US011179417B2

(12) United States Patent
Bauer et al.

(10) Patent No.: US 11,179,417 B2
(45) Date of Patent: Nov. 23, 2021

(54) METHOD FOR OBTAINING GLOBALLY ACTIVATED MONOCYTES

(71) Applicants: TRANSIMMUNE AG, Dusseldorf (DE); YALE UNIVERSITY, New Haven, CT (US)

(72) Inventors: Gunter Bauer, Schmalfeld (DE); Justin Duckworth, Surrey (GB); Robert Tigelaar, New Haven, CT (US); Richard Edelson, Westport, CT (US); Michael Girardi, Madison, CT (US); Karsten Henco, Dusseldorf (DE); Adrian Hayday, Kent (GB)

(73) Assignees: Transimmune AG, Düsseldorf (DE); Yale University, New Haven, CT (US)

( * ) Notice: Subject to any disclaimer, the term of this patent is extended or adjusted under 35 U.S.C. 154(b) by 432 days.

(21) Appl. No.: 15/323,219

(22) PCT Filed: Jul. 3, 2015

(86) PCT No.: PCT/EP2015/065199
§ 371 (c)(1),
(2) Date: Dec. 30, 2016

(87) PCT Pub. No.: WO2016/001405
PCT Pub. Date: Jan. 7, 2016

(65) Prior Publication Data

US 2017/0128490 A1 May 11, 2017

Related U.S. Application Data

(60) Provisional application No. 62/020,547, filed on Jul. 3, 2014.

(30) Foreign Application Priority Data

Aug. 1, 2014 (GB) .................................... 1413665

(51) Int. Cl.
*A61K 35/15* (2015.01)
*C12N 5/0784* (2010.01)
*A61K 39/395* (2006.01)
*C12N 5/0786* (2010.01)

(52) U.S. Cl.
CPC ........ *A61K 35/15* (2013.01); *A61K 39/39558* (2013.01); *C12N 5/0639* (2013.01); *C12N 5/0645* (2013.01); *C12N 2502/115* (2013.01); *C12N 2521/00* (2013.01)

(58) Field of Classification Search
CPC .............. A61K 35/15; A61K 39/39558; C12N 5/0645; C12N 5/0639
USPC ........................................................ 435/325
See application file for complete search history.

(56) References Cited

U.S. PATENT DOCUMENTS

| | | | |
|---|---|---|---|
| 6,252,052 B1 | 6/2001 | Stockert et al. | |
| 6,524,855 B2 | 2/2003 | Edelson et al. | |
| 7,109,031 B2 * | 9/2006 | Edelson ............ | A61K 39/0011 435/325 |
| 8,053,234 B2 | 11/2011 | Hochrein et al. | |
| 8,524,495 B2 | 9/2013 | Edelson | |
| 9,321,991 B2 | 4/2016 | Edelson | |
| 10,087,418 B2 | 10/2018 | Edelson | |
| 2003/0118588 A1 | 6/2003 | Diehl et al. | |
| 2003/0133914 A1 | 7/2003 | Edelson et al. | |
| 2003/0219420 A1 | 11/2003 | Edelson et al. | |
| 2004/0110226 A1 | 6/2004 | Lazar et al. | |
| 2005/0084966 A1 | 4/2005 | Edelson et al. | |
| 2008/0199471 A1 | 8/2008 | Bernett et al. | |
| 2008/0241815 A1 | 10/2008 | Edelson et al. | |
| 2009/0053251 A1 | 2/2009 | Pogue-Caley et al. | |
| 2009/0074787 A1 | 3/2009 | Gomez-Navarro et al. | |
| 2009/0130715 A1 | 5/2009 | Bedian et al. | |
| 2010/0023458 A1 | 1/2010 | Kociuba | |
| 2010/0234578 A1 | 9/2010 | Mikayama et al. | |
| 2010/0267137 A1 | 10/2010 | Edelson | |
| 2011/0033449 A1 | 2/2011 | Glennie et al. | |
| 2013/0295091 A1 | 11/2013 | Esslinger et al. | |
| 2013/0323710 A1 | 12/2013 | Edelson | |
| 2013/0336976 A1 | 12/2013 | Glennie et al. | |
| 2016/0130552 A1 | 5/2016 | Henco et al. | |
| 2016/0194606 A1 | 7/2016 | Edelson | |
| 2016/0298082 A1 | 10/2016 | Henco et al. | |
| 2017/0128490 A1 | 5/2017 | Bauer et al. | |
| 2018/0195042 A1 | 7/2018 | Bauer et al. | |
| 2019/0017025 A1 | 1/2019 | Edelson | |

FOREIGN PATENT DOCUMENTS

| | | | |
|---|---|---|---|
| CN | 1646566 | A | 7/2005 |
| JP | 2003-514873 | A | 4/2003 |
| JP | 2006-265245 | A | 10/2006 |
| JP | 2007-277242 | A | 10/2007 |
| JP | 2010-506925 | A | 3/2010 |
| WO | WO-01/37870 | A1 | 5/2001 |

(Continued)

OTHER PUBLICATIONS

Woodhead et al. (Immunology, 1998, 94: 552-559).*

(Continued)

*Primary Examiner* — Yan Xiao
(74) *Attorney, Agent, or Firm* — Clark & Elbing LLP

(57) ABSTRACT

The present invention relates to methods for producing immuno-stimulatory autologous dendritic cells. The present invention further relates to the use of such cells for treating patients suffering from hyper-proliferative disease such as cancer.

5 Claims, 30 Drawing Sheets

Figure 1:
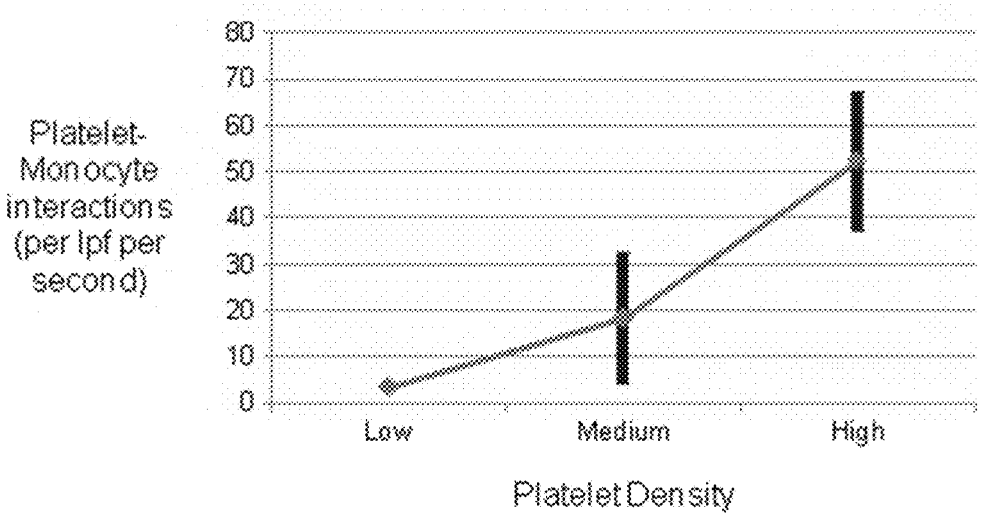
Figure 1:
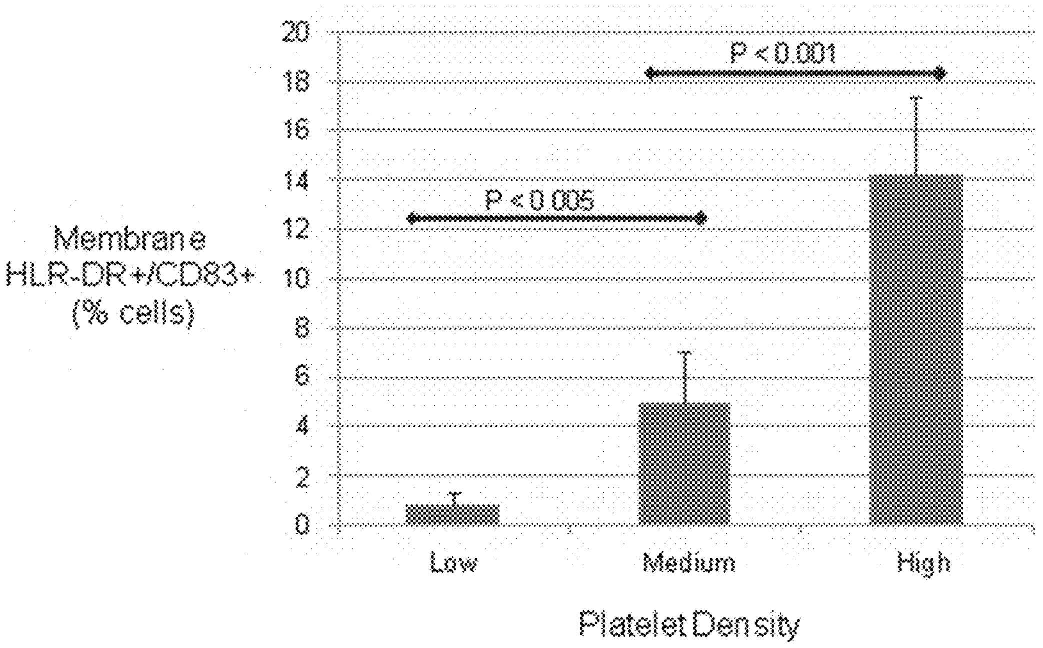

Specification includes a Sequence Listing.

(56) References Cited

FOREIGN PATENT DOCUMENTS

| | | | | |
|---|---|---|---|---|
| WO | WO-2005/000870 A2 | | 1/2005 | |
| WO | WO-2005/032475 A2 | | 4/2005 | |
| WO | WO-2005/105139 A2 | | 11/2005 | |
| WO | WO-2007/113648 A2 | | 10/2007 | |
| WO | WO-2008/110372 A1 | | 9/2008 | |
| WO | WO-2009/089260 A2 | | 7/2009 | |
| WO | WO-2011/137365 A1 | | 11/2011 | |
| WO | WO 2011137365 | * | 11/2011 | A61M 1/36 |
| WO | WO-2012/088272 A1 | | 6/2012 | |
| WO | 2014/106629 A1 | | 7/2014 | |
| WO | 2014/106631 A1 | | 7/2014 | |

OTHER PUBLICATIONS

Heinzelmann et al. (Cellular Immunology 1997, 176, 127-134).*
NCBI_MeSH_PLAUR (Jul. 29, 2008).*
Anguille et al., "Dendritic Cells as Pharmacological Tools for Cancer Immunotherapy," Pharmacol Rev. 67(4): 731-53 (2015).
Communication Pursuant to Article 94(3) EPC for European Patent Application No. 14700050.9, dated Jul. 13, 2017 (5 pages).
English Translation of Notice of Preliminary Rejection for Korean Patent Application No. 10-2015-7020667, dated Dec. 16, 2016 (4 pages).
English Translation of Decision of Rejection for Japanese Patent Application No. 2015-551179, dated Jun. 27, 2017 (5 pages).
English Translation of Notice of Reasons for Rejection for Japanese Patent Application No. 2015-551178, dated Oct. 11, 2016 (5 pages).
EPO Communication for European Patent Application No. 14700050.9 dated Nov. 27, 2018 (4 pages).
Examination Report for Australian Patent Application No. 2014204346, dated Sep. 6, 2016 (3 pages).
Harry et al., "Generation and characterisation of therapeutic tolerogenic dendritic cells for rheumatoid arthritis," Ann Rheum Dis. 69(11): 2042-2050 (2010) (11 pages).
International Search Report and Written Opinion for PCT Patent Application No. PCT/EP2014/050012, dated May 9, 2014 (12 pages).
Office Action for Canadian Patent Application No. 2,897,113, dated Oct. 6, 2016 (4 pages).
Office Action for United Kingdom Patent Application No. 1300052. 6, dated Jul. 1, 2013 (10 pages).
Phillips et al., "Clinical Tolerogenic Dendritic Cells: Exploring Therapeutic Impact on Human Autoimmune Disease," Front Immunol. 8(1279): 1-9 (2017).
Result of consultation for European Patent Application No. 14700025.1 dated Jun. 26, 2019 (3 pages).
Summons to Attend Oral Proceedings Pursuant to Rule 115(1) EPC for European Patent Application No. 14700025.1, dated May 3, 2019 (4 pages).
Ventura et al., "Extracorporeal Photochemotherapy Drives Monocyte-to-Dendritic Cell Maturation to Induce Anti-Cancer Immunity," author manuscript published online first on May 15, 2018, published in final edited form as: Cancer Res. 78(14): 4045-58 (2018) (29 pages).
Wilcox, "Cutaneous T-cell lymphoma: 2016 update on diagnosis, risk-stratification, and management," available in PMC Jan. 1, 2017, published in final edited form as: Am J Hematol. 91(1): 151-65 (2016) (38 pages).
Brash et al., "Adsorption on glass and polyethylene from solutions of fibrinogen and albumin," Thrombosis Research. 9:249-259 (1976) (12 pages).
Translation of Japanese Office Action dated Sep. 4, 2018 in application No. JP 2015-551178 (8 pages).
Durazzo et al., "Induction of monocyte-to-dendritic cell maturation by extracorporeal photochemotherapy: Initiation via direct platelet signaling," Transfusion and Apheresis Science 50:370-378 (2014).
Edelson, "Mechanistic insights into extracorporeal photochemotherapy: Efficient induction of monocyte-to-dendritic cell maturation," Transfusion and Apheresis Science 50:322-329 (2014).
Zimmer et al., "Identification of a New Phenotype of Tolerogenic Human Dendritic Cells Induced by Fungal Proteases from Aspergillus orzyae," J Immunol. 186:3966-3976 (2011) (12 pages).
Krzysiek, "Role of Glucocorticoid-Induced Leucine Zipper (GILZ) Expression by Dendritic Cells in Tolerance induction," Transplantation Proceedings. 42(8):3331-3332 (2010).
European Office Action dated Jul. 12, 2017 in application No. 14700025.1 (6 pages).
Korean Office Action dated Jun. 27, 2017 in application No. 10-2015-7020665 (8 pages) (English language translation provided).
Durazzo, "Platelet Induction of Monocyte to Dendritic Cell Differentiation," Yale Medicine Thesis Digital Library, Paper 1549, pp. 1-64 (Jan. 2011).
Canadian Office Action dated Oct. 7, 2016 in application No. CA2897109 (4 pages).
Japanese Office Action dated Oct. 11, 2016 in application No. 2015-551178 (10 pages) (English language translation provided).
Australian Office Action dated Sep. 6, 2016 in application No. 2014204344 (3 pages).
Berger et al., "Induction of Human Tumor-Loaded Dendritic Cells," Int. J. Cancer, 91:438-447 (2001).
Spisek et al., "Maturation state of dendritic cells during the extracorporeal photopheresis and its relevance for the treatment of chronic graft-versus-host disease," Transfusion. 46(1):55-65 (2006).
Baird et al., "Generation of immature dendritic cells by modified extracorporeal photophoresis," Journal of Investigative Dermatology, vol. 30, No. Suppl. 1 p. S136, abstract, No. 813 (2010).
Hu et al., "Tolerogenic dendritic cells and their potential applications," Immunology, vol. 132, pp. 307-314 (2010).
Rudikoff et al., "Single amino acid substitution altering antigen-binding specificity," Immunology, 79, pp. 1979-1983 (1982) (5 pages).
Colman, "Effects of amino acid sequence changes on antibody-antigen interactions," Research in Immunology, 145, pp. 33-36 (1994) (4 pages).
Kussie et al., "A Single Engineered Amino Acid Substitution Changes Antibody Fine Specificity," Journal of Immunology, 152, pp. 146-152 (1994).
Chen et al., "Enhancement and destruction of antibody function by somatic mutation: unequal occurence is controlled by V gene combinatorial associations," The EMBO Journal, 14(12), pp. 2784-2794 (1995).
Kono et al., Trastuzumab (Herceptin) Enhances Class I-Restricted Antigen Presentation Recognized by HER-w/ neu-Specific T Cytotoxic Lymphocytes, Clinical Cancer Research, 10, pp. 2538-2544 (2004).
Gupta et al., "A novel human-derived antibody against NY-ESO-1 improves the efficacy of chemotherapy", Cancer Immunity, vol. 13, pp. 1-9 (2013).
Nicholaou et al., "Directions in the immune targeting of cancer: Lesson learned from cancer-testis Ag NY-ESO-1," Immunology and Cell Biology, vol. 84, pp. 303-317 (2006).
Vonderheide et al., "Clinical Activity and Immune Modulation in Cancer Patients Treated With CP-870,893, a Novel CD40 Agonist Monoclonal Antibody", Journal of Clinical Oncology, vol. 25, No. 7, pp. 876-883 (2007).
Carpenter et al., "Activation of Human B Cells by the Agonist CD40 Antibody CP-870-893 and Augmentation Nith Simultaneous Toll-Like Receptor," Journal of Translational Medicine, vol. 7 (2009) (10 pages).
Law et al., "Preclinical Antilymphoma Activity of a Humanized Anti-CD40 Monoclonal Antibody, SGN-40", Cancer Research, vol. 65, No. 18, pp. 8331-8338 (2005) (9 pages).
Kelley et al., "Preclinical Pharmacokinetics, Pharmacodynamics, and Activity of a Humanized Anti-CD40 Antibody (SGN-40) in Rodents and Non-Human Primates," British Journal of Pharmacology, vol. 148, No. 8, pp. 1116-1123 (2006) (8 pages).
Aoki et al., "Antibody Responses Against NY-ESO-1 and HER2 Antigens in Patients Vaccinated with combinations of Cholesteryl Pullulan (CHP)-NY-ESO-1 and CHP-HER2 With OK-432," Vaccine. 27(49):6854-61 (2009).
Gnjatic et al., "NY-ESO-1: Review of an Immunogenic Tumor Antigen," Advances in Cancer Res., 1-30 (2006) (30 pages).

(56) References Cited

OTHER PUBLICATIONS

Kawabata et al., "Antibody Response Against NY-ESO-1 in CHP-NY-ESO-1 Vaccinated Patients," Int. J Cancer. 120(10):2178-2184 (2007).
Lohmann et al., "Primary Malignant Melanoma of the Oesophagus: A clinical and Pathological Study with Emphasis on the Immunophenotype of the Tumours for Melanocyte Differentiation Markers and Cancer/Testis Antigens," Melanoma Res., 13(6):595-601 (2003).
Schultz-Thater et al., "NY-ESO-1 Tumour Associated Antigen is a Cytoplasmic Protein Detectable by Specific Monoclonal Antibodies in Cell Lines and Clinical Specimens," Br. J. Cancer, 83(2):204-08 (2000).
Valmori et al., "Identification of B Cell Epitopes Recognized by Antibodies Specific for the Tumor Antigen NY-ESO-1 in Cancer Patients with Spontaneous Immune Responses," Clin. Immunol. 117(1):24-30 (2005).
Berger et al., "Rapid Generation of Maturationally Synchronized Human Dendritic Cells: Contribution to the Clinical Efficacy of Extracorporeal Photochemotherapy," Blood, vol. 116, No. 23, pp. 4838-4847 (2010) (11 pages).
Hoffmann et al., "Induction of Immunomodulatory Dendritic Cells by Transimimunization," Journal of Investigative Dermatology, vol. 127, S117, p. 8117, abstract No. 701 (2007) (1 page).
Engberg et al., Generation of Tumor-Specific Anti-Melanoma T-Cell Responses by Extracorporeal Photochemotherapy-Induced Dendritic Cells, Journal of Investigative Dermatology, vol. 131, S94, p. 894, abstract No. 562 (2011) (1 page).
Khalil et al., "Conversion of Monocytes to Dendritic Cells by Platelet Signaling," Journal of Investigative Dermatology, vol. 132, S101, p. 8101, abstract No. 595 (2012) (1 page).
Durazzo et al., "Platelet Induction of Monocyte-to-Dendritic Cell Maturation," Journal of Investigative Dermatology, vol. 130, S121, p. 8121, abstract No. 721 (2010) (1 page).
Salskov-Iversen et al., "Rapid Construction of a Dendritic Cell Vaccine Through Physical Pertubation and Apoptotic Malignant T Cell Loading," Journal of Immune Based Therapies and Vaccines. 3:4 (2005) (16 pages).
Cohen et al., "GILZ expression in human dendritic cells redirects their maturation and prevents antigen-specific T lymphocyte response," Blood, vol. 107, No. 5, pp. 2037-2044 (2006) (9 pages).
UK Office Action dated Jul. 1, 2013 in application No. GB130049.2 (10 pages).
International Search Report and Written Opinion for International Application No. PCT/EP2014/050010, dated May 9, 2014 (14 pages).
European Office Action dated Jul. 13, 2017 in application No. 14700050.9 (5 pages).
Japanese Office Action dated Jun. 27, 2017 in application No. 2015-551179 (10 pages) (English language translation provided).
Notice of Reasons for Rejection for Japanese Patent Application No. 2015-551178, dated Oct. 11, 2016 (5 pages).
Notice of Reasons for Rejection for Japanese Patent Application No. 2015-551178, dated Sep. 4, 2018 (8 pages).
Office Action for Canadian Patent Application No. 2897109, dated Oct. 7, 2016 (4 pages).
Office Action for European Patent Application No. 14700025.1, dated Jul. 12, 2017 (6 pages).
Baird, "Baird, 8-Mop/uva inhibits maturation of extracorporeal photochemotherapy (ECP) generated dendritic cells," Yale Medicine Thesis Digital Library, 1537, pp. 1-47 (2011) (48 pages).
UK Office Action dated Jul. 1, 2013 in application No. GB1300052.6 (10 pages).
International Search Report and Written Opinion for International Application No. PCT/EP2014/050012, dated May 9, 2014 (14 pages).
Canadian Office Action dated Oct. 6, 2016 in application No. 2897113 (4 pages).
Australian Office Action dated Sep. 6, 2016 in application No. 2014204346 (3 pages).
Japanese Office Action dated Oct. 11, 2016 in application No. 2015-551179 (8 pages) (English language translation provided).
Korean Office Action dated Dec. 16, 2016 in application No. 10-2015-7020667 (10 pages) (English language translation provided).
Restriction Requirement for U.S. Appl. No. 14/759,016 dated May 17, 2017 (7 pages).
Non-Final Office action for U.S. Appl. No. 14/759,016 dated Oct. 19, 2017 (8 pages).
Final Office Action for U.S. Appl. No. 14/759,016 dated Apr. 6, 2018 (9 pages).
Non-Final Office Action for U.S. Appl. No. 14/759,016 dated Feb. 8, 2019 (9 pages).
Final Office Action for U.S. Appl. No. 14/759,016 dated Dec. 17, 2019 (10 pages).
Restriction Requirement for U.S. Appl. No. 14/759,012 dated Feb. 1, 2017 (10 pages).
Non-Final Office Action for U.S. Appl. No. 14/759,012 dated May 3, 2017 (12 pages).
Non-Final Office Action for U.S. Appl. No. 14/759,012 dated Oct. 24, 2017 (13 pages).
Final Office Action for U.S. Appl. No. 14/759,012 dated May 23, 2018 (14 pages).
Non-Final Office Action for U.S. Appl. No. 14/759,012 dated Jan. 22, 2019 (15 pages).
Non-Final Office Action for U.S. Appl. No. 14/759,012 dated Apr. 30, 2019 (16 pages).
Final Office Action for U.S. Appl. No. 14/759,012 dated Sep. 12, 2019 (15 pages).
Restriction Requirement for U.S. Appl. No. 15/741,384 dated Sep. 16, 2019 (7 pages).
Hank et al., "Activation of Multiple Effector Mechanisms to Enhance Tumor Immunotherapy," J Immunol. 14:329-335 (1993).
UK Office Action for Application No. GB1413665.9 dated Apr. 29, 2015 (8 pages).
"Regenerative Medicine," Wikipedia, <https://en.wikipedia.org/wiki/Regenerative_medicine>, accessed Jan. 2, 2018 (5 pages).
International Search Report and Written Opinion for International Application No. PCT/EP2015/065199 dated Sep. 14, 2015 (13 pages).

* cited by examiner a)

b)

a)

b)

a)

b)

c)

d)

A)

B)

| | HLA-DR | CD86 | ICAM-1 | PLAUR | FSC/SSC Complexity |
|---|---|---|---|---|---|
| Fresh (Ficoll) PBMC | 0 | 0 | 0 | 0 | 0 |
| D1 PBMC | ++ | 0 | ++ | ++ | + |
| PP D1 PBMC | +++ | + | ++++ | ++++ | +++ |
| Immature Fast DC | ++++ | +++ | ++ | – | ? |

A)

B)

Growth Inhibition of YUMM Tumors (Exp 1)

METHOD FOR OBTAINING GLOBALLY ACTIVATED MONOCYTES

FIELD OF THE INVENTION

The present invention relates to methods for producing globally activated monocytes and uses thereof.

BACKGROUND OF THE INVENTION

Dendritic cells (DC) are recognized to be potent antigen presenting cells for the initiation and control of cellular immunologic responses in humans. Since DC can either be immuno-stimulatory or immuno-suppressive, depending on which set of their potential properties they express at the moment of interaction with responsive specific clones of T cells, they are considered profoundly important pivotal players in T cell-mediated immune reactions. As a broad, but widely held generalization, immature DC are more "tolerogenic" than their more mature counterparts, while mature DC are thought to be more "immunogenic" than their immature precursors. The capacity of DC, generated ex vivo from monocytes and armed with specific antigen, to function effectively in either immunologic direction, is dependent on their viability and vigor after being returned to the patient. It is logically concluded that the balance between counteractive immuno-stimulatory and immunosuppressive DC will be a major determinant of both the direction and potency of DC-dependent therapeutic immune responses.

The production of immuno-stimulatory or immune-suppressive antigen presenting cells including dendritic cells by a process called transimmunization has been described in PCT/EP2014/050010 and PCT/EP2014/050012, respectively. The methods described therein build on deciphering certain mechanistic aspects of extracorporeal photopheresis (ECP).

Extracorporeal Photopheresis (ECP) has been used successfully to treat cutaneous T-cell lymphoma (CTCL) in subsets of patients. In ECP, patients suffering from CTCL receive the photoactivatable compound 8-methoxypsoralen (8-MOP). Patients are then leukapheresed to obtain buffy coats and these buffy coats are passed through a continuous closed circuit ultraviolet exposure device to irradiate the leukapheresed buffy coats and thereby lethally damage exposed lymphocytes. In this manner, 8-MOP is induced to covalently crosslink base pairs of DNA. The concept of ECP is to destroy proliferating metastatic T-cells of CTCL and to then to intravenously re-introduce the dying cells to the patient. It has been learned that this process additionally leads to conversion of passaged blood monocytes to DC without the need for stimulation by addition of exogenous cytokines. These ECP-induced DCs are furthermore assumed to internalize, process and display antigens from the tumor cells, which were destroyed by the combination of 8-MOP and UV irradiation. It has been hypothesized that reintroduction of these loaded dendritic cells to the patient account for at least part of the success of ECP when treating CTLC.

However, it has also been found that ECP or ECP-like process lead to truncated, i.e. immuno-suppressive or tolerogenic DC, likely contributing heavily to ECP's clinical efficacy in the treatment of Graft versus Host Disease, which commonly follows post-bone marrow stem allotransplants. The precise mechanistic aspects of ECP on differentiation of monocytes into either immuno-stimulatory or immuno-suppressive DC have remained elusive (for review of the ECP process see Girardi et al. (2002), *Transfusion and Apheresis Science,* 26, 181-190).

ECP and ECP-like processes are thus conceived to lead to complex mixtures of immuno-stimulatory and immuno-suppressive DC. Of course, from inter alia a clinical perspective, it would be important to understand how the ECP and ECP-like processes can be modified to overcome these limitations and how one can obtain purposively and selectively preferentially immuno-stimulatory over immuno-suppressive DC and vice versa. Further, the classical ECP process is, in principle an in vivo method as the obtained dendritic cell mixtures are reinfused into the patient. It would, however, be desirable to have methods available that allow preferential production of immuno-stimulatory over immuno-suppressive DC and vice versa outside the human or animal body.

The transimmunization processes described in PCT/EP2014/050010 and PCT/EP2014/050012 allow preferential production of immune-stimulatory or immune-suppressive antigen-presenting cells including dendritic cells. Monocytes are activated through physical forces such as mechanical stress and potentially interaction with plasma components such as platelets. These activated monocytes can develop into antigen-presenting cells such as dendritic cells, which can be supported by co-incubation with e.g. apoptotic disease antigen shedding cells. The activation process can be monitored by co-expression of e.g. HLA-$DR^+$/$CD83^+$. However, differentiation of these activated monocytes may also be channeled towards immuno-suppressive antigen-presenting cells such as dendritic cells by applying e.g. 8-methoxypsoralen (8-MOP) and UV-A. Differentiation into immuno-suppressive antigen-presenting cells such as dendritic cells may be monitored e.g. by increased expression of GILZ.

The immuno-stimulatory or immuno-suppressive antigen-presenting cells such as dendritic cells as described in PCT/EP2014/050010 and PCT/EP2014/050012 provide for certain benefits. They can be produced in comparatively large amounts with minimal interference by other factors and are patient-specific. Other than the common methods, generation of such immuno-stimulatory dendritic cells does not require complex and rather expensive cytokine cocktails. In those standard methods, the cytokines are employed at concentrations very much higher (often by orders of magnitude) than those encountered in vivo under physiological conditions.

OBJECTIVES AND SUMMARY OF THE INVENTION

The inventors have realized that the transimmunization processes described in PCT/EP2014/050010 and PCT/EP2014/050012 allow to obtain globally activated monocytes (GAMs) and that these GAM can not only be used for obtaining immuno-stimulatory or immuno-suppressive antigen-presenting cells such as dendritic cells, but may, in view of their phagocytizing properties, be also used for direct tumor killing, e.g. of tumors being treated with e.g. a therapeutically active antibody, for wound-healing, and/or for purposes in regenerative medicine.

One objective of the present invention is to provide methods for producing globally activated monocytes.

Another objective of the present invention is use such globally activated monocytes for anti-tumor therapy, wound healing, and regenerative medicine.

These and other objectives as they will become apparent from the ensuing description hereinafter are solved by the subject matter of the independent claims. Some of the preferred embodiments of the present invention form the subject matter of the dependent claims. Yet other embodiments of the present invention may be taken from the ensuing description.

The present invention is based to some extent on the realization that the transimmunization processes described in PCT/EP2014/050010 and PCT/EP2014/050012 allow obtaining globally activated monocytes (GAMs). Further, such GAMs may have phagocytizing activity and may thus be used for treatment of cancers, wound healing, and/or regenerative medicine. They may also be used for differentiation into immuno-stimulatory or immuno-suppressive antigen-presenting cells such as dendritic cells. These aspects are schematically summarized in FIG. 24.

It is assumed that GAMs may be used for e.g. killing tumor cells by way of their phagocytizing activity because it has been shown that therapeutic-antibody mediated therapy may include phagocytosis of antibody-labeled tumor cells by macrophages (see e.g. Tseng et al., *PNAS,* 110 (27), 11103-11108 (2013) or Gül et al., *The Journal of Clinical Investigation,* 124(2), 812-823 (2014)).

Similarly phagocytozing macrophages have been involved in wound healing processes (see e.g. Willenborg et al. *Blood,* 120 (3), 613-625, 2012). Moreover, the occurrence of wounds and the initiation of the wound healing process bears some resemblance with the methods described herein for obtaining GAMs (see also FIG. 25). Thus, in the methods described herein monocytes are activated by e.g. mechanical stress.

The concept of monocyte-derived cells and their uses has moreover been discussed e.g. in Hume et al., *J. Leukoc Biol.;* 92:433 (2012).

The data presented hereinafter, which for a miniaturized and scalable device allowed (i) to mimic some aspects of the classical ECP procedure, (ii) to elucidate the cellular, molecular mechanism and biophysical conditions of induction of differentiation of monocytes into immuno-stimulatory autologous dendritic cells in an extracorporeal amount of blood. This data shows that the activation of platelets and binding of monocytes to such activated platelets under conditions of shear force is beneficial for obtaining immuno-stimulatory autologous dendritic cells. As is shown by the experiments described hereinafter, these immuno-stimulatory autologous dendritic cells can be characterized by expression of molecular markers indicative of immuno-stimulatory autologous dendritic cells. The data also shows that conditions that lead to an increased expression of Glucocorticoid-induced Leucine Zipper (GILZ) will favorably allow monocytes to differentiate into immuno-suppressive autologous dendritic cells. The data moreover suggests that the process of obtaining immuno-stimulatory dendritic cells seems to include a global monocyte activation step and a subsequent monocyte to immuno-stimulatory antigen-presenting cell (e.g. dendritic cell) differentiation step. These steps seem to be initially dependent on physical activation of monocytes with the physical forces occurring during e.g. initial purification or enrichment of monocytes being sufficient for activation even though passage of e.g. initially activated monocytes through devices as described herein may allow improvement of activation and differentiation. Further, if activation and differentiation take place in the absence of photoactivatable agents and UV-A (as it is and was used in ECP processes), formation of immuno-suppressive dendritic cells seems to be favorably reduced as expression of GILZ is reduced. The present data further shed light on the nature of molecular markers that can be used to identify immuno-stimulatory dendritic cells.

Some of the embodiments, which are based on this data, are described in more detail hereinafter.

In a first aspect, the invention relates to a method for obtaining globally activated monocytes, said method comprising at least the steps of:

a) subjecting an extracorporeal quantity of a mammalian subject's blood sample, which comprises monocytes, to a physical force such that said monocytes are globally activated, wherein said globally activated monocytes are characterized by increased expression of at least HLA-DR, PLAUR and ICAM-1.

In general, suitable molecular markers are described hereinafter and may be taken from e.g. Table 6. Markers like HLA-DR, PLAUR and ICAM-1 may be considered to be indicative of global monocyte activation. Globally activated monocytes may preferably be characterized by increased expression of additionally at least ABCA1, CCL2, CCL7, CD68, CRK, FAS, IL 10, RAB7B, RALA, SCARF1, and/or THBS1. Further such globally activated monocytes may be characterized by increased expression of additionally at least CXCL1, CXCL2, CXCL5, CXCL16, ITGA5, ITGAV, MMP9, MSR1, OLR1, PLAU, PLAUR, SIRPa, TIMP1, and/or TNF. Globally activated monocytes may thus be also identifiable by increased expression of at least 3, 4, 5, 6, 7, 8, 9, 10, 15, 20, or 25 markers of Table 6. In general, globally activated monocytes will not show an increased expression of GILZ. Increased expression refers to a comparison of the expression of these markers before and after subjecting the cells to physical forces such as mechanical stress.

In one embodiment of this first aspect, global activation of monocytes is inter alia achieved in that said extracorporeal quantity of said mammalian subject's blood sample is subjected to a physical force by passing or cycling said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample.

Thus, global activation of monocytes and induction of globally activated monocytes can be achieved and influenced by varying the flow forces of the extracorporeal quantity of the mammalian subject's blood sample through the flow chamber of such a device, by varying the geometry of the flow path of the flow chamber, by varying the dimensions of the flow chamber, by varying the temperature of the flow chamber and thus of the extracorporeal quantity of the mammalian subject's blood sample, by changing the biophysical and geometric surface properties of the flow path, by allowing the exposure of the extracorporeal quantity of the mammalian subject's blood sample in the flow chamber to visible or UV light, etc.

As is shown hereinafter, global activation of monocytes and e.g. subsequent induction of differentiation into immuno-stimulatory autologous dendritic cells may be optimized dependent on interaction of monocytes with activated platelets and/or specific plasma components in a situation where the monocytes experience physical force which may be provided by a device as described hereinafter.

In another embodiment of this first aspect, the present invention thus relates to global activation of monocytes, which experience a physical force and which interact with activated platelets and/or plasma components such as fibrinogen or fibronectin. Activation may be a process of subsequent steps including the steps of (i) immobilizing plasma components such as fibrinogen or fibronectin either as isolated components or as part of the extracorporeal quantity of the mammalian subject's blood sample in the flow chamber of said device (ii) passing platelets, which may be obtained as a purified fraction from the extracorporeal quantity of the mammalian subject's blood sample or as part of the extracorporeal quantity of the mammalian subject's blood sample, through the flow chamber such that the platelets can interact with and become activated by the plasma components and (iii) passing monocytes, which may be obtained as a purified fraction from the extracorporeal quantity of the mammalian subject's blood sample or as part of the extracorporeal quantity of the mammalian subject's blood sample, through the flow chamber such that the monocytes can interact with and become activated by the activated platelets and/or the plasma components.

Thus, in addition and/or alternatively to the above described parameters and variable touching on the architecture of and the conditions under which the device is operated, global activation of monocytes and e.g. subsequent induction of differentiation into immuno-stimulatory autologous dendritic cells can be achieved and influenced by varying the nature, purity and concentrations of the plasma components, the nature, purity and concentration of the platelets, the order of steps by which the plasma components and/or the platelets are passed through and/or disposed on the flow chamber, the density by which the flow chamber is coated with the plasma components and/or the platelets, the flow forces of the extracorporeal quantity of the mammalian subject's blood sample and in particular the platelets and/or the monocytes are passed through the flow chamber of such a device, the temperature and/or time at which the extracorporeal quantity of the mammalian subject's blood sample and in particular the platelets and/or the monocytes are passed through the flow chamber of such a device, etc., the nature, purity and concentrations of additional factors such as 8-MOP and/or cytokines are added to the extracorporeal quantity of the mammalian subject's blood sample and in particular to the monocytes, etc.

It needs, however, to be understood that while such devices may be particularly effective in inducing global monocyte activation, physical forces which monocytes experience during initial purification or enrichment such as during Ficoll-Hypaque enrichment as described hereinafter may already be sufficient to activate monocytes and to induce their differentiation into globally activated monocytes and subsequent induction of e.g. immuno-stimulatory antigen-presenting cells such as dendritic cells. Similarly even though activated platelets and/or specific plasma components may be helpful in increasing global monocyte activation and differentiation into immuno-stimulatory antigen-presenting cells such as dendritic cells they may not be absolutely necessary. In order to effect global monocyte activation the invention thus contemplates as a minimal requirement the application of physical forces. In order to let this process proceed as uninfluenced as possible, the invention as a preferred embodiment always considers to not apply molecular cocktails to achieve maturation and differentiation of monocytes into e.g. immuno-stimulatory autologous dendritic cells and to avoid conditions that lead to e.g. increased expression of GILZ such as co-application of photoactivatable agents and UV-A.

Globally activated monocytes may be identified by the markers above and may be differentiated from immune-stimulatory antigen-presenting cells such as dendritic cells. Markers for immuno-stimulatory dendritic cells derived from globally activated monocytes include PLAUR, NEU1, CD80, CCR7, LOX1, CD83, ADAM Decysin, FPRL2, GPNMB, ICAM-1, HLA-DR, and/or CD86.

Additionally or alternatively to these embodiments, the invention also relates to such methods which are conducted under conditions which avoid an increased expression of GILZ and/or an increased number of $CD4^+CD25^+Foxp3^+$ cells and/or a down-regulations of CD80, CD86 and CD83. The invention thus relates to e.g. methods, which are conducted in the absence of a photoactivatable agent such as 8-MOP and without exposure to light such as UV-A.

Another embodiment relates to globally activated monocytes as described herein for use in treating cancer. Treatment of cancer takes preferably place by phagocytosis of tumor cells by globally activated monocytes. This process may be initiated by treatment of an individual suffering from cancer, which is treated with a therapeutically active antibody as cancer cells recognized by such antibodies may be phagocytosed by globally activated monocytes. Treatment of cancer may preferably be considered for patients undergoing chemotherapy and/or radiation therapy such as gamma-irradiation therapy. In view of the data presented herein (see in particular Experiment 9), it seems reasonable to assume that the globally activated monocytes as they are described herein may take up the tumor-associated antigens released in such patients as a consequence of chemotherapy, radiation therapy or combinations thereof and thereby further develop into immutable-stimulatory antigen-presenting cells such as dendritic cells displaying tumor-associated antigens and thereby mediating an anti-tumor response. In such patients, globally activated monocytes may provide for an anti-tumor activity even if the patient is not undergoing therapy with therapeutically active antibodies. In fact, globally activated monocytes as they are described herein and are obtainable by the methods described herein are considered for use in treating patients suffering from other disease is as long as the patient is undergoing therapy mediating release of disease-associated antigens.

Thus, the invention also relates to globally activated monocytes as described herein for use in treating cancer in individuals, which receive antibody therapy. Globally activated monocytes may thus be used for treating cancer in a non-antigen specific manner.

The invention also relates to globally activated monocytes as described herein for use in wound healing. Such wounds are chronic wounds, diabetic wounds, vascular compromised wounds including venous stasis, post-surgical wounds, etc.

The invention also relates to globally activated monocytes as described herein for use in regenerative medicine such as stimulation of tissue repair (beyond wound healing), as in degenerative joint disease or degenerative neurologic and brain diseases (e.g. Alzheimer's disease), hair growth/regrowth (e.g. androgenetic alopecia).

In general, the invention also relates to globally activated monocytes as described herein for use in phagocytozing cells. Such phagocytized cells may include antibody-coated cells including antibody-coated tumor cells, apoptotic cells including apoptotic tumor cells, etc. Formation of cells with phagocytozing activity has been observed for samples undergoing an ECP process. This observation together with the finding that the methods of the present invention allow obtaining globally activated monocytes as detectable by increased FSC/SSC complexity suggests that the globally activated monocytes will also have phagocytozing activity.

This phagocytozing activity can be responsible for recognizing the information shed by apoptotic or necrotic cells and, e.g. in the context of wound healing and/or regenerative medicine, shutting down such destructive information, cleaning up the damage, and stimulating regeneration.

In view of their phagocytozing activity, the globally activated monocytes may also be used for treating inflammatory diseases.

The globally activated monocytes may be administered systemically by re-infusing the cells into the body or by local delivery, e.g. where the wound or inflammation occurred.

It needs to be understood that wherever the present invention uses the terminology "globally activated monocytes as described herein for use in treating . . . " or "globally activated monocytes as described herein for use in . . . " such as "globally activated monocytes as described herein for use in treating cancer" or "globally activated monocytes as described herein for use in wound-healing", this means to disclose a corresponding "method of treatment" or "method of use", e.g. "method of treating cancer" or "method of wound-healing" by administering globally activated monocytes. Similarly, this phraseology intends to disclose "the use of globally activated monocytes for the manufacturing of a medicament for treating" or the "the use of globally activated monocytes for the manufacturing of a medicament for use in" such as "the use of globally activated monocytes for the manufacturing of a medicament for treating cancer" or the "the use of globally activated monocytes for the manufacturing of a medicament wound healing".

Further embodiments will be described hereinafter.

FIGURE LEGENDS

FIG. 1 Effect of platelet density on number of monocyte-platelet interactions and subsequent monocyte phenotype. Monocytes were passed through parallel plates coated with platelets at low, medium, or high density. (A) The number of monocyte-platelet interactions increased substantially for plates coated with higher densities of platelets. (B) After overnight incubation, monocytes which were exposed to high levels of platelets were significantly more likely to develop a phenotype consistent with DC differentiation, as assessed by expression of membrane CD83 and HLA-DR (high versus medium or low density: $p<0.0001$; medium versus low density: $p<0.005$). Data shown are the means (+/−SD) of at least 6 independent experiments. lpf, low power field.

Figure 2:
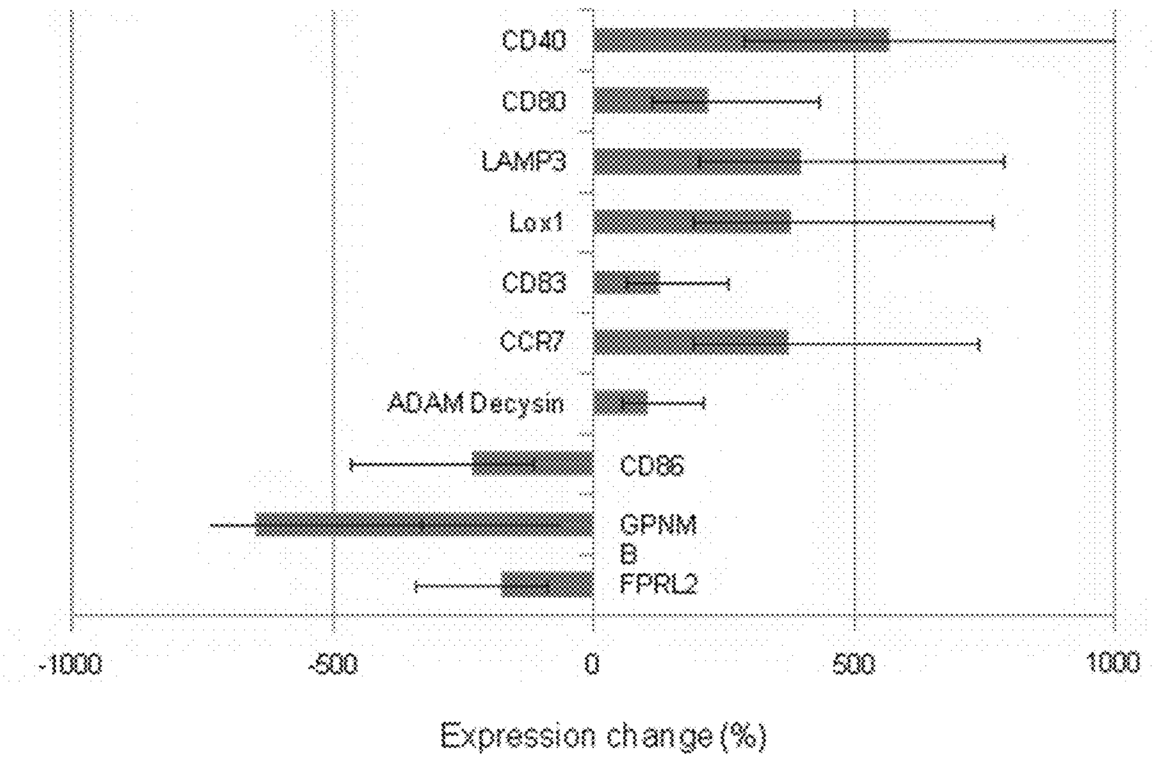

FIG. 2 Gene expression following exposure to platelets. Monocytes were exposed to high or low levels of platelets in flow. Following overnight incubation, cells were assessed for differences in gene expression using RT-PCR. FIG. 2 shows gene expression changes in monocytes exposed to high levels of platelets relative to those exposed to low levels. Seven genes associated with DC-differentiation and/or function were found to be upregulated, while three were downregulated. Of the genes downregulated, GPNMB and FPRL2 have known functions in decreasing cytokine production and inhibiting DC maturation, respectively. Of the genes upregulated, all have either pro-immune functions or miscellaneous roles in DC biology. See text for specific description of genes. Data shown are the means (+/−SD) of 2 independent experiments.

Figure 3:
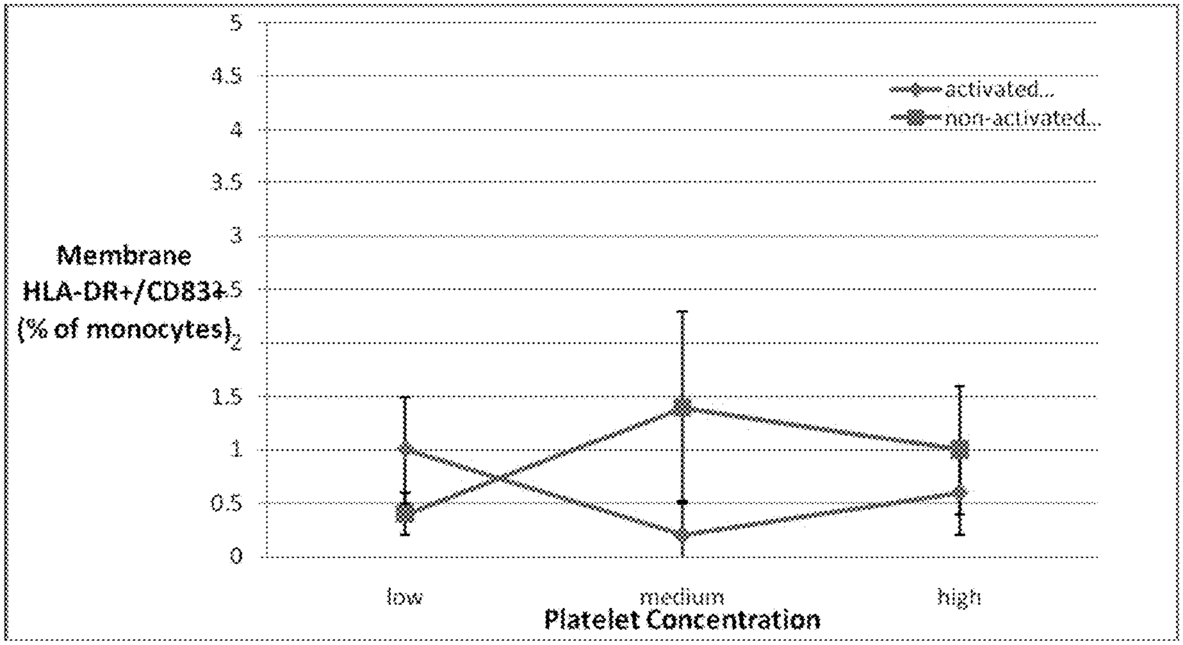

FIG. 3 Platelet influence on monocyte differentiation in static conditions. Monocytes were co-cultured for 18 hours with low, medium, or high concentrations of platelets in static conditions lacking flow. Under these conditions, there was no observable platelet influence on DC differentiation; all conditions resulted in low, baseline levels of cells expressing DC markers. Furthermore, activating platelets with thrombin in culture (blue line) did not cause a discernible difference in monocyte differentiation relative to those cultures containing platelets not activated by thrombin (red line).

Figure 4:
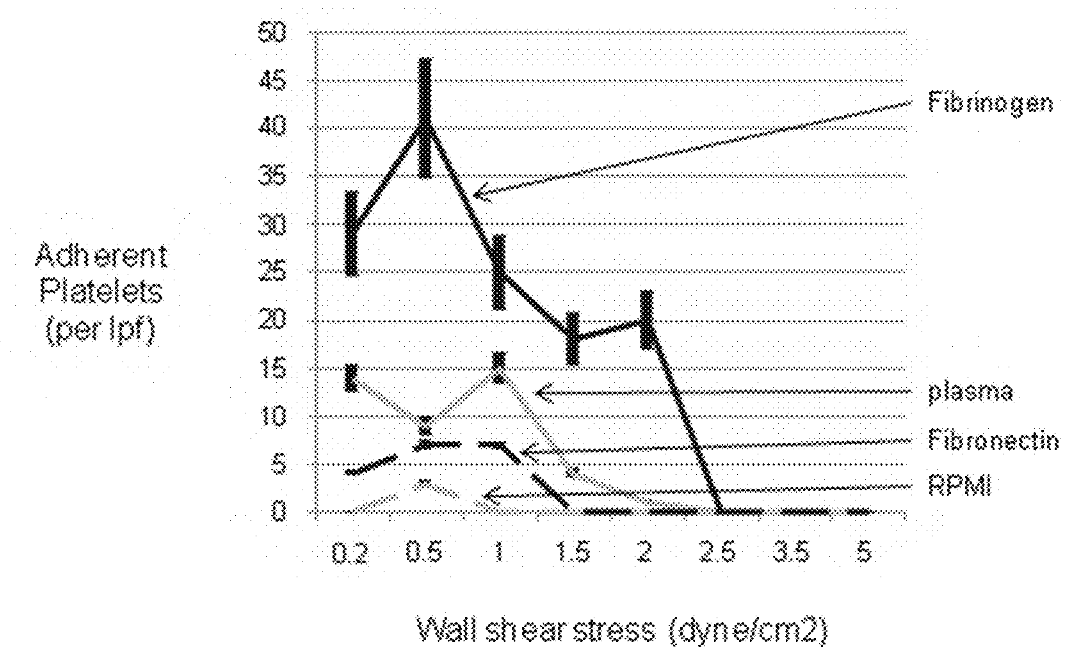

FIG. 4 Plasma protein influence on platelet adhesion to plates. Platelets were passed through plates coated with fibrinogen, plasma, fibronectin, or RMPI at the shear stress level indicated by the x-axis. Platelets in flow adhered optimally to fibronectin. For all proteins, platelet adhesion occurred maximally between 0.5 and 1.0 dyne/$cm^2$ lpf, low power field. Data shown are the means (+/−SD) of at least 2 independent experiments.

Figure 5:
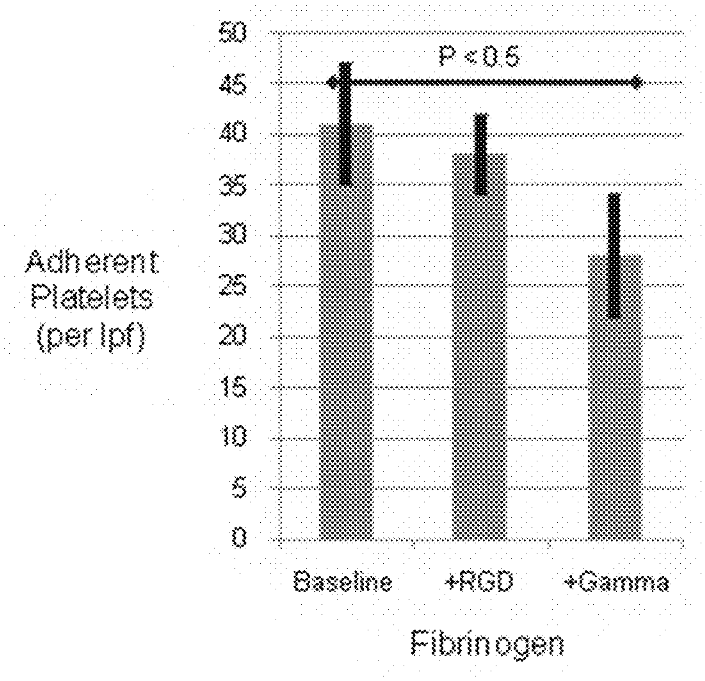
Figure 5:
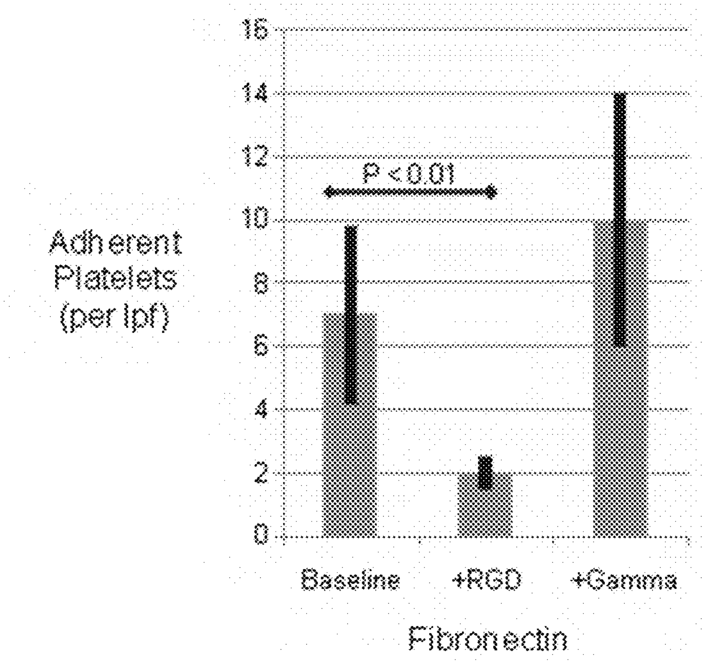

FIG. 5 Plasma protein influence on platelet adhesion to plates coated with Fibrinogen (A) or Fibronectin (B). Platelets were either untreated (baseline), or pretreated with either RGD fragments (+RGD) or gamma fragments (+Gamma) and their subsequent adhesion to fibrinogen (left panel) and fibronectin (right panel) was assessed. Platelet binding to fibrinogen was decreased by gamma fragments ($p<0.05$), while binding to fibronectin was decreased by RGD peptides ($p<0.001$). lpf, low power field. Data shown are the means (+/−SD) of at least 2 independent experiments.

Figure 6:
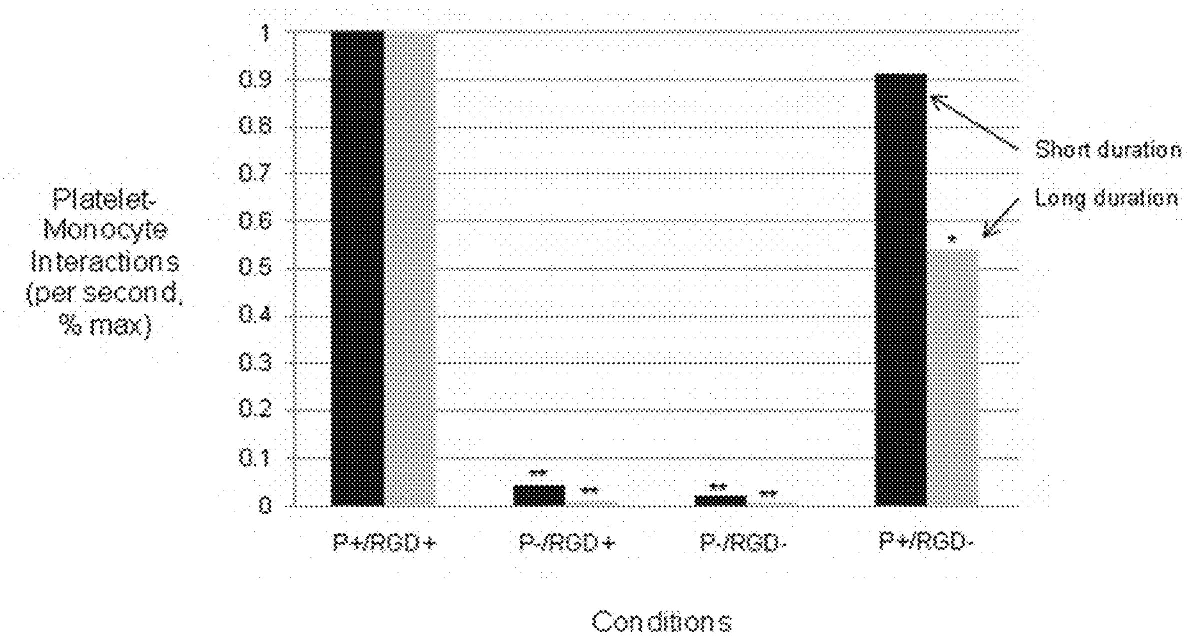

FIG. 6 Proteins involved in monocyte-platelet interactions. Monocytes were passed between platelet-coated plates at a wall shear stress of 0.5 dyne/cm2 under the conditions indicated by the x-axis: platelets were either pretreated with anti-P-selectin (P−) or an isotype control (P+); monocytes were either pretreated with RGD peptides (RGD−) or a control fragment (RGD+). Monocyte-platelet interactions were quantified under each set of conditions using digital microscopy, and are expressed in the figure as a fraction of the maximum seen under conditions of P+/RGD+. Interactions were divided into those lasting less than 3 second (short duration, black bars) and those lasting greater than 3 seconds, including stable binding (long-duration, gray bars). All conditions which involved blocking with anti-P-selectin (P−) resulted in a significant decrease in both short and long duration interactions (**, $p<0.01$); Blocking only RGD (RGD−) resulted in a significant decrease in long-duration interactions (*, $p<0.05$) but no change in short-duration interactions. Data shown are the means (+/−SD) of 3 independent experiments.

Figure 7:
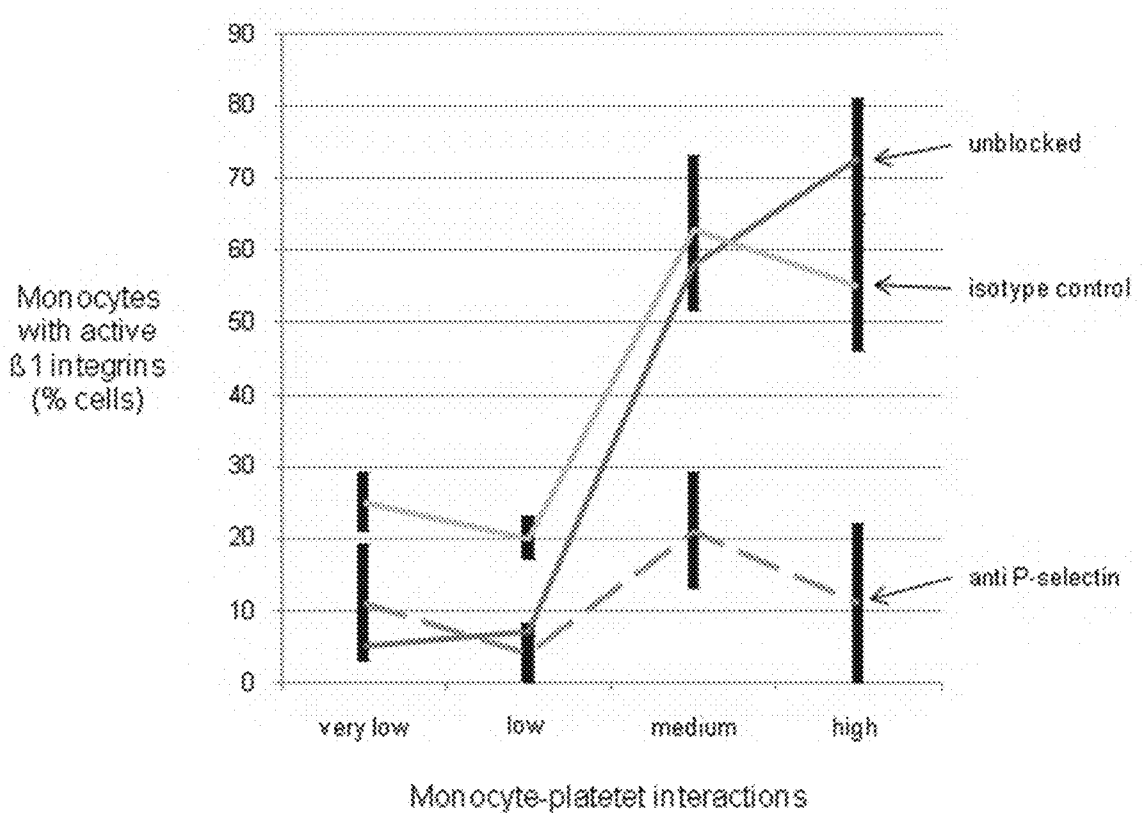

FIG. 7 Effect of p-Selectin exposure on monocyte integrins. Plastic plates were coated with platelets at the relative density indicated by the x-axis. Platelets were then pretreated with anti p-selectin (dashed line) or an isotype control (gray line), or received no pretreatment (black line). Monocytes were passed through the plates at 0.5 dyne/cm2 and then immediately assessed by flow cytometry for expression of active (31 integrins. The y-axis indicates the percent of monocyte, which bound an antibody directed at an epitope only exposed when the integrin is in the open confirmation. Data shown are the means (+/−SD) of 3 independent experiments.

Figure 8:
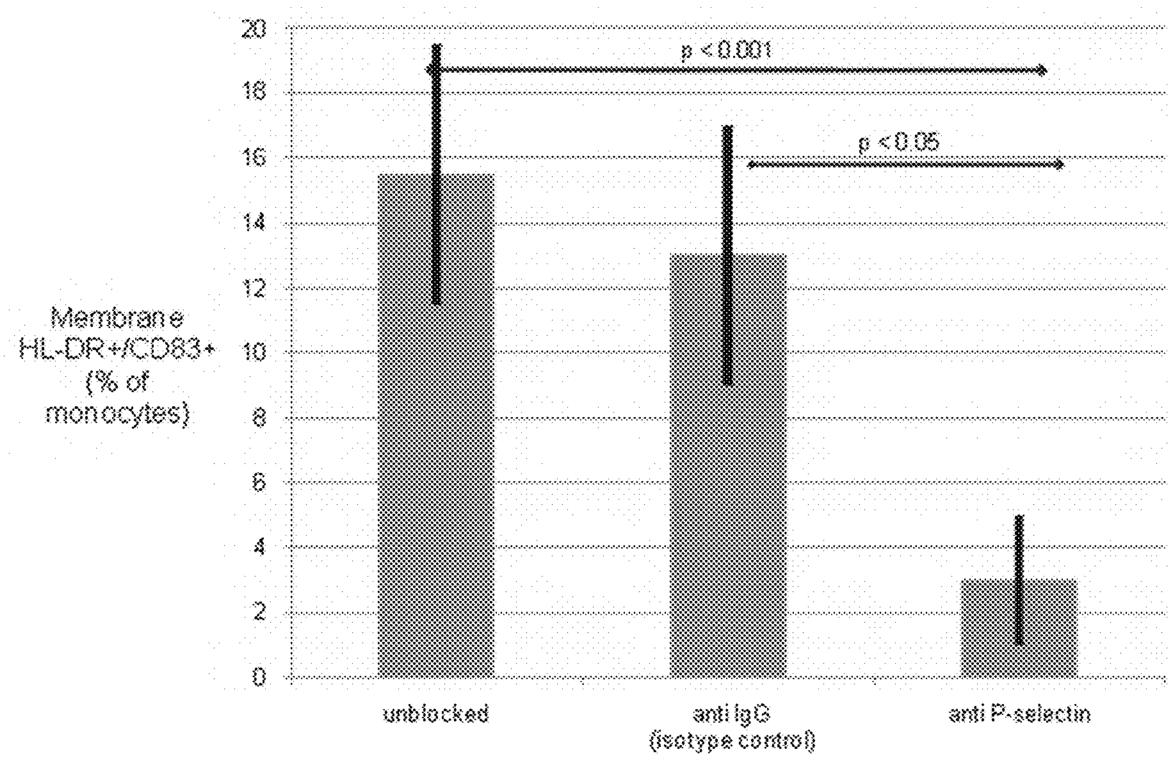

FIG. 8 Effect of P-selectin exposure on monocyte phenotype after overnight incubation. Platelet-coated plates were either untreated (first column), or pretreated with an isotype control (second column) or anti-P-selectin (third column). Monocytes were passed through the plates at 0.5 dyne/cm2 then incubated overnight. The y-axis indicates the percent of monocytes, which developed a phenotype consistent with DC differentiation, i.e., membrane HLA-DR+/CD83+. Data shown are the means (+/−SD) of 3 independent experiments.

Figure 9:
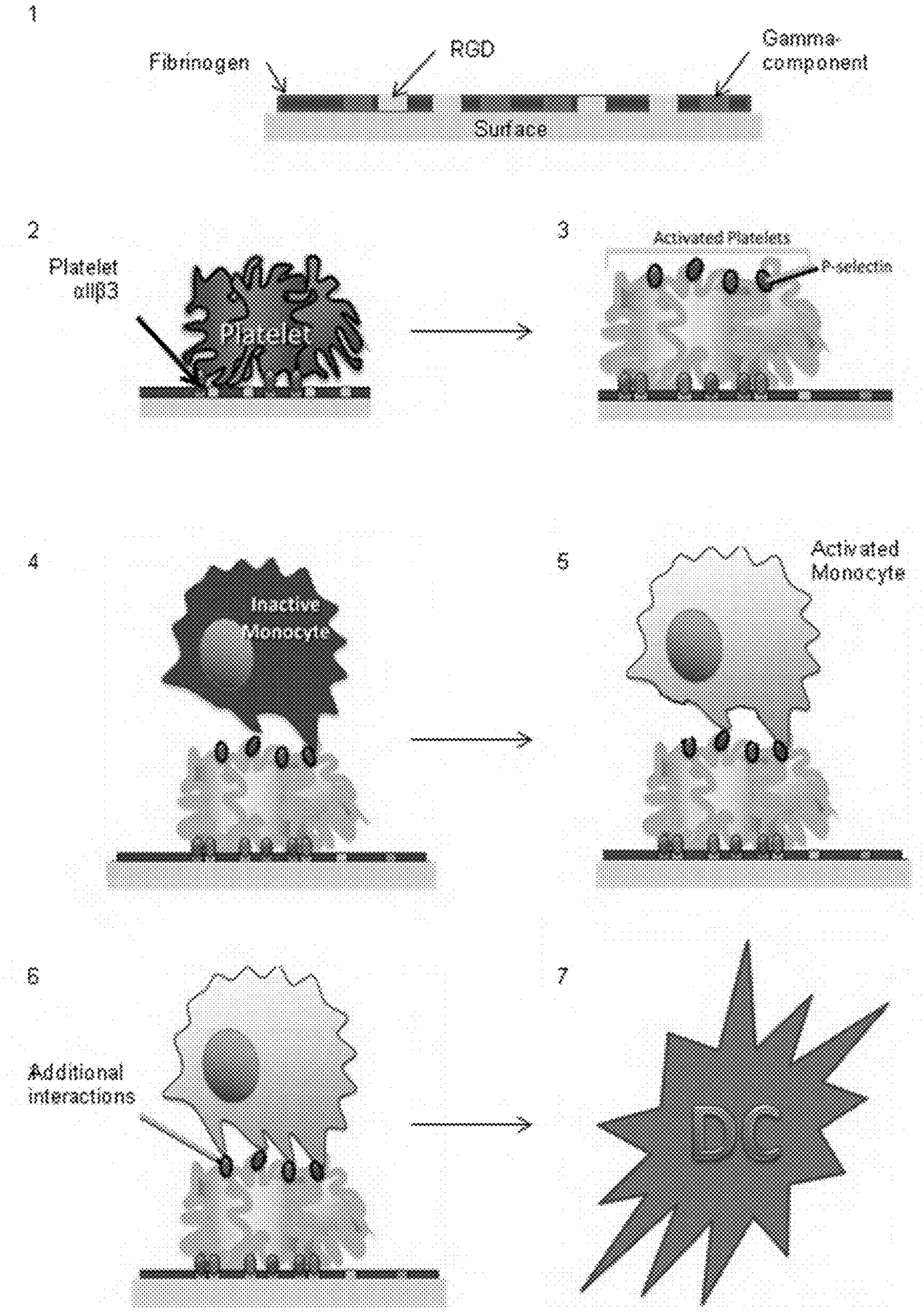

FIG. 9 Proposed mechanism for induction of monocyte-to-DC differentiation. Based on data presented in this manuscript, the following sequence of events is postulated: (1) plasma fibrinogen coats the plastic surface of the flow chamber; (2) through their αIIbβ3 receptor, unactivated platelets bind to the gamma-component of immobilized fibrinogen; (3) platelets become activated and instantaneously express preformed P-selectin and other surface proteins; (4) passaged monocytes transiently bind P-selectin via PSGL-1, causing partial monocyte activation and integrin receptor conformational changes; (5) partially-activated monocytes, now capable of further interactions, bind additional platelet-expressed ligands, including those containing RGD domains; (6) finally, so influenced, monocytes efficiently enter the DC maturational pathway within 18 hours. Note that, in-vivo, step (1) above may be replaced physiologically by inflammatory signals from tissue acting on local endothelium, causing it to recruit and activate platelets in a similar manner.

Figure 10:
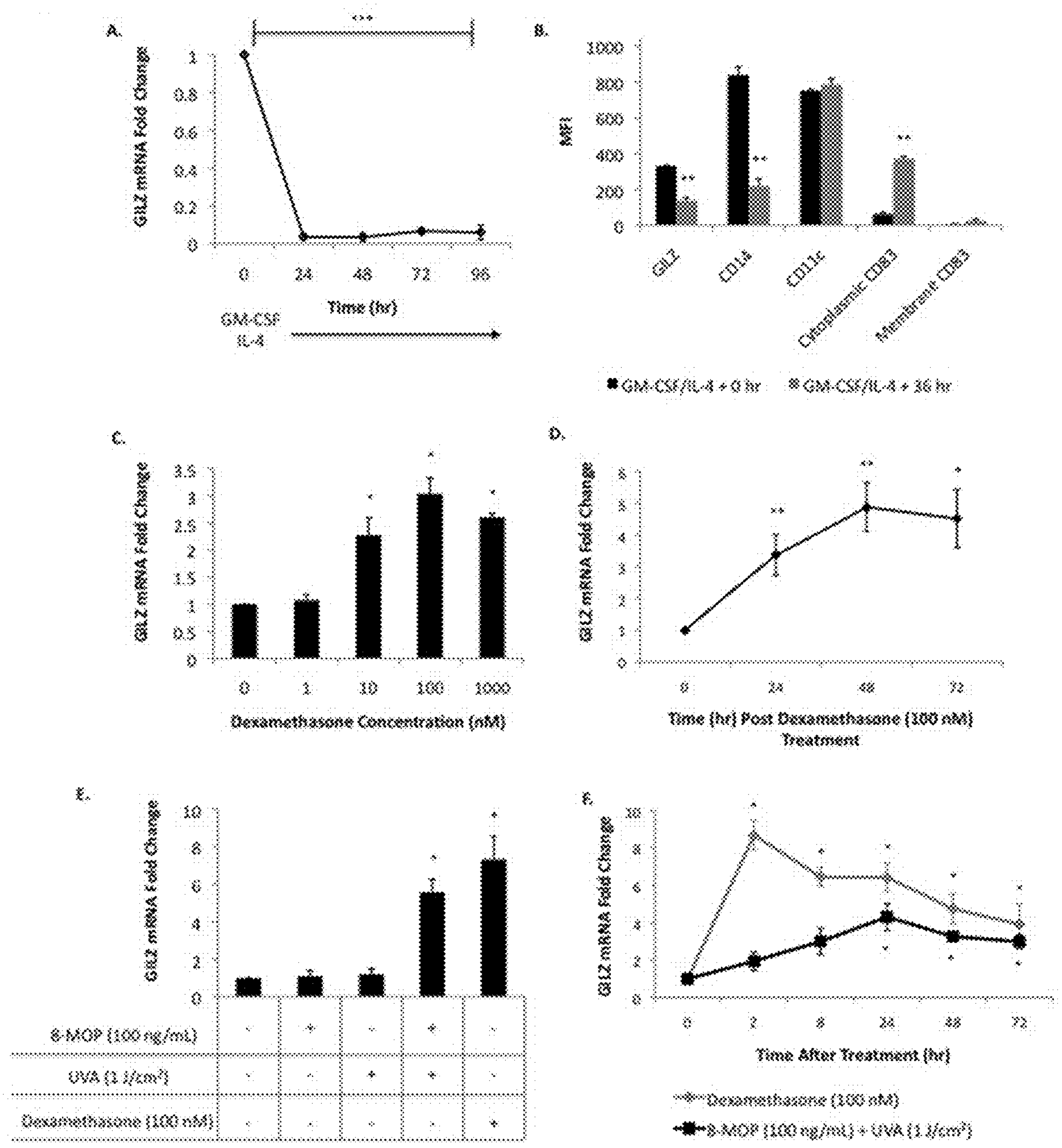

FIG. 10: Expression of GILZ is rapidly down-regulated as monocytes differentiate into immature MoDC, and up-regulated after exposure to dexamethasone. A.) GILZ mRNA expression in CD11c+ MoDC is presented as a fold change relative to freshly isolated monocytes. B.) Median fluorescence intensities for intracellular and cell surface markers after 0 and 36 hr. C.) GILZ mRNA expression in CD11c+ MoDC after 24 hr is presented as a fold change relative to MoDC receiving no dexamethasone. D.) GILZ mRNA expression in CD11c+ MoDC is presented as a fold change relative to MoDC at time 0 hr. E.) GILZ mRNA expression in CD11c+ MoDC after 24 hr is presented as a fold change relative to untreated MoDC. F.) GILZ mRNA expression in CD11c+ MoDC is presented as a fold change relative to untreated MoDC. All data are expressed as mean±standard deviation for a minimum of 3 independent experiments. For differential gene expression: *≥2.5-fold change and p<0.05, ≥2.5-fold change and p<0.01, *≥2.5-fold change and p<0.001

Figure 11:
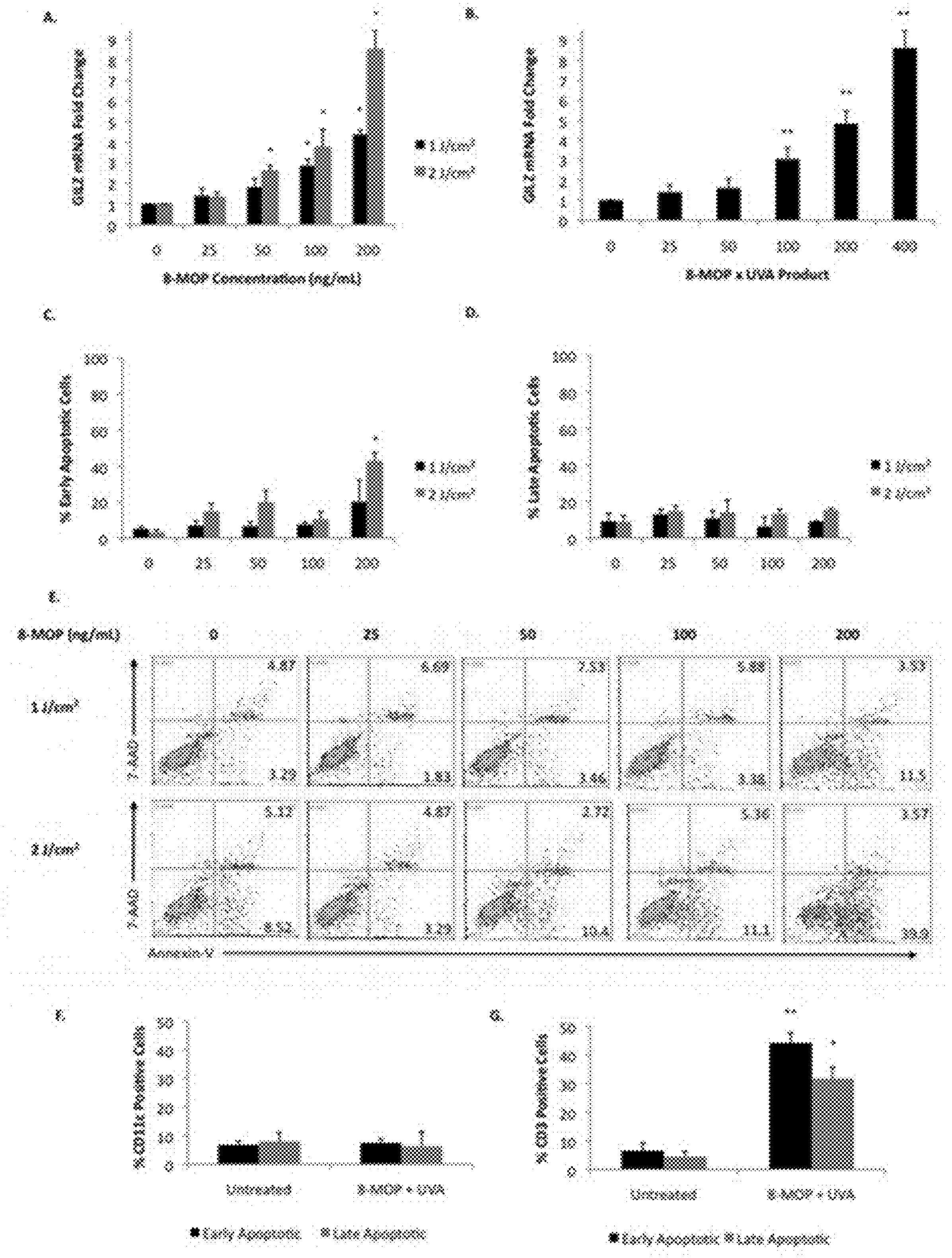

FIG. 11: 8-MOP plus UVA light up-regulates GILZ in immature MoDC in a dose-dependent fashion. A.) GILZ expression is presented as a function of the 8-MOP concentration at 1 J/cm2 and 2 J/cm2 of UVA light. GILZ mRNA expression in CD11c+ MoDC 24 hr after PUVA treatment is presented as a fold change relative to MoDC receiving no 8-MOP. B.) GILZ expression is presented as a function of the 8-MOP concentration multiplied by the UVA dose. C.) The percentage of early apoptotic CD11c+ cells after 24 hr. D.) The percentage of late apoptotic CD11c+ cells after 24 hr E.) Dot plots of CD11c+-gated cells for UVA doses of 1 J/cm2 and 2 J/cm2 are shown for 1 representative experiment of 4. The percentage of CD11c+ cells displaying Annexin-V+/7-AAD− or Annexin-V+/7-AAD+ phenotypes are indicated. The percentage of F.) CD11c+ cells and G.) CD3+ cells expressing early and late apoptotic markers were quantified 24 hr after treatment with 8-MOP (100 ng/mL) and UVA light (1 J/cm2). All data represent mean±standard deviation of at least 4 independent experiments. For differential gene expression: *≥2.5-fold change and p<0.05, **≥2.5-fold change and p<0.01

Figure 12:
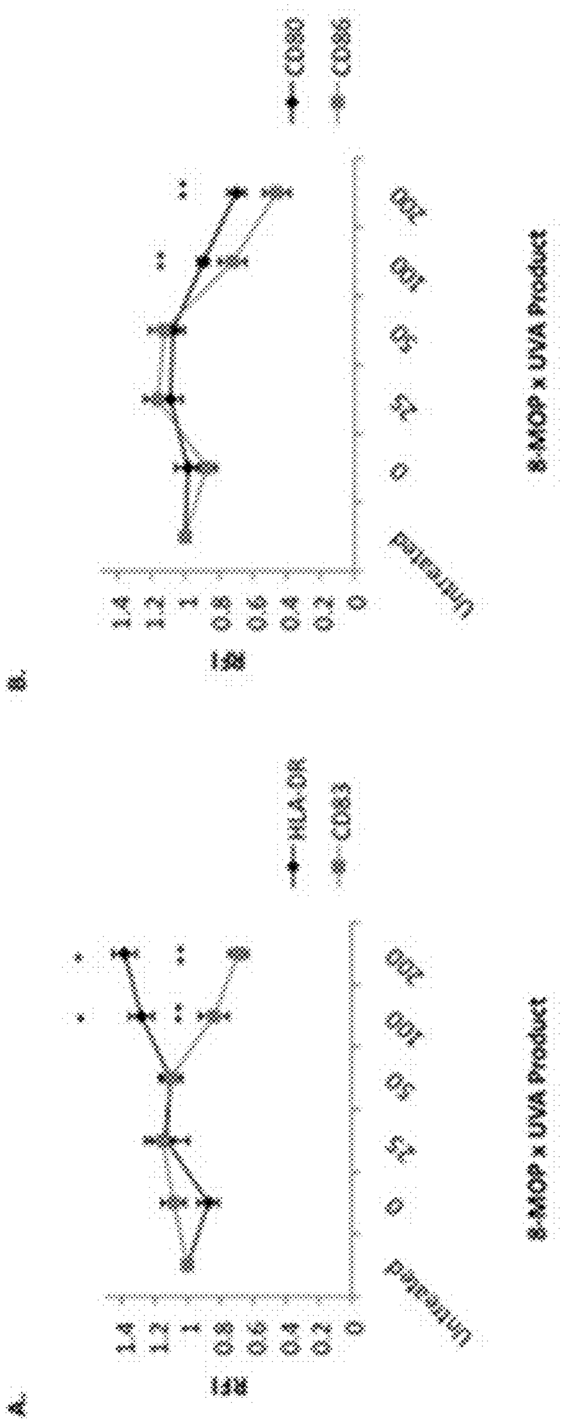

FIG. 12: 8-MOP plus UVA light down-regulates CD83, CD80 and CD86 and up-regulates HLA-DR in immature MoDC in a dose-dependent manner. Relative fluorescence intensities for membrane expression of A.) HLA-DR and CD83, and B.) CD80 and CD86 are presented as a function of the 8-MOP concentration (0 to 200 ng/mL) multiplied by the UVA dose (1 or 2 J/cm2) 24 hr after PUVA treatment. Untreated MoDC served as controls and were assigned an RFI value of 1. Data represent mean±standard deviation of 4 independent experiments. *p<0.05, **p<0.01

Figure 13:
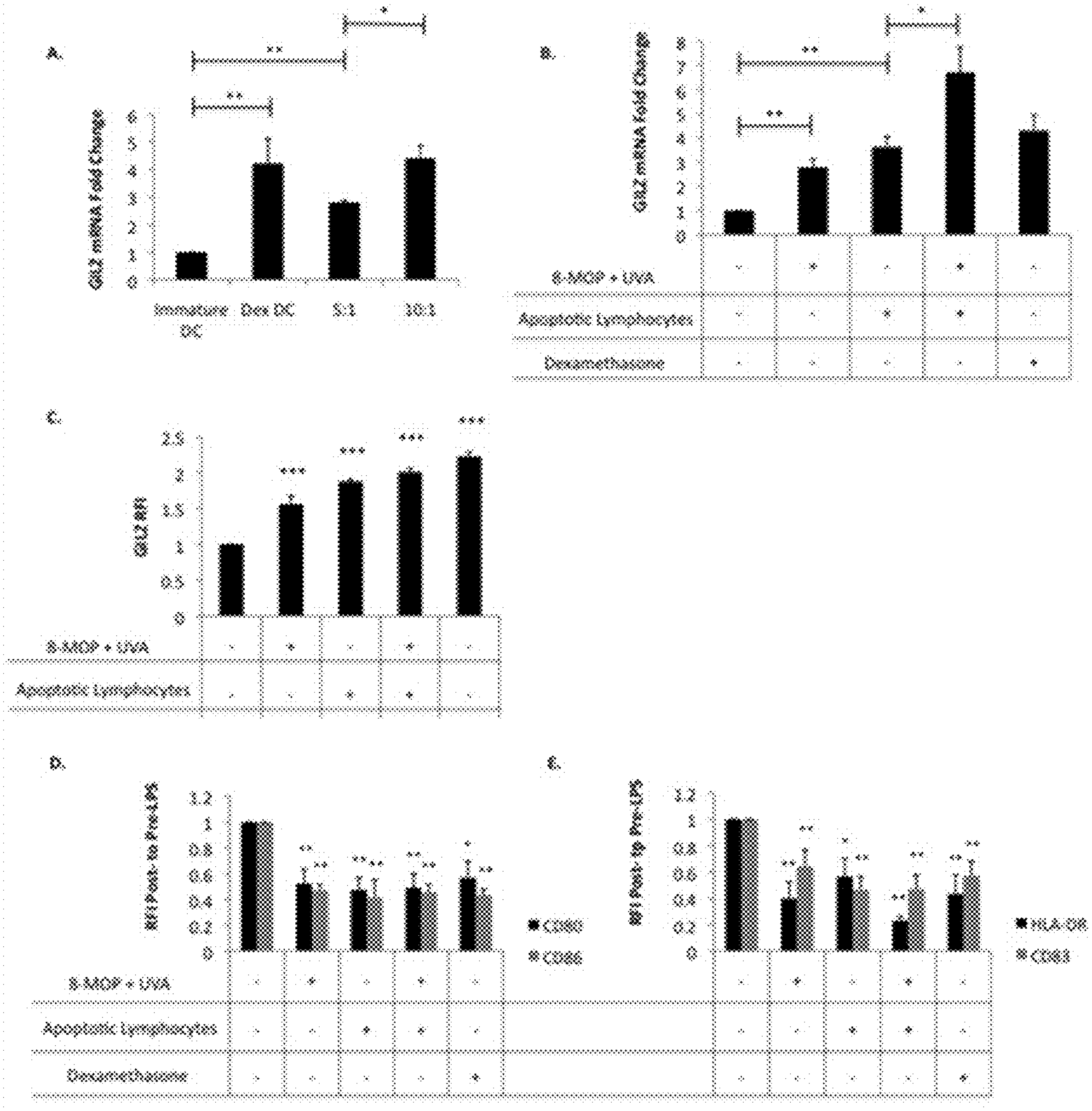

FIG. 13: Immature MoDC exposed to apoptotic lymphocytes up-regulate GILZ. A.) GILZ mRNA expression in CD11c+ MoDC 24 hr after co-culture is presented as a fold change relative to untreated MoDC that were cultured alone. B.) GILZ mRNA expression in CD11c+ MoDC 24 hr after co-culture is presented as a fold change relative to untreated MoDC that were cultured alone. C.) Relative fluorescence intensity for intracellular GILZ 24 hr after co-culture. Relative fluorescence intensities post- to pre-LPS stimulation for D.) CD80 and CD86 and E.) HLA-DR and CD83 were calculated as follows: (MFItreated after LPS−MFItreated before LPS)/(MFIuntreated after LPS−MFIuntreated before LPS). Data represent mean±standard deviation for at least 4 independent experiments. For differential gene expression: *≥2.5-fold change and p<0.05

Figure 14:
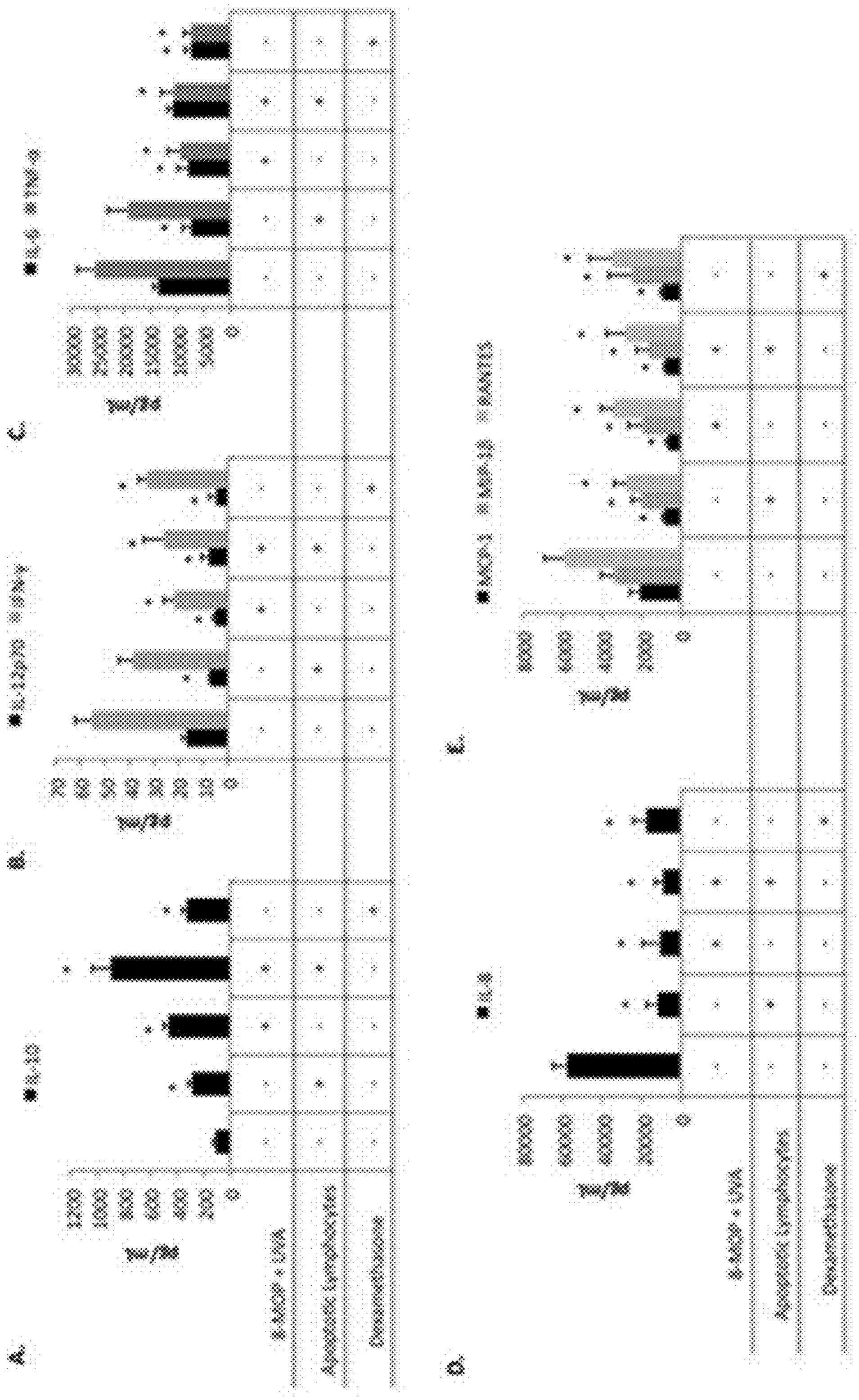

FIG. 14: MoDC expressing GILZ increase production of IL-10, and decrease production of various pro-inflammatory cytokines and chemokines. 24 hr after LPS stimulation, culture supernatants were harvested for cytokine quantification by magnetic bead multiplex immunoassays for A.) IL-10, and the pro-inflammatory cytokines B.) IL-12p70 and IFN-γ, C.) IL-6 and TNF-α. The same analysis was performed for the pro-inflammatory chemokines D.) IL-8, and E.) MCP-1, MIP-1β and RANTES. Data are presented as mean±standard deviation of 3 independent experiments. * p<0.05 compared to the untreated MoDC group.

Figure 15:
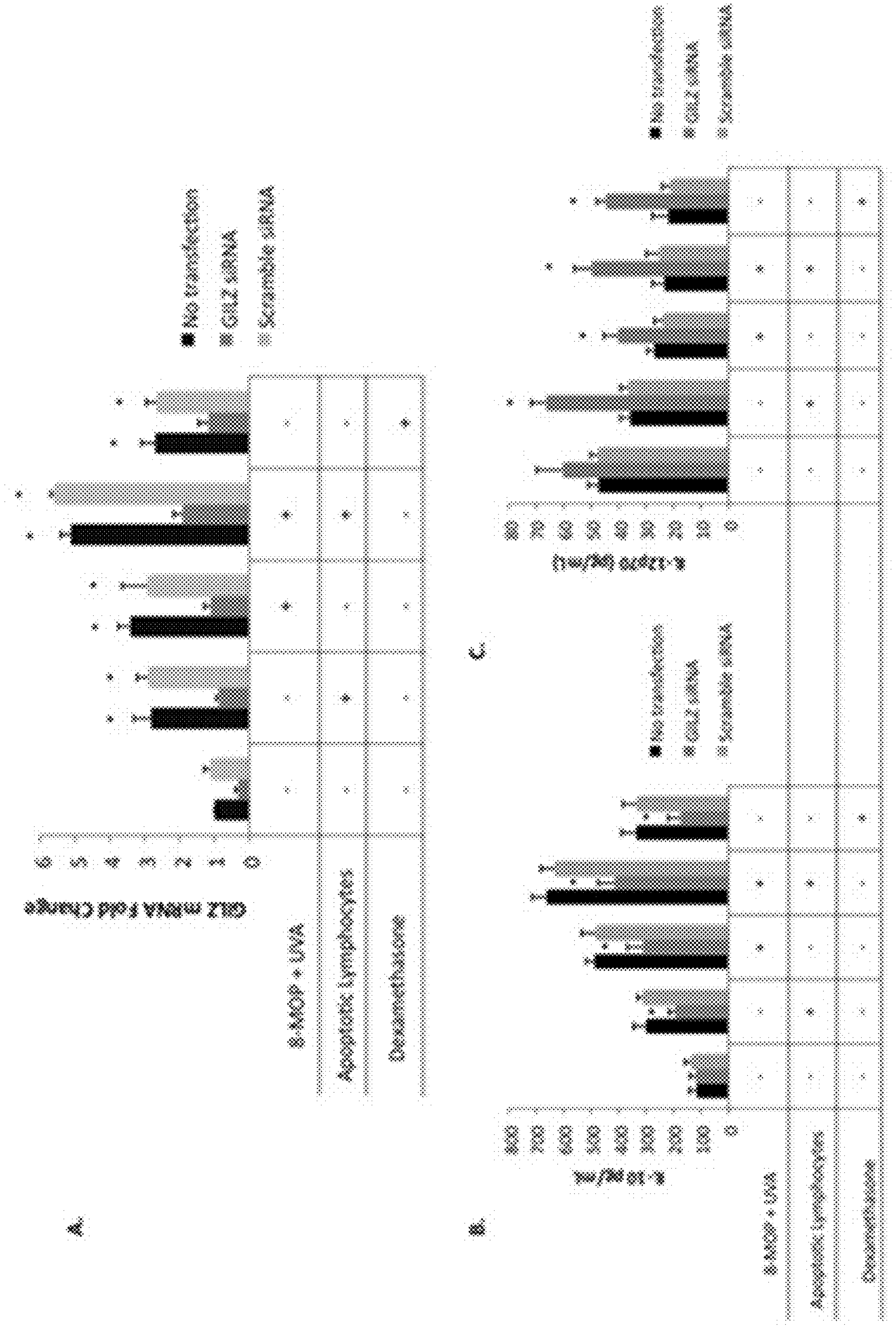

FIG. 15: siRNA-mediated knockdown of GILZ abolishes the increased IL-10 to IL-12p70 ratio characteristic of tolerogenic DC. A.) GILZ mRNA expression is presented as fold change compared to untreated MoDC that were cultured alone. *≥2.5-fold change and p<0.05. B.) Quantification of IL-10 and IL-12p70 protein levels in culture supernatants after LPS stimulation. Data represent mean±standard deviation of 3 independent experiments. *p<0.05, compared to identically treated MoDC not transfected with siRNA.

Figure 16:
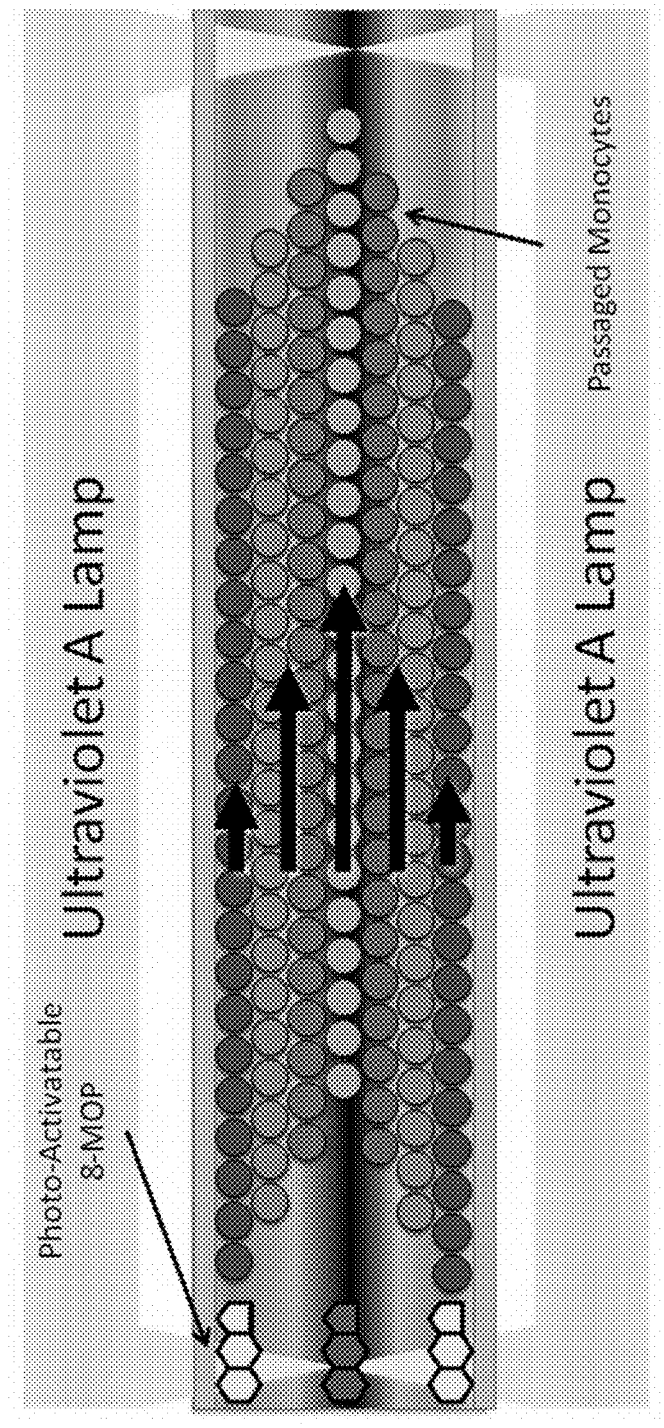

FIG. 16: depicts the flow of monocytes in a classical ECP process in the presence of UVA and 8-MOP. The monocytes in the middle experience lower UVA exposure than the monocytes towards the surfaces of the channels.

Figure 17:
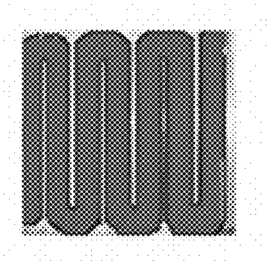

FIG. 17: depicts the design of the channels of the device used in a classical ECP process.

Figure 18:
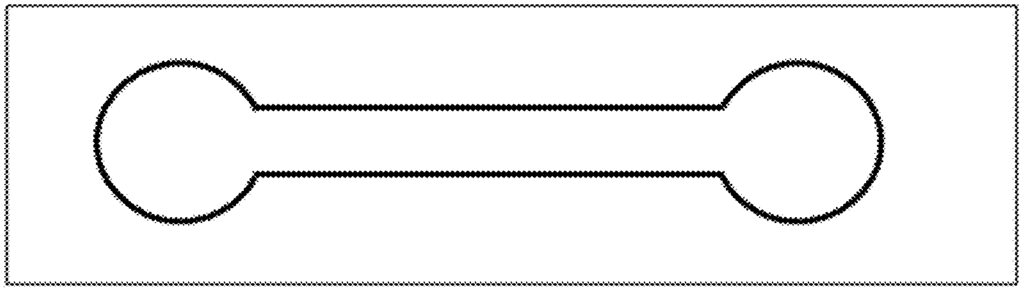
Figure 18:
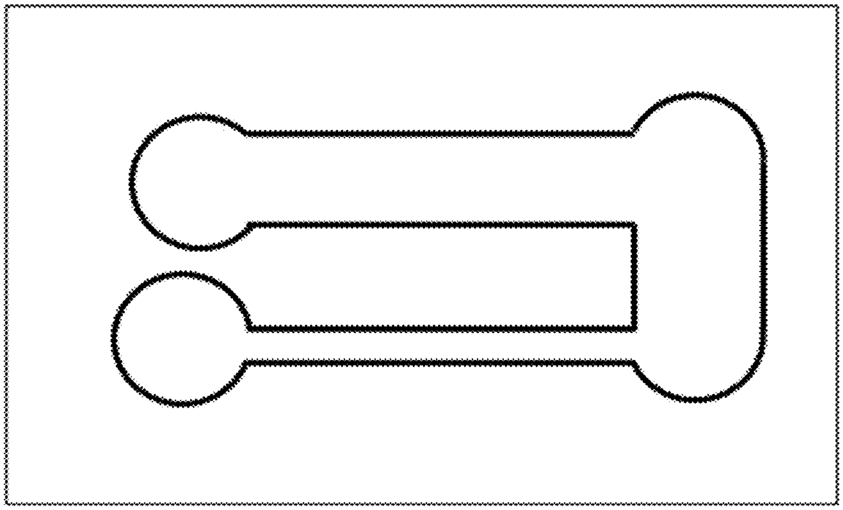
Figure 18:
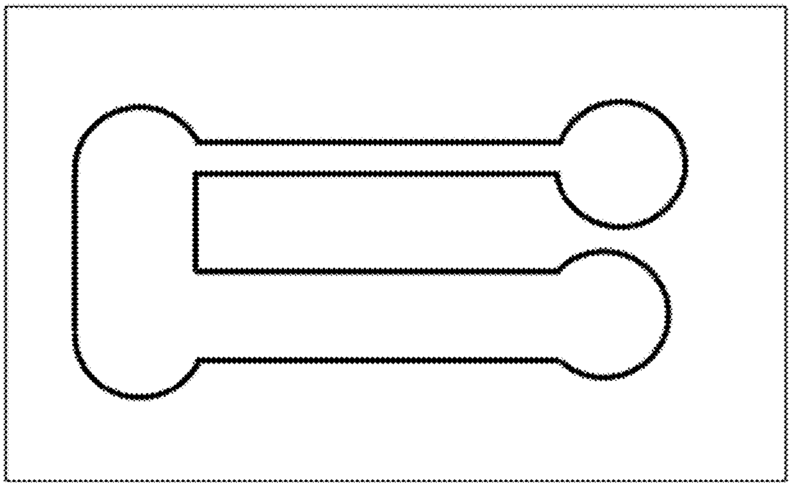
Figure 18:
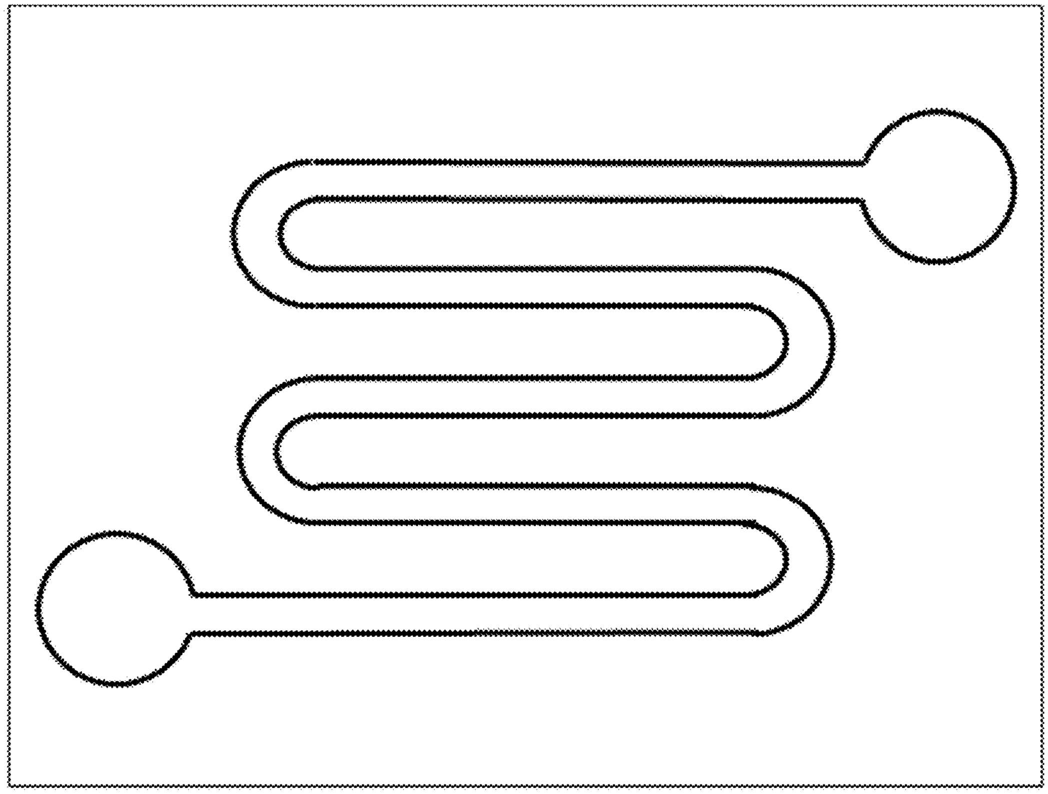

FIG. 18: a) to d) depict different geometries of the flow chamber of a device that may be used for the methods of the invention.

Figure 19:
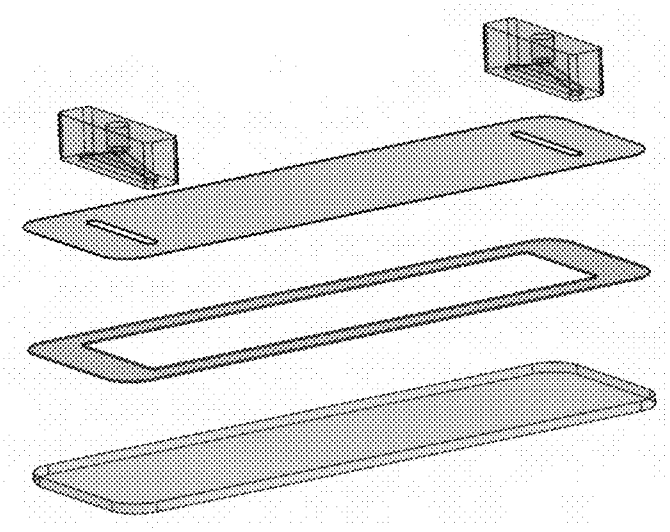
Figure 19:
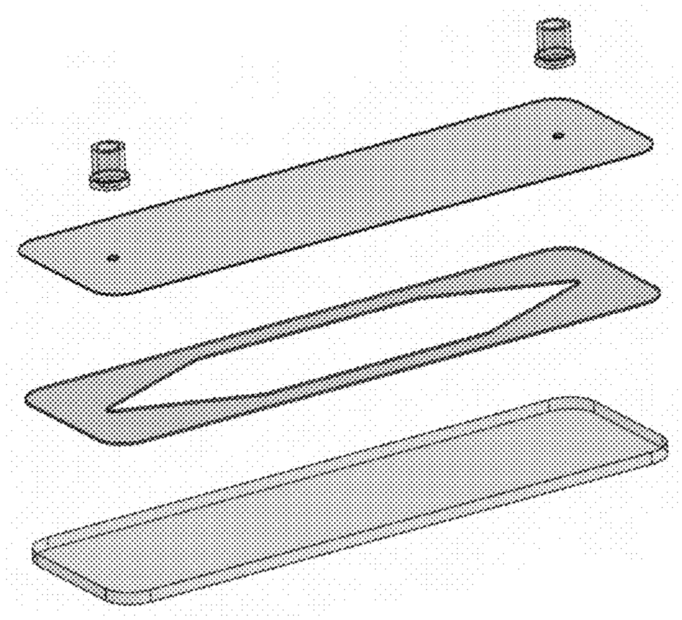

FIG. 19: A) depicts the geometry of a device used in some of the examples. B) depicts the geometry of an alternative device.

Figure 20:
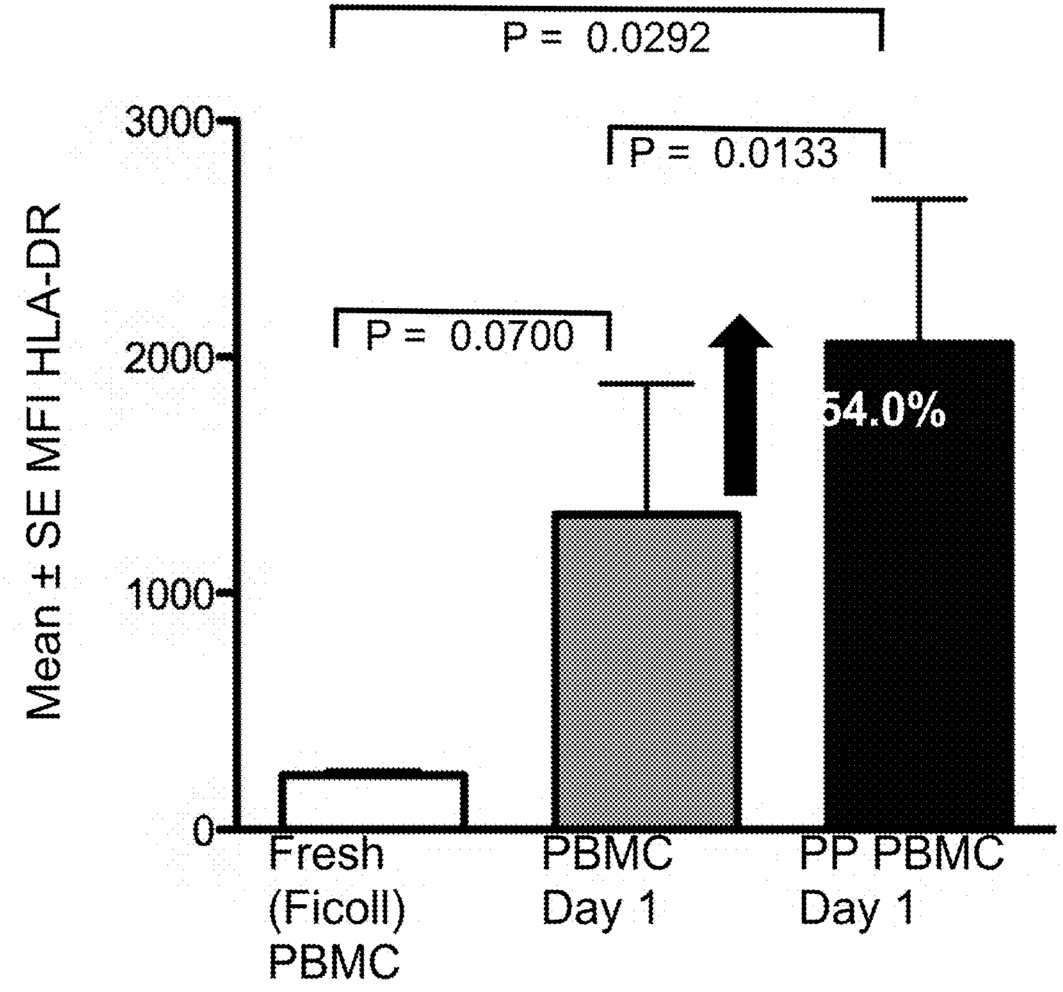

FIG. 20: depicts increase of expression of HLA-DR upon physical activation of monocytes through a device of FIG. 19

Figure 21:
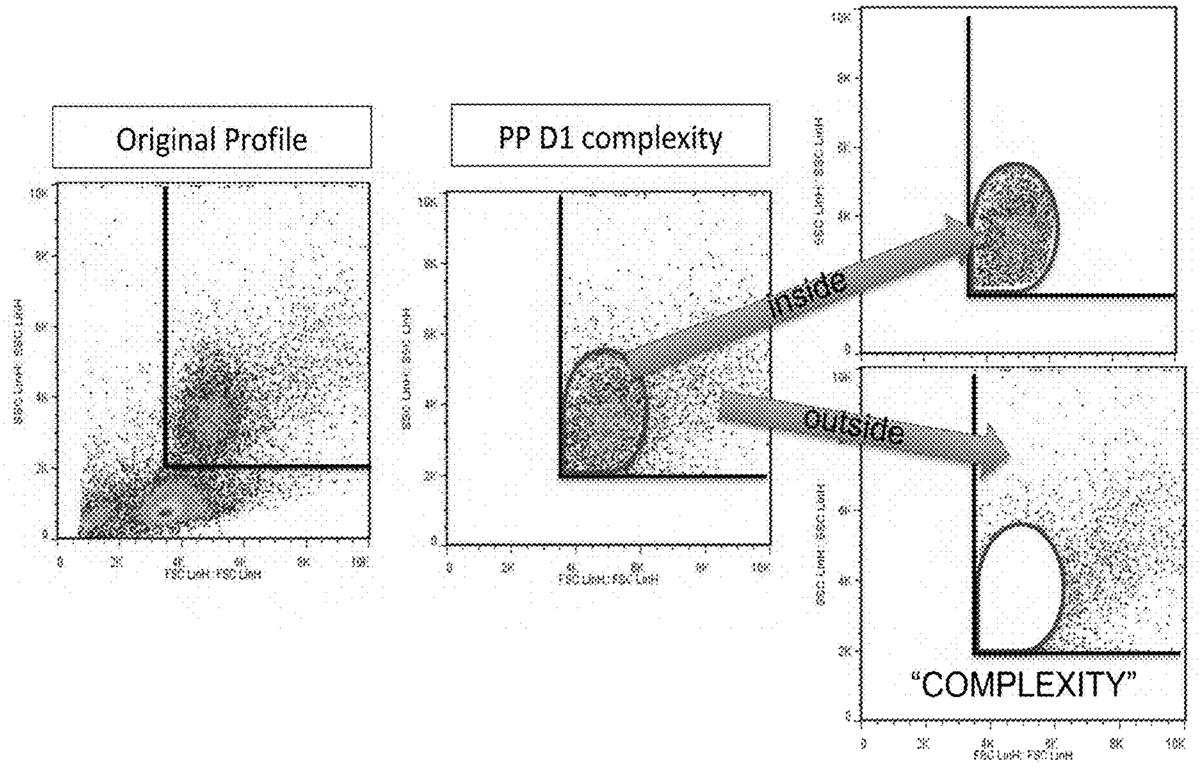

FIG. 21: depicts increase of FSC/SSC complexity upon physical activation of monocytes through a device of FIG. 19

Figure 22:
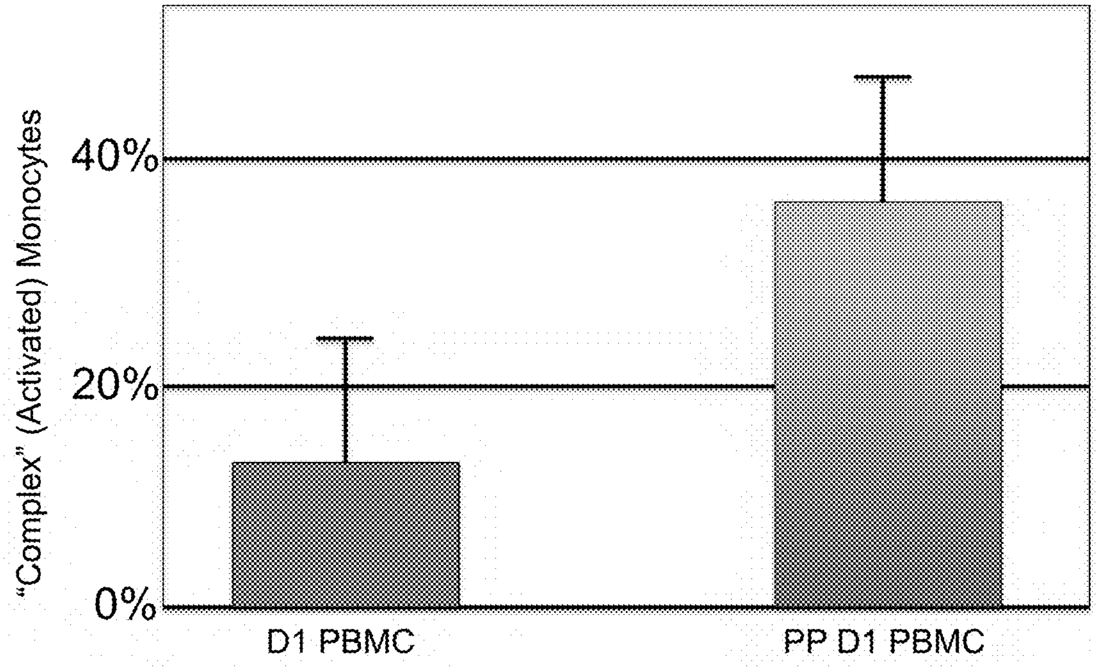

FIG. 22: depicts increase of FSC/SSC complexity upon physical activation of monocytes by passing through a device of FIG. 19

Figures 23, 24:
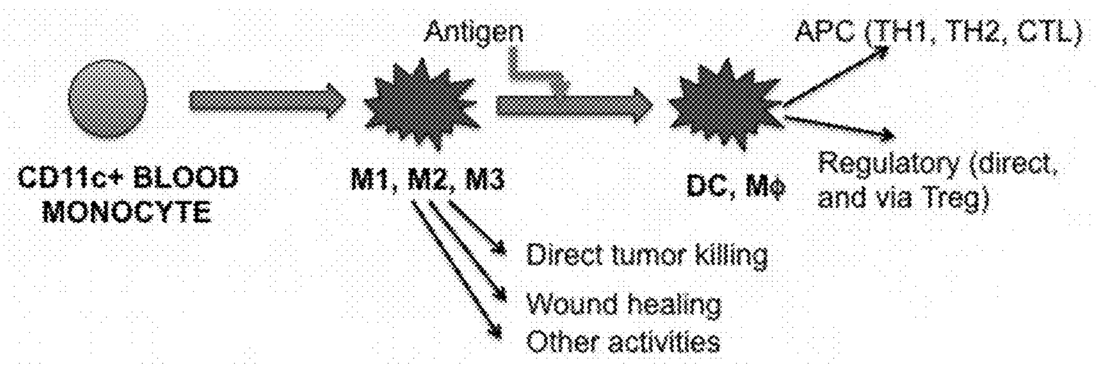

FIG. 23: depicts increase of expression of HLA-DR, CD86, ICAM-1, PLAUR and or FSC/SSC complexity upon physical activation of monocytes through a device of FIG. 19

Figure 25:
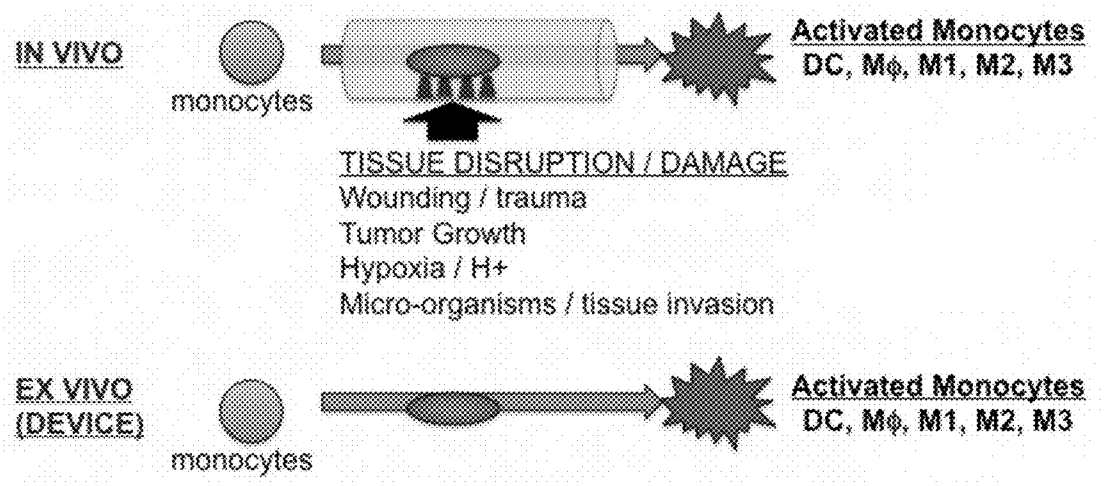
Figure 26:
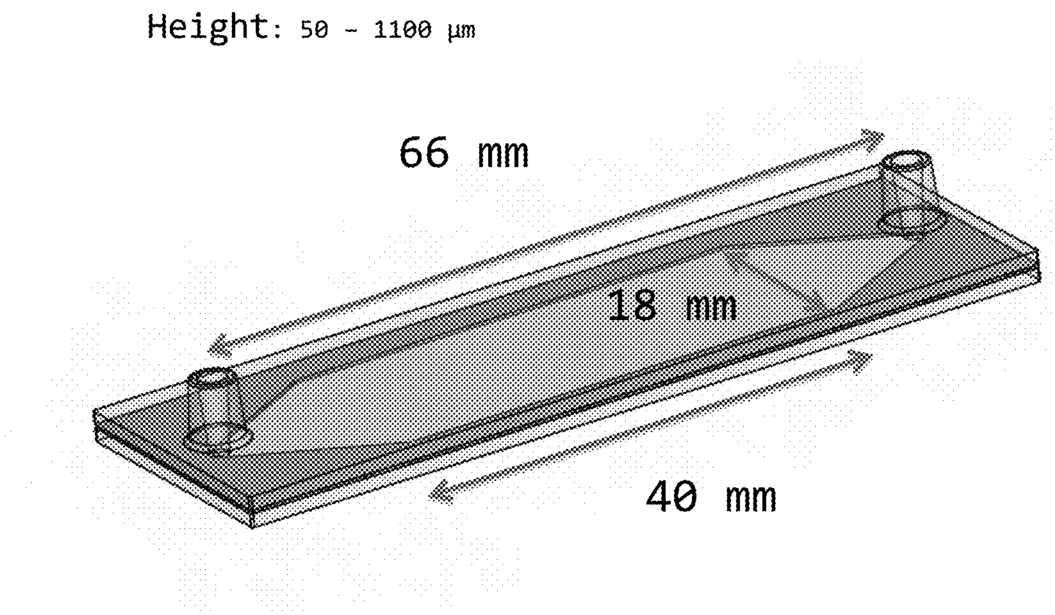
Figure 26:
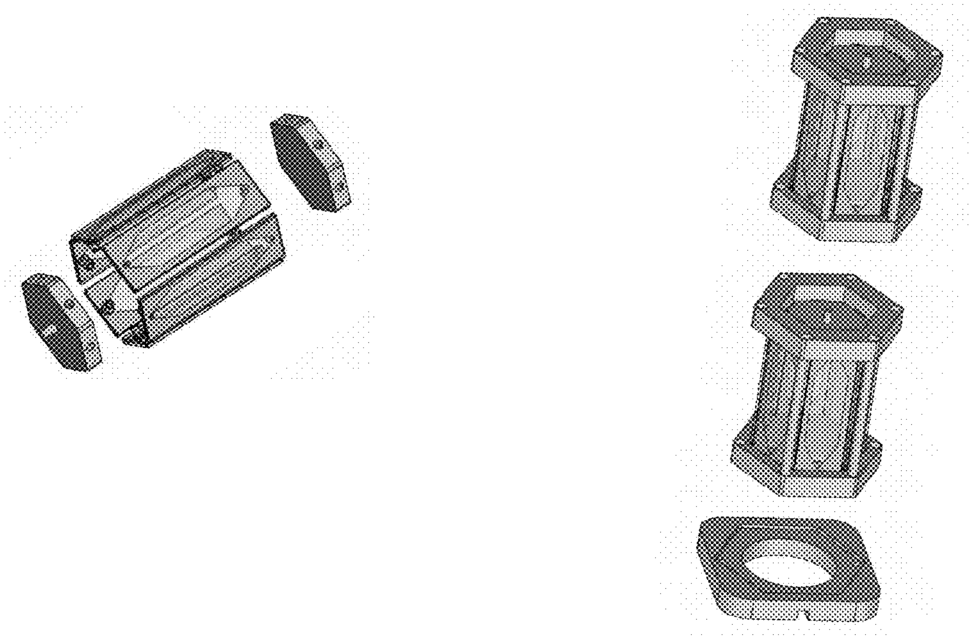

FIG. 24: depicts schematically a potential global activation of monocytes with M1, M2, M3 indicating a e.g. continuum of globally activated macrophages FIG. 25: depicts schematically aspects of wound healing FIG. 26 A) depicts a flow chamber as used in Experiments 7, 8 and 9. B) depicts one option of assembling flow chambers depicted in A).

Figure 27:
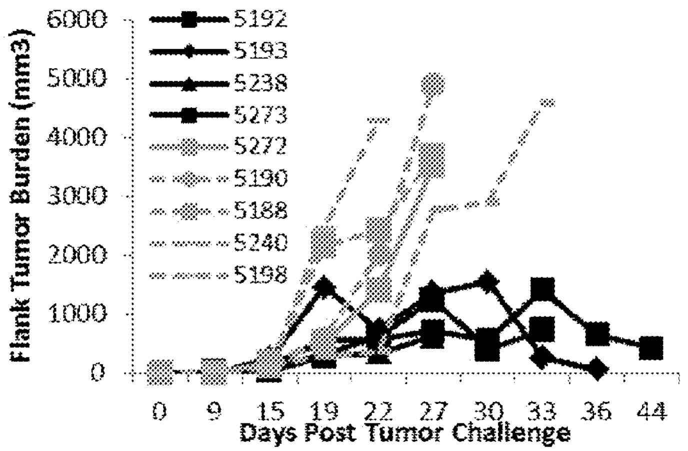

FIG. 27 depicts growth inhibition of YUMM tumors for individual mice. 8-MOP/UVA-treated Yumm 1.7 cells were mixed with PBMCs or PBS and passed through the same flow chamber and subjected to 8-MOP/UVA. Dashed lines depict tumor size of individual control group mice not being treated with flow chamber passaged PBMCs. Solid lines depict tumor size of individual treatment group mice being treated with flow chamber passaged PBMCs. Tumor volume was determined by cell counting.

Figure 28:
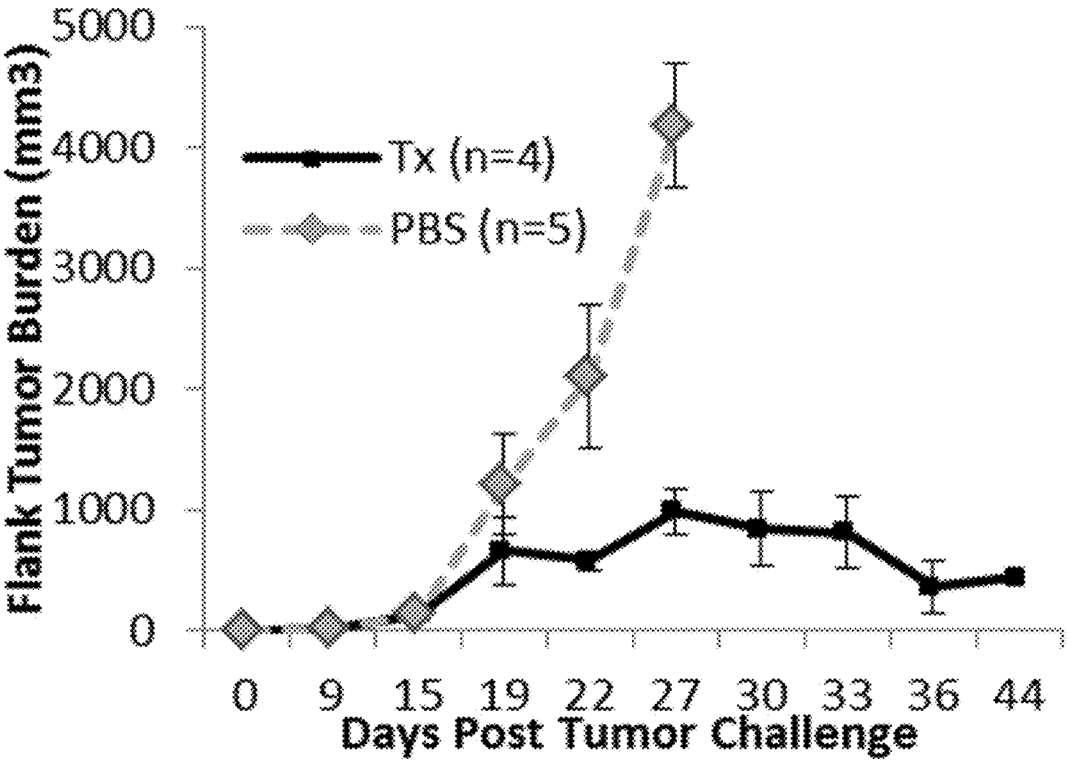

FIG. 28 depicts combined growth inhibition of YUMM tumors of FIG. 27 averaged across control and treatment groups. Dashed lines depict tumor size of control group where mice were not treated with flow chamber passaged PBMCs. Solid lines depict tumor size of treatment group where mice were treated with flow chamber passaged PBMCs. Tumor volume was determined by cell counting.

Figure 29:

FIG. 29 depicts some of the treated mice of Experiment 7.

Figure 30:
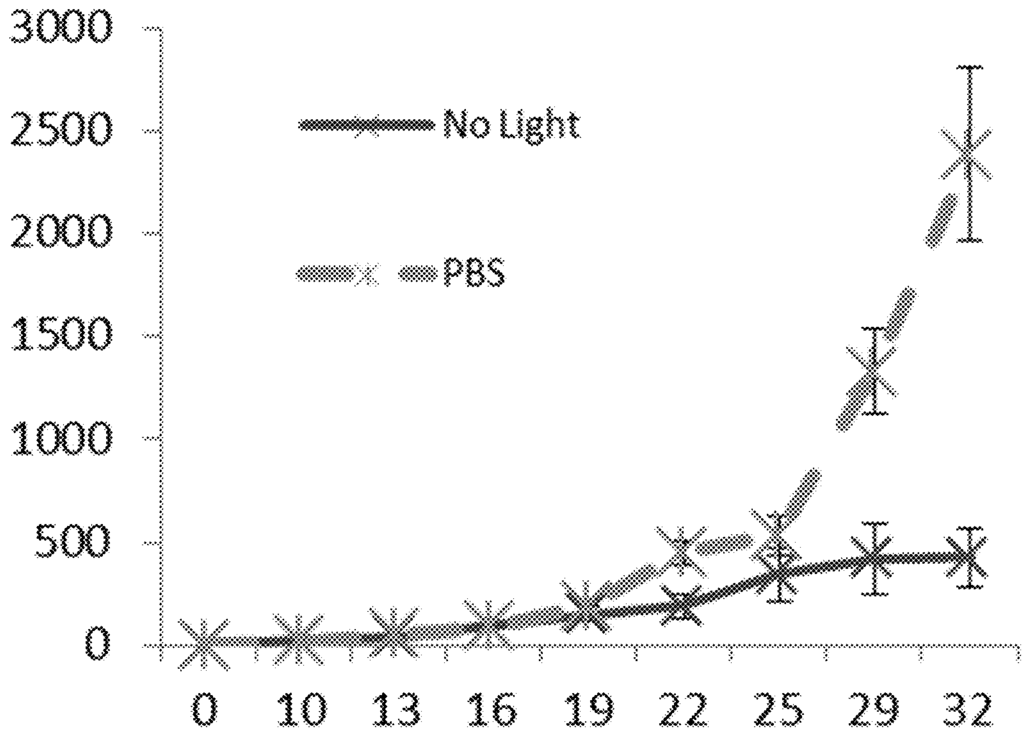

FIG. 30 depicts combined growth inhibition of YUMM tumors averaged across control and treatment groups. 8-MOP/UVA-treated Yumm 1.7 cells were mixed with PBMCs or PBS and passed through the same flow chamber but not subjected to 8-MOP/UVA. Dashed lines depict tumor size of individual control group mice not being treated with flow chamber passaged PBMCs. Solid lines depict tumor size of individual treatment group mice being treated with flow chamber passaged PBMCs. Tumor volume was determined by cell counting.

Figure 31:
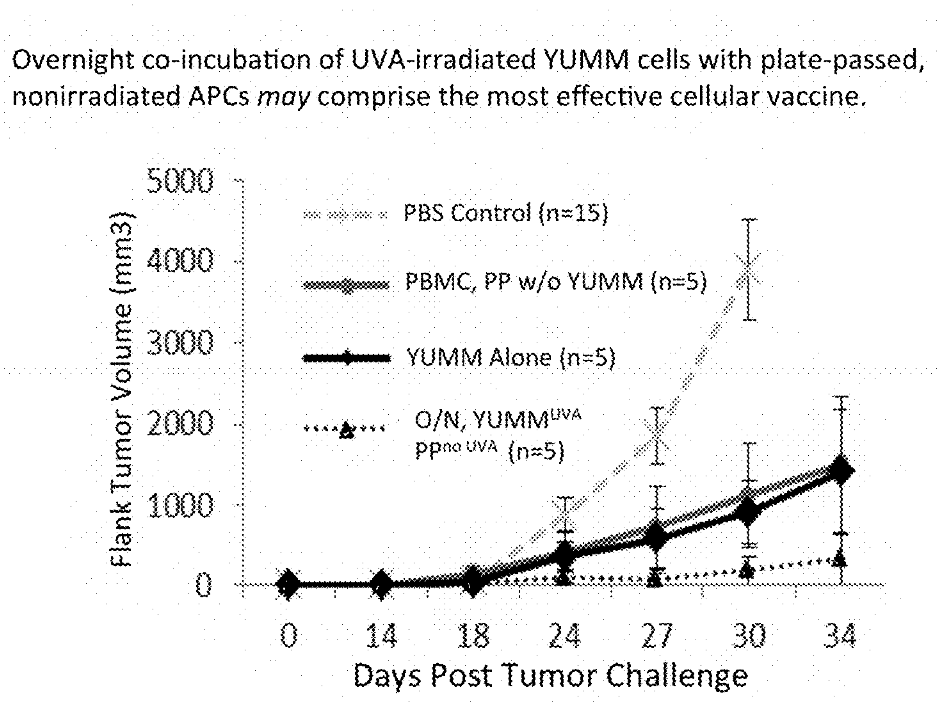

FIG. 31 depicts combined growth inhibition of YUMM tumors averaged across control and treatment groups The three treatment groups (five mice each) received only 8-MOP/UVA-treated flow chamber-passaged Yumm 1.7 (YUMM alone), only PBMCs which had been passed through the flow chamber but not subjected to 8-MOP/UVA (PBMC, PP w/o YUMM), PBMCs which had been passed through the flow chamber but not subjected to 8-MOP/UVA, and co-incubated with -MOP/UVA-treated flow chamber-passaged Yumm 1.7 cells overnight (Group 4, O/N YUMM$^{UVA}$ PP$^{noUVA}$), or PBS. Tumor volume was determined by cell counting.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody, which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

As already mentioned, the present invention is based to some extent on data presented hereinafter, which for a miniaturized device allowed (i) to mimic some aspects of the classical ECP procedure and (ii) to elucidate the cellular and molecular mechanism of global monocyte activation and e.g. subsequent induction of differentiation of such globally activated monocytes into immuno-stimulatory dendritic cells in an extracorporeal amount of blood.

The data presented hereinafter suggest that shear stress is in principle responsible for global monocyte activation and the subsequent induction of DC. By using e.g. the miniaturized model device as described hereinafter, it was shown that induction of immuno-stimulatory DC occurs even if substantially lower amounts of extracorporeal blood, which has not been obtained by apheresis such as leukapheresis, are used, even if 8-MOP is not added to the extracorporeal amount of blood and even if no irradiation with UV-A takes place. Thus, global monocyte activation and induction of DC occurred despite omission of central steps of the classical ECP procedure. However, shear stress seems to be one factor that is crucial for first globally activating monocytes and subsequently obtaining immuno-stimulatory DC. Other steps with a positive influence for global monocyte activation and e.g. subsequent induction of DC formation seem to be the activation of platelets by plasma components and the activation of monocytes by such activated platelets. The data further suggests that, if shear-stress induced induction of DC formation takes place in the presence of 8-MOP and irradiation with UVA, expression of the Glucocorticoid-induced Leucine Zipper (GILZ) is increased, which in turn activates a pathway leading to formation of truncated, i.e. immuno-suppressant tolerogenic DC (see Example 2). The fact that shear-stress induced induction of immuno-stimulatory DC could be achieved by applying shear stress without the addition of 8-MOP and without irradiation with UV-A further suggests that in the classical ECP procedure due to the dimensions of the plastic channels some of the initially shear-stress induced DC were not effectively irradiated with the consequence that these DC could further develop into immuno-stimulatory DC (see FIG. 16). This previous data was obtained using a device having the general architecture of FIG. 17. However, in the classical ECP and ECP-like procedures, mixtures of immuno-stimulatory autologous and immuno-suppressive autologous dendritic cells were obtained. Based on the data presented hereinafter, it is now possible to e.g. dispense with some of the requirements of the ECP and ECP-like processes of the prior art, e.g. to use large amounts of blood which needs to be processed by apheresis such as leukapheresis. Further, one can now deliberately adapt the process parameters and the design of the device, which is used to exert a physical force on monocytes, to deliberately obtain either immuno-stimulatory autologous or immuno-suppressive autologous dendritic cells.

Further, the data and conclusions presented herein suggest that the process of obtaining immuno-stimulatory dendritic cells seems to include a global monocyte activation step and a monocyte to immuno-stimulatory antigen-presenting cell (e.g. dendritic cell) differentiation step. These different steps seem to be traceable by molecular markers as described above, by Forward Scattering/Side Scattering Complexity (FSC/SSC Complexity), which is determinable by FACS analysis and by the phagocytozing activity observed for cells undergoing ECP. The molecular markers may moreover be grouped according to their know function as e.g. molecular markers of antigen-presentation, molecular markers of cellular adhesion etc. HLA-DR, CD86, and CD 80 may be considered to representative of antigen-presentation. PLAUR, and ICAM-1 may be considered to representative of cell adhesion. Markers like HLA-DR, PLAUR and ICAM-1 as well as FSC/SSC complexity may be moreover considered to be indicative of global monocyte activation while increased expression of e.g. CD83, ADAM-Decysin, CD40, CD80, LAMP-3, and CCR7 seems indicative of monocyte to dendritic cell differentiation.

The method as described hereinafter may be performed without the need of molecular cocktails to achieve global monocyte activation and subsequent maturation and differentiation into e.g. antigen-presenting cells such as immuno-stimulatory autologous dendritic cells. Further, as the invention is based on globally activating monocytes contained in an extracorporeal quantity of mammalian subject's blood sample, the activation and subsequent differentiation process is not limited to the molecular events, which can be triggered by typical cytokine cocktails. Rather, globally activated monocytes and dendritic cells as obtainable with the methods described hereinafter seem to have more complex molecular, albeit synchronized patterns, which seem representative of a broader functionality of these cells.

In a first aspect, the invention thus relates to a method for obtaining globally activated monocytes, said method comprising at least the steps of:

a) subjecting an extracorporeal quantity of a mammalian subject's blood sample, which comprises monocytes, to a physical force such that said monocytes are globally activated, wherein said globally activated monocytes are characterized by increased expression of at least HLA-DR, PLAUR and ICAM-1.

In general, suitable molecular markers are described hereinafter and may be taken from e.g. Table 6. Markers like HLA-DR, PLAUR and ICAM-1 may be considered to be indicative of global monocyte activation. Globally activated monocytes may preferably be characterized by increased expression of additionally at least ABCA1, CCL2, CCL7, CD68, CRK, FAS, IL 10, RAB7B, RALA, SCARF1, and/or THBS1.

Further such globally activated monocytes may be characterized by increased expression of additionally at least CXCL1, CXCL2, CXCL5, CXCL16, ITGA5, ITGAV, MMP9, MSR1, OLR1, PLAU, PLAUR, SIRPa, TIMP1, and/or TNF. Globally activated monocytes may thus be also identifiable by increased expression of at least 3, 4, 5, 6, 7, 8, 9, 10, 15, 20, or 25 markers of Table 6. Globally activated monocytes may not show an increased expression of GILZ. Increased expression refers to a comparison of the expression of these markers before and after subjecting the cells to physical forces such as mechanical stress.

As has already been mentioned, the methods described hereinafter have been shown to allow, after global monocyte activation, production of immuno-stimulatory and immuno-suppressive cells, which due to their molecular markers seem to be related to if not correspond to cells that are commonly named dendritic cells. Thus the immune-stimulatory cells according to the invention have been named immune-stimulatory dendritic cells. However, dendritic cells are representatives of a broader class of cells, which may be designated as antigen-presenting cells. Thus, the methods as described hereinafter generally refer to the production of immune-stimulatory antigen-presenting cells with immune-stimulatory dendritic cells being preferred.

The term "immuno-stimulatory autologous dendritic cells" thus refers to cells derivable from monocytes by treating the monocytes contained in an extracorporeal quantity of said mammalian subject's blood sample as it is described herein and identifiable by molecular markers as described in the following. These molecular markers have been discussed in the literature for dendritic cells which can present antigens by way of MHC I and MHC II. It is to be understood that the immuno-stimulatory autologous dendritic cells as obtainable by the methods described herein and identifiable by the molecular markers described herein may be considered as dendritic cells, which have already differentiated enough and internalized and even display e.g. tumor-specific antigens from apoptotic cells such as cytotoxic T-cells, which are contained in the extracorporeal quantity of a respective mammalian subject's blood sample, or e.g. viral or bacterial antigens, which are contained in the extracorporeal quantity of a respective mammalian subject's blood sample, such that they can be considered to be immuno-stimulatory autologous antigen-presenting dendritic cells. However, the process can also be conducted in a way such that the dendritic cells express molecular markers indicative of immuno-stimulatory dendritic cells, which have not yet internalized and display antigens. The term "immuno-stimulatory autologous dendritic cells" in one embodiment thus encompasses immuno-stimulatory autologous antigen-presenting dendritic cells. It needs to be understood that where immuno-stimulatory antigen-presenting cells such as dendritic cells are mentioned herein, this refers to immuno-stimulatory antigen-presenting cells such as dendritic cells which have the capacity of displaying e.g.

disease-specific antigens in their surfaces after these cells have been contacted with such antigens.

As is described in the examples, molecular markers which are indicative of immuno-stimulatory autologous dendritic cells obtainable by the methods described herein were identified by subjecting monocytes contained in the extra-corporeal quantity of mammalian subjects' blood samples derived either from healthy volunteers to the process using a miniaturized device (see markers 88 to 99 of Table 1). Further, as is also described in the example, molecular markers, which are indicative of immuno-stimulatory autologous dendritic cells, were identified by subjecting monocytes contained in the extracorporeal quantity of mammalian subjects' blood samples derived either from healthy volunteers or from patients suffering from CTCL or from GvH disease (GvHD) to an ECP process (see markers 1 to 87 of Table 1). The dendritic cells were then isolated and up-regulated expression of molecular markers, which are known or suspected to play a role in immuno-stimulatory dendritic cells, was analyzed. Some of the markers identified for the ECP process, which is assumed to lead to a complex mixture of immune-stimulatory and immune-suppressive dendritic cells, are the same as they were observed for the dendritic cells obtained by the process with the miniaturized device, which should lead to immune-stimulatory dendritic cells only. Thus to the extents that the ECP process leads to up-regulation of molecular markers, which can be associated with dendritic cell function, it seems justified to assume that these markers will also be suitable to identify immune-stimulatory dendritic cells as they are obtainable by the processes described herein such as with the miniaturized device. A set of overall 99 molecular markers was identified as being upregulated for immuno-stimulatory autologous dendritic cells obtainable by methods described herein. This set may be extended by further molecular markers in the future through comparable analysis Thus, the data of examples 1 and 3 lead to a set of 99 markers, which are considered indicative of immuno-stimulatory autologous dendritic cells. These markers are summarized in Table 1.

TABLE 1

| No. | Marker | NCBI Gene ID No. | mRNA REF | SEQ ID No. |
|---|---|---|---|---|
| 1 | ABCA1 | 19 | NM_005502.3 | 1 |
| 2 | ACVR1B | 91 | NM_004302.4 | 2 |
| 3 | ANPEP | 290 | NM_001150.2 | 3 |
| 4 | AQP9 | 366 | NM_020980.3 | 4 |
| 5 | ATP6V0B | 533 | NM_001039457.1 | 5 |
| 6 | BASP1 | 10409 | NM_001271606.1 | 6 |
| 7 | BEST1 | 7439 | NM_001139443.1 | 7 |
| 8 | CD63 | 967 | NM_001257389.1 | 8 |
| 9 | CD68 | 968 | NM_001040059.1 | 9 |
| 10 | CDCP1 | 64866 | NM_022842.3 | 10 |
| 11 | CPM | 1368 | NM_001005502.2 | 11 |
| 12 | CRK | 1398 | NM_005206.4 | 12 |
| 13 | CSF2RA | 1438 | NM_001161529.1 | 13 |
| 14 | CTNND1 | 1500 | NM_001085458.1 | 14 |
| 15 | CTSB | 1508 | NM_001908.3 | 15 |
| 16 | CXCL16 | 58191 | NM_001100812.1 | 16 |
| 17 | EMP1 | 2012 | NM_001423.2 | 17 |
| 18 | ENG | 2022 | NM_000118.2 | 18 |
| 19 | EPB41L3 | 23136 | NM_012307.2 | 19 |
| 20 | FLOT1 | 10211 | NM_005803.2 | 20 |
| 21 | GNA15 | 2769 | NM_002068.2 | 21 |
| 22 | GPNMB | 93695 | NM_053110.4 | 22 |
| 23 | GPR137B | 83924 | NM_031999.2 | 23 |
| 24 | GPR157 | 269604 | NM_177366.3 | 24 |
| 25 | HEXB | 3074 | NM_000521.3 | 25 |
| 26 | HOMER3 | 9454 | NM_001145721.1 | 26 |

TABLE 1-continued

| No. | Marker | NCBI Gene ID No. | mRNA REF | SEQ ID No. |
|---|---|---|---|---|
| 27 | ICAM1 | 3383 | NM_000201.2 | 27 |
| 28 | IL1R1 | 3554 | NM_000877.2 | 28 |
| 29 | IRAK1 | 3654 | NM_001025242.1 | 29 |
| 30 | ITGA5 | 3678 | NM_002205.2 | 30 |
| 31 | ITGB8 | 3696 | NM_002214.2 | 31 |
| 32 | KCTD11 | 147040 | NM_001002914.2 | 32 |
| 33 | LAMP2 | 3920 | NM_001122606.1 | 33 |
| 34 | LEPROT | 54741 | NM_001198681.1 | 34 |
| 35 | LGALS3 | 3958 | NM_001177388.1 | 35 |
| 36 | LILRB4 | 11006 | NM_001081438.1 | 36 |
| 37 | MARCKSL1 | 65108 | NM_023009.6 | 37 |
| 38 | MCOLN1 | 57192 | NM_020533.2 | 38 |
| 39 | MFAP3 | 4238 | NM_001135037.1 | 39 |
| 40 | MGAT4B | 11282 | NM_014275.4 | 40 |
| 41 | MR1 | 3140 | NM_001194999.1 | 41 |
| 42 | MRAS | 22808 | NM_001085049.2 | 42 |
| 43 | MSR1 | 4481 | NM_002445.3 | 43 |
| 44 | NEU1 | 4758 | NM_000434.3 | 44 |
| 45 | NPC1 | 4864 | NM_000271.4 | 45 |
| 46 | OLR1 (LOX1) | 4973 | NM_001172632.1 | 46 |
| 47 | OMG | 4974 | NM_002544.4 | 47 |
| 48 | P2RX4 | 5025 | NM_001256796.1 | 48 |
| 49 | PI4K2A | 55361 | NM_018425.2 | 49 |
| 50 | PLAUR | 5329 | NM_001005376.2 | 50 |
| 51 | PMP22 | 5376 | NM_000304.2 | 51 |
| 52 | PPAP2B | 8613 | NM_003713.4 | 52 |
| 53 | PSEN1 | 5663 | NM_000021.3 | 53 |
| 54 | PVRL2 | 5819 | NM_001042724.1 | 54 |
| 55 | RAB13 | 5872 | NM_002870.2 | 55 |
| 56 | RAB8B | 51762 | NM_016530.2 | 56 |
| 57 | RAB9A | 9367 | NM_001195328.1 | 57 |
| 58 | RALA | 5898 | NM_005402.3 | 58 |
| 59 | RHEB | 6009 | NM_005614.3 | 59 |
| 60 | RNASE1 | 6035 | NM_002933.4 | 60 |
| 61 | SC5DL | 6309 | NM_001024956.2 | 61 |
| 62 | SDC2 | 6383 | NM_002998.3 | 62 |
| 63 | SEMA6B | 10501 | NM_032108.3 | 63 |
| 64 | SIRPA | 140885 | NM_001040022.1 | 64 |
| 65 | SLC17A5 | 26503 | NM_012434.4 | 65 |
| 66 | SLC1A4 | 6509 | NM_001193493.1 | 66 |
| 67 | SLC22A4 | 6583 | NM_003059.2 | 67 |
| 68 | SLC31A1 | 1317 | NM_001859.3 | 68 |
| 69 | SLC35E3 | 55508 | NM_018656.2 | 69 |
| 70 | SLC39A6 | 25800 | NM_001099406.1 | 70 |
| 71 | SLC6A6 | 6533 | NM_001134367.1 | 71 |
| 72 | SLC6A8 | 6535 | NM_001142805.1 | 72 |
| 73 | SLC7A11 | 23657 | NM_014331.3 | 73 |
| 74 | STX3 | 6809 | NM_001178040.1 | 74 |
| 75 | STX6 | 10228 | NM_005819.4 | 75 |
| 76 | TM9SF1 | 10548 | NM_001014842.1 | 76 |
| 77 | TMBIM1 | 64114 | NM_022152.4 | 77 |
| 78 | TMEM33 | 55161 | NM_018126.2 | 78 |
| 79 | TNFRSF10B | 8795 | NM_003842.4 | 79 |
| 80 | TNFRSF11A | 8792 | NM_001270949.1 | 80 |
| 81 | TNFRSF1A | 7132 | NM_001065.3 | 81 |
| 82 | TNFRSF1B | 7133 | NM_001066.2 | 82 |
| 83 | TNFSF14 | 8740 | NM_003807.3 | 83 |
| 84 | TNFSF9 | 8744 | NM_003811.3 | 84 |
| 85 | TRIP10 | 9322 | NM_004240.2 | 85 |
| 86 | TRIP6 | 7205 | NM_003302.2 | 86 |
| 87 | YKT6 | 10652 | NM_006555.3 | 87 |
| 88 | DC-LAMP (LAMP3) | 27074 | NM_014398.3 | 88 |
| 89 | CLEC5A | 23601 | NM_013252.2 | 89 |
| 90 | SPC2 (PCSK2) | 5126 | NM_002594.3 | 90 |
| 91 | THBS1 | 7057 | NM_003246.2 | 91 |
| 92 | CD14 | 929 | NM_000591.3 | 92 |
| 93 | CD40 | 958 | NM_001250.4 | 93 |
| 94 | CD80 | 941 | NM_005191.3 | 94 |
| 95 | CCR7 | 1236 | NM_001838.3 | 95 |
| 96 | CD83 | 9308 | NM_001251901.1 | 96 |
| 97 | ADAM Decysin | 27299 | NM_014479.3 | 97 |
| 98 | FPRL2 (FPR3) | 2359 | NM_002030.3 | 98 |
| 99 | CD86 | 942 | NM_006889.4 | 99 |

Of the 87 genes (markers 1 to 87 of Table 1) that represent surface markers/functional mediators of immuno-stimulatory DC function, 66 were found to be uniquely identified in the ECP-induced process (plate passaged, overnight cultured, see example) dendritic cells, after comparison to expression databases for "classical" dendritic cells. These are: ABCA1, ACVR1B, ATP6V0B, BASP1, BEST1, CPM, CRK, CSF2RA, CTNND1, CTSB, CXCL16, ENG, FLOT1, GNA15, GPR137B, GPR157, HEXB, HOMER3, ICAM1, IRAK1, ITGA5, ITGB8, KCTD11, LAMP2, LEPROT, MARCKSL1, MCOLN1, MFAP3, MGAT4B, MR1, MRAS, MSR1, NEU1, OLR1, OMG, PI4K2A, PLAUR, PMP22, PVRL2, RAB13, RAB8B, RAB9A, RALA, RNASE1, SCSDL, SEMA6B, SIRPA, SLC1A4, SLC22A4, SLC31A1, SLC35E3, SLC39A6, SLC6A6, SLC6A8, STX3, STX6, TM9SF1, TMBIM1, TMEM33, TNFRSF10B, TNFRSF11A, TNFRSF1A, TNFRSF1B, TNFSF14, TNFSF9, YKT6.

Immuno-stimulatory autologous dendritic cells are thus identifiable by determining expression of at least one molecular marker for the immuno-stimulatory autologous dendritic cells obtainable by the methods described herein and by comparing its expression for monocytes contained within the extracorporeal quantity of a mammalian subject's blood sample. If an increased expression for immuno-stimulatory autologous dendritic cells vs. monocytes is observed, this is indicative of the differentiation of monocytes to immuno-stimulatory autologous dendritic cells.

Preferably, immuno-stimulatory autologous dendritic cells are identifiable by determining expression for at least 2, 3, 4, 5, 6, 7, 8, 9, 10, 15, 20, 25, 30, 35, 40, 45, 50, or more molecular markers selectable from Table 1. For example, one may identify immuno-stimulatory autologous dendritic cells by determining expression for at least 1, 2, 3, 4, 5, 6, 7, 8, 9, 10, 11, 12, 13, 14, 15, 16, 17, 18, 19, 20, 21 or 22 molecular markers selectable from the group comprising PLAUR, NEU1, CTSB, CXCL16, ICAM1, MSR1, OLR1, SIRPa, TNFRSF1A, TNFSF14, TNFSF9, PMB22, CD40, LAMP3, CD80, CCR7, LOX1, CD83, ADAM Decysin, FPRL2, GPNMB and/or CD86. More preferably, one may identify immuno-stimulatory autologous dendritic cells by determining expression for at least 1, 2, 3, 4, 5, 6, 7, 8, 9, or 10 molecular markers selectable from the group comprising PLAUR, NEU1, CD80, CCR7, LOX1, CD83, ADAM Decysin, FPRL2, GPNMB and/or CD86. The most preferred markers, which are considered indicative of immuno-stimulatory autologous dendritic cells are PLAUR, NEU1, CD80, CD83, and/or CD86.

The data and conclusions presented herein suggest that the process of obtaining immuno-stimulatory dendritic cells seems to include a global monocyte activation step and a monocyte to immuno-stimulatory antigen-presenting cell (e.g. dendritic cell) differentiation step. These different steps seem to be traceable by molecular markers as described above and by Forward Scattering/Side Scattering Complexity (FSC/SSC Complexity), which is determinable by FACS analysis. The molecular markers may moreover be grouped according to their know function as e.g. molecular markers of antigen-presentation, molecular markers of cellular adhesion etc. HLA-DR, CD86, and CD 80 may be considered to representative of antigen-presentation. PLAUR, and ICAM-1 may be considered to representative of cell adhesion. Markers like HLA-DR, PLAUR and ICAM-1 as well as FSC/SSC complexity may be moreover considered to be indicative of global monocyte activation while increased expression of e.g. CD83, ADAM-Decysin, CD40, CD80, LAMP-3, and CCR7 seems indicative of monocyte to dendritic cell differentiation.

A set of markers, which may be used for identification of globally activated monocytes and for differentiation vs immune-stimulatory antigen presenting cells or immune-suppressive antigen-presenting cells is found in below Table 6. After identifying global monocyte activation by increased FSC/SSC complexity (see Experiment 5), results of Experiments 3 and 4 were re-evaluated by comparing the upregulated genes (466 genes with fold-change>2, P<0.05) with genes identified in the literature or as commercial sets associated with phagocytosis or wound healing. This led to a set of 26 genes identified in Experiment 3 and 4 and associated with phagocytosis or wound healing The GEO2R software was used to compare all PreECP samples vs all PostECP samples in Experiments 3 and 4. GEO2R reports Log 2 fold change and adjusted P<0.05 values

TABLE 6

| No. | Marker | NCBI Gene ID No. | mRNA REF | SEQ ID No. |
|---|---|---|---|---|
| 1 | ABCA1 | 19 | NM_005502.3 | 106 |
| 2 | ANXA5 | 308 | NM_001154.3 | 107 |
| 3 | CCL2 | 6347 | NM_002982.3 | 108 |
| 4 | CCL7 | 6354 | NM_006273.3 | 109 |
| 5 | CD68 | 968 | NM_001251.2, NM_001040059.1 | 110 |
| 6 | CRK | 1398 | NM_016823.3 NM_005206.4 | 111 |
| 7 | CXCL1 | 2919 | NM_001511.3 | 112 |
| 8 | CXCL2 | 2920 | NM_002089.3 | 113 |
| 9 | CXCL5 | 6374 | NM_002994.4 | 114 |
| 10 | CXCL16 | 58191 | NM_022059.3 | 115 |
| 11 | FAS | 355 | NM_152871.2, NM_000043.4, NM_152872.2 | 116 |
| 12 | IL10 | 3586 | NM_000572.2 | 117 |
| 13 | ITGA5 | 3678 | NM_002205.2 | 118 |
| 14 | ITGAV | 3685 | EF560727.1 | 119 |
| 15 | MMP9 | 4318 | NM_004994.2 | 120 |
| 16 | MSR1 | 4481 | NM_138715.2, NM_138716.2, NM_002445.3 | 121 |
| 17 | OLR1 | 4973 | NM_002543.3, NM_001172633.1, NM_001172632.1 | 122 |
| 18 | PLAU | 5328 | NM_002658.3, NM_001145031.1 | 123 |
| 19 | PLAUR | 5329 | NM_001005377.2, NM_001005376.2, NM_002659.3 | 124 |
| 20 | RAB7B | 338382 | NM_001164522.1, NM_177403.4 | 125 |
| 21 | RALA | 5898 | NM_005402.3 | 126 |
| 22 | SCARF1 | 8578 | NM_003693.3, NM_145350.2 | 127 |
| 23 | SIRPA | 140885 | NM_001040022.1, NM_001040023.1 | 128 |
| 24 | THBS1 | 7057 | NM_003246.2 | 129 |
| 25 | TIMP1 | 7076 | NM_003254.2 | 130 |
| 26 | TNF | 7124 | NM_000594.3 | 131 |

As is described herein, if the methods are conducted to allow an increased expression of GILZ (SEQ ID No.: 100), IDO (Indoleamine) (SEQ ID No.: 101), KMO (kynurenine 3-hydroxylase) (SEQ ID No.: 102), transforming growth factor-beta (TGFβ) (SEQ ID No.: 103), and/or IL-10 (Interleukin 10) (SEQ ID No.: 104), globally activated monocytes contained within the extracorporeal quantity of a mammalian subject's blood sample will not differentiate into immuno-stimulatory autologous dendritic cells, but rather into immature, so-called truncated or immuno-suppressive dendritic cells. Thus, globally activated monocytes as well as immuno-stimulatory autologous dendritic cells are identifiable not only by determining expression of the aforementioned molecular markers, but also by determining that expression of GILZ, IDO, KMO, TGFβ, and/or IL-10 is not increased for immuno-stimulatory autologous dendritic cells vs. monocytes. If increased GILZ, IDO, KMO, TGFβ and/or IL-10 expression was determined, this would be considered indicative of at least some for immuno-suppressive dendritic cells having formed. The preferred molecular marker, which is considered indicative for immune-suppressive dendritic cells, is currently GILZ.

As mentioned above, the method as described hereinafter may be performed without the need of molecular cocktails to achieve global monocyte active and subsequent maturation and differentiation of monocytes into immuno-stimulatory autologous dendritic cells. Such cocktails may comprise factors such as e.g. IL-4, GM-CSF, LPS, IFN-γ, IL-1β and TNF-α.

Given that one now has the understanding and correspondingly the tools, e.g. the molecular markers at hand to distinguish between globally activated monocytes, immuno-stimulatory autologous antigen-presenting cells and the immuno-suppressive autologous antigen-presenting cells, one can now deliberately vary both the design of the device and the flow chamber through which the extracorporeal quantity of a mammalian subject's blood sample and thus the monocytes are passed to experience a physical force, and the parameters at which the process of global monocyte activation and subsequent induction of differentiation of monocytes into globally activated monocytes and subsequently immuno-stimulatory autologous dendritic cells is performed.

As mentioned above, an extracorporeal quantity of a mammalian subject's blood sample is passed through a flow chamber of a device, such that a shear force is applied to said monocytes contained within said mammalian subject's blood sample. Alterations of the design of the device and the flow chamber which have an influence on the global activation of monocytes include variation of flow forces, variation of the geometry of the flow path of the flow chamber, variation of the dimensions of the flow chamber, the possibility to adjust temperature, the possibility of exposure of the extracorporeal quantity of the mammalian subject's blood sample in the flow chamber to visible or UV light, etc. Application of a physical force may not only be achieved by e.g. passing an extracorporeal amount of blood sample through a flow chamber, but also by placing such an extracorporeal amount of blood sample in e.g. an EVA plastic bag as obtainable from Macopharma and gently moving or shaking this blood sample-filled bag (see e.g. Andreu et al., (1994), *Trans. Sci.,* 15(4), 443-454)

As also mentioned above and shown hereinafter, global activation of monocytes and subsequent induction of differentiation into immuno-stimulatory autologous dendritic cells is dependent on interaction of monocytes with activated platelets and/or specific plasma components in a situation where the monocytes experience physical force, which may be provided by a device as described hereinafter. Variation of process parameters thus include varying the nature, purity and concentrations of plasma components; the nature, purity and concentration of platelets; the order of steps by which plasma components and/or platelets are passed through and/or disposed on the flow chamber; the density by which the flow chamber is coated with plasma components and/or platelets, the flow forces of the extracorporeal quantity of the mammalian subject's blood sample and in particular the platelets and/or the monocytes are passed through the flow chamber of such a flow chamber, the temperature and/or time at which the extracorporeal quantity of the mammalian subject's blood sample and in particular the platelets and/or the monocytes are passed through the flow chamber of such a device, etc., the nature, purity and concentrations of additional factors such as 8-MOP and/or cytokines are added to the extracorporeal quantity of the mammalian subject's blood sample and in particular to the monocytes, etc.

Factors relating to the design of the device and the flow chamber as well as to process parameter will now be discussed in more detail as regards their relevance for global activation of monocytes and subsequent differentiation into immuno-stimulatory autologous dendritic cells. It is to be understood that for any of the embodiments discussed in the following global activation of monocytes is achieved wherein globally activated monocytes are identifiable by determining expression of molecular markers described above and/or by determining expression of GILZ. Further, for all embodiments discussed in the following it is to be understood that monocytes that are contained in an extracorporeal quantity of a mammalian subject's blood sample are subjected to a physical force such as shear stress in order to allow them to be globally activated.

In one embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample, and wherein said flow chamber of said device has a design allowing to apply a shear force to said monocytes contained within said mammalian subject's blood sample.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device, which allows adjustment of the flow rate of said extracorporeal quantity of said mammalian subject's blood sample through said flow chamber of said device such that a shear force is applied to said monocytes contained within said mammalian subject's blood sample, and wherein said device additionally allows for adjustment of at least one parameter selected from the group comprising temperature, and light exposure.

In another embodiment of the first aspect, the invention relates to a method of globally activating monocytes contained in an extracorporeal quantity of a mammalian subject's blood sample, wherein said extracorporeal quantity of said mammalian subject's blood sample is subjected to a physical force by passing said extracorporeal quantity of said mammalian subject's blood sample through a flow chamber of a device as mentioned before and wherein said monocytes are globally activated through interaction with activated platelets and/or plasma components.

For example, in one embodiment of the first aspect, the invention relates to a method of globally activating monocytes contained in an extracorporeal quantity of a mammalian subject's blood sample, wherein said method comprises at least the steps of:

a) applying said extracorporeal quantity of said mammalian subject's blood sample comprising at least monocytes to a device, which is configured to provide for a flow chamber through which said extracorporeal quantity of said mammalian subject's blood sample can be passed,
b) activating platelets, which may be comprised within said extracorporeal quantity of said mammalian subject's blood or which may be provided separate from said mammalian subject's blood sample comprising at least monocytes,
c) treating said extracorporeal quantity of said mammalian subject's blood sample comprising at least monocytes in said device by applying a physical force to the monocytes contained within said extracorporeal quantity of said mammalian subject's blood sample such that said monocytes are globally activated by binding to said activated platelets obtained in step b).

In another embodiment of the first aspect, the invention relates to a method of globally activating monocytes contained in an extracorporeal quantity of a mammalian subject's blood sample, wherein said method comprises at least the steps of:

a) applying said extracorporeal quantity of said mammalian subject's blood sample comprising at least monocytes to a device, which is configured to provide for a flow chamber through which said extracorporeal quantity of said mammalian subject's blood sample can be passed,
b) passing plasma components, which may be comprised within said extracorporeal quantity of said mammalian subject's blood sample or which may be provided separate from said mammalian subject's blood sample,
c) treating said extracorporeal quantity of said mammalian subject's blood sample comprising at least monocytes in said device by applying a physical force to the monocytes contained within said extracorporeal quantity of said mammalian subject's blood sample such that said monocytes are globally activated by binding to said plasma components obtained in step b).

In yet another embodiment of the first aspect, the invention relates to a method of globally activating monocytes contained in an extracorporeal quantity of a mammalian subject's blood sample, wherein said method comprises at least the steps of:

a) applying said extracorporeal quantity of said mammalian subject's blood sample comprising at least monocytes to a device, which is configured to provide for a flow chamber through which said extracorporeal quantity of said mammalian subject's blood sample can be passed,
b) passing plasma components, which may be comprised within said extracorporeal quantity of said mammalian subject's blood or which may be provided separate from said mammalian subject's blood sample,
c) activating platelets, which may be comprised within said extracorporeal quantity of said mammalian subject's blood sample or which may be provided separate from said mammalian subject's blood sample comprising at least monocytes,
d) treating said extracorporeal quantity of said mammalian subject's blood comprising at least monocytes in said device by applying a physical force to the monocytes contained within said extracorporeal quantity of said mammalian subject's blood sample such that said monocytes are globally activated by binding to said activated platelets and/or plasma components obtained in steps b) and c).

In yet another embodiment of the first aspect, the invention relates to a method of globally activating monocytes contained in an extracorporeal quantity of a mammalian subject's blood sample, wherein said method comprises at least the steps of:

a) optionally passing platelets-rich plasma through a device, which is configured to provide for a flow chamber through which said extracorporeal quantity of said mammalian subject's blood sample can be passed,
b) applying said extracorporeal quantity of said mammalian subject's blood sample comprising at least monocytes to a device, which is configured to provide for a flow chamber through which said extracorporeal quantity of said mammalian subject's blood sample can be passed,
c) treating said extracorporeal quantity of said mammalian subject's blood comprising at least monocytes in said device by applying a physical force to the monocytes contained within said extracorporeal quantity of said mammalian subject's blood sample such that said monocytes are globally activated optionally by binding to said platelets-rich plasma of steps a).

The steps of activating platelets and the subsequent activation of monocytes will be discussed in the following for the embodiment that (i) plasma components such as plasma proteins are passed through the flow chamber of the device so that these components adhere to the walls of the flow chamber, that (ii) platelets are passed through the flow chamber and are activated by binding to the plasma components and that (iii) monocytes-containing fractions such as an extracorporeal quantity of said mammalian subject's blood comprising at least monocytes are passed through the flow chamber and are activated by binding to the activated platelets. It is, however, to be understood that these activities also occur if the plasma fraction or plasma proteins or fragments thereof, the platelet fraction and the monocytes-containing fraction are passed simultaneously through the channels or channel-like structures as is the case for a whole blood fraction if obtained from the extracorporeal amount of blood as described below. It is further to be understood that the process may be performed even though not with same effectiveness by adhering only plasma components to the walls of the flow chamber and letting monocytes interact with the plasma components. Nevertheless, in the following these aspect will be discussed for a preferred embodiment, i.e. where steps (i), (ii), and (iii) are realized.

As regards the first step, plasma components including proteins like fibrinogen or fibronectin, or fragments thereof like the gamma component of fibrinogen may be provided either as fractions obtained from the extracorporeal amount of blood sample or in purified form from other resources e.g. in the form of recombinantly expressed proteins. Even though it seems that activation of platelets by plasma proteins such as fibrinogen and fibronectin is sufficient so that recombinantly expressed forms of these proteins are sufficient, it can be preferred to use plasma fractions which are obtained from the extracorporeal amount of blood sample and comprise these proteins as these plasma fractions have a more complex composition and may comprise all plasma components, which provide for an optimal activation of platelets.

Plasma protein fractions, plasma proteins or fragments thereof may be passed through the flow chamber, which may be made of plastic or non-plastic materials such as glass in order to adhere to the walls of the channels or channel-like structures. There is no requirement that the plasma fractions or plasma proteins are passed through the flow chamber at a specific physical force such as e.g. a specific pressure. However, in order to streamline the process, it is envisaged to pass the plasma fractions or plasma proteins through the flow chamber at a shear stress, which is comparable if not identical to the shear stress required for monocyte activation being described in more detail below. In general, the plasma fractions or plasma proteins are first pumped through the flow chamber to coat the surfaces thereof with plasma proteins, including fibronectin and fibrinogen. The flow rate of the plasma protein fractions, plasma proteins or fragments thereof through the flow chamber is controlled to obtain a desired level of protein adherence to the plastic surfaces. If desired, the flow can be stopped for a period of time and the plasma component can “soak” the surfaces of the flow chamber. By controlling the speed and timing of the pump that propels the plasma components through the flow chamber, the degree of coating of can be controlled. In one approach, the plasma fractions or plasma proteins are exposed to the surfaces of the flow chamber structures for a period between about 1 to 60 min, between about 1 to about 30 min, between about 1 to about 20 min, or between about 1 to about 10 min. To enhance plasma protein adherence to the surfaces of the flow chamber, the flow may be temporarily discontinued (for up to about 60 min), before resumption, or the flow rate may be slowed from the filling rate (up to 100 ml/minute) to as low as 5 ml/minute, during this phase of the procedure.

One can also envisage a scenario, where a device with a flow chamber is used for which the surfaces of the flow chamber have been pre-coated with e.g. purified plasma proteins or fragments thereof such as the gamma component of fibrinogen. Such pre-coated devices may be used if the whole process s conducted in a handheld device comprising a cartridge providing the flow chamber, which is configured for e.g. one time use. One can also envisage a scenario, where a device with a flow chamber is used for which the surfaces of the flow chamber have been pre-coated with e.g. platelets-rich plasma.

After the plasma fractions or plasma proteins or fragments thereof have been passed through the channels or channel-like structures and the surfaces thereof have been coated with plasma proteins, the platelet fraction is passed by e.g. pumping into and through the channels or channel-like structures. The flow rate and residence time of the platelets within the channels or channel-like structures is selected to allow the platelets to bind to the plasma components or proteins or fragments thereof which have adhered before to the surfaces of the channels or channel-like structures and to thereby activated.

The data presented herein suggest that activation of platelets by plasma components is a sequential process in which inactivated platelets first bind to the gamma component of fibronectin, get activated thereby and can then bind to the RGD motif (Arginine, Glycine, Aspartic Acid) which is found in many plasma proteins such as fibronectin or fibrinogen. If purified and/or recombinantly expressed plasma proteins or fragments thereof are used for activation of platelets, it can therefore be envisaged to pre-coat channels or channel-like structures with at least the gamma-component of fibrinogen and optionally additionally with RGD peptides. These plasma protein fragments and peptides may allow for efficient activation of platelets and at the same time for an optimal control of the coating process of the surfaces of the channels or channel-like structures. Of course, all of these components are present if a plasma fraction obtained from the extracorporeal amount of blood is used for coating and activation.

For efficient binding of the platelets to the plasma components and activation thereby, the flow rate may be adjusted upward or downward compared to the coating step of the plasma components, or flow may be stopped for a period of time, to obtain the desired level of platelets bound to the plasma components. The flow rates for plasma activation can typically be in the range of about 5 ml/min to about 200 ml/min, of about 10 ml/min to about 150 ml/min, of about 10 ml/min to about 100 ml/min, or of about 5 ml/min to about 50 ml/min depending on the selected device. Typically, it will be desirable to allow between about 1 to 60 min, between about 1 to about 30 min, between about 1 to about 20 min, or between about 1 to about 10 min for the platelets to bind to the plasma components.

Even though shear stress does not seem to of the same importance for activation of platelets as for global activation of monocytes, it can be preferred to pass the platelets fraction through the flow chamber under a shear force of about 0.01 to about 100.0 dynes/$cm^2$, of about 0.05 to about 50.0 dynes/$cm^2$, of about 0.1 to about 20.0 dynes/$cm^2$, of about 0.2 to about 15.0 dynes/$cm^2$, of about 0.3 to about 10.0 dynes/$cm^2$ such as from about 0.2 to about 0.4, to about 0.5, to about 0.6, to about 0.7, to about 0.8, to about 0.9, to about 1, to about 2, to about 3, to about 4, to about 5, or to about 6 dynes/$cm^2$. Typical flow rates of the platelets-containing fraction may be in the range of about 5 ml/min to about 200 ml/min, of about 10 ml/min to about 150 ml/min, of about 10 ml/min to about 100 ml/min, or of about 5 ml/min to about 50 ml/min depending on the respective device. The flow rates will depend to some extent on the size and geometry of the flow chamber and can particularly be used if flow chamber of the below-mentioned dimensions are used. In general, one will select flow rates to achieve the afore-mentioned shear stress values.

Thus, it is contemplated to pass the platelets-containing fraction through the channels or channel-like structures with a flow rate of about 10 ml/minute to about 200 ml/minute to produce a shear force of about 0.1 to about 10.0 dynes/$cm^2$.

After the platelets have been passed through the channels or channel-like structures and have been activated by the plasma proteins or fragments thereof, which have been disposed on the surfaces of the channels or channel-like structures thereof, the monocytes-containing fraction, e.g. the extracorporeal quantity of said mammalian subject’s blood sample or the below-mentioned leukocyte or buffy coat fraction, which have been obtained from the extracorporeal amount of blood sample, is passed by e.g. pumping into and through the channels or channel-like structures, by applying a physical force. It is to be understood that activation of platelets through interaction with plasma components will lead to adherence of platelets to plasma components.

It is also to be understood that the same events as described above will happen if an extracorporeal quantity of a mammalian subject's blood sample comprising platelets and plasma components is passed through the flow chamber. In this case, plasma components will adhere to the walls to the flow chamber and then activate platelets. However, in this scenario the process may be less controllable and account may be taken of this by increasing the residence time of the extracorporeal quantity of a mammalian subject's blood sample comprising platelets and plasma components in the flow chamber.

It is further to be noticed that instead of activated platelets, factors derived from platelets may be used, which are sufficient to activate monocytes. These factors include e.g. fibronectin and may also include factors such as P-selectin, Integrin a5β1 the C-type lectin receptor, CD61, CD36, CD47 and complement inhibitors such as CD55 and CD59, or TREM-like transcript-1. Such platelet-derived factors may also be disposed directly on the surfaces of the flow chamber either as e.g. mixtures of purified components or mixtures of components obtained by e.g. lysis of platelets contained within the extracorporeal quantity of a mammalian subject's blood sample. In this case, the need for e.g. coating the surfaces of the flow chamber with plasma components may be bypassed.

The data presented herein suggest that once platelets have been activated, proteins such as P-selectin and RGD-containing ligands are expressed by the activated platelets, which can then interact with monocytes and activate their differentiation into immuno-stimulatory dendritic cells. Moreover, it was found that monocyte activation and dendritic cell induction by activated platelets do not occur under static conditions. Rather monocytes need to be passed through the channels or channel-like structures under application of a physical force. Given that platelets upon activation need about 60 to about 120 min to express factors such as P-selectin, which then activates monocytes, passing of monocytes may be delayed until platelets have started to express these factors, e.g. for about 60 to about 120 min. If an extracorporeal quantity of a mammalian subject's blood sample comprising monocytes, platelets and plasma components is passed through the flow chamber, this time period may have to be adjusted to longer times.

It is to be understood that interaction of monocytes with activated platelets, platelet-derived factors or plasma components is not sufficient for global activation of monocytes without the application of a physical force at the same time.

Application of a physical force for moving the monocytes-containing fraction through the flow chamber preferably may mean that a monocytes-containing fraction such as the extracorporeal quantity of a mammalian subject's blood sample is moved through the flow chamber under shear stress. Typically, monocytes-containing fraction may be passed through the flow chamber under a shear force of about 0.01 to about 100.0 dynes/$cm^2$, of about 0.05 to about 50.0 dynes/$cm^2$, of about 0.1 to about 20.0 dynes/$cm^2$, of about 0.2 to about 10.0 dynes/$cm^2$, such as from about 0.2 to about 0.3, to about 0.4, to about 0.5, to about 0.6, to about 0.7, to about 0.8, to about 0.9, to about 1, to about 1.5, or to about 2 dynes/$cm^2$. The flow rates will depend to some extent on the size and geometry of the flow chamber and can particularly be used if channels or channel-like structures of the below-mentioned dimensions are used. In general, one will select flow rates to achieve the afore-mentioned shear stress values.

Suitable shear forces allowing for activation of monocytes may be achieved by a flow chamber having the aforementioned width to height ratio of about 40:1 to about 400:1 such as about 50:1 to about 300:1 or about 50:1 to about 250:1. Temperature is another factor to influence global activation of monocytes. The methods in accordance with the invention may be performed in a range of about 18° C. to about 42° C., preferably in a range of about 22° C. to about 41° C. and more preferably in a range of about 37° C. to about 41° C.

One parameter that can also be varied to tune global activation of monocytes is the density by which the flow chamber is coated with plasma components and thus with platelets that bind to the plasma components. In general, the denser the surfaces of the flow chamber are coated with plasma components and platelets, the more efficient will be the monocyte activation.

It has been mentioned above that platelets are activated by binding to plasma components. The term "activated platelets" in accordance with the invention is used to refer to platelets which show an increased expression of P-selectin, αIIb-f33 integrin and/or RGD-containing proteins such as fibronectin, fibrinogen or vitronectin as a consequence of binding of platelets to plasma components such as fibronectin and/or fibrinogen. Expression may be determined by conventional methods such as RT-PCR, Western-Blotting or FACS analysis. The term "unactivated platelets" in accordance with the invention is used to refer to platelets for which binding to plasma proteins such as fibronectin or fibrinogen cannot be reduced by pre-incubating platelets with the gamma component of fibrinogen.

It has been mentioned above, that monocytes are globally activated and start to differentiate into immuno-stimulatory autologous dendritic cells by binding to activated platelets under shear stress conditions.

The finding, that activation of monocytes and subsequent induction of differentiation of these monocytes into immuno-stimulatory autologous DC can be achieved in a miniaturized device, allows to conduct the process of global monocyte activation with smaller amounts of an extracorporeal blood sample. As mentioned above, the classical ECP procedure requires processing of 2.5 L to 6 L blood, which is typically obtained from patients by apheresis such as leukapheresis, to obtain a final volume of about 200 ml to 500 ml comprising leukocytes including monocytes as well as plasma components and platelets.

However, the methods in accordance with the invention may require substantial lower amount of blood samples thus bypassing the need of apheresis such as leukapheresis or other processes, which are a considerable burden to patients.

Thus, the present invention can be performed without the need for apheresis such as leukapheresis and the whole process of obtaining such globally activated monocytes may be performed in a handheld device.

Thus, in one embodiment of the first aspect of the invention, which may be combined with the above described embodiments, it is contemplated to perform the method in accordance with the first aspect, wherein said extracorporeal quantity of said mammalian subject's blood is not obtained by apheresis such as leukapheresis.

Said extracorporeal quantity of said mammalian subject's blood may typically be between 0.1%-10% of total blood volume of the respective subject. The quantity of said mammalian subject's blood may be about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal blood of said mammalian subject to give a final volume between about 1 ml to about 100 ml, between about 1 ml to about 50 ml, between about 1 ml to about 40 ml, or between about 1 ml to about 30 ml an extracorporeal amount of a mammalian's blood sample.

The quantity of extracorporeal blood withdrawn and applied to the device may be whole blood. Alternatively, said extracorporeal quantity of said mammalian subject's blood may be obtained by isolating leukocytes from between $0.5*10^6$-$50*10^6$ mononuclear cells. Leukocytes may be isolated from about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal whole blood of said mammalian subject.

Said extracorporeal quantity of said mammalian subject's blood may also be obtained by isolating buffy coats from between about 5 ml to about 500 ml, between about 10 ml to about 450 ml, between about 20 ml to about 400 ml, between about 30 ml to about 350 ml, between about 40 ml to about 300 ml, or between about 50 ml to about 200 ml or between about 50 ml to about 100 ml of extracorporeal whole blood of said mammalian subject.

In all of the afore-mentioned cases (whole blood, leukocyte fraction, buffy coats), said extracorporeal amount of blood will typically comprise between about $1\times10^4$ to about $1\times10^8$ such as about $5\times10^6$ mononuclear cells/ml.

The person skilled in the art is familiar how to obtain whole blood, a leukocyte fraction thereof or a buffy coat fraction thereof (see e.g. Bruil et al., *Transfusion Medicine Reviews* (1995), IX (2), 145-166) an include filtration, differential centrifugation. A preferred method relies on filters as they are available from e.g. Pall. Such filters may be incorporated into the device such that processing of the extracorporeal sample can be done in the handheld device. As a source one can also use e.g. blood of the umbilical cord.

If one uses centrifugation, one may obtain whole blood through a syringe with e.g. a 17 or 18 gauge-gauge needle. Such a whole blood sample may be centrifuged to remove debris and other components. The whole blood sample may then be filtered through common filters, as they are available from Pall.

For obtaining a mononuclear leukocyte fraction, one may obtain a whole blood sample as described and then layer such a sample on e.g. Ficoll-Hypaque. Subsequently a centrifugation step is performed at e.g. about 100 g to about 200 g such as 180 g and the mononuclear leukocyte fraction can then be collected from the interface and washed with common buffers such as HBSS. The washed mononuclear leukocyte fraction can then be resuspended in serum-free cell culture medium such as RPMI-1640 medium (GIBCO). Other methods for obtaining mononuclear leukocyte fractions include elutriation, filtration, density centrifugation, etc.

Monocytes, before global activation, may be identified in a blood sample as $CD13^+$ cells.

As pointed out above, crucial steps for the global monocyte activation and induction of DC formation seem to involve the activation of platelets by plasma components and the activation of monocytes by such activated platelets. In principle, one could pass a whole blood sample through the device under shear stress. The plasma components of such a sample will then bind to the surfaces of the flow chamber and allow for adherence and activation of platelets within such a sample by plasma-components. The monocytes of such a sample will then bind to the activated platelets and be activated themselves.

Similarly one may obtain combinations of the various components such as a platelet-rich plasma containing fraction which may be obtained by centrifuging a whole blood sample which has been obtained as described above at about 100 g to about 180 g such as about 150 g for about 10 min to about 20 min such as about 15 min to separate the debris of the whole blood sample. The platelet-rich plasma layer is then collected and recentrifuged at about 700 g to about 1000 g such as about 900 g for about 3 min to about 10 min such as about 5 min. The resultant pellet is then resuspended in serum-free cell culture medium.

However, in order to have the best control over the process, it may be desirable to first pass plasma components through the flow chamber and let them adhere, then platelets and then the monocytes-containing fraction. For this approach, it may be desirable to obtain a leukocyte fraction comprising a monocytes- or buffy-coat fraction comprising monocytes, which does not comprise plasma components and which does not comprise platelets. Such plasma- and platelet-free monocytes-containing fractions may be obtained as is described in the art. If leukocyte or buffy-coat fractions are obtained as described above, they will be sufficiently free of plasma or platelets for the purposes of the invention. For this approach, it may also be desirable to have platelet- and/or plasma-fractions.

Thus, the invention contemplate to use platelets which have been separated from the extracorporeal quantity of said mammalian subject's blood before said extracorporeal quantity of said mammalian subject's blood is applied to said device. These platelets may then be passed through the flow chamber, which has been coated with plasma components such as fibronectin.

In another embodiment, the invention considers to use plasma components, which have been separated from the extracorporeal quantity of said mammalian subject's blood before said extracorporeal quantity of said mammalian subject's blood is applied to said device. These plasma components may then be passed through flow chamber so that they can adhere.

Instead of using plasma components which have been obtained from the extracorporeal amount of blood, one may also use plasma components, which have been isolated from other sources such as e.g. by recombinant protein expression. Such plasma components include fibrinogen, fibronectin, P-selectin, and fragments thereof such as the gamma component of fibrinogen.

Even though it may be preferred to use an extracorporeal amount of blood, which has not been obtained by apheresis such as leukapheresis, using an extracorporeal amount of blood, which was obtained by apheresis such as leukapheresis is not excluded by the invention.

Thus, in another embodiment of the first aspect of the invention it is contemplated to perform the method as described above, wherein said extracorporeal quantity of said mammalian subject's blood is obtained by apheresis such as leukapheresis.

Apheresis such as leukapheresis may be performed as is known in the art. Thus, an extracorporeal quantity of blood such as 2.5 L to 6 l may be obtained from a subject and treated by conventional leukapheresis to obtain three fractions, namely the plasma, the platelets and the buffy coats. The plasma, which contains proteins such as fibronectin and fibrinogen, is the lightest blood fraction, and therefore is the first portion of the blood selectively removed from the centrifuge and passaged through channels or channel-like structures. After the plasma has been pumped through the channels or channel-like structures and the surfaces thereof have been coated with plasma proteins, the second lightest component in the leukapheresis centrifuge, the platelet fraction, is pumped into and through the channels or channel-like structures. The third lightest fraction to be eluted from the leukapheresis centrifuge is the buffy coat, which contains the white blood cells, including the blood monocytes. The buffy coat including the monocytes is then pumped through the channels or channel-like structures. Blood sample may be obtained using the Therakos device, the Spectra cell separator (see Andreu et al., (1994), *Transf. Sci.,* 15(4), 443-454), or the Theraflex device from Macopharma.

Thus, the invention in one embodiment the invention considers to use platelets which have been separated from the extracorporeal quantity of said mammalian subject's blood obtained by apheresis such as leukapheresis before said extracorporeal quantity of said mammalian subject's blood comprising monocytes is applied to said device.

In another embodiment the invention considers to use plasma components, which have been separated from the extracorporeal quantity of said mammalian subject's blood obtained by apheresis such as leukapheresis before said extracorporeal quantity of said mammalian subject's blood comprising monocytes and/or platelets is applied to said device.

Instead of using plasma components which have been obtained from the extracorporeal amount of blood, one may use also either plasma components which have been isolated from other sources such as e.g. by recombinant protein expression. Such plasma components include fibrinogen, fibronectin, or P-selectin. One can also use fragments of plasma proteins such as the gamma component of fibrinogen, which corresponds to amino acids 400-411 (SEQ ID NO.: 105, His-His-Leu-Gly-Gly-Ala-Lys-Gln-Ala-Gly-Asp-Val). This gamma component is shown by the data presented herein to be able to activate platelets. It can therefore be preferred to use plasma fractions, which at least, if not predominantly comprise fibronectin. Similarly, it can be preferred to use e.g. recombinantly expressed and/or purified fibronectin or the gamma component thereof to activate platelets.

For both embodiments of the first aspect of the invention where the extracorporeal amount of blood is obtained or not obtained by apheresis such as leukapheresis, it may be considered to pass all three fractions, namely plasma components, platelets and the monocytes-containing fraction at once, e.g. even in the form of a whole blood sample or by using only pre-purified fractions of whole blood, through the flow chamber even though the afore-described sequential passing of these fractions through the flow chamber may provide for better control over the process. Pre-purified fractions of whole blood may be obtained by e.g. centrifuging a blood bag and squeezing out the supernatant, which would be enriched in white blood cells and platelets.

As mentioned the flow rate through flow chamber and thus the resulting shear stress can be adjusted to effect global activation of monocytes. The design and the dimensions of the flow chamber may also be used to manipulate and even improve the application of a physical force to the monocytes.

A device having a flow chamber with channels or channel-like structures may be suitable. Such a flow chamber having the general architecture, albeit at smaller dimensions, of a device, which is used for the classical ECP procedure is depicted in FIG. 17.

However, other geometries such as those depicted in FIG. 18 *a*) to *d*) or FIG. 26 may also be used. Thus, the findings described herein allow to consider flow chambers of significantly simplified geometry, which also allows having better control over the process in terms of turbulences and shear stress occurring during the process.

A device having a multiplicity of flow chambers may be suitable. Such a flow chamber having the general architecture, albeit at smaller dimensions, of a device, which is used for the classical ECP procedure is depicted in FIG. 17.

The flow chamber such as channels may in principle have any cross-sectional shape suitable for the above-described purposes. They thus may have a rectangular, round, elliptical, or other cross-sectional form. Even though the dimensions of such flow chamber will be discussed in the following mainly with respect to a rectangular cross-section, it can be preferred that flow chamber such as channels with an elliptical or round cross-section are used as such cross-sections should allow for e.g. more homogenous coating with plasma components and/or more continuous flow properties with less turbulences.

Flow chambers may in general have a height of about 20 μm to up to about 2000 μm of height, a width of about 5 mm to about 200 mm and length of about 10 mm to about 400 mm of length allows for efficient activation by ensuring that monocytes have a sufficient surface for attaching to and thereby getting activated.

An even more preferred embodiment relates to a flow chamber having a width to height ratio of about 40:1 to about 400:1 such as about 50:1 to about 300:1 or about 50:1 to about 250:1. Such dimensions allow for efficient activation of monocytes.

If having a rectangular cross-section, flow chamber such as channels may have dimensions of about 5 μm to up to about 500 μm of height and of about 5 μm to up to about 500 μm of width. The channels or channel-like structures may also have dimensions of about 10 μm to up to and including about 400 μm of height and of about 5 mm to up to and including about 2000 mm of width, of about 10 μm to up to and including about 300 μm of height and of about 10 μm to up to and including about 300 μm of width, of about 10 μm to up to and including about 250 μm of height and of about 10 μm to up to and including about 250 μm of width, of about 10 μm to up to and including about 100 μm of height and of about 10 μm to up to and including about 100 μm of width, or of about 10 μm to up to and including about 50 μm of height and of about 10 μm to up to and including about 50 μm of width. Such flow chambers may have a width to height ratio of about 40:1 to about 400:1 such as about 50:1 to about 300:1 or about 50:1 to about 250:1.

If flow chambers such as channels of elliptical cross-section are used, the afore-mentioned dimensions of height and width would have to be adapted correspondingly to allow for a comparable volume.

If flow chambers such as channels of round cross-sections are used, the diameter may typically be in the range of about 5 μm to up to and including about 500 μm, of about 10 μm to up to and including about 400 μm, of about 10 μm to up to and including about 300 μm, of about 10 μm to up to and including about 250 μm, of about 10 μm to up to and including about 100 μm, or of about 10 μm to up to and including about 50 μm.

Smaller dimensions are generally preferred for the flow chambers with a particular preference for height, widths or diameters of below 100 μm such as 50 μm the reason being that it is assumed that for such smaller dimensions interaction of monocytes with platelets is more efficient and uniform and flow properties at the surfaces and in the center of the flow chamber are more comparable.

The length of the flow chamber such as channels channel-like structures is usually selected such that the flow chamber allows for passage of the volume of extracorporeal blood. For example the flow chamber and the device may be configured to allow for passing of an overall volume of between about 1 ml to about 50 ml, between about 1 ml to about 40 ml, or between about 1 ml to about 30 ml.

A flow chamber as depicted in FIG. 26 is particularly preferred. Such flow chambers may have a height of about 20 μm to up to about 2000 μm of height, a width of about 5 mm to about 100 mm and length of about 40 mm to about 100 mm of length allows for efficient activation by ensuring that monocytes have a sufficient surface for attaching to and thereby getting activated. An even more preferred embodiment relates to a flow chamber having a width to height ratio of about 40:1 to about 400:1 such as about 50:1 to about 300:1 or about 50:1 to about 250:1.

The afore-mentioned width to height ratio may be a particularly preferred parameter when performing the methods described herein for activating monocytes. They may be combined with flow rates and shear stress as mentioned above.

The flow chamber may have internal sub-structures to increase the surface area or to make the flow conditions less heterogeneous.

The flow chamber may be filled with particles to increase the surface area or to make the flow conditions less heterogeneous.

The material of the flow chamber may be plastic or non-plastic.

If non-plastic materials are considered, one may use glass.

The surface of the chamber may be coated covalently or via adsorption.

Materials for auxiliary tubing, chambers, valves etc. may be selected to for having reduced interactions with blood components.

Surfaces of auxiliary tubing, chambers, valves etc. may be treated/coated for having reduced interactions with blood components.

If plastic materials are considered, one may use acrylics, polycarbonate, polyetherimide, polysulfone, polyphenylsulfone, styrenes, polyurethane, polyethylene, teflon or any other appropriate medical grade plastic. In a preferred embodiment of the present invention, the flow chamber is made from an acrylic plastic.

The flow chamber may be made of a material that provides a degree of transparency such that the sample within the flow chamber such as the monocytes-containing fractions can be irradiated with visible or UV light, preferably with UV-A. As is shown by the experiments, exposure to UV-A and 8-MOP leads to increased expression of GILZ and thus to global activation of monocytes and differentiation into immuno-suppressive autologous dendritic cells. Thus exposure to light such as UV-A and DNA-cross linking agents such as 8-MOP should be generally avoided when producing globally activated monocytes.

A typical flow chamber may have the geometry depicted in FIG. 19A). The flow path has dimensions of 20 mm by 80 mm. The chamber is made of polystyrene, PET (polyethylenteherephtalate), PMMA (poly (methyl mathacrylate)) and silicon. A blood sample may be spun at low speed through a Ficoll gradient to obtain e.g. 8 ml of sample with a concentration of white blood cells of e.g. $10^{10}$ cells/ml. The chamber may be pre-coated with platelets-rich plasma. The sample may be passed through the chamber at about 0.028 Pa for some minutes. The chamber may then be washed with about 3 ml RPMI at 0.028 Pa. A second wash with 30-55 ml RPMI may be performed at about 1.2 Pa. The collected activated monocytes will then be combined and used for further analysis.

Once globally activated monocytes have been obtained by methods in accordance with the invention, they can be generally further processed for specific purposes. They may be differentiated into immuno-stimulatory dendritic cells or immuno-suppressive dendritic cells. Immuno-stimulatory dendritic cells can for example be incubated under standard conditions to allow completion of their maturation. Culturing of these immuno-stimulatory dendritic cells can be performed under standard conditions, e.g. at 37° C. and 5% $CO_2$ in standard mediums for culturing of human cells such as in RPMI-1640 medium (obtainable e.g. from GIBCO), supplemented with 15% AB serum (obtainable from e.g. Gemini Bio-Products).

However, globally activated monocytes may, as mentioned above, also be used for e.g. therapeutic treatments such as treatment of cancers or for wound healing. As it is assumed that the globally active monocytes will have some phagocytozing activity, they may be used e.g. for treatment of cancer patients receiving therapy with therapeutically active antibodies.

Globally activated monocytes are obtainable by conducting the method in accordance with the first aspect and its embodiments as they are described above (e.g. by using flow chambers, platelet and/or plasma components, etc.) in the absence of any apoptotic agent, in particular in the absence of 8-MOP/UVA. Thus, the method in accordance with the first aspect is used for activating monocytes which are outside the human or animal body in the absence of any apoptotic agent, in particular in the absence of 8-MOP/UVA as long as the monocytes are outside the human or animal body. Globally activated monocytes which have been obtained by this embodiment of the first aspect are in particular suitable for treating cancer in patients undergoing chemotherapy, radiation therapy such as gamma-irradiation therapy or combinations thereof. Chemotherapy may include treatment with therapeutically active antibodies, but may also be include treatment with cytotoxic agents such as taxanes including docetaxel and paclitaxel, anthracyclines, cyclophosphamide, vinca alkaloids, cisplatin, carboplatin, 5-fluoro-uracil, gemcitabine, capecitabin, navelbine or zoledronate in the absence of therapeutically active antibodies. Radiation therapy may include photon therapy such as X-ray therapy and gamma-irradiation therapy; and particle therapy such as electron-, proton-, neutron-, carbon ion-, alpha particle-, and beta particle-therapy.

In such patients there will be tumor-associated antigens which may have been released by e.g. chemotherapy, radiation therapy such as gamma-irradiation therapy or combinations thereof. If globally activated monocytes as their obtainable by the methods in accordance with the first aspect and in particular in the absence of apoptotic agents as long as the monocytes are outside the human or animal body are reintroduced into such patients there assumed to take up such tumor-associated antigens and thereby mature into antigen-displaying antigen-presenting cells such as dendritic cells which can then launch an anti-tumor response. However, as the monocytes have been activated outside the human or animal body in the absence of apoptotic agents and in particular in the absence of 8-MOP/UVA it is assumed that truncating and/or tolerogenizing effects of 8-MOP/UVA are reduced. As a consequence immuno-stimulatory antigen-presenting cells should favorably be formed over tolerogenic dendritic cells reducing the likelihood for the tumor to escape immune surveillance.

Such globally activated monocytes may be used for treatment of cancers in patients undergoing chemotherapy and/or radiation therapy and suffering either from lymphatic cancers or solid tumors such as solid tumors selected from the group comprising lung cancer, breast cancer, colon cancer, prostate cancer, head and neck cancer, brain cancer, ovarian, muscle, connective tissue, kidney cancer or skin cancers such as melanoma.

Such globally activated monocytes may of course also be used in patients suffering from cancer and undergoing chemotherapy, radiation therapy or combinations thereof including treatment with therapeutically active antibodies. In fact, it is assumed that such globally activated monocytes will allow treatment of other disease is than cancer in patients undergoing the treatment regimen leading to the release of disease-associated antigens in the human body.

The invention is now described with respect to some specific examples, which, however, are for illustrative purposes and not to be construed in a limiting manner.

EXPERIMENTS

Experiment 1—Shear Stress and Platelet Activation for Inducing Monocyte Activation Materials and Methods Procurement of Leukocytes and Platelets All samples were acquired from young, healthy subjects not taking medications, including aspirin, known to influence platelet function. Samples were obtained under the guidelines of the Yale Human Investigational Review Board, and informed consent was provided according to the Declaration of Helsinki. Peripheral blood specimens were collected through a 19-gauge needle from the antecubital vein into syringes containing heparin, then layered on Ficoll-Hypaque (Gallard-Schlessinger, Carle Place, N.Y.). Following centrifugation at 180 g, the interface containing the mononuclear leukocyte fraction was collected and washed twice in HBSS, then resuspended in RPMI-1640 medium (GIBCO) to a final concentration of $5\times10^6$ mononuclear cells/ml. Cells were utilized within one hour of being acquired.

Preparation of Platelet-Rich-Plasma

Whole blood was centrifuged at 150 g for 15 min at room temperature. The platelet-rich-plasma (PRP) layer was collected and centrifuged at 900 g for 5 min, and the platelet pellet resuspended in RPMI 1640 to the desired concentration.

Preparation of Parallel-Plates

Two likes of parallel-plate flow chambers were used to model the flow dynamics of ECP. Experiments involving the assessment of cell phenotype post-flow were conducted using the larger Glycotech system (Glycotech, Rockville, Md.). This system consisted of a volumetric flow path measuring 20000×10000×254 microns (length×width×height). The bottom plate in this system was composed of a 15 mm petri dish (BD Biosciences, Durham, N.C.) separated by a gasket and vacuum-connected to an acrylic flow deck, which formed the upper plate. For experiments requiring the plates to be pre-coated with platelets, prior to assembling the flow chamber, 20 drops of the desired concentration of PRP was placed in the center of the petri dish and platelets allowed to settle for 20 minutes at room temperature. The petri dish was washed twice with 2 ml of RPMI, and the flow chamber then assembled.

For experiments not involving the collection and phenotyping of cells post-flow, Vena8 biochips (Cellix Ltd, Dublin, Ireland) were used to generate laminar flow. The volumetric flow path for a channel of the Vena8 biochips measured 20000×400×100 microns (length×width×height). Protein coating of these chips is described in the appropriate section below.

Experiments Using Parallel-Plates

The parallel-plate flow chamber was mounted on the stage of a phase contrast optical microscope (CK40, Olympus, Japan) with a 10× objective. All runs were performed at room temperature. A uniform laminar flow field was simulated by use of a syringe pump (KD Scientific, New Hope, Pa.) capable of generating near-constant volumetric flow rates. The components of the configuration were devised to minimize tubing. Prior to infusing cell suspensions through the plates, the system was washed with 5 ml of RPMI at a flow rate producing a wall shear stress of approximately 1 dyne/$cm^2$. Cell suspensions of interest were then passed through the chamber at a fixed flow rate and wall shear stress.

All experiments were viewed in real time, recorded at 15.2 frames per second using a DP 200 digital camera and software (DeltaPix, Maalov, Denmark), and analyzed using Image J software (NIH).

Overnight Culture

When overnight culture was required, cells were centrifuged and resuspended in RPMI-1640 medium (GIBCO), supplemented with 15% AB serum (Gemini Bio-Products) to a final concentration of 5×106 cells/ml. Cells were cultured overnight for 18 hours in 12-well polystyrene tissue culture plates (2 ml per well) at 37° C. in 5% CO2.

Immunophenotyping

Monoclonal antibodies for immunophenotyping included CD14 (LPS receptor; monocytes), CD11c (integrin subunit; monocytes and DC), HLA-DR (class II MHC molecule), CD83 (DC marker), CD62p (P-selectin; activated platelets), and CD61 (integrin subunit; platelets). Antibodies were obtained from Beckman Coulter (CD14, CD11c, HLADR, CD83) or Sigma (CD62p, CD61) and used at their pre-determined optimal dilutions. Background staining was established with appropriate isotype controls, and immunofluorescence was analyzed using a FC500 flow cytometer (Beckman Coulter). Two-color membrane staining was performed by adding the pre-determined optimal concentrations of both antibodies directly conjugated to FITC or PE and incubating for 20 min at 4° C., followed by washing to remove unbound antibodies. Combined membrane and cytoplasmic staining was performed following manufacturer's instructions for cell fixation and permeabilization (Intraprep kit, Beckman Coulter).

Quantitative Real-Time PCR

Gene expression was compared between cells exposed during flow through the parallel plates to low (10±5/low power field [lpf]) versus high (102±32/lpf) levels of platelets, followed by overnight culture. Cell RNA was isolated using RNeasy Mini Kit columns with on-column DNase I treatment (QIAGEN). RNA yield and purity were measured using a NanoDrop ND-1000 Spectrophotometer and an Agilent 2100 Bioanalyzer. RNA was reverse transcribed to cDNA using the High Capacity cDNA Reverse Transcription Kit (Applied Biosystems). Reverse transcription was carried out in a 96-well thermocycler (MJ Research PTC-200) in the following conditions: 25° C., 10 minutes, 37° C., 120 minutes, 85° C., 5 seconds. TaqMan real-time PCR was used to detect transcripts of DC-LAMP, CD40, ADAM Decysin, Lox1, CCR7, CD80, CD83, CD86, FPRL2, and GPNMB. Primers and probes for each sequence were obtained as inventoried Taqman Gene Expression Assays (Applied Biosystems). HPRT1 was used as a reference gene.

Co-Cultures of Platelets with Monocytes

Experiments involving co-cultures of monocytes with additional platelets were performed as described in the Overnight Culture section, with a few necessary modifications. Following Ficoll-Hypaque separation, mononuclear cells were resuspended in 30% AB serum/RMPI to a final concentration of 10×106 cells/ml, of which 1 ml was allocated to each well of a 16-well plate. An additional 1 ml of platelets (suspended in RPMI, at 2× the desired final concentration) or RPMI without platelets was then added to each well. To activate platelets, 500 μl containing 2 units of thrombin was added to half the wells, and 500 μl of RPMI was added to the others to balance the volume. Cells were then incubated as described previously.

Platelet Adhesion Studies

Platelet adhesion experiments were performed using the Vena8 flow chamber described above. Fibrinogen and fibronectin (Sigma) were dissolved in PBS to a final concentration of 200 mcg/ml. Channels of the Vena8 chips were incubated at room temperature in a humidified chamber for 2 hours with the protein solution, autologous plasma, or PBS alone. The channels were washed with 5× the volume RPMI. Platelet-rich-plasma was then perfused through the protein-coated channel at the indicated shear-stress, held constant. For each channel, still images were acquired exactly 90 seconds into the experiment at 4 pre-defined low power fields located along the flow path (fields were centered at 2500, 7500, 12500, and 17500 microns from the start point of infusion).

Some experiments involved pre-treating platelet-rich-plasma with protein fragments prior to infusion through the channels. Small RGD peptides, containing the amino-acid sequence Arg-Gly-Asp-Ser; DRG peptides, contain the amino-acid sequence Ser-Asp-Gly-Arg; or fragment 400-411 of fibrinogen, containing the amino-acid sequence His-His-Leu-Gly-Gly-Ala-Lys-Gln-Ala-Gly-Asp-Val, were incubated at a concentration of 2 mM with PRP for 20 minutes at room temperature. The PRP was then perfused through the channels as previously described.

Receptor-Ligand Studies

Platelet-coated Vena8 channels were pre-treated with either 40 μg/ml anti-P-selectin (R&D Systems) or 40 μg/ml of an isotype control for 30 minutes at room temperature, then washed with 5× the volume RPMI. Mononuclear cell suspensions were pre-treated with either RGD or DGR peptides at a concentration of 2.5 mM. Video samples lasting 400 frames (26.3 seconds) were recorded 60 seconds after commencement of flow using a lower power field of view spanning 400 microns and centered at 7500 microns from the flow start point.

β-1 integrin conformation was assessed using the Glycotech flow chamber. 15 mm platelet-coated petri dishes (described above) were pre-treated with 40 μg/ml anti-P-selectin or an isotype control for 20 minutes at room temperature, then washed with 5× the volume RPMI. Immediately following perfusion through the platelets, cells were immunophenotyped with anti-CD29 HUTS-21 (BD Biosciences), an antibody that specifically binds to the active (open) conformation of 01 integrins.

Results

Monocytes in Flow Transiently Interact with Immobilized Platelets

ECP was initially developed as a means to enable extracorporeal chemotherapeutic exposure of pathogenic leukocytes to ultraviolet A (UVA)-activated 8-methoxypsoralen (8-MOP), a DNA-cross-linking drug. Therefore, ECP involves the flow of leukapheresed blood between large transparent plastic parallel-plates separated by 1 mm. To permit detailed analysis of the flow dynamics involved during ECP, independent of UVA/8-MOP exposure, the flow conditions of ECP were reproduced using miniature parallel plates with surface area of only 0.8 $mm^2$, separated by 100 microns. This model permitted visualization using digital microscopy. Studies using the model revealed the following sequence (determined by video analysis): initial adherence of platelets from the flow stream to the plate, followed by transient binding of passaged monocytes to the immobilized platelets.

DC Induction Correlates with the Number of Monocyte Platelet Interactions

Based on the initial qualitative observations described above, platelets were hypothesized to induce monocyte-to-DC differentiation under conditions of flow. To test the influence of platelets on monocyte-to-DC differentiation, monocytes were passed between parallel plates pre-coated with autologous platelets at low (10±5/low power field [lpf]), medium (44±20/lpf), and high (102±32/lpf) densities. Cells were passed through the plates at a flow rate producing a wall shear stress of 0.5 dyne/$cm^2$, analogous to the wall shear stress in post-capillary venules. The number of monocyte-platelet interactions per unit time increased in proportion to augmented density of platelets (determined by video analysis). An average of 52.3+15 monocyte-platelet interactions per lpf per second were observed with the high-density plate, dropping to 18.3±14 and 3.4±1 interactions per second with the medium and low-density plates, respectively (FIG. 1*a*).

Following overnight incubation, a correlation was found between the percentage of cells which developed a DC phenotype and the frequency of monocyte-platelet physical interactions observed the previous day (FIG. 1*b*). An increasing number of monocyte-platelet interactions correlated with increasing proportion of cells expressing markers consistent with DC differentiation, membrane HLA-DR and CD83. An average of 14.2% of monocytes exposed to the high-density platelet-coated plate were HLA-DR+/CD83+ after overnight incubation, compared to 4.9% and 0.8% of monocytes exposed to plates coated with medium and low levels of platelets, respectively.

Monocyte Exposure to Platelets Results in Changes in Gene Expression

To supplement the described changes in monocyte phenotype observed following platelet exposure, RT-PCR was performed to assess for changes in gene expression. Monocytes were passed through parallel plates coated with high or low densities of platelets as described in the previous section. Following overnight incubation, RNA was extracted and RT-PCR performed to determine level of expression for 10 genes associated with DC (FIG. 2). CD40, a costimulatory molecule with known expression on mature DC (Cella et al., 1996, see reference list), was found to be upregulated by over 567% in monocytes exposed to high densities of platelets relative to monocytes exposed to low levels. LAMP3, a marker specific to DC differentiation (de Saint-Vis at al., 1998, see reference list), was upregulated by 398%. CD80 is a costimulatory molecule known to be upregulated upon APC activation (Slavik et al., 1999, see reference list), upregulated by 220% in monocytes exposed to high levels of platelets. CCR7, a chemokine receptor known to play a role in DC migration to lymphoid organs, was upregulated by 376%. LOX1, CD83, CCR7, and ADAM Decysin, all genes associated with DC (Berger et al., 2010, see reference list), were also upregulated in the monocytes exposed to high levels of platelets. FPRL2, GPNMB, and CD86 were all downregulated in monocytes exposed to high levels of platelets. FPRL2 is a receptor that when activated is known to inhibit DC maturation (Kang et al., 2005, see reference list) GPNMB is a protein involved in decreasing cytokine production (Ripoll et al., 2007, see reference list); CD86 is a costimulatory molecule expressed by APCs.

DC Induction in the Presence of Platelets does not Occur Under Static Conditions Platelets could potentially influence monocytes through direct receptor-ligand interaction, or via cytokines and other secreted mediators. To determine whether the platelet induction of monocyte-to-DC differentiation requires flow dynamics, we tested the role of platelets under static conditions. Monocytes were co-cultured with low (<50,000/$mm^3$), medium (100-200,000/$mm^3$) and high (>400,000/$mm^3$) concentrations of platelets, with platelets in either an inactive or active state (induced by the addition of thrombin). After overnight incubation in static conditions (shear stress=0), we found that neither activated nor non-activated platelets were capable of inducting DC differentiation of monocytes in the absence of flow (see FIG. 3).

Platelets Suspended in Flow Bind to Serum Proteins Adsorbed onto the Plate

Several proteins abundantly present in plasma, including fibronectin and fibrinogen, are well known adsorb onto glass and plastic surfaces; the contribution of adherent plasma proteins on platelet adhesion and activation was therefore assessed. Parallel plates were pre-coated either with fibrinogen, fibronectin, plasma, or saline. Unactivated platelets were then passed through at shear rates producing wall shear stresses ranging from 0.2 to 6.0 dyne/$cm^2$. The highest concentrations of platelets adhered to plates coated with fibrinogen (FIG. 4). Adhesion to fibronectin-coated, plasma-coated, and uncoated plates was observed as well, but to a significantly lower extent ($p<0.05$). In the absence of flow, platelet adherence was equivalent on all protein substrates.

Both fibrinogen and fibronectin contain segments with the amino acid sequence arginine (R)-glycine (G)-aspartate (D), RGD. RGD segments are well-known to interact with many integrin receptors, particularly the FA domain of beta subunits, which are exposed when the integrins are in the active conformation (Xiong et al., 2002, see references). In experiments using fibrinogen-coated plates, platelet adhesion was not significantly altered by pre-incubation of platelets with RGD peptides; however, adhesion was significantly decreased ($p<0.05$) by pre-incubation of platelets with peptide fragments corresponding to amino acids 400-411 of fibrinogen, the gamma component of the protein (FIG. 5 *a*). In experiments using fibronectin-coated plates, pre-incubating platelets with RGD peptides decreased adhesion significantly, while pre-incubating platelets with peptide fragments corresponding to amino acids 400-411 of fibrinogen had no effect, (FIG. 5*b*). Interestingly, it should be noted that unlike the I/A domain of integrins, which is known to interact with RGD domains of proteins, the region of the integrin found to interact with the gamma component of fibrinogen is exposed in the integrin's inactive state (Weisel et al., 1992, see references). Therefore, this data suggests that unactivated platelets in flow bind to the gamma-component of fibrinogen-coated plates. The potential for platelets in the unactivated state to bind fibrinogen may explain the greater level of platelet adhesion seen on fibrinogen-coated plates explained in the previous paragraph.

Platelets are Activated by Adhesion to the Plate

Platelets physiologically circulate in an inactive state, with an array of proteins stored in intracellular granules. Upon encountering stimuli such as damaged endothelium or thrombin, platelets become activated and almost instantaneously translocate these intracellular proteins to the plasma membrane (Kaplan et al., 1979, see references). It was postulated that platelet adhesion to the plastic plate/absorbed proteins caused platelet activation similar to that caused by well-known stimuli. To test this hypothesis, surface expression of P-selectin, a well-known marker of platelet activation, was assessed before and after adhesion. Prior to adhesion, 6±3% of platelets were found to express P-selectin, with a mean fluorescence intensity (MFI) of 12.4±6.9; following adhesion, P-selectin positivity increased to 64±13% (MFI 98.2±14). The positive control, platelets activated with thrombin, was 71±18% P-selectin positive (MFI 108.3±23). Expression of P-selectin was further assessed at 30, 60, and 90 minutes following platelet adhesion; P-selectin expression remained stable at all time points, with 72±11% of platelets P-selectin positive 90 minutes after adhesion, indicating that platelets remain in an active state for the duration of the procedure. Similar trends were found in assessment of $\alpha$IIb-$\beta$3, a fibrinogen-binding integrin, with surface expression of this protein increasing from 4±3% prior to adhesion, to 49±18% post-adhesion.

Monocytes Interact with P-Selectin and RGD-Containing Ligands Expressed on Activated Platelets The monocyte-platelet interactions observed on video were divided into two categories: (1) short-acting, arbitrarily defined as contact occurring for less than 3 seconds (46 frames), and (2) long-acting, defined as contact longer than 3 seconds, including stable binding. Since it had been previously determined that the platelets in the ECP system were in an activated state, and that activated platelets express an array of proteins including P-selectin and RGD containing proteins (e.g. fibronectin, fibrinogen, and vitronectin), it was sought to determine the involvement, if any, of these proteins in either short or long-duration interactions. Plates were pre-coated with platelets, and four conditions tested: (1) platelets pre-treated with an irrelevant isotype control, and monocytes untreated (P+RGD+); (2) platelets pre-treated with an irrelevant isotype control, and monocytes pre-incubated with RGD peptides (P+RGD−); (3) platelets pre-treated with anti-P-selectin, and monocytes untreated (P−RGD+); (4) platelets pre-treated with anti-P-selectin, and monocytes pre-treated with RGD peptides (P−RGD−). It was assumed that pre-treating monocytes with RGD peptides should result in a decreased in the number of free RGD-recognizing receptors available to interact with RGD-containing proteins expressed by the platelets. Thus, the four conditions tested represent every permutation of potential interaction with two platelet ligands, P-selectin and RGD-containing-proteins. As shown by FIG. 6, both short-acting and long-acting interactions were maximal when neither RGD nor P-selectin were blocked (P+RGD+); the level of interaction in all other conditions was expressed as a percentage of this maximum. Blocking with anti-P-selectin alone (P−RGD+) resulted in a decrease of both short and long monocyte-platelet interactions to almost zero ($p<0.01$; FIG. 6, also confirmed by video analysis). In contrast, blocking RGD alone (P+RGD−) did not significantly alter the number of short-duration interactions, but decreased the long-duration monocyte-platelet interactions by 44% ($p<0.05$; FIG. 6). Blocking both P-selectin and RGD simultaneously (P−RGD−) resulted in a pattern similar to that seen when only P-selectin was blocked, with both long and short duration interactions reduced to near zero. The most appropriate conclusions, based on the pattern of interactions observed in each of the four conditions, are as follows: (1) P-selectin is predominantly responsible for the short-duration interactions; (2) RGD-containing proteins expressed by the platelet are involved in long-duration interactions, but not short-duration interactions; (3) monocyte interaction with P-selectin must occur upstream of monocyte interaction with RGD-containing proteins expressed by platelets. This last conclusion is based on the observation that conditions of P−RGD+ decreased both short and long duration interactions to near zero, while P+RGD-conditions only decreased long-duration interactions. If the interactions were not sequential, conditions of P−RGD+ should have produced similar results to P+RGD+ in terms of long-duration interactions. Furthermore, the ordering of the interactions, i.e. that P-selectin acts upstream of RGD-interactions, is apparent by the finding that conditions of P+RGD− only influenced long duration interactions, while conditions of P−RGD+ produced similar results to those of P−RGD−.

Monocyte Exposure to P-Selectin Results in Downstream Monocyte Integrin-Activation Integrin receptors, in their open conformation, are known to interact with RGD-containing ligands (Ruoslathi et al., 1996, see references). Using an antibody that recognizes an epitope exposed only when the β1 integrin is in its open conformation, we assessed the conformation of monocyte integrins before and after flow through the model. FIG. 7 shows that as the number of short-acting monocyte-platelet interactions increased, there was corresponding increase in the percentage of monocytes expressing integrins in their open conformation immediately post-flow. The black line shows that an average of 71% of monocytes which had received a high number of platelet-interactions (>61±19/lpf×sec) expressed (31 in the active form, compared to 9% of monocytes which had received a low number of platelet interactions (<5.1±2/lpf×sec). These results were not significantly affected by pre-treating the adherent platelets with an irrelevant isotype control (gray line). In contrast, pretreating platelets with anti-P-selectin reduced the monocyte-platelet interactions to near zero, and monocytes emerging from flow in these conditions (dashed line) displayed low levels of active β1 integrins, irrespective of the density of platelets to which they were exposed. It is noteworthy that all cell populations prior to passage through the plates demonstrated similar low levels of baseline integrin activation (<10%); therefore, differences seen in short-duration monocyte-platelet interactions were not the result of differences in integrin conformation pre-flow.

Monocyte Exposure to P-Selectin is Required for DC Differentiation

Given the dependence of monocyte-platelet interactions on platelet P-selectin, we set out to determine if there was a relationship between monocyte exposure to P-selectin at time 0, and the phenotype later developed by the monocyte after overnight incubation, time 18-hours (FIG. 8). Monocytes were passed though parallel plates coated with high densities (108±36/lpf) of platelets that were either untreated (unblocked), or pretreated with either anti-P-selectin or an isotype control. 15.5±4% of monocytes exposed to unblocked platelets became membrane HLA-DR+/CD83+ (markers of maturing DC) after overnight incubation, and 13±4% of those exposed to platelets blocked with the irrelevant isotype control. In contrast, only 3±2% of the monocytes exposed to platelets blocked with anti-P-selectin became HLA-DR+/CD83+ after overnight incubation.

Experiment 2—Identification of Molecular Markers for Immuno-Suppressive Dendritic Cells Materials and Methods Sample Collection and Monocyte Enrichment Peripheral blood specimens were acquired from healthy subjects under the guidelines of the Yale Human Investigational Review Board, and informed consent was provided according to the Declaration of Helsinki. PBMC were isolated by centrifugation over a Ficoll-Hypaque gradient (Isolymph, CTL Scientific). Monocytes were enriched from freshly isolated PBMC by: 1) plastic adherence for dexamethasone dose-titration experiments (purity: 71.6±5.6% $CD14^+$); 2) CD14 magnetic bead positive selection (Miltenyi Biotec) for PUVA dose-titration experiments (purity: 88.1±3.5% $CD14^+$), and; 3) Monocyte Isolation Kit II (Miltenyi Biotec) for LPS stimulation experiments (purity: 83.8±3.8% $CD14^+$).

Generation of Monocyte-Derived DC (MoDC)

Monocytes were cultured at a density of $5\times10^6$ cells/mL in 6- and 12-well polystyrene tissue culture plates at 37° C. and 5% $CO_2$ in RPMI-1640 (Gibco) supplemented with heat-inactivated 15% AB serum (Gemini) and 1% penicillin/streptomycin (now referred to as complete media). 800 IU/mL recombinant human GM-CSF (R&D Systems) and 1000 IU/mL recombinant human IL-4 (R&D Systems) were added to cultures for 36 hr to induce monocyte to DC differentiation as described.

8-MOP and UFA Light Treatment

Cultures were incubated with 8-MOP (Uvadex, 20 μg/mL) for 30 min in the dark, and then irradiated with a desktop UVA light box containing a series of 12 linear fluorescent tubes. The tubes emitted UVA light ranging from 320 to 400 nm. The UVA irradiance (power, $W/m^2$) was measured using a photodiode. Given a measured irradiance and the absorption properties of the various components of the system, it was possible to determine the time (sec) needed to expose the cells to deliver a given dose of UVA radiation ($J/cm^2$).

MoDC/Lymphocyte Co-Cultures

Non-adherent cells (purity: 66.0±4.5% $CD3^+$) removed during plastic adherence will now be generally referred to as lymphocytes. Lymphocytes were treated with 8-MOP (100 ng/mL) and UVA (1 $J/cm^2$), washed with PBS, and co-cultured in complete media at 37° C. and 5% $CO_2$ with either PUVA-treated or untreated-MoDC in a ratio of 5 or 10 lymphocytes to 1 MoDC. MoDC treated for 24 hr with 100 nM dexamethasone (Sigma) served as the positive control group. After 24 hr, cells were harvested and MoDC were re-purified. To ensure that RNA was not isolated in significant amounts from lymphocytes, it was critical to re-purify MoDC from all cultures using CD11c magnetic bead (Miltenyi Biotec) positive selection (purity: 96.4±1.0% $CD11c^+$). $CD11c^+$ MoDC were re-plated at $0.5\text{-}1.0\times10^6$ cells/mL in complete media and stimulated with 100 ng/mL LPS (Sigma). 24 hr after LPS stimulation, cells were harvested for RNA isolation and immunophenotyping, and supernatants were collected for cytokine quantification. As negative controls, parallel groups did not receive LPS.

siRNA Experiments

Silencer select pre-designed and validated GILZ siRNA (Invitrogen), with off-target prediction algorithms, was used to knockdown GILZ expression. Mo-DC were transfected using Lipofectamine RNAiMAX Reagent (Invitrogen). $RNA_1$ duplex and lipofectamine reagent were incubated together for 20 min, then added to MoDC cultures and incubated for 2 hr at 37° C. and 5% $CO_2$. Transfected MoDC were treated in an identical fashion as described for the MoDC/lymphocyte co-cultures. MoDC were also transfected with scramble siRNA.

Immunophenotyping

Monoclonal antibodies included HLA-DR, CD80, CD83, CD3, CD86, CD14, CD11c and GILZ. Antibodies were obtained from Beckman-Coulter and eBioscience and were used at their pre-determined optimal dilutions. Apoptosis was assessed using the Annexin-V Apoptosis Detection Kit (eBioscience), with Annexin-V recognizing phosphatidylserine (PS) on the surface of apoptotic cells. 7-AAD substituted for PI as the cell viability dye. Cells displaying an Annexin-$V^+$/7-$AAD^-$ phenotype were classified as early apoptotic cells, and cells displaying an Annexin-$V^+$/7-$AAD^+$ phenotype were classified as late apoptotic cells. Dual membrane and intracytoplasmic staining was performed using the IntraPrep fix and permeabilization kit (Beckman-Coulter). Background staining was established with appropriate isotype and fluorescence minus one controls. Immunofluorescence was analyzed using a FACSCalibur L (BD Biosciences) within 2 hr of fixation with 2% paraformaldehyde. A minimum of 10,000 events were collected for each group.

Quantitative Real-Time PCR

RNA was isolated from $CD11c^+$ MoDC using QIAShredder columns (QIAGEN) and the RNeasy Mini Kit (QIAGEN) with on-column Dnase I treatment (QIAGEN). RNA yield and purity were assessed using a NanoDrop ND-1000 spectrophotometer. cDNA was obtained using the High Capacity cDNA Reverse Transcription Kit (Applied Biosystems) in a 96-well thermocycler (MJ Research PTC-200). TaqMan real-time PCR was used to detect transcripts of GILZ, CD80, and CD86. Primers and probes were obtained as pre-designed and validated Taqman Gene Expression Assays (Applied Biosystems). SYBR green real-time PCR (Applied Biosystems) was used to detect transcripts of IL-12, IL-10, IL-6, TNF-alpha, and TGF-β. Primers were designed to span intron junctions using Primer3Plus. Primer melting curves were obtained to confirm a single product. HPRT-1 and GAPDH were used as reference genes. Samples were run in triplicate on a 7500 Real Time PCR System (Applied Biosystems). The delta-delta C(t) method was used to calculate the fold change.

Cytokine Quantification

Culture supernatants were analyzed in a multiplex format utilizing magnetic beads to IL-6, IL-8, IL-10, IL-12p70, IFN-γ, TNF-α, RANTES, MCP-1, and MIP-1β (BioRad Laboratories). For siRNA experiments, supernatants were analyzed with enzyme-linked immunosorbent assay (ELISA) kits for IL-10 (R&D Systems) and IL-12p70 (Enzo Life Science). All samples and standards were run in duplicate and analyzed using the LUMINEX 200 (LUMINEX), or the BioTek EL800 (BioTek).

Statistical Analysis

Student's t-tests were used for statistical comparisons between groups, with p-values<0.05 considered statistically significant. Differential gene expression was considered statistically significant with a ≥2.5-fold change and a p-value<0.05.

Results

Expression of GILZ is Rapidly Down-Regulated as Monocytes Differentiate into Immature MoDC Freshly isolated $CD14^+$ monocytes express GILZ, but rapidly down-regulate GILZ by more than 99% as they differentiate into immature MoDC (FIG. 10A). A reduction in GILZ mRNA was confirmed by a 61% decrease in GILZ protein levels (FIG. 10B). GILZ down-regulation correlated with reduced expression of CD14 (monocyte-specific marker, see Zhou et al., references), and increased expression of cytoplasmic CD83, (immature MoDC marker, see Klein et al., references). Importantly, MoDC remained immature, expressing low membrane CD83 (mature DC marker, see Renzo et al., references, p=0.16). MoDC up-regulate GILZ after treatment with dexamethasone (dex) in a dose-dependent manner (FIG. 10C). Treatment with 100 nM dex for 24 hr was selected as the positive control for inducing GILZ expression in MoDC (Dex-DC) (FIG. 10D).

8-MOP or UVA treatment alone did not effect GILZ expression (FIG. 10E). However, when MoDC were treated with the combination of 8-MOP and UVA light (PUVA-DC), GILZ expression increased 5.5-fold. The induction of GILZ exhibited a slow time course, peaking 24 hr after treatment, and remaining significantly elevated for 72 hr (FIG. 10F). In comparison, Dex-DC up-regulated GILZ as little as 2 hr after treatment.

Immature MoDC Treated with the Combination of 8-MOP and UFA Light Up-Regulate GILZ and Assume a Tolerogenic, Immuno-Suppressive Phenotype It was next examined if there was a PUVA dose-dependent effect on GILZ expression. MoDC treated with 1 $J/cm^2$ UVA and 100 or 200 ng/mL 8-MOP up-regulated GILZ 2.9- and 4.4-fold respectively (FIG. 11A). A similar dose-dependent phenomenon was observed with 2 $J/cm^2$, starting at an 8-MOP concentration of 50 ng/mL. Treatment with 0.5 $J/cm^2$ had no effect on GILZ expression until the 8-MOP concentration reached 200 ng/mL, and treatment with 4 $J/cm^2$ resulted in high levels of non-specific cell death (data not shown). The number of photo-adducts formed per $10^6$ base pairs is directly related to the product of the 8-MOP concentration and UVA dose, see Gasparro et al., references. As the product of 8-MOP and UVA reached 100, GILZ was up-regulated 3-fold, and as the product increased to 200 and 400, GILZ was up-regulated 4.8- and 8.6-fold respectively (FIG. 11B).

The percentage of early apoptotic $CD11c^+$ cells was minimally (p>0.05) higher at 2 $J/cm^2$ as compared to 1 $J/cm^2$ for all doses of 8-MOP tested (FIG. 11C). At 2 $J/cm^2$ and 200 ng/mL, there was an increase in the percentage of early apoptotic $CD11c^+$ cells as compared to untreated MoDC (FIG. 11C). The percentage of late apoptotic $CD11c^+$ cells remained less than 13% at 1 $J/cm^2$, and less than 16% at 2 $J/cm^2$ for all doses of 8-MOP tested (FIG. 11D). Moreover, dot plots highlight the relative resistance of MoDC to the pro-apoptotic effect of escalating doses of PUVA (FIG. 11E). The number of cells recovered from cultures did not statistically differ in any group treated with 1 or 2 $J/cm^2$ (data not shown), and greater than 90% $CD11c^+$ cells (range 91.0-97.5%) were harvested after treatment.

In contrast, lymphocytes display Annexin-V as early as 2 hr after treatment with 1 $J/cm^2$ and 100 ng/mL (data not shown). In contrast to MoDC treated with 100 ng/mL and 1 $J/cm^2$ (FIG. 11F), 24 hr after treatment with the same dose of PUVA, the percentage of early apoptotic lymphocytes increased from 6.6% in untreated MoDC to 44.3% in PUVA-DC, and the percentage of late apoptotic lymphocytes increased from 4.5% to 33.7% (FIG. 11G). Given that 64.3±3.2% of lymphocytes were Annexin-$V^+$24 hr after treatment, PUVA-treated lymphocytes are subsequently referred to as apoptotic lymphocytes (ApoL).

The PUVA dose-dependent induction of GILZ correlated with a decrease in cell surface expression of CD80, CD86, and CD83 (FIG. 12A, 3B). Down-regulation of these markers paralleled the induction of GILZ (see FIG. 11B), beginning at 8-MOP concentrations of 100 ng/mL for both 1 and 2 J/$cm^2$. As the product of 8-MOP and UVA exceeded 100, CD83, CD80 and CD86 expression were reduced by 31%, 30% and 54% respectively, and HLA-DR expression increased by 38%.

MoDC Exposed to Apoptotic Lymphocytes Up-Regulate GILZ and are Resistant to LPS-Induced Full Maturation To dissect the individual contributions of PUVA and exposure to apoptotic cells, MoDC were first co-cultured with varying ratios of ApoL. GILZ was up-regulated in an ApoL dose-dependent fashion (FIG. 13A). When PUVA-DC were exposed to ApoL, GILZ was expressed at higher levels than in PUVA-DC cultured alone (FIG. 13B). PUVA-DC exposed to ApoL also expressed GILZ at higher levels than in untreated MoDC exposed to ApoL (6.7-fold and 3.6-fold higher, respectively). There was a corresponding 1.5-fold increase in the GILZ protein level in all groups in which GILZ mRNA was up-regulated (FIG. 13C). Induction of GILZ was not related to an increase in the number of early or late apoptotic CD11c+ cells, as there were <12% early apoptotic (range 3.8-11.4%) and late apoptotic (range 6.3-11.5%) $CD11c^+$ cells in all groups demonstrating up-regulation of GILZ.

MoDC expressing GILZ greater than 2.5-fold above untreated MoDC were resistant to full maturation by LPS and exhibited a semi-mature, tolerogenic phenotype. LPS stimulation increased CD80 expression in MoDC up-regulating GILZ to only 50% of the levels seen after LPS stimulation in untreated MoDC (FIG. 13D, range 0.48-0.57%), and increased CD86 expression to only 45% of untreated MoDC (FIG. 13D, range 0.42-0.47%). Similar results were obtained for HLA-DR and CD83 (FIG. 14E, range 47-65% and 23-57% of untreated MoDC after LPS respectively). In addition, MoDC up-regulating GILZ expressed 6% of the CD80 mRNA of untreated MoDC (range 4.5-7.5%), and expressed 50% of the CD86 mRNA of untreated MoDC (range 12.4-85.1%), as assessed by qRT-PCR.

MoDC Expressing GILZ Display a Tolerogenic Cytokine Profile, and Knockdown of GILZ Reduces the IL-10 to IL-12p70 Ratio Supernatants were harvested from co-cultures as described in FIG. 13B. Dex-DC up-regulated GILZ 4.29-fold (see FIG. 13B), increased production of IL-10 (FIG. 14A), and decreased production of all pro-inflammatory cytokines (FIG. 14B, 14C) and chemokines (FIG. 14D, 14E) tested. In comparison, PUVA-DC up-regulated GILZ 2.78-fold (see FIG. 13B), increased production of IL-10, and decreased production of all pro-inflammatory cytokines and chemokines tested, except TNF-α and IFN-γ. PUVA-DC or untreated MoDC, exposed to ApoL expressed GILZ at higher levels that PUVA-DC cultured alone (3.6- and 6.7-fold higher, respectively; see FIG. 13B). These two groups increased production of IL-10, and decreased production of all pro-inflammatory cytokines and chemokines tested. Cytokine levels were confirmed at the RNA level, with MoDC that up-regulated GILZ also demonstrating up-regulation of IL-10 mRNA 8-fold above untreated MoDC (range 5.5-11.8, p<0.01). Reductions in IL-12, TNF-α, and IL-6 were also confirmed at the RNA level (data not shown). TGF-β was up-regulated 2.5-fold in MoDC up-regulating GILZ (data not shown). TGF-β was not included in the multiplex analysis and therefore was only analyzed at the mRNA level.

The IL-10 to IL-12p70 ratio is a useful indicator of tolerogenicity, since tolerogenic DC are characterized by an increased IL-10 to IL-12p70 ratio, see Steinman et al., references). The ratio of IL-10 to IL-12p70 increased from 6.7 in untreated MoDC to 67.7 in Dex-DC. Similarly, the IL-10 to IL-12p70 ratio increased to 38.7 in PUVA-DC, and to 89.4 and 114.9 in untreated MoDC and PUVA-DC exposed to ApoL, respectively (p<0.05).

To assess whether induction of GILZ was mediating the tolerogenic cytokine profile, MoDC were transfected with siRNA to knockdown GILZ expression. Transfection with GILZ siRNA reduced GILZ expression in Mo-DC by 68% (FIG. 15A, range 59-79%). Transfection with scramble siRNA did not significantly change GILZ expression. There was also no significant difference in the number of cells recovered from any groups transfected with siRNA as compared to non-transfected groups (data not shown).

Treated MoDC up-regulating GILZ 2.5-fold higher than untreated MoDC produced higher levels of IL-10 (FIG. 15B), and knockdown of GILZ reduced IL-10 production by 39% (range 34-48%, p<0.05). Treated MoDC up-regulating GILZ 2.5-fold higher than untreated MoDC also produced lower amounts of IL-12p70 (FIG. 15C), and knockdown of GILZ increased IL-12p70 production by 188% (range 149-214%, p<0.05). Treatment with scramble siRNA had no appreciable effect on the production of IL-10 or IL-12p'70. Knockdown of GILZ reduced the IL-10 to IL-12p70 ratio that had been elevated after GILZ induction. Dex-DC treated with GILZ siRNA demonstrated a reduction in the IL-10 to IL-12p70 ratio from 15.3 in non-transfected MoDC to 3.9 in transfected Dex-DC. In PUVA-DC the ratio decreased from 8.4 in non-transfected MoDC to 2.9 in PUVA-DC, and in untreated MoDC and PUVA-DC exposed to ApoL, reductions in the ratio from 18.1 to 7.8 and 28.4 to 8.3, respectively, were observed.

These results demonstrates that like other immunosuppressive mediators, PUVA induces the expression of GILZ and generates tolerogenic immuno-suppressive dendritic cells, characterized by low expression of the co-stimulatory molecules CD80 and CD86, and the maturation marker CD83. GILZ induction is necessary for the polarization towards a tolerogenic cytokine profile, characterized by increased IL-10 production, and decreased pro-inflammatory cytokine and chemokine production, including IL-12p70. These results further implicate GILZ as the molecular switch mediating the immunosuppressive effects of apoptotic cells.

Experiment 3—Identification of Further Molecular Markers for Immuno-Stimulatory Dendritic Cells Materials and Methods Patient Samples Leukocytes from patients undergoing ECP using the UVAR XTS Photopheresis System (Therakos) were obtained under the guidelines of the Yale Human Investigational Review Board. Informed consent was provided according to the Declaration of Helsinki. Aliquots were procured at 3 time points: before treatment (Pre ECP), immediately after 8-MOP/ultraviolet A (UVA) exposure (ECP Day 0) or after 18-hour incubation of treated blood mononuclear leukocytes (ECP Day 1) in a 1-L platelet storage bag (PL-2410; Baxter).

Normal Subjects

To determine whether ECP induces monocytes from healthy subjects to convert to DC, mononuclear leukocytes from normal subjects were examined in 2 ways. Leukapheresed leukocytes from normal subjects (N=3) were studied pretreatment (pre-ECP), immediately after ECP (ECP Day 0), and 18 hours after ECP (ECP Day 1). A desktop apparatus, incorporating a UVA light source and a plastic exposure plate, enabled laboratory reproduction of the clinical ECP system and sample access for parallel RNA isolation, immunophenotyping, and functional studies. Alternatively, a unit of blood from normal subjects was drawn into a transfer bag and passed through the ECP treatment apparatus in an identical fashion to that of treated patients (N=3). The cells obtained from the unit of normal blood were used for microarrays and antigen presentation assays.

Psoralen Addition

As is routinely done during ECP, the standard 8-MOP concentrated solution (Therakos) was added directly to the clinical ECP apparatus and to the laboratory model system. That mode of introduction enabled precise 100-200 ng/mL concentrations throughout the clinical procedures and experimentation.

Overnight Culture

In ECP, it is not possible to examine phenotypic and functional changes in treated monocytes, because those cells are immediately reinfused into patients. Therefore, after ECP, cells were cultured for 18 hours (RPMI 1640/15% autologous serum) to study induced monocyte gene activation, maturation and function. Prior to (pre-ECP) and immediately after ECP (ECP Day 0), patient and normal subject samples were isolated by centrifugation over a Ficoll-Hypaque gradient. The cells were resuspended in RPMI-1640 medium (Gibco), supplemented with 7.5% AB serum, 7.5% autologous serum (Gemini Bio-Products) and cultured (for patients) in 6-well polystyrene tissue-culture plates at a density of $5*10^6$ cells/mL and in Baxter platelet storage bags (for normal subjects 37° C., 5% $CO_2$). After overnight culture (ECP Day 1), cells were harvested before undergoing monocyte enrichment. To generate DC for comparative phenotypic analysis, cells were cultured in RPMI 1640 15% serum in the presence of 1 mL of GMCSF and IL4 (25 ng/mL; R&D Systems) for 6 days.

Magnetic Bead Enrichment of the Monocyte Population

To enable determination of whether ECP activates genes directing monocytes into the dendritic cell maturational pathway, it was necessary to develop a gentle negative monocyte enrichment method that eliminates contribution of lymphocytes to the transcriptome analysis while minimizing monocyte physical or cell membrane perturbation. Monocytes were enriched from the mononuclear cell pool by single passage through affinity columns. This negative selection method limited physical perturbation, whereas lymphocytes adherent to magnetic microbeads (Miltenyi Biotec), conjugated to relevant monoclonal antibodies (anti-CD4, CD8, CD19), were depleted. However, enrichment of ECP Day 1 monocytes beyond 60%-80% proved challenging, because diminished surface display of lymphocyte markers by ECP-damaged lymphocytes permitted a fraction of T and B cells to escape retention in the columns. Repetitive passes through the affinity column, to further enhance monocyte purity, was not an option because that approach compounds the physical perturbation of passively filtered monocytes. Fortuitously, a series of analyses revealed that ECP's preferential damage of lymphocytes precluded the necessity of full purification of monocytes for accurate assessment of level of DC gene activation. Due to their extreme sensitivity to UVA-activated 8-MOP, 99% of ECP-processed lymphocytes were apoptotic after overnight incubation (as determined by staining with APO2-PE, Trypan blue, and/or annexin-fluorescein isothiocynate FITC/propidium iodide). Because ECP causes global lymphocyte apoptosis, 90%-95% of viable mononuclear leukocytes in the ECP day 1 fraction were monocytes. This phenomenon accounts for the observation that multiple step magnetic bead removal of apoptotic lymphocytes, performed as follows and yielding monocyte purity of greater than 95%, does not alter levels of observed gene expression in the studied cell populations. To accomplish that comparison we modified the monocyte purification procedure by adapting a negative selection protocol using magnetic beads and the EasySep magnet. Peripheral blood mononuclear cells were centrifuged at low speed (120 g for 10 minutes) to remove platelets. Cells were then labeled using the Monocyte Isolation Kit II (Miltenyi Biotec) following the manufacturers procedure with the following modifications: (1) buffer consisted of ice-cold phosphate-buffered saline containing 2% autologous serum and 1 mM EDTA (ethylenediaminetetraacetic acid); (2) blocking time was increased to 10 minutes; (3) labeling with the Biotin-Antibody Cocktail was increased to 20 minutes; and (4) cells were washed once between labeling with the Biotin-Antibody Cocktail and the Anti-Biotin Microbeads. To avoid stimulating the monocytes by passing them over a column, the magnetically labeled cells were instead separated from the unlabeled monocytes using the EasySep magnet (StemCell Technologies). Cells, in 2 mL of buffer in a 5-mL polystyrene tube, were placed in the magnet for 10 minutes, and then the unlabeled cells were carefully poured off into a new tube. This procedure was repeated 2×, to maximally enhance monocyte purity. At this point, because the purity was still insufficient, cells were relabeled with the Monocyte Isolation Kit II reagents and placed in the EasySep magnet for an additional 10 minutes, and the unlabeled monocytes were eluted. Final purity (X=96%+4.5) was assessed by flow cytometric analysis of CD14 staining.

Immunophenotyping

Monoclonal antibodies specific for monocytes and dendritic cells, included: CD14 (lipopolysaccharide [LPS] receptor, monocytes); CD36 (receptor for apoptotic cells, monocytes); human leukocyte antigen DR-1 (HLA-DR; class II major histocompatibility complex [MHC] molecule); CD83 (dendritic cell marker); cytoplasmic dendritic cell-lysosome-associated membrane protein (DC-LAMP; dendritic cell marker); and CD80 and CD86 (B7.1 and B7.2 costimulatory molecules). Antibodies were obtained from Beckman Coulter and used at their predetermined optimal dilutions. Background staining was established with appropriate isotype controls, and immunofluorescence was analyzed using a FC500 flow cytometer (Beckman Coulter). Combined membrane and cytoplasmic staining was performed following manufacturer's instructions for cell fixation and permeabilization (Intraprep kit; Beckman Coulter).

Antigen Presentation Assay

Volunteer freshly isolated, magnetic bead-enriched, antigen-experienced $CD4^+$ populations ($2*10^6$/mL, 50 μL/well)

were added to monocytes ($2*10^6$/mL, 50 μL/well) in the presence of tetanus toxoid (10 μg/mL, 100 μL/well) and RPMI medium 1640/15% autologous serum. After 5 days of culture, the cells received 1 μCi of [$^3$H]-thymidine and were incubated overnight, harvested, and counted in a Beta liquid scintillation counter (PerkinElmer). Results are presented as the mean and standard deviation of 5 replicate cultures.

MLR/CML Assay

To assess whether ECP-processed monocytes are functionally capable of stimulating MHC class I-restricted cytotoxicity by CD8 T cells, mononuclear leukocytes from 3 normal subjects were studied. One unit of anti-coagulated blood, freshly procured from each of 3 HLA-A2-positive volunteers, served as sources of stimulator monocyte/dendritic cells, before and after being processed through the clinical ECP apparatus in a manner identical to the actual ECP procedure. Mononuclear fractions were isolated from the blood immediately prior to ECP processing (pre-ECP) and immediately after ECP (ECP DO). After gamma irradiation (3000 rad, Cesium source) to ensure unidirectional T-cell stimulation, the Pre ECP fraction was serially diluted in RPMI 1640/15% autologous serum, and 100 μL containing from 25 000 to 250 cells was plated in round-bottom microtiter plate wells, in 5 replicates. The ECP D0 fraction was incubated for 18 hours in large well plates and harvested by scraping the wells to free adherent cells. The re-suspended cells were then serially diluted and plated as above. An A-2-negative normal donor served as the source of responder CD4 and CD8 T cells, purified by positive selection on Miltenyi magnetic bead columns (average purity 98%). Responder T cells (50 000/well in 100 μL) were then added to the wells containing either Pre-ECP or ECP-DO stimulators, and the plates were cultured for 7 days at 37° C. in a CO2 incubator. For target cells, the A-2-positive T-B hybridoma lymphoblast line, 174×CWM.T1, was labeled with $^{51}$Cr and added to the MLR cultures at $10^4$ cells/well. After 4-hour incubation, plates were centrifuged, and 100 μL of supernatant was removed from each well for counting in a gamma counter. "Percent-specific lysis" was defined as 100 times the following fraction:

Mean *cpm* (sample)−Mean *cpm* (*T* cell only) Mean *cpm* (detergent maximum release)−mean *cpm* (*T* cells only)

RNA Isolation and Microarray Hybridization

Total RNA was isolated using RNeasy Mini Kit columns with on-column DNase I treatment (QIAGEN). RNA yield and purity were measured using the NanoDrop ND-1000 Spectrophotometer and the Agilent 2100 Bioanalyzer. Fragmented cRNAs were hybridized on Affymetrix HG U133 Plus 2.0 human chips, and screening for approximately 47 400 human genes and ESTs was performed by the Yale University W. M. Keck Resource Laboratory. The microarray results are available on Gene Expression Omnibus under accession number GSE23604.

Data Analysis

Raw data without normalization generated from Affymetrix GeneChip Operating Software Version 1.2 (GCOS 1.2; Affymetrix) were analyzed using GeneSpring software 7.2 (Agilent Technologies-Silicon Genetics). Data were normalized using Robust Multi-Array. Only probe sets with a minimal fold change of >2.0 combined with an average signal intensity of 500 or higher in either leukapheresis or treated samples were included in the analysis. Differential gene expression was considered as a ≥2-fold change and P≤0.05. Principal component analysis (PCA) of the induced transcriptomes was performed by standard methodology. Signal transduction pathway involvement was identified with MetaCore Software Version 1.0 (GeneGo).

Quantitative Real-Time PCR

Microarray expression of selected genes was confirmed in aliquots of the same RNA samples, using quantitative real-time polymerase chain reaction (PCR). RNA was reverse transcribed to cDNA using the High Capacity cDNA Reverse Transcription Kit (Applied Biosystems). Reverse transcription was carried out in a 96-well thermocycler (MJ Research PTC-200) in the following conditions: 25° C., 10 minutes, 37° C., 120 minutes, 85° C., 5 seconds. TaqMan real-time PCR was used to detect transcripts of DC-LAMP, CCR7, CD80, CD86, and CD14. Primers and probes for each sequence were obtained as inventoried Taqman Gene Expression Assays (Applied Biosystems). HPRT1 was used as a reference gene.

Results

Large ECP-Induced Changes in Individual Gene Expressions

The stimulation by ECP of individual gene activation in monocytes was expressed as the ratio of ECP Day 1 to pre-ECP expression for the relevant gene. To preclude inadvertent gene induction during monocyte enrichment, a negative column purification method was used, whereby lymphocytes were retained, and monocytes were passively filtered. The results revealed that the ECP-processed monocytes from both patients and normal subjects remain sufficiently viable to reproducibly express a shared transcriptome signature.

Genes were considered significantly up- or down-regulated by ECP if fold change was ≥2 and significance was P≤0.05 compared with pre ECP. Levels of RNA transcripts from approximately 3000 genes were significantly changed in each patient group and in normal subjects (Table 2). Overall, 1129 genes were up- or down-regulated in common by ECP-processed monocytes from both CTCL and GVHD patients and from normal subjects, indicating commonality in ECP-induced gene activation.

TABLE 2

Number of Monocyte Genes with Altered Expression after ECP.

| Monocyte Source | Total | Up-regulated | Down-regulated |
|---|---|---|---|
| Normal Subjects (alone): N = 6 | 3,666 | 1494 (41%) | 2172 (59%) |
| CTCL (alone): N = 3 | 4,315 | 2613 (61%) | 1702 (38%) |
| GVHD (alone): N = 3 | 4,350 | 2658 (61%) | 1692 (39%) |

Number of genes significantly induced or suppressed by ECP.

Increased expression of numerous genes associated with dendritic cell differentiation, adhesion, and function (Table 3) further support ECP stimulation of entry of monocytes into that pathway.

TABLE 3

ECP-Enhanced Expression of DC Marker Genes, Ratio* of Post-ECP/Pre-ECP Levels

| Gene | Attributes | CTCL and GVHD (N-6) Induced Expression Ratio | Normal Subjects (N-6) Induced Expression Ratio |
|---|---|---|---|
| DC-LAMP | DC Lysomal Protein | 27.6<br>$p = 1.2 \times 10^{-09}$ | 17.2<br>$p = 1.4 \times 10^{-07}$ |
| GPNMB | Transmembrane glycoprotein | 205.7<br>$p = 9.6 \times 10^{-15}$ | 123.3<br>$p = 2.8 \times 10^{-14}$ |
| CD80 | Co-stimulatory molecule, B7.1 | 13.4<br>$p = 2.3 \times 10^{-13}$ | NC |
| CD86 | Co-stimulatory molecule, B7.2[8] | NC | 5.0<br>$p = 1.4 \times 10^{-05}$ |
| CD40 | Involved in DC survival | 2.3<br>$p = 5.7^{-04}$ | NC |
| Decysin | ADAM-like, Expressed in LPS matured DC | 26.5<br>$p = 1.0 \times 10^{-09}$ | 7.1<br>$p = 5.6 \times 10^{-04}$ |
| CCR7 | Lymph node homing molecule | 2.6<br>$p = 7.0 \times 10^{-03}$ | NC |
| CD83 | DC maturation molecule | NC | 2.3<br>$p = 0.03$ |
| OLR1 | Lox1, lectin-like receptor | 13.6<br>$p = 3.3 \times 10^{-05}$ | 100.1<br>$p = 8.3 \times 10^{-08}$ |
| CLEC5A | MDL-1 | 10.9<br>$p = 9.5 \times 10^{-07}$ | 45.5<br>$p = 1.6 \times 10^{-08}$ |
| FPRL2 | Formyl peptide receptor-like-2 | 33.9<br>$p = 2.1 \times 10^{-08}$ | 43.2<br>$p = 1.9 \times 10^{-08}$ |
| SDC2 | Syndecan, cell surface proteoglycan | 21.7<br>$p = 9.3 \times 10^{-08}$ | 98.9<br>$p = 3.3 \times 10^{-09}$ |
| THBS1 | Thrombospondin 1 | 6.2<br>$p = 7.8 \times 10^{-08}$ | 10.4<br>$p = 4.7 \times 10^{-09}$ |

*Ratio = (Pre-ECP Gene Expression) to (Post-ECP Gene Expression), Fold increase in expression of multiple genes involved in DC maturation and function induced by ECP. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Further genes, the expression of which was found to be increased, and which can be considered to be molecular markers of immune-stimulatory dendritic cells are depicted in Table 1.

As would be expected during monocyte-to-dendritic cell maturation, CD14 (monocyte marker) expression was diminished, as assessed by measuring the mean fluorescence intensity on the monocyte populations of all patients and normal subjects, after overnight culture of ECP-processed monocytes. This result was confirmed in RT-PCR studies of the patients' post-ECP cells (results not shown). Further factors, the expression of which was reduced indicating monocyte-to-dendritic cell maturation are shown in Table 4.

TABLE 4

ECP-Reduced Expression of Monocyte Marker Genes, Ratio* of Post-ECP/Pre-ECP Levels

| Gene | Attributes | CTCL and GVHD (N = 6) Induced Expression Ratio | Normal Subjects (N = 6) Induced Expression Ratio |
|---|---|---|---|
| CD33 | Cell surface protein expressed on monocytes | −2.2<br>$p = 4.5 \times 10^{-04}$ | NC |
| CD36 | Receptor for apoptotic cells | −7.4<br>$p = 7.9 \times 10^{-05}$ | NC |
| FCGR1A | Receptor for IgGFc fragment 1A | −6.9<br>$p = 6.6 \times 10^{-05}$ | −4.4<br>$p = 2.1 \times 10^{-03}$ |

*Ratio = (Pre-ECP Gene Expression) to (Post-ECP Gene Expression), Fold decrease in expression of genes distinctive of monocytes induced by ECP, as the monocytes differentiate into DC. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Further factors, the expression of which was reduced and thus indicating monocyte-to-immuno suppressive dendritic cell maturation are shown in Table 5.

TABLE 5

ECP-Enhanced Expression of Immunosuppression-Associated Genes, Ratio* of Post-ECP/Pre-ECP Levels.

| Gene | Attributes Normal | CTCL and GVHD (N-6) Induced Expression Ratio | Normal Subjects (N-6) Induced Expression Ratio |
|---|---|---|---|
| IDO | Indoleamine | 27.8<br>$p = 4.0 \times 10^{-10}$ | 9.4<br>$p = 1.1 \times 10^{-06}$ |
| KMO | kynurenine 3-hydroxylase | 6.0<br>$p = 2.5 \times 10^{-06}$ | NC |
| IL10 | Interleukin 10 | 6.3<br>$p = 9.2 \times 10^{-06}$ | 8.6<br>$p = 5.7 \times 10^{-06}$ |

*Ratio = (Pre-ECP Gene Expression) to (Post-ECP Gene Expression), ECP-induced fold increase in expression of genes which contribute to DC capacity suppress T cell-mediated immunologic reactions. Impact of treatment on gene expression is displayed as an Induced Expression Ratio (ratio of post-ECP to pre-ECP expression for the relevant gene). RNA was isolated from 3 CTCL patients and 3 GVHD patients and 6 normal subjects at the relevant time points.

Experiment 4—Surface Molecule Markers and Functional Mediators of Immuno-Stimulatory DC Further analysis of the ECP-induced dendritic cells transcriptome was performed to identify a subset of surface molecule gene products as markers and functional mediators of immuno-stimulatory dendritic cells. Of 466 genes upregulated in ECP-induced dendritic cells were cross-referenced to approximately 2000 known or presumed full-length human transmembrane genes to identify 87 shared surface proteins.

Materials and Methods

Procurement of Leukocytes and Platelets

All samples were acquired from young, healthy subjects not taking medications, including aspirin, known to influence platelet function. Samples were obtained under the guidelines of the Yale Human Investigational Review Board, and informed consent was provided according to the Declaration of Helsinki. Peripheral blood specimens were collected through a 19-gauge needle from the antecubital vein into syringes containing heparin, then layered on Ficoll-Hypaque (Gallard-Schlessinger, Carle Place, N.Y.). Following centrifugation at 180 g, the interface containing the mononuclear leukocyte fraction was collected and washed twice in HBSS, then resuspended in RPMI-1640 medium (GIBCO) to a final concentration of $5\times10^6$ mononuclear cells/ml. Cells were utilized within one hour of being acquired.

Preparation of Platelet-Rich-Plasma

Whole blood was centrifuged at 150 g for 15 min at room temperature. The platelet-rich-plasma (PRP) layer was collected and centrifuged at 900 g for 5 min, and the platelet pellet resuspended in RPMI 1640 to the desired concentration.

Preparation of Plates

Plate passage was conducted using a Glycotech system (Glycotech, Rockville, Md.). This system consisted of a volumetric flow path measuring 20000×10000×254 microns (length×width×height). The bottom plate in this system was composed of a 15 mm petri dish (BD Biosciences, Durham, N.C.) separated by a gasket and vacuum-connected to an acrylic flow deck, which formed the upper plate. For precoating with platelets, prior to assembling the flow chamber, 20 drops of the desired concentration of PRP was placed in the center of the petri dish and platelets allowed to settle for 20 minutes at room temperature. The petri dish was washed twice with 2 ml of RPMI, and the flow chamber then assembled.

Overnight Culture

When overnight culture was required, cells were centrifuged and resuspended in RPMI-1640 medium (GIBCO), supplemented with 15% AB serum (Gemini Bio-Products) to a final concentration of 5×106 cells/ml. Cells were cultured overnight for 18 hours in 12-well polystyrene tissue culture plates (2 ml per well) at 37° C. in 5% CO2.

Immunophenotyping

Monoclonal antibodies for immunophenotyping included CD14 (LPS receptor; monocytes), CD11c (integrin subunit; monocytes and DC), HLA-DR (class II MHC molecule), CD83 (DC marker), CD62p (P-selectin; activated platelets), and CD61 (integrin subunit; platelets). Antibodies were obtained from Beckman Coulter (CD14, CD11c, HLADR, CD83) or Sigma (CD62p, CD61) and used at their predetermined optimal dilutions. Background staining was established with appropriate isotype controls, and immunofluorescence was analyzed using a FC500 flow cytometer (Beckman Coulter). Two-color membrane staining was performed by adding the pre-determined optimal concentrations of both antibodies directly conjugated to FITC or PE and incubating for 20 min at 4° C., followed by washing to remove unbound antibodies. Combined membrane and cytoplasmic staining was performed following manufacturer's instructions for cell fixation and permeabilization (Intraprep kit, Beckman Coulter).

Results

Plate-passed and/or PBMC D1 populations showed significant upregulation of analyzed surface expression of SIRPa, ICAM1, CXCL16, LIGHT, PLAUR (CD87, plasminogen activator, urokinase receptor), MSR1, Neul (sialidase), CD137L, and CATB (CTSB, cathepsin B).

Experiment 5—Determining Expression of Molecular Markers and FSC/SSC Complexity after Passing Monocytes Through Flow Chamber Materials and Methods Monocytes were passed through a device depicted in FIG. 19. In brief, a blood sample was spun at low speed through a Ficoll gradient to obtain e.g. 8 ml of sample with a concentration of peripheral blood mononuclear cells (PBMC) of e.g. $10^{10}$ cells/ml.

The chamber was pre-coated with platelets. The sample was passed through the chamber at about 0.028 Pa. The chamber and then washed with about 3 ml RPMI at 0.028 Pa. A second wash with 30-55 ml RPMI was performed at about 1.2 Pa. The collected activated monocytes were combined, incubated for a day and used for further analysis (PP D1 PBMC). As a control PBMCs were not passed through the device and incubated for a day (D1 PBMC). As another control immature fast DC were obtained by directly cultivating PBMC in the presence of GM-CSF and IL-4 (immature Fast DC). Further, PBMC were analyzed directly after harvest through a Ficoll gradient (Fresh (Ficoll) PBMC).

The cells and controls were then analyzed for expression of HLA-DR, CD86, ICAM-1, and PLAUR. They were further analyzed for FSC/SSC complexity. The results are depicted for HLA-DR in FIG. 20 and for FSC/SSC complexity in FIGS. 21 and 22. A summary is shown in FIG. 23.

Results

The results show that cells subjected to centrifugation through a Ficoll gradient already seem to experience enough physical forces to start differentiating as becomes apparent from incubating these cells for one day (D1 PBMC). However, activation and differentiation is more pronounced upon plate passage through the device (PP D1 PDMC). The dendritic cells obtained by methods in accordance with the invention in the absence of e.g. 8-MOP and UV-A moreover have a more complex and distinct pattern than immature Fast DC obtained with cytokine cocktails.

Experiment 6—Determining Phagocytizing Activity

Plate-passaged ECP cells of Experiment 3 are incubated with an anti-CD3 antibody, which marks T-cells, and recorded. It is observed that cells with phagocytozing activity have formed

Experiment 7

Materials and Methods

Generation of Melanoma Mouse Model

The known YUMA/I 1.7 melanoma cell line (Theodosakis, N et al., *Mol Cancer Ther*. Published OnlineFirst May 6, 2015; doi:10.1158/1535-7163.MCT-15-0080) was used for generating melanoma tumors in male C57BL/6 mice. $10^5$ YUMM 1.7 cells in PBS were injected subcutaneously in nine 4 week old male C57BL/6 mice under the right flank to induce tumor formation.

Mice were grown for approximately 11-13 days to establish small tumors at about 10 $mm^3$. The mice were then divided into two cohorts. One cohort (four mice) was designated as the treatment group (Group 1) and the second cohort (five mice) was designated as the PBS control group (Group 2).

After days 11-13, each treatment for Group 1 was started by bleeding the mice and taking 200 μl of entire blood per mouse. Blood was spun through a Ficoll gradient to remove red blood cells and to obtain peripheral blood mononuclear cells (PBMC) at an amount of $8.33*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

8-MOP/UVA-treated Yumm 1.7 cells were then mixed with PBMCs and passed through the same flow chamber. The flow rate was 0.1 ml/min and subjected to 8-MOP and UVA treatment (2 $J/cm^2$ and 100 ng/ml 8-MOP).

Cells were spun down, resuspended in mice's serum (100 μl per mouse) and intravenously injected back inside the retrorbital sinus of the mice.

For Group 2, the same procedure was performed except that PBMC were replaced by PBS buffer. This procedure was repeated twice a week over the next three weeks (overall six treatments). Subsequently tumor volume was determined by cell counting.

Results

The results for the individual mice are shown in FIG. 27. The combined results are shown in FIG. 28. FIG. 4 depicts some of the treated mice. The results are shown in FIG. 29. A clear reduction of tumor volume is observed for Group 1, but not for Group 2.

Experiment 8

Materials and Methods

YUMM 1.7 cells were subcutaneously injected to generate as described in Experiment 7.

Mice were grown for approximately 11-13 days to establish small tumors at about 10 $mm^3$. The mice were then divided into two cohorts. One cohort (five mice) was designated as the treatment group (Group 1) and the second cohort (five mice) was designated as the PBS control group (Group 2).

After days 11-13, each treatment for Group 1 was started by bleeding the mice and taking 200 μl of entire blood per mouse. Blood was spun through a Ficoll gradient to remove red blood cells and to obtain PBMCs at an amount of $8.3*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

8-MOP/UVA-treated Yumm 1.7 cells were then mixed with PBMCs and passed through the same flow chamber but other than in Experiment 7 without applying 8-MOP and UVA. The PBMCs were thus not subject to any apoptotic challenge.

Cells were spun down, resuspended in mice's serum (100 μl per mouse) and intravenously injected back inside the retrorbital sinus of the mice.

For Group 2, the same procedure was performed except that PBMC were replaced by PBS buffer. This procedure was repeated twice a week over the next three weeks (overall six treatments). Subsequently tumor volume was determined by cell counting.

Results

The results are shown in FIG. 30. A clear reduction of tumor volume is observed for Group 1, but not for Group 2.

Experiment 9

Materials and Methods

YUMM 1.7 cells were subcutaneously injected to generate as described in Experiment 7.

Mice were grown for approximately 11-13 days to establish small tumors at about 10 $mm^3$. The mice were then divided into four cohorts. One cohort (five mice) was designated as the PBS control group (Group 1); three cohorts (Groups 2 to 4, each five mice) were treatment groups.

After days 11-13, each treatment for Group 2 was started by bleeding the mice and taking 200 μl of entire blood per mouse. Blood was spun through a Ficoll gradient to remove red blood cells and to obtain PBMCs at an amount of $8.3*10^8$ cells/ml. In parallel, the same number of YUMM 1.7 cells was suspended in PBS and subjected to 8-MOP and UVA treatment (4 $J/cm^2$ and 100 ng/ml 8-MOP) by passing the Yumm 1.7 cells through a flow chamber as depicted in FIG. 26. The flow rate was 0.1 ml/min.

Yumm 1.7 cells were spun down, resuspended in mice's serum (100 μl per mouse) and intravenously injected back inside the retrorbital sinus of the mice without PBMCs (Yumm alone). This procedure was repeated twice a week over the next three weeks (overall six treatments). Subsequently tumor volume was determined by cell counting.

For Group 1, the same treatment procedure was performed except that pure PBS (without Yumm cells or PBMCs) was injected into mice.

For Group 3, PBMCs were obtained as described for Group 1. PBMCs were resuspended in PBS and passed through the flow chamber of FIG. 1 at a flow rate of 0.1 ml/min without 8-MOP/UVA treatment. Flow-chamber passaged PBMCs were spun down, resuspended in mice's serum (100 μl per mouse) and intravenously injected without Yumm cells back inside the retrorbital sinus of the mice (PBMC, PP w/o YUMM). This procedure was repeated twice a week over the next three weeks (overall six treatments). Subsequently tumor volume was determined by cell counting.

For Group 4, PBMCs were obtained as for Group 3 and passed through the flow chamber of FIG. 1 at a flow rate of 0.1 ml/min without 8-MOP/UVA treatment. In parallel, YUMM 1.7 cells were suspended in PBS and subjected to 8-MOP and UVA treatment (4 $J/cm^2$ and 100 ng/ml 8-MOP) by passing the Yumm 1.7 cells through the flow chamber as depicted in FIG. 26 at a flow rate was 0.1 ml/min.

8-MOP/UVA-treated Yumm 1.7 cells and PBMCs were then co-incubated overnight at 37° C. and 5% $CO_2$ in $CO_2$ in RPMI medium supplemented with 15% mouse plasma. Cells were spun down, resuspended in mice's serum (100 μl per mouse) and intravenously injected back inside the retrorbital sinus of the mice (0/N $YUMM^{UVA}$ $PP^{noUVA}$). This procedure was repeated twice a week over the next three weeks (overall six treatments). Subsequently tumor volume was determined by cell counting.

Results

The results are shown in FIG. 31. A clear reduction of tumor volume is observed for Group 2 and Group 3 vs the control Group 1. Tumor reduction is most advanced with Group 4.

REFERENCES

1. Berger C, Hoffmann K, Vasquez J G, Mane S, Lewis J, Filler R et al. Rapid generation of maturationally synchronized human dendritic cells: contribution to the clinical efficacy of extracorporeal photochemotherapy. Blood 2010; 116(23): 4838-4847.
2. Cella M, Scheidegger D, PalmerLehmann K, Lane P, Lanzavecchia A, Alber G. Ligation of CD40 on dendritic cells triggers production of high levels of interleukin-12 and enhances T cell stimulatory capacity: T-T help via APC activation. Journal of Experimental Medicine 1996; 184(2): 747-752.
3. de Saint-Vis B, Vincent J, Vandenabeele S, Vanbervliet B, Pin J J, Ait-Yahia S et al. A novel lysosome-associated membrane glycoprotein, DC-LAMP, induced upon DC maturation, is transiently expressed in MHC class II compartment. Immunity 1998; 9(3): 325-336.
4. Slavik J M, Hutchcroft J E, Bierer B E. CD80 and CD86 are not equivalent in their ability to induce the tyrosine phosphorylation of CD28. Journal of Biological Chemistry 1999; 274(5): 3116-3124.
5. Kang H K, Lee H Y, Kim M K, Park K S, Park Y M, Kwak J Y et al. The synthetic peptide Trp-Lys-Tyr-Met-Val-D-Met inhibits human monocyte-derived dendritic cell maturation via formyl peptide receptor and formyl peptide receptor-like 2. Journal of Immunology 2005; 175(2): 685-692.
6. Ripoll V M, Irvine K M, Ravasi T, Sweet M J, Hume D A. Gpnmb is induced in macrophages by IFN-gamma and lipopolysaccharide and acts as a feedback regulator of proinflammatory responses. Journal of Immunology 2007; 178(10): 6557-6566.
7. Chen S Q, Springer T A. Selectin receptor-ligand bonds: Formation limited by shear rate and dissociation governed by the Bell model. Proceedings of the National Academy of Sciences of the United States of America 2001; 98(3): 950-955.
8. Thomas W E. Understanding the counterintuitive phenomenon of catch bonds. Current Nanoscience 2007; 3: 63-83.
9. Xiong J P, Stehle T, Zhang R G, Joachimiak A, Frech M, Goodman S L et al. Crystal structure of the extracellular segment of integrin alpha V beta 3 in complex with an Arg-Gly-Asp ligand. Science 2002; 296(5565): 151-155.
10. Weisel J W, Nagaswami C, Vilaire G, Bennett J S. Examination of the Platelet Membrane Glycoprotein-IIB-IIIA Complex and its Interaction with Fibrinogen and Other Ligands by Electron-Microscopy. Journal of Biological Chemistry 1992; 267(23): 16637-16643.
11. Kaplan K L, Broekman M J, Chernoff A, Lesznik G R, Drillings M. Platelet alpha-granule proteins—studies on release and subcellular-localization. Blood 1979; 53(4): 604-618.
12. Ruoslahti E. RGD and other recognition sequences for integrins. Annual Review of Cell and Developmental Biology 1996; 12: 697-715.
13. Zhou L J, Tedder T F. CD14+ blood monocytes can differentiate into functionally mature CD83+ dendritic cells. Proc. Natl. Acad. Sci. U.S.A. 1996; 93(6):2588-2592.
14. Klein E. CD83 localization in a recycling compartment of immature human monocyte-derived dendritic cells. International Immunology. 2005; 17(4):477-487.
15. Renzo M D, Rubegni P, Pasqui A L, et al. Extracorporeal photopheresis affects interleukin (IL)-10 and IL-12 production by monocytes in patients with chronic graft-versus-host disease. Br J Dermatol. 2005; 153(1):59-65.
16. Gasparro F P, Bevilacqua P M, Goldminz D, et al. Repair of 8-MOP photoadducts in human lymphocyte. In DNA Damage and Repair in Human Tissues (edited by B. M. Sutherland and A. D. Woodhead). Plenum Press, New York.
17. Steinman R M, Hawiger D, Nussenzweig M C. Tolerogenic dendritic cells. Annu. Rev. Immunol. 2003; 21:685-711.

The invention claimed is:

1. A method for treating cancer in a mammalian subject comprising the step of:

subjecting tumor cells present in the mammalian subject to phagocytosis by globally activated monocytes, wherein said globally activated monocytes are obtained by a method comprising the steps of:

(a) applying an extracorporeal quantity of said mammalian subject's blood comprising at least monocytes to a device, which provides for a flow chamber;

(b) providing platelets in said flow chamber, which may be comprised within said blood sample or which may be provided separate from said blood sample;

(c) subjecting said blood sample, which comprises monocytes, to a physical force such that said monocytes are globally activated, and (d) identifying said globally activated monocytes by increased expression of at least HLA-DR, PLAUR and ICAM-1.

2. The method according to claim 1 further comprising administering the globally activated monocytes to the mammalian subject in need thereof.

3. The method according to claim 2, wherein said mammalian subject is undergoing chemotherapy, radiation therapy or combinations thereof.

4. The method according to claim 2, wherein said cancer is treated in combination with an anti-tumor therapeutic antibody.

5. The method of claim 1, wherein said globally activated monocytes are not presented with an antigen prior to administration to the subject.

* * * * *

SEQUENCE LISTING

```
<160> NUMBER OF SEQ ID NOS: 131

<210> SEQ ID NO 1
<211> LENGTH: 10515
<212> TYPE: DNA
<213> ORGANISM: Homo sapiens

<400> SEQUENCE: 1

ggaggaggga gagcacaggc tttgaccgat agtaacctct gcgctcggtg cagccgaatc      60

tataaaagga actagtcccg gcaaaaaccc cgtaattgcg agcgagagtg agtggggccg     120

ggacccgcag agccgagccg acccttctct cccgggctgc ggcagggcag ggcggggagc     180

tccgcgcacc aacagagccg gttctcaggg cgctttgctc cttgtttttt ccccggttct     240

gttttctccc cttctccgga aggcttgtca aggggtagga gaaagagacg caaacacaaa     300

agtggaaaac agttaatgac cagccacggc gtccctgctg tgagctctgg ccgctgcctt     360

ccagggctcc cgagccacac gctgggggtg ctggctgagg gaacatggct tgttggcctc     420

agctgaggtt gctgctgtgg aagaacctca ctttcagaag aagacaaaca tgtcagctgc     480

tgctggaagt ggcctggcct ctatttatct tcctgatcct gatctctgtt cggctgagct     540

acccaccccta tgaacaacat gaatgccatt ttccaaataa agccatgccc tctgcaggaa    600

cacttccttg ggttcagggg attatctgta atgccaacaa cccctgtttc cgttacccga     660

ctcctgggga ggctcccgga gttgttggaa actttaacaa atccattgtg gctcgcctgt     720
```

-continued

```
tctcagatgc tcggaggctt cttttataca gccagaaaga caccagcatg aaggacatgc    780
gcaaagttct gagaacatta cagcagatca agaaatccag ctcaaacttg aagcttcaag    840
atttcctggt ggacaatgaa accttctctg ggttcctgta tcacaacctc tctctcccaa    900
agtctactgt ggacaagatg ctgagggctg atgtcattct ccacaaggta tttttgcaag    960
gctaccagtt acatttgaca agtctgtgca atggatcaaa atcagaagag atgattcaac   1020
ttggtgacca agaagtttct gagctttgtg gcctaccaag ggagaaactg gctgcagcag   1080
agcgagtact tcgttccaac atggacatcc tgaagccaat cctgagaaca ctaaactcta   1140
catctccctt cccgagcaag gagctggctg aagccacaaa aacattgctg catagtcttg   1200
ggactctggc ccaggagctg ttcagcatga gaagctggag tgacatgcga caggaggtga   1260
tgtttctgac caatgtgaac agctccagct cctccaccca aatctaccag gctgtgtctc   1320
gtattgtctg cgggcatccc gagggagggg ggctgaagat caagtctctc aactggtatg   1380
aggacaacaa ctacaaagcc ctctttggag gcaatggcac tgaggaagat gctgaaacct   1440
tctatgacaa ctctacaact ccttactgca atgatttgat gaagaatttg gagtctagtc   1500
ctctttcccg cattatctgg aaagctctga agccgctgct cgttgggaag atcctgtata   1560
cacctgacac tccagccaca aggcaggtca tggctgaggt gaacaagacc ttccaggaac   1620
tggctgtgtt ccatgatctg gaaggcatgt gggaggaact cagccccaag atctggacct   1680
tcatggagaa cagccaagaa atggaccttg tccggatgct gttggacagc agggacaatg   1740
accacttttg ggaacagcag ttggatggct tagattggac agcccaagac atcgtggcgt   1800
ttttggccaa gcacccagag gatgtccagt ccagtaatgg ttctgtgtac acctggagag   1860
aagctttcaa cgagactaac caggcaatcc ggaccatatc tcgcttcatg gagtgtgtca   1920
acctgaacaa gctagaaccc atagcaacag aagtctggct catcaacaag tccatggagc   1980
tgctggatga gaggaagttc tgggctggta ttgtgttcac tggaattact ccaggcagca   2040
ttgagctgcc ccatcatgtc aagtacaaga tccgaatgga cattgacaat gtggagagga   2100
caaataaaat caaggatggg tactgggacc ctggtcctcg agctgacccc tttgaggaca   2160
tgcggtacgt ctgggggggc ttcgcctact tgcaggatgt ggtggagcag gcaatcatca   2220
gggtgctgac gggcaccgag aagaaaactg gtgtctatat gcaacagatg ccctatccct   2280
gttacgttga tgacatcttt ctgcgggtga tgagccggtc aatgcccctc ttcatgacgc   2340
tggcctggat ttactcagtg gctgtgatca tcaagggcat cgtgtatgag aaggaggcac   2400
ggctgaaaga gaccatgcgg atcatgggcc tggacaacag catcctctgg tttagctggt   2460
tcattagtag cctcattcct cttcttgtga gcgctggcct gctagtggtc atcctgaagt   2520
taggaaacct gctgccctac agtgatccca gcgtggtgtt tgtcttcctg tccgtgtttg   2580
ctgtggtgac aatcctgcag tgcttcctga ttagcacact cttctccaga gccaacctgg   2640
cagcagcctg tgggggcatc atctacttca cgctgtacct gccctacgtc ctgtgtgtgg   2700
catggcagga ctacgtgggc ttcacactca agatcttcgc tagcctgctg tctcctgtgg   2760
cttttgggtt tggctgtgag tactttgccc tttttgagga gcagggcatt ggagtgcagt   2820
gggacaacct gtttgagagt cctgtggagg aagatggctt caatctcacc acttcggtct   2880
ccatgatgct gtttgacacc ttcctctatg gggtgatgac ctggtacatt gaggctgtct   2940
ttccaggcca gtacggaatt cccaggccct ggtattttcc ttgcaccaag tcctactggt   3000
ttggcgagga aagtgatgag aagagccacc ctggttccaa ccagaagaga atatcagaaa   3060
```

-continued

```
tctgcatgga ggaggaaccc acccacttga agctgggcgt gtccattcag aacctggtaa   3120
aagtctaccg agatgggatg aaggtggctg tcgatggcct ggcactgaat ttttatgagg   3180
gccagatcac ctccttcctg ggccacaatg gagcggggaa gacgaccacc atgtcaatcc   3240
tgaccgggtt gttcccccg acctcgggca ccgcctacat cctgggaaaa gacattcgct   3300
ctgagatgag caccatccgg cagaacctgg gggtctgtcc ccagcataac gtgctgtttg   3360
acatgctgac tgtcgaagaa cacatctggt tctatgcccg cttgaaaggg ctctctgaga   3420
agcacgtgaa ggcggagatg gagcagatgg ccctggatgt tggtttgcca tcaagcaagc   3480
tgaaaagcaa aacaagccag ctgtcaggtg gaatgcagag aaagctatct gtggccttgg   3540
cctttgtcgg gggatctaag gttgtcattc tggatgaacc cacagctggt gtggaccctt   3600
actcccgcag gggaatatgg gagctgctgc tgaaataccg acaaggccgc accattattc   3660
tctctacaca ccacatggat gaagcggacg tcctggggga caggattgcc atcatctccc   3720
atgggaagct gtgctgtgtg ggctcctccc tgtttctgaa gaaccagctg ggaacaggct   3780
actacctgac cttggtcaag aaagatgtgg aatcctccct cagttcctgc agaaacagta   3840
gtagcactgt gtcatacctg aaaaaggagg acagtgtttc tcagagcagt tctgatgctg   3900
gcctgggcag cgaccatgag agtgacacgc tgaccatcga tgtctctgct atctccaacc   3960
tcatcaggaa gcatgtgtct gaagcccggc tggtggaaga catagggcat gagctgacct   4020
atgtgctgcc atatgaagct gctaaggagg gagcctttgt ggaactcttt catgagattg   4080
atgaccggct ctcagacctg ggcatttcta gttatggcat ctcagagacg accctggaag   4140
aaatattcct caaggtggcc gaagagagtg gggtggatgc tgagacctca gatggtacct   4200
tgccagcaag acgaaacagg cgggccttcg gggacaagca gagctgtctt cgcccgttca   4260
ctgaagatga tgctgctgat ccaaatgatt ctgacataga cccagaatcc agagagacag   4320
acttgctcag tgggatggat ggcaaagggt cctaccaggt gaaaggctgg aaacttacac   4380
agcaacagtt tgtggccctt ttgtggaaga gactgctaat tgccagacgg agtcggaaag   4440
gatttttgc tcagattgtc ttgccagctg tgtttgtctg cattgccctt gtgttcagcc   4500
tgatcgtgcc accctttggc aagtacccca gcctggaact tcagccctgg atgtacaacg   4560
aacagtacac atttgtcagc aatgatgctc ctgaggacac gggaaccctg gaactcttaa   4620
acgccctcac caaagaccct ggcttcggga cccgctgtat ggaaggaaac ccaatcccag   4680
acacgccctg ccaggcaggg gaggaagagt ggaccactgc cccagttccc cagaccatca   4740
tggacctctt ccagaatggg aactggacaa tgcagaaccc ttcacctgca tgccagtgta   4800
gcagcgacaa aatcaagaag atgctgcctg tgtgtccccc aggggcaggg gggctgcctc   4860
ctccacaaag aaaacaaaac actgcagata tccttcagga cctgacagga agaaacattt   4920
cggattatct ggtgaagacg tatgtgcaga tcatagccaa aagcttaaag aacaagatct   4980
gggtgaatga gtttaggtat ggcggctttt ccctgggtgt cagtaatact caagcacttc   5040
ctccgagtca agaagttaat gatgccatca aacaaatgaa gaaacaccta aagctggcca   5100
aggacagttc tgcagatcga tttctcaaca gcttgggaag atttatgaca ggactggaca   5160
ccaaaaataa tgtcaaggtg tggttcaata acaagggctg gcatgcaatc agctctttcc   5220
tgaatgtcat caacaatgcc attctccggg ccaacctgca aaagggagag aaccctagcc   5280
attatggaat tactgctttc aatcatcccc tgaatctcac caagcagcag ctctcagagg   5340
tggctctgat gaccacatca gtggatgtcc ttgtgtccat ctgtgtcatc tttgcaatgt   5400
ccttcgtccc agccagcttt gtcgtattcc tgatccagga gcgggtcagc aaagcaaaac   5460
```

-continued

```
acctgcagtt catcagtgga gtgaagcctg tcatctactg gctctctaat tttgtctggg   5520
atatgtgcaa ttacgttgtc cctgccacac tggtcattat catcttcatc tgcttccagc   5580
agaagtccta tgtgtcctcc accaatctgc ctgtgctagc ccttctactt ttgctgtatg   5640
ggtggtcaat cacacctctc atgtacccag cctcctttgt gttcaagatc cccagcacag   5700
cctatgtggt gctcaccagc gtgaacctct tcattggcat taatggcagc gtggccacct   5760
ttgtgctgga gctgttcacc gacaataagc tgaataatat caatgatatc ctgaagtccg   5820
tgttcttgat cttcccacat ttttgcctgg gacgagggct catcgacatg gtgaaaaacc   5880
aggcaatggc tgatgccctg gaaaggtttg gggagaatcg ctttgtgtca ccattatctt   5940
gggacttggt gggacgaaac ctcttcgcca tggccgtgga aggggtggtg ttcttcctca   6000
ttactgttct gatccagtac agattcttca tcaggcccag acctgtaaat gcaaagctat   6060
ctcctctgaa tgatgaagat gaagatgtga ggcgggaaag acagagaatt cttgatggtg   6120
gaggccagaa tgacatctta gaaatcaagg agttgacgaa gatatataga aggaagcgga   6180
agcctgctgt tgacaggatt tgcgtgggca ttcctcctgg tgagtgcttt gggctcctgg   6240
gagttaatgg ggctggaaaa tcatcaactt tcaagatgtt aacaggagat accactgtta   6300
ccagaggaga tgctttcctt aacaaaaata gtatcttatc aaacatccat gaagtacatc   6360
agaacatggg ctactgccct cagtttgatg ccatcacaga gctgttgact gggagagaac   6420
acgtggagtt ctttgccctt ttgagaggag tcccagagaa agaagttggc aaggttggtg   6480
agtgggcgat tcggaaactg ggcctcgtga agtatggaga aaaatatgct ggtaactata   6540
gtggaggcaa caaacgcaag ctctctacag ccatggcttt gatcggcggg cctcctgtgg   6600
tgtttctgga tgaacccacc acaggcatgg atcccaaagc ccggcggttc ttgtggaatt   6660
gtgccctaag tgttgtcaag gaggggagat cagtagtgct tacatctcat agtatggaag   6720
aatgtgaagc tctttgcact aggatggcaa tcatggtcaa tggaaggttc aggtgccttg   6780
gcagtgtcca gcatctaaaa aataggtttg gagatggtta tacaatagtt gtacgaatag   6840
cagggtccaa cccggacctg aagcctgtcc aggatttctt tggacttgca tttcctggaa   6900
gtgttctaaa agagaaacac cggaacatgc tacaatacca gcttccatct tcattatctt   6960
ctctggccag gatattcagc atcctctccc agagcaaaaa gcgactccac atagaagact   7020
actctgtttc tcagacaaca cttgaccaag tatttgtgaa ctttgccaag gaccaaagtg   7080
atgatgacca cttaaaagac ctctcattac acaaaaacca gacagtagtg gacgttgcag   7140
ttctcacatc ttttctacag gatgagaaag tgaaagaaag ctatgtatga agaatcctgt   7200
tcatacgggg tggctgaaag taaagaggaa ctagactttc ctttgcacca tgtgaagtgt   7260
tgtggagaaa agagccagaa gttgatgtgg gaagaagtaa actggatact gtactgatac   7320
tattcaatgc aatgcaattc aatgcaatga aaacaaaatt ccattacagg ggcagtgcct   7380
ttgtagccta tgtcttgtat ggctctcaag tgaaagactt gaatttagtt ttttacctat   7440
acctatgtga aactctatta tggaacccaa tggacatatg ggtttgaact cacacttttt   7500
tttttttttt tgttcctgtg tattctcatt ggggttgcaa caataattca tcaagtaatc   7560
atggccagcg attattgatc aaaatcaaaa ggtaatgcac atcctcattc actaagccat   7620
gccatgccca ggagactggt ttcccggtga cacatccatt gctggcaatg agtgtgccag   7680
agttattagt gccaagtttt tcagaaagtt tgaagcacca tggtgtgtca tgctcacttt   7740
tgtgaaagct gctctgctca gagtctatca acattgaata tcagttgaca gaatggtgcc   7800
```

-continued

```
atgcgtggct aacatcctgc tttgattccc tctgataagc tgttctggtg gcagtaacat   7860
gcaacaaaaa tgtgggtgtc tccaggcacg ggaaacttgg ttccattgtt atattgtcct   7920
atgcttcgag ccatgggtct acagggtcat ccttatgaga ctcttaaata tacttagatc   7980
ctggtaagag gcaaagaatc aacagccaaa ctgctggggc tgcaagctgc tgaagccagg   8040
gcatgggatt aaagagattg tgcgttcaaa cctagggaag cctgtgccca tttgtcctga   8100
ctgtctgcta acatggtaca ctgcatctca agatgtttat ctgacacaag tgtattattt   8160
ctggcttttt gaattaatct agaaaatgaa aagatggagt tgtattttga caaaaatgtt   8220
tgtacttttt aatgttattt ggaattttaa gttctatcag tgacttctga atccttagaa   8280
tggcctcttt gtagaaccct gtggtataga ggagtatggc cactgcccca ctatttttat   8340
tttcttatgt aagtttgcat atcagtcatg actagtgcct agaaagcaat gtgatggtca   8400
ggatctcatg acattatatt tgagtttctt tcagatcatt taggatactc ttaatctcac   8460
ttcatcaatc aaatattttt tgagtgtatg ctgtagctga aagagtatgt acgtacgtat   8520
aagactagag agatattaag tctcagtaca cttcctgtgc catgttattc agctcactgg   8580
tttacaaata taggttgtct tgtggttgta ggagcccact gtaacaatac tgggcagcct   8640
tttttttttt ttttttaatt gcaacaatgc aaaagccaag aaagtataag ggtcacaagt   8700
ctaaacaatg aattcttcaa cagggaaaac agctagcttg aaaacttgct gaaaaacaca   8760
acttgtgttt atggcattta gtaccttcaa ataattggct ttgcagatat tggataccc    8820
attaaatctg acagtctcaa atttttcatc tcttcaatca ctagtcaaga aaaatataaa   8880
aacaacaaat acttccatat ggagcatttt tcagagtttt ctaacccagt cttatttttc   8940
tagtcagtaa acatttgtaa aaatactgtt tcactaatac ttactgttaa ctgtcttgag   9000
agaaaagaaa aatatgagag aactattgtt tggggaagtt caagtgatct ttcaatatca   9060
ttactaactt cttccacttt ttccagaatt tgaatattaa cgctaaaggt gtaagacttc   9120
agatttcaaa ttaatctttc tatatttttt aaatttacag aatattatat aacccactgc   9180
tgaaaaagaa aaaaatgatt gttttagaag ttaaagtcaa tattgatttt aaatataagt   9240
aatgaaggca tatttccaat aactagtgat atggcatcgt tgcattttac agtatcttca   9300
aaaatacaga atttatagaa taatttctcc tcatttaata tttttcaaaa tcaaagttat   9360
ggtttcctca ttttactaaa atcgtattct aattcttcat tatagtaaat ctatgagcaa   9420
ctccttactt cggttcctct gatttcaagg ccatatttta aaaaatcaaa aggcactgtg   9480
aactattttg aagaaaacac aacattttaa tacagattga aaggacctct tctgaagcta   9540
gaaacaatct atagttatac atcttcatta atactgtgtt accttttaaa atagtaattt   9600
tttacatttt cctgtgtaaa cctaattgtg gtagaaattt ttaccaactc tatactcaat   9660
caagcaaaat ttctgtatat tccctgtgga atgtacctat gtgagtttca gaaattctca   9720
aaatacgtgt tcaaaaattt ctgcttttgc atctttggga cacctcagaa aacttattaa   9780
caactgtgaa tatgagaaat acagaagaaa ataataagcc ctctatacat aaatgcccag   9840
cacaattcat tgttaaaaaa caaccaaacc tcacactact gtatttcatt atctgtactg   9900
aaagcaaatg ctttgtgact attaaatgtt gcacatcatt cattcactgt atagtaatca   9960
ttgactaaag ccatttgtct gtgttttctt cttgtggttg tatatatcag gtaaaatatt  10020
ttccaaagag ccatgtgtca tgtaatactg aaccactttg atattgagac attaatttgt  10080
acccttgtta ttatctacta gtaataatgt aatactgtag aaatattgct ctaattcttt  10140
tcaaaattgt tgcatccccc ttagaatgtt tctatttcca taaggattta ggtatgctat  10200
```

-continued tatcccttct tataccctaa gatgaagctg tttttgtgct ctttgttcat cattggccct 10260
cattccaagc actttacgct gtctgtaatg ggatctattt ttgcactgga atatctgaga 10320
attgcaaaac tagacaaaag tttcacaaca gatttctaag ttaaatcatt ttcattaaaa 10380
ggaaaaaaga aaaaaaattt tgtatgtcaa taactttata tgaagtatta aaatgcatat 10440
ttctatgttg taatataatg agtcacaaaa taaagctgtg acagttctgt tggtctacag 10500
aaaaaaaaaa aaaaa 10515

<210> SEQ ID NO 2
<211> LENGTH: 4564
<212> TYPE: DNA
<213> ORGANISM: Homo sapiens

<400> SEQUENCE: 2
ggggaggcgc cgggggcgcg cgcgcgcgcg ctgggcgctg ctgggctgcg gcggcggcgg 60
cggcggcggt ggttactatg gcggagtcgg ccggagcctc ctccttcttc cccccttgttg 120 tcctcctgct cgccggcagc ggcgggtccg ggccccgggg ggtccaggct ctgctgtgtg 180
cgtgcaccag ctgcctccag gccaactaca cgtgtgagac agatggggcc tgcatggttt 240
ccattttcaa tctggatggg atggagcacc atgtgcgcac ctgcatcccc aaagtggagc 300
tggtccctgc cgggaagccc ttctactgcc tgagctcgga ggacctgcgc aacacccact 360
gctgctacac tgactactgc aacaggatcg acttgagggt gcccagtggt cacctcaagg 420
agcctgagca cccgtccatg tggggcccgg tggagctggt aggcatcatc gccggcccgg 480
tgttcctcct gttcctcatc atcatcattg ttttccttgt cattaactat catcagcgtg 540
tctatcacaa ccgccagaga ctggacatgg aagatccctc atgtgagatg tgtctctcca 600
aagacaagac gctccaggat cttgtctacg atctctccac ctcagggtct ggctcagggt 660 taccccctctt tgtccagcgc acagtggccc gaaccatcgt tttacaagag attattggca 720
agggtcggtt tggggaagta tggcggggcc gctggagggg tggtgatgtg gctgtgaaaa 780
tattctcttc tcgtgaagaa cggtcttggt tcagggaagc agagatatac cagacggtca 840
tgctgcgcca tgaaaacatc cttggattta ttgctgctga caataaagat aatggcacct 900
ggacacagct gtggcttgtt tctgactatc atgagcacgg gtccctgttt gattatctga 960
accggtacac agtgacaatt gaggggatga ttaagctggc cttgtctgct gctagtgggc 1020
tggcacacct gcacatggag atcgtgggca cccaagggaa gcctggaatt gctcatcgag 1080
acttaaagtc aaagaacatt ctggtgaaga aaaatggcat gtgtgccata gcagacctgg 1140
gcctggctgt ccgtcatgat gcagtcactg acaccattga cattgccccg aatcagaggg 1200
tggggaccaa acgatacatg gcccctgaag tacttgatga aaccattaat atgaaacact 1260
ttgactcctt taaatgtgct gatatttatg ccctcgggct tgtatattgg gagattgctc 1320
gaagatgcaa ttctggagga gtccatgaag aatatcagct gccatattac gacttagtgc 1380
cctctgaccc ttccattgag gaaatgcgaa aggttgtatg tgatcagaag ctgcgtccca 1440
acatccccaa ctggtggcag agttatgagg cactgcgggt gatggggaag atgatgcgag 1500
agtgttggta tgccaacggc gcagcccgcc tgacggccct gcgcatcaag aagaccctct 1560
cccagctcag cgtgcaggaa gacgtgaaga tctaactgct ccctctctcc acacggagct 1620
cctggcagcg agaactacgc acagctgccg cgttgagcgt acgatggagg cctacctctc 1680
gtttctgccc agccctctgt ggccaggagc cctggcccgc aagagggaca gagcccggga 1740

-continued

```
gagactcgct cactcccatg ttgggtttga gacagacacc ttttctattt acctcctaat   1800
ggcatggaga ctctgagagc gaattgtgtg gagaactcag tgccacacct cgaactggtt   1860
gtagtgggaa gtcccgcgaa acccggtgca tctggcacgt ggccaggagc catgacaggg   1920
gcgcttggga ggggccggag gaaccgaggt gttgccagtg ctaagctgcc ctgagggttt   1980
ccttcgggga ccagcccaca gcacaccaag gtggcccgga agaaccagaa gtgcagcccc   2040
tctcacaggc agctctgagc cgcgctttcc cctcctccct gggatggacg ctgccgggag   2100
actgccagtg gagacggaat ctgccgcttt gtctgtccag ccgtgtgtgc atgtgccgag   2160
gtgcgtcccc cgttgtgcct ggttcgtgcc atgcccttac acgtgcgtgt gagtgtgtgt   2220
gtgtgtctgt aggtgcgcac ttacctgctt gagctttctg tgcatgtgca ggtcgggggt   2280
gtggtcgtca tgctgtccgt gcttgctggt gcctcttttc agtagtgagc agcatctagt   2340
ttccctggtg cccttccctg gaggtctctc cctcccccag agcccctcat gccacagtgg   2400
tactctgtgt ctggcaggct actctgccca ccccagcatc agcacagctc tcctcctcca   2460
tctcagactg tggaaccaaa gctggcccag ttgtccatga caaaagaggc ttttgggcca   2520
aaatgtgagg gtggtgggtg ggatgggcag ggaaggaatc ctggtggaag tcttgggtgt   2580
tagtgtcagc catgggaaat gagccagccc aagggcatca tcctcagcag catcgaggaa   2640
gggccgagga atgtgaagcc agatctcggg actcagattg gaatgttaca tctgtctttc   2700
atctcccaga tcctggaaac agcagtgtat atttttggtg gtggtgggtt tggggtgggg   2760
aagggaaggg cgggcaagga gtggggaggg agtctggggt gggagggagg catctgcatg   2820
ggtcttcttt tactggactg tctgatcagg gtggagggaa ggtgagaggt ttgcatccac   2880
ttcaggagcc ctactgaagg gaacagcctg agccgaacat gttatttaac ctgagtatag   2940
tatttaacga agcctagaag cacggctgtg ggtggtgatt tggtcagcat atcttaggta   3000
tataataact ttgaagccat aacttttaac tggagtggtt tgatttcttt ttttaatttt   3060
attgggaggg tttggatttt aacttttttt aatgttgtta aatattaagt ttttgtaaaa   3120
ggaaaaccat ctctgtgatt acctctcaat ctatttgttt ttaaagaaat ccctaaaaaa   3180
aaaaattatc caattgaacg cacatagctc aatcacactg gaaatgtttg tccttgcacc   3240
tgagcctgtt cccactcagc agtgagagtt cctctttgcc ctgaggctca gtctctctcg   3300
tattttgtcc ccaccccaa ttccttgagt ggtttttgct ctagggccct ttcttgcact   3360
gtccagctgg ttgtaccctc tccaggcatt tattcaacaa atgtgggtga agtgcctgct   3420
gggtgccagg tgctgggaat acatctgtgg acaagacatg cttgggtcct actcctggag   3480
cactgtaaaa agagctgatt caagtaagta gatgcctgtt ttgagaccag aaggtttcat   3540
aattggttct acgacccttt tgagcctaga attattgttc ttatataaga tcactgaaga   3600
aagaggaacc cccacaaccc cctccacaaa gagaccaggg gcgggtgatg agacctgggg   3660
tttagaaccc caggtgagac ctcaaatcac tgcattcatt ctgagccccc ttcctgtccc   3720
caggggaggt gtattgtgta tgtagcctta gagcatctct gcctccaacc cagcagttct   3780
ctgccaaagc ttgtggagga gggagagccc tgtccctgcc ctcaggctcc ccagtgctcc   3840
tggcccttct atttatttga ctgattattg cttctttcct tgcattaaag gagatcttcc   3900
cctaaccttt gggccaattt actggccact aatttcgttt aaataccatt gtgtcattgg   3960
ggggaccgtc tttaccccctg ctgacctccc acctatccgc cctgcagcag aaccttggcg   4020
gtttataggt aatgatggaa cttagactcc tcttcccaga gtcacaagta gcctctggga   4080
tctgccaaca cacgtccact cccaagccac tagcccactc cccagttggc ccttctgccc   4140
```

-continued

```
ttaccccaca cacagtccaa ctcttccacc tctggggaag atggagcagg tctttgggaa   4200

gctcccacac ccacctctgc cactcttaac actaagtgag agttggggag aaactgaagc   4260

cgtgtttttg gccccccgag gctaaccctg atccatagtg ctacctgcac ctctggattc   4320

tggattcaca gaccaagtcc aagcccgttc ttacgtcgcc ataaaggccc ccgaacggca   4380

ttctcggtac ttctgtttgt ttttgtacat tttattagaa aggactgtaa aatagccact   4440

tagacacttt acctcttcag tatgcaaatg taaataaatt gtaatatagg aaatcttttg   4500

ttttaatata agaatgagcc tgtccaattt ctgctgtaca ttattaaaag ttttattcac   4560

agag                                                                4564


<210> SEQ ID NO 3
<211> LENGTH: 3740
<212> TYPE: DNA
<213> ORGANISM: Homo sapiens

<400> SEQUENCE: 3

gggacggcgg cggcgcagct cggaacccgc cagggtccag ggtccaggtt ccagcgcccg     60

gcggcccagg caccccccga gcccagctcc acacaccgtt cctggatctc ctctccccag    120

gcggagcgtg cccctgccca gtccagtgac cttcgcctgt tggagccctg gttaattttt    180

gcccagtctg cctgttgtgg ggctcctccc ctttggggat ataagcccgg cctggggctg    240

ctccgttctc tgcctggcct gaggctccct gagccgcctc cccaccatca ccatggccaa    300

gggcttctat atttccaagt ccctgggcat cctggggatc ctcctgggcg tggcagccgt    360

gtgcacaatc atcgcactgt cagtggtgta ctcccaggag aagaacaaga acgccaacag    420

ctcccccgtg gcctccacca ccccgtccgc ctcagccacc accaaccccg cctcggccac    480

caccttggac caaagtaaag cgtggaatcg ttaccgcctc cccaacacgc tgaaacccga    540

ttcctaccgg gtgacgctga gaccgtacct cacccccaat gacaggggcc tgtacgtttt    600

taagggctcc agcaccgtcc gtttcacctg caaggaggcc actgacgtca tcatcatcca    660

cagcaagaag ctcaactaca ccctcagcca ggggcacagg gtggtcctgc gtggtgtggg    720

aggctcccag ccccccgaca ttgacaagac tgagctggtg gagcccaccg agtacctggt    780

ggtgcacctc aagggctccc tggtgaagga cagccagtat gagatggaca gcgagttcga    840

gggggagttg gcagatgacc tggcgggctt ctaccgcagc gagtacatgg agggcaatgt    900

cagaaaggtg gtggccacta cacagatgca ggctgcagat gcccggaagt ccttcccatg    960

cttcgatgag ccggccatga aggccgagtt caacatcacg cttatccacc ccaaggacct   1020

gacagccctg tccaacatgc ttcccaaagg tcccagcacc ccacttccag aagaccccaa   1080

ctggaatgtc actgagttcc acaccacgcc caagatgtcc acgtacttgc tggccttcat   1140

tgtcagtgag ttcgactacg tggagaagca ggcatccaat ggtgtcttga tccggatctg   1200

ggcccggccc agtgccattg cggcgggcca cggcgattat gccctgaacg tgacgggccc   1260

catccttaac ttctttgctg gtcattatga cacaccctac ccactcccaa aatcagacca   1320

gattggcctg ccagacttca acgccggcgc catggagaac tggggactgg tgacctaccg   1380

ggagaactcc ctgctgttcg acccccctgtc ctcctccagc agcaacaagg agcgggtggt   1440

cactgtgatt gctcatgagc tggcccacca gtggttcggg aacctggtga ccatagagtg   1500

gtggaatgac ctgtggctga acgagggctt cgcctcctac gtggagtacc tgggtgctga   1560

ctatgcggag cccacctgga acttgaaaga cctcatggtg ctgaatgatg tgtaccgcgt   1620
```

-continued gatggcagtg gatgcactgg cctcctccca cccgctgtcc acacccgcct cggagatcaa 1680
cacgccggcc cagatcagtg agctgtttga cgccatctcc tacagcaagg gcgcctcagt 1740
cctcaggatg ctctccagct tcctgtccga ggacgtattc aagcagggcc tggcgtccta 1800
cctccacacc tttgcctacc agaacaccat ctacctgaac ctgtgggacc acctgcagga 1860
ggctgtgaac aaccggtcca tccaactccc caccaccgtg cgggacatca tgaaccgctg 1920
gaccctgcag atgggcttcc cggtcatcac ggtggatacc agcacgggga ccctttccca 1980
ggagcacttc ctccttgacc ccgattccaa tgttacccgc ccctcagaat tcaactacgt 2040
gtggattgtg cccatcacat ccatcagaga tggcagacag cagcaggact actggctgat 2100
agatgtaaga gcccagaacg atctcttcag cacatcaggc aatgagtggg tcctgctgaa 2160
cctcaatgtg acgggctatt accgggtgaa ctacgacgaa gagaactgga ggaagattca 2220
gactcagctg cagagagacc actcggccat ccctgtcatc aatcgggcac agatcattaa 2280
tgacgccttc aacctggcca gtgcccataa ggtccctgtc actctggcgc tgaacaacac 2340
cctcttcctg attgaagaga gacagtacat gccctgggag gccgccctga gcagcctgag 2400
ctacttcaag ctcatgtttg accgctccga ggtctatggc cccatgaaga actacctgaa 2460
gaagcaggtc acacccctct tcattcactt cagaaataat accaacaact ggagggagat 2520
cccagaaaac ctgatggacc agtacagcga ggttaatgcc atcagcaccg cctgctccaa 2580
cggagttcca gagtgtgagg agatggtctc tggccttttc aagcagtgga tggagaaccc 2640
caataataac ccgatccacc ccaacctgcg gtccaccgtc tactgcaacg ctatcgccca 2700
gggcggggag gaggagtggg acttcgcctg ggagcagttc cgaaatgcca cactggtcaa 2760
tgaggctgac aagctccggg cagccctggc ctgcagcaaa gagttgtgga tcctgaacag 2820
gtacctgagc tacaccctga acccggactt aatccggaag caggacgcca cctctaccat 2880
catcagcatt accaacaacg tcattgggca aggtctggtc tgggactttg tccagagcaa 2940
ctggaagaag ctttttaacg attatggtgg tggctcgttc tccttctcca acctcatcca 3000
ggcagtgaca cgacgattct ccaccgagta tgagctgcag cagctggagc agttcaagaa 3060
ggacaacgag gaaacaggct tcggctcagg cacccgggcc ctggagcaag ccctggagaa 3120
gacgaaagcc aacatcaagt gggtgaagga gaacaaggag gtggtgctcc agtggttcac 3180
agaaaacagc aaatagtccc cagcccttga agtcacccgg cccccatgca aggtgcccac 3240
atgtgtccat cccagcggct ggtgcagggc ctccattcct ggagcccgag gcaccagtgt 3300
cctcccctca aggacaaagt ctccagccca cgttctctct gcctgtgagc cagtctagtt 3360
cctgatgacc caggctgcct gagcacctcc cagcccctgc ccctcatgcc aaccccgccc 3420
taggcctggc atggcacctg tcgcccagtg ccctggggct gatctcaggg aagcccagct 3480
ccagggccag atgagcagaa gctctcgatg gacaatgaac ggccttgctg ggggccgccc 3540
tgtaccctct ttcacctttc cctaaagacc ctaaatctga ggaatcaaca gggcagcaga 3600
tctgtatatt tttttctaag agaaaatgta aataaaggat ttctagatga aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa 3740

<210> SEQ ID NO 4
<211> LENGTH: 3033
<212> TYPE: DNA
<213> ORGANISM: Homo sapiens

<400> SEQUENCE: 4

```
aacacaactg gcacatctct tttctcatct cttgaaaaaa accaacagag aaaaaagtac     60
cttgagaata aaggtaatga ttaatctgtc aggcacaaaa gggattgttt tggggatttc    120
gggttctaag tcgcagattc aaacaaatag cagcgaacag ggaatgacag ttccaccaga    180
agacgattaa gccacagcct ctaattggaa cggcatttgt acagtcagag actcttacca    240
gacatctcca ggaatctgtg agccattgtc aaaacgtcca ttttcatctg gctgtgaaag    300
tgaggaccac aacaggtagg tattggtaga aacaggagtc ctcagagaag ccccaagatg    360
cagcctgagg gagcagaaaa gggaaaaagc ttcaagcaga gactggtctt gaagagcagc    420
ttagcgaaag aaaccctctc tgagttcttg ggcacgttca tcttgattgt ccttggatgt    480
ggctgtgttg cccaagctat tctcagtcga ggacgttttg gaggggtcat cactatcaat    540
gttggatttt caatggcagt tgcaatggcc atttatgtgg ctggcggtgt ctctggtggt    600
cacatcaacc cagctgtgtc tttagcaatg tgtctctttg gacggatgaa atggttcaaa    660
ttgccatttt atgtgggagc ccagttcttg ggagcctttg tgggggctgc aaccgtcttt    720
ggcatttact atgatggact tatgtccttt gctggtggaa aactgctgat cgtgggagaa    780
aatgcaacag cacacatttt tgcaacatac ccagctccgt atctatctct ggcgaacgca    840
tttgcagatc aagtggtggc caccatgata ctcctcataa tcgtctttgc catctttgac    900
tccagaaact tgggagcccc cagaggccta gagcccattg ccatcggcct cctgattatt    960
gtcattgctt cctccctggg actgaacagt ggctgtgcca tgaacccagc tcgagacctg   1020
agtcccagac ttttcactgc cttggcaggc tgggggtttg aagtcttcag agctggaaac   1080
aacttctggt ggattcctgt agtgggccct ttggttggtg ctgtcattgg aggcctcatc   1140
tatgttcttg tcattgaaat ccaccatcca gagcctgact cagtctttaa gacagaacaa   1200
tctgaggaca aaccagagaa atatgaactc agtgtcatca tgtagtggca tgctcagctc   1260
tggatttgca gtcagtttgg gattctcttc agaaagatgg catctaagtg tctgtgttct   1320
tgtaagcctg aggtggaatc cacccagttt tgtctgctag ccatatggga catctaattg   1380
gaaaagcatc tgcataaaag tttggaaaca atgaccactt ctctaccatt gtcccccacc   1440
cccacccccc agaataacgc tgactgtccc ctgaaacagc cttctctcct gccctgttta   1500
tttcatcctc gatgggaatt cttgctaggt aagcactaat aactcggcat cttgacgata   1560
gtcccatttg ggtggtttca gctgcactat ctgtatgaaa tggtgtcacc aaaacccttt   1620
tcttcagtat cgacaaagat tacattctga gtaccaacca aaccctaaat tgaaagacaa   1680
aactatggtt tcagtcaaca tattcatgaa ttagggagct aatgggttaa gcttccagtt   1740
cccgctatgc tactggattt gtataaatac tgatattctc caaacctagt ggtgtaggga   1800
gcaagagaat gcagctggaa ggcacaaggg gaggacattg tggcattcag aaactgcagg   1860
agacaagatg aatttgagaa gccaaatgga atttttaatg gaaaccattt atcagattaa   1920
tctcttgctc tcctgcattt tagaggacac caattaattt cctggtcttt agtatataat   1980
aacctaaaat accattgtaa cctcagtcat gaaaaataca tcactctgtc tttttagctc   2040
aaatgtattt tcctaattgc ccacttgaga acagacattt gacaagttat atcaacgact   2100
gtgcttgtcc attattttac acatgcccta gaagccaaaa ctgaaagcca ctggatcctg   2160
gtctagctga atcttcagag tgggaggtct ccaaaaagat attaccttat tgggcttaac   2220
aattcacaag gcactttcac acccattatc taatttaatc ctcataatga ctatgtgagg   2280
caaatgccac attgcccatt tttcagataa agaaacaaaa tcttagggaa gataagttga   2340
```

-continued gttgtccaag agcacactga aagttgaatg ttatctaatg cattcctcta cctttcagaa 2400
gatcagtagc tggctgagaa tctttgccaa atcttccttg ctagccagaa gtggaattgg 2460
cagcttctag aatatgtaca cctctggaca aaatgttcct caatcttaag atacaaagac 2520
cctcattgtc tgggtctatt cccacactta ctgagtacag atgaaggaaa gtggtagcaa 2580
tttaatcata actttcattt gctgaaaaac attatgagaa ggcctccctt cctaagccac 2640
ctctggtctt gctaagtctt gatcttgctt cctgccagca ccaaacatta cattcagggg 2700
atttcctctg gctcagtctt ttccccttga agttctctaa tagatgttac ttttgacaaa 2760
agatcgccta tgagttacaa gcaccagggg atgctctaca tcaagggatg caccttcagt 2820
caaactgtca aaaagcccag aattcccaaa ggcattaggt ttcccaactg ctttgtgctg 2880
atatcagaac agcagaaatt aaatgtgaaa tgtttctgat gacttatgtt ctacaatcta 2940
tggacatacg ggattttttt ttcttgcttt gaagctacct ggatatttcc tatttgaaat 3000
aaaattgttc ggtcattgtt gaaaaaaaaa aaa 3033

<210> SEQ ID NO 5
<211> LENGTH: 979
<212> TYPE: DNA
<213> ORGANISM: Homo sapiens

<400> SEQUENCE: 5
gagttaggtg acgctgcggg gcgggcggac agactgcggg acggacggtg gacgctggga 60
cgcgtttgta gctccggccc cgccgttccg acccccgccg ccgtcgccgc catgacgggg 120
ctagcactgc tctactccgg ggtcttcgtg gccttctggg cctgcgcgct ggccgtgggt 180
tcctgacgga gacttcgccc ttcatgtggt ccaacctggg cattggccta gctatctccc 240
tgtctgtggt tggggcagcc tggggcatct atattaccgg ctcctccatc attggtggag 300
gagtgaaggc ccccaggatc aagaccaaga acctggtcag catcatcttc tgtgaggctg 360
tggccatcta cggcatcatc atggcaattg tcattagcaa catggctgag cctttcagtg 420
ccacagaccc caaggccatc ggccatcgga actaccatgc aggctactcc atgtttgggg 480
ctggcctcac cgtaggcctg tctaacctct tctgtggagt ctgcgtgggc atcgtgggca 540
gtggggctgc cctggccgat gctcagaacc ccagcctctt tgtaaagatt ctcatcgtgg 600
agatctttgg cagcgccatt ggcctctttg gggtcatcgt cgcaattctt cagacctcca 660
gagtgaagat gggtgactag atgatatgtg tgggtggggc cgtgcctcac ttttatttat 720
tgctggtttt cctgggacag ctggagctgt gtcccttagc ctttcagagg cttggtgttc 780
agggccctcc ctgcactccc ctcttgctgc gtgttgattt ggaggcactg cagtccaggc 840
cgagtcctca gtgcggggag caggctgctg ctgctgactc tgtgcagctg cgcacctgtg 900
tcccccacct ccaccctcaa cccatcttcc tagtgtttgt gaaataaact tggtatttgt 960
ctgggtcagt gcaaaaaaa 979

<210> SEQ ID NO 6
<211> LENGTH: 1727
<212> TYPE: DNA
<213> ORGANISM: Homo sapiens

<400> SEQUENCE: 6
gcgcaactcg tttgcagcgg cgcagcccag acgcgcctgc agctggggct caccccaacc 60
tcgctgccag ccgagaactc caagatggga ggcaagctca gcaagaagaa gaagggctac 120
aatgtgaacg acgagaaagc caaggagaaa gacaagaagg ccgagggcgc ggcgacggaa 180

-continued

```
gaggaggggga ccccgaagga gagtgagccc caggcggccg cagagcccgc cgaggccaag    240

gagggcaagg agaagcccga ccaggacgcc gagggcaagg ccgaggagaa ggagggcgag    300

aaggacgcgg cggctgccaa ggaggaggcc ccgaaggcgg agcccgagaa gacggagggc    360

gcggcagagg ccaaggctga gcccccgaag gcgcccgagc aggagcaggc ggcccccggc    420

cccgctgcgg gcggcgaggc cccccaaagct gctgaggccg ccgcggcccc ggccgagagc    480

gcggcccctg ccgccgggga ggagcccagc aaggaggaag gggaacccaa aaagactgag    540

gcgcccgcag ctcctgccgc ccaggagacc aaaagtgacg gggccccagc ttcagactca    600

aaacccggca gctcggaggc tgccccctct tccaaggaga cccccgcagc cacggaagcg    660

cctagttcca cacccaaggc ccagggcccc gcagcctctg cagaagagcc caagccggtg    720

gaggccccgg cagctaattc cgaccaaacc gtaaccgtga aagagtgaca aggacagcct    780

ataggaaaaa caataccact taaaacaatc tcctctctct ctctctctct ctctctctat    840

ctctctctct atctcctctc tctctctcct ctcctatctc tcctctctct ctctcctata    900

ctaacttgtt tcaaattgga agtaatgata tgtattgccc aaggaaaaat acaggatgtt    960

gtcccatcaa gggagggagg gggtgggaga atccaaatag tattttttgtg gggaaatatc    1020

taatatacct tcagtcaact ttaccaagaa gtcctggatt tccaagatcc gcgtctgaaa    1080

gtgcagtaca tcgtttgtac ctgaaactgc cgccacatgc actcctccac cgctgagagt    1140

tgaatagctt ttcttctgca atgggagttg ggagtgatgc gtttgattct gcccacaggg    1200

cctgtgccaa ggcaatcaga tctttatgag agcagtattt tctgtgtttt ctttttaatt    1260

tacagccttt cttattttga tattttttta atgttgtgga tgaatgccag ctttcagaca    1320

gagcccactt agcttgtcca catggatctc aatgccaatc ctccattctt cctctccaga    1380

tatttttggg agtgacaaac attctctcat cctacttagc ctacctagat ttctcatgac    1440

gagttaatgc atgtccgtgg ttgggtgcac ctgtagttct gtttattggt cagtggaaat    1500

gaaaaaaaaa aaaaaaaaaa gtctgcgttc attgcagttc cagtttctct tccattctgt    1560

gtcacagaca ccaacacacc actcattgga aaatggaaaa aaaaaacaaa aaaaaaacaa    1620

aaaaatgtac aatggatgca ttgaaattat atgtaattgt ataaatggtg caacagtaat    1680

aaagttaaac aattaaaaag aagtaataaa gacaaaaaaa aaaaaaa                    1727
```

```
<210> SEQ ID NO 7
<211> LENGTH: 2852
<212> TYPE: DNA
<213> ORGANISM: Homo sapiens

<400> SEQUENCE: 7
```

```
caaggctggg accagaaacc aggactgttg actgcagccc ggtattcatt ctttccatag     60

cccacagggc tgtcaaagac cccagggcct agtcagaggc tcctccttcc tggagagttc    120

ctggcacaga agttgaagct cagcacagcc ccctaacccc caactctctc tgcaaggcct    180

caggggtcag aacactggtg gagcagatcc tttagcctct ggattttagg gccatggtag    240

agggggtgtt gccctaaatt ccagccctgg tctcagccca acaccctcca agaagaaatt    300

agaggggcca tggccaggct gtgctagccg ttgcttctga gcagattaca agaagggact    360

aagacaagga ctcctttgtg gaggtcctgg cttagggagt caagtgacgg cggctcagca    420

ctcacgtggg cagtgccagc ctctaagagt gggcaggggc actggccaca gagtcccagg    480

gagtcccacc agcctagtcg ccagaccttc tgtgggatca tcggacccac ctggaacccc    540
```

-continued

```
acctgctggc cctcacggaa gaacaacagc tgatgtttga gaaactgact ctgtattgcg    600
acagctacat ccagctcatc cccatttcct tcgtgctggg cttctacgtg acgctggtcg    660
tgacccgctg gtggaaccag tacgagaacc tgccgtggcc cgaccgcctc atgagcctgg    720
tgtcgggctt cgtcgaaggc aaggacgagc aaggccggct gctgcggcgc acgctcatcc    780
gctacgccaa cctgggcaac gtgctcatcc tgcgcagcgt cagcaccgca gtctacaagc    840
gcttccccag cgcccagcac ctggtgcaag caggctttat gactccggca gaacacaagc    900
agttggagaa actgagccta ccacacaaca tgttctgggt gccctgggtg tggtttgcca    960
acctgtcaat gaaggcgtgg cttggaggtc gaatccggga ccctatcctg ctccagagcc   1020
tgctgaacga gatgaacacc ttgcgtactc agtgtggaca cctgtatgcc tacgactgga   1080
ttagtatccc actggtgtat acacaggtgg tgactgtggc ggtgtacagc ttcttcctga   1140
cttgtctagt tgggcggcag tttctgaacc cagccaaggc ctaccctggc catgagctgg   1200
acctcgttgt gcccgtcttc acgttcctgc agttcttctt ctatgttggc tggctgaagg   1260
tggcagagca gctcatcaac ccctttggag aggatgatga tgattttgag accaactgga   1320
ttgtcgacag gaatttgcag gtgtccctgt tggctgtgga tgagatgcac caggacctgc   1380
ctcggatgga gccggacatg tactggaata agcccgagcc acagcccccc tacacagctg   1440
cttccgccca gttccgtcga gcctccttta tgggctccac cttcaacatc agcctgaaca   1500
aagaggagat ggagttccag cccaatcagg aggacgagga ggatgctcac gctggcatca   1560
ttggccgctt cctaggcctg cagtcccatg atcaccatcc tcccagggca aactcaagga   1620
ccaaactact gtggcccaag agggaatccc ttctccacga gggcctgccc aaaaaccaca   1680
aggcagccaa acagaacgtt aggggccagg aagacaacaa ggcctggaag cttaaggctg   1740
tggacgcctt caagtctgcc ccactgtatc agaggccagg ctactacagt gccccacaga   1800
cgcccctcag ccccactccc atgttcttcc ccctagaacc atcagcgccg tcaaagcttc   1860
acagtgtcac aggcatagac accaaagaca aaagcttaaa gactgtgagt tctggggcca   1920
agaaaagttt tgaattgctc tcagagagcg atggggcctt gatggagcac ccagaagtat   1980
ctcaagtgag gaggaaaact gtggagttta acctgacgga tatgccagag atccccgaaa   2040
atcacctcaa agaacctttg gaacaatcac caaccaacat acacactaca ctcaaagatc   2100
acatggatcc ttattgggcc ttggaaaaca ggtctgtcct ccacctgaac caggggcact   2160
gcattgccct gtgccccacc ccagcttccc ttgctctgag cctacccttc ctccacaatt   2220
tcctagggtt ccatcactgc cagagcacac tggacctacg cccagcactg gcttggggta   2280
tatacttggc caccttcaca gggatcctag ggaagtgttc gggacctttt ctcacttcac   2340
cctggtatca cccggaagac ttcttgggac caggtgaagg aagatgaggt tgtgctgacc   2400
agaatgctgc tggagaactg ccccagggct gacaggccag gcttagctga gcagatgtta   2460
tcactggccc caacttactt tgagcaaggg tggctgaccc aaaaccatga ggtggcagtc   2520
agctggatga cagatgaaca cttcccccat aactatttag ggtagtaccc aagcactaca   2580
ggaaagggtg gcaggaactg cctcactcct aggaactggt agatggtgag gttgagggtg   2640
tccagcgccc ttaggtcatt ttctcactgc ctgggaacct caccaaaata cttcttgctt   2700
ccttggggtc agcccaaagc tgtcacaaaa tcagatattt ccctttattc cagatttcct   2760
ggacactttc acccaattat aaacacccca cttcagcccc aatcacgtgg gaggaagtgt   2820
aacttccctt ttaaaaaaaa aaaaaaaaaa aa                                 2852
```

-continued

<210> SEQ ID NO 8
<211> LENGTH: 1238
<212> TYPE: DNA
<213> ORGANISM: Homo sapiens

<400> SEQUENCE: 8

```
agactaggat ccctggaaaa tggagaagct gtgctaatag aggggggcca gaaatcccca     60

ctctagaatg ctgtagaatg ttgggagaca cccaggatgt gagccaggga ctttctggaa    120

gtgtttgttc tggccccacc cgaccccagg cagtccccag ctgtctgcac agtcggatgg    180

ggagggggct tgcacagagt tggagccaga ggagagagct ggctcatccc ctacggtagg    240

atggggaaac ctcacagacc acattgtcac ccggcctcag ctctccgccc cggcgctcag    300

agggtaactc tcacccacct cgtccgcttc tctgaaccag agtgacccag gctgcgctcc    360

gccccgctct cctaccccga gttggcacgg aggcccggca gccatggcgg tggaaggagg    420

aatgaaatgt gtgaagttct tgctctacgt cctcctgctg gccttttgcg cctgtgcagt    480

gggactgatt gccgtgggtg tcggggcaca gcttgtcctg agtcagacca taatccaggg    540

ggctacccct ggctctctgt tgccagtggt catcatcgca gtgggtgtct tcctcttcct    600

ggtggctttt gtgggctgct gcggggcctg caaggagaac tattgtctta tgatcacgtt    660

tgccatcttt ctgtctctta tcatgttggt ggaggtggcc gcagccattg ctggctatgt    720

gtttagagat aaggtgatgt cagagtttaa taacaacttc cggcagcaga tggagaatta    780

cccgaaaaac aaccacactg cttcgatcct ggacaggatg caggcagatt ttaagtgctg    840

tggggctgct aactacacag attgggagaa aatcccttcc atgtcgaaga accgagtccc    900

cgactcctgc tgcattaatg ttactgtggg ctgtgggatt aatttcaacg agaaggcgat    960

ccataaggag ggctgtgtgg agaagattgg gggctggctg aggaaaaatg tgctggtggt   1020

agctgcagca gcccttggaa ttgcttttgt cgaggttttg ggaattgtct ttgcctgctg   1080

cctcgtgaag agtatcagaa gtggctacga ggtgatgtag ggtctggtc tcctcagcct   1140

cctcatctgg gggagtggaa tagtatcctc caggtttttc aattaaacgg attatttttt   1200

cagaccgaaa agagatggtc tgagtttgtc ttagagtg                          1238
```

<210> SEQ ID NO 9
<211> LENGTH: 1790
<212> TYPE: DNA
<213> ORGANISM: Homo sapiens

<400> SEQUENCE: 9

```
taattacaaa aactaatgac taagagagag gtggctagag ctgaggcccc tgagtcaggc     60

tgtgggtggg atcatctcca gtacaggaag tgagactttc atttcctcct ttccaagaga    120

gggctgaggg agcagggttg agcaactggt gcagacagcc tagctggact ttgggtgagg    180

cggttcagcc atgaggctgg ctgtgctttt ctcgggggcc ctgctggggc tactggcaga    240

gagcactgga acaaccagcc acaggactac caagagccac aaaaccacca ctcacaggac    300

aaccaccaca ggcaccacca gccacggacc cacgactgcc actcacaacc ccaccaccac    360

cagccatgga aacgtcacag ttcatccaac aagcaatagc actgccacca gccagggacc    420

ctcaactgcc actcacagtc ctgccaccac tagtcatgga aatgccacgg ttcatccaac    480

aagcaacagc actgccacca gcccaggatt caccagttct gcccacccag aaccacctcc    540

accctctccg agtcctagcc caacctccaa ggagaccatt ggagactaca cgtggaccaa    600

tggttcccag ccctgtgtcc acctccaagc ccagattcag attcgagtca tgtacacaac    660
```

ccagggtgga ggagaggcct ggggcatctc tgtactgaac cccaacaaaa ccaaggtcca 720
gggaagctgt gagggtgccc atccccacct gcttctctca ttcccctatg gacacctcag 780
ctttggattc atgcaggacc tccagcagaa ggttgtctac ctgagctaca tggcggtgga 840
gtacaatgtg tccttccccc acgcagcaca gtggacattc tcggctcaga atgcatccct 900
tcgagatctc caagcacccc tggggcagag cttcagttgc agcaactcga gcatcattct 960
ttcaccagct gtccacctcg acctgctctc cctgaggctc caggctgctc agctgcccca 1020
cacaggggtc tttgggcaaa gtttctcctg ccccagtgac cggtccatct tgctgcctct 1080
catcatcggc ctgatccttc ttggcctcct cgccctggtg cttattgctt tctgcatcat 1140
ccggagacgc ccatccgcct accaggccct ctgagcattt gcttcaaacc ccagggcact 1200
gagggggttg ggtgtggtg ggggggtacc cttatttcct cgacacgcaa ctggctcaaa 1260
gacaatgtta ttttccttcc ctttcttgaa gaacaaaaag aaagccgggc atgacggctc 1320
atgcctgtaa tcccagcact ttgggaggct gaggcaggtg gatcactgga ggtcaggagt 1380
ttgagaccag cctggccaac atggtgaaac cctgtctcta ctaaaaatac aattagccag 1440
gtgtggcggc gtaatcccag ctggcctgta atcccagcta cttgggaggc tgaggcagaa 1500
ctgcttgaac ccaggaggtg gaggttgcag tgagccgtca tcgcgccact aagccaagat 1560
cgcgccactg cactccagcc tgggcgacag agccagactg tctcaaataa ataaatatga 1620
gataatgcag tcgggagaag ggagggagag aattttatta aatgtgacga actgcccccc 1680
cccccccccc agcaggagag cagcaaaatt tatgcaaatc tttgacgggg ttttccttgt 1740
cctgccagga ttaaaagcca tgagtttctt gtcaaaaaaa aaaaaaaaaa 1790

<210> SEQ ID NO 10
<211> LENGTH: 6017
<212> TYPE: DNA
<213> ORGANISM: Homo sapiens

<400> SEQUENCE: 10
gggcggggct cgggccggtc cgcccgcgcg caggtgagtg agccagggcg gagcgcagct 60
gcgccgggct tgggcgcctg gggccgccgc tccccaccgt cgttttcccc accgaggccg 120
aggcgtcccg gagtcatggc cggcctgaac tgcggggtct ctatcgcact gctaggggtt 180
ctgctgctgg gtgcggcgcg cctgccgcgc ggggcagaag cttttgagat tgctctgcca 240
cgagaaagca acattacagt tctcataaag ctggggaccc cgactctgct ggcaaaaccc 300
tgttacatcg tcatttctaa aagacatata accatgttgt ccatcaagtc tggagaaaga 360
atagtcttta cctttagctg ccagagtcct gagaatcact ttgtcataga gatccagaaa 420
aatattgact gtatgtcagg cccatgtcct tttggggagg ttcagcttca gccctcgaca 480
tcgttgttgc ctaccctcaa cagaactttc atctgggatg tcaaagctca taagagcatc 540
ggtttagagc tgcagttttc catccctcgc ctgaggcaga tcggtccggg tgagagctgc 600
ccagacggag tcactcactc catcagcggc cgaatcgatg ccaccgtggt caggatcgga 660
accttctgca gcaatggcac tgtgtcccgg atcaagatgc aagaaggagt gaaaatggcc 720
ttacacctcc catggttcca ccccagaaat gtctccggct tcagcattgc aaaccgctca 780
tctataaaac gtctgtgcat catcgagtct gtgtttgagg gtgaaggctc agcaaccctg 840
atgtctgcca actacccaga aggcttccct gaggatgagc tcatgacgtg gcagtttgtc 900
gttcctgcac acctgcgggc cagcgtctcc ttcctcaact tcaacctctc caactgtgag 960
aggaaggagg agcgggttga atactacatc ccgggctcca ccaccaaccc cgaggtgttc 1020
aagctggagg acaagcagcc tgggaacatg gcggggaact tcaacctctc tctgcaaggc 1080
tgtgaccaag atgcccaaag tccagggatc ctccggctgc agttccaagt tttggtccaa 1140
catccacaaa atgaaagcaa taaaatctac gtggttgact tgagtaatga gcgagccatg 1200
tcactcacca tcgagccacg gcccgtcaaa cagagccgca agtttgtccc tggctgtttc 1260
gtgtgtctag aatctcggac ctgcagtagc aacctcaccc tgacatctgg ctccaaacac 1320
aaaatctcct tcctttgtga tgatctgaca cgtctgtgga tgaatgtgga aaaaaccata 1380
agctgcacag accaccggta ctgccaaagg aaatcctact cactccaggt gcccagtgac 1440
atcctccacc tgcctgtgga gctgcatgac ttctcctgga agctgctggt gcccaaggac 1500
aggctcagcc tggtgctggt gccagcccag aagctgcagc agcatacaca cgagaagccc 1560
tgcaacacca gcttcagcta cctcgtggcc agtgccatac ccagccagga cctgtacttc 1620
ggctccttct gcccgggagg ctctatcaag cagatccagg tgaagcagaa catctcggtg 1680
acccttcgca cctttgcccc cagcttccaa caagaggcct ccaggcaggg tctgacggtg 1740
tcctttatac cttatttcaa agaggaaggc gttttcacgg tgacccctga cacaaaaagc 1800
aaggtctacc tgaggacccc caactgggac cggggcctgc catccctcac ctctgtgtcc 1860
tggaacatca gcgtgcccag agaccaggtg gcctgcctga ctttctttaa ggagcggagc 1920
ggcgtggtct gccagacagg gcgcgcattc atgatcatcc aggagcagcg gacccgggct 1980
gaggagatct tcagcctgga cgaggatgtg ctccccaagc caagcttcca ccatcacagc 2040
ttctgggtca acatctctaa ctgcagcccc acgagcggca agcagctaga cctgctcttc 2100
tcggtgacac ttaccccaag gactgtggac ttgactgtca tcctcatcgc agcggtggga 2160
ggtggagtct tactgctgtc tgccctcggg ctcatcattt gctgtgtgaa aaagaagaaa 2220
aagaagacaa acaagggccc cgctgtgggt atctacaatg acaacatcaa tactgagatg 2280
ccgaggcagc caaaaaagtt tcagaaaggg cgaaaggaca atgactccca tgtgtatgca 2340
gtcatcgagg acaccatggt atatgggcat ctgctacagg attccagcgg ctccttcctg 2400
cagccagagg tggacaccta ccggccgttc cagggcacca tgggggtctg tcctccctcc 2460
ccacccacca tatgctccag ggccccaact gcaaagttgg ccactgagga gccacctcct 2520
cgctcccctc ctgagtctga gagtgaaccg tacaccttct cccatcccaa caatggggat 2580
gtaagcagca aggacacaga cattccctta ctgaacactc aggagcccat ggagccagca 2640
gaataacttg atccattcca gacgctttgc tgagtttcat aaagcagggc actgagacac 2700
ccgtccgtgt tcctaaccag aaatcctaaa gaagaggaat tatacagaag gaacagcagg 2760
aggttttcct ggacaccgcc aacttcacat tgctcagtgg actcattcta agggcaagac 2820
attgaaaatg atgaattcca atctggatac agtcatgaca gctcatgtgc tcctcaactt 2880
aggctgtgcg gttagccagc ctgtaatgag aggagagagg cctgagtcac ctagcatagg 2940
gttgcagcaa gccctggatt cagagtgtta aacagaggct tgccctcttc aggacaacag 3000
ttccaattcc aaggagccta cctgaggtcc ctactctcac tggggtcccc aggatgaaaa 3060
cgacaatgtg ccttttttatt attatttatt tggtggtcct gtgttattta agagatcaaa 3120
tgtataacca cctagctctt ttcacctgac ttagtaataa ctcatactaa ctggtttgga 3180
tgcctgggtt gtgacttcta ctgaccgcta gataaacgtg tgcctgtccc ccaggtggtg 3240
ggaataattt acaatctgtc caaccagaaa agaatgtgtg tgtttgagca gcattgacac 3300
atatctgctt tgataagaga cttcctgatt ctctaggtcg gttcgtggtt atcccattgt 3360

-continued

```
ggaaattcat cttgaatccc attgtcctat agtcctagca ataagagaaa tttcctcaag   3420
tttccatgtg cggttctcct agctgcagca atactttgac atttaaagag aaatttagag   3480
aatattctca tcctctaaaa atgtttaaat atataccaaa cagtggcccc ctgcattagt   3540
tttctgttgc cactgcaacc tattacttgg tagcttaaaa acaacacatt agcttatagt   3600
cctggggatc agaattccaa aatggatgtc cctgaatgaa aatcaaggtg tcagcagagc   3660
tgtgctcctt ctgaaggctc tagggagaag ccggttcctt gccatttcaa gcttctagag   3720
gctggctgca ttcccaggct ccagtggctg gtcaagcttt tctcacatgg catcactgtg   3780
acactggccc tcccacttcc ctctttgact tacaaagccc accaggaaga tccaggataa   3840
tctctccatc taaagttcct tcatcatcct ggaagagcct tttgccatgc aagacaacat   3900
agccacaggt ggggattagg accagaacat ctttggggtg ctgttattct gcctaccaca   3960
ccttcctgcc actgactccc acaggagagg ctacaaaatg atctggcgca cagggatgtt   4020
ttgtttagct tgcggactct aacacttaaa aaaaaaccca gatcagaaga tctggccatg   4080
ctggggctca cattctcacc tagcaacaac tggctggagc tgggcaccag ctctgccttt   4140
agaaggggtg tccacttcac caggtcacca cagcccacac tacgccctat cacttcccac   4200
aatgaggctg agtgtttgtt tctactgatc aatgcccctg caggttgcat ttattgtaat   4260
gaaaaagaaa gactgggatt aatctctaat caggtgagta gaccatgaga ccaatgtgtg   4320
ctcacattac cctttttctt tttttctttt ttctttttct tttttttttt aatgtgagac   4380
aggatctcat tctgttgcct aggctggagt gcagtggcgc aatctcggct cactgcaacc   4440
tctgcctcct gggctcaagc aattctccca cctcagcctc ccaaatagct gggatcactg   4500
gcacaaacca ccatgcccag ctaattttgt atttttttgta gagacagggt ttcaccatgt   4560
tgcccaggct ggtctcaacc tcctgggctc aagcaatcct cctgcctcgg cctcccaaag   4620
tgctgggatt acagatgtga gccaccgcat ccagccccac accctcattt ataccaatta   4680
cctgcccagt aactgtggac ttttgcttcc tcacccctgc tctgatctgg aaggagaggg   4740
attatgttat agcttgtcag cacagtccca agttcaatat ttctgcggca aaaacttcct   4800
tcaaaaaata aatgtacttc attgtattca atgaattcac cttggaaatg caccgcctca   4860
acttgttcac atggcataaa tgaaaggaat tttatagtct cctaaatggc gtgtactgca   4920
agacctcttg aacactttcc agaggatagg atatttaagt catgcccttg gcgttgccta   4980
tggcaccttt cccttctgaa agtctggttc ctgcccagtg acccttggcc ttgtgagccg   5040
agatgctgac cctgcataaa gggccaaagg agggctgcgg cttccttccc tcactgaaga   5100
gcccttattt gaattcactg tgtggagccc tagccctcca ttctcgacat tccccaacct   5160
cccagcccct tccaagcagg actaggtgcc ctgcattcca cccaaggtgg gattggcctt   5220
ccttaggctg gctacttgtc accatcaccg acatcactgt tgcctgcaag gacaccacgt   5280
ggccattttc cttcaactga gggctcaaaa ctcctggaca agttgctggc tcctgagacc   5340
agtatttcct ggagctgtgc ctcagtgaag gggcccagcc tgaggaaccc tggctctttt   5400
ctttaaagcc caggccccac ttacgtaaaa catttcaggg tcactggaaa cagtgaagtg   5460
ccatttgttg aagcctactg catgccagcc cactgctcat ccacgtggtc tgccatgcct   5520
acgaggaagg ccagcgcatg caggactggt ctctaatgct gtggtcattg cacagaaggg   5580
aaaggtctca aggaagagtc aactggaaca agcacaagcc caccggacat ggccttggta   5640
aaggttagca gactggtgtg tgtggatctg cagtgcttca ctggaaataa tttattcatt   5700
gcagatactt tttaggtggc attttattca tttcctgtgc tttaaataaa caaatgtacc   5760
```

-continued aaaaaacaag tatcaagctg tttaagtgct tcggctactt gtcccctggt tcagtagagg 5820
ccccggtttc ccagttgttg actgtgacag gctcagcatg ggctcagcag atgctgtctt 5880
aatttgtgga tgatacagaa agccaggctt tgggatacaa gttctttcct cttcatttga 5940
tgccgtgcac tgtgtgaagc agatgttttt gtccggaaat aaaaataata gtcttggagt 6000
ctcgccaaaa aaaaaaa 6017

<210> SEQ ID NO 11
<211> LENGTH: 6651
<212> TYPE: DNA
<213> ORGANISM: Homo sapiens

<400> SEQUENCE: 11
ataacacccg gccccgccgg gcggccgcgg gtgggtagag aacatggact tcccgtgcct 60
ctggctaggg ctgttgctgc ctttggtagc tgcgctggat ttcaactacc accgccagga 120
agggatggaa gcgtttttga agactgttgc ccaaaactac agttctgtca ctcacttaca 180
cagtattggg aaatctgtga aaggtagaaa cctgtgggtt cttgttgtgg ggcggtttcc 240
aaaggaacac agaattggga ttccagagtt caaatacgtg gcaaatatgc atggagatga 300
gactgttggg cgggagctgc tgctccatct gattgactat ctcgtaacca gtgatggcaa 360
agaccctgaa atcacaaatc tgatcaatag tacccggata cacatcatgc cttccatgaa 420
cccagatgga tttgaagccg tcaaaaagcc tgactgttat tacagcatcg gaagggaaaa 480
ttataaccag tatgacttga atcgaaattt ccccgatgct tttgaatata ataatgtctc 540
aaggcagcct gaaactgtgg cagtcatgaa gtggctgaaa acagagacgt ttgtcctctc 600
tgcaaacctc catggtggtg ccctcgtggc cagttaccca tttgataatg gtgttcaagc 660
aactggggca ttatactccc gaagcttaac gcctgatgat gatgtttttc aatatcttgc 720
acatacctat gcttcaagaa atcccaacat gaagaaagga gacgagtgta aaaacaaaat 780
gaactttcct aatggtgtta caaatggata ctcttggtat ccactccaag gtggaatgca 840
agattacaac tacatctggg cccagtgttt tgaaattacg ttggagctgt catgctgtaa 900
atatcctcgt gaggagaagc ttccatcctt ttggaataat aacaaagcct cattaattga 960
atatataaag caggtgcacc taggtgtaaa gggtcaagtt tttgatcaga atggaaatcc 1020
attacccaat gtaattgtgg aagtccaaga cagaaaacat atctgcccct atagaaccaa 1080
caaatatgga gagtattatc tccttctctt gcctgggtct tatataataa atgttacagt 1140
ccctggacat gatccacaca tcacaaaggt gattattccg gagaaatccc agaacttcag 1200
tgctcttaaa aaggatattc tacttccatt ccaagggcaa ttggattcta tcccagtatc 1260
aaatccttca tgcccaatga ttcctctata cagaaatttg ccagaccact cagctgcaac 1320
aaagcctagt ttgttcttat ttttagtgag tcttttgcac atattcttca aataaagtaa 1380
aatgtgaaac tcaacccaca tcaccacctg gaatcaggga ttgctcactc caggttactg 1440
caaccctaac tcactctagt gggaccttga ctggagaaac tccacgatct tcctgaagaa 1500
gagaaatgga tgtttccaaa ttccacaata agcaatatgt ggtgataatg aaaagaatga 1560
ttcagtcttg acggtgaatg gaagacactt acctaacaag tactgctcat ttacactcaa 1620
attaatcttg aagtagtctt aaaatgtgta agaagttaaa acttgagaag caaaaaaatg 1680
cctgcaaaaa gaagatcatt ttgtatacag agaaccggat gaatataagc aatgaagatg 1740
aacatttatt gatcttctac atacaagact tcaccataag gccaggagca gtggctcaca 1800

-continued ccttgtaatc ccagcacttt gggaggccaa ggtgggcgga tcaccctgag gtcaggagtt 1860
caaaaccagc ctgaccaaca tggtgaaacc ctgtctctac taaatattag cggggtgtgg 1920
tggcgggcac ctgtaatcgc agcctttcag gaggctgaga caggagaatc gcttgaaccc 1980
tagaggcgga gtttgcagtg agccgagata gtgccattgt actccagctt gggcaacaga 2040
gtaagactct gtctcaaaaa aaaaaaaaca aaaacaaaca aacaaaaaaa acacctcacc 2100
atgagtgcta catgtgaata gatattaagt gccatatata attagttctc agaagaaggg 2160
agaaatgatc ataggactgg gaattgtttt gcaaacgttc taggagatgt gagagaaaat 2220
atgtaaccac atcttagtgg cccaagaaaa tacaggcctg aagggataag attgtgtctc 2280
tatagagctt caaagcatac aggtcaatta agaaagcccc tctctctcca gagccgtttc 2340
cctagctttt ggcacctgga tgccacagtc ctccattagg ctgatgactc caaagatgta 2400
actctagcct cttgcctgag cttcagactc gcgtcccact gcccacagga cacatccacc 2460
tggatgtgac tcacaggtac ctccaaccca tcatgtggag atactcatcc tgttcccccct 2520
agagctgctc ttcctgctgc attctctctc tcaattactg ggaccaccaa gctaggaacc 2580
tgggagtcat ccttgatact ttctcttcct ccttaatcct gtgtattcag caagtaacta 2640
aaggttggtg ttggccaggc atggtggctc atgcctgtaa tcccagcatt ttgggaggcc 2700
aaggcgggcg gatcacttga ggtcaggagc tcaagaccag cctggccaac atggtgaaac 2760
cccatctcta ctaaaaaaaa aaaaaaaatt agtcgggcgt ggtggtgcat gcctgtaatc 2820
ccagctactg gggaggctga ggcaggagaa tcgcttgaac ctgggaggca gaggttgcag 2880
tgagccggga ttgcgccatt gtactccagc ctgggtgaag aagtgagact ctgtcttaaa 2940
aaaaaaaatt ggtgctgata aatattgatg aattctgctc tctgctctct atggttgtca 3000
acactgcaga gttgaggcct catatctcac ctgcactgct gcaacagctt actggtccct 3060
tgctcccagc cttctcctct tcagtccatc gtccacacag cactggggaa ggggagccac 3120
ttgaaacaaa agtcaacaac tggttgtagt tcataaacac agagctgttt gtgtcccctg 3180
tatctggaat gccattatga cccactacat tttttcttc ctacccctct taaaactcag 3240
ttcaggtagc agctccacta ggaagccttg gctgaccata atcccattca attccatttc 3300
acctcttcgc aggcagtctg gggttaggga ccctttctct ttgctcccca aaataaactg 3360
gttatctcta ctattggatt tacaacattg tattataatc ttctccatgt gtgccttctc 3420
tagtagaatg tgagctcttt gaggccaagg tctatttaat ttgtttgaaa aattcattgt 3480
tatatcctca aagcctagca catagtaggt actgaatgaa tgaatgaaca aggggtgcca 3540
ggagactgct actcccagtc cttcccagaa actgcctagg gctttgagtc attttatgaa 3600
gctaggtctt aatgcgtagg caacctccca gctcactatg aacgctgaca gaagagtgtt 3660
ttcatgtcta taatcaagaa ttccagatac attcctttta ctgaaccttg aattgatcct 3720
aagattggta gtaaaggtat tatgttacct cctaacagca ctacaaagta cctttttta 3780
tcagaaaaaa attttaccat taggactcaa tttgaagtac taatgcttct caagttctcc 3840
actatgagag ttaccctgta ttagaccgtt acctataaga attaaggggt aaagcactaa 3900
acagaaaaga aaaaaaaaat agcaactctg gtgagcagat ttctttcctt tcttccttcc 3960
ttctcctctt cctaccttcc tccctccttt ccctctcctc cccttctctc cctttccctc 4020
cccttccctt ccttttcttc tttcctccgc tcccctcccc ttccctcccc ttcccatcct 4080
tctttctctt ttttttactt aatccccagt gtgacagtaa tataggctga tttctagaag 4140
tgtggtgtat tactcatgga aagtgagttg ccttggttat tactttcaat tgaaagttct 4200
atgggatcta gaaatgagac atactggcat ggagagtgag aacgacaaag gaatgaagag 4260
ctacaggagc atttaggcca tttctatgcc aagcttattc tacatgcaca aaatcataca 4320
tgttaataaa tataaacaaa ttggaggctt atttaaacca attatgaaat ctggtaattt 4380
gtgcagcagc aatagatgat aaccaaaaaa aactcataat aatctgaata tcttgatcat 4440
ttgtatttaa agaagcagta attatatact tgaaagtaca taatatagta ttgcaaaaat 4500
gactttggta tattacaaat taaaagtata taagatgaaa cttgatttgc tatcaagccc 4560
caagcaattt ttcaactggg cattgaattc taacttttct aagatagcaa tttttgaaga 4620
gacacgaaca aaaatctgaa ttagttcatg agccttaatg taaatctctt gctgaaatag 4680
tttttaaaat cagaatttag ttatctatca gactcaaaat catttaaaga ctaacaaaac 4740
acaatcatga tattctaact gtggtcaaac caggtaccca agccacctcc ctgcccaacg 4800
cctttccggc ttttcccctc cctcttgggc tggtggttat gctcctccag ctctagttca 4860
gctataattc cttttataga gaaaccaacc tgatacacac tttcatgatg ggagaaaaat 4920
gtgggagtga aatggtattt agaaagcagc agtcaggcac ggtggctcat gcctgtaatc 4980
ccagcacttt gggaggctga ggcaggcgga tcacttgagg tcaggagctc gagaccagcc 5040
tggccaacac ggtgaaaccc catctctact aaaaaaaaat acaaaaatta gccgggcgtg 5100
gtggcaggca cctgtaatcc cagctacttg ggaggctgag gcaggagaaa tcgcctgaac 5160
ccagaaggca gaggttgcag tgagccaaga tcacatcact gcactgcact ccagccgggg 5220
tgacagagcg aacctctgtc tcaaaaaaaa aaaaagaaaa aagaaagaaa gaaaaaaggc 5280
agaagccctg gattcaaatc cgccacacat tcagtttctt tatctgtaaa atggagacca 5340
ccccccgcca cgctgaacgg tgattctgtg actggtaaga gatgctacat ttttggtgct 5400
tgttcaggtg gaggaaagat gatagttaac actcaggtaa taagtatttt gaaggcagta 5460
taatatacct tcttaaagag tatacctact caaatgttgg taaatgttga catgattgaa 5520
tctaaatggc aaagagtatt ttagaaaaac attaagtccc tgcagataaa tgacagtgtt 5580
gatttggatg cttaattaca ttcagacatg aactgttgga tgtatctgaa atgttaaaag 5640
ctttttctca acatttccaa aagtctttcc aagaaatcaa tgttatgttt tgttccagaa 5700
gcaaatttgc atttgtgatc tgtttctaaa aatggtacaa gttagctctg tttagaaagt 5760
aaaaatatct gatgttagat tggaagtatc tcttcctggg gaatccagaa agataagcat 5820
agcatattgt cttactgcaa tagataagtt gcttattgag aagtctggtt gttattctat 5880
atggtaacaa tacagttgat gtatatttta tgatagatcc tttatatttt cctcatgact 5940
ttagaagggg gaagggggag aaaattatga tgaccagact agttaaagag cattgaaagt 6000
ccacagtact gtagctaaag tagaagtttg ggtttgttat agactttaca ttatatcaac 6060
taataagcag atactgtaca gtattgctca ccattttatc atacttttgc atatgaacta 6120
ctccattgcc ttttatagat gttttatagc tgatcttacc agttttcctg gtaacttttt 6180
ttatttcttt tttttttttt tgagacggag tctcgcccta acacccaggt tggagtgcag 6240
tgccgtgatc tcggctcact gcaacctctg cctcccgggt tcaagcaatt ctcctgtctc 6300
agcctcccga gtacctggga ctaccggtgc ctgtctccac gcccggctaa tttttgtat 6360
ttgtagtaga gacggggttt caccgtgtta gccaggatgg tctcgatctc ctgacctcat 6420
gatctgcctg cctctgcctg gacctcccaa agtgctggga ttacaggcgt gagcccccgc 6480
gcccagccac tttctttaat actataacta agaatttatt aaaatgcaca aattgtctaa 6540

-continued gactgtaaag tttattgggg agaggccatg actacctctg aatttagtaa atttaaaata 6600
tttctgattc tcaataaaga actaatatcc atataaaaaa aaaaaaaaaa a 6651

<210> SEQ ID NO 12
<211> LENGTH: 3055
<212> TYPE: DNA
<213> ORGANISM: Homo sapiens

<400> SEQUENCE: 12
atttccggag ggggaggccc gcggctgccg ccgccatttc gggcgctgct gtgaagctga 60
aaccggagcc ggtccgctgg gcggcgggcg ccgggggccg gaggggcgcg cgcggcggcg 120
gcaccccagc gtttaggcgc ggaggcagcc atggcgggca acttcgactc ggaggagcgg 180
agtagctggt actgggggag gttgagtcgg caggaggcgg tggcgctgct gcagggccag 240
cggcacgggg tgttcctggt gcgggactcg agcaccagcc ccggggacta tgtgctcagc 300
gtctcagaga actcgcgcgt ctcccactac atcatcaaca gcagcggccc gcgcccgccg 360
gtgccaccgt cgcccgccca gcctccgccc ggggtgagcc cctccagact ccgaatagga 420
gatcaagagt ttgattcatt gcctgcttta ctggaattct acaaaataca ctatttggac 480
actacaacgt tgatagaacc agtttccaga tccaggcagg gtagtggagt gattctcagg 540
caggaggagg cggagtatgt gcgagccctc tttgacttta atgggaatga tgaggaagat 600 cttccccttta agaaaggaga catcttgaga atccgggaca agcctgaaga gcagtggtgg 660
aatgcggagg acagcgaagg caagagaggg atgattccag tcccttacgt cgagaagtat 720
agacctgcct ccgcctcagt atcggctctg attggaggtc ggtgagctgg taaaggttac 780
gaagattaat gtgagtggtc agtgggaagg ggagtgtaat ggcaaacgag gtcacttccc 840
attcacacat gtccgtctgc tggatcaaca gaatcccgat gaggacttca gctgagtata 900
gttcaacagt tttgctgaca gatgggaaca atcttttttt ttttttccca actgccatct 960
atacaatttt cttacagatg tcaaaagcag tctagtttat ataagcattc tgttacctgt 1020
gatatttttt agactgaact gctccattcc tagtcttaat taccatattc agggtacgaa 1080
ctggagggct tgtgtgttag cttctgaatt ggcaattgga ggcggtagtg gtcgtgcctg 1140
tgtgtatcag aagggatagg tatcttgcct cctttctctc aggcagtgca aatcaccctg 1200
tggaaaaccg atggacagga aggagtgtta cacactgctt accctgattt attcagtggt 1260
tttgttttca ttctggaacc atactatcaa atggcgacag actgttccgt tccacccccg 1320
tgaagtaatc atgcaccgtg tgaatagtat caagcaggat tgctttcatt gtatggagca 1380
tgaccagcgt gtgactcatt ctgacatttc agatcctaag aattctaaga acactactag 1440
aagcatttgt tccctcctag tcaatgcttc atactttttc ttgggattct tttagccctt 1500
gacattcttg tcccccaaac ctgtaagtag gtgaattcct aagataagtg tgtattttca 1560
ttccaggtga aaagcaggat gtaccgagca ctttattcag tgcatagctt taagccagtg 1620
ttggattcac taagtggaca gccagtctcc cagctctctg ccttccccaa aagggtcgta 1680
gtaggtcacc cttctacagc agctaactag agtcctaact aatgggatcc agcagggcca 1740
tttctccaga gggccagtat cctattagga gactcttgga attcttaggt tctactcaag 1800
agtggaagga ccaatcacct ctgatattct gtggaaggtt ttggggtcaa attctgccct 1860
ctgcattctg tgcaacttgt ataaaagtca agttagtatt acatgaattt ggggtagggt 1920
tagtgctttg aaaaaatgtt gaaccggctg ggcgcggtgg ctcacgtctg taatcccagc 1980
actttgggag gccgaggcgg gtggatcatg aggtcaggag ttcgagacca gcctggccaa 2040
catagtgaaa ccccatctct gctaaagata taaaaaatta gcccggcgtg gtggtgcacg 2100
cctgtaatcc cagctactcg ggaggctgag gcaggagaat tgcttcaacc tgggaggtgg 2160
aggctgcagt gagccgagat cgcaccactg cgttccagcc tgagcgacag ggcaagactc 2220
agtctcaaaa aaaaaaaaaa ggaaaaaaaa aagaaaaaaa aatgttgaac caattgtgaa 2280
ttacttatgt attattcatt tctcatgggg agagtaatgc tgttgaagaa cattacattg 2340
taaactgcct tcatttttgg ctctttgttt atgttcaggt ttagtttaca aacccattta 2400
agtatggaat gatttatatg gggtcaggtg ctccacaaaa tagacctatg agaccaaaaa 2460
tgacctaggc tatttagacg acagcatgaa acttccacgt tagttctcag tctataaagg 2520
cacttaccgg tctctggtgt ggtatgacca atagaaacac cttatagttt gctttggacc 2580
tcattttgga aaaataatct gcctttctaa ttgttctgca taggttaaaa tgataaattt 2640
acattctttg aacctatacc agattgtggt gtccgagtga ccggcacact gtctgacaca 2700
cagtcagtgt gcacgtattt gtctgagtga atgaggagac ctgagaaacc ggtgacgtgg 2760
cacagggaag ccagctggcc caggattccg tacatggccg caagcagact aacgcgttga 2820
cgctaattta atgtatttta cctcacacta aggtcatgct tgataaagac gttaaactca 2880
acttgtaaaa tggtagccca gtgctatgca cagagtgggt gctcattagt gttgaatgaa 2940
cacatttgta atactacatg taattccatc tgactgcttt gttaaatttt cagttagaac 3000
gtagatactg taaagtccac acacacatta aatcttgttt tcctgaaagt atggc 3055

<210> SEQ ID NO 13
<211> LENGTH: 1983
<212> TYPE: DNA
<213> ORGANISM: Homo sapiens

<400> SEQUENCE: 13
ctctgaaggg agctactcag aagcgggagt ctccgagaga agaaaagcag gtggaaggag 60
aggaagcgga tgccgtgggg tttacagcag gaaaatccgt ggagacagca gatccgagaa 120
gcggcgatgt ttgcgtagaa ccctgtcagc tgagccatga cccatgaacc atggaagctt 180
gactctagat tgaccatctt gagatgccaa agatgtccac gtcctaatcc catgtgggag 240
acagaataat ggccctgcag accttcccag ctggccatga cccctcattt gaccagctct 300
tcccttctct ctgaccagca ccatgcttct cctggtgaca agccttctgc tctgtgagtt 360
accacaccca gcattcctcc tgatcccaga gaaatcggat ctgcgaacag tggcaccagc 420
ctctagtctc aatgtgaggt ttgactccag gacgatgaat ttaagctggg actgccaaga 480
aaacacaacc ttcagcaagt gtttcttaac tgacaagaag aacagagtcg tggaacccag 540
gctcagtaac aacgaatgtt cgtgcacatt tcgtgaaatt tgtctgcatg aaggagtcac 600
atttgaggtt cacgtgaata ctagtcaaag aggatttcaa cagaaactgc tttatccaaa 660
ttcaggaagg gagggtaccg ctgctcagaa tttctcctgt ttcatctaca atgcggattt 720
aatgaactgt acctgggcga ggggtccgac ggcccccgt gacgtccagt attttttgta 780
catacgaaac tcaaagagaa ggagggagat ccggtgtcct tattacatac aagactcagg 840
aacccatgtg ggatgtcacc tggataacct gtcaggatta acgtctcgca attactttct 900
ggttaacgga accagccgag aaattggcat ccaattcttt gattcacttt tggacacaaa 960
gaaaatagaa cgattcaacc ctcccagcaa tgtcaccgta cgttgcaaca cgacgcactg 1020
cctcgtacgg tggaaacagc ccaggaccta tcagaagctg tcgtacctgg actttcagta 1080

-continued

```
ccagctggac gtccacagaa agaataccca gcctggcacg gaaaacctac tgattaatgt   1140
ttctggtgat ttggaaaata gatacaactt tccaagctct gagcccagag caaaacacag   1200
tgtgaagatc agagctgcag acgtccgcat cttgaattgg agctcctgga gtgaagccat   1260
tgaatttggt tctgacgacg ggaacctcgg ctctgtgtac atttatgtgc tcctaatcgt   1320
gggaaccctt gtctgtggca tcgtcctcgg cttcctcttt aaaaggttcc ttaggataca   1380
gcggctgttc ccgccagttc cacagatcaa agacaaactg aatgataacc atgaggtgga   1440
agacgagatc atctgggagg aattcacccc agaggaaggg aaaggctacc gcgaagaggt   1500
cttgaccgtg aaggaaatta cctgagaccc agagggtgta ggaatggcat ggacatctcc   1560
gcctccgcga cacgggggaa ctgttttctt gatgatgctg tgaaccttta tatcattttc   1620
tatgttttta tttaaaaaca tgacatttgg ggccaggcgc ggtggctcac gcctgtaatc   1680
ccagcacttt gggaggccaa ggcaggcgga tcacctgagg tcaggagttc aagaccagcc   1740
tgcccaacat ggtgaaaccc catctggact aaaaatgcag aaatttaccc aggcacggcg   1800
gcggacgccc atcatcccag ctacttggga ggctgaggca ggagaattgc ttgaacccgt   1860
gaggcggagg ttgtagtgag ccaagatcgc accattgcac accaacctgc gtgacagagc   1920
aagattgcat ctcaaaacaa acaataataa taaataataa aaacctgata tttggctggg   1980
caa                                                                  1983
```

<210> SEQ ID NO 14
<211> LENGTH: 6363
<212> TYPE: DNA
<213> ORGANISM: Homo sapiens

<400> SEQUENCE: 14

```
ggctgacatc acttaggaaa gcgaaggggg tagggctgcc agatcagttt gtcaccaccc     60
aggctccctt gcctttggct gggtgcaact tccattttag gtgttggatc tgagggggaa    120
aaaaaagaga gagggagaga gagagaaaga agagcaggaa agatcccgaa aggaggaaga    180
ggtggcgaaa aatcaactgc cctgctggat ttgtctttct cagcaccttg gcgaagcctt    240
gggtttcttt cttaaaggac tgatttttag aactccacat ttgaggtgtg tggcttttga    300
agaaaatgta tgtactgacg ggaaaaggag gataagcaag tcgaattttt gtcttacgct    360
ctctccttcc tgcttcctcc ttgctgtggt ggctgggatg cttcttccat gattttttga    420
atctagactg ggctgttctc tgtgttaaac caatcagttg cgaccttctc ttaacagtgt    480
gaagtgaggg ggtctctctc cctccttctc cttcctctgt gattcacctt cctttttacc    540
ctgccctgcg gcggctccgc cccttacctt catggacgac tcagaggtgg agtcgaccgc    600
cagcatcttg gcctctgtga aggaacaaga ggcccagttt gagaagctga cccgggcgct    660
ggaggaggaa cggcgccacg tctcggcgca gctggaacgc gtccgggtct caccacaaga    720
tgccaaccca ctcatggcca acggcacact cacccgccgg catcagaacg gccggtttgt    780
gggcgatgct gaccttgaaa gacagaaatt ttcagatttg aaactcaacg gaccccagga    840
tcacagtcac cttctatata gcaccatccc caggatgcag gagccggggc agattgtgga    900
gacctacacg gaggaggatc ctgagggagc catgtctgta gtctctgtgg agacctcaga    960
tgatgggacc actcggcgca cagagaccac ggtcaagaaa gtagtgaaga ctgtgacaac   1020
acggacagta cagccagtcg ctatgggacc agacgggttg cctgtggatg cttcatcagt   1080
ttctaacaac tatatccaga ctttgggtcg tgatttccgc aagaatggca atgggggacc   1140
tggtccctat gtggggcaag ctggcactgc taccctttcct aggaacttcc actaccctcc   1200
```

-continued tgatggttat agtcgccact atgaagatgg ttatccaggt ggcagtgata actatggcag 1260
tctgtcccgg gtgacccgca ttgaggagcg gtataggccc agcatggaag gctaccgggc 1320
acctagtaga caggatgtgt atgggcccca accccaggtt cgggtaggtg ggagcagcgt 1380
ggatctgcat cgctttcatc cagagcctta tgggctagag gatgaccagc gtagtatggg 1440
ctatgatgac ctggattatg gtatgatgtc tgattatggc actgcccgtc ggactgggac 1500
accctctgac cctcgtcggc gcctcaggag ctatgaagac atgattggtg aggaggtgcc 1560
atcggatcaa tactactggg ctcctttggc ccagcatgag cgaggaagtt tagcaagctt 1620
ggatagcctg cgcaaaggag ggcctccacc tcctaattgg agacagccag agctgccaga 1680
ggtgatcgcc atgcttggat tccgcttgga tgctgtcaag tccaatgcag ctgcatacct 1740
gcaacactta tgctaccgca atgacaaggt gaagactgac gtgcggaagc tcaagggcat 1800
cccagtactg gtgggattgt tagaccatcc caaaaaggaa gtgcaccttg gagcctgtgg 1860
agctctcaag aatatctctt ttggacgtga ccaggataac aagattgcca taaaaaactg 1920
tgatggtgtg cctgcccttg tgcgattgct tcgaaaggct cgtgatatgg accttactga 1980
agttattacc ggaaccctgt ggaatctttc atcccatgac tcaatcaaaa tggagattgt 2040
ggaccatgca ctgcatgcct tgacagatga agtgatcatt cctcattctg gttgggagcg 2100
ggaacctaat gaagactgta agccacgcca tattgagtgg gaatcggtgc tcaccaacac 2160
agctggctgc cttaggaatg taagctcaga gaggagtgaa gctcgccgga aacttcggga 2220
atgtgatggt ttagttgatg ccctcatttt cattgttcag gctgagattg ggcagaagga 2280
ttcagacagc aagcttgtag agaactgtgt ttgccttctt cggaacttat catatcaagt 2340
tcaccgggag atcccacagg cagagcgtta ccaagaggca gctcccaatg ttgccaacaa 2400
tactgggcca catgctgcca gttgctttgg ggccaagaag ggcaaagatg agtggttctc 2460
cagagggaaa aaacctatag aggatccagc aaacgataca gtggatttcc ctaaaagaac 2520
gagtccagct cgaggctatg agctcttatt tcagccagag gtggttcgga tatacatctc 2580
acttcttaag gagagcaaga ctcctgccat cctagaagcc tcagctggag ctatccagaa 2640
cttgtgtgct gggcgctgga cgtatggtcg atacatccgc tctgctctgc gtcaagagaa 2700
ggctctttct gccatagctg acctcctgac taatgaacat gaacgggtgg tgaaagctgc 2760
atctggagca ctgagaaacc tggctgtgga tgctcgcaac aaagaattaa ttggtaaaca 2820
tgctattcct aacttggtaa agaatctgcc aggaggacag cagaactcct cttggaattt 2880
ctctgaggac actgtcatct ctattttgaa cactatcaac gaggttatcg ctgagaactt 2940
ggaggctgcc aaaaagcttc gagagacaca gggtattgag aagctggtgt tgatcaacaa 3000
atcagggaac cgctcagaaa aagaagttcg agcagcagca cttgtattac agacaatctg 3060
gggatataag gaactgcgga agccactgga aaaagaagga tggaagaaat cagactttca 3120
ggtgaatcta aacaatgctt cccgaagcca gagcagtcat tcatatgatg atagtactct 3180
ccctctcatt gaccggaacc aaaaatcaga taagaaacct gatcgggaag aaattcagat 3240
gagcaatatg ggatcaaaca caaaatcact agataacaac tattccacac caaatgagag 3300
aggagaccac aatagaacac tggatcgatc gggggatcta ggcgacatgg agccattgaa 3360
gggaacaaca cccttgatgc aggacgaggg gcaggaatct ctggaggaag agttggatgt 3420
gttggttttg gatgatgagg ggggccaagt gtcttacccc tccatgcaga agatttagca 3480
ccactatctc cgttccatct gggcttatat gtacttttat tttttggtgg tgaaattgac 3540

-continued

```
tgatgatttt cctttttctt cgctggacta ttgtgccaac tgccaggctg cctcctgccc   3600
ttacagccct aagtggctgc cttctttcca tcaactccca acttcttcct gtgaagttta   3660
attgtctcaa cgcctccccc tcccccattc cctccatttt tctcccaaga aacctgactc   3720
aattatttgc atattttgag aaactgctgc agattagttc tttttgccag ttttccctgg   3780
aactcctggc cttttgtgga ggggagggat ggagagaata ggaatcttca ctagaagccg   3840
tgggaagaat tggaagttac atgctgtata tgcaatgtcc agcagtctga taaactgacg   3900
attcttaatc aagatttttt tcctgatggg gaagggactt ttattttctt ttagagaggg   3960
gaaagtgtga gctcttccct tattcctaat ggctattttt gaagcaaaga aggccagcaa   4020
cattggcaca tgccacctgg caaaggaccc ttgagtaagt gaaggtctcc taaaactggg   4080
attaagaaac cttgctctcc tcatctccaa ggcagggacc atcaagaacc tacagactcc   4140
atctcttctg caagcctcat gccaaccctg ggctattgct gctgcccctt aaacacaggc   4200
tgtccttaac ccacctctcc tgccctgtga tatgtctgct gagttggcct ggccatttcc   4260
aagaggctgt agaaaggggga gaatgtcaag gaagactttt ggtagagaag gagcagaaag   4320
atgtgttttt gggaagaaga agacctctag gaggagctag taggaatgta catgaagcaa   4380
ttagtctgaa actggcttcc ccactccccc gtttctcctt ttcctatcct tataggcctg   4440
tcccttgcct ctgccctgga ttggttggca aactaaagga cttgatgtac ataactcctg   4500
tccctttcc cttacaaggt ggggattgcc cctggctttg cctcttcttt gtgcctttgg   4560
cctggggtgc atctcctccc gcccttccat gtgcctttct ttgcctctgc agtctcattt   4620
ctcataattt tgcaaattat atttgttgc tttcttacct actattggcc ctaaatagca   4680
gaaagaagag aagtgaccga gagaacctca gattcttcat tgaggattgg tatagccatg   4740
atttcagtca tagcaagctt ttgctcaaca gcatatgggt gggattttgc aaaaatccta   4800
ttctgatgaa tctcaaagta aggctggtaa gagaagtgag tggtgtgact cttactcctt   4860
aggtgcccag aatttaccat catctctgaa ggagttacag ggaagtggtc tccccaattc   4920
tcccctccct ccagtattgc cccctctcac tttagcatat attaattagc aggttgggct   4980
agagaaatca gctgctatgc gggttgatta ttattattat ttctaatcct tttccttatt   5040
tgccttctac tccccttaat ctaatctaaa agctctgttc catgcaactg gagttcctta   5100
tccctctctt ccccttccct tatatattga ggctatgggg taggagaaaa gtgcacaacc   5160
caccaccccc tttactcgtg cattaaaatt tcttatttac ccttttcccc cttcccattt   5220
cttcccactt tcatctacct tttctggcaa aaaggagcct tttgctctct gtgaccctaa   5280
gagcacactg cacagggaaa attgccccat ccagacctgg ctccactctt gatctctctt   5340
gtcctcttct gctcttttcc tggtgctctt ttttctcggt ggggtgtggg taatagaaca   5400
gccgtgggct tttggggacc tttaactttt ttttctctct tttgtttata aaaaacacta   5460
aacattcaat tccagagaac caaaaatccc accttcccac cgaacactac taaggggctt   5520
gtgttctgct ccataccttt tctcttttct ttctgtcttg ttaatgcttt taaaaacaaa   5580
tgagtttttt atataaataa agtttttaaa gtgtgtatgt ggggggtctg tgtcatttct   5640
tcacttcaag ctgttatttc ttccctgctt tgcatctttg ttacttcctt atgtatcagt   5700
gtcctttcca gagcaaccag aaggaggtta taccaggatt tattttgagc tcagccccaa   5760
ctctttatca agcaacattc ttgttaacta tatgtgaaac attttttctt ctgaagattc   5820
ttaaaaattg aatgtggctg aagttgaaca tgggagctta ttgctaattt agagatagga   5880
aactgaagca taaagaatta atgacttact ttaattactg gaattcttct gcaacatttg   5940
```

-continued

```
acaaaactaa ccttgaataa ggcccactgt aatacgtagc tctcttaaat ataacactta   6000

ggactagaag attagaaact accaatccca actacgtaat aggaaaatgt aggatcaaaa   6060

ggcccatgta tataagtact gaccactggg ccataatgtt gcttctcagg ctatatgcag   6120

tcctttagtc agaagtcaat aggcctattt attaatattt tacagaccat attacctgga   6180

ttaccaggga ctatctttgc tgcagagatc aagggttaag atctatggga agatacttat   6240

ttttctgagg tccttatgtc ctgtcatata attaaagact caagagaatt tatgtgaaat   6300

gctttctgta tgcccaaatc tttagattaa aattatatag ctgctcctga aaaaaaaaaa   6360

aaa                                                                 6363
```

<210> SEQ ID NO 15
<211> LENGTH: 3783
<212> TYPE: DNA
<213> ORGANISM: Homo sapiens

<400> SEQUENCE: 15

```
ggggcggggc cgggagggta cttagggccg gggctggccc aggctacggc ggctgcaggg     60

ctccggcaac cgctccggca acgccaaccg ctccgctgcg cgcaggctgg gctgcaggct    120

ctcggctgca gcgctgggtg gatctaggat ccggcttcca acatgtggca gctctgggcc    180

tccctctgct gcctgctggt gttggccaat gcccggagca ggccctcttt ccatcccctg    240

tcggatgagc tggtcaacta tgtcaacaaa cggaatacca cgtggcaggc cgggcacaac    300

ttctacaacg tggacatgag ctacttgaag aggctatgtg gtaccttcct gggtgggccc    360

aagccacccc agagagttat gtttaccgag gacctgaagc tgcctgcaag cttcgatgca    420

cgggaacaat ggccacagtg tcccaccatc aaagagatca gagaccaggg ctcctgtggc    480

tcctgctggg ccttcggggc tgtggaagcc atctctgacc ggatctgcat ccacaccaat    540

gcgcacgtca gcgtggaggt gtcggcggag gacctgctca catgctgtgg cagcatgtgt    600

ggggacggct gtaatggtgg ctatcctgct gaagcttgga acttctggac aagaaaaggc    660

ctggtttctg gtggcctcta tgaatcccat gtagggtgca gaccgtactc catccctccc    720

tgtgagcacc acgtcaacgg ctcccggccc ccatgcacgg gggagggaga tacccccaag    780

tgtagcaaga tctgtgagcc tggctacagc ccgacctaca aacaggacaa gcactacgga    840

tacaattcct acagcgtctc caatagcgag aaggacatca tggccgagat ctacaaaaac    900

ggccccgtgg agggagcttt ctctgtgtat tcggacttcc tgctctacaa gtcaggagtg    960

taccaacacg tcaccggaga gatgatgggt ggccatgcca tccgcatcct gggctgggga   1020

gtggagaatg gcacacccta ctggctggtt gccaactcct ggaacactga ctggggtgac   1080

aatggcttct ttaaaatact cagaggacag gatcactgtg gaatcgaatc agaagtggtg   1140

gctggaattc cacgcaccga tcagtactgg gaaaagatct aatctgccgt gggcctgtcg   1200

tgccagtcct gggggcgaga tcggggtaga aatgcatttt attctttaag ttcacgtaag   1260

atacaagttt cagacagggt ctgaaggact ggattggcca aacatcagac ctgtcttcca   1320

aggagaccaa gtcctggcta catcccagcc tgtggttaca gtgcagacag gccatgtgag   1380

ccaccgctgc cagcacagag cgtccttccc cctgtagact agtgccgtag ggagtacctg   1440

ctgccccagc tgactgtggc cccctccgtg atccatccat ctccagggag caagacagag   1500

acgcaggaat ggaaagcgga gttcctaaca ggatgaaagt tcccccatca gttcccccag   1560

tacctccaag caagtagctt tccacatttg tcacagaaat cagaggagag acggtgttgg   1620
```

-continued gagccctttg gagaacgcca gtctcccagg ccccctgcat ctatcgagtt tgcaatgtca 1680
caacctctct gatcttgtgc tcagcatgat tctttaatag aagttttatt ttttcgtgca 1740
ctctgctaat catgtgggtg agccagtgga acagcgggag acctgtgcta gttttacaga 1800
ttgcctcctt atgacgcggc tcaaaaggaa accaagtggt caggagttgt ttctgaccca 1860
ctgatctcta ctaccacaag gaaaatagtt taggagaaac cagcttttac tgtttttgaa 1920
aaattacagc ttcaccctgt caagttaaca aggaatgcct gtgccaataa aagttttctc 1980
caacttgaag tctactctga tgggatctca gatcctttgt cactgcctat agacttgtag 2040
ctgctgtctc tctttgtccc tgcagagaat cacgtcctgg aactgcatgt tcttgcgact 2100
cttgggactt catcttaact tctcgctgcc ccagccatgt tttcaaccat ggcatccctc 2160
ccccaattag ttccctgtca tcctcgtcaa ccttctctgt aagtgcctgg taagcttgcc 2220
cttgcttaag aactcaaaac atagctgtgc tctatttttt tgttgttgtt gtgactgaca 2280
gagtgagatt ccgtctccca ggctggagtg cagtggcgcc ttctcagctc actgcaacct 2340
gcagcctcct agattcaagc gattctcctg cttcagcctt ccgagtagct gggatgacag 2400
gcactcacca atatgcctgg gtaatttttg tatttttaag tacatacagg atttcaccat 2460
gttggccagg ctagtttcaa actcccggcc tcaggtggtc tgcctgcctc agcctcccaa 2520
agtgttggga ttacaggcgt gagccactgg gccctgcctg tatttttat cagccacaaa 2580 tccagcaaca agctgaggat tcagctcata aaacaggctt ggtgtcttgg tgatctcaca 2640
taaccaagat gctaccccgt ggggaaccac atccccctgg atgccctcca gccttggttt 2700
gggctggagt cagggcctgt atacagtatt ttgaatttgt atgccactgg tttgcattgc 2760
tggtcaggaa ctctagtgct ttgcatagcc ctggtttaga aacatgttat agcagttctt 2820
ggtatagagc aaactagaag aaccagcaat cattccactg tcctgccaag gtacacctca 2880
gtactcccct tcccaactga agtggtatga ggctagctct ttccaaaagc attcaagttt 2940
ggcttctgat gtgactcaga atttaggaac cagatgctag atcaaataag ctctgaaaat 3000
ctgaggaaca ttgtaggaaa ggtttgttaa gcatctctta agtgccatga tgagcataac 3060
agccggccgt cgtggctcac gcctgtaatc ccagcacttt gggaggccaa ggtgggagga 3120
tgacaaggtc aggagttcaa gaccagcctg gccaacatgc tgaaacctca cctctactaa 3180
aaatacaaaa attagctggg catggtggca catgcctgta atcccagcta cttgggaggc 3240
tgaggcagga gaatcgcttg aacccgggag gcggaggttg cagtgagcca agacagtgcc 3300
agtgcactcc agcctcggtg acagcgcaag gctccgtctc aataattaaa aaaaaaaaaa 3360
aaaaaaaaaa ggccgggcgc agtggctcaa gcctgtaatc ccagcacttt gggaggctga 3420
ggcgggcaga tcacctgagg tcaggagttt tgagatcagc cttggcaaca cggtgaaacc 3480
ccatctctac taaaaataca aaattagcca agcatgctgg cacatgcctg taatcccagc 3540
tactcgggag gctgaggtac gagaatcgct tgaacctggg aggcagagga tgcagtgagc 3600
cgagatcacg ccattgcact ccagcctggg ggacaagagt gaatctgtgt ctcaccaaaa 3660
aaaaaaagaa aaagaaagat gcttaacaaa ggttaccata agccacaaat tcataaccac 3720
ttatccttcc agtttcaagt agaatatatt cataacctca ataaagttct ccctgctccc 3780
aaa 3783

<210> SEQ ID NO 16
<211> LENGTH: 1466
<212> TYPE: DNA
<213> ORGANISM: Homo sapiens

<400> SEQUENCE: 16
ggtgcgtccg cgggtggctg ccccgcaggt gcgcgcggcc ggggctggcg gcgactctct 60
ccaccgggcc gcccgggagg ctcatgcagc gcggctgggt cccgcggcgc ccggatcggg 120
gaagtgaaag tgcctcggag gaggagggcc ggtccggcag tgcagccgcc tcacaggtcg 180
gcggacgggc caggcgggcg gcctcctgaa ccgaaccgaa tcggctcctc gggccgtcgt 240
cctcccgccc ctcctcgccc gccgccggag ttttctttcg gtttcttcca agattcctgg 300
ccttccctcg acggagccgg gcccagtgcg ggggcgcagg gcgcgggagc tccacctcct 360
cggctttccc tgcgtccaga ggctggcatg gcgcgggccg agtactgagc gcacggtcgg 420
ggcacagcag ggccgggggg tgcagctggc tcgcgcctcc tctccggccg ccgtctcctc 480
cggtccccgg cgaaagccat tgagacacca gctggacgtc acgcgccgga gcatgtctgg 540
gagtcagagc gaggtggctc catccccgca gagtccgcgg agccccgaga tgggacggga 600
cttgcggccc gggtcccgcg tgctcctgct cctgcttctg ctcctgctgg tgtacctgac 660
tcagccaggc aatggcaacg agggcagcgt cactggaagt tgttattgtg gtaaaagaat 720
ttcttccgac tccccgccat cggttcagtt catgaatcgt ctccggaaac acctgagagc 780
ttaccatcgg tgtctatact acacgaggtt ccagctcctt tcctggagcg tgtgtggggg 840
caacaaggac ccatgggttc aggaattgat gagctgtctt gatctcaaag aatgtggaca 900
tgcttactcg ggattgtgg cccaccagaa gcatttactt cctaccagcc ccccaatttc 960
tcaggcctca gagggggcat cttcagatat ccacacccct gcccagatgc tcctgtccac 1020
cttgcagtcc actcagcgcc ccaccctccc agtaggatca ctgtcctcgg acaaagagct 1080
cactcgtccc aatgaaacca ccattcacac tgcgggccac agtctggcag ctgggcctga 1140
ggctggggag aaccagaagc agccggaaaa aaatgctggt cccacagcca ggacatcagc 1200
cacagtgcca gtcctgtgcc tcctggccat catcttcatc ctcaccgcag ccctttccta 1260
tgtgctgtgc aagaggagga gggggcagtc accgcagtcc tctccagatc tgccggttca 1320
ttatatacct gtggcacctg actctaatac ctgagccaag aatggaagct tgtgagggta 1380
aactgtggct tattcttaca aaaagtgtaa taaaggagac tgacccctga caacatggta 1440
ggcactgtat aaaaaaaaaa aaaaaa 1466

<210> SEQ ID NO 17
<211> LENGTH: 2804
<212> TYPE: DNA
<213> ORGANISM: Homo sapiens

<400> SEQUENCE: 17
aaagccagac tgattcatag aaactccttt aaaacacggt gaaaagaaac cgcccattac 60
acaccccagt acaccagcag aggaaactta taacctcggg aggcaggtcc ttcccctcag 120
tgcggtcaca tacttccaga agagcggacc agggctgctg ccagcacctg ccactcagag 180
cgcctctgtc gctgggaccc ttcagaactc tctttgctca caagttacca aaaaaaaaag 240
agccaacatg ttggtattgc tggctggtat ctttgtggtc cacatcgcta ctgttattat 300
gctatttgtt agcaccattg ccaatgtctg gttggtttcc aatacggtag atgcatcagt 360
aggtctttgg aaaaactgta ccaacattag ctgcagtgac agcctgtcat atgccagtga 420
agatgccctc aagacagtgc aggccttcat gattctctct atcatcttct gtgtcattgc 480
cctcctggtc ttcgtgttcc agctcttcac catggagaag ggaaaccggt tcttcctctc 540

-continued

```
aggggccacc acactggtgt gctggctgtg cattcttgtg ggggtgtcca tctacactag    600
tcattatgcg aatcgtgatg gaacgcagta tcaccacggc tattcctaca tcctgggctg    660
gatctgcttc tgcttcagct tcatcatcgg cgttctctat ctggtcctga gaaagaaata    720
aggccggacg agttcatggg gatctggggg gtggggagga ggaagccgtt gaatctggga    780
gggaagtgga ggttgctgta caggaaaaac cgagataggg gagggggag ggggaagcaa    840
aggggggagg tcaaatccca aaccattact gaggggattc tctactgcca agcccctgcc    900
ctggggagaa agtagttggc tagtactttg atgctccctt gatggggtcc agagagcctc    960
cctgcagcca ccagacttgg cctccagctg ttcttagtga cacacactgt ctggggcccc   1020
atcagctgcc acaacaccag ccccacttct gggtcatgca ctgaggtcca cagacctact   1080
gcactgagtt aaaatagcgg tacaagttct ggcaagagca gatactgtct ttgtgctgaa   1140
tacgctaagc ctggaagcca tcctgccctt ctgacccaaa gcaaaacatc acattccagt   1200
ctgaagtgcc tactgggggg ctttggcctg tgagccattg tccctctttg gaacagatat   1260
ttagctctgt ggaattcagt gacaaaatgg gaggaggaaa gagagtttgt aaggtcatgc   1320
tggtgggtta gctaaaccaa gaaggagacc ttttcacaat ggaaaacctg gggatggtc    1380
agagcccagt cgagacctca cacacggctg tccctcatgg agacctcatg ccatggtctt   1440
tgctaggcct cttgctgaaa gccaaggcag ctcttctgga gtttctctaa agtcactagt   1500
gaacaattcg gtggtaaaag taccacacaa actatgggat ccaaggggca gtcttgcaac   1560
agtgccatgt tagggttatg tttttaggat tcccctcaat gcagtcagtg tttcttttaa   1620
gtatacaaca ggagagagat ggacatggct cattgtagca caatcctatt actcttcctc   1680
taacattttt gaggaagttt tgtctaatta tcaatattga ggatcagggc tcctaggctc   1740
agtggtagct ctggcttaga caccacctgg agtgatcacc tcttggggac cctgcctatc   1800
ccacttcaca ggtgaggcat ggcaattctg gaagctgatt aaaacacaca taaaccaaaa   1860
ccaaacaaca ggcccttggg tgaaaggtgc tatataattg tgaagtatta agcctaccgt   1920
atttcagcca tgataagaac agagtgcctg cattcccagg aaaatacgaa aatcccatga   1980
gataaataaa aatataggtg atgggcagat cttttcttta aaataaaaaa gcaaaaactc   2040
ttgtggtacc tagtcagatg gtagacgagc tgtctgctgc cgcaggagca cctctataca   2100
ggacttagaa gtagtatgtt attcctggtt aagcaggcat tgctttgccc tggagcagct   2160
attttaagcc atctcagatt ctgtctaaag gggttttttg ggaagacgtt ttctttatcg   2220
ccctgagaag atctacccca gggagaatct gagacatctt gcctactttt ctttattagc   2280
tttctcctca tccatttctt ttataccttt cctttttggg gagttgttat gccatgattt   2340
ttggtattta tgtaaaagga ttattactaa ttctatttct ctatgtttat tctagttaag   2400
gaaatgttga gggcaagcca ccaaattacc taggctgagg ttagagagat tggccagcaa   2460
aaactgtggg aagatgaact ttgtcattat gatttcatta tcacatgatt atagaaggct   2520
gtcttagtgc aaaaaacata cttacatttc agacatatcc aaagggaata ctcacatttt   2580
gttaagaagt tgaactatga ctggagtaaa ccatgtattc ccttatcttt tacttttttt   2640
ctgtgacatt tatgtctcat gtaatttgca ttactctggt ggattgttct agtactgtat   2700
tgggcttctt cgttaataga ttatttcata tactataatt gtaaatattt tgatacaaat   2760
gtttataact ctagggatat aaaaacagat tctgattccc ttca                    2804
```

```
<210> SEQ ID NO 18
<211> LENGTH: 3196
```

<212> TYPE: DNA
<213> ORGANISM: Homo sapiens

<400> SEQUENCE: 18

```
ctctacccgg ttggcaggcg gcctggccca gccccttctc taaggaagcg catttcctgc     60
ctccctgggc cggccgggct ggatgagccg ggagctccct gctgccggtc ataccacagc    120
cttcatctgc gccctggggc caggactgct gctgtcactg ccatccattg gagcccagca    180
ccccctcccc gcccatcctt cggacagcaa ctccagccca gccccgcgtc cctgtgtcca    240
cttctcctga cccctcggcc gccaccccag aaggctggag cagggacgcc gtcgctccgg    300
ccgcctgctc ccctcgggtc cccgtgcgag cccacgccgg ccccggtgcc cgcccgcagc    360
cctgccactg gacacaggat aaggcccagc gcacaggccc ccacgtggac agcatggacc    420
gcggcacgct ccctctggct gttgccctgc tgctggccag ctgcagcctc agccccacaa    480
gtcttgcaga aacagtccat tgtgaccttc agcctgtggg ccccgagagg ggcgaggtga    540
catataccac tagccaggtc tcgaagggct gcgtggctca ggcccccaat gccatccttg    600
aagtccatgt cctcttcctg gagttcccaa cgggcccgtc acagctggag ctgactctcc    660
aggcatccaa gcaaaatggc acctggcccc gagaggtgct tctggtcctc agtgtaaaca    720
gcagtgtctt cctgcatctc caggccctgg gaatcccact gcacttggcc tacaattcca    780
gcctggtcac cttccaagag cccccggggg tcaacaccac agagctgcca tccttcccca    840
agacccagat ccttgagtgg gcagctgaga ggggccccat cacctctgct gctgagctga    900
atgaccccca gagcatcctc ctccgactgg gccaagccca ggggtcactg tccttctgca    960
tgctggaagc cagccaggac atgggccgca cgctcgagtg gcggccgcgt actccagcct   1020
tggtccgggg ctgccacttg gaaggcgtgg ccggccacaa ggaggcgcac atcctgaggg   1080
tcctgccggg ccactcggcc gggccccgga cggtgacggt gaaggtggaa ctgagctgcg   1140
cacccgggga tctcgatgcc gtcctcatcc tgcagggtcc cccctacgtg tcctggctca   1200
tcgacgccaa ccacaacatg cagatctgga ccactggaga atactccttc aagatctttc   1260
cagagaaaaa cattcgtggc ttcaagctcc cagacacacc tcaaggcctc ctgggggagg   1320
cccggatgct caatgccagc attgtggcat ccttcgtgga gctaccgctg gccagcattg   1380
tctcacttca tgcctccagc tgcggtggta ggctgcagac ctcacccgca ccgatccaga   1440
ccactcctcc caaggacact tgtagcccgg agctgctcat gtccttgatc cagacaaagt   1500
gtgccgacga cgccatgacc ctggtactaa agaaagagct tgttgcgcat ttgaagtgca   1560
ccatcacggg cctgaccttc tgggacccca gctgtgaggc agaggacagg ggtgacaagt   1620
ttgtcttgcg cagtgcttac tccagctgtg gcatgcaggt gtcagcaagt atgatcagca   1680
atgaggcggt ggtcaatatc ctgtcgagct catcaccaca gcggaaaaag gtgcactgcc   1740
tcaacatgga cagcctctct ttccagctgg gcctctacct cagcccacac ttcctccagg   1800
cctccaacac catcgagccg gggcagcaga gctttgtgca ggtcagagtg tccccatccg   1860
tctccgagtt cctgctccag ttagacagct gccacctgga cttggggcct gagggaggca   1920
ccgtggaact catccagggc cgggcggcca agggcaactg tgtgagcctg ctgtccccaa   1980
gccccgaggg tgacccgcgc ttcagcttcc tcctccactt ctacacagta cccataccca   2040
aaaccggcac cctcagctgc acggtagccc tgcgtcccaa gaccgggtct caagaccagg   2100
aagtccatag gactgtcttc atgcgcttga acatcatcag ccctgacctg tctggttgca   2160
caagcaaagg cctcgtcctg cccgccgtgc tgggcatcac ctttggtgcc ttcctcatcg   2220
```

-continued

```
gggccctgct cactgctgca ctctggtaca tctactcgca cacgcgtgag taccccaggc   2280
ccccacagtg agcatgccgg gcccctccat ccacccgggg gagcccagtg aagcctctga   2340
gggattgagg ggccctggcc aggaccctga cctccgcccc tgcccccgct cccgctccca   2400
ggttccccca gcaagcggga gcccgtggtg gcggtggctg ccccggcctc ctcggagagc   2460
agcagcacca accacagcat cgggagcacc cagagcaccc cctgctccac cagcagcatg   2520
gcatagcccc ggcccccgc gctcgcccag caggagagac tgagcagccg ccagctggga   2580
gcactggtgt gaactcaccc tgggagccag tcctccactc gacccagaat ggagcctgct   2640
ctccgcgcct acccttcccg cctccctctc agaggcctgc tgccagtgca gccactggct   2700
tggaacacct tggggtccct ccaccccaca gaaccttcaa cccagtgggt ctgggatatg   2760
gctgcccagg agacagacca cttgccacgc tgttgtaaaa acccaagtcc ctgtcatttg   2820
aacctggatc cagcactggt gaactgagct gggcaggaag ggagaacttg aaacagattc   2880
aggccagccc agccaggcca acagcacctc cccgctggga agagaagagg gcccagccca   2940
gagccacctg gatctatccc tgcggcctcc acacctgaac ttgcctaact aactggcagg   3000
ggagacagga gcctagcgga gcccagcctg ggagcccaga gggtggcaag aacagtgggc   3060
gttgggagcc tagctcctgc cacatggagc cccctctgcc ggtcgggcag ccagcagagg   3120
gggagtagcc aagctgcttg tcctgggcct gcccctgtgt attcaccacc aataaatcag   3180
accatgaaac cagtga                                                 3196
```

<210> SEQ ID NO 19
<211> LENGTH: 4446
<212> TYPE: DNA
<213> ORGANISM: Homo sapiens

<400> SEQUENCE: 19

```
cgcaccgccg ccgaggacgc gcgcccgagc ctagtcccca cgccgcggcg cgcccgggct     60
ccctgctgat cccagaacaa tcaaccatga cgaccgaatc tggatcagac tcggaatcca    120
agccggacca ggaggccgag ccccaggagg cggcgggggc gcaggggcgc gcgggggcgc    180
ccgtgccgga gccgcccaag gaggagcagc agcaggccct ggagcagttc gccgccgctg    240
cagcgcacag caccccggtg cggagggagg tcactgacaa ggaacaggag tttgctgcca    300
gggctgcaaa acagctcgaa tatcagcaat tagaagacga taaactttct cagaaatcat    360
ctagcagtaa actctctcgg tctccattaa agattgtcaa aaagcctaaa agcatgcagt    420
gcaaagtgat acttctcgat ggatcagaat atacctgtga tgtagagaaa cgctccagag    480
gacaagtgct gtttgataaa gtgtgtgaac acttgaactt gctagagaaa gactactttg    540
ggcttacgta tcgagatgct gaaaaccaga agaattggtt ggaccctgct aaggaaataa    600
aaaaacaggt tcgaagtggt gcttggcact tttcatttaa tgtgaaattt tatccaccag    660
accctgccca actatctgaa gatatcacca ggtactacct ctgcttgcag ttgcgagatg    720
acatcgtgtc cggaaggctg ccctgctcct ttgttaccct ggccttgctg ggctcctaca    780
ctgtccagtc agagctcgga gactatgacc cagatgaatg tgggagcgat tacattagtg    840
agttccgctt tgcaccaaac cacactaaag aactggaaga caaagtgatc gagctgcaca    900
agagccacag aggaatgacg ccagcagaag cagagatgca tttcttggaa aatgccaaaa    960
aattatcaat gtatggggta gatttacatc atgctaagga ctcagaaggg gtagaaatta   1020
tgttaggagt ttgtgcaagt ggtctgttga tatatcgcga ccggctgcga ataaacagat   1080
ttgcctggcc caaggttcta aagatttcat acaaacggaa caacttttac attaagatcc   1140
```

ggccgggaga gtttgaacaa tttgaaagca ccattgggtt taagctgcca aaccatcgag 1200
ctgccaagcg tttatggaaa gtatgtgttg agcatcatac atttttcaga ctactgttac 1260
cagaagcacc tcccaagaaa ttcctaacct tgggttccaa gtttcgttat agtggcagga 1320
cacaagcgca aacgagaaga gccagtgcgt tgatagatcg cccagcacct tactttgaac 1380
gctcatccag caaacgttat accatgtctc gcagcttgga tggagaggtt ggtactggcc 1440
agtacgccac aacaaaaggc atctctcaga ccaacttgat caccactgtg actccggaga 1500
agaaggctga ggaggagcgg gacgaggaag aggacaaacg gaggaagggg gaagaagtca 1560
cgcccatctc ggccatccgg cacgagggaa agtcacctgg gcttggcact gactcatgtc 1620
ccttgtcacc cccatccacc cattgtgccc ccacatctcc cacagagctc cgtaggaggt 1680
gtaaggagaa tgactgcaaa ctgccaggtt atgagccgtc cagagctgag cacctgcctg 1740
gagagcccgc cttggactct gatggcccag ggaggcctta cctaggggat caagatgtgg 1800
cttttagcta cagacagcaa actggcaagg ggaccaccct gttctccttc tccttgcagc 1860
tccctgagtc attcccctcc ctcctagatg atgatggata cctctctttc cccaaccttt 1920
ctgaaaccaa cctcctgccc cagagcttgc agcattacct cccgatccgc tcaccgtccc 1980
ttgtgccctg tttcctcttc atctttttct ttctgctgtc tgcctccttc tcagtgccat 2040
acgctctcac tctctccttc cctctggctc tgtgcctctg ctacctggag cccaaggcgg 2100
cctccttgag cgcctcccta gacaatgacc cgagtgacag ttcagaggaa gagactgaca 2160
gtgagcgcac ggacaccgca gccgacgggg agaccaccgc cactgagtcg gaccaggagg 2220
aagatgcaga gctcaaggca caggagctag aaaaaactca agatgacctg atgaaacatc 2280
aaaccaacat tagcgagctg aaaagaacct tcttagaaac ctcaacagac actgccgtaa 2340
cgaatgaatg ggagaagagg ctttccacct cccccgtgcg actggccgcc aggcaggagg 2400
atgcccccat gatcgaacca cttgtccctg aagagactaa gcagtcttct ggggaaaagc 2460
tcatggatgg ctctgaaatc ttcagtttat tagagtctgc gcgaaaacca acagaattca 2520
taggaggggt tacttctact tctcaaagct gggttcagaa aatggaaacc aagacggagt 2580
ccagtggaat agagacggaa cccaccgtgc accacctgcc gcttagcact gagaaggtgg 2640
tgcaggagac cgtgttggtg gaggagcggc gtgtggtgca cgcgagtggg gatgcttctt 2700
actcggcggg agacagcggg gatgctgcag cacagcccgc attcacaggc attaaaggga 2760
aagagggctc tgccttgacg gagggggcta aagaggaagg aggggaggag gtcgctaaag 2820
ctgtcctgga acaggaagag acagccgctg cttcccgtga gcgacaagag gagcagagtg 2880
cagccatcca catttcagaa actttggaac aaaaacctca ttttgagtcc tcaacggtga 2940
agacggaaac catcagtttt ggcagtgttt caccgggagg agtaaagcta gaaatttcca 3000
cgaaggaagt gccagtagtt cacaccgaaa ccaaaaccat cacatatgaa tcatcacagg 3060
tcgatccagg cacagatctg gagccaggcg tgctgatgag tgcacagacg atcacatctg 3120
aaaccaccag taccaccacc actacgcaca tcaccaaaac tgtgaaaggg ggcatttcag 3180
agacaagaat tgagaagcga atagtcatca cgggggatgc agacattgac catgaccagg 3240
cgctggctca ggcaattaaa gaggccaaag agcagcaccc tgacatgtca gtgaccaaag 3300
tagtggtcca taaagagaca gagatcacac cagaagatgg agaggattga ccagaggaat 3360
aacttagctt gcacatgaat gcagtcatgc aaaccgttag gaaaaccaga gcctatatgg 3420
agttccctct tctaacccaa ctgacttgta tctgtccgtg gaaaatttca gtccagaaga 3480

-continued attgaccttg accattaata aagacactgg cagagagatc ttcccataat aaagcaatct 3540
gattcagcat cactaaaccg ataatgcatg aagcaacgat aaaattacaa aagagcagca 3600
tttttaattt tcacaaaatg tctcagtttt cagctatacc tgcacgttca taaccaacaa 3660
tataaaccgt ggtctcatgt aacacataaa caattcatgc ctttcatagt ttattattat 3720
taaagtctaa acaaaattgc aatttcttag gtaaccttat atttacaata aatgaagatt 3780
accctcaaat gctagaagct gtctaggtcc gtccggtgtg tcagattttc ctcagattag 3840
atgtgccaat aaccaagttt attcagtaaa caacttgtac ttgtttcatc tggttttatt 3900
actctcaccc ataaacagta atgactctct gaccctctgg aaatatgtaa tgcttccaat 3960
cttgctttgt gtatctcatt taatttgtta taaggtagta ctgattttag catattaatg 4020
cgatttcttc cttgttgttt gctttggtct gtgttcaatc cagagagctt aaattgtcat 4080
tattttggga agaaaacctg tatttttgtt agtttacaat attatgaaat ttcacttcag 4140
gagaaactgc tgggcttcct gtggctttgt tttcttagtt actttttccg tgccgtgtat 4200
tttttaattg atttttcttc ttttacttga aaagaaagtg ttttattttc aaatctggtc 4260
catatttaca ttctagttca gagccaagcc ttaaactgta cagaatttcc actgtaatta 4320
aaactattta gtgttagtta taaatagcct tcaaaaagag agattctcca ttacacgatc 4380
acctgcatca cagcccatgg tgaatgtatg tttctgcata gcgaaataaa aatggcaaat 4440
gcactg 4446

<210> SEQ ID NO 20
<211> LENGTH: 1839
<212> TYPE: DNA
<213> ORGANISM: Homo sapiens

<400> SEQUENCE: 20
agcaacgggg tgcggcaggg tggggaacgc gggagcgggg ccagctccca ggaaagctgg 60
tctgcgagcg gcccctgccc ggctcccagg tccctgcgcg accccgccct tcccgagacc 120
ccagccgggc tgccgcccgc gtcccggaag ctccagcctg aaccatgttt ttcacttgtg 180
gcccaaatga ggccatggtg gtctccgggt tctgccgaag ccccccagtc atggtggctg 240
gagggcgtgt ctttgtcctg ccctgcatcc aacagatcca gaggatctct ctcaacacac 300
tgaccctcaa tgtcaagagt gaaaaggttt acactcgcca tggggtcccc atctcagtca 360
ctggcattgc ccaggtaaaa atccaggggc agaacaagga gatgttggcg gccgcctgtc 420
agatgttcct ggggaagacg gaggctgaga ttgcccacat tgccctggag acgttagagg 480
gccaccagag ggccatcatg gcccacatga ctgtggagga gatctataag gacaggcaga 540
aattctcaga acaggttttc aaagtggcct cctcagacct ggtcaacatg ggcatcagtg 600
tggttagcta cactctgaag gacattcacg atgaccagga ctatttgcac tctttgggga 660
aggctcgaac agctcaagtc caaaaagatg cacggattgg agaagcagag gccaagagag 720
atgctgggat ccgggaagct aaagccaagc aggaaaaggt gtctgctcag tacctgagtg 780
agatcgagat ggccaaggca cagagagatt acgaactgaa gaaggccgcc tatgacatcg 840
aggtcaacac ccgccgagca caggctgacc tggcctatca gcttcaggtg gccaagacta 900
agcagcagat tgaggagcag cgggtgcagg tgcaggtggt ggagcgggcc cagcaggtgg 960
cagtgcagga gcaggagatc gcccggcggg agaaggagct ggaggcccgg gtgcggaagc 1020
cagcggaagc ggagcgctac aagctggagc gcctagccga ggcagagaag tcccaactaa 1080
ttatgcaggc ggaggcagaa gccgcgtctg tgcggatgcg tggggaagct gaggcctttg 1140

-continued

```
ccataggggc ccgagcccga gccgaggctg agcagatggc caagaaggca gaagccttcc   1200
agctgtacca agaggctgct cagctggaca tgctgctaga gaagctgccc caggtggcag   1260
aggagatcag tggtcccttg acttcagcca ataagatcac actggtgtcc agcggcagtg   1320
ggaccatggg ggcagccaaa gtgactgggg aagtactgga cattctaact cgcctgccag   1380
agagtgtgga aagactcaca ggcgtgagca tctcccaggt gaatcacaag cctttgagaa   1440
cagcctgagc cttcagccct cacagatgcc cagcctcata gctgaagttg cctgaatgat   1500
cctcctgttg catgtaaccc actggcctcc ctgagcatgt ccattgacag tgaggtccca   1560
cccctcatct ctccttgcca aatagtttgt gccttgtctt gaagggggtt gctccccttg   1620
ccaacctcac actgctatga ttgccaactc cagcggtccc atgtcagcct tctgatgatc   1680
ccactccacc ccacctcaac ttatttaact tcctaattaa atcagactgt ttgagcctgt   1740
tgtctagaat attttcctga ccaagactga gggatgggct ggaggttttc aactttgcta   1800
cccaaataaa ttgctgtaag taagtactaa aaaaaaaaa                          1839
```

<210> SEQ ID NO 21
<211> LENGTH: 2132
<212> TYPE: DNA
<213> ORGANISM: Homo sapiens

<400> SEQUENCE: 21

```
ggggagccct ggcctcccca cctcctcccg tccccaccct gttcccagca ctcaagcctt     60
gccaccgccg agccgggctt cctgggtgtt tcaggcaagg aagtctaggt ccctgggggg    120
tgacccccaa ggaaaaggca gcctccctgc gcacccggtt gcccggagcc ctctccaggg    180
ccggctgggc tgggggttgc cctggccagc aggggcccgg gggcgatgcc acccggtgcc    240
gactgaggcc accgcaccat ggcccgctcg ctgacctggc gctgctgccc ctggtgcctg    300
acggaggatg agaaggccgc cgcccgggtg gaccaggaga tcaacaggat cctcttggag    360
cagaagaagc aggaccgcgg ggagctgaag ctgctgcttt tgggcccagg cgagagcggg    420
aagagcacct tcatcaagca gatgcggatc atccacggcg ccggctactc ggaggaggag    480
cgcaagggct tccggcccct ggtctaccag aacatcttcg tgtccatgcg ggccatgatc    540
gaggccatgg agcggctgca gattccattc agcaggcccg agagcaagca ccacgctagc    600
ctggtcatga gccaggaccc ctataaagtg accacgtttg agaagcgcta cgctgcggcc    660
atgcagtggc tgtggaggga tgccggcatc cgggcctact atgagcgtcg gcgggaattc    720
cacctgctcg attcagccgt gtactacctg tcccacctgg agcgcatcac cgaggagggc    780
tacgtcccca cagctcagga cgtgctccgc agccgcatgc ccaccactgg catcaacgag    840
tactgcttct ccgtgcagaa aaccaacctg cggatcgtgg acgtcggggg ccagaagtca    900
gagcgtaaga aatggatcca ttgtttcgag aacgtgatcg ccctcatcta cctggcctca    960
ctgagtgaat acgaccagtg cctggaggag aacaaccagg agaaccgcat gaaggagagc   1020
ctcgcattgt ttgggactat cctggaacta ccctggttca aaagcacatc cgtcatcctc   1080
tttctcaaca aaaccgacat cctggaggag aaaatcccca cctcccacct ggctacctat   1140
ttccccagtt tccagggccc taagcaggat gctgaggcag ccaagaggtt catcctggac   1200
atgtacacga ggatgtacac cgggtgcgtg gacggccccg agggcagcaa gaagggcgca   1260
cgatcccgac gcctcttcag ccactacaca tgtgccacag acacacagaa catccgcaag   1320
gtcttcaagg acgtgcggga ctcggtgctc gcccgctacc tggacgagat caacctgctg   1380
```

```
tgacccaggc cccacctggg gcaggcggca ccggcgggcg ggtgggaggt gggagtggct   1440

gcagggaccc ctagtgtccc tggtctatct ctccagcctc ggcccacacg caagggagtc   1500

gggggacgga cggcccgctg ctggccgctc tcttctctgc ctctcaccag gacagccgcc   1560

ccccagggta ctcctgccct tgcttgactc agtttccctc ctttgaaagg gaaggagcaa   1620

aacggccatt tgggatgcca gggtggatga aaaggtgaag aaatcagggg attgaggact   1680

tgggtgggtg ggcatctctc aggagcccca tctccgggcg tgtcacctcc tgggcagggt   1740

tctgggaccc tctgtgggtg acgcacaccc tgggatgggg ctagtagagc cttcaggcgc   1800

cttcgggcgt ggactctggc gcactctagt ggacaggaga aggaacgcct tccaggaacc   1860

tgtggactag gggtgcaggg acttcccttt gcaaggggta acagaccgct ggaaaacact   1920

gtcactttca gagctcggtg gctcacagcg tgtcctgccc cggtttgcgg acgagagaaa   1980

tcgcggccca caagcatccc cccatccctt gcaggctggg ggctgggcat gctgcatctt   2040

aacctttgt atttattccc tcaccttctg cagggctccg tgcgggctga aattaaagat   2100

ttcttagagg ctgcgtcgcc agcgtcctgt tt                                2132
```

<210> SEQ ID NO 22
<211> LENGTH: 3798
<212> TYPE: DNA
<213> ORGANISM: Homo sapiens

<400> SEQUENCE: 22

```
ggggcaagtg actcatgagc acgagttgtt aagcgatgga atttgggaga tcaagccaca     60

ctgcttaaaa catcacatga tctccctctg gccccgtatt tcataaaaca gagcggatcg    120

caggaggccg acactgtgac tcctggtgga tgggactggg gagtcagagt caagccctga    180

ctggttgcag gcgctcggag tcagcatgga aagtctctgc ggggtcctgg gatttctgct    240

gctggctgca ggactgcctc tccaggctgc caagcgattt cgtgatgtgc tgggccatga    300

acagtatccc gatcacatga gagagcacaa ccaattacgt ggctggtctt cggatgaaaa    360

tgaatgggat gaacacctgt atccagtgtg gaggaggggga gacggcaggt ggaaggactc    420

ctgggaagga ggccgtgtgc aggcagtcct gaccagtgac tcaccggctc tggtgggttc    480

caatatcact tttgtggtga acctggtgtt ccccagatgc cagaaggaag atgctaatgg    540

caatatcgtc tatgagaaga actgcaggaa tgatttggga ctgacatctg acctgcatgt    600

ctacaactgg actgcagggg cagatgatgg tgactgggaa gatggcacca gccgaagcca    660

gcatctcagg ttcccggaca ggaggccctt ccctcgcccc catggatgga agaaatggag    720

ctttgtctac gtctttcaca cacttggcca gtatttccaa aaactgggtc ggtgttcagc    780

acgggtttct ataaacacag tcaacttgac agctggccct caggtcatgg aagtgactgt    840

ctttcgaaga tacggccggg catacattcc catctcgaag gtgaaagatg tgtatgtgat    900

aacagatcag atccctgtat tcgtgaccat gtcccagaag aatgacagga acttgtctga    960

tgagatcttc ctcagagacc tccccatcgt cttcgatgtc ctcattcatg atcccagcca   1020

cttcctcaac gactctgcca tttcctacaa gtggaacttt ggggacaaca ctggcctgtt   1080

tgtctccaac aatcacactt tgaatcacac ttatgtgctc aatggaacct tcaaccttaa   1140

cctcaccgtg caaactgcag tgcccgggcc atgccctccc ccttcgcctt cgactccgcc   1200

tccaccttca actccgccct cacctccgcc ctcacctctg cccacattat caacacctag   1260

cccctcttta atgcctactg gttacaaatc catggagctg agtgacattt ccaatgaaaa   1320

ctgccgaata aacagatatg gctacttcag agccaccatc acaattgtag aggggatcct   1380
```

-continued

```
ggaagtcagc atcatgcaga tagcagatgt ccccatgccc acaccgcagc ctgccaactc   1440
cctgatggac ttcactgtga cctgcaaagg ggccaccccc atggaagcct gtacgatcat   1500
ctccgacccc acctgccaga tcgcccagaa ccgggtctgc agccctgtgg ctgtggatgg   1560
gctgtgcctg ctgtctgtga gaagagcctt caatgggtct ggcacctact gtgtgaattt   1620
cactctggga gatgatgcaa gcctggccct caccagcacc ctgatctcta tccctggcaa   1680
agacccagac tcccctctga gagcagtgaa tggtgtcctg atctccatcg gctgcctggc   1740
tgtgcttgtc accatggtta ccatcttgct gtacaaaaaa cacaaggcgt acaagccaat   1800
aggaaactgc cccaggaaca cggtcaaggg caagggcctg agtgttctcc tcagtcacgc   1860
gaaagccccg ttcttccgag gagaccagga gaaggatcca ttgctccagg acaagccaag   1920
gacactctaa gtctttggcc ttccctctga ccaggaaccc actcttctgt gcatgtatgt   1980
gagctgtgca gaagtatgtg gctgggaact gttgttctct aaggattatt gtaaaatgta   2040
tatcgtggct tagggagtgt ggttaaatag cattttagag aagacatggg aagacttagt   2100
gtttcttccc atctgtattg tggtttttac actgttcgtg gggtggacac gctgtgtctg   2160
aaggggaggt ggggtcactg ctacttaagg tcctaggtta actgggggag ataccacaga   2220
tgcctcagct ttccacataa catgggcatg aacccagcta atcaccacct gaaggccatg   2280
cttcatctgc cttccaactc actgagcatg cctgagctcc tgacaaaatt ataatgggcc   2340
cgggctttgt gtatggtgcg tgtgtgtaca tattctactc attaaaaagg cagtctaata   2400
agctgtgtga ttattatatt ggggagaaaa ttttccctgt gtagttcagt gaactaccca   2460
tccattcatt tatccatgga cacttataaa gcatgtggtg ggctgcactt gacctatgag   2520
accttgtcta ttctatacca gcagaccctt aatagcaacc aagtgagatc tgagagtcca   2580
gactgtatct accttgatga aggtagacaa ctggataaat atgatggtat tatagaatga   2640
ctgctcattt ttgaggcatt gtggaggacc aacattcagt ctggtacttt gacacccccc   2700
ccccccacta ggtggcctag aagcaaaaag aagctttttg tttggaaatt gtctccaaag   2760
aatgtaaaaa ttgctgacca cttaggacag ggcctctcag ccaggagtgt ttggcaatgt   2820
ttggagagat ttgtggttgt caaaactagg gtggggtgct actggcatct agtggggaga   2880
gcccagggct gctgaacacc ctgtgcctgc gggacagccc cacagccaag gagcccagag   2940
caactgaagg agtcctgggc acaggcatcc caacagcagc cttgtatctg aaccgagccc   3000
tgacatctaa agctttgtga cctagtgaca tggcatgtta ggagtctttt ctgcctctgt   3060
ctcagctgta gaaggggtat gctgtccctc tctgactcac ttcacatggc cgctactgct   3120
cctgatggaa gaatgagtgc aggtacagcc ttgtgttaca gtctcagcct ggggacagaa   3180
acacgtgaag aagcttgatt gattgattga ttgattgatt gattgattga ttgattgatt   3240
gattgatttt tacatactaa ggagcccgtt cactagtacc caaaacagga cattgatttc   3300
aggttgctgc agaatccaca gaccgcttag actccacccc atggttccaa acactgtctt   3360
gtggaggtgg gaccccataa tttggatttc tgagaaacca acagagaatc cttattctgc   3420
tggttccagg acaagaatga gcaaggctgg gcttgggatc acttccttgc tcaggtcaac   3480
agggggcagc agagaacagc agatacagaa cagccaccaa agcggcaggt ccatgacttt   3540
gtttatctag cttcatctaa acaaatttta atctagtagt aggaaagaag tctgaaatag   3600
taaattgtgt cgatttatat tttccaagtg accctggtaa gggaactgtc tgcagaatgg   3660
aagaaatagc ctaagagaca gggatggctt gattgatgtt ggctgagaat taaaacttct   3720
```

-continued cacgaaaagt acatgtgtat gtaacaaatt attccaggaa ttgcttattt ctagggcttt 3780
tataaatgtc tgcatcct 3798

<210> SEQ ID NO 23
<211> LENGTH: 2996
<212> TYPE: DNA
<213> ORGANISM: Homo sapiens

<400> SEQUENCE: 23
atgtggtgcg gcgggaggaa gtgcggcttg ttttcccggc taggctctgg agcggcgggc 60
gcggcgcgat gcgcgggtac ccgggagcga acggctgcga gccctgatga agctcgagca 120
gccccagcct gatggaggcg cctccgtggg agccggtgcg caatgactcc ctgcctccca 180
cgctgagccc cgcggtgccg ccctacgtga agctcggcct caccgcggtc tacaccgtct 240
tctacgcgct cctcttcgtg ttcatctatg cgcagctctg gctggtgctg cgctaccgtc 300
acaagcggct cagctaccag agcgtcttcc tcttcctttg cctcttctgg gcctcgctgc 360
gtaccgtgct cttctccttt tacttccgag acttcgtggc agccaactcg ttcagcccct 420
tcgtcttctg gctgctctac tgcttccccg tgtgtctaca gttcttcacc ctcacgctca 480
tgaacttgta cttcacgcag gtgattttca aggccaagtc aaaatattct ccagagctac 540
tcaaataccg gttacccctc tacctggcct cacttttcat cagcctcgtt ttcctgttgg 600
tgaatctgac ctgtgctgtg ctggtgaaga cgggagactg ggacaggaag gttatcgtct 660
ctgtgagagt ggccatcaat gacacactct ttgtgctgtg tgctatctct ctctccatct 720
gcctctacaa aatctccaag atgtccctgg ccaacatcta cttggagtca aagggctcat 780
cagtgtgtca ggtaactgcc attggtgtca ccgtcatctt gctctacacc tctcgggcct 840
gctacaacct gttcatcttg tcattttctc agatcaagaa cgtccattcc tttgattatg 900
actggtacaa tgtatccgac caggcagatc tgaagagcca gctgggtgac gccggctacg 960
tagtgtttgg cgtggtgctt ttcgtgtggg agctcctacc caccaccttg gtggtttatt 1020
tcttccgagt cagaaatccc acgaaggatc ttaccaatcc tgggatggtc cccagccatg 1080
gattcagtcc cagatcttac ttctttgaca acccccgaag atatgacagt gatgatgacc 1140
ttgcctggaa cattgcccct cagggacttc agggaagttt tgctccagac tactatgatt 1200
ggggacaaca aaataacagc ttcctggcac aagcaggaac tttgcatcaa gactccactt 1260
tggatccaga caaagcaagc caagggtagc agcagctgac acagccctat ggaagagttc 1320
tctgttgaaa gccttcagcc agacagaccg gatgacagct gagttgctaa ggcagttttc 1380
cttaggaaac agaactctag tttttgctat agctttctca tggctccaca gggctaagca 1440
ataatttaga gcaataaact ctttagtact agcagagaat ctggctattt cagtgggtat 1500
aatttaaact tataaaagag gttctgtact tttataaaga tgtattttat ataacttaaa 1560
tactaatgct aaagtatact aggtttttcc ttgattgtta attgcaacgt atgttgtagt 1620
ttgcacagac tttcatgcat aattcacttt aaaacgtata gaatacgtgg tctaatagtt 1680
taaagctttg gggaaagttt ccacaaatct tacctctgaa ggtccctctt gtgagtgcca 1740
cgtggtgggc tcctttcacc gccactcaag cattccaagt tcaggagaag cagagtacca 1800
tggtctgtac gtaacaggct caacagcagc agcagcagca gcagcagcag cagcaatttc 1860
tcgtaaactc tgtcctaagc ctggtccttc ttcatctgaa agcactacta caagcactcc 1920
agtaacaagt ggatactgtt aagatgtagt tgctgacact attaaacctc ctctgctgtg 1980
tgtgtagcca ttttgtagag ttttcttcag cccggtgtaa ctgaatactc actacctcag 2040

```
tacctcagta ggatgcaagg actgtgcctt ctttgactca gccagtgctt gctatagtca   2100
ggctacaagc caagaggtcc ccacagagta ttaacaataa atacttctgg ccttcaagct   2160
ctaaaggatt gcagactcct gacagctttt ctgtaagaca tgcctgtcat ttgtatgagg   2220
ctgacacggg gctcactgcc tgttattttt agatagtgtt ctattaaaag ctatgtgtat   2280
gagaaagtag gctctgccta cgtggcggca gcatccccat atcagccaga gagtgttcca   2340
gacagtggtc ctcttgtgcc atctccgtgc tgtcctggga aaacgctgga acaacgtggc   2400
cctcctggag gccggatgct ctggcttctt ctggtcctat aggtcacaga gccacgccca   2460
ctttctccca ttttgttata tttaagattg ggagcccagt ttccagtggg ttgtaatggg   2520
gtcttcgttg tacagaggac gacgtggagg aacttgcgca gccccgcccc acaccctgcc   2580
tttgggtttg agtaaacatc tgggttgcaa gccatttaaa attgcttctt tgccagggtg   2640
aattctggca aagcctacac aaatcgcctg tacgatagca ctgtataaaa gtttatctgt   2700
caccatacct gcaatgattt ggctgttgca gccagtgccc acagctcctg tgtccttgtc   2760
tctagcaggg cggtacctgt cagcagccaa gggcaaggct tgctggaaag cacagcctca   2820
ttaaggctgt tctgtttgca cccattttgt agcacatgca cactttacag ttggtgaatg   2880
ctgggcgtct gttttcttac agtaacaagc aagctatcat ccatttttac aataaagttg   2940
tcagcattca tgtcagcaat aaaaagacta cagctcttaa aaaaaaaaaa aaaaaa       2996
```

<210> SEQ ID NO 24
<211> LENGTH: 4762
<212> TYPE: DNA
<213> ORGANISM: Homo sapiens

<400> SEQUENCE: 24

```
aagggaggga cctggaggac tcagggtagg attgtagagc tcagggacag ggagtggagg     60
gcgccgcggt gagaccgctg ttgtgtagtt gttagactgg gcggggctgg gacgcaggcg    120
ggacccgtgg ggacgcgagc ccgggcgcca aatgcccaga cagaggcgac cgcgggctcg    180
gcttggccac gacctctcgg caccccttagg cctgtgcacc ctggctgtct gcccttggtc   240
cccaacccac catgccctca cccgcgcctc ccaccgagct gctgccgtgg gagcgcgcgg    300
tggtgctgct gtcgtgtgcg ctgtcagctc tgggctcggg cctcctggtg gccacgcacg    360
ccctgtggcc tgacctgcgt agccgggcgc ggcgcctgct actcttcctg tcgctagcgg    420
acctgctctc ggctgcctcg tacttctacg gagtgctgca ggactttgcg ggcacttcgt    480
gggattgcgt ccttcagggc gctctctcta ctttcgccaa caccagctcc ttcttctgga    540
cggtggccat cgccctctac ctatacctca gcatcgtccg aactacgcgc gggccctcca    600
cggaccacct aatctgggct tttcacctca tcagctgggg tgtcccgttg gccatcacag    660
tggcagccgt ctctctaaag aagataggct atgatgcctc ggatgtgtct gtgggctggt    720
gctggatcaa cctggaggct gaggaccgtg tcctgtggat gctactgacc gggaagctgt    780
gggagatgct ggcttatatc ttgctacctc tgctgtacct tttggtcaga aagcacatca    840
acagggcgca ccaggcgctc tcggagtacc ggcccatctg cgaggggcgc cagctgcagc    900
gaggctcctc cacttccacg gcagataaga agttggtcct cattccgctc atattcatct    960
gcctccgcgt ctggagcacc gtgcgctttg tcctgacgct ctgtggttcc ccggctgtac   1020
agacacccgt gctggttgtt ctgcatggca ttggaaacac cttccaggga ggggccaact   1080
gcatcatgtt cgtcctctgt acccgggcag tccgcacaag gctcttttct ctttgctgct   1140
```

-continued

```
gctgtcctcg gccctccacc cagagccctc cgggggctcc tacgcccccc aagataggag   1200
aatctcagga atccagacgg accccagaag tgcccagcac ttgagcggtt ggctttcctc   1260
cctgtccgta ctggcgctgc cttcctggtt cctgcttcag gattaggaga ccaagcatgc   1320
tgtcagcctg gcctaaagtg aagatcggag cccagtggag ggacagccat cagtatggac   1380
tcttctacct cccagacttg caggcaggca gtgtgttcct tgcacactca tgtcctggtt   1440
cagtggggtt tgtttgtgta agcacaaaga ccgtgagact cagctatgcg ggataccgcc   1500
agggcattgg ttctcagtgt ccccggccac caacgttgtt tacagttgga gggatccgta   1560
cctgtggacc catcccaggc ttgactgaat aataatgaac accatcttgg atcccagaca   1620
tcgcagtatg gagtccgggc ttgccagggc gttgagaatc cctagagacc ctgggggtaa   1680
ttagcagtgc tggtcagctg agggtaatat ccttaaacta ggtcccaagt ccacggaagt   1740
cacaggagac tgccatcatt gatgaaaacc acccgggcac acactcatgg gcatctcacg   1800
gaatctctgc gtgggtcatc gcccctcagt gtttattaca tctgaatttc agcacaggcc   1860
agagtccaga gtcctgtcca ttagtcaatc acttaacatc ctcgttccct ccaggtacca   1920
ggacagaagg cagctcagct ccagccccta tggacaatta ccagttcacc tactgttctc   1980
acagagccct ctcctcacgg tgactcatac agggggaggg ggtctggctc tgcactttgc   2040
ttaggaaagg tgaccagtga atggatctga ttccaccctg aaggtgaatg tttgaagagt   2100
cagcctcggg ctggcctgta gctccgtgta gtttccaggt tggtcctagc accccaaata   2160
cttaaaaggc ctttgtgttt tgtagttatc tgggggatat agaaatagga ttctgagatg   2220
attacatttt attttgtttt tttgagacag ggtctcatgt ggacatgctg gcctggaact   2280
tgttatgtag atcaggctgg cctccaactc acagagatcc acctgcctct gcctcctgat   2340
agttacattt ttaaaaaaat gttgtgttgt gttgtgcctg ttaggcaggt gctccgccac   2400
tgagttcaat cccatgcccc tccccactcc cttttttttg agacataatc ttactaagtt   2460
gcctagactg gccttcaact ctcagtcgac caggctggtc ttgaacttaa gattttccta   2520
cctcaacttc ccaggaagct agaattgtcg cctttggcta gcaagcctgg ccagagcggg   2580
gcttaactga gatctgctca gtggctcttc cacccacaca tccctcattt cagaaagcag   2640
tgtgtgccga cgtgcaggct ctcggtgtgg gaagtgtgcc cgccaccttg cagtcaaggt   2700
gaggtagcgc ccttggattc tgtcaatacc ctcacaaaac cgagaggatg ctcagagcct   2760
ggctcaagat ggaagcagag tcacacgggg catcagcgcc catctctatc aggaaaggaa   2820
tagtcgcgca gagggctgtg tctgtatgct cctcttctgg cttcctaaag catttcttta   2880
ggaaactcta caagaggtgg gttccctttt gggagtctaa gaaagctcct tggcttggta   2940
ctctgtctgc ttacaaaacc agtctgtgta gggtgtcctg agatcctgtg aagatattac   3000
agccaatgtg tgcactgtca gcgtgtagcg cagcggtaat ggatctcctg gcttctaaaa   3060
tggaacagaa attctaggaa tttgtctcct ggaggggaga aaataaacca ccaaatacta   3120
cggaggaaat gatgttggat aaacccagct ggacagagca gtgtgaaacc ctggctgttt   3180
ggggctttgt tcaaggaaag gcaggcaggg ggcatccgaa agccctgctc ctggagcctg   3240
gggcttaccc aagttttctc tgatgccact ggccaggatt gctgtccgta aaaccccccta  3300
caaagtctac acttggctct ttccatctgt ttcccatgct gccctgtcac cgaaggtggc   3360
tggtggtgac ccgaggcccg gtgcctgacc tctagcccta cgtgctcaca gacatcaacc   3420
ttagctcagc cggtggccaa gtgggtcttc taggcagcca gggttcagag ctgaagagga   3480
atagaagaat ccttggggcc aggaggggcc ttagcaccgg tgaggaccag ctcccctttg   3540
```

-continued ctttgctcag cctcgtgggt tcctatctct actaggaagt gtcattaata tctgtctgtc 3600
cgtgttcctc tgtcacccaa atgtgacctc agccttaatg ggtgctacag cccccacacc 3660
cttcttaagc actttatgaa ttttttttt ccgagacagg gtttctctgt atagccctgg 3720
ctgtcctgga actcactctg tagaccaggc tggcctcgaa ctcagaaatc cgcctgcctc 3780
tgcctcctga gtgctgggat taaagacgtg tgtcaccacc gcctggtaca ctttgtgaat 3840
cttgttctgc aaatccgttg ccagctgctt cctgcctttg actttctgag gcagagagag 3900
agagagggag agagggagag agggagagag agagggagag aatgtgtgtg tgcgtgagat 3960
attatgctct agcatttatc tctcttcatt ttttttttt gttttgtttt ttaagtttcg 4020
aaacagggtt ctcaggctgg agagatggct cagcggctaa gagcactgac tgctcttccg 4080
aaggtcctga gttcaaattc cagcaaccac atggtggctc acaaccattt gtaatgagat 4140
ctgatgccct cttctggtgt gtctgaggac agatacagtg tacttatata taataaataa 4200
ataaatcgtt aatttttttt ttaaaaaaga atcagggttc tcactacttg tccaggcagg 4260
ccttaagcag ttttactgtt tctgggatta caggcctatg ccaccccgag ccggcttttt 4320
agtttgttct ctctgtctct ctgtctctct gtctctctct ctctctctct ctctctctct 4380
ctctctctct ctctctctct ctttctctct ctatgtgtgt ctctttctct ctctgcctct 4440
ctgtctgtct gtctctctct ctgcttctct ctctgaaaat aaaaataaaa actattatgt 4500
gtccaaagta caaatgagac catatgtgtt tgtttgtatg tgtacgggta ttttgtgtgt 4560
acgcagttcc cttagaggcc agagggactc tgatcccctg aatctggagt catagctgtg 4620
aactctgggc aaagggaact aagcctgggt cctttgcagg aacagcaacg ctcttatctg 4680
ttgagctagc tctccagccc tctctgcaaa tgtttgtgtg aactcacagt tgtggtataa 4740
ttaaacctgg catgagattt tt 4762

<210> SEQ ID NO 25
<211> LENGTH: 1919
<212> TYPE: DNA
<213> ORGANISM: Homo sapiens

<400> SEQUENCE: 25
gcagtcatct gactcggtga ctcacccgcg gccgcgcttc ctctgatccg ggccgggcgg 60
gaagtcgggt cccgaggctc cggctcggca gaccgggcgg aaagcagccg agcggccatg 120
gagctgtgcg ggctggggct gccccggccg cccatgctgc tggcgctgct gttggcgaca 180
ctgctggcgg cgatgttggc gctgctgact caggtggcgc tggtggtgca ggtggcggag 240
gcggctcggg ccccgagcgt ctcggccaag ccggggccgg cgctgtggcc cctgccgctc 300
tcggtgaaga tgaccccgaa cctgctgcat ctcgccccgg agaacttcta catcagccac 360
agccccaatt ccacggcggg cccctcctgc accctgctgg aggaagcgtt tcgacgatat 420
catggctata tttttggttt ctacaagtgg catcatgaac ctgctgaatt ccaggctaaa 480
acccaggttc agcaacttct tgtctcaatc acccttcagt cagagtgtga tgctttcccc 540
aacatatctt cagatgagtc ttatacttta cttgtgaaag aaccagtggc tgtccttaag 600
gccaacagag tttggggagc attacgaggt ttagagacct ttagccagtt agtttatcaa 660
gattcttatg gaactttcac catcaatgaa tccaccatta ttgattctcc aaggttttct 720
cacagaggaa ttttgattga tacatccaga cattatctgc cagttaagat tattcttaaa 780
actctggatg ccatggcttt taataagttt aatgttcttc actggcacat agttgatgac 840
cagtctttcc catatcagag catcactttt cctgagttaa gcaataaagg aagctattct 900
ttgtctcatg tttatacacc aaatgatgtc cgtatggtga ttgaatatgc cagattacga 960
ggaattcgag tcctgccaga atttgatacc cctgggcata cactatcttg ggaaaaggt 1020 cagaaagacc tcctgactcc atgttacagt agacaaaaca agttggactc ttttggacct 1080
ataaacccta ctctgaatac aacatacagc ttccttacta catttttcaa agaaattagt 1140
gaggtgtttc cagatcaatt cattcatttg ggaggagatg aagtggaatt taaatgttgg 1200
gaatcaaatc caaaaattca agatttcatg aggcaaaaag gctttggcac agattttaag 1260
aaactagaat ctttctacat tcaaaaggtt ttggatatta ttgcaaccat aaacaaggga 1320
tccattgtct ggcaggaggt tttgatgat aaagcaaagc ttgcgccggg cacaatagtt 1380
gaagtatgga aagacagcgc atatcctgag gaactcagta gagtcacagc atctggcttc 1440
cctgtaatcc tttctgctcc ttggtactta gatttgatta gctatggaca agattggagg 1500
aaatactata aagtggaacc tcttgatttt ggcggtactc agaaacagaa acaacttttc 1560
attggtggag aagcttgtct atggggagaa tatgtggatg caactaacct cactccaaga 1620
ttatggcctc gggcaagtgc tgttggtgag agactctgga gttccaaaga tgtcagagat 1680
atggatgacg cctatgacag actgacaagg caccgctgca ggatggtcga acgtggaata 1740
gctgcacaac ctctttatgc tggatattgt aaccatgaga acatgtaaaa aatggagggg 1800
aaaaaggcca cagcaatctg tactacaatc aactttattt tgaaatcatg taaaataaga 1860
tattagactg ttttttgaat aaaatatttt tattgattga aaaaaaaaaa aaaaaaaaa 1919

<210> SEQ ID NO 26
<211> LENGTH: 1428
<212> TYPE: DNA
<213> ORGANISM: Homo sapiens

<400> SEQUENCE: 26
ggccggcggc atccgaggcg catgactagt tggggccaaa ccagtgctcc tgccacctct 60
ctggctgccc cctagagcct gcccatccca gcctgaccaa tgtccacagc cagggagcag 120
ccaatcttca gcacacgggc gcacgtgttc caaattgacc cagccaccaa gcgaaactgg 180
atcccagcgg gcaagcacgc actcactgtc tcctatttct acgatgccac ccgcaatgtg 240
taccgcatca tcagcatcgg aggcgccaag gccatcatca acagcactgt cactcccaac 300
atgaccttca ccaaaacttc ccagaagttc gggcagtggg ccgacagtcg cgccaacaca 360
gtctacggcc tgggctttgc ctctgaacag catctgacac agtttgccga gaagttccag 420
gaagtgaagg aagcagccag gctggccagg gagaaatctc aggatggcgg ggagctcacc 480
agtccagccc tggggctcgc ctcccaccag gtgcccccga gccctctcgt cagtgccaac 540
ggccccggcg aggaaaaact gttccgcagc cagagcgctg atgcccccgg ccccacagag 600
cgcgagcggc taaagaagat gttgtctgag ggctccgtgg gcgaggtaca gtgggaggcc 660
gagtttttcg cactgcagga cagcaacaac aagctggcag gcgccctgcg agaggccaac 720
gccgccgcag cccagtggag gcagcagctg gaggctcagc gtgcagaggc cgagcggctg 780
cggcagcggg tggctgagct ggaggctcag gcagcttcag aggtgacccc caccggtgag 840
aaggaggggc tgggccaggg ccagtcgctg gaacagctgg aagctctggt gcaaaccaag 900
gaccaggaga ttcagaccct gaagagtcag actgggggc cccgcgaggc cctggaggct 960
gccgagcgtg aggagactca gcagaaggtg cagacccgca atgcggagtt ggagcaccag 1020
ctgcgggcga tggagcgcag cctggaggag gcacgggcag agcgggagcg ggcgcgggct 1080

```
gaggtgggcc gggcagcgca gctgctggac gtcagcctgt ttgagctgag tgagctgcgt   1140
gagggcctgg cccgcctggc tgaggctgcg ccctgagccg ggctggtttt tctatgaacg   1200
attccggcct gggatgcggg ccaggctgca ggcggcatag ttgggcccat tcgtcctgga   1260
aagggactgg ggggtcccaa cttagccctg ggtgggccgg gccgggctgg gctggggtgg   1320
gccccagtcg gctctggttg ttggcagctt tggggctgtt tttgagcttc tcattgtgta   1380
gaatttctag atcccccgat tacatttcta agcgtggcaa aaaaaaaa                1428
```

<210> SEQ ID NO 27
<211> LENGTH: 3249
<212> TYPE: DNA
<213> ORGANISM: Homo sapiens

<400> SEQUENCE: 27

```
caagcttagc ctggccggga aacgggaggc gtggaggccg ggagcagccc ccggggtcat     60
cgccctgcca ccgccgcccg attgctttag cttggaaatt ccggagctga agcggccagc    120
gagggaggat gaccctctcg gcccgggcac cctgtcagtc cggaaataac tgcagcattt    180
gttccggagg ggaaggcgcg aggtttccgg gaaagcagca ccgccccttg gcccccaggt    240
ggctagcgct ataaaggatc acgcgcccca gtcgacgctg agctcctctg ctactcagag    300
ttgcaacctc agcctcgcta tggctcccag cagcccccgg cccgcgctgc ccgcactcct    360
ggtcctgctc ggggctctgt tcccaggacc tggcaatgcc cagacatctg tgtccccctc    420
aaaagtcatc ctgccccggg gaggctccgt gctggtgaca tgcagcacct cctgtgacca    480
gcccaagttg ttgggcatag agaccccgtt gcctaaaaag gagttgctcc tgcctgggaa    540
caaccggaag gtgtatgaac tgagcaatgt gcaagaagat agccaaccaa tgtgctattc    600
aaactgccct gatgggcagt caacagctaa aaccttcctc accgtgtact ggactccaga    660
acgggtggaa ctggcacccc tcccctcttg gcagccagtg ggcaagaacc ttaccctacg    720
ctgccaggtg gagggtgggg caccccgggc caacctcacc gtggtgctgc tccgtgggga    780
gaaggagctg aaacgggagc cagctgtggg ggagcccgct gaggtcacga ccacggtgct    840
ggtgaggaga gatcaccatg gagccaattt ctcgtgccgc actgaactgg acctgcggcc    900
ccaagggctg gagctgtttg agaacacctc ggccccctac cagctccaga cctttgtcct    960
gccagcgact cccccacaac ttgtcagccc ccgggtccta gaggtggaca cgcaggggac   1020
cgtggtctgt tccctggacg ggctgttccc agtctcggag gcccaggtcc acctggcact   1080
gggggaccag aggttgaacc ccacagtcac ctatggcaac gactccttct cggccaaggc   1140
ctcagtcagt gtgaccgcag aggacgaggg cacccagcgg ctgacgtgtg cagtaatact   1200
ggggaaccag agccaggaga cactgcagac agtgaccatc tacagctttc cggcgcccaa   1260
cgtgattctg acgaagccag aggtctcaga agggaccgag gtgacagtga agtgtgaggc   1320
ccaccctaga gccaaggtga cgctgaatgg ggttccagcc cagccactgg gcccgagggc   1380
ccagctcctg ctgaaggcca ccccagagga caacgggcgc agcttctcct gctctgcaac   1440
cctggaggtg gccggccagc ttatacacaa gaaccagacc cgggagcttc gtgtcctgta   1500
tggcccccga ctggacgaga gggattgtcc gggaaactgg acgtggccag aaaattccca   1560
gcagactcca atgtgccagg cttgggggaa cccattgccc gagctcaagt gtctaaagga   1620
tggcactttc ccactgccca tcggggaatc agtgactgtc actcgagatc ttgagggcac   1680
ctacctctgt cgggccagga gcactcaagg ggaggtcacc cgcaaggtga ccgtgaatgt   1740
```

gctctccccc cggtatgaga ttgtcatcat cactgtggta gcagccgcag tcataatggg 1800
cactgcaggc ctcagcacgt acctctataa ccgccagcgg aagatcaaga aatacagact 1860
acaacaggcc caaaaaggga cccccatgaa accgaacaca caagccacgc ctccctgaac 1920
ctatcccggg acagggcctc ttcctcggcc ttcccatatt ggtggcagtg gtgccacact 1980
gaacagagtg gaagacatat gccatgcagc tacacctacc ggccctggga cgccggagga 2040
cagggcattg tcctcagtca gatacaacag catttggggc catggtacct gcacacctaa 2100
aacactaggc cacgcatctg atctgtagtc acatgactaa gccaagagga aggagcaaga 2160
ctcaagacat gattgatgga tgttaaagtc tagcctgatg agaggggaag tggtgggggga 2220 gacatagccc caccatgagg acatacaact gggaaatact gaaacttgct gcctattggg 2280
tatgctgagg ccccacagac ttacagaaga agtggccctc catagacatg tgtagcatca 2340
aaacacaaag gcccacactt cctgacggat gccagcttgg gcactgctgt ctactgaccc 2400
caacccttga tgatatgtat ttattcattt gttattttac cagctattta ttgagtgtct 2460
tttatgtagg ctaaatgaac ataggtctct ggcctcacgg agctcccagt cctaatcaca 2520
ttcaaggtca ccaggtacag ttgtacaggt tgtacactgc aggagagtgc ctggcaaaaa 2580
gatcaaatgg ggctgggact tctcattggc caacctgcct ttccccagaa ggagtgattt 2640
ttctatcggc acaaaagcac tatatggact ggtaatggtt acaggttcag agattaccca 2700
gtgaggcctt attcctccct tccccccaaa actgacacct ttgttagcca cctccccacc 2760
cacatacatt tctgccagtg ttcacaatga cactcagcgg tcatgtctgg acatgagtgc 2820
ccagggaata tgcccaagct atgccttgtc ctcttgtcct gtttgcattt cactgggagc 2880
ttgcactatg cagctccagt ttcctgcagt gatcagggtc ctgcaagcag tggggaaggg 2940
ggccaaggta ttggaggact ccctcccagc tttggaagcc tcatccgcgt gtgtgtgtgt 3000
gtgtatgtgt agacaagctc tcgctctgtc acccaggctg gagtgcagtg gtgcaatcat 3060
ggttcactgc agtcttgacc ttttgggctc aagtgatcct cccacctcag cctcctgagt 3120
agctgggacc ataggctcac aacaccacac ctggcaaatt tgattttttt ttttttttcca 3180 gagacggggt ctcgcaacat tgcccagact tcctttgtgt tagttaataa agctttctca 3240
actgccaaa 3249

<210> SEQ ID NO 28
<211> LENGTH: 4909
<212> TYPE: DNA
<213> ORGANISM: Homo sapiens

<400> SEQUENCE: 28
tagacgcacc ctctgaagat ggtgactccc tcctgagaag ctggacccct tggtaaaaga 60
caaggccttc tccaagaaga atatgaaagt gttactcaga cttatttgtt tcatagctct 120
actgatttct tctctggagg ctgataaatg caaggaacgt gaagaaaaaa taattttagt 180
gtcatctgca aatgaaattg atgttcgtcc ctgtcctctt aacccaaatg aacacaaagg 240
cactataact tggtataaag atgacagcaa gacacctgta tctacagaac aagcctccag 300
gattcatcaa cacaaagaga aactttggtt tgttcctgct aaggtggagg attcaggaca 360
ttactattgc gtggtaagaa attcatctta ctgcctcaga attaaaataa gtgcaaaatt 420
tgtggagaat gagcctaact tatgttataa tgcacaagcc atatttaagc agaaactacc 480
cgttgcagga gacggaggac ttgtgtgccc ttatatggag ttttttaaaa atgaaaataa 540
tgagttacct aaattacagt ggtataagga ttgcaaacct ctacttcttg acaatataca 600

-continued ctttagtgga gtcaaagata ggctcatcgt gatgaatgtg gctgaaaagc atagagggaa 660
ctatacttgt catgcatcct acacatactt gggcaagcaa tatcctatta cccgggtaat 720
agaatttatt actctagagg aaaacaaacc cacaaggcct gtgattgtga gcccagctaa 780
tgagacaatg gaagtagact tgggatccca gatacaattg atctgtaatg tcaccggcca 840
gttgagtgac attgcttact ggaagtggaa tgggtcagta attgatgaag atgacccagt 900
gctaggggaa gactattaca gtgtggaaaa tcctgcaaac aaaagaagga gtaccctcat 960
cacagtgctt aatatatcgg aaattgaaag tagattttat aaacatccat ttacctgttt 1020
tgccaagaat acacatggta tagatgcagc atatatccag ttaatatatc cagtcactaa 1080
tttccagaag cacatgattg gtatatgtgt cacgttgaca gtcataattg tgtgttctgt 1140
tttcatctat aaaatcttca agattgacat tgtgctttgg tacagggatt cctgctatga 1200
ttttctccca ataaaagctt cagatggaaa gacctatgac gcatatatac tgtatccaaa 1260
gactgttggg gaagggtcta cctctgactg tgatattttt gtgtttaaag tcttgcctga 1320
ggtcttggaa aaacagtgtg gatataagct gttcatttat ggaagggatg actacgttgg 1380
ggaagacatt gttgaggtca ttaatgaaaa cgtaaagaaa agcagaagac tgattatcat 1440
tttagtcaga gaaacatcag gcttcagctg gctgggtggt tcatctgaag agcaaatagc 1500
catgtataat gctcttgttc aggatggaat taaagttgtc ctgcttgagc tggagaaaat 1560
ccaagactat gagaaaatgc cagaatcgat taaattcatt aagcagaaac atggggctat 1620
ccgctggtca ggggacttta cacagggacc acagtctgca aagacaaggt tctggaagaa 1680
tgtcaggtac cacatgccag tccagcgacg gtcaccttca tctaaacacc agttactgtc 1740
accagccact aaggagaaac tgcaaagaga ggctcacgtg cctctcgggt agcatggaga 1800
agttgccaag agttctttag gtgcctcctg tcttatggcg ttgcaggcca ggttatgcct 1860
catgctgact tgcagagttc atggaatgta actatatcat cctttatccc tgaggtcacc 1920
tggaatcaga ttattaaggg aataagccat gacgtcaata gcagcccagg gcacttcaga 1980
gtagagggct tgggaagatc ttttaaaaag gcagtaggcc cggtgtggtg gctcacgcct 2040
ataatcccag cactttggga ggctgaagtg ggtggatcac cagaggtcag gagttcgaga 2100
ccagcccagc caacatggca aaaccccatc tctactaaaa atacaaaaat gagctaggca 2160
tggtggcaca cgcctgtaat cccagctaca cctgaggctg aggcaggaga attgcttgaa 2220
ccggggagac ggaggttgca gtgagccgag tttgggccac tgcactctag cctggcaaca 2280
gagcaagact ccgtctcaaa aaaagggcaa taaatgccct ctctgaatgt ttgaactgcc 2340
aagaaaaggc atggagacag cgaactagaa gaaagggcaa gaaggaaata gccaccgtct 2400
acagatggct tagttaagtc atccacagcc caagggcggg gctatgcctt gtctggggac 2460
cctgtagagt cactgaccct ggagcggctc tcctgagagg tgctgcaggc aaagtgagac 2520
tgacacctca ctgaggaagg gagacatatt cttggagaac tttccatctg cttgtatttt 2580
ccatacacat ccccagccag aagttagtgt ccgaagaccg aattttattt tacagagctt 2640
gaaaactcac ttcaatgaac aaagggattc tccaggattc caaagttttg aagtcatctt 2700
agctttccac aggagggaga gaacttaaaa aagcaacagt agcagggaat tgatccactt 2760
cttaatgctt tcctccctgg catgaccatc ctgtcctttg ttattatcct gcattttacg 2820
tctttggagg aacagctccc tagtggcttc ctccgtctgc aatgtccctt gcacagccca 2880
cacatgaacc atccttccca tgatgccgct cttctgtcat cccgctcctg ctgaaacacc 2940

```
tcccaggggc tccacctgtt caggagctga agcccatgct ttcccaccag catgtcactc   3000
ccagaccacc tccctgccct gtcctccagc ttcccctcgc tgtcctgctg tgtgaattcc   3060
caggttggcc tggtggccat gtcgcctgcc cccagcactc ctctgtctct gctcttgcct   3120
cgacccttcc tcctcctttg cctaggaggc cttctcgcat ttctctagc tgatcagaat    3180
tttaccaaaa ttcagaacat cctccaattc cacagtctct gggagacttt ccctaagagg   3240
cgacttcctc tccagccttc tctctctggt caggcccact gcagagatgg tggtgagcac   3300
atctgggagg ctggtctccc tccagctgga attgctgctc tctgagggag aggctgtggt   3360
ggctgtctct gtccctcact gccttccagg agcaatttgc acatgtaaca tagatttatg   3420
taatgcttta tgtttaaaaa cattccccaa ttatcttatt taatttttgc aattattcta   3480
attttatata tagagaaagt gacctatttt ttaaaaaaat cacactctaa gttctattga   3540
acctaggact tgagcctcca tttctggctt ctagtctggt gttctgagta cttgatttca   3600
ggtcaataac ggtcccccct cactccacac tggcacgttt gtgagaagaa atgacatttt   3660
gctaggaagt gaccgagtct aggaatgctt ttattcaaga caccaaattc caaacttcta   3720
aatgttggaa ttttcaaaaa ttgtgtttag attttatgaa aaactcttct actttcatct   3780
attctttccc tagaggcaaa catttcttaa aatgtttcat tttcattaaa aatgaaagcc   3840
aaatttatat gccaccgatt gcaggacaca agcacagttt taagagttgt atgaacatgg   3900
agaggacttt tggtttttat atttctcgta tttaatatgg gtgaacacca acttttattt   3960
ggaataataa ttttcctcct aaacaaaaac acattgagtt taagtctctg actcttgcct   4020
ttccacctgc tttctcctgg gcccgctttg cctgcttgaa ggaacagtgc tgttctggag   4080
ctgctgttcc aacagacagg gcctagcttt catttgacac acagactaca gccagaagcc   4140
catggagcag ggatgtcacg tcttgaaaag cctattagat gttttacaaa tttaattttg   4200
cagattattt tagtctgtca tccagaaaat gtgtcagcat gcatagtgct aagaaagcaa   4260
gccaatttgg aaacttaggt tagtgacaaa attggccaga gagtgggggt gatgatgacc   4320
aagaattaca agtagaatgg cagctggaat ttaaggaggg acaagaatca atggataagc   4380
gtgggtggag gaagatccaa acagaaaagt gcaaagttat tccccatctt ccaagggttg   4440
aattctggag gaagaagaca cattcctagt tccccgtgaa cttcctttga cttattgtcc   4500
ccactaaaac aaaacaaaaa acttttaatg ccttccacat taattagatt ttcttgcagt   4560
ttttttatgg catttttttta aagatgccct aagtgttgaa gaagagtttg caaatgcaac   4620
aaaatattta attaccggtt gttaaaactg gtttagcaca atttatattt tccctctctt   4680
gcctttctta tttgcaataa aaggtattga gccatttttt aaatgacatt tttgataaat   4740
tatgtttgta ctagttgatg aaggagtttt ttttaacctg tttatataat tttgcagcag   4800
aagccaaatt ttttgtatat taaagcacca aattcatgta cagcatgcat cacggatcaa   4860
tagactgtac ttattttcca ataaaatttt caaactttgt actgttaaa               4909
```

<210> SEQ ID NO 29
<211> LENGTH: 3499
<212> TYPE: DNA
<213> ORGANISM: Homo sapiens

<400> SEQUENCE: 29

```
cgcggacccg gccggcccag gcccgcgccc gccgcggccc tgagaggccc cggcaggtcc     60
cggcccggcg gcggcagcca tggccggggg gccgggcccg ggggagcccg cagccccccgg   120
cgcccagcac ttcttgtacg aggtgccgcc ctgggtcatg tgccgcttct acaaagtgat    180
```

```
ggacgccctg gagcccgccg actggtgcca gttcgccgcc ctgatcgtgc gcgaccagac    240
cgagctgcgg ctgtgcgagc gctccgggca gcgcacggcc agcgtcctgt ggccctggat    300
caaccgcaac gcccgtgtgg ccgacctcgt gcacatcctc acgcacctgc agctgctccg    360
tgcgcgggac atcatcacag cctggcaccc tcccgccccg cttccgtccc caggcaccac    420
tgccccgagg cccagcagca tccctgcacc cgccgaggcc gaggcctgga gcccccggaa    480
gttgccatcc tcagcctcca ccttcctctc cccagctttt ccaggctccc agacccattc    540
agggcctgag ctcggcctgg tcccaagccc tgcttccctg tggcctccac cgccatctcc    600
agccccttct tctaccaagc caggcccaga gagctcagtg tccctcctgc agggagcccg    660
cccctttccg ttttgctggc ccctctgtga gatttcccgg ggcacccaca acttctcgga    720
ggagctcaag atcggggagg gtggctttgg gtgcgtgtac cgggcggtga tgaggaacac    780
ggtgtatgct gtgaagaggc tgaaggagaa cgctgacctg gagtggactg cagtgaagca    840
gagcttcctg accgaggtgg agcagctgtc caggtttcgt cacccaaaca ttgtggactt    900
tgctggctac tgtgctcaga acggcttcta ctgcctggtg tacggcttcc tgcccaacgg    960
ctccctggag gaccgtctcc actgccagac ccaggcctgc ccacctctct cctggcctca   1020
gcgactggac atccttctgg gtacagcccg ggcaattcag tttctacatc aggacagccc   1080
cagcctcatc catggagaca tcaagagttc caacgtcctt ctggatgaga ggctgacacc   1140
caagctggga gactttggcc tggcccggtt cagccgcttt gccgggtcca gccccagcca   1200
gagcagcatg gtggcccgga cacagacagt gcggggcacc ctggcctacc tgcccgagga   1260
gtacatcaag acgggaaggc tggctgtgga cacggacacc ttcagctttg ggtggtagt    1320
gctagagacc ttggctggtc agagggctgt gaagacgcac ggtgccagga ccaagtatct   1380
gaaagacctg gtggaagagg aggctgagga ggctggagtg gctttgagaa gcacccagag   1440
cacactgcaa gcaggtctgg ctgcagatgc ctgggctgct cccatcgcca tgcagatcta   1500
caagaagcac ctggacccca ggcccgggcc ctgcccacct gagctgggcc tgggcctggg   1560
ccagctggcc tgctgctgcc tgcaccgccg ggccaaaagg aggcctccta tgacccagga   1620
gaactcctac gtgtccagca ctggcagagc ccacagtggg gctgctccat ggcagcccct   1680
ggcagcgcca tcaggagcca gtgcccaggc agcagagcag ctgcagagag gccccaacca   1740
gcccgtggag agtgacgaga gcctaggcgg cctctctgct gccctgcgct cctggcactt   1800
gactccaagc tgccctctgg acccagcacc cctcagggag gccggctgtc ctcaggggga   1860
cacggcagga gaatcgagct gggggagtgg cccaggatcc cggcccacag ccgtggaagg   1920
actggccctt ggcagctctg catcatcgtc gtcagagcca ccgcagatta tcatcaaccc   1980
tgcccgacag aagatggtcc agaagctggc cctgtacgag gatggggccc tggacagcct   2040
gcagctgctg tcgtccagct ccctcccagg cttgggcctg gaacaggaca ggcaggggcc   2100
cgaagaaagt gatgaatttc agagctgatg tgttcacctg ggcagatccc ccaaatccgg   2160
aagtcaaagt tctcatggtc agaagttctc atggtgcacg agtcctcagc actctgccgg   2220
cagtgggggt gggggcccat gcccgcgggg gagagaagga ggtggccctg ctgttctagg   2280
ctctgtgggc ataggcaggc agagtggaac cctgcctcca tgccagcatc tgggggcaag   2340
gaaggctggc atcatccagt gaggaggctg gcgcatgttg ggaggctgct ggctgcacag   2400
acccgtgagg ggaggagagg ggctgctgtg caggggtgtg gagtagggag ctggctcccc   2460
tgagagccat gcagggcgtc tgcagcccag gcctctggca gcagctcttt gcccatctct   2520
```

```
ttggacagtg gccaccctgc acaatggggc cgacgaggcc tagggccctc ctacctgctt   2580

acaatttgga aaagtgtggc cgggtgcggt ggctcacgcc tgtaatccca gcactttggg   2640

aggccaaggc aggaggatcg ctggagccca gtaggtcaag accagccagg gcaacatgat   2700

gagaccctgt ctctgccaaa aaattttta aactattagc ctggcgtggt agcgcacgcc   2760

tgtggtccca gctgctgggg aggctgaagt aggaggatca tttatgcttg ggaggtcgag   2820

gctgcagtga gtcatgattg tatgactgca ctccagcctg ggtgacagag caagaccctg   2880

tttcaaaaag aaaaaccctg ggaaaagtga agtatggctg taagtctcat ggttcagtcc   2940

tagcaagaag cgagaattct gagatcctcc agaaagtcga gcagcaccca cctccaacct   3000

cgggccagtg tcttcaggct ttactgggga cctgcgagct ggcctaatgt ggtggcctgc   3060

aagccaggcc atccctgggc gccacagacg agctccgagc caggtcaggc ttcggaggcc   3120

acaagctcag cctcaggccc aggcactgat tgtggcagag gggccactac ccaaggtcta   3180

gctaggccca agacctagtt acccagacag tgagaagccc ctggaaggca gaaaagttgg   3240

gagcatggca gacagggaag ggaaacattt tcagggaaaa gacatgtatc acatgtcttc   3300

agaagcaagt caggtttcat gtaaccgagt gtcctcttgc gtgtccaaaa gtagcccagg   3360

gctgtagcac aggcttcaca gtgattttgt gttcagccgt gagtcacact acatgccccc   3420

gtgaagctgg gcattggtga cgtccaggtt gtccttgagt aataaaaacg tatgttgcaa   3480

taaaaaaaaa aaaaaaaaa                                               3499
```

<210> SEQ ID NO 30
<211> LENGTH: 4267
<212> TYPE: DNA
<213> ORGANISM: Homo sapiens

<400> SEQUENCE: 30

```
attcgcctct gggaggttta ggaagcggct ccgggtcggt ggccccagga cagggaagag     60

cgggcgctat ggggagccgg acgccagagt cccctctcca cgccgtgcag ctgcgctggg    120

gcccccggcg ccgacccccg ctgctgccgc tgctgttgct gctgctgccg ccgccaccca    180

gggtcggggg cttcaactta gacgcggagg ccccagcagt actctcgggg cccccgggct    240

ccttcttcgg attctcagtg gagttttacc ggccgggaac agacggggtc agtgtgctgg    300

tgggagcacc caaggctaat accagccagc caggagtgct gcagggtggt gctgtctacc    360

tctgtccttg ggtgccagc cccacacagt gcacccccat tgaatttgac agcaaaggct    420

ctcggctcct ggagtcctca ctgtccagct cagagggaga ggagcctgtg gagtacaagt    480

ccttgcagtg gttcggggca acagttcgag cccatggctc ctccatcttg gcatgcgctc    540

cactgtacag ctggcgcaca gagaaggagc cactgagcga ccccgtgggc acctgctacc    600

tctccacaga taacttcacc cgaattctgg agtatgcacc ctgccgctca gatttcagct    660

gggcagcagg acagggttac tgccaaggag gcttcagtgc cgagttcacc aagactggcc    720

gtgtggtttt aggtggacca ggaagctatt tctggcaagg ccagatcctg tctgccactc    780

aggagcagat tgcagaatct tattaccccg agtacctgat caacctggtt caggggcagc    840

tgcagactcg ccaggccagt tccatctatg atgacagcta cctaggatac tctgtggctg    900

ttggtgaatt cagtggtgat gacacagaag actttgttgc tggtgtgccc aaagggaacc    960

tcacttacgg ctatgtcacc atccttaatg gctcagacat tcgatccctc tacaacttct   1020

caggggaaca gatggcctcc tactttggct atgcagtggc cgccacagac gtcaatgggg   1080

acgggctgga tgacttgctg gtgggggcac ccctgctcat ggatcggacc cctgacgggc   1140
```

-continued

```
ggcctcagga ggtgggcagg gtctacgtct acctgcagca cccagccggc atagagccca   1200
cgcccaccct taccctcact ggccatgatg agtttggccg atttggcagc tccttgaccc   1260
ccctggggga cctggaccag gatggctaca atgatgtggc catcggggct ccctttggtg   1320
gggagaccca gcagggagta gtgtttgtat ttcctggggg cccaggaggg ctgggctcta   1380
agccttccca ggttctgcag cccctgtggg cagccagcca caccccagac ttctttggct   1440
ctgcccttcg aggaggccga gacctggatg gcaatggata tcctgatctg attgtggggt   1500
cctttggtgt ggacaaggct gtggtataca ggggccgccc catcgtgtcc gctagtgcct   1560
ccctcaccat cttccccgcc atgttcaacc cagaggagcg gagctgcagc ttagagggga   1620
accctgtggc ctgcatcaac cttagcttct gcctcaatgc ttctggaaaa cacgttgctg   1680
actccattgg tttcacagtg gaacttcagc tggactggca gaagcagaag ggaggggtac   1740
ggcgggcact gttcctggcc tccaggcagg caaccctgac ccagaccctg ctcatccaga   1800
atggggctcg agaggattgc agagagatga agatctacct caggaacgag tcagaatttc   1860
gagacaaact ctcgccgatt cacatcgctc tcaacttctc cttggacccc caagccccag   1920
tggacagcca cggcctcagg ccagccctac attatcagag caagagccgg atagaggaca   1980
aggctcagat cttgctggac tgtggagaag acaacatctg tgtgcctgac ctgcagctgg   2040
aagtgtttgg ggagcagaac catgtgtacc tgggtgacaa gaatgccctg aacctcactt   2100
tccatgccca gaatgtgggt gagggtggcg cctatgaggc tgagcttcgg gtcaccgccc   2160
ctccagaggc tgagtactca ggactcgtca gacacccagg gaacttctcc agcctgagct   2220
gtgactactt tgccgtgaac cagagccgcc tgctggtgtg tgacctgggc aaccccatga   2280
aggcaggagc cagtctgtgg ggtggccttc ggtttacagt ccctcatctc cgggacacta   2340
agaaaaccat ccagtttgac ttccagatcc tcagcaagaa tctcaacaac tcgcaaagcg   2400
acgtggtttc ctttcggctc tccgtggagg ctcaggccca ggtcaccctg aacggtgtct   2460
ccaagcctga ggcagtgcta ttcccagtaa gcgactggca tccccgagac cagcctcaga   2520
aggaggagga cctgggacct gctgtccacc atgtctatga gctcatcaac caaggcccca   2580
gctccattag ccagggtgtg ctggaactca gctgtcccca ggctctggaa ggtcagcagc   2640
tcctatatgt gaccagagtt acgggactca actgcaccac caatcacccc attaacccaa   2700
agggcctgga gttggatccc gagggttccc tgcaccacca gcaaaaacgg gaagctccaa   2760
gccgcagctc tgcttcctcg ggacctcaga tcctgaaatg cccggaggct gagtgtttca   2820
ggctgcgctg tgagctcggg cccctgcacc aacaagagag ccaaagtctg cagttgcatt   2880
tccgagtctg ggccaagact ttcttgcagc gggagcacca gccatttagc ctgcagtgtg   2940
aggctgtgta caaagccctg aagatgccct accgaatcct gcctcggcag ctgccccaaa   3000
aagagcgtca ggtggccaca gctgtgcaat ggaccaaggc agaaggcagc tatggcgtcc   3060
cactgtggat catcatccta gccatcctgt ttggcctcct gctcctaggt ctactcatct   3120
acatcctcta caagcttgga ttcttcaaac gctccctccc atatggcacc gccatggaaa   3180
aagctcagct caagcctcca gccacctctg atgcctgagt cctcccaatt tcagactccc   3240
attcctgaag aaccagtccc cccaccctca ttctactgaa aaggaggggt ctgggtactt   3300
cttgaaggtg ctgacggcca gggagaagct cctctcccca gcccagagac atacttgaag   3360
ggccagagcc agggggggtga ggagctgggg atccctcccc cccatgcact gtgaaggacc   3420
cttgtttaca catacccctct tcatggatgg gggaactcag atccagggac agaggcccca   3480
```

gcctccctga agcctttgca ttttggagag tttcctgaaa caacttggaa agataactag 3540
gaaatccatt cacagttctt tgggccagac atgccacaag gacttcctgt ccagctccaa 3600
cctgcaaaga tctgtcctca gccttgccag agatccaaaa gaagccccca gctaagaacc 3660
tggaacttgg ggagttaaga cctggcagct ctggacagcc ccaccctggt gggccaacaa 3720
agaacactaa ctatgcatgg tgccccagga ccagctcagg acagatgcca cacaaggata 3780
gatgctggcc cagggcccag agcccagctc caaggggaat cagaactcaa atggggccag 3840
atccagcctg gggtctggag ttgatctgga acccagactc agacattggc acctaatcca 3900
ggcagatcca ggactatatt tgggcctgct ccagacctga tcctggaggc ccagttcacc 3960
ctgatttagg agaagccagg aatttcccag gaccctgaag ggccatgat ggcaacagat 4020 ctggaacctc agcctggcca gacacaggcc ctccctgttc cccagagaaa ggggagccca 4080
ctgtcctggg cctgcagaat ttgggttctg cctgccagct gcactgatgc tgcccctcat 4140
ctctctgccc aacccttccc tcaccttggc accagacacc caggacttat ttaaactctg 4200
ttgcaagtgc aataaatctg acccagtgcc cccactgacc agaactagaa aaaaaaaaaa 4260
aaaaaaa 4267

<210> SEQ ID NO 31
<211> LENGTH: 8787
<212> TYPE: DNA
<213> ORGANISM: Homo sapiens

<400> SEQUENCE: 31
ggcgggtgct tctagggcgc tcccagagcc gcctcccccct gttgctggca tcccgagctt 60
cctcccttgc cagccaggac gctgccgact tgtctttgcc cgctgctccg cagacggggc 120
tgcaaagctg caactaatgg tgttggcctc cctgcccacc tgtggaagca actgcgctga 180
ttgatgcgcc acagactttt ttcccctcga cctcgccggc gtcccctccc acagatccag 240
catcacccag tgaatgtaca ttagggtggt ttcccccca gcttcgggct ttgtttgggt 300
ttgattgtgt ttggctcttc gctaagctga tttatgcagc agaagcccca ccggctggag 360
agaaacaaaa gctcttttct ttgtcccgga gcaggctgcg gagcccttgc agagccctct 420
ctccagtcgc cgccggggcc cttggccgtc gaaggaggtg cttctcgcgg agaccgcggg 480
acccgccgtg ccgagccggg agggccgcag gggccctgag atgccgagcg gtgcccgggc 540
ccgcttacct gcaccgcttg ctccgagccg cggggtccgc ctgctaggcc tgcggaaaac 600
gtcctagcga cactcggccc gcgggccccg aggtgcgccc gggaggcgcg agcccgcgtc 660
cggaaggcag tcaggcggcg ggcgcggggc gggctgtttt gcattatgtg cggctcggcc 720
ctggcttttt ttaccgctgc atttgtctgc ctgcaaaacg accggcgagg tcccgcctcg 780
ttcctctggg cagcctgggt gttttcactt gttcttggac tgggccaagg tgaagacaat 840
agatgtgcat cttcaaatgc agcatcctgt gccaggtgcc ttgcgctggg tccagaatgt 900
ggatggtgtg ttcaagagga tttcatttca ggtggatcaa gaagtgaacg ttgtgatatt 960
gtttccaatt taataagcaa aggctgctca gttgattcaa tagaataccc atctgtgcat 1020
gttataatac ccactgaaaa tgaaattaat acccaggtga caccaggaga agtgtctatc 1080
cagctgcgtc caggagccga agctaatttt atgctgaaag ttcatcctct gaagaaatat 1140
cctgtggatc tttattatct tgttgatgtc tcagcatcaa tgcacaataa tatagaaaaa 1200
ttaaattccg ttggaaacga tttatctaga aaaatggcat tttctcccg tgactttcgt 1260 cttggatttg gctcatacgt tgataaaaca gtttcaccat acattagcat ccaccccgaa 1320
aggattcata atcaatgcag tgactacaat ttagactgca tgcctcccca tggatacatc 1380
catgtgctgt ctttgacaga gaacatcact gagtttgaga aagcagttca tagacagaag 1440
atctctggaa acatagatac accagaagga ggttttgacg ccatgcttca ggcagctgtc 1500
tgtgaaagtc atatcggatg gcgaaaagag gctaaaagat tgctgctggt gatgacagat 1560
cagacgtctc atctcgctct tgatagcaaa ttggcaggca tagtggtgcc caatgacgga 1620
aactgtcatc tgaaaaacaa cgtctatgtc aaatcgacaa ccatggaaca cccctcacta 1680
ggccaacttt cagagaaatt aatagacaac aacattaatg tcatctttgc agttcaagga 1740
aaacaatttc attggtataa ggatcttcta cccctcttgc caggcaccat tgctggtgaa 1800
atagaatcaa aggctgcaaa cctcaataat ttggtagtgg aagcctatca gaagctcatt 1860
tcagaagtga aagttcaggt ggaaaaccag gtacaaggca tctattttaa cattaccgcc 1920
atctgtccag atgggtccag aaagccaggc atggaaggat gcagaaacgt gacgagcaat 1980
gatgaagttc ttttcaatgt aacagttaca atgaaaaaat gtgatgtcac aggaggaaaa 2040
aactatgcaa taatcaaacc tattggtttt aatgaaaccg ctaaaattca tatacacaga 2100
aactgcagct gtcagtgtga ggacaacaga ggacctaaag gaaagtgtgt agatgaaact 2160
tttctagatt ccaagtgttt ccagtgtgat gagaataaat gtcattttga tgaagatcag 2220
ttttcttctg agagttgcaa gtcacacaag gatcagcctg tttgcagtgg tcgaggagtt 2280
tgtgtttgtg ggaaatgttc atgtcacaaa attaagcttg gaaaagtgta tggaaaatac 2340
tgtgaaaagg atgacttttc ttgtccatat caccatggaa atctgtgtgc tgggcatgga 2400
gagtgtgaag caggcagatg ccaatgcttc agtggctggg aaggtgatcg atgccagtgc 2460
ccttcagcag cagcccagca ctgtgtcaat tcaaagggcc aagtgtgcag tggaagaggc 2520
acgtgtgtgt gtggaaggtg tgagtgcacc gatcccagga gcatcggccg cttctgtgaa 2580
cactgcccca cctgttatac agcctgcaag gaaaactgga attgtatgca atgccttcac 2640
cctcacaatt tgtctcaggc tatacttgat cagtgcaaaa cctcatgtgc tctcatggaa 2700
caacagcatt atgtcgacca aacttcagaa tgtttctcca gcccaagcta cttgagaata 2760
tttttcatca ttttcatagt tacattcttg attgggttgc ttaaagtcct gatcattaga 2820
caggtgatac tacaatggaa tagtaataaa attaagtcct catcagatta cagagtgtca 2880
gcctcaaaaa aggataagtt gattctgcaa agtgtttgca caagagcagt cacctaccga 2940
cgtgagaagc ctgaagaaat aaaaatggat atcagcaaat taaatgctca tgaaactttc 3000
aggtgcaact tctaaaaaaa gatttttaaa cacttaatgg gaaactggaa ttgttaataa 3060
ttgctcctaa agattataat tttaaaagtc acaggaggag acaaattgct cacggtcatg 3120
ccagttgctg gttgtacact cgaacgaaga ctgacaagta tcctcatcat gatgtgactc 3180
acatagctgc tgacttttc agagaaaaat gtgtcttact actgtttgag actagtgtcg 3240
ttgtagcact ttactgtaat atataactta tttagatcag catagaatgt agatcctctg 3300
aagagcactg attacacttt acaggtacct gttatcccta cgcttcccag agagaacaat 3360
gctgtgagag agtttagcat tgtgtcacta caagggtaca gtaatccctg cactggacat 3420
gtgaggaaaa aaataatctg gcaagtatat tctaaggttg ccaaacactt caacagttgg 3480
tggttgaata gacaagaaca gctagatgaa taaatgattc gtgtttcact ctttcaagag 3540
gtgaacagat acaaccttaa tcttaaaaga ttattgcttt ttaaagtgtg tagttttatg 3600
catgtgtgtt tatggtttgc ttatttttgc aagatggata ctaattccag cattctctcc 3660

-continued

```
tctttgcctt tatgttttgt tttctttttt acaggataag tttatgtatg tcacagatga   3720
ctggattaat taagtgctaa gttactactg ccataaaaaa ctaataatac aatgtcactt   3780
tatcagaata ctagttttaa aagctgaatg ttaatagggg acactgtaaa gtatcatcaa   3840
aacctgaata gcttcattgt gcacaagtgt ggagttttgt atcctcttac ctggtaaact   3900
gaagggattg tttggccatt tcatttatct tatcattaat tcacaagata gttagaaatt   3960
ctgcctcaag caaagtacca cattttgaat gttttcttag attttgattg caagtagata   4020
tcagcatttt ttaaatgaaa agctatatta tcttctccct tcaaggcagc ctaaggatgt   4080
tctttcccag aatcactcca acccttcttg ccagaattca taaaagtaca aaattggaga   4140
atagatgata tcttagaaat aagctttttt tttttttttt tttttttttg agacggagtt   4200
tcactcttgt cacccaggct gaagtgcaat ggcgcaatta gggttcactg caacctctgc   4260
ctcccgggtt caagcagttc tcctgcctca gcctcctgag tagctgggat tacaggcatc   4320
caccaccgtg cccagctaat ttttgtattt ttagtagaga cggggttttg ccatgttgga   4380
caggttgatc tcaaactcct gacctcaggt gatctaccct cctcggcctc ccagagtgtt   4440
gggattacag gcatgagcca ccatgccagg ctgctaattc tcctttttag tgagttaggg   4500
aactgagcct cagaaaactt aaacgatttc tcagaaaaca ctcaagtgat aaagtggcca   4560
cattggaaag gagtttttat cttctcattg tcaggccagt gttcattgca caatatcatg   4620
ctacctcttg aatctttaaa atattcaatt ggcaaatgtt tttcaatgtg atttactcat   4680
gtcttaagtg tatgaggaaa gttcaaagca aaatagaaag gaataattca aactgaattg   4740
tccataatca gcttccagtc tttcatgcta atcagcttct taagagactg aagtatggca   4800
tacctacagg ggaattcctt cgcaccatag cctgtatgaa cagtgttccc tggagttctc   4860
cagtgctcag cttgagacct tgatacacgg gccatgagcc ctgtcttccc caatggaaat   4920
ttatttacac ttaccttatc cctatggact tagtctgatt ttattggcta ggagtctaac   4980
agtcctgtgt ggatatacag ttttgcccat gacaacaaag gaatctatcc gaaatatctt   5040
tttttttata ataaacttcc aagatttgct gtcttccagc acttgagtta aagtactaga   5100
tactgcattt tgatgaagac taaccccatc tcatattcta ccctaaagag aactgaaaaa   5160
cctataataa gttgttctgg agccaataaa cacagcagct ctgttagatg tcctctacag   5220
ccaagcactt tcaatgctaa cttgaactgc atttccttcc tcaaatgaga gattgacata   5280
attcagtact gtgagtcact tgtataagaa acctttgatc actaaaaata atgtaaaaat   5340
tgggtttagt agcctaatac acataacgtt cttcttaaaa aggaaaatgg atggatgcct   5400
gacaaccctc caaaagaaaa aagtgtaaga tagccattaa gatgatgaca atttttgaaa   5460
tgaacattat gatatttatg aacaataaac aaatttccgt atggaatgaa ttatccaaaa   5520
agagtataac aaaatgaaat ccttaaaaat ccagagttta tatttttttt ataccctcac   5580
ttgtttgcac taactttata gtggaccaag gctgttacca taggaaggga caaacttcct   5640
tgtaggcaac tcagtgttag acgatgattg tggttatgct tgcaaagtct tgtgcttatc   5700
tttttgttt ttacttaaaa agctaatttt taaagattgt agggcttgta ttttacttga   5760
ataattgata tcttcctgtg taatgatttg tgagatgaga attaatattt gactagttag   5820
aattaattaa atggtaaggg aacacagggt actcttaggt taaataatgt atgcaaatag   5880
agtctatttt caactaatat ggccacagga gccttttgag attcattgat attaaacaca   5940
attaatgaaa ttttaaattg ttaacagaat tgagaacttg aacaacactt ttagtactgc   6000
agcattttg tgccctaaag tatgtaatga tttataaatg tgccatacat acactacaac   6060
```

ataacatttg ctttgttatg cattttattt ctctggggac accattgcac tgcagtgcac 6120
acgtatttat aaacatttgt tatatttttg gaaacttgct aatatttatt aagtcataga 6180
cttttctgga ggacttaaaa attcactaaa aatctgatta tgtcttaaat gttcagttta 6240
tctttggttt attaaaataa aaaaaaaatc taagattaaa cacagtagat atctctggag 6300
gcaattttcc aaaactcaac attaaaattt gtggatgcat gagatgcaat ccttcaaaga 6360
atgaatctga aatatatttt taatatttac ttaatatcca ctgaagatat ctttatgcaa 6420
gacaagagtc agccatcaga cactgaaata tattatgata gattatgaag aattttctct 6480
gtagaattat attcttcctg gaacctggta gagtagatta gactcaaagg ctttttcttc 6540
cttttcttac tcctgttttt tccactcact cttcccaaga gatttcctaa agcttcaagc 6600
ttaataagcc taatagtgaa aaataactga atttaatggt ataatgaagt tcttcatttc 6660
cagacatctt taattgatct taaagctcat ttgagtcttt gcccctgaac aaagacagac 6720
ccattaaaat ctaagaattc taaattttca caactgtttg agcttctttt cattttgaag 6780
gatttggaat atatatgttt tcataaaagt atcaagtgaa atatagttac atgggagctc 6840
aatcatgtgc agattgcatt ctgttatgtt gactcaatat ttaatttaca actatcctta 6900
tttatattga cctcaagaac tccattttat gcaatgcaga ccactgagat atagctaaca 6960
ttctttcaaa taattttcct tttcttttat aattcctcta tagcaaattt ttatgtataa 7020
ctgattatac atatccatat ttatatttca ttgattccaa gacatcactt tttcaattta 7080
acatctctga aattgtgaca tttcttgcaa ctgttggcac ttcagatgca gtgtttaaaa 7140
ttatgcttga ataaatatta cactaatcca actttaccta aatgtttatg catctaggca 7200
aattttgttt tcttataaag atttgagagc ccatttatga caaaatatga aggcgaaatt 7260
taaggacaac tgagtcacgc acaactcaac atggagccta actgattatc agctcagatc 7320
ccgcatatct tgagtttaca aaagctcttt caggtcccca tttatacttt acgtgagtgc 7380
gaatgatttc agcaaaccct aacttaacta acaagaatgg gtaggtatgt ctacgtttca 7440
ttaacaaatt tttattattt ttattctatt atatgagatc cttttatatt atcatctcac 7500
ttttaaacaa aattaactgg aaaaatatta catggaactg tcatagttag gttttgcagc 7560
atcttacatg tcttgtatca atggcaggag aaaaatatga taaaaacaat cagtgctgtg 7620
aaaaacaact ttcttctaga gtcctcttac tttttattct tctttatcat ttgtgggttt 7680 ttccccttg gctctgatca ctttaacttc aagcttatgt aacgactgtt ataaaactgc 7740
atatttaaat tatttgaatt atatgaaata attgttcagc tatctgggca gctgttaatg 7800
taaacctgag agtaataaca ctactctttt atctacctgg aatacttttc tgcataaaat 7860
ttatctttgt aagctaactc tattaatcag gtttcttcta gcctctgcaa cctacttcag 7920
ttagaattgt ctaatactgc tctattaatc aggtttctag cctctacaac ctacttcagt 7980
taaaattgtc taatacagca atatttaaaa aaaaaacact gcaattgtca aggatggaaa 8040
atgtgtgatt tgtgtaaaca atttttacca actttacatt ttcctacaga taaatgtgaa 8100
attttgataa gaagtctacg caatgacaag tatggtacat aaattttatt aagaatattg 8160
agtataaagt actttaattc taaattataa gaaaatatac atttgcacat attaatatag 8220
aaattcattt tgtgtatatt taacatagct tttaaactat tttacattag ctacttcatt 8280
atggtttctt gaacttctga aaaaaattag aaatgtatta aacttatcag taacataaaa 8340
acttattttg tttcacctaa cgaatactgc gtttgtaaaa ataaatttaa tatagaatat 8400

```
atttttaaat taaatatttg aatataaaat agctctaaga aagaagcaaa ttatcactga   8460

acatatttct tattatttct ggctttgaat tatacgtaac ttaaattgtc ttaaatgata   8520

cagaatattg gagaatatga tactttcaca taatatacta tgaacctgtt catataactc   8580

tgattgacta ctaacttctg ttttatgtat ttattaaaga gctgacactg tagtttgtgg   8640

tgagatgttt atttttctaa cagagcttat aacagttagg acaaggcatt taattaatgc   8700

atcattctgt ttagtagtag gtgttaatca atatgaaatt ctctgtttta aaataaaaat   8760

gtaaaaatct aagaataaaa aaaaaaa                                         8787


<210> SEQ ID NO 32
<211> LENGTH: 3081
<212> TYPE: DNA
<213> ORGANISM: Homo sapiens

<400> SEQUENCE: 32

attagaggct ccagccccgc cgacttgcag acgtgagatc gggcacacct gagcggcggc     60

ggggcggtcg tggccacatc cggggcgacg tgcctgagtc accccgtccc gccagcgtct    120

gccagtccag ccagtccgcc cagtctctcg cgtccgagac tcgcctccag cctcccacct    180

ccgcccgggc cgcgcgagcc tcgcgggggc gggggcgggg cgccaagggg cggggctgtc    240

tcttaaaggg ccccgggccg ctgcccttag gccacttcct gggggcggag aggacctcag    300

cggctgcggc gacacccagg gaaggcggcg cggccgggtc ccgaaactcc tggctgtttc    360

catcagagcc ctcggacact cccagcccgg gctgagcacg catcgtcgct ccccggcgga    420

tacaaggggg ctccgccatc cgctcccgtc agttcggcct ccatctcctg ggacccgcgc    480

cggcagccag gccaggcctc tgagtggccc cagagccctg gctggactcg tccacggcgg    540

cagcgatctg cccggggtct cggaggccat cccttcagag tcggccctgt gctcgccacc    600

gtcacctgct ggttggattc cggaaaccca ctgtctgaag accacagagg ggtgtcgctg    660

accaccccaa atcggatacg tccagacctc aagctccctt cccctctctg gctgccctct    720

gctcttttca tctcttctct caaccttttg gggatttctg tgtcctgaca ccacctcccc    780

atccaccacc aaagtagccg gggtgagccc caaaccttac tgggtgtgct ccacctgtgc    840

ctccaaccca gcgaatctga cagcttcgac ccaattctgc acacacccag gaagttctgc    900

cttttctttt ctttcggtgt ctcctgtact tcccaaaatt tctcctcctc ctgtgccctc    960

ttcgcccccc tcctttgggg gccccgtgac cctgaatgtg gggggcacac tatattccac   1020

cactttggag accctgaccc gcttcccaga ctctatgctg gggggccatgt ttagggccgg   1080

cacccccatg ccccccaacc tcaattccca aggaggcggc cactacttca tcgaccggga   1140

tggcaaggcc ttccggcaca tcctcaattt cctgaggctg ggccgcctgg acctgccccg   1200

tgggtacgga gagacagcgc tgctcagggc agaggctgac ttctaccaga tccggcccct   1260

cctggacgcg ctgcgggaac tggaggcctc tcaggggacc cctgcaccca cagctgccct   1320

gctccacgca gatgtagatg tcagccccccg cctggtgcac ttctctgctc gccggggacc   1380

ccatcactat gagctgagct ccgtccaggt ggacaccttc cgagccaacc ttttctgcac   1440

cgactctgag tgtctaggtg ctttgcgggc ccgatttggt gtggccagtg gggatagggc   1500

agaggggagc ccacattttc atctggagtg ggcccccccgc cccgtggaac tccccgaggt   1560

ggagtatggg agactggggc tgcagccgct gtggactggg gggccaggag agcggcggga   1620

ggtggtgggc accccaagct tcctggagga ggtgctgcgg gtggctctcg agcacggctt   1680

ccgactagac tctgtcttcc ccgaccccga agacctgctc aactccaggt ctctgcgctt   1740
```

```
tgtccggcac tgaggatgct gttctcagtt tgactgtggg gaggagagag aatggggtac   1800
tagcacccct gaagcctctt tccagctctg cttcaggagc tatgagagtc gggactctcc   1860
tgcacctgac tggagctcag atgtgggcag gaattcccaa acctgagccc accaaggact   1920
cacaagtggt ccagaaggtc tcaacctgtg ctgaccctgg gaggggtagg gaaggttctc   1980
tcagcttgtt cttgcctaag gctgagcacc tccagtctct ccttgatttg gagctcagtg   2040
tttaagggct tggaaaaggg gggaacatct ctttacccag actagaccta gcaaaaccct   2100
ggaaggatat tgaggtctgg ggaaaaggga ggactttgca ttttcccaat gcggtctctt   2160
ggaccatggc ttctactcct gaagctgggt ggcctggcct ggcctgacca atgagaggcc   2220
agaacactct ggaacatcgg aagaggagtt ctttgctatg ttccaagcca tctactgagg   2280
gaggcagaaa ggccacaacc caccctaggt tgatgtatgg gagctaggac agtccccatg   2340
gcaatggggc tggagcatcc ctcatctgga agaatcccat actgatggca gggctggcca   2400
gggggaagag ggtagtatct gtgggtcctg gcctttcttc atgtgtgcgt gcatatcagc   2460
ccgtgtggct gactgatgta taggtccctg gcatcctggt tcatatctgt gttgctgact   2520
acagtgtctg tgatgtccgc atgtccaggc ctgtttgggg ttgcctagcg actcttctgg   2580
cacagggtgt gtctgtggta tacctgtgag gtggttgaca attagtagtt taatcacagg   2640
gtgtgtgtgt gtgtgtgtgt gtgtgtgttt atgtgcacgc atgtatatgc atcaccacgt   2700
agccaggagg ggcctgttgg ggtttgagtc actgggatct tcctggtgag aggtaagaga   2760
agtcactggg cttagctggg cctctgaggc ctgtatggaa ctcttggttg ctgaggcaac   2820
catggacctg ttgctaggag atagctgggg aaggcccaag gccgcccagg gcagagagag   2880
gagacgaaga gtttgggaca gtgggggagg agatgggaag ggatgggatt tctgggtccc   2940
agagcgggtg ggatactcac gcacagcttc ttcactggtg gggggtgggg cacacattat   3000
ttctcactgg tcatgattta caagaagaaa aataaaactg cttttggaac cacaaaaaaa   3060
aaaaaaaaaa aaaaaaaaaa a                                             3081
```

<210> SEQ ID NO 33
<211> LENGTH: 3767
<212> TYPE: DNA
<213> ORGANISM: Homo sapiens

<400> SEQUENCE: 33

```
aagaaagagc cccgccccta gtcttatgac tcgcactgaa gcgccgattc ctggcttttg     60
caaggctgtg gtcggtggtc atcagtgctc ttgacccagg tccagcgagc cttttccctg    120
gtgttgcagc tgttgttgta ccgccgccgt cgccgccgtc gccgcctgct ctgcggggtc    180
atggtgtgct tccgcctctt cccggttccg ggctcagggc tcgttctggt ctgcctagtc    240
ctgggagctg tgcggtctta tgcattggaa cttaatttga cagattcaga aaatgccact    300
tgcctttatg caaaatggca gatgaatttc acagtacgct atgaaactac aaataaaact    360
tataaaactg taaccatttc agaccatggc actgtgacat ataatggaag catttgtggg    420
gatgatcaga atggtcccaa aatagcagtg cagttcggac ctggcttttc ctggattgcg    480
aattttacca aggcagcatc tacttattca attgacagcg tctcattttc ctacaacact    540
ggtgataaca caacatttcc tgatgctgaa gataaaggaa ttcttactgt tgatgaactt    600
ttggccatca gaattccatt gaatgacctt tttagatgca atagtttatc aactttggaa    660
aagaatgatg ttgtccaaca ctactgggat gttcttgtac aagcttttgt ccaaaatggc    720
```

-continued

```
acagtgagca caaatgagtt cctgtgtgat aaagacaaaa cttcaacagt ggcacccacc    780
atacacacca ctgtgccatc tcctactaca acacctactc caaaggaaaa accagaagct    840
ggaacctatt cagttaataa tggcaatgat acttgtctgc tggctaccat ggggctgcag    900
ctgaacatca ctcaggataa ggttgcttca gttattaaca tcaaccccaa tacaactcac    960
tccacaggca gctgccgttc tcacactgct ctacttagac tcaatagcag caccattaag   1020
tatctagact ttgtctttgc tgtgaaaaat gaaaaccgat tttatctgaa ggaagtgaac   1080
atcagcatgt atttggttaa tggctccgtt ttcagcattg caaataacaa tctcagctac   1140
tgggatgccc ccctgggaag ttcttatatg tgcaacaaag agcagactgt ttcagtgtct   1200
ggagcatttc agataaatac ctttgatcta agggttcagc ctttcaatgt gacacaagga   1260
aagtattcta cagctgaaga atgttctgct gactctgacc tcaactttct tattcctgtt   1320
gcagtgggtg tggccttggg cttccttata attgttgtct ttatctctta tatgattgga   1380
agaaggaaaa gtcgtactgg ttatcagtct gtgtaatcag ttaaatctag tgtttgtttg   1440
tttttttcaa ttagaagtta cgtttccatt ggctaaaagc caggacatgc tgtgcaatag   1500
attgtttaag atatgcagac taacttcagt gagttcctag ctaacttggg catgagtaca   1560
cttatttaag acaaaatata ttaggaccaa tttttttctg ttttttttct tcctttgtta   1620
aagtataatt aaaagaaaaa ttgtggctta gaattttttta agtaaataat gattttaagc   1680
ccctggatcc aattatgaaa gcatttttgc tgatgtgtaa ttttatatgt tacagttact   1740
tatattttac tactttgatg ttatttgcaa aatcaaaggt gttaaagaat ttaacttgct   1800
tcaggaaata aattcaagaa catagtggat tcattttcat tggtggcaga cacgaaattt   1860
ggttcatgat aagacttcct ttccccacct cctgatcagc attatttaaa tctgtatttt   1920
tctgttagtt aagaaagaaa tggcttcatg atattgtatt taatagcaaa agtttggctg   1980
tcttcttcat tactgttaat agctactata ttttaacaag gagatttctt tttttgttgt   2040
tgttgttcta gagtttggaa tatactgatt atctcagact tgacatttat actgaaggat   2100
gaagtaagac ctccagcttt ttttaaaaaa ggtgttgatt tggaacacct gtatgggtta   2160
tggtttatta aggttatggt ttagaaagtt tttttccctc agagccttaa cttgttaaga   2220
aggttcattt atcctgcact gaaaacaaaa actctatata ctttgtttgt gtgcctcctg   2280
cactctccca ttccctatgt gaatatgctc tagttgatat ttttaatata ttgatttctt   2340
ttttctcaca gcaacaagtg cttactctag aggttagtgg gccctgatat gtcatcagtc   2400
agatgcctgc ctagccaaag ctggactaag attattctgt acatttgttg atcttgatat   2460
agacttatat ccctgtaggg actgctaatg gctccggctt ctggagtaag gtactggaga   2520
ccactcatcc ctgtgtctgc ttgattggtt cagctgttga attgcccttt tatttggaag   2580
cagtgttgaa gttgtctagg gttcaaatgg ctgctttgta cacctgtcat tagtataagg   2640
cagatgttta ttttatcaag ctattttatc tctacattta actaaaaaca aaagttccca   2700
aagatctgcc ttcacttcag aaattttttt tggattaaaa aaattaagcc tgaaccttaa   2760
ataaagtgag ttggttattc attccaagga ttaagtccca atctacctct cagcacaatg   2820
cagaagctca ccactgtatt gctgccatta actcatgcca gaaccctttg ccaataactg   2880
gaattacaaa tttttgttaa agaaaattta tcaagatctt tctttactgc cttctctata   2940
tgtacatctc aaaaacatgt acatctcaaa aactggagta gaaagttaga ttgctcaact   3000
acaactcctc tagaactcta tagctctgac atacagattc acactctcct ctatttgcta   3060
agtatgtaaa gaatgttttc ttttaaaatg ttctcttttg agaacaactg cttatttgtt   3120
```

ataaaagcat ttggttaaaa tgatgtcatc ataaaaaaca gtggctttgt ttcaatacat 3180
atttttgaga tgattatcta gaagccagat taataaaatc agcttgtgac cttgctaagc 3240
atataaactg gaaattcaga tacattcaaa attatgggtt catttaaaag tgttctacct 3300
tttgggtatg agactaatat cactaattcc tcaatagtta tcatggctct atcttaatta 3360
attagaaaat atgtgtgttt aattctttga gaattaaaat agagaatatt aacagagggt 3420
taaaaactgc ttcaactcca ataagataaa ggaagctcaa aatctatgag ctgagtgttc 3480
aattagcttt gcctactgag ttcaatttta tgtcaataca acagtggatc agacagtacg 3540
actttgaact ggtgaatgta aacaattgtt tttcacctaa gctgctttgg aagaactgat 3600
gcttgctgct aactaaagtt ttggatgtat cgatttagag aaccaattaa tacctgcaaa 3660
ataaagcata ctgtggtact tctgtttgat ctagtatgtg tgattttaga ttgatggatt 3720
aaaaattaat aaagatcata cattccatac caaaaaaaaa aaaaaaa 3767

<210> SEQ ID NO 34
<211> LENGTH: 4625
<212> TYPE: DNA
<213> ORGANISM: Homo sapiens

<400> SEQUENCE: 34
tcgggagaca tggcgggcgt taaagagaag aaaccagtgt gtgtgtagta tgtgtttttt 60
gcatggggca gttggtaaaa acaccgcgtc ccttatctgt atggcttcag agcaatgcga 120
gacggaaaag gtttttgca aggcttcctg tattttgctc tcgtggcatt atccttcagt 180
ggggctattg gactgacttt tcttatgctg ggatgtgcct tagaggatta tggcgtttac 240
tggcccttat tcgtcctgat tttccacgcc atctccccca tcccccattt cattgccaaa 300
agagtcacct atgactcaga tgcaaccagt agtgcctgtc gggaactggc atatttcttc 360
actactggaa ttgttgtttc tgcctttgga tttcctgtta ttcttgctcg tgtggctgtg 420
atcaaatggg gagcctgcgg ccttgtgttg gcaggcaatg cagtcatttt ccttacaatt 480
caagggtttt tccttatatt tggaagagga gatgatttta gctgggagca gtggtagcac 540
tttattctga ttacagtgca ttgaatttct tagaactcat actatctgta tacatgtgca 600
catgcggcat tttactatga aatttaatat gctgggtttt ttaatacctt tatatatcat 660
gttcacttta agaaagactt cataagtagg agatgagttt tattctcagc aaatagacct 720
gtcaaattta gattatgtta ctcaaattat gttacttgtt tggctgttca tgtagtcacg 780
gtgctctcag aaaatatatt aacgcagtct tgtaggcagc tgccacctta tgcagtgcat 840
cgaaaccttt tgcttgggga tgtgcttgga gaggcagata acgctgaagc aggcctctca 900
tgacccagga aggccggggt ggatccctct ttgtgttgta gtccatgcta ttaaaagtgt 960
ggcccacaga ccaagagcct caacatttcc tagagcctta ttagaaatgc agaatctgaa 1020
gccccactct ggacccagga cattttgatg agatccaaag gagttgtatg cacatgaaag 1080
tttgagaagc atcatcatag agaagtaaac atcacaccca acttccttat ctttccagtg 1140
gctaaaccac ttaacctctc tgggtgttac ctgctcattt gtttaaaaaa aaaaaaaaag 1200
tctcacctgc tttcatgctg aggacaagtt cagatgttca agcctataat atttaggcag 1260
ttcctcaaat ttatgaaaag tgttctcaga attgggagac agtcaaaggg tacaaagcct 1320
cagttaggag gaataagtgt gatttttttt taaagatcac ttgcacagca tgctaaatat 1380
aggaataatt gaatgtatat ttcaatattg ctaagagagt aaatttctaa tgttctcata 1440

-continued

```
aaaaagttaa atatttgaga tcatatgtta attagtgtaa tcattccacc ttatattcaa   1500
aaatcataaa accgtattgt accctataaa aatatacaat aatttgtcaa tatataatca   1560
aaataaaaaa caaaacatac tctctccccc aaaaaaacat ctcagtgggg aacagatgta   1620
tcttttcatc tgaaagacaa tgctggggga agagctccac tgagatgcgg gcagggaggc   1680
tgggctcgag ccagcccctg cgttagcagg agggggagaa cagataggta actcttttac   1740
atttccttta tgatctggca cttctcccca gctccttccc tctgcccccc acccctactc   1800
ctcaacagtt ctggtttgcc ctgacttctc tacggctctg gcttcttccc gaagagatat   1860
aggagccatg taagcacgca gtgggtgaac tgcttaattt cactacgtgt tgatgtactt   1920
gtcttccgtc ctgtaggtct tttctatata actttatgcc acccttaaat gaatcattgg   1980
gtatacctgt catgttggat cctgtaatca cagttttccc tgctcacctt tttgtctaag   2040
atctattgag aaagggaaat atgggaagga gaaccatttg atcagaatac aaccaatagt   2100
ctttaagcat tgttaaagta tgaaactgaa atacattcaa aacacttaat ccttgaggct   2160
tgtgatctga gtaattagca ggtatgatgc tgggactgga aaatagaaag taataactaa   2220
agggttaatg tgcaacgtta ttttttggcc ttgttcatga ttttatgttt tcagtgtcct   2280
gtgtacatat agaattgtta aagttgtcat ttccaatatt tatattagaa aaattattta   2340
gatactttat aattttaacc ggcattttta ataatgacac ttgcatttat tgtattgtaa   2400
taaatttcac ttttaacttt aaaagtttaa ctttaaaatt tttttgtgat gttgccttgc   2460
ctgaaaagat aacaaaaatg agagaatttc ttgatgtttt aaaatgggca gttttgagca   2520
ataatctgtc ctaacagaac agtagcaata agttttagga taccatcttg aatgtctagt   2580
tggtgtgcaa tagcttttct ttctaagatg gcaataatga ttcatttcta ctacattttg   2640
caaaagtgtt tttgttgctt atacacattt tcaataacca aggtagcctt catatgtagc   2700
cttaaagcat tacctcttga ttgtatcttt agattgatat aaagtacttg catatagagt   2760
atttgaagtg atagattatt agatttgctc tatgtctgaa aagagagcta ttctgcagtg   2820
cctaaatatc atttaaacag taaatattaa taggaaatat tgctatatct gaatatataa   2880
tacaaaagtt tgatcatggt gacacaaatg ttggacattt ttttccttat aaaaggctct   2940
ttttttatat attgtacaat atatttggag attcagagca tagtgactat agtcgaaaac   3000
tgagattgca cttccaaaat tggccacaag taaataatct tatgaaggga ttctttatca   3060
tgtttcaaac aagtgggtta caagcagact ttgagacact tttccacaga aacaatacta   3120
tgaattggtg attgagttcc caggccaagc ctccctcaac aggttcaact ctaatatacc   3180
taacctgtga tactgaaggt gcctgcctga gttttgggtc tctgagacag ggtagtgtga   3240
gtagtttgga ggaaggacag tgcaactttc caccccttt cctaagaaca aggtctttct   3300
ccttttaatt tttccactca ttttcacctc ctaatgccct tgagatccag gtacactcct   3360
gggagttttg ttcacctctc ccaactgaga accttcccac tgggctccat cctccctcct   3420
gaggttcttc atattccaga gtcacccacc cttctcctcc cattagtcag ttctctaagt   3480
acagctgatg tcatgtggtg ctgagaagaa agcagatcac acttcatcac agaaagaatg   3540
ccttgtgatt atcttctcca catctgaaat tccttttgac acctgcattg ggccgactgc   3600
cattcccatg actgctgcac ctgcgttttt agagaatgcc tcataaccca ctgattctca   3660
ttcacagaga atgggagaac ggaatgaaga aagattccag cagcttatag aaggatagca   3720
atattttggg acagggaaaa tcctgtcata cctcatctct tcctcaggag gagttctgag   3780
ctggtcctgc ttttcatagt tgtttctttt cttccactta agaactcata gatttttctt   3840
```

-continued actgtcctaa ggaagtcctt acctctgagg tatctcctca atgaatactg ttttcaaggc 3900
tgaaatagtt cattatgtta ataaccttct ttatgttctc agggaaatgc ttaggtggtg 3960
tcacaaaatg tgccttttct tttctttttt tttttttttt tttgaggcag agtctcgctc 4020
tgttgcccag gctggagtgc agtggtgcga tcttggctca ctgcaagctc cgcctcccgg 4080
gttcacgcca ttctcctgcc tcagcctccc aaggagctgg gactacaggc tcccgccacc 4140
acgcctggct aatttttttg tatttttagt aaagacgggt ttcatcgtgt tagccaggat 4200
ggtctcgatc tcctgacctc atgatccgcc cgcctctgcc tcccaaagtg ctgggattac 4260
aggcctgagc cactgtgccc agccaaaatg tgcctttgca aagtttgcga aatcagattt 4320
tgtatcccaa tagaaccaaa atatttatga ggatgctagc attttccaag catagtaatt 4380
agttcacaac tgagaaatat tatgtctgta gtagataaat attagttgtg cattttaatt 4440
taattctcct ttttccattt tgtctcatga agtaccttat tgcaaaaatc ccactgagta 4500
atagctcata aattataatc tttcaaatag ccatgctacc agcgtacaac agtgatacat 4560
gtaaccccaa atgtgatgtg agaggacgat tactttgtaa ataaaacttg ttattgacat 4620
tttaa 4625

<210> SEQ ID NO 35
<211> LENGTH: 744
<212> TYPE: DNA
<213> ORGANISM: Homo sapiens

<400> SEQUENCE: 35
gagtatttga ggctcggagc caccgccccg ccggcgcccg cagcacctcc tcgccagcag 60
ccgtccggag ccagccaacg agcggaaaat ggcagacaat tttcgctcc atgatgcgtt 120 atctgggtct ggaaacccaa accctcaagg atggcctggc gcatgggggga accagcctgc 180 tggggcaggg ggctacccag gggcttccta tcctggggcc taccccgggc aggcaccccc 240
aggggcttat cctggacagg cacctccagg cgcctaccct ggagcacctg gagcttatcc 300
cggagcacct gcacctggag tctacccagg gccacccagc ggccctgggg cctacccatc 360
ttctggacag ccaagtgcca ccggagccta ccctgccact ggcccctatg gcgcccctgc 420
tgggccactg attgtgcctt ataacctgcc tttgcctggg ggagtggtgc ctcgcatgct 480
gataacaatt ctgggcacgg tgaagcccaa tgcaaacaga attgctttag atttccaaag 540
agggaatgat gttgccttcc actttaaccc acgcttcaat gagaacaaca ggagagtcat 600
tgtttgcact tacatgtgta aaggtttcat gttcactgtg agtgaaaatt tttacattca 660
tcaatatccc tcttgtaagt catctactta ataaatatta cagtgaatta cctgtctcaa 720
tatgtcaaaa aaaaaaaaaa aaaa 744

<210> SEQ ID NO 36
<211> LENGTH: 2094
<212> TYPE: DNA
<213> ORGANISM: Homo sapiens

<400> SEQUENCE: 36
cacttgttca atgatgtacc cccagtgtca ggcgctttgc aaacacacga tacatacggg 60
ttgatgtttg gtcaagagag gaattaagac caggcagaca gcaggctggg atcagagaga 120
ccccatttct gtctgaaatg tctgcagaga acctggtgcc tgcctcagcc ctagctctgg 180
ggaaatgaaa gccaggctgg ggttcaaatg agggcagttt cccttcctgt gggctgctga 240

```
tggaacaacc ccatgacgag aaggacccag cctccaagcg gccacaccct gtgtgtctct    300
ttgtcctgcc ggcactgagg actcatccat ctgcacagct ggggcccctg ggaggagacg    360
ccatgatccc caccttcacg gctctgctct gcctcgggct gagtctgggc cccaggaccc    420
acatgcaggc agggcccctc cccaaaccca ccctctgggc tgagccaggc tctgtgatca    480
gctgggggaa ctctgtgacc atctggtgtc aggggaccct ggaggctcgg gagtaccgtc    540
tggataaaga ggaaagccca gcaccctggg acagacagaa cccactggag cccaagaaca    600
aggccagatt ctccatccca tccatgacag aggactatgc agggagatac cgctgttact    660
atcgcagccc tgtaggctgg tcacagccca gtgaccccct ggagctggtg atgacaggag    720
cctacagtaa acccaccctt tcagccctgc cgagtcctct tgtgacctca ggaaagagcg    780
tgaccctgct gtgtcagtca cggagcccaa tggacacttt ccttctgatc aaggagcggg    840
cagcccatcc cctactgcat ctgagatcag agcacggagc tcagcagcac caggctgaat    900
tccccatgag tcctgtgacc tcagtgcacg gggggaccta caggtgcttc agctcacacg    960
gcttctccca ctacctgctg tcacacccca gtgaccccct ggagctcata gtctcaggat   1020
ccttggagga tcccaggccc tcacccacaa ggtccgtctc aacagctgca ggccctgagg   1080
accagcccct catgcctaca gggtcagtcc cccacagtgg tctgagaagg cactgggagg   1140
tactgatcgg ggtcttggtg gtctccatcc tgcttctctc cctcctcctc ttcctcctcc   1200
tccaacactg gcgtcaggga aaacacagga cattggccca gagacaggct gatttccaac   1260
gtcctccagg ggctgccgag ccagagccca aggacggggg cctacagagg aggtccagcc   1320
cagctgctga cgtccaggga gaaaacttct gtgctgccgt gaagaacaca cagcctgagg   1380
acggggtgga aatggacact cggagcccac acgatgaaga cccccaggca gtgacgtatg   1440
ccaaggtgaa acactccaga cctaggagag aaatggcctc tcctccctcc ccactgtctg   1500
gggaattcct ggacacaaag gacagacagg cagaagagga cagacagatg gacactgagg   1560
ctgctgcatc tgaagccccc caggatgtga cctacgccca gctgcacagc tttaccctca   1620
gacagaaggc aactgagcct cctccatccc aggaaggggc ctctccagct gagcccagtg   1680
tctatgccac tctggccatc cactaatcca gggggggaccc agaccccaca agccatggag   1740
actcaggacc ccagaaggca tggaagctgc ctccagtaga catcactgaa ccccagccag   1800
cccagacccc tgacacagac cactagaaga ttccgggaac gttgggagtc acctgattct   1860
gcaaagataa ataatatccc tgcattatca aaataaagta gcagacctct caattcacaa   1920
tgagttaact gataaaacaa aacagaagtc agacaatgtt ttaaattgaa tgatcatgta   1980
aatattacac atcaaaccaa tgacatggga aaatgggagc ttctaatgag gacaaacaaa   2040
aaatagagaa aaattaataa agtcaaaatg tttattcttg aaaaaaaaaa aaaa         2094
```

<210> SEQ ID NO 37
<211> LENGTH: 1562
<212> TYPE: DNA
<213> ORGANISM: Homo sapiens

<400> SEQUENCE: 37

```
gcgggcggca ttctggcgcg gagcggagcg gcggcgggcg cagctagcgg gtcggccgcg     60
gagcggaggt gcagctcggc ttcccccggc acccctcccc ctcgggcgcc agccccaccc    120
ctccgccggc cgggccgacc ccgccgtact atcccctgcg gcgcgagccc ggggcggctc    180
caagcgcccc ccagcagacc cccatcatgg gcagccagag ctccaaggct ccccggggcg    240
acgtgaccgc cgaggaggca gcaggcgctt cccccgcgaa ggccaacggc caggagaatg    300
```

```
gccacgtgaa aagcaatgga gacttatccc ccaagggtga aggggagtcg ccccctgtga    360

acggaacaga tgaggcagcc ggggccactg gcgatgccat cgagccagca ccccctagcc    420

agggtgctga ggccaagggg gaggtccccc ccaaggagac ccccaagaag aagaagaaat    480

tctctttcaa gaagcctttc aaattgagcg gcctgtcctt caagagaaat cggaaggagg    540

gtgggggtga ttcttctgcc tcctcaccca cagaggaaga gcaggagcag gggggagatcg    600

gtgcctgcag cgacgagggc actgctcagg aagggaaggc cgcagccacc cctgagagcc    660

aggaacccca ggccaagggg gcagaggcta gtgcagcctc agaagaagag gcagggcccc    720

aggctacaga gccatccact ccctcggggc cggagagtgg ccctacacca gccagcgctg    780

agcagaatga gtagctaggt aggggcaggt gggtgatctc taagctgcaa aaactgtgct    840

gtccttgtga ggtcactgcc tggacctggt gccctggctg ccttcctgtg cccagaaagg    900

aaggggctat tgcctcctcc cagccacgtt ccctttcctc ctctccctcc tgtggattct    960

cccatcagcc atctggttct cctcttaagg ccagttgaag atggtccctt acagcttccc   1020

aagttaggtt agtgatgtga aatgctcctg tccctggccc tacctccttc cctgtcccca   1080

cccctgcata aggcagttgt tggttttctt ccccaattct tttccaagta ggttttgttt   1140

accctactcc ccaaatccct gagccagaag tggggtgctt atactcccaa accttgagtg   1200

tccagccttc ccctgttgtt tttagtctct tgtgctgtgc ctagtggcac ctgggctggg   1260

gaggacactg ccccgtctag gtttttataa atgtcttact caagttcaaa cctccagcct   1320

gtgaatcaac tgtgtctctt ttttgacttg gtaagcaagt attaggcttt ggggtggggg   1380

gaggtctgta atgtgaaaca acttcttgtc tttttttctc ccactgttgt aaataacttt   1440

taatggccaa accccagatt tgtacttttt ttttttttct aactgctaaa accattctct   1500

tccacctggt tttactgtaa catttggaaa aggaataaat gtcgtccctt tagtggtgct   1560

tt                                                                  1562
```

<210> SEQ ID NO 38
<211> LENGTH: 2118
<212> TYPE: DNA
<213> ORGANISM: Homo sapiens

<400> SEQUENCE: 38

```
cacgtgaccg aggcacagat cagctgatgc cggagggttt gaagccgcgc cgcgagggag     60

cgaggtcgca gtgacagcgg cgggcgatcg gacccaggct gccccgccgt acccgcctgc    120

gtcccgcgct cccgccccag catgacagcc ccggcgggtc cgcgcggctc agagaccgag    180

cggcttctga cccccaaccc cgggtatggg acccaggcgg ggccttcacc ggcccctccg    240

acacccccag aagaggaaga ccttcgccgt cgtctcaaat actttttcat gagtccctgc    300

gacaagtttc gagccaaggg ccgcaagccc tgcaagctga tgctgcaagt ggtcaagatc    360

ctggtggtca cggtgcagct catcctgttt gggctcagta atcagctggc tgtgacattc    420

cgggaagaga acaccatcgc cttccgacac ctcttcctgc tgggctactc ggacggagcg    480

gatgacacct tcgcagccta cacgcgggag cagctgtacc aggccatctt ccatgctgtg    540

gaccagtacc tggcgttgcc tgacgtgtca ctgggccggt atgcgtatgt ccgtggtggg    600

ggtgaccctt ggaccaatgg ctcagggctt gctctctgcc agcggtacta ccaccgaggc    660

cacgtggacc cggccaacga cacatttgac attgatccga tggtggttac tgactgcatc    720

caggtggatc cccccgagcg gccccctccg ccccccagcg acgatctcac cctcttggaa    780
```

-continued agcagctcca gttacaagaa cctcacgctc aaattccaca agctggtcaa tgtcaccatc 840
cacttccggc tgaagaccat taacctccag agcctcatca ataatgagat cccggactgc 900
tataccttca gcgtcctgat cacgtttgac aacaaagcac acagtgggcg gatccccatc 960
agcctggaga cccaggccca catccaggag tgtaagcacc ccagtgtctt ccagcacgga 1020
gacaacagct tccggctcct gtttgacgtg gtggtcatcc tcacctgctc cctgtccttc 1080
ctcctctgcg cccgctcact ccttcgaggc ttcctgctgc agaacgagtt tgtggggttc 1140
atgtggcggc agcggggacg ggtcatcagc ctgtgggagc ggctggaatt tgtcaatggc 1200
tggtacatcc tgctcgtcac cagcgatgtg ctcaccatct cgggcaccat catgaagatc 1260
ggcatcgagg ccaagaactt ggcgagctac gacgtctgca gcatcctcct gggcacctcg 1320
acgctgctgg tgtgggtggg cgtgatccgc tacctgacct tcttccacaa ctacaatatc 1380
ctcatcgcca cactgcgggt ggccctgccc agcgtcatgc gcttctgctg ctgcgtggct 1440
gtcatctacc tgggctactg cttctgtggc tggatcgtgc tggggcccta tcatgtgaag 1500
ttccgctcac tctccatggt gtctgagtgc ctgttctcgc tcatcaatgg ggacgacatg 1560
tttgtgacgt tcgccgccat gcaggcgcag cagggccgca gcagcctggt gtggctcttc 1620
tcccagctct acctttactc cttcatcagc ctcttcatct acatggtgct cagcctcttc 1680
atcgcgctca tcaccggcgc ctacgacacc atcaagcatc ccggcggcgc aggcgcagag 1740
gagagcgagc tgcaggccta catcgcacag tgccaggaca gccccacctc cggcaagttc 1800
cgccgcggga gcggctcggc ctgcagcctt ctctgctgct gcggaaggga cccctcggag 1860
gagcattcgc tgctggtgaa ttgattcgac ctgactgccg ttggaccgta ggccctggac 1920
tgcagagacc cccgcccccg accccgctta tttatttgta gggtttgctt ttaaggatcg 1980
gctccctgtc gcgcccgagg agggcctgga cctttcgtgt cggacccttg gggggcgggga 2040 gactgggtgg ggagggtgtt gaataaaagg gaaaataaat gtgtcgtttt catttttaaa 2100
aaaaaaaaaa aaaaaaaa 2118

<210> SEQ ID NO 39
<211> LENGTH: 4588
<212> TYPE: DNA
<213> ORGANISM: Homo sapiens

<400> SEQUENCE: 39
aaacttccga gttaagccgc cgctgaggcc ggaaggagct agacggcggt cgggtggaaa 60
gtggttggtt tctgataact tcctaaacat caccaatgta gcttttgatg accgtgggct 120
ctatacctgt ttcgtcacct ctccaattcg tgcctcctac tctgtcaccc tacgtgttat 180
cttcacctcg ggagacatga gtgtctatta catgattgtt tgcctgattg cctttacaat 240
cacactcatc ttgaatgtca cacggctgtg catgatgagc agccatcttc gcaagactga 300
gaaggctatc aatgagttct ttagaactga aggggctgag aaacttcaga aggcctttga 360
gattgcaaaa cgtatcccca tcattacctc agccaaaact ctggagctcg ccaaagtcac 420
acaatttaag accatggagt ttgctcgtta tattgaagaa ctggcaagaa gtgtccctct 480
tccacctctt attctaaact gtcgagcctt tgttgaggag atgtttgagg ctgtgcgagt 540
ggacgaccct gatgacctgg gtgaaagaat taaagagaga cctgccttga atgctcaagg 600
tggcatctat gtcattaacc cagagatggg acggagtaat tcaccaggag gagattcaga 660
tgatggctct ctgaatgaac aaggccagga aatagcagtt caggtttctg tccaccttca 720
gtcagaaacc aaaagtattg atacagagtc tcaaggcagc agtcatttca gtccacctga 780

-continued

```
tgatatagga tctgcagaat ctaactgtaa ctacaaagat ggggcatatg aaaactgtca    840
gctgtaacct acaatgctgt aacccagtac ctacaaaatc agctcgctct cagaaaagga    900
acctgtttct tagaagaagt aacatttttg ccaaaagatg actggggttt tccgtttgtt    960
aatattaagc acatcagaac gtgaattgcc aaagtcttca ttagaaggca gcatttttcc   1020
tctctgatac ttttcagtca ttttccttag agctttatta aattatgcat gctaagattt   1080
aaaggagccc cagataaaca tgatggggaa aagcactgaa ctaagagtcc catggtttct   1140
cttctggtca cagttcttcc attggttgga tctgatactt atcttgggac ttcagttttt   1200
ccgtcaataa gatgagggat taggtgagat ctgaagttgt ttctagctct atagcttctt   1260
aacccatcac ctttaaatta ccagaatctt cactcatctc taagtaaacc tttcccggga   1320
cttttactcg cttcttttgg aaaggattaa gctgagatct aaatttccac accaatgtca   1380
taatgcacag aggtttttga aaaacatctg agtgtttttc agatgttttg ccatgtggag   1440
catataatga tatgtgcaag attgaatctt ttcaatgtag cacatgtctg tagggttata   1500
cagatgtcag agagctaact gctctgtaaa ctactttcca tgagtaaatt ggtccttggt   1560
gggggtgtat catattttta acttactgag atatcatttt agttcattga ggttggcagg   1620
gattgcctaa ctgatcttcc aaagtgagca gtttatttct aaggtataac gtctttgatg   1680
cttttagaat aagaacagtg tcaaatcatc tgtcttctgg aaaatcatgg attttcatat   1740
ttctgttaac agaatttctc aggctttccc tttttaaaag tattggactc tacaaatagg   1800
ttctatattt gggatctcat cctaggagaa aacccaaaac tggattcctc ttaagacctc   1860
tgtcaaccct cctgcccttt gtggtcttag gtatggtgct ataggttgca tgcgtcttta   1920
tcttgtttgt ttggttaata ttttgttgtt gaggttttta tttttgttta cttcagatac   1980
ataattctga gctatggctg cttttgtagc ctttccaaga agcactaacc tgaaataaga   2040
ttagataatt gtgagggtgt gttactatat taaaatacac acacaactga tctagacatc   2100
aagaggaaga aaaatgatgg atgatgccac ctgcttcaac tgtatataat aaacacttat   2160
gatgacattt cttgcctggc tgagatctga tataatggaa ttgtaaatac tcttcagaac   2220
aatttcttca gctacaggaa gcgtggtgcc atataatttt aagaacttgg cagtggagct   2280
ccatttgggg cttcacgttt cttcatatga cttctgatta ttgaagcatt acttcagcta   2340
gaggctcctg agggaaatgt tcagaggagg ttttatcagg attttaattt aaggtttcaa   2400
acaggggaag acaggaaatt caaagcgtga cgggataaaa ctcatgcctc cctttgtcca   2460
ggcttatcag aagtaataca tctgctctga atagcatgaa tgaatcaatg tgcagtttta   2520
tcagatggca tcatggataa agatgataat gctgcctttt ctgtctctca ggctgtttcc   2580
atggaaacct ctagagccaa ataaaagcta accaatcatt tagccaaagc ttgccttggc   2640
tcatagactg gtatttcttt aaggaaaatt gtttttatat atttgactat aagagcaaag   2700
gctcttgaac atatcctaga ttatggaaca ctttttccct tccctttttct ctggaaaaat   2760
taaatttttt ttctgtccac tgagactgga gtgcagtggc aagatcatag ctcactgcag   2820
cctccaactc ctggggtcaa gcgatcgtcc tgcttcagcc tcccaagcag ctaggactac   2880
aggtgtgcac cacctttcct ggctaatttt tttttatttt ttgtagagat gggggtctca   2940
ctttgttgcc caggctgacc ttgtacttgt ggcttcaaat gatcctcctg ccttacctcc   3000
caaagtgttg agattacagg catgagccac tgtgcctggc caaaaaacat tttaaatccc   3060
ttgtctgggg gtcagtcctc taaacatccc tcagatttca gatagtactt tcaaccctgt   3120
```

```
cctaacatag caggtttgca gtaatctttt agaatatagc ttgtcaaatt agagaatggt   3180

tttaccccac atgttctcat aggagacatt attatttaga accctaaggt agacatgttt   3240

aaaatcaaag tcctaagaaa cagaactttg gaaaaatgga ggaaatgttt ttaaagtctg   3300

taagtttgca cgatactgta tagtaactaa atgcatgcta ctccgttgta tcctagttat   3360

tttagaaaca gaggtggcct aatttggtgg ccaaagtaac tggtttactt tgagtgtacc   3420

agcttatggt gccattgatg aggaattaaa gtaggtcaaa atttaattgg agttggtatt   3480

acttcgtaaa gctagttttc aagaggaaga aaaccacact tactaatgtt ttctgtatct   3540

aatcaaatac tcttcatata taattaagcc tcatgttatc ttttttttaa atcaaccttt   3600

tgaacttcaa ctacagtcta aaagtcttga tggtaactat agtgtaatta tctttttgtc   3660

tcactggatt ttatagttag tggaaaatgc ctttacaaaa tgtatttaaa atagctgtca   3720

tctcatttgt aaattttgtc gtgtattgtg atatagtgaa ccttattgtc cttatgaaat   3780

ggtagctttg tgaaatacat tcaccaaaaa tcaaaatttg aacatcttta tgattcctta   3840

ccagctgaag ccagatagac aggtattaat tgagctgatg ccccacttga gtttatagac   3900

tgtttgataa ctgcctgtcc tccaaattgt gtatgtatat gttacgatgg tttaattctt   3960

gagtcagggc cagcacgcat ttatattttc taccaattac cttgatagaa atatcttaga   4020

aattgctgac ctggaacggt tgtgagaaga ctcctggctt ctttcttgcc tcacttaaca   4080

aatattttaa ggtcaaagca atatctgtgc acggctttcc ttttgctcct ccagacaagt   4140

gaggctgttg gtatagtcct cttcaccctc tgcatgtagc ttcaccctag atcagacttt   4200

tgtctcttgg gtcccagatg gcacaggagc actgcatgct tgttttctag agcccagcca   4260

gtcatgggtg ctagcctagt ctccacacac cagcaagtag aacccaagtg tattgtataa   4320

atatttcctg agtaccagta agagaatgca ttcttttctc atctaggcca ggaatgttga   4380

aaatgctcag ccttacatag aaactcctag attttcacta acgcatttca caaaagtaaa   4440

taagtatttc atataattca gaggatgttt aaattgtcag cattttaata aatacttgca   4500

ttataatttt gtctcttttt taaagaaagt catacttgaa tataatttat taaacgttca   4560

atggagtata tagtctattt gaaatttt                                      4588
```

<210> SEQ ID NO 40
<211> LENGTH: 2482
<212> TYPE: DNA
<213> ORGANISM: Homo sapiens

<400> SEQUENCE: 40

```
cccagatcca ggccgggccg cggctctcgc cgcccagccc agcccagccc ggcccggccc     60

ggccctgccg cggaggcgag gccgccagtg tcccgcgccc ctgatatctg cagtgagcct    120

gatacctgcc tctgcccttc tgagcctgtt cctcttccct gagtacaggg cacaaagctt    180

gcgccctgag gggcggccgg cgcgctccct ggcccggtcc ccgcccggcc ccgggccccc    240

cgcccctccc cgacccgggg ccggggcccc tgccgccgcc gccgccgcct tccgacccct    300

gcgccccggc cccggtcccc cgggccatgc agcctcggcc ccgcgggcgc ccgccgcgca    360

cccgaggaga tgaggctccg caatggcacc ttcctgacgc tgctgctctt ctgcctgtgc    420

gccttcctct cgctgtcctg gtacgcggca ctcagcggcc agaaaggcga cgttgtggac    480

gtttaccagc gggagttcct ggcgctgcgc gatcggttgc acgcagctga gcaggagagc    540

ctcaagcgct ccaaggagct caacctggtg ctggacgaga tcaagagggc cgtgtcagaa    600

aggcaggcgc tgcgagacgg agacggcaat cgcacctggg gccgcctaac agaggacccc    660
```

```
cgattgaagc cgtggaacgg ctcacaccgg cacgtgctgc acctgcccac cgtcttccat    720

cacctgccac acctgctggc caaggagagc agtctgcagc ccgcggtgcg cgtgggccag    780

ggccgcaccg gagtgtcggt ggtgatgggc atcccgagcg tgcggcgcga ggtgcactcg    840

tacctgactg acactctgca ctcgctcatc tccgagctga gcccgcagga gaaggaggac    900

tcggtcatcg tggtgctgat cgccgagact gactcacagt acacttcggc agtgacagag    960

aacatcaagg ccttgttccc cacggagatc cattctgggc tcctggaggt catctcaccc   1020

tccccccact tctaccctga cttctcccgc ctccgagagt cctttgggga ccccaaggag   1080

agagtcaggt ggaggaccaa acagaacctc gattactgct tcctcatgat gtacgcgcag   1140

tccaaaggca tctactacgt gcagctggag gatgacatcg tggccaagcc caactacctg   1200

agcaccatga agaactttgc actgcagcag ccttcagagg actggatgat cctggagttc   1260

tcccagctgg gcttcattgg taagatgttc aagtcgctgg acctgagcct gattgtagag   1320

ttcattctca tgttctaccg ggacaagccc atcgactggc tcctggacca tattctgtgg   1380

gtgaaagtct gcaaccccga gaaggatgcg aagcactgtg accggcagaa agccaacctg   1440

cggatccgct tcaaaccgtc cctcttccag cacgtgggca ctcactcctc gctggctggc   1500

aagatccaga aactgaagga caaagacttt ggaaagcagg cgctgcggaa ggagcatgtg   1560

aacccgccag cagaggtgag cacgagcctg aagacatacc agcacttcac cctggagaaa   1620

gcctacctgc gcgaggactt cttctgggcc ttcacccctg ccgcggggga cttcatccgc   1680

ttccgcttct tccaacctct aagactggag cggttcttct tccgcagtgg gaacatcgag   1740

cacccggagg acaagctctt caacacgtct gtggaggtgc tgcccttcga caaccctcag   1800

tcagacaagg aggccctgca ggagggccgc accgccaccc tccggtaccc tcggagcccc   1860

gacggctacc tccagatcgg ctccttctac aagggagtgg cagagggaga ggtggaccca   1920

gccttcggcc ctctggaagc actgcgcctc tcgatccaga cggactcccc tgtgtgggtg   1980

attctgagcg agatcttcct gaaaaaggcc gactaagctg cgggcttctg agggtaccct   2040

gtggccagcc ctgaagccca catttctggg ggtgtcgtca ctgccgtccc cggagggcca   2100

gatacggccc cgcccaaagg gttctgcctg gcgtcgggct tgggccggcc tggggtccgc   2160

cgctggcccg gaggccctag gagctggtgc tgccccccgcc cgccgggccg cggaggaggc   2220

aggcggcccc cacactgtgc ctgaggcccg gaaccgttcg cacccggcct gccccagtca   2280

ggccgtttta gaagagcttt tacttgggcg cccgccgtct ctggcgcgaa cactggaatg   2340

catatactac tttatgtgct gtgtttttta ttcttggata catttgattt tttcacgtaa   2400

gtccacatat acttctataa gagcgtgact tgtaataaag ggttaatgaa gtgtgtgcct   2460

caaaaaaaaa aaaaaaaaaa aa                                            2482
```

<210> SEQ ID NO 41
<211> LENGTH: 7725
<212> TYPE: DNA
<213> ORGANISM: Homo sapiens

<400> SEQUENCE: 41

```
agaatcttct gtaggccttt ctcttgcctt cttttattca caactgatga cactgcatat     60

cttcccctgt tcttattggg agaaggcctt gtgtgtcacc aagaggttct cagaagggac    120

ctgtcagttt ttggttaaaa gaacccggaa agagaaggac tatgggggaa ctgatggcgt    180

tcctgttacc tctcatcatt gtgttaatgg tgaagcacag cgattcccgg acgcactctc    240
```

-continued

```
tgagatattt tcgcctgggc gtttcggatc ccatccatgg ggtccctgaa tttatttcgg    300
ttgggtacgt ggactcgcac cctatcacca catatgacag tgtcactcgg cagaaggagc    360
cacgggcccc atggatggca gagaacctcg cgcctgatca ctgggagagg tacactcagc    420
tgctgagggg ctggcagcag atgttcaagg tggaactgaa gcgcctacag aggcactaca    480
atcactcaga taatgtggct cacaccatca agcaggcatg ggaggccaat cagcatgagt    540
tgctgtatca aaagaattgg ctggaagaag aatgtattgc ctggctaaag agattcctgg    600
agtatgggaa agacacccta caaagaacag agccccccact ggtcagagta aatcgcaaag    660
aaacttttcc aggggttaca gctctcttct gcaaagctca tggcttttac cccccagaaa    720
tttacatgac atggatgaaa aacggggaag aaattgtcca agaaattgat tatggagaca    780
ttcttcccag tggggatgga acctatcagg cgtgggcatc aattgagctt gatcctcaga    840
gcagcaacct ttactcctgt catgtggagc actgcggtgt ccacatggtt cttcaggtcc    900
cccaggaatc agaaactatc cctcttgtga tgaaagctgt ctctgggtcc attgtccttg    960
tcattgtgct ggctggagtt ggtgttctag tctggagaag aaggccccga gagcaaaatg   1020
gagccatcta ccttccaaca ccagatcgat gattgcagat ccctcttttc cagttctcct   1080
tcctctagga gccatgttat cctctgtccc ccatagagtc aagcctagtg cttgaaggtc   1140
ctgacgacac ccacaacata catgagagta atgggattga gcatttatgg cagcaacaga   1200
ggagccacaa aatgttcttt gttctttggc tccaaaaaga ctgtcagctt tcagtctctt   1260
ttgatggact gttttatcag agttgacttt aaatacagct tgtctcatga cacaacgctt   1320
ccctacattc tatttgtcaa tgatgatttg caactagttg gagattctca gagcaggaag   1380
gaatcttttc aaccagagca ggaactgtct tctgcaatgc cttggacttg agcctccagc   1440
ctccacttga acaccatgtg aagggaacct cagtacttca taaaatggcc tttctcattc   1500
atctttcatg ggaacattta ttgtacaagc gctttgaata tcatgggcac catgactgtg   1560
accctacagg taggattgga tcactccatg agagtagccg gcaggtttct acaatggcct   1620
gggaatggac tgattatttt tatacatttt ctggcctgag agaaagccaa agtcccctgc   1680
tgttcacagc aaccctgcct gggagcttgg aatcttggta atctgcccgg ttggatctat   1740
ggaggtagtc tcaccctttt tgtcttttgt gggaaattaa gagaaataat tatcagacat   1800
atcatcacct ccagtggaac tacagagacc tggacccagc tgcactattt taatgtaaaa   1860
ataacagtat ggccaggtgc agtggctcac gcctgtaatc ccatcacttt gagcagccaa   1920
ggcgggcgga tcacgaggtc aggagattaa gaccatcctg gccaatatgg tgaaaccctg   1980
tctctactaa aatacaaaaa attagctggg catggtgttg cgtgcctgta gtcccagcta   2040
cttgggaggc tgagacaggg gaattgcttg aacccgggag gcagagattg cagtgagccg   2100
agatcacgcc actgcactcc agcctggcga cagagtgaga ctctatctca aaataataat   2160
aataataata ataataataa taataataat aacagtatat ttggtgtcag gagagggctc   2220
aattctcatt tctgcctttc ctgtgctggc tcatggtagc tgggcatgac ttgccttcct   2280
acataggttg tcttcataca tatgcactgg gaatcaataa aagcccatgg tgagaatgaa   2340
catcccctta atgttcctta ctatccccaa cccctgaggc ctcacctact gccctgccat   2400
gtggagctac ttgccctggg gctgccagtc acacattcct cggtcctact tctctgaccc   2460
cgtttgactc tgcacctgag ccctaatgct tacttcagtg acctgaactt tgacaagtgg   2520
cttttgtcct gcacctcagg tttgacctct gctctccctt gaccttgact gtgacatttg   2580
acctttggct ttaatcatta cagcctcaga taaaggtacc ttcagcccgg gcacagtggc   2640
```

-continued

```
tcacgcctgt aatcctagca ctttgggagg ctgaggcagg cggattccct gagctcagga   2700
gttcaagacc agcctgggca acacggtgaa accctgtctc tactaaaata caaataatta   2760
gctgggcatg gtggcatgtg cctatagtcc cagctacttg ggaggctaag gcaggagaat   2820
cacttgaatc tataaggcag aggtggcagt gagccgagat cacaccactg cactccagcc   2880
tgggcaacgg agcaagactc tgtctccaaa aaaaaaaaga aagataccct cagtgtgcca   2940
ggcctctaag agctcacctg ccaggcttcc tccttgctcc actgtcccat gtaattccat   3000
atatgaagct accactgtac atctctcttt tccggtgcct gttgagttgc atagaagcac   3060
agttgtgttt attttgtttt tagggttgcc atgggcaatt tccgtgccac ttttaagcag   3120
tgttgcactg tgaagagaat gtaggcaagt ttatttctgg aatggtttct tcttacaatc   3180
agaatagtta ggatgtaata tatttttggg tgggcattta aagtgaaaag gtacatattt   3240
acatagacac aggtgataat gtatctatgt aaatgccttt tgattctgca actgcaggat   3300
actctcatca aagacacaga taaaaagcct ctgtgtttcc aaggccttgc cctacaccta   3360
acacataata tgtccaaatg gatgaagagg aggcaaggac aaggatgtga tgacaaaaca   3420
ttctgttatg cacttgtagc atttatgttt cttcctgggg gattttataa tactaaaaga   3480
atcataatat aaagagatga ttaaaaaaaa aatactgccg ggcacggtgg ctcatgcctg   3540
taatcccagc attttgggag gccgaggtgg gcagatcacc tgaggtcggg agttcgagac   3600
cagcctgacc aacatggaga aaccctgtct ctaccaaaca tacaaaatta gccggggatg   3660
gtggcgcatg cctataatcc cagctactcg ggagtctgag gcagaagaac cgcttgaacc   3720
cgggaggcag aggttgtggt gagccgagat cgcgccatcg cactctagcc tgggcaacaa   3780
gagtgaaact ccatctcaaa aaaataaaaa taaaataagt aagtaatacc taaaattctg   3840
caaccttcat tttactatag atggttgaag attatattac ttcttaattg ttttagcctt   3900
gttattgctt cattacttca tggttgttga gtacagatgc tcagtaatca taacctatga   3960
aatatttgac accatgatct aaacattaaa aacaaataac tgtgctattg ccacagctat   4020
gttttggctt tgaattttct ttactgaata ttttggatca agaacactag atgagaaacc   4080
tgttcaactc tgttcttttt ttttttttta actccactgt atttattacc tgtttttgtt   4140
ttttttgttt gtttgttttt gatgtgcata tagaccaaga tgtggtaaat ttaaatggca   4200
gatgtttttg atgtggtaca tttaagggag agaaagcagt ttaaagagca gggtgaaaaa   4260
tccaacaaga ctccatcgag agtttctgag ctctcccatc aggggccagt cctcctttcc   4320
tctctcctct tactcccatg atttccaagt tgtgatcctt tccttatttc tgaggaatga   4380
cttggtttct cctcttcttt ttttggcctg agagaagatg tttttgcact tgtagctatg   4440
aggaacagat tgtccactag ggaggccagc tgatcatttt ctgccagagt cacacagagc   4500
agtcacacct tattttgaaa accactgtct ggggtctttg tcctcacata tgcaggtcta   4560
gtgtccccac aaagtgatca gatggatata taaagtggag tgccaatgta ttaatttact   4620
gtgagaaaca caattgctaa gtgggtcaga tatctgtctc agctggtcag tacaccttcc   4680
agcaggaaaa tctacataag aacaactaaa tcacaatctg tagagtgctt gatgacccca   4740
gaattggtgc aaggggacac attcttgctt gttagcacct gctctctgga gtttgctatt   4800
ttctcacaca cagtgtatta gttcacagaa tgttctccaa ggaggacagg gggctttgcc   4860
catagccatg tgctgtgggc agcagagcta ggaagaagca caggcatctc ccagcccagg   4920
tgtttcccac ttaactgcat tgccctttc atcttttttt tttccccaat agcttcagga   4980
```

-continued

```
cattcagtac attgtgcttt ttagaggttg atgattccac tgcctgagct gccttcacct   5040
ctctttcttt ggaaattgcc atctttgagc attgtatgtc tctgtaacat ctctgcatct   5100
ccttttcact ctggcctccc tttctccatt gtccttctag cttctggttg ccccaaaccc   5160
cacagactgt gtaacaaaac ccaaaaccta ttggtttaaa acaataccca ttttattttc   5220
tttcatagtt tctatgggtc aggaatttgg atatggcttg ggtaagcagt tctggcttct   5280
catggagttg gaggcaagtg gtggctggaa cagaaatggg gcagccaggg gtggtggcca   5340
ggcatcagct acatctcctc catgtagtct caggaactct ccatgtaatc tctctgtgtg   5400
ggttgggctt cctcacaaca tggtggcctc agggcagtca ctgcttacat ggcagctagc   5460
ttccctcaga gtgagtatcc caagagatca cagtcaaagt gcatagcatt tatataatct   5520
aatcttggaa gtcacaaaat gtcattcttg tgatactctc attggtgaag aagtcataaa   5580
atcctgctca ggttcaaaaa gagggtgtat agaacccaac actcaatagg aagattgtca   5640
gagttacatt gtaagaagag catgtagttg ggagatatca ttgtggccat tttgggaaag   5700
atgcaacatg tcacaatgtc atgttctcca tcgtctcccc gttccacctt gtactggttt   5760
ccaagggtag tcgtttaaaa gtaccacaaa aactgggtgg cttggaacaa cagaaattta   5820
ttgtttcaca gttctggagg ccagaagttc aaaatgaagt gttggcagaa acatgctgcc   5880
tctaaaggga ctgggaaagg atctgttcca ggcttccctc ctatcttctg gttgttcctt   5940
gccttctggc tgcgtaactc tagtcttcat ttggtgttct ccctgcatgc atggctttgt   6000
gtccaaattt cctttttca tgaggccatc agtcatactg gattagggac ccactctact   6060
actgcaggat gacctcacct tcccaaatta catctgcaac aaccctattt ccaaagaagg   6120
ccacattctg aggtactggg ggttataact tcaacatgaa ttttttggag gaaacaattc   6180
aactcctaac acatctctac ccaacctctg taggttccct caatccacca aaattttttg   6240
gctccactgg attatctagc agttaggaaa ccaagatcat taaatgaatt caccgcaact   6300
acagtgagac tgactacctt agcttacctc tgtgaaagga gttaagccaa aggaatctgt   6360
ggaattttgg agagtttggg agcatttggg ggcaggaggc aaatgttctt cctttaaatc   6420
acaacactta gttctcttcc atttataaga ctcacccctc catcccaacc cctgcaccac   6480
aggacaagga agtgttcttg gtcttcaact ttcatccctg atggtgaaag cagttgctcc   6540
tgacctattt gcccaccagc ttctcctctg gagcctgagg cttctgatgc ctgcctggct   6600
ggttctcagt aagaaggtca agttcaacca gaggggagat gctgatgcct ttcagtactt   6660
aaatatgagt tcagaccctg gggcctggac ataagatttg gggtcccctg gatataagat   6720
ttctgaaaac actcagactg tggagacccc tgctgaggga gaagccccaa actgtggctt   6780
caggggaatg caccaaggct ctcattgagg ccaccttctc caacaagctc ccctcctgct   6840
tccccatggc tggcatggct gaggaaaaag gacactgagc acagcccgtg catgagcggc   6900
ttgccatgca acaggataaa acccataatg ccactcagca agccttggtt gtaaatctag   6960
tttgattaca tttgtaatca aatgatggcc atttgttctg tttctggttt gtgaaccaac   7020
tgaagacata agcagggcct cagctaaccc acaaatagca catgtgtgca aactggaaaa   7080
atgaaccctt cttctgggag gacgccagcc caggccaggt cacccggctt ggccagcaga   7140
acacagagta gattttggtc ccgtttgttc cccagtgggg tatctatcct tgtgcagggc   7200
acaagcctac atggtggctc tggtcatatc attagaaaat agacagaaat gggctgcaca   7260
ccagaatgaa tgaattgaat tgaaagggag gagtgatggt ggaaaaaaaa acaagtcaat   7320
tcatttagac tggtagaacc agaaccactg tgtagtacat ccaaacggtt aaaattccct   7380
```

ggaagatgtt acataatcct atcatggtgt ttatttatgg aaatctattt taaaaatttt 7440
atgtaatact gcacagtctg tttgcatgat gccttgtacg tagtagcaac tcagtaaata 7500
ctttttgaat gaactagtat agtattttaa ttagctagtc ttcatgtact ggtacaaaag 7560
aacagtgtca tcttacagct gaagtcatag aggggaaata tcccactcaa gatcatataa 7620
cattccaggt actcaggatg aatggtttga ggactggtct gaattcttca aaggtttcag 7680
ctgtattaac attctccatc taataaactt tatcttgtca ttgca 7725

<210> SEQ ID NO 42
<211> LENGTH: 4033
<212> TYPE: DNA
<213> ORGANISM: Homo sapiens

<400> SEQUENCE: 42
cggcggccgc ggggcccggc gggcgcgacg ctgcctcctc accggcgcag gctaggaggg 60
ggcggcctga gtgccgtagc cgagccgggg ctggagcgcg cggtctgacc tacgagaaac 120
atggcaacca gcgccgtccc cagtgacaac ctccccacat acaagctggt ggtggtgggg 180
gatgggggtg tgggcaaaag tgccctcacc atccagtttt tccagaagat ctttgtgcct 240
gactatgacc ccaccattga agactcctac ctgaaacata cggagattga caatcaatgg 300
gccatcttgg acgttctgga cacagctggg caggaggaat tcagcgccat gcgggagcaa 360
tacatgcgca cgggggatgg cttcctcatc gtctactccg tcactgacaa ggccagcttt 420
gagcacgtgg accgcttcca ccagcttatc ctgcgcgtca aagacaggga gtcattcccg 480
atgatcctcg tggccaacaa ggtcgatttg atgcacttga ggaagatcac cagggagcaa 540
ggaaaagaaa tggcgaccaa acacaatatt ccgtacatag aaaccagtgc caaggaccca 600
cctctcaatg tcgacaaagc cttccatgac ctcgttagag taattaggca acagattccg 660
gaaaaaagcc agaagaagaa gaagaaaacc aaatggcggg gagaccgggc cacaggcacc 720
cacaaactgc aatgtgtgat cttgtgacag gcctgaggcc ctgggcacag tgacggtggc 780
ctggccagcc ctcgggaccc ctccccacct aactgcactg aaaccatttc taaccacaac 840
ccttggccca aggacttggt acaggaaggg agaagggcag gtgggcaggg agcagacagg 900
gtctggcttt gcccagaggg cacgggcttt cccacctctc aaagagacaa ggaagccacc 960
tgtaagcaga agcagcatcc aagtgcccct ggccccccca tgtgttgatt caacccggtt 1020
cctccccctc tctcggtggg tgtgttgttt attgtaacta catagtgttg gtttgatgtg 1080
gaagtgttta tccacataca aagtacaaaa caagccatga acaagcttct ttcccttacc 1140
ccccatccac aatgtctgag cttggatgtc ttttatagat ttttaaatta ttttagtgat 1200
tattatttta ttaaaggggt ctgggctcac tgcctggtga agtttcaagt gttcagcaga 1260
cctctctggt aacatatctg gaatattgtt gttgtttttt aaccgagttt tcccatcagt 1320
gccaaaactc aactcaatct gaaagtagag tgtctgagag gacagaaggt aatgggaact 1380
gtagctggag gcctcaggcc atgggtcaaa cctgggaggg aaagagaccc tacacatggc 1440
ctagaaatga gagaagagag aggtatttac ccagaggatt ttcctatggt tggggatgca 1500
aatattagaa aacagattgt attttgctga ggggagtggc tgtcatgagc atgtcagttc 1560
taaaaggggt tttcattatc ctggaaatgt ataaactaaa gtaagctgat tggctttgca 1620
aacatgttca tttgtttttc agacagtatg ggttaagttc tctgccctcc ccaggggtct 1680
gaggaggctc tgggtttctc agatctgtct cttgctgcgt tttcacatca gctgtgctgc 1740

-continued

```
ttggtgcctc tctgatacga atacactgac acgtcaaagt aacctaatgt ggacaccatc   1800
cagaaaactc cagttcatgc tggatcttaa ccaaaaatga ttcaatactg ttatcactaa   1860
aacagcacca agacctgaag ccatcttccc ttggagtcaa ctgactacca cctctataag   1920
cctagtcaat gagcagaccc cttccagtat ttgtaaaagt agtactaggt tgcctttttg   1980
gcaattttta ttgacctgtt gaatcttgac tataaaatga tctgagaagt aaggaaggct   2040
gggctgatgt gtggctctca tataccttct gcaagggggc agtctcccca gctccctgat   2100
gatgctcacc cccgcccccc cacctcaggt gctgctggtg tgagccaaag actggagttt   2160
ttccagctgg ggtgggagtg gagagacaac aggaacaacg ctgcaccaaa gaaaaggtca   2220
gaataaaagg cagcacagct ggtgacctta ttttctagat gttacaaatc aggtcactat   2280
gcaaactaga atatcctcag caggtggcct ggccactctg gagaaagaaa cccaaggaaa   2340
gtgagcaccc aactggatgc caagacaccc gggttctgaa aatgtgctgt gttcctacct   2400
cggcaagatc accagcactg aggggcccag ctggagaatg attctgctac aaaaggagac   2460
agttgagact tttgcttgtt ggaaatcaaa cttcttattt gtctaaattg ccccttttc   2520
tgttcctaaa aggaaggata agagagaaca ttccaggtga ggcacttcaa agtttcctta   2580
gaccctatag tgttaagagg tattttaaac actaaaagga caaagctctt cccaatcctt   2640
atgcttccct aagtggtatc tgcagcagtt tgttgtgtgc agtttgatgg cagctgcaaa   2700
ctggaggtga ggcggaggaa aggcaggtag gaaggagtaa ggatggagat gctcagaatc   2760
aagagcatgg cggagtagga gaagaagccc tgcacacagg gcagtgtcca cagccagaaa   2820
actcctgctg ggcaccaacc actacgagca taccccatgc ccaccgtgga gctgcaactc   2880
ctcgacagca ctgagtttga tagtctcact ggaagcagat cagctgatgt agaacagaga   2940
cctcggccat aaaggtgaga agacataggg atttcaacca cacagttggg acagaaggga   3000
cagtgcatct gttcatccat cctgcacttg gcccacgttg aactccatgg tgcctgagag   3060
agactagtta agggttggtc ttctgtatcc tctgctgttg agcctctggt aagctttcat   3120
ctcccatgaa ctcatttccc cataaatgaa atgggtaaat aatgccccat ttgtagaagt   3180
gggccctcat gactgaggta gcttccagat aggccagagt agagtgtaga gtgtgccccg   3240
tgacatccct ccatcttctc ctccattatc atctagcagg gtcagactgg gaaacctggt   3300
tggccacgcc acaccatgac cgaggagcca actgggactt ctggctgttt gacatcctca   3360
tgttcccgtt ggtcttccgg agaatagtgc taccctcaca tcccctggag cacagccttc   3420
ctgaaatgcc ctcaccccat gcctttgcca ttgtgtgctc tcagatttct tccactgttt   3480
gacaccctcc ttagagggct gctctttttt ttccagagat aatcctagcc atcctctcca   3540
ctcccacggc tggggacaat ggccacttac tacctgtgca ctttgccact cgggacacct   3600
ggatggtttc tcttaggact ttgcccacct ccttctcatg gcacttgctg tggaaaatgc   3660
ctggctggcc tcgtggggcc tgtctcactt ttccaggaga catgacccac taacgtggca   3720
actttaaccc aaaggcccct cagacatgtt acagcaaatc tggagccaca gacaggttcc   3780
ctccattggc agcccattgt gtttgaaatt ccatgtcggg tttacttgga atgaaagata   3840
cttgaattat tgtgcgcctg tgagcgccca gcttctgttt catagtctta acaggtggcc   3900
attgtcgtga aacgagtgat gcctgaagat ctcagtgatg tttgaacctt ctgtgtaact   3960
ttttattaag tctttgtatc tctcgactga ttaataaaga agagaaacac gtaaaaaaaa   4020
aaaaaaaaaa aaa                                                      4033
```

<210> SEQ ID NO 43
<211> LENGTH: 2960
<212> TYPE: DNA
<213> ORGANISM: Homo sapiens

<400> SEQUENCE: 43
aaatttagat tttgcaaacc tgtgcattga tgagagtgct attgaaacac attaagaaag 60
attttcaacg caggaatgtg tcatttcctt tcttcatgta ccagatgctg aaatactatg 120
agataaagat tttaggtttc aattgtaaag agagagaagt ggataaatca gtgctgcttt 180
ctttaggacg aaagaagtat ggagcagtgg gatcactttc acaatcaaca ggaggacact 240
gatagctgct ccgaatctgt gaaatttgat gctcgctcaa tgacagcttt gcttcctccg 300
aatcctaaaa acagcccttc ccttcaagag aaactgaagt ccttcaaagc tgcactgatt 360
gccctttacc tcctcgtgtt tgcagttctc atccctctca ttggaatagt ggcagctcaa 420
ctcctgaagt gggaaacgaa gaattgctca gttagttcaa ctaatgcaaa tgatataact 480
caaagtctca cgggaaaagg aaatgacagc gaagaggaaa tgagatttca agaagtcttt 540
atggaacaca tgagcaacat ggagaagaga atccagcata ttttagacat ggaagccaac 600
ctcatggaca cagagcattt ccaaaatttc agcatgacaa ctgatcaaag atttaatgac 660
attcttctgc agctaagtac cttgttttcc tcagtccagg gacatgggaa tgcaatagat 720
gaaatctcca agtccttaat aagtttgaat accacattgc ttgatttgca gctcaacata 780
gaaaatctga atggcaaaat ccaagagaat accttcaaac aacaagagga aatcagtaaa 840
ttagaggagc gtgtttacaa tgtatcagca gaaattatgg ctatgaaaga agaacaagtg 900
catttggaac aggaaataaa aggagaagtg aaagtactga ataacatcac taatgatctc 960
agactgaaag attgggaaca ttctcagacc ttgagaaata tcactttaat tcaaggtcct 1020
cctggacccc cgggtgaaaa aggagatcga ggtcccactg gagaaagtgg tccacgagga 1080
tttccaggtc caataggtcc tccgggtctt aaaggtgatc ggggagcaat tggctttcct 1140
ggaagtcgag gactcccagg atatgccgga aggccaggaa attctggacc aaaaggccag 1200
aaaggggaaa aggggagtgg aaacacatta agaccagtac aactcactga tcatattagg 1260
gcagggccct cttaagatca ggtgggttgg gcgggacatc ctctgctacc atctcattaa 1320
aaggcccttc acctctggac aagtcatctg cacaactgac ttccaagatc cttttgtgac 1380
tcctccaaat gactttggtt cccgtgttgt acctgacttc cacatggcct tctctcctgg 1440
tccctggtgc tgtttgggcc tctgctccca tgctcatacc tcttcttact ccaattactc 1500
caccatcacc tctctcccct atcacccccca gcctggacac ctctcatgca cggactggag 1560
ggctgctcca accagtcctc agttctctgc cacccattga cctagagtct tgaacccaat 1620
ttaatttatt gggttctagg agaactgctg tgttctcacc ctaacttgga agagtgatgt 1680
ttcagtcaag caaagcgatt cctaccatac aatataacac ttgtgtgagg ctctgtccta 1740
aatatctcaa ttaccaatat gtggtttggt agtatttctc gccatgcttt gctcatgcgc 1800
aatgagacta caactagggt gtaaatttta agtatcccat ctaaaactca tacaatgata 1860
ggaaaaatcc atttgttttt catttgattt ttactgagga atcagctcaa tcttcaatga 1920
atactggtct ctttccaaag catttttgat caaagtaaag actgagtcaa gggctttttt 1980
tttttctttt tcttgtttta agagacagag ccttgttcta ttgcacaggc tggactacac 2040
gcattcacct agagtctaga acacaattta atttattggg ttctaggaga actgtcatga 2100
gtattgataa tatgagagtt ctttatattc aaacattatt ctcaaccaga gatagggatg 2160
tcatagaaga aaatccattc attcaatcat taattcacat gtccattatg tacctccatg 2220
agctggacat aacagctaat aagagataat tgtctctggt tttacagagc taattgtccc 2280
taagagatgt agacaaatga acaagcaatt acaatacatc taagctatac tgggggagga 2340
acagggctgg ataggtatgc agaggagata aaaaaatttt aattccttag aatatttttt 2400
aaaaattgat tcttatttta ccttctcatc ttcttatttt ccaaattaca gcatatatat 2460
atatatatat atatatatat atatatatat atatatatat attttttttt tttttttttt 2520
ttttttttta agttttgaag tgtagtcgag cttgggcaat ttatccaacc catttaaacc 2580
aaaaataaaa cttttcatgt attacctggt catttcaaac aaaaatattt tgatcatgaa 2640
aaagaatacc aatattcttt tgttctaaaa atctcttatg ggattacatg ttatattttt 2700
ggtttctctc tactgatcaa cagactacat tttcacaact cttctttcct ttacgtttta 2760
acacacagac ccaagattca tactattaag attctagtag aactctagat ggtatgcctc 2820
tgtgtatctc agcattttta ttcccactct tgtataatga acatgttaac acctacctca 2880
cagggttgtt gtgaggatca agtaagatat tgtgtgtgtg aagatgctct gtgaaatcat 2940
aaagtccttt aaagatgtaa 2960

<210> SEQ ID NO 44
<211> LENGTH: 2088
<212> TYPE: DNA
<213> ORGANISM: Homo sapiens

<400> SEQUENCE: 44
gagctacttg aagaccaatt agagtccggg aagcgcggcg gggcctccag accggggcgg 60
gcttaagggt gacatctgcg ctttaaaggg tccgggtcag ctgactcccg actctgtgga 120
gtctagctgc cagggtcgcg gcagctgcgg ggagagatga ctggggagcg acccagcacg 180
gcgctcccgg acagacgctg gggccgcgg attctgggct tctggggagg ctgtagggtt 240
tgggtgtttg ccgcgatctt cctgctgctg tctctggcag cctcctggtc caaggctgag 300
aacgacttcg gtctggtgca gccgctggtg accatggagc aactgctgtg ggtgagcggg 360
agacagatcg gctcagtgga caccttccgc atcccgctca tcacagccac tccgcggggc 420
actcttctcg cctttgctga ggcgaggaaa atgtcctcat ccgatgaggg ggccaagttc 480
atcgccctgc ggaggtccat ggaccagggc agcacatggt ctcctacagc gttcattgtc 540
aatgatgggg atgtccccga tgggctgaac cttggggcag tagtgagcga tgttgagaca 600
ggagtagtat ttcttttcta ctccctttgt gctcacaagg ccggctgcca ggtggcctct 660
accatgttgg tatggagcaa ggatgatggt gtttcctgga gcacaccccg gaatctctcc 720
ctggatattg gcactgaagt gtttgcccct ggaccgggct ctggtattca gaaacagcgg 780
gagccacgga agggccgcct catcgtgtgt ggccatggga cgctggagcg ggacggagtc 840
ttctgtctcc tcagcgatga tcatggtgcc tcctggcgct acggaagtgg ggtcagcggc 900
atcccctacg gtcagcccaa gcaggaaaat gatttcaatc ctgatgaatg ccagccctat 960
gagctcccag atggctcagt cgtcatcaat gcccgaaacc agaacaacta ccactgccac 1020
tgccgaattg tcctccgcag ctatgatgcc tgtgatacac taaggccccg tgatgtgacc 1080
ttcgaccctg agctcgtgga ccctgtggta gctgcaggag ctgtagtcac cagctccggc 1140
attgtcttct tctccaaccc agcacatcca gagttccgag tgaacctgac cctgcgatgg 1200
agcttcagca atggtacctc atggcggaaa gagacagtcc agctatggcc aggccccagt 1260
ggctattcat ccctggcaac cctggagggc agcatggatg gagaggagca ggccccccag 1320

```
ctctacgtcc tgtatgagaa aggccggaac cactacacag agagcatctc cgtggccaaa   1380

atcagtgtct atgggacact ctgagctgtg ccactgccac aggggtattc tgccttcagg   1440

actctgcctt caggaacacg ggtctgtaga gggtctgctg gagacgcctg aaagacagtt   1500

ccatcttcct ttagactcca gccttggcaa aatcaccttc cctttaccag ggaaatcact   1560

tcctttagga ctgaaagcta ggcgtcctct cccacaaaaa agtcctgccc tcatctgaga   1620

atactgtctt tccatatggc taagtgtggc cccaccaccc tctctgccct cccgggacat   1680

tgattggtcc tgtcttgggc aggtctagtg agctgtagaa ttgaatcaat gtgaactcag   1740

ggaactgggg aaggctgagc ctcctctttg gtgttgcggt aagataaccg acagggctgg   1800

tgaaagtccc cagatggcag gatatttggt ttcagagtaa ggactaggtg caccaccatg   1860

actgactatc aatcaaaatg tttgtaactt aaaattttta atgaaggata atgaatattt   1920

gtagagtctc tatggttctg tcaatgcaca tcttcgtgtc tgttttcctc atgtatcctt   1980

gtgagcctgg gtgagttctg gggagagacc tgatgtgcgt actgcctgtg aaaatctgac   2040

tttggcaaat caaatcctct tttcctttg aaaaaaaaaa aaaaaaaa                2088
```

<210> SEQ ID NO 45
<211> LENGTH: 4827
<212> TYPE: DNA
<213> ORGANISM: Homo sapiens

<400> SEQUENCE: 45

```
gaagggcaac acggggacct tgaagcgggg tcgcggcggc gccccagccc gggccaggga     60

gtcccggcag cggcacctcc cagaaagggc ggagccgacg acgccttctt ccttcctgac    120

cggcgcgcgc agcctgctgc cgcggtcagc gcctgctcct gctcctccgc tcctcctgcg    180

cggggtgctg aaacagcccg gggaagtaga gccgcctccg gggagcccaa ccagccgaac    240

gccgccggcg tcagcagcct tgcgcggcca cagcatgacc gctcgcggcc tggcccttgg    300

cctcctcctg ctgctactgt gtccagcgca ggtgttttca cagtcctgtg tttggtatgg    360

agagtgtgga attgcatatg gggacaagag gtacaattgc gaatattctg gcccaccaaa    420

accattgcca aaggatggat atgacttagt gcaggaactc tgtccaggat tcttctttgg    480

caatgtcagt ctctgttgtg atgttcggca gcttcagaca ctaaaagaca acctgcagct    540

gcctctacag tttctgtcca gatgtccatc ctgtttttat aacctactga acctgttttg    600

tgagctgaca tgtagccctc gacagagtca gtttttgaat gttacagcta ctgaagatta    660

tgttgatcct gttacaaacc agacgaaaac aaatgtgaaa gagttacaat actacgtcgg    720

acagagtttt gccaatgcaa tgtacaatgc ctgccgggat gtggaggccc cctcaagtaa    780

tgacaaggcc ctgggactcc tgtgtgggaa ggacgctgac gcctgtaatg ccaccaactg    840

gattgaatac atgttcaata aggacaatgg acaggcacct tttaccatca ctcctgtgtt    900

ttcagatttt ccagtccatg ggatggagcc catgaacaat gccaccaaag gctgtgacga    960

gtctgtggat gaggtcacag caccatgtag ctgccaagac tgctctattg tctgtggccc   1020

caagccccag cccccacctc ctcctgctcc ctggacgatc cttggcttgg acgccatgta   1080

tgtcatcatg tggatcacct acatggcgtt tttgcttgtg ttttttggag catttttttgc   1140

agtgtggtgc tacagaaaac ggtattttgt ctccgagtac actcccatcg atagcaatat   1200

agctttttct gttaatgcaa gtgacaaagg agaggcgtcc tgctgtgacc ctgtcagcgc   1260

agcatttgag ggctgcttga ggcggctgtt cacacgctgg gggtctttct gcgtccgaaa   1320
```

-continued

```
ccctggctgt gtcattttct tctcgctggt cttcattact gcgtgttcgt caggcctggt   1380
gtttgtccgg gtcacaacca atccagttga cctctggtca gcccccagca gccaggctcg   1440
cctggaaaaa gagtactttg accagcactt tgggcctttc ttccggacgg agcagctcat   1500
catccgggcc cctctcactg acaaacacat ttaccagcca tacccttcgg gagctgatgt   1560
accctttgga cctccgcttg acatacagat actgcaccag gttcttgact tacaaatagc   1620
catcgaaaac attactgcct cttatgacaa tgagactgtg acacttcaag acatctgctt   1680
ggcccctctt tcaccgtata acacgaactg caccattttg agtgtgttaa attacttcca   1740
gaacagccat tccgtgctgg accacaagaa aggggacgac ttctttgtgt atgccgatta   1800
ccacacgcac tttctgtact gcgtacgggc tcctgcctct ctgaatgata caagtttgct   1860
ccatgaccct tgtctgggta cgtttggtgg accagtgttc ccgtggcttg tgttgggagg   1920
ctatgatgat caaaactaca ataacgccac tgcccttgtg attaccttcc ctgtcaataa   1980
ttactataat gatacagaga agctccagag ggcccaggcc tgggaaaaag agtttattaa   2040
ttttgtgaaa aactacaaga atcccaatct gaccatttcc ttcactgctg aacgaagtat   2100
tgaagatgaa ctaaatcgtg aaagtgacag tgatgtcttc accgttgtaa ttagctatgc   2160
catcatgttt ctatatattt ccctagcctt ggggcacatg aaaagctgtc gcaggcttct   2220
ggtggattcg aaggtctcac taggcatcgc gggcatcttg atcgtgctga gctcggtggc   2280
ttgctccttg ggtgtcttca gctacattgg gttgcccttg accctcattg tgattgaagt   2340
catcccgttc ctggtgctgg ctgttggagt ggacaacatc ttcattctgg tgcaggccta   2400
ccagagagat gaacgtcttc aaggggaaac cctggatcag cagctgggca gggtcctagg   2460
agaagtggct cccagtatgt tcctgtcatc cttttctgag actgtagcat ttttcttagg   2520
agcattgtcc gtgatgccag ccgtgcacac cttctctctc tttgcgggat tggcagtctt   2580
cattgacttt cttctgcaga ttacctgttt cgtgagtctc ttggggttag acattaaacg   2640
tcaagagaaa aatcggctag acatcttttg ctgtgtcaga ggtgctgaag atggaacaag   2700
cgtccaggcc tcagagagct gtttgtttcg cttcttcaaa aactcctatt ctccacttct   2760
gctaaaggac tggatgagac caattgtgat agcaatattt gtgggtgttc tgtcattcag   2820
catcgcagtc ctgaacaaag tagatattgg attggatcag tctctttcga tgccagatga   2880
ctcctacatg gtggattatt tcaaatccat cagtcagtac ctgcatgcgg gtccgcctgt   2940
gtactttgtc ctggaggaag ggcacgacta cacttcttcc aaggggcaga acatggtgtg   3000
cggcggcatg ggctgcaaca atgattccct ggtgcagcag atatttaacg cggcgcagct   3060
ggacaactat acccgaatag gcttcgcccc ctcgtcctgg atcgacgatt atttcgactg   3120
ggtgaagcca cagtcgtctt gctgtcgagt ggacaatatc actgaccagt tctgcaatgc   3180
ttcagtggtt gaccctgcct gcgttcgctg caggcctctg actccggaag gcaaacagag   3240
gcctcagggg ggagacttca tgagattcct gcccatgttc ctttcggata accctaaccc   3300
caagtgtggc aaagggggac atgctgccta tagttctgca gttaacatcc tccttggcca   3360
tggcaccagg gtcggagcca cgtacttcat gacctaccac accgtgctgc agacctctgc   3420
tgactttatt gacgctctga agaaagcccg acttatagcc agtaatgtca ccgaaaccat   3480
gggcattaac ggcagtgcct accgagtatt tccttacagt gtgttttatg tcttctacga   3540
acagtacctg accatcattg acgacactat cttcaacctc ggtgtgtccc tgggcgcgat   3600
atttctggtg accatggtcc tcctgggctg tgagctctgg tctgcagtca tcatgtgtgc   3660
caccatcgcc atggtcttgg tcaacatgtt tggagttatg tggctctggg gcatcagtct   3720
```

```
gaacgctgta tccttggtca acctggtgat gagctgtggc atctccgtgg agttctgcag   3780

ccacataacc agagcgttca cggtgagcat gaaaggcagc cgcgtggagc gcgcggaaga   3840

ggcacttgcc cacatgggca gctccgtgtt cagtggaatc acacttacaa aatttggagg   3900

gattgtggtg ttggcttttg ccaaatctca aattttccag atattctact tcaggatgta   3960

tttggccatg gtcttactgg gagccactca cggattaata tttctccctg tcttactcag   4020

ttacataggg ccatcagtaa ataaagccaa aagttgtgcc actgaagagc gatacaaagg   4080

aacagagcgc gaacggcttc taaatttcta gccctctcgc agggcatcct gactgaactg   4140

tgtctaaggg tcggtcggtt taccactgga cgggtgctgc atcggcaagg ccaagttgaa   4200

caccggatgg tgccaaccat cggttgtttg gcagcagctt tgaacgtagc gcctgtgaac   4260

tcaggaatgc acagttgact tgggaagcag tattactaga tctggaggca accacaggac   4320

actaaacttc tcccagcctc ttcaggaaag aaacctcatt ctttggcaag caggaggtga   4380

cactagatgg ctgtgaatgt gatccgctca ctgacactct gtaaaggcca atcaatgcac   4440

tgtctgtctc tccttttagg agtaagccat cccacaagtt ctataccata tttttagtga   4500

cagttgaggt tgtagataca ctttataaca ttttatagtt taaagagctt tattaatgca   4560

ataaattaac tttgtacaca tttttatata aaaaaacagc aagtgatttc agaatgttgt   4620

aggcctcatt agagcttggt ctccaaaaat ctgtttgaaa aaagcaacat gttcttcaca   4680

gtgttcccct agaaaggaag agatttaatt gccagttaga tgtggcatga aatgagggac   4740

aaagaaagca tctcgtaggt gtgtctactg ggttttaact tatttttctt taataaaata   4800

cattgttttc ctaaaaaaaa aaaaaaa                                       4827
```

```
<210> SEQ ID NO 46
<211> LENGTH: 2393
<212> TYPE: DNA
<213> ORGANISM: Homo sapiens

<400> SEQUENCE: 46
```

```
attcttctat tagataacag tagctattta aatacttctg cagaagctca catattttta     60

gtttgttgaa gttcgtgact gcttcactct ctcattctta gcttgaattt ggaaatgact    120

tttgatgacc taaagatcca gactgtgaag gaccagcctg atgagaagtc aaatggaaaa    180

aaagctaaag gtcttcagtt tctttactct ccatggtggt gcctggctgc tgcgactcta    240

ggggtccttt gcctgggatt agtagtgacc attatggtgc tgggcatgca attatcccag    300

gtgtctgacc tcctaacaca agagcaagca aacctaactc accagaaaaa gaaactggag    360

ggacagatct cagcccggca acaagcagaa gaagcttcac aggagtcaga aaacgaactc    420

aaggaaatga tagaaaccct tgctcggaag ctgaatgaga aatccaaaga gcaaatggaa    480

cttcaccacc agaatctgaa tctccaagaa acactgaaga gagtagcaaa ttgttcagga    540

cttcatccag caagcaattt cctattccag ttttccattc tggatggggc tgtctcggag    600

gaaccccagc tacccatggc tctgggagga cggttctcct ttgatgcccc acttatttag    660

agtccgaggc gctgtctccc agacataccc ttcaggtacc tgtgcatata tacaacgagg    720

agctgtttat gcggaaaact gcattttagc tgccttcagt atatgtcaga agaaggcaaa    780

cctaagagca cagtgaattt gaaggctctg gaagaaaaga aaaaagtctt tgagttttat    840

tctggaattt aagctattct ttgtcacttg ggtgccaaac atgagagccc agaaaactgt    900

catttagctg gctgcagaac tcctttgcag aaactggggt tccaggtgcc tggcaccttt    960
```

atgtcaacat ttttgattct agctacctgt attatttcac ctagcttgtc ccaagcttcc 1020
ctgccagcct gaagtccatt ttcccctttt tattttaaaa tttgactcct cttcaagctt 1080
gaaaaccctc tgaactcagt cttctttacc tcattatcac cttcccctca cactcctaaa 1140
attgcatgaa agacagaaca tggagaactt gctcaagtgc aggcagagag caaaaagggg 1200
aaatatgtct gggaaaaagt gcacgtgaag aaacaaagaa ggacagaggc cattccgaaa 1260
tcaagaaact catgttctta actttaaaaa aggtatcaat ccttggtttt taaactgtgg 1320
tccatctcca gactctacca cttacggaca gacagacaga cagacacaca cacacacaca 1380
cacacacatt ttgggacaag tggggagccc aagaaagtaa ttagtaagtg agtggtcttt 1440
tctgtaagct aatccacaac ctgttaccac ttcctgaatc agttattatt tcttcatttt 1500
tttttctacc agaggacaga ttaatagatt taacccttca caacagttct tgttagaatc 1560
atgggatgtg tggcccagag gtaagaatag aatttctttc cctaaagaac ataccttttg 1620
tagatgaact cttctcaact ctgttttgct atgctataat tccgaaacat acaagacaaa 1680
aaaaatgaag acactcaatc tagaacaaac taagccaggt atgcaaatat cgctgaatag 1740
aaacagatgg aattagaaat atatcttcta tttttaggct tctatttcct ttccacccac 1800
tcttcacagg ctattctact ttaaaggaag cctttttatt ttgctgcaca caatctagca 1860
ggaatctttt ttttttttta agagctgtgt catccttatg taggcaagag atgtttgctt 1920
ttgttaaaag ctttattgag atataattaa cataaaataa actgaacata tttaaagtgt 1980
actatttgat aagttttcac accttgtgga gaacatgcat actacaatta agagagtgaa 2040
catatccatc atccctcaaa gtgtcacaat gctcctcctg atgactcctc cccagaaaac 2100
caccaatcgg ctttcatttt gcattttgta gttttatgtg aatggaatca tatagtatgt 2160
cttttttttt tgtctggctt ctttcacttt gcataattat tttgagattc atatgtctcc 2220
atcttgatgc tcgtatgaat tcattctttt aaatgttgaa tattcccttg tatggatata 2280
ccacaattca tttacccatt tacttgttga tgacatttgg gttgttttag ttttgggata 2340
ttacaaataa agctgctgtg aacatttgtg tacaagaaaa aaaaaaaaaa aaa 2393

<210> SEQ ID NO 47
<211> LENGTH: 1945
<212> TYPE: DNA
<213> ORGANISM: Homo sapiens

<400> SEQUENCE: 47
ataaatttga gtcagcacca gcgacagctc tgcagtcctc ctatgtggta ctgatcaggt 60
ggttgcagag cttcagctca cagcaacaca atgcagctga gcaggcaagc acagcccaca 120
gccagaaaca gttccgactc tacagaacaa gacgaccttt aagtttccca gagaaaatga 180
gatgctgatg ttgaagacga caccacggct ttgatggaat atcagatatt gaaaatgtct 240
ctctgcctgt tcatccttct gtttctcaca cctggtattt tatgcatttg tcctctccaa 300
tgtatatgca cagagaggca caggcatgtg gactgttcag gcagaaactt gtctacatta 360
ccatctggac tgcaagagaa tattatacat ttaaacctgt cttataacca ctttactgat 420
ctgcataacc agttaaccca atataccaat ctgaggaccc tggacatttc aaacaacagg 480
cttgaaagcc tgcctgctca cttacctcgg tctctgtgga acatgtctgc tgctaacaac 540
aacattaaac ttcttgacaa atctgatact gcttatcagt ggaatcttaa atatctggat 600
gtttctaaga acatgctgga aaaggttgtc ctcattaaaa atacactaag aagtctcgag 660
gttctcaacc tcagtagtaa caaactttgg acagttccaa ccaacatgcc ctccaaacta 720
catatcgtgg acctgtctaa taattctttg acacaaattc ttccaggtac attaataaac 780
ctgacaaatc tcacacatct ttacctgcac aacaataagt tcacattcat tccagaccaa 840
tcttttgacc aactctttca gttgcaagag ataacccttt acaataacag gtggtcatgt 900
gaccacaaac aaaacattac ttacttactg aagtggatga tggaaacaaa agcccatgtg 960
atagggactc catgttctac ccaaatatca tctttaaagg aacataacat gtatcccaca 1020
ccttctggat ttacctcaag cttattcact gtaagtggga tgcagacagt ggacaccatt 1080
aactctctga gtgtggtaac tcaacccaaa gtgaccaaaa tacccaaaca atatcgaaca 1140
aaggaaacaa cgtttggtgc cactctaagc aaagacacca cctttactag cactgataag 1200
gcttttgtgc cctatccaga agatacatcc acagagacta tcaattcaca tgaagcagca 1260
gctgcaactc taactattca tctccaagat ggaatggtca caaacacaag cctcactagc 1320
tcaacaaaat catccccaac acccatgacc ctaagtatca ctagtggcat gccaaataat 1380
ttctctgaaa tgcctcaaca aagcacaacc cttaacttat ggagggaaga gacaaccaca 1440
aatgtaaaga ctccattacc ttctgtggca aatgcttgga aagtaaatgc ttcatttctc 1500
ttattgctca atgttgtggt catgctggct gtctgagggt ctgcattttc tgaaactaat 1560
gaaagcactc ctccctgatg tacagttggg aaaatatgtc catatctaac cagtgattcg 1620
agctatattt aagtattcaa gaaagccagt cttaacattt ctaactctga tgtaaatgaa 1680
gtaacttgtc ttaaataaaa gaaatgcaca atgtcttggt acttgctgct attttactgt 1740
cttaattaag taaactaatg agtttctttt ataaaaaaaa tgaaatgttt taaggcttca 1800
atttattgca caaaatataa agcatctaaa ctttaatatg tattttatgt atgtttacac 1860
tgtcaaacat ctggaaaata aaaggtctat gctcaaaaaa aaaaaaaaaa aaaaaaaaaa 1920
aaaaaaaaaa aaaaaaaaaa aaaaa 1945

<210> SEQ ID NO 48
<211> LENGTH: 2091
<212> TYPE: DNA
<213> ORGANISM: Homo sapiens

<400> SEQUENCE: 48
aagtgctggg atgacaggtg tgagccaccg cccccggccc ctcgcccgcc ttttgaagga 60
gcctttcgtc ctcaagggcg aggccactcc cccccgcga gttccatgcc ccctagaggg 120
tcatcgttcc cgacggggag gtggcgccct cccccgggcc ccgggccccg accgcccgtg 180
ctgcctcctt ccgggccctc ctccgcgatg acggcgccgc cagcaggcca ggcggactgg 240
gcggggctcc gagcggggac tgggacccag accgactagg ggactgggag cgggcggcgc 300
ggccatggcg ggctgctgcg ccgcgctggc ggccttcctg ttcgagtacg acacgccgcg 360
catcgtgctc atccgcagcc gcaaagtggg gctcatgaac cgcgccgtgc aactgctcat 420
cctggcctac gtcatcgggt gctaccatcc ccatttggca gaagtggaaa tggagtcccc 480
tagaaggtgg gtgtttgtgt gggaaaaggg ctaccaggaa actgactccg tggtcagctc 540
cgttacgacc aaggtcaagg gcgtggctgt gaccaacact tctaaacttg gattccggat 600
ctgggatgtg gcggattatg tgataccagc tcaggaggaa aactccctct tcgtcatgac 660
caacgtgatc ctcaccatga accagacaca gggcctgtgc cccgagattc cagatgcgac 720
cactgtgtgt aaatcagatg ccagctgtac tgccggctct gccggcaccc acagcaacgg 780
agtctcaaca ggcaggtgcg tagctttcaa cgggtctgtc aagacgtgtg aggtggcggc 840
ctggtgcccg gtggaggatg acacacacgt gccacaacct gctttttttaa aggctgcaga 900 aaacttcact cttttggtta agaacaacat ctggtatccc aaatttaatt tcagcaagag 960
gaatatcctt cccaacatca ccactactta cctcaagtcg tgcatttatg atgctaaaac 1020
agatcccttc tgccccatat tccgtcttgg caaaatagtg gagaacgcag gacacagttt 1080
ccaggacatg gccgtggagg gaggcatcat gggcatccag gtcaactggg actgcaacct 1140
ggacagagcc gcctccctct gcttgcccag gtactccttc cgccgcctcg atacacggga 1200
cgttgagcac aacgtatctc ctggctacaa tttcaggttt gccaagtact acagagacct 1260
ggctggcaac gagcagcgca cgctcatcaa ggcctatggc atccgcttcg acatcattgt 1320
gtttgggaag gcagggaaat ttgacatcat ccccactatg atcaacatcg gctctggcct 1380
ggcactgcta ggcatggcga ccgtgctgtg tgacatcata gtcctctact gcatgaagaa 1440
aagactctac tatcgggaga agaaatataa atatgtggaa gattacgagc agggtcttgc 1500
tagtgagctg gaccagtgag gcctacccca cacctgggct ctccacagcc ccatcaaaga 1560
acagagagga ggaggaggga gaaatggcca ccacatcacc ccagagaaat ttctggaatc 1620
tgattgagtc tccactccac aagcactcag ggttccccag cagctcctgt gtgttgtgtg 1680
caggatctgt ttgcccactc ggcccaggag gtcagcagtc tgttcttggc tgggtcaact 1740
ctgcttttcc cgcaacctgg ggttgtcggg ggagcgctgg cccgacgcag tggcactgct 1800
gtggctttca gggctggagc tggctttgct cagaagcctc ctgtctccag ctctctccag 1860
gacaggccca gtcctctgag gcacggcggc tctgttcaag cactttatgc ggcaggggag 1920
gccgcctggc tgcagtcact agacttgtag caggcctggg ctgcaggctt ccccccgacc 1980
attccctgca gccatgcggc agagctggca tttctcctca gagaagcgct gtgctaaggt 2040
gatcgaggac cagacattaa agcgtgattt tcttaaaaaa aaaaaaaaaa a 2091

<210> SEQ ID NO 49
<211> LENGTH: 4185
<212> TYPE: DNA
<213> ORGANISM: Homo sapiens

<400> SEQUENCE: 49
cggccgcgag cgcagtggtg tggagcgcgc cgggtcccgg agccggctgt ctgagggatg 60
gacgagacga gcccactagt gtcccccgag cgggcccaac ccccggacta caccttcccg 120
tcgggctcgg gcgctcactt tccgcaggtg cccgggggcg cggtccgagt ggcggcggcg 180
gccggctcgg gcccctctcc gccaggctcg ccgggccacg accgcgagcg gcagccactg 240
ttggatcggg cccggggcgc ggcggcccag ggccagaccc aaaccgtggc ggcgcaggcc 300
caggctctgg ccgctcaggc cgcggcggca gcccacgccg ctcaggccca ccgcgagcgg 360
aacgagttcc cggaggatcc tgagttcgag gcggtggtgc ggcaggccga gctggccatc 420
gagcgctgca tctttcccga gcgcatctac cagggctcca gcggaagcta cttcgtcaag 480
gaccctcagg ggaggatcat tgctgtcttc aaacccaaga atgaagagcc ctatgggcat 540
cttaatccta agtggaccaa gtggctgcag aagctgtgct gtccttgctg ctttggccgt 600
gactgccttg tccttaacca gggctatctc tcagaagcag gggccagcct ggtggaccaa 660
aaactggaac tcaacattgt tccccgtaca aaggtagtat acctggccag tgagaccttc 720
aactatagtg ccattgaccg agtgaagtcc aggggcaagc ggcttgcact agagaaagtg 780
ccaaaagttg gacagcggtt taaccgcatc gggctaccac caaaggttgg ttcattccag 840
ctctttgttg aaggctacaa agatgcagac tattggctgc ggcgttttga agcagaacct 900

-continued

```
cttcctgaga acactaaccg gcaactactg ctccagtttg agcggttggt ggtgctggat    960
tacatcatcc gcaacactga tcgaggcaat gacaactggc tgattaaata tgactgtcca   1020
atggatagtt ctagctctcg ggacacagac tgggtggtgg tgaaggagcc tgttatcaag   1080
gtggctgcca tagacaatgg gctggccttc ccactgaagc atcctgactc ctggagggca   1140
tatccttttt actgggcctg gttgccccag gcgaaagtcc cattttctca ggagatcaaa   1200
gatctgatcc ttccaaagat atcggaccct aacttcgtca aggacttgga agaggaccta   1260
tatgaactct tcaagaaaga tcctggtttc gacaggggcc agttccataa gcagattgct   1320
gtcatgcggg gccagatctt aaatctgacc caggccttga aagacaacaa gagtcccctg   1380
cacctcgtcc agatgccacc tgtgattgtc gagacggccc gttcccacca gcggtcttct   1440
agcgagtcct acacacagag ctttcagagc cggaagccct tcttttcatg gtggtagctc   1500
cagaggcagg cagaggaaat attgtcagag actggtggga ggaagcctgg ggagtggggt   1560
gcaggaaaag ccagagaagc cggtggagag cagcaccttt aagagccctc tctctctgct   1620
tgccaccctg ctcagagctt tccacccaca gggagaagca caatcaggaa cagtgagtgc   1680
tcctcgccct tctgatgtgg gggaggctgg agctccatgc acgtagtcca gatgcctggg   1740
aaggaacatc tcccttccag catctgctgg tagcaggctg ggacagtccc ttccttccct   1800
gaaaccctgc tctattgcaa ttccctatta tattctgcat cagaaaaaca aacaaaacaa   1860
aaacaacttt aaatgcttgt agcagaaccc cgggtcatct catgtcagaa acctttaatc   1920
caggcctaaa tttgcataga cctgacattc agctgccttg cagttgcttc ctcccatgag   1980
ccaaggtggt gtcagagggc aactggatga ctcgcagtac cacagcactg ggacagacag   2040
aagccacacc tttcttttgg gtttttgcca agcctcctcc atctcccatc agtgctgtgg   2100
gctggctgca agcctcgaaa cagttctcct ggaagggagg tttttgcttt acccccgcca   2160
gcacttccgc acacaatcat agagaacctc tctgctctct gctggcctac agcttgtctg   2220
tttctcaagc agaggcagga agagctagtc ttagcattta tattttaata ggaagttgac   2280
tcccagcatg taaaagtgat ccacgcagcc ggagtgtatg ccgggagcta agtggtctat   2340
gggtgaacat atcccacctt gcttcctgag tccttggtcc caatcttctc atttgttcct   2400
ctcgttttaa attttttccc cccaactctt ttgatgtaag agttcagttt gtcttcggga   2460
gtgggtctct gcaagggctc tgggatgagt cttggcttcc aagaggacag gctattaggt   2520
tcttggactt ttttctgtgc taccgctgct gcttggtgga agtaacagga cgtggattct   2580
gcctcataag tggcagtttc ccttttctct ctgacttgtc ctaggccgat ttctctatgg   2640
cttccctgag aaaggtgagg cccaaaggag agaggccttc aaactgtccc aggtcctgcg   2700
cagctcagtg cgtatcttct tgcttccatg tgtcttttcc cctgctgcct cactccccac   2760
ccccacttgc caggtgtttg agccatttct acaccaaagc aaagtacggc ctcaggaggg   2820
agtaaaaagg gtgccatctg tgtctggagg ggcagctgtg ttcatgccct gtgctactgg   2880
acatttcaca attctggcac cttgcgattg gtcagtcaac ctcagaaagt aactatcttg   2940
aaggtttgaa aaacaaccaa agaaagggag tgaggactat ggctgcatgt cctctgcttg   3000
cccggctgca gagcagagat gtgcagccct ctggtcagct ggtccaggct ggtccccgcc   3060
ggtccccttc cagtccagcc accaagagtc cacttgtccc gggcttccac ctggctgaca   3120
ggaagaattt ctgagagctg gatgtgcatg ccctgtggac gaaggtacag ctcgcctgcc   3180
tgccccaatc ccagccccga caatcacatg cagctgactc ggacactggc cttgggaaca   3240
```

-continued atgttcgaga gaacacttgc cccttgactg taggagccag aaggggaccc aggtgtgcat 3300
agctctctgt agacattttt acccaaacct gttggtaaag tgcccatctg gtgctcaaga 3360
gagcctgggg gtctaacagg gagcccggct gcctcacctg gccacagcct ccacaccaga 3420
tctccacatt gtcttgatcc agaccagctc tgtgatcaga aggaaattgg gtccagtgta 3480
ggagagagct ggtcctgggc ctggcaggca agagtgtggg catcctttcc tggcctttct 3540
ccactctccc tcaagcctgt gctcaggttg ccttgaatgt ggactctgga agagccaggg 3600
gcccagaatg ccgggggagg cttctgagtg gcactcatgg aacaccgtcc ctctgccagc 3660
cataggccct gcctccagtg tcagggaatg gaggctgggc tgcgagagtg ttgctgcccc 3720
ctgtgtcatt cttctaatcc aatgtagaaa ttgtacgtaa tgtatttaaa tcaacgcaaa 3780
tgtatgaata acaaatacag ttctgacctt ttttgtccag tttctttggg ggaaggaaga 3840
caaagaaggt aggaacggaa ttttgagggc aaagaaacct gtgtttccat ggaattgctg 3900
agacgtggct cctggggcta tttctcccta ataaaggatg atccaggtcc tcatttccaa 3960
agtcccaatg ctctgaaaac caaaagtatt ttcataaccc atttgaaacc aaacctgacc 4020
tgaacttaca ctgataggaa gctatgggta attatgatgt gttcctttta gtgtgattct 4080
ttgttgcaga aatgtcaata tattttatga catggttccc tactagggat tatacagtat 4140
ttgctgacta cttcctaaga gccaaaaata aaaaatctga attcc 4185

<210> SEQ ID NO 50
<211> LENGTH: 1455
<212> TYPE: DNA
<213> ORGANISM: Homo sapiens

<400> SEQUENCE: 50
gccgagccag ccccttcacc accagccggc cgcgccccgg gaagggaagt ttgtggcgga 60
ggaggttcgt acgggaggag ggggaggcgc ccacgcatct ggggctgact cgctctttcg 120
caaaacgtct gggaggagtc cctggggcca caaaactgcc tccttcctga ggccagaagg 180
agagaagacg tgcagggacc ccgcgcacag gagctgccct cgcgacatgg gtcacccgcc 240
gctgctgccg ctgctgctgc tgctccacac ctgcgtccca gcctcttggg gcctgcggtg 300
catgcagtgt aagaccaacg gggattgccg tgtggaagag tgcgccctgg gacaggacct 360
ctgcaggacc acgatcgtgc gcttgtggga agaaggagaa gagctggagc tggtggagaa 420
aagctgtacc cactcagaga agaccaacag gaccctgagc tatcggactg gcttgaagat 480
caccagcctt accgaggttg tgtgtgggtt agacttgtgc aaccagggca actctggccg 540
ggctgtcacc tattcccgaa gccgttacct cgaatgcatt tcctgtggct catcagacat 600
gagctgtgag aggggccggc accagagcct gcagtgccgc agccctgaag aacagtgcct 660
ggatgtggtg acccactgga tccaggaagg tgaagaaggg cgtccaaagg atgaccgcca 720
cctccgtggc tgtggctacc ttcccggctg cccgggctcc aatggtttcc acaacaacga 780
caccttccac ttcctgaaat gctgcaacac caccaaatgc aacgagggcc caatcctgga 840
gcttgaaaat ctgccgcaga atggccgcca gtgttacagc tgcaagggga acagcaccca 900
tggatgctcc tctgaagaga ctttcctcat tgactgccga ggccccatga atcaatgtct 960
ggtagccacc ggcactcacg aacgctcact ctggggaagc tggttgccat gtaaaagtac 1020
tactgccctg agaccaccat gctgtgagga agcccaagct actcatgtat aaatgccatg 1080
tggagataga gccccagatg tttcagccat ctcagcccag gcaccagaca agtgggtgaa 1140
gaagccacct tggacatgta gccccagcag atgtgatata gagaagaaac aggaaacttg 1200
gctatattag tttcctaggg ctgcctgtga taaattatta caaactttat aaactaacac 1260
attgtgtgcc tatatcaaaa catcatggaa ggacaggcac agtggctcat gcctgtagtc 1320
ctagcacttt gggagggtga gaaaggaaga tctcttgagc tcaggagttc aagatcagcc 1380
tgggcaacac agtgagacct catctccact aaaaataaaa aaaaattggc tggaaaaaaa 1440
aaaaaaaaaa aaaaa 1455

<210> SEQ ID NO 51
<211> LENGTH: 1828
<212> TYPE: DNA
<213> ORGANISM: Homo sapiens

<400> SEQUENCE: 51
cagttacagg gagcaccacc agggaacatc tcggggagcc tggttggaag ctgcaggctt 60
agtctgtcgg ctgcgggtct ctgactgccc tgtggggagg gtcttgcctt aacatccctt 120
gcatttggct gcaaagaaat ctgcttggaa gaaggggtta cgctgtttgg ccgggcagaa 180
actccgctga gcagaacttg ccgccagaat gctcctcctg ttgctgagta tcatcgtcct 240
ccacgtcgcg gtgctggtgc tgctgttcgt ctccacgatc gtcagccaat ggatcgtggg 300
caatggacac gcaactgatc tctggcagaa ctgtagcacc tcttcctcag gaaatgtcca 360
ccactgtttc tcatcatcac caaacgaatg gctgcagtct gtccaggcca ccatgatcct 420
gtcgatcatc ttcagcattc tgtctctgtt cctgttcttc tgccaactct tcaccctcac 480 caagggggc aggttttaca tcactggaat cttccaaatt cttgctggtc tgtgcgtgat 540
gagtgctgcg gccatctaca cggtgaggca cccggagtgg catctcaact cggattactc 600
ctacggtttc gcctacatcc tggcctgggt ggccttcccc ctggcccttc tcagcggtgt 660
catctatgtg atcttgcgga aacgcgaatg aggcgcccag acggtctgtc tgaggctctg 720
agcgtacata gggaaggag gaagggaaaa cagaaagcag acaaagaaaa aagagctagc 780
ccaaaatccc aaactcaaac caaaccaaac agaaagcagt ggaggtgggg gttgctgttg 840
attgaagatg tatataatat ctccggttta taaaacctat ttataacact ttttacatat 900
atgtacatag tattgtttgc tttttatgtt gaccatcagc ctcgtgttga gccttaaaga 960
agtagctaag gaactttaca tcctaacagt ataatccagc tcagtatttt tgttttgttt 1020
tttgtttgtt tgttttgttt tacccagaaa taagataact ccatctcgcc ccttcccttt 1080
catctgaaag aagatacctc cctcccagtc cacctcattt agaaaaccaa agtgtgggta 1140
gaaaccccaa atgtccaaaa gcccttttct ggtgggtgac ccagtgcatc caacagaaac 1200
agccgctgcc cgaacctctg tgtgaagctt tacgcgcaca cggacaaaat gcccaaactg 1260
gagcccttgc aaaaacacgg cttgtggcat tggcatactt gcccttacag gtggagtatc 1320
ttcgtcacac atctaaatga gaaatcagtg acaacaagtc tttgaaatgg tgctatggat 1380
ttaccattcc ttattatcac taatcatcta aacaactcac tggaaatcca attaacaatt 1440
ttacaacata agatagaatg gagacctgaa taattctgtg taatataaat ggtttataac 1500
tgcttttgta cctagctagg ctgctattat tactataatg agtaaatcat aaagccttca 1560
tcactcccac atttttctta cggtcggagc atcagaacaa gcgtctagac tccttgggac 1620
cgtgagttcc tagagcttgg ctgggtctag gctgttctgt gcctccaagg actgtctggc 1680
aatgacttgt attggccacc aactgtagat gtatatatgg tgcccttctg atgctaagac 1740
tccagacctt ttgtttttgc tttgcatttt ctgattttat accaactgtg tggactaaga 1800

```
tgcattaaaa taaacatcag agtaactc                                      1828


<210> SEQ ID NO 52
<211> LENGTH: 3324
<212> TYPE: DNA
<213> ORGANISM: Homo sapiens

<400> SEQUENCE: 52

gacctcgtga aataaaagtg cagaaaacaa acccaggcga tcacagcagc agccgccgcg      60

gcagcagcac caacagcagg aggagcagga ggagccggag gaggaggagg aggaggaggc     120

aaagttagag ttggggctgg cgctccggag ttgctgggct cagcgcagct cccattcatt     180

aaggaaccag ctgcggagga aggtggccga gcgcccgcgc tgcccactcg ctcgctcgcg     240

cactcagacg cgcgccacaa cagcgcgccc caagctgcgc agctctgcaa aagtttctgc     300

tcgggatctg gctctcttcc ccttggactt tagaacgatt tagggttgac agaggaaagc     360

agaggcgcgc aggaggagca gaaaacacca ccttctgcag ttggaggcag gcagccccgg     420

ctgcactcta gccgccgcgc ccggagccgg ggccgacccg ccactatccg cagcagcctc     480

ggccaggagg cgacccgggc gcctgggtgt gtggctgctg ttgcgggacg tcttcgcggg     540

gcgggaggct cgcgccgcag ccagcgccat gcaaaactac aagtacgaca aagcgatcgt     600

cccggagagc aagaacggcg gcagcccggc gctcaacaac aacccgagga ggagcggcag     660

caagcgggtg ctgctcatct gcctcgacct cttctgcctc ttcatggcgg gcctcccctt     720

cctcatcatc gagacaagca ccatcaagcc ttaccaccga gggtttttact gcaatgatga     780

gagcatcaag tacccactga aactggtga gacaataaat gacgctgtgc tctgtgccgt      840

ggggatcgtc attgccatcc tcgcgatcat cacgggggaa ttctaccgga tctattacct     900

gaagaagtcg cggtcgacga ttcagaaccc ctacgtggca gcactctata agcaagtggg     960

ctgcttcctc tttggctgtg ccatcagcca gtctttcaca gacattgcca aagtgtccat    1020

agggcgcctg cgtcctcact tcttgagtgt ctgcaaccct gatttcagcc agatcaactg    1080

ctctgaaggc tacattcaga actacagatg cagaggtgat gacagcaaag tccaggaagc    1140

caggaagtcc ttcttctctg gccatgcctc cttctccatg tacactatgc tgtatttggt    1200

gctataccctg caggcccgct tcacttggcg aggagcccgc ctgctccggc ccctcctgca   1260

gttcaccttg atcatgatgg ccttctacac gggactgtct cgcgtatcag accacaagca    1320

ccatcccagt gatgttctgg caggatttgc tcaaggagcc ctggtggcct gctgcatagt    1380

tttcttcgtg tctgacctct tcaagactaa gacgacgctc tccctgcctg cccctgctat    1440

ccggaaggaa atcctttcac ctgtggacat tattgacagg aacaatcacc acaacatgat    1500

gtaggtgcca cccacctcct gagctgtttt tgtaaaatga ctgctgacag caagttcttg    1560

ctgctctcca atctcatcag acagtagaat gtagggaaaa acttttgccc gactgatttt    1620

taaaaaggaa aaaaaaaatg ttttactatg tggccttcca aaataggtag tgtttgccta    1680

tgtggaaaca acagcaaact aacaccaagt gccagagtcc tggatgtgca attggtttaa    1740

gtgttcatgt tctagtgaac acagcttgtt caggaacaaa cactaaaacg atttgagtag    1800

aggctgctgg tcaccttttg tgacctgagg aatcccaggc ctgtgagaaa agcaaaaatt    1860

cacattgcag cacatgatgc cagaaatagc actgaatcaa gaaaatagcc attgcggagc    1920

tgccctcttg agtctttctg tccatcccat tctattctgt actgtgactt tagttcagga    1980

agttttgttt tgtgttttaa ataaaaggaa agagcaagtt tgctcagtca agtgatcaga    2040

tcccgaatct agattcccag ttctaaggcc ttatcacctc cctgcccat aggccaacaa     2100
```

ccatagttcc tcacattagt gattagcaga ctctttgtgg acgagtgaat ttcacaaaca 2160
gcacaatttc agaagaaatc gagggcacag gccctcactt ttcttctttt gacgcatcat 2220
cctgtgatgt tgaaatgtca attgcaggat gctgatgttg tgcacgtcaa tcaccgggca 2280
cttgcatact cttagaaaca gttcgacttc ggttactgcc ttctcccttg aaatccttgc 2340
tgcgtgccca ccaggatttc ctgtgagggc ccaggaatga gcaaggcatg gtctgccacc 2400
agctgacgga aagcagcctt ctgtacaaca gatgggaggg tgaagggggc agaatgaaaa 2460
tcgaaccaac cttttagctg ttgcaaatca gaaggagcca gagaagcagg cagtctcatg 2520
catgagaggt tacccttcag gatgacagag ctgagggtct ttgtaggagt tgctcttgct 2580
gtgtaaagca ctattgtctt ggggttgagc cctagggcag ttcttggtag gttctgctgg 2640
gcagaacata tgggttaaat ctcggtagag agtttccctc atcctctatc cgtaagtgtc 2700
cttccatgca aggtcccact ctaggtgata gacagggacc ccttctactg aacctttgag 2760
gaaaggagga aggaagaaat gcgtttagat cttggatgca gacctttcaa agggttaaat 2820
gtaaccatat ggatcaacca catgcacatc cttactacag aatccgtcct ttcatttcaa 2880
cttatagcaa gctatgattt ttatatataa atattatata aataatgtat aaaacattaa 2940
aagttaacta tgtaagatat tatttctgaa acaatttagc tatatccact atgattataa 3000
actgtgtctc gacctgtgtt atttacatta gctgcttaaa aaagcattga gttaattttt 3060
ttaaatatca actaaaatat catagttctg tggtagacat tgttttataa tgaaataact 3120
gcaactagag aaaactgtat aaaaacatta aattgtcagt atttttgtaa ggttccattt 3180
tgtaaagaga ataatattca aagacttttg tagcatacaa agtgaaaact tgtatctgcg 3240
aaactatact tgtattaaat gtgcttttta aataaaagct cgtaacacaa ctaattaagg 3300
acttgcaaaa aaaaaaaaaa aaaa 3324

<210> SEQ ID NO 53
<211> LENGTH: 6107
<212> TYPE: DNA
<213> ORGANISM: Homo sapiens

<400> SEQUENCE: 53
aaatgacgac aacggtgagg gttctcgggc ggggcctggg acaggcagct ccggggtccg 60
cggtttcaca tcggaaacaa aacagcggct ggtctggaag gaacctgagc tacgagccgc 120
ggcggcagcg gggcggcggg gaagcgtata cctaatctgg gagcctgcaa gtgacaacag 180
cctttgcggt ccttagacag cttggcctgg aggagaacac atgaaagaaa gaacctcaag 240
aggctttgtt ttctgtgaaa cagtatttct atacagttgc tccaatgaca gagttacctg 300
caccgttgtc ctacttccag aatgcacaga tgtctgagga caaccacctg agcaatactg 360
tacgtagcca gaatgacaat agagaacggc aggagcacaa cgacagacgg agccttggcc 420
accctgagcc attatctaat ggacgacccc agggtaactc ccggcaggtg gtggagcaag 480
atgaggaaga agatgaggag ctgacattga aatatggcgc caagcatgtg atcatgctct 540
ttgtccctgt gactctctgc atggtggtgg tcgtggctac cattaagtca gtcagctttt 600
atacccggaa ggatgggcag ctaatctata ccccattcac agaagatacc gagactgtgg 660
gccagagagc cctgcactca attctgaatg ctgccatcat gatcagtgtc attgttgtca 720
tgactatcct cctggtggtt ctgtataaat acaggtgcta taaggtcatc catgcctggc 780
ttattatatc atctctattg ttgctgttct ttttttcatt catttacttg gggaagtgt 840

-continued

```
ttaaaaccta taacgttgct gtggactaca ttactgttgc actcctgatc tggaattttg    900
gtgtggtggg aatgatttcc attcactgga aaggtccact tcgactccag caggcatatc    960
tcattatgat tagtgccctc atggccctgg tgtttatcaa gtacctccct gaatggactg   1020
cgtggctcat cttggctgtg atttcagtat atgatttagt ggctgttttg tgtccgaaag   1080
gtccacttcg tatgctggtt gaaacagctc aggagagaaa tgaaacgctt tttccagctc   1140
tcatttactc ctcaacaatg gtgtggttgg tgaatatggc agaaggagac ccggaagctc   1200
aaaggagagt atccaaaaat tccaagtata atgcagaaag cacagaaagg gagtcacaag   1260
acactgttgc agagaatgat gatggcgggt tcagtgagga atgggaagcc cagagggaca   1320
gtcatctagg gcctcatcgc tctacacctg agtcacgagc tgctgtccag gaactttcca   1380
gcagtatcct cgctggtgaa gacccagagg aaaggggagt aaaacttgga ttgggagatt   1440
tcattttcta cagtgttctg gttggtaaag cctcagcaac agccagtgga gactggaaca   1500
caaccatagc ctgtttcgta gccatattaa ttggtttgtg ccttacatta ttactccttg   1560
ccattttcaa gaaagcattg ccagctcttc caatctccat cacctttggg cttgttttct   1620
actttgccac agattatctt gtacagcctt ttatggacca attagcattc catcaatttt   1680
atatctagca tatttgcggt tagaatccca tggatgtttc ttctttgact ataacaaaat   1740
ctggggagga caaaggtgat ttcctgtgt ccacatctaa caaagtcaag attcccggct    1800
ggacttttgc agcttccttc caagtcttcc tgaccacctt gcactattgg actttggaag   1860
gaggtgccta tagaaaacga ttttgaacat acttcatcgc agtggactgt gtccctcggt   1920
gcagaaacta ccagatttga gggacgaggt caaggagata tgataggccc ggaagttgct   1980
gtgccccatc agcagcttga cgcgtggtca caggacgatt tcactgacac tgcgaactct   2040
caggactacc gttaccaaga ggttaggtga agtggtttaa accaaacgga actcttcatc   2100
ttaaactaca cgttgaaaat caacccaata attctgtatt aactgaattc tgaacttttc   2160
aggaggtact gtgaggaaga gcaggcacca gcagcagaat ggggaatgga gaggtgggca   2220
ggggttccag cttccctttg attttttgct gcagactcat cctttttaaa tgagacttgt   2280
tttcccctct ctttgagtca agtcaaatat gtagattgcc tttggcaatt cttcttctca   2340
agcactgaca ctcattaccg tctgtgattg ccatttcttc ccaaggccag tctgaacctg   2400
aggttgcttt atcctaaaag ttttaacctc aggttccaaa ttcagtaaat tttggaaaca   2460
gtacagctat ttctcatcaa ttctctatca tgttgaagtc aaatttggat tttccaccaa   2520
attctgaatt tgtagacata cttgtacgct cacttgcccc agatgcctcc tctgtcctca   2580
ttcttctctc ccacacaagc agtctttttc tacagccagt aaggcagctc tgtcgtggta   2640
gcagatggtc ccattattct agggtcttac tctttgtatg atgaaaagaa tgtgttatga   2700
atcggtgctg tcagccctgc tgtcagacct tcttccacag caaatgagat gtatgcccaa   2760
agacggtaga attaaagaag agtaaaatgg ctgttgaagc actttctgtc ctggtatttt   2820
gtttttgctt ttgccacaca gtagctcaga atttgaacaa atagccaaaa gctggtggtt   2880
gatgaattat gaactagttg tatcaacaca aagcaagagt tggggaaagc catatttaac   2940
ttggtgagct gtgggagaac ctggtggcag aaggagaacc aactgccaag gggaaagaga   3000
aggggcctcc agcagcgaag gggatacagt gagctaatga tgtcaaggag gagtttcagg   3060
ttattctcgt cagctccaca aatgggtgct ttgtggtctc tgcccgcgtt acctttcctc   3120
tcaatgtacc tttgtgtgaa ctgggcagtg gaggtgcctg ctgcagttac catggagttc   3180
aggctctggg cagctcagtc aggcaaaaca cacaaacagc catcagcctg tgtgggctca   3240
```

gggcacctct ggacaaaggc ttgtggggca taaccttctt taccacagag agcccttagc 3300
tatgctgatc agaccgtaag cgtttatgag aaacttagtt tcctcctgtg gctgaggagg 3360
ggccagcttt ttcttctttt gcctgctgtt ttctctccca atctatgata tgatatgacc 3420
tggtttgggg ctgtctttgg tgtttagaat atttgttttc tgtcccagga tatttcttat 3480
aagaacctaa cttcaagagt agtgtgcgag tactgatctg aatttaaatt aaaattggct 3540
tatattaggc agtcacagac aggaaaaata agagctatgc aaagaaaggg ggatttaaag 3600
tagtaggttc tatcatctca attcattttt ttccatgaaa tcccttcttc caagattcat 3660
tccctctctc agacatgtgc tagcatgggt attatcattg agaaagcaca gctacagcaa 3720
agccacctga atagcaattt gtgattggaa gcattcttga gggatcccta atctagagta 3780
atttatttgt gtaaggatcc caaatgtgtt gcacctttca tgatacattt cttctctgaa 3840
gagggtacgt ggggtgtgtg tatttaaatc catcctatgt attactgatt gtcctgtgta 3900
gaaagatggc aattattctg tctctttctc caagtttgag ccacatctca gccacattgt 3960
tagacagtgt acagagaacc tatctttcct tttttttttt ttaaaggaca ggattttgct 4020
gtgttgccca ggctagactt gaactcctgg gctcaagtaa tccacctcag cctgagtagc 4080
tgagactaca gcccatctta tttctttaaa tcattcatct caggcagaga acttttccct 4140
caaacattct ttttagaatt agttcagtca ttcctaaaac atccaaatgc tagtcttcca 4200
ccatgaaaaa tagattgtca ctggaaagaa cagtagcaat ttccataagg atgtgccttc 4260
actcacacgg gacaggcggt ggttatagag tcgggcaaaa ccagcagtag agtatgacca 4320
gccaagccaa tctgcttaat aaaaagatgg aagacagtaa ggaaggaaag tagccactaa 4380
gagtctgagt ctgactgggc tacagaataa agggtattta tggacagaat gtcattacat 4440
gcctatggga ataccaatca tatttggaag atttgcagat ttttttttcag agaggaaaga 4500
ctcaccttcc tgtttttggt tctcagtagg ttcgtgtgtg ttcctagaat cacagctctg 4560
actccaaatg actcaatttc tcaattagaa aaagtagaag ctttctaagc aacttggaag 4620
aaaacagtca taagtaagca atttgttgat tttactacag aagcaacaac tgaagaggca 4680
gtgtttttac tttcagactc cgggattccc attctgtagt ctctctgctt ttaaaaaccc 4740
tccttttgca atagatgccc aaacagatga tgtttattac ttgttattta cgtggcctca 4800
gacagtgtat gtattctcga tataacttgt agagtgtgaa atataagttt aactaccaaa 4860
taaggtctcc cagggttaga tgactgcggg aagcctttga tcccaacccc caaggctttg 4920
tatatttgat catttgtgat ctaaccctgg aagaaaaaga gctcagaaac cactatgaaa 4980
aaatttgttc agtgttttct gtgttcccgt aggttctgga gtctgaggat gcaaagatga 5040
ataagataaa ttctcagaat gtagttataa tctcttgttt tctggtatat gccatctttc 5100
tttaacttct ctaaaatatt gggtatttgt caaataacca cttttaacag ttaccattac 5160
tgagggctta tacattggtg ttataaaagt gacttgattc agaaatcaat ccattcagta 5220
aagtactcct tctctaaatt tgctgttatg tctataagga acagtttgac ctgcccttct 5280
cctcacctcc tcacctgcct tccaacattg aatttggaag gagacgtgaa aattggacat 5340
ttggttttgc ccttgggctg gaaactatca tataatcata agtttgagcc tagaagtgat 5400
ccttgtgatc ttctcacctc tttaaattcc cacaacacaa gagattaaaa acagaggttt 5460
cagctcttca tagtgcgttg tgaaatggct ggccagagtg taccaacaaa gctgtcatcg 5520
ggctcacagc tcagagacat ctgcatgtga tcatctgcat agtcctctcc tctaacggga 5580

-continued

```
aacacctcag atttgcatat aaaaaagcac cctggtgctg aaatgaaccc ctttcttgaa   5640

catcaaagct gtctcccaca gccttgggca gcagggtgcc tcttagtgga tgtgctgggt   5700

ccaccctgag ccctgacatg tggtggcagc attgccagtt ggtctgtgtg tctgtgtagc   5760

agggacgatt tcccagaaag caattttcct tttgaaatac gtaattgttg agactaggca   5820

gtttcaaagt cagctgcata tagtagcaag tacaggactg tcttgttttt ggtgtccttg   5880

gaggtgctgg ggtgagggtt tcagtgggat catttactct cacatgttgt ctgccttctg   5940

cttctgtgga cactgctttg tacttaattc agacagactg tgaatacacc tttttataa    6000

ataccttca aattcttggt aagatataat tttgatagct gattgcagat tttctgtatt    6060

tgtcagatta ataaagactg catgaatcca aaaaaaaaaa aaaaaaa                 6107
```

<210> SEQ ID NO 54
<211> LENGTH: 2869
<212> TYPE: DNA
<213> ORGANISM: Homo sapiens

<400> SEQUENCE: 54

```
agaattcttt ggcaggggcg accttagaat cctggggagg agcgagaatg gaatcccggg     60

gaggaacagg ggtggaatcc ggggggcggg gtcagaacgc caggaggggg cggggccgga    120

gccagggtcg gcttgactcg gggagcagc gggtggatcc tgtgacgtca gcgggttcga     180

accgccggag ctgagcgaga ggccgggggt gccgagccgg gcggggagag ctgggccggg    240

agagcagaac agggaggcta gagcgcagcg ggaaccggcc cggagccgga gccggagccc    300

cacaggcacc tactaaaccg cccagccgat cggcccccac agagtggccc gcgggcctcc    360

ggccgggccc agtcccctcc cgggccctcc atggcccggg ccgctgccct cctgccgtcg    420

agatcgccgc cgacgccgct gctgtggccg ctgctgctgc tgctgctcct ggaaaccgga    480

gcccaggatg tgcgagttca agtgctaccc gaggtgcgag gccagctcgg gggcaccgtg    540

gagctgccgt gccacctgct gccacctgtt cctggactgt acatctccct ggtgacctgg    600

cagcgcccag atgcacctgc gaaccaccag aatgtggccg ccttccaccc taagatgggt    660

cccagcttcc ccagcccgaa gcctggcagc gagcggctgt ccttcgtctc tgccaagcag    720

agcactgggc aagacacaga ggcagagctc caggacgcca cgctggccct ccacgggctc    780

acggtggagg acgagggcaa ctacacttgc gagtttgcca ccttccccaa ggggtccgtc    840

cgagggatga cctggctcag agtcatagcc aagcccaaga accaagctga ggcccagaag    900

gtcacgttca gccaggaccc tacgacagtg gccctctgca tctccaaaga gggccgccca    960

cctgcccgga tctcctggct ctcatccctg gactgggaag ccaaagagac tcaggtgtca   1020

gggaccctgg ccggaactgt cactgtcacc agccgcttca ccttggtgcc ctcgggccga   1080

gcagatggtg tcacggtcac ctgcaaagtg gagcatgaga gcttcgagga accagccctg   1140

atacctgtga ccctctctgt acgctaccct cctgaagtgt ccatctccgg ctatgatgac   1200

aactggtacc tcggccgtac tgatgccacc ctgagctgtg acgtccgcag caacccagag   1260

cccacgggct atgactggag cacgacctca ggcaccttcc cgacctccgc agtggcccag   1320

ggctcccagc tggtcatcca cgcagtggac agtctgttca ataccacctt cgtctgcaca   1380

gtcaccaatg ccgtgggcat gggccgcgct gagcaggtca tctttgtccg agagaccccc   1440

aacacagcag gcgcaggggc cacaggcggc atcatcgggg gcatcatcgc cgccatcatt   1500

gctactgctg tggctgccac gggcatcctt atctgccggc agcagcggaa ggagcagacg   1560

ctgcaggggg cagaggagga cgaagacctg gagggacctc cctcctacaa gccaccgacc   1620
```

```
ccaaaagcga agctggaggc acaggagatg ccctcccagc tcttcactct gggggcctcg   1680
gagcacagcc cactcaagac cccctacttt gatgctggcg cctcatgcac tgagcaggaa   1740
atgcctcgat accatgagct gcccaccttg gaagaacggt caggaccctt gcaccctgga   1800
gccacaagcc tggggtcccc catcccggtg cctccagggc cacctgctgt ggaagacgtt   1860
tccctggatc tagaggatga ggagggggag gaggaggaag agtatctgga caagatcaac   1920
cccatctatg atgctctgtc ctatagcagc ccctctgatt cctaccaggg caaaggcttt   1980
gtcatgtccc gggccatgta tgtgtgagct gccatgcgcc tggcgtctca catctcacct   2040
gttgatccct tagctttctt gccaaggatc tagtgccccc tgacctctgg ccaggccact   2100
gtcagttaac acatatgcat tccatttgtg atgtctacct tggtggctcc actatgaccc   2160
ctaacccatg agcccagaga aattcaccgt gataatggaa tcctggcaac cttatctcat   2220
gaggcaggag gtggggaagg tgcttctgca caacctctga tcccaaggac tcctctccca   2280
gactgtgacc ttagaccata cctctcaccc cccaatgcct cgactccccc aaaatcacaa   2340
agaagaccct agacctataa tttgtcttca ggtagtaaat tcccaatagg tctgctggag   2400
tgggcgctga gggctccctg ctgctcagac ctgagccctc caggcagcag ggtcccactt   2460
acccctccc cacccctgttc cccaaaggtg ggaaagaggg gattccccag cccaaggcag   2520
ggttttccca gcaccctcct gtaagcagaa gtctcagggt ccagaccctt ccctgagccc   2580
ccaccccac cccaattcct gcctaccaag caagcagccc cagcctaggg tcagacaggg   2640
tgagcctcat acagactgtg ccttgatggc cccagccttg ggagaagaat ttactgttaa   2700
cctggaagac tactgaatca ttttaccctt gcccagtgga ataggaccta aacatccccc   2760
ttccggggaa agtgggtcat ctgaattggg ggtagcaatt gatactgttt tgtaaactac   2820
atttcctaca aaatatgaat ttatactttg accaggaaaa aaaaaaaaa               2869
```

<210> SEQ ID NO 55
<211> LENGTH: 1211
<212> TYPE: DNA
<213> ORGANISM: Homo sapiens

<400> SEQUENCE: 55

```
ctgggctccg tgccgctctg tttgccaacc gtccagtccc gcctaccagt gccgggcgct     60
ccccacccct cccccggctc ccccggtgtc cgccatggcc aaagcctacg accacctctt    120
caagttgctg ctgatcgggg actcgggggt gggcaagact tgtctgatca ttcgctttgc    180
agaggacaac ttcaacaaca cttacatctc caccatcgga attgatttca agatccgcac    240
tgtggatata gaggggaaga agatcaaact acaagtctgg gacacggctg gccaagagcg    300
gttcaagaca ataactactg cctactaccg tggagccatg ggcattatcc tagtatacga    360
catcacggat gagaaatctt tcgagaatat tcagaactgg atgaaaagca tcaaggagaa    420
tgcctcggct ggggtggagc gcctcttgct ggggaacaaa tgtgacatgg aggccaagag    480
gaaggtgcag aaggagcagg ccgataagtt ggctcgagag catggaatcc gatttttcga    540
aactagtgct aaatccagta tgaatgtgga tgaggctttt agttccctgg cccgggacat    600
cttgctcaag tcaggaggcc ggagatcagg aaacggcaac aagcctccca gtactgacct    660
gaaaacttgt gacaagaaga acaccaacaa gtgctccctg ggctgaggac cctttcttgc    720
ctccccaccc cggaagctga acctgaggga gacaacggca gagggagtga gcaggggaga    780
aatagcagag gggcttggag ggtcacatag gtagatggta aagagaatga ggagaaaaag    840
```

```
gagaaaaggg aaaagcagaa aggaaaaaaa ggaagagaga ggaagggaga agggagagga    900

atgaattgag gaagtgaaag aaggcaagga ggtaggaaga gagggaggag gaaaggaagg    960

agagatgcct caggcttcag accttacctg ggttttcagg gcaaacataa atgtaaatac   1020

actgatttat tctgttacta gatcaggttt tagggtcctg caaaaggcta gctcggcact   1080

acactaggga atttgctcct gttctgtcac ttgtcatggt ctttcttggt attaaaggcc   1140

accatttgca caaaaaaaaa aaaaaaaaaa aaaaaaaaaa aaaaaaaaaa aaaaaaaaaa   1200

aaaaaaaaaa a                                                        1211
```

<210> SEQ ID NO 56
<211> LENGTH: 4877
<212> TYPE: DNA
<213> ORGANISM: Homo sapiens

<400> SEQUENCE: 56

```
ggcggattgg cgggcacgcc ccctcgcccg cggccccctc cccgcctctc tccaccgcct     60

cctctggctc cccggtcaga gggccggagc gagaagatgg cgaagacgta cgattatctc    120

ttcaagctcc tgctgatcgg cgactcgggg gtaggcaaga cctgcctcct gttccgcttc    180

tcagaggacg ccttcaacac caccttcatc tccaccatcg gaattgattt taaaattaga    240

acgatagaac tagatggaaa gaaaattaag cttcagatat gggacacagc gggtcaggaa    300

agattccgaa caatcacgac agcgtactac agaggagcca tgggcattat gctggtctat    360

gacatcacaa atgaaaaatc ctttgacaat attaaaaatt ggatcagaaa cattgaagag    420

catgcctctt ccgatgtcga aagaatgatc ctgggtaaca aatgtgatat gaatgacaaa    480

agacaagtgt caaaagaaag aggggagaag ctagcaattg actatgggat taaattcttg    540

gagacaagcg caaaatccag tgcaaatgta gaagaggcat tttttacact tgcacgagat    600

ataatgacaa aactcaacag aaaaatgaat gacagcaatt cagcaggagc aggtggacca    660

gtgaaaataa cagaaaaccg atcaaagaag accagtttct ttcgttgctc gctactttga    720

tgaactcttt ctgagagact gcagcacacc tagagggccc tttcctgctt ctctgaaagc    780

acaggtcacc cagcctcaga atcacacctc ccggctgctg ctgagagcac cactgaactt    840

agacctctca acacagtatg ccaagtggat tccagcctca tggcctagca aaagaacaga    900

ctcccttttt caaacatgga agcaatgaag tggagacaca tgcaggacct aactcgtttt    960

ttccttgttt tattacctgt tgcagaagcg gttatctttc ttttttactt tgcacatcag   1020

tgttagcctt tccctatttc agcacaatct tagactcata tttgcacact tttgtgtcgt   1080

gaagttctag acaaatttgt acatgtggca atgttaaaag agcatttaca gcagaggtta   1140

atatactaaa attaaagggt atttggtctg gttcatatgg tcaaatatta ctgccttggt   1200

agcatttatt taagggcttt ttcttaaata agaatcatta aagtcattaa aaaaatttac   1260

tgaaatgccc atcttgtcat caaaggccac aatttcttta tttcttcaga ttaagagctt   1320

tgcctcatcc ccgacctgtt ttccagagtc tgggtagctg aatgaatcac tttaaaatga   1380

ttacctctgc ctaatctata gaaactgcat ttggaaatca ccataatctc atttttccct   1440

ggggtttgta tttgctattc tttcccatgt ttgacttaag tgtaatcact cttaagtaat   1500

atttgaacat tattatctgt ttctatttgt gaacttcttg agctgaaatt ttacgtgggc   1560

tgagagatat accatttagg gttttagtgc agcatctaac tgtgattctg tcaataagga   1620

tatgtaatat attttttctt aggttcactc cttagctggc tggtttagtt gtaataccaa   1680

attcctacca taatccctgt ctacaaaagt taggtttaga ttttagtttg cggaaacctt   1740
```

```
ccctatatag agacagatta acttgttgat ataaatttaa tagagctagc tcttggtaat   1800
ggtgaaaata atgagttttg gttggtttta tttggcagat gtttttagaa ataaaagtac   1860
ttagacctag tgcagcctct aggaaaagtc ttgccttttc attagagaaa acaggaccaa   1920
ggtttcagtt ttcaaacagc tgttgttgat tgtgtagaac ccagttccat ctgttttggt   1980
tcattgttac agaacttagt ccagtcattt gggctaaagc caaccaaaag cttagttgcc   2040
tttctcaaca aacactggta ctggtatact tttgtagatg aaaccatcac aaggtattta   2100
gtgttaactt gtgtgccaaa ttcagatcac tatgtcgttg ttgctctagc cttcagtgtc   2160
ataacacagg ggggataaaa cagaggggat gagggaaatg aattctgtta ataattattc   2220
ttcctggtat gcctgttttg cttcacaaag gctactatca tgctggatag ataagaacag   2280
gagatggcag tggaaaggga ttgcttgtta ccacagagaa ttctcttcaa attaagatat   2340
gtcattagaa tgcttggacc agtcaatctt ttgtacttat ttgaaaatat aggaacaatt   2400
tagcagctgc aaatatgccc aagctatttt taatagatat actaaactta ttgttgacaa   2460
atttcagcct ccttaatttt tttttttttg gtaattacct ataggcttaa aagtcattcg   2520
ttgctgttct agtataatta gtagttccgt gattgaaagt ttattgtaat tctactatct   2580
tcaaattaga tacattttca aaaggaaaag ataatttttt agaaacatct taatattcac   2640
tatttcctga aaaaatccaa gcagttaacg ctttctggat ggtaacaaag taccttctaa   2700
aagataagtg ctatgacacc atgtatgaat gtaattctct tagtaattta cctctgacta   2760
tttggtgtct taacgctttg gtttatataa tctcaggggt tgtctgcaaa ccaaaactga   2820
catattctgt ggttagcttt tattactttt ttttttaaca gaatgctttg ctttggttat   2880
atttcttctt tcttcttttg tcttatatgg attaataact agtctccatg aacttcactt   2940
gaaagagcct gtaaaagtta gatgagtcta aaagtgctct ttgaagtagc agcaaattgg   3000
gagtatatgc tctgttatat agaaataaat tgtccttgct attttcttac atttagcttt   3060
gctagattgt atatacattg agctaagacc ttaggaaatt cactttctgc atgataaaat   3120
gacccaataa atattccact ttgcttaata atgtacatac agtgcattat tttttctatt   3180
tgtagatgaa tttaatgaca gataattgtc tgttccccgc tgaaactgaa gaaatctagt   3240
tttttgtga acatttttgt ggtcttatgg ataaggtaca tgaagatttt tgcagcagta   3300
ttagtggttc agtggctgca ctttattaat cagtgtgtta atttttgaca gtgattggac   3360
tagacctttt caaatagagt ctgagggtat cagacagtga aaatgtgctg taactaagta   3420
gcatgtaaat cagttgattg taaaacgttt cgctgggaac ttattttagc tatattttac   3480
ttcagacaga ttatgataca ataatctacc tgtgcatcag ttagtaggtg ctgcagggtt   3540
tcttactatt tacagaaaca ttttgtgcag tctttgttat aaattttcag aagactatac   3600
tctttacttt gaaggtctat tttttaatta tacctcattt agctaactag tattctaata   3660
cctggtagaa aaacagtgag ccagccttta agcatctaac aaaatttaga ctctttgttt   3720
tgttttgaac tgaagacatc attgggaaag gtaggaaata ttagtttagg atagagcata   3780
catgtcatat ccagtagcat aaaaaaagta ttatctccct gtctccatta ataaatttag   3840
ctgtgcaata taggtgcgtt tttgcagaag tttctagtaa gagattataa ctccatttta   3900
caggttctga atgctcagag tctatattaa ggcttataaa gtttttcctg tgatcagtaa   3960
gtgacacatt taagcagaca ttcttttcaa gttcatgact tagattcctt tacaaattta   4020
gttctcaatc tttaaaaacc acatttcatt atgttggtta attattataa attttaagca   4080
```

ctcatttctg caatcaggtt tctcagaatt tttttttttt aaacagaaga gacattcctt 4140
tttccttgtt acatccaagg ggggcacagg ggtgggtgga aaggaatgtc taaaaatgaa 4200
atcccttgat atagagggac ctagacggac aggatatgct aaaataattt caaattctag 4260
cacaatttta gagtagaata agtcattttt ttagactaat aaaattaatg gctgtcatgt 4320
tcactctgaa aaaaatctaa atgactgaaa tgtacagaaa taaaaattag caaacaatta 4380
ttctagggat attttcagat tttacttcat ttcttgaaat gcgtgtgcca tatgcaattg 4440
catttcttgt gccaagaaac taatagaact tatttcactt taccttttt taaaatgtga 4500 atttagttat tatagttcaa ttttatggcc ttacagatgg cttttatttt gtttgcagct 4560
gacactgcag ttcctttcat gcaaaatacc ataaactgtt tgatgaaaat catgccccta 4620
atggaaactc tctagttttt ccatataact atcctactgt acatgtttaa acatatttta 4680
tttttgctcc aatggcttaa tgtgaaaagc tcctgcagat aagtggacct gtcatgtggt 4740
taatcttgtt taagccaatt cattaactgt gtactgatac tgatgctatg ttttttttaa 4800
atggatttta ttccaggtga actttttttt tataataatg ttcgtctaaa ataaaaacta 4860
cataatgaaa atgaaaa 4877

<210> SEQ ID NO 57
<211> LENGTH: 1288
<212> TYPE: DNA
<213> ORGANISM: Homo sapiens

<400> SEQUENCE: 57
cgtcgccatg ttgttccctc cgcgctggac gggagcagct ggagcgggag cctggctgcg 60
ctaccgcggc tgcctcctgc tgtgcaggtc cccgaccctc tctctgtcct cattgcgccc 120
agacgggccg gcccagagct cccgggtcgt ctttcgtgtg gccgcgaggg ttcttgaagc 180
ttttgagatt aacaatggca ggaaaatcat cactttttaa agtaattctc cttggagatg 240
gtggagttgg gaagagttca cttatgaaca gatatgtaac taataagttt gatacccagc 300
tcttccatac aataggtgtg gaatttttaa ataaagattt ggaagtggat ggacattttg 360
ttaccatgca gatttgggac acggcaggtc aggagcgatt ccgaagcctg aggacaccat 420
tttacagagg ttctgactgc tgcctgctta cttttagtgt cgatgattca caaagcttcc 480
agaacttaag taactggaag aaagaattca tatattatgc agatgtgaaa gagcctgaga 540
gctttccttt tgtgattctg ggtaacaaga ttgacataag cgaacggcag gtgtctacag 600
aagaagccca agcttggtgc agggacaacg gcgactatcc ttatttgaa acaagtgcaa 660 aagatgccac aaatgtggca gcagcctttg aggaagcggt tcgaagagtt cttgctaccg 720
aggataggtc agatcatttg attcagacag acacagtcaa tcttcaccga aagcccaagc 780
ctagctcatc ttgctgttga ttgttagatt gttgatgcat tctaaccaac tcacacatat 840
acacaaaatc aacatgggga tggagaagag aattagcgtt tgcagcagtg tatcatctac 900
taataaaatt aaactaatgt tgctgcttca ttagttggtg ggagaaggga cacatccact 960
cttggaggaa tatatttact caataatggc accttacatt tataaattgt aacagttgtc 1020
taataacgtt tctttaattt aaatatgtaa gttgcagagc taataaatga aatgaccaag 1080
actttaatta taataaaaat aagaaacttg actattctag aagttatact tggatttttt 1140
cctgggaaaa tggagaacta ctttttatat gtgtatgttt ttatgcaatt agcattgtat 1200
tcttggttca gggaaatact ttcctaaagc aataatgtta gatattaaag attaaaatct 1260
aatgtatttg caaaaaaaaa aaaaaaaa 1288

<210> SEQ ID NO 58
<211> LENGTH: 2828
<212> TYPE: DNA
<213> ORGANISM: Homo sapiens

<400> SEQUENCE: 58
agcgccccgg aagtgatctg tggcggctgc tgcagagccg ccaggaggag ggtggatctc 60
cccagagcaa agcgtcggag tcctcctcct ccttctcctc ctcctcctcc tcctcctcca 120
gccgcccagg ctcccccgcc acccgtcaga ctcctccttc gaccgctccc ggcgcggggc 180
cttccaggcg acaaggaccg agtaccctcc ggccggagcc acgcagccgc ggcttccgga 240
gccctcgggg cggcggactg gctcgcggtg cagattcttc ttaatccttt ggtgaaaact 300
gagacacaaa atggctgcaa ataagcccaa gggtcagaat tctttggctt tacacaaagt 360
catcatggtg ggcagtggtg gcgtgggcaa gtcagctctg actctacagt tcatgtacga 420
tgagtttgtg gaggactatg agcctaccaa agcagacagc tatcggaaga aggtagtgct 480
agatggggag gaagtccaga tcgatatctt agatacagct gggcaggagg actacgctgc 540
aattagagac aactacttcc gaagtgggga ggggttcctc tgtgttttct ctattacaga 600
aatggaatcc tttgcagcta cagctgactt cagggagcag attttaagag taaaagaaga 660
tgagaatgtt ccatttctac tggttggtaa caaatcagat ttagaagata aaagacaggt 720
ttctgtagaa gaggcaaaaa acagagctga gcagtggaat gttaactacg tggaaacatc 780
tgctaaaaca cgagctaatg ttgacaaggt attttttgat ttaatgagag aaattcgagc 840
gagaaagatg gaagacagca aagaaaagaa tggaaaaaag aagaggaaaa gtttagccaa 900
gagaatcaga gaaagatgct gcattttata atcaaagccc aaactccttt cttatcttga 960
ccatactaat aaatataatt tataagcatt gccattgaag gcttaattga ctgaaattac 1020
tttaacattt tggaaattgt tgtatatcac taaaagcatg aattggaact gcaatgaaag 1080
tcaaatttac tttaaaaaga aattaatatg gcttcaccaa gaagcaaagt tcaacttatt 1140
tcataattgc ctacatttat catggtcctg aatgtagcgt gtaagcttgt gtttcttggg 1200
cagtctttct tgaaattgaa gaggtgaaat gggggtgggg agtgggagga aaggtgactt 1260
cctctggtgt ttattataaa gcttaaattt tatatcattt taaaatgtct tggtcttcta 1320
ctgccttgaa aaatgacaat tgtgaacatg atagttaaac taccactttt tttaaccatt 1380
attatgcaaa atttagaaga aaagttattg gcatggttgt tgcatatagt taaactgaga 1440
gtaattcatc tgtgaatctg ctttaattac ctggtgagta acttagaaaa gtggtgtaaa 1500
cttgtacatg gaatttttttg aatatgcctt aatttagaaa ctgaaaaata tctggttata 1560
tcattctggg tgtgttctta ctgacaccag gggtccgctg ccccatgtgt cctggtgaga 1620
aaatatatgc ctggcacagc ttttgtatag aaaattcttg agaagtaact gtccgctaga 1680
agtctgtcca aatttaaaat gtgtgccata ttctggttct tgaaaataag attccagagc 1740
tctttgatcg cttttaataa actgcaagtt cattttaaat gaagggccag catatatact 1800
tgcaagataa ttttcagctg caaggattca gcaccagtta tgtttgaatg aaccctcctt 1860
ttctctgaga ttctggtccc tggaaatccc tttctgctag tggtgagcat gtaagtgtta 1920
agtttttaat ctgggagcag ggcataggaa gaaaatgtca gtagtgctaa tgcattttgc 1980
actagaacgc ttcgggaaaa tattcatgct tgccatctgt tcatttctaa atttatattc 2040
ataaagttac agtttgatac aggaattatt aggagtaatt cttttctgtt tctgtttata 2100
atgaagaaca ctgtagctac attttcagaa gttaacatca agccatcaaa cctgggtata 2160
gtgcagaaaa cgtggcacac actgaccaca cattaggctg tgtcaccatt gtgtggtgta 2220
cctgctggaa gaattctagc atgctacttg ggacataat ttcagtggga aatatgccac 2280
tgaccgattt tttttttttc ctctttgcag tggggctagg acagttgatt caacaaagta 2340
tttttttctt ttttctcagt cctaatttga acaggtcaaa gatgtgttca ggcattccag 2400
gtaacaggtg tgtatgtaaa gttaaaaata ggctttttag gaactcactc tttagatatt 2460
tacatccagc ttctcatgtt aaatatttgt ccttaaaggg tttgagatgt acatctttca 2520
tttcgtattt ctcataggct atgccatgtg cggaattcaa gttaccaatg taacactggc 2580
cagcgggccc agcaatctcc atgtgtactt attacagtct tatttaacca ggggtcctaa 2640
ccactaacat tgtgactttg ctttgagacc tttcctctcc tgggtactga ggtgctatga 2700
agccaactga caaagatgca tcacgtgtct taggctgatg ccactacccg atttgtttat 2760
ttgcaatttg agccatttaa agaccaataa acttcctttt ttaaaatgtt aaaaaaaaaa 2820
aaaaaaaa 2828

<210> SEQ ID NO 59
<211> LENGTH: 2092
<212> TYPE: DNA
<213> ORGANISM: Homo sapiens

<400> SEQUENCE: 59
ggcgtaatta aaaagcggcg gaagaaggtg ggagggtcat gacgcagcga gtttcagtcg 60
tgacttttct gggggcatcg cggcgtcccc tttttttgcc tttaaagtaa aacgtcgccc 120
cgacgcaccc cccgcgtatt tcgggggggcg gaggcggcgg gccacggcgc gaagaggggc 180
ggtgctgacg ccggccggtc acgtgggcgt gttgtggggg ggaggggcgc cgccgcgcgg 240
tcggttccgg gcggttggga gcgcgcgagc tagcgagcga gaggcagccg cgcccgccgc 300
cgcccctgct ctgtatgccg ctctctcccg gcgcggccgc cgccgatcac agcagcagga 360
gccaccgccg ccgcggttga tgtggttggg ccggggctga ggaggccgcc aagatgccgc 420
agtccaagtc ccggaagatc gcgatcctgg gctaccggtc tgtggggaaa tcctcattga 480
cgattcaatt tgttgaaggc caatttgtgg actcctacga tccaaccata gaaaacactt 540
ttacaaagtt gatcacagta aatggacaag aatatcatct tcaacttgta gacacagccg 600
ggcaagatga atattctatc tttcctcaga catactccat agatattaat ggctatattc 660
ttgtgtattc tgttacatca atcaaaagtt ttgaagtgat taaagttatc catggcaaat 720
tgttggatat ggtggggaaa gtacaaatac ctattatgtt ggttgggaat aagaaagacc 780
tgcatatgga aagggtgatc agttatgaag aagggaaagc tttggcagaa tcttggaatg 840
cagctttttt ggaatcttct gctaaagaaa atcagactgc tgtggatgtt tttcgaagga 900
taattttgga ggcagaaaaa atggacgggg cagcttcaca aggcaagtct tcatgctcgg 960
tgatgtgatt ctgctgcaaa gcctgaggac actgggaata tattctacct gaagaagcaa 1020
actgcccgtt ctccttgaag ataaactatg cttctttttt cttctgttaa cctgaaagat 1080
atcatttggg tcagagctcc cctcccttca gattatgtta actctgagtc tgtccaaatg 1140
agttcacttc cattttcaaa ttttaagcaa tcatattttc aatttatata ttgtatttct 1200
taatattatg accaagaatt ttatcggcat taatttttca gtgtagtttg ttgtttaaaa 1260
taatgtaatc atcaaaatga tgcatattgt tacactacta ttaactaggc ttcagtatat 1320
cagtgtttat ttcattgtgt taaatgtata cttgtaaata aaatagctgc aaacctcagt 1380

-continued

```
cctttgtgct acttgatgtg gctttcaaag aagagaagcc ttgtcctgag tttctcactt   1440

ggcttcagga aggccccagg ttggattcca gaaaccagtg aagatgtggc cacaggagga   1500

ggtgtgctga ggtggctgct gaccgtggac tccctgcgca gtggcctgca gatgttgggg   1560

ctgggttaca gctgattgaa gctgagtggc cctggggggt ctgtgagggg agttcctccc   1620

cagtgatgaa attctctcct tccaccctca aatccctaga ccttgactga aatgctccgt   1680

ggtcgggagc ctggtcaagg aggaggagct gctgagaggc attgttcgcc cttgctcata   1740

gcttagctcg atgtccgtgt cagacaggag atgattgaga acagccttgc ctgtcactgt   1800

cctagaacac cctggagttt agtgttctgt gtcagagtct tgggagcctc cttcagaccc   1860

agatgacggg cctccctctg tccaaggagc agctgtaaag gagaagaggg atttcatttg   1920

tttggtggct gttaccttgt ctgtaagtca aacttggagt tgagcagtgc tttttaaacg   1980

attccctttt gcagctaaaa tttcacaggg ctatttctaa tacgtaagca aatgttacca   2040

ttgactttat taataaaata tagttttgct ttgcaaaaaa aaaaaaaaaa aa           2092
```

<210> SEQ ID NO 60
<211> LENGTH: 820
<212> TYPE: DNA
<213> ORGANISM: Homo sapiens

<400> SEQUENCE: 60

```
gtataaggtc cacaccccgg gagctgagtg attgcagaaa ctggccttcc atctctctca     60

gacaccaagc tgcagatcca ggcttttctg ggaaagtgag gccaccatgg ctctggagaa    120

gtctcttgtc cggctccttc tgcttgtcct gatactgctg gtgctgggct gggtccagcc    180

ttccctgggc aaggaatccc gggccaagaa attccagcgg cagcatatgg actcagacag    240

ttcccccagc agcagctcca cctactgtaa ccaaatgatg aggcgccgga atatgacaca    300

ggggcggtgc aaaccagtga acacctttgt gcacgagccc ctggtagatg tccagaatgt    360

ctgtttccag gaaaaggtca cctgcaagaa cgggcagggc aactgctaca agagcaactc    420

cagcatgcac atcacagact gccgcctgac aaacggctcc aggtacccca actgtgcata    480

ccggaccagc ccgaaggaga gacacatcat tgtggcctgt gaagggagcc catatgtgcc    540

agtccacttt gatgcttctg tggaggactc tacctaaggt cagagcagcg agatacccca    600

cctccctcaa cctcatcctc tccacagctg cctcttccct cttccttccc tgctgtgaaa    660

gaagtaacta cagttagggc tcctattcaa cacacacatg cttccctttc ctgagtccca    720

tccctgcgtg attttggggg tgaagagtgg gttgtgaggt gggcccccatg ttaacccctc    780

cactctttct ttcaataaaa cgcagttgca aacacctgaa                          820
```

<210> SEQ ID NO 61
<211> LENGTH: 7019
<212> TYPE: DNA
<213> ORGANISM: Homo sapiens

<400> SEQUENCE: 61

```
gggccggggg gcgatggaat aaaagaagat ggagagactt cagcgcctgg gactcgggtg     60

ggcgaggcgg aaggtgtcct cgcagcacgg cttttctccg cgccgcggtt ggttagcgag    120

tgccctctgg gtgctaggcg ttgggcggat ggtaggatcg cggtagcata cggatccgag    180

tcctgcgccg agtgagagga gaggctggca ggggctaagt gatggatctt gtactccgtg    240

ttgcagatta ctattttttt acaccatacg tgtatccagc cacatggcca gaagatgaca    300
```

-continued

```
tcttccgaca agctattagt cttctgattg taacaaatgt tggtgcttac atcctttatt    360
tctttctgtgc aacactgagc tattattttg tcttcgatca tgcattaatg aaacatccac   420
aatttttaaa gaatcaagtc cgtcgagaga ttaagtttac tgtccaggca ttgccatgga    480
taagtattct tactgttgca ctgttcttgc tggagataag aggttacagc aaattacatg    540
atgacctagg agagtttcca tatggattgt ttgaacttgt cgttagtata atatctttcc    600
tctttttcac tgacatgttc atctactgga ttcacagagg ccttcatcat agactggtat    660
ataagcgcct acataaacct caccatattt ggaagattcc tactccattt gcaagtcatg    720
cttttcaccc tattgatggc tttcttcaga gtctacctta ccatatatac ccttttatct    780
ttccattaca caaggtggtt tatttaagtc tgtacatctt ggttaatatc tggacaattt    840
ccattcatga cggtgatttt cgtgtccccc aaatcttaca gccatttatt aatggctcag    900
ctcatcatac agaccaccat atgttctttg actataatta tggacaatat ttcactttgt    960
gggataggat tggcggctca ttcaaaaatc cttcatcctt tgaggggaag ggaccgctca   1020
gttatgtgaa ggagatgaca gagggaaagc gcagcagcca ttcaggaaat ggctgtaaga   1080
atgaaaaatt attcaatgga gagtttacaa agactgaata gattattgcc cagttattct   1140
taagtaagga caaagaagga aatatcatcg tatttctttt ttttaataag gaaaaaataa   1200
tatccataca gtcaagatac atagtaaatg gtatcatttg gaaatcagca tcgtgggcac   1260
tgctgaggaa tgatcctagt ggtaggtcag aagaagatgc tgtgaacacc aggactttaa   1320
tcttatgctt aaaatgccag atgttgttcg ggggacaact tgtatctttc tagcagcaga   1380
tctgtagttt gtatagcctc aacaacaatt ttaaataaga tggagaataa attattgagg   1440
ggactaggct atatgcattt gccttcatcc acccatgttt attaagaatc attgtgctta   1500
ataataccaa gactaagcac cataaccaag aaatactaat gtaaagattg tttcttgttt   1560
caggaatggt taattcttca acgttggtat gataatgata acttgttttg acttgaataa   1620
agtactacat cagtgtggaa aaaaattctg atacattagc agctatgtaa atgacctaat   1680
tgatagcagg tgtaataaga ctatcgtctt cctacacata ggaggctcat tctctggaca   1740
cactatcacc tattacattt tactgattaa caaataaatt ggaatttaaa aatatcgata   1800
tcaccatgat ttaatccaga tctgggatta tgtagctaaa cattgtgatg attattattt   1860
aaaaccatta tttaataaga gtaaaaatat gtgaatctgg atatatttaa aaaaagaaat   1920
ttgatgccca gataatatat taggcactac tgattttta gttaaattga tgcactacac     1980
ttttgatgtt tgaagttaca aacctgtaat ttttttgtaa aggaaataat tgccaaatac   2040
ctaggcccat tgctgacgat tagttctaaa atcttattcc tcctcttctc ccctcacttt   2100
tccctacttc ctctgcaaaa agatttaaca aatacattca taaggaaatg tgtgttgtaa   2160
caaatatatt gcaaaaacat agtttgtaaa ggcattctat aagctattta tgtaaaatca   2220
ataaaagttg atcataatta aactgtatca gttgagtatt atagcagcac aaagtattct   2280
ttgtacagat tttgtgccaa tttgaagcca cagaaatgat gtggattgtt aattgtgttt   2340
tagaacatcc ccggacactc agtgtcacag ggggaaagaa gtgggtacca cattctgttt   2400
atatttcaca ttttaactag atttgagtgt ttttagcaag aaatcagtct taaaatctaa   2460
tgtctgggat ccagaagaaa atgtctttaa tctgtgagtt attgtcacaa tgtcatctta   2520
tttaaatgta ccaattagca ttttgtaata ggcaaatgtc atttagtgct tttcaccaat   2580
cccactcacc cccggtgctc cgccttgcct aagaaaaaga aattaaggag aagtaaactt   2640
tatttcctaa tataatgtca gctgatattt attgagcttt tcctctttgc ccagagacta   2700
```

-continued ggacccaaag aagttaagta actattccca ggtttatttc tctctcatat gatgtcccat 2760
gtggatgttt gtggtcagtg gacagctttc cacctagtct ttctgcgacc caggctcctt 2820
cctcttgggg ctctgccttt ctctcagtcc atagagccct ctttgttgaa agagcacata 2880
ggaaaagaag gaaaagtctg tgtggaaaat gtttctgggt caggcctgga agtggtgcat 2940
atctcttccg cccatgttcc tttggacaga actccgtcac atggcccacc tagagagatt 3000
ttgggaaatg tgtccagctg tgtgcctggg aggaaggggg caccattttc ttgagcagct 3060
agacagtttg ccgtatttgt ggtgttctcc tcttgttgat gttgaaatgg tgaatgagcc 3120
ataaagtatt tcaggttatc cacacactaa tcatctcagt gtctttaatt cttaactcca 3180
atatgaatgt ttaaagcttc ctctagattc ttattcctat ataactaata gagaagaaag 3240
gacagcttcc tatggggaag acagaggctt cctcatagat gttaggaata atcaaacttg 3300
cccctgccct ttcacccgtc tcaaattctg gtcttttaaa gcagcgttat gttaagtagt 3360
cctaacattg taatatacag tactgccaca ttctcctact ttctattaga ggaagtcaga 3420
gaatatttat ggaagtgagg acccaaatta ccttctacag atgactttta tagttacagg 3480
acagaaagtg aaaatcaagg ttacgttttc tacttttgtg gtagaaattg agaagtgggt 3540
ggatatggtt cgagaagacc tttcagaaac acagagactg agtctttgtc ttccatgctg 3600
tctctgcagt actgagtgaa tttccttata cccttgtatc atgttttcct cccatcttct 3660
agaagctggg gacagatttg gaagagaatt acacaagttc agtttttga tacatggatt 3720 ttacagtgca tgcaggttat ttatgtagag aggaggtctg ggagaaagat ggaaactagg 3780
gagatgactg agaacaaaga tatttgggat taacacagat agaagaaaag tttgaaacca 3840
tgagattgtc acagcatgaa aaaagatatt caaagacact aaccaacttg aggggtgcag 3900
tggtctgaat gtgtcctcca aaattcaaat gtggaaatgt atttgccagt gagatagtat 3960
gtagaggtgg ggccttgagg aagtgattaa gtcatgaggg ctctgggatt aatgacttaa 4020
aaagaggtgt gaggcagctg ttcagccctt ctgtctcctg tcccttttt tttttttt 4080 tttgagatgg agtcttgctc tgttgcccca ggctggagtg cagtggcgtg atcttggttc 4140
actgcaagct ccacctcccg ggttcacgcc attctcctgc ctcagcctcc cgagtagctg 4200
ggactacagg tgcccgccac caccacgccc ggctaatttt ttatattttt agtagagatg 4260
gggtttcacc gtgttagcca ggatggtctt gatctcctga cctcatgatc tgcctgcctc 4320
ggcctcccaa agtgctggga ttataggtgt gagccaccat gcccagcccc ttctgtccct 4380
tctaacgtga ggacccagca acaaggtacc atcttgaaag cagcaactgg ggactcagca 4440
gacaccaaac caactggtgc ttaaccgtga cttcccagcc tccagagctg taagaaaata 4500
aatttctatt atttatagat tacccagttg aagatacttt gttaaggcag tacaaatgga 4560
ctaagacaag gggaagaaa tttgcattcc tgatcttccc aacttcttca aattcacaac 4620
acttgaatga cagtcttatt tcagcactta ctgctatcac ctattacttt tatgtgtgtc 4680
ttacctattt gagatgccag attccttgga agtagagacc gtgtctgaat catcattgta 4740
ttaaaccact catccttaac aaatgcccaa gccatggtta aagttcaata aatactttgt 4800
tgaatttatt aataaaatgg cagaaatgtc attctcttcc atatatgttt aataaatccc 4860
tgataggtgc taagcactgc actaggtaaa aattctcttc tgatgctgtc tttttggcca 4920
accatttttt tatcatttat tcattagctg acatttgcta agtgctttgg aggggtcaaa 4980
aggggaagta atgagaaatc aaagatggtc cctacatcaa ggataaacta tcttttttta 5040

-continued

```
gtcactcaaa gtcataaccc tttggaaaca aaacccacca gtaccccaga ttttgaccac   5100
agatgaatca gtactacaag gactggttag agggttgaat gaatctgtat actcagcact   5160
taacacagca ctctgggtaa aagaaaaaag atcctcaaag atattagttg gttacatcaa   5220
gaaaggacaa acttaggtta atctataact tcatctcaga ggaacaggaa ctttggagat   5280
aaacagggct ctgccacttg caagttgcac catccctggt ttctccatct gtaaattgat   5340
taaaacactg cctatctaat aagattaaat aagttagaag cattcagtta aatgtcaact   5400
gaaactattg ttcatgtaaa ttgtgcttga tgctttttct ttctagattc aatgattatt   5460
gtcattttac ctccataggc cctcaataga aatcagttgc agagggcaga agcctagata   5520
ttttcacctt aaaattggag ggtgaaagac attgaggtga agtagagata gagggtacac   5580
agaaaaatcg tataagtaaa actaacatcg ttaacattat ttactgtaag ttatctttgt   5640
aagagtggta aaatacattg tgttgttaaa taatttcatt taaaaaatgc atcactttgt   5700
gtgtttttat attgctaaaa ccataaggcc agtctacaag gtttgtagat aaaatagaaa   5760
catacctccc ttgaaaagca gaataaattt tttaaaggca ggaaggaagt gtttgaacca   5820
tgtgtcaaca agctttactg tcaaagcagg cttttggtat gggaagaaaa atacttataa   5880
atacttgttt taatatttgc tttattaaaa tacatttaaa atacagcatt tttaaatctc   5940
taagctcaac ttgaagatat aagaacagta aatttgataa aaatgagaaa ttacattccc   6000
atttctttaa caatttgtaa attccaatta tcctgaacat ttaataccat ttacatattt   6060
tattaatcac attttcttaa acatttgata agagatttaa tattttgatc caactaccaa   6120
aaaagcagac ttgtgtactt gacagatttt tctaaacact tcacaactca cgattcaaac   6180
aaagacaaaa tagcatatca aaagttaatc actcagttgg aaagcactca taccataggc   6240
ttttattcat ttcttgaata attttgttat atcttcctct tttaggctgc aatgagctat   6300
aattgcacta ctgcactcca cgctgggtga cagagcaaga ccctatctct aaaaataaaa   6360
aagtatatat atataaaaat atcttcctct attataattt aactcattaa gccatttatt   6420
tagatgtaaa cttgcccccc tgacatgtgg tatgaaacaa atagaaacct agaaatttag   6480
tgcatattca aatattaaga cagacactgg tgtggtgact tttgtctgtc gcttcattgg   6540
gacgtttttt ctttctgatc aacttaatga aattataatt tactataatt aagtgtagcc   6600
atttttactg tagagttcaa tgatctttga tgaacgtgta cacccatgta accaccaccc   6660
ccaatcaaag taaagaacat tttcttacca gaataaattt cctctccgtt tgcagtcatt   6720
ctccccagcc ctaggtcacc actgatccac cttctgttac tggaaggtta gttttcttcc   6780
ctgatttaga atttcatata aattaaatca gatagtatat actcttgtgt ttagtttctt   6840
tagcttaaca tgtttagaga tatttgctgt tgcctgtgtc tgtagctttt tgttttcatt   6900
gctgaatagt atttcattgt aatataccac agttggttta tgtatttgct gatgaatatt   6960
tgtgttattt ccagcgtggg attattatga ataaagttgc tacaaacatt tgtatacaa    7019
```

<210> SEQ ID NO 62
<211> LENGTH: 3485
<212> TYPE: DNA
<213> ORGANISM: Homo sapiens

<400> SEQUENCE: 62

```
agtcgcccag gggagcccgg agaagcaggc tcaggaggga gggagccaga ggaaaagaag     60
aggaggagaa ggaggaggac ccggggaggg aggcgcggcg cgggaggagg aggggcgcag    120
ccgcggagcc agtggccccg cttggacgcg ctgctctcca gataccccccg gagctccagc    180
```

-continued

```
cgcgcggatc gcgcgctccc gccgctctgc ccctaaactt ctgccgtagc tccctttcaa    240
gccagcgaat ttattcctta aaaccagaaa ctgaacctcg gcacgggaaa ggagtccgcg    300
gaggagcaaa accacagcag agcaagaaga gcttcagaga gcagccttcc cggagcacca    360
actccgtgtc gggagtgcag aaaccaacaa gtgagagggc gccgcgttcc cggggcgcag    420
ctgcgggcgg cgggagcagg cgcaggagga ggaagcgagc gcccccgagc cccgagcccg    480
agtccccgag cctgagccgc aatcgctgcg gtactctgct ccggattcgt gtgcgcgggc    540
tgcgccgagc gctgggcagg aggcttcgtt ttgccctggt tgcaagcagc ggctgggagc    600
agccggtccc tggggaatat gcggcgcgcg tggatcctgc tcaccttggg cttggtggcc    660
tgcgtgtcgg cggagtcgag agcagagctg acatctgata aagacatgta ccttgacaac    720
agctccattg aagaagcttc aggagtgtat cctattgatg acgatgacta cgcttctgcg    780
tctggctcgg gagctgatga ggatgtagag agtccagagc tgacaacatc tcgaccactt    840
ccaaagatac tgttgactag tgctgctcca aaagtggaaa ccacgacgct gaatatacag    900
aacaagatac ctgctcagac aaagtcacct gaagaaactg ataaagagaa agttcacctc    960
tctgactcag aaaggaaaat ggacccagcc gaagaggata caaatgtgta tactgagaaa   1020
cactcagaca gtctgtttaa acggacagaa gtcctagcag ctgtcattgc tggtggagtt   1080
attggctttc tctttgcaat ttttcttatc ctgctgttgg tgtatcgcat gagaaagaag   1140
gatgaaggaa gctatgacct tggagaacgc aaaccatcca gtgctgctta tcagaaggca   1200
cctactaagg agttttatgc gtaaaactcc aacttagtgt ctctatttat gagatcactg   1260
aacttttcaa aataaagctt ttgcatagaa taatgaagat ctttgttttt tgttttcatt   1320
aaagagccat tctggcactt taatgataaa atcccattgt atttaaaaca tttcatgtat   1380
ttctttagaa caacataaaa ttaaaattta acatctgcag tgttctgtga atagcagtgg   1440
caaaatatta tgttatgaaa accctcgatg ttcatggaat tggtttaaac ttttatgcgc   1500
aaatacaaaa tgattgtctt tttcctatga ctcaaagatg aaagctgttt catttgtgtc   1560
agcatgtctc agattgacct taccaagttg gtcttacttt gttaatttat ctgttgtccc   1620
cttcctctcc tctgccctcc cttcttgtgc ccttaaaacc aaaccctatg ccttttgtag   1680
ctgtcatggt gcaatttgtc tttggaaaat tcagataatg gtaatttagt gtatatgtga   1740
ttttcaaata tgtaaacttt aacttccact ttgtataaat ttttaagtgt cagactatcc   1800
attttacact tgctttattt ttcattacct gtagctttgg gcagatttgc aacagcaaat   1860
taatgtgtaa aattggatta ttactacaaa accgtttagt catatctatc taatcagatc   1920
ttcttttggg aggatttgat gtaagttact gacaagcctc agcaaaccca aagatgttaa   1980
cagtatttta agaagttgct gcagattcct ttggccactg tatttgttaa tttcttgcaa   2040
tttgaaggta cgagtagagg tttaaagaaa aatcagtttt tgttcttaaa aatgcattta   2100
agttgtaaac gtctttttaa gcctttgaag tgcctctgat tctatgtaac ttgttgcaga   2160
ctggtgttaa tgagtatatg taacagttta aaaaaaaagt tggtatttta taagcacaga   2220
caattctaat ggtaactttt gtagtcttat gaatagacat aaattgtaat ttgggaacat   2280
aaaaactact gaataaatca tgtggcctaa tattgaaaat gtcactgtta taaattttgt   2340
acatttttga tcaaatgtac atctcccctt tgctaacggc cgtctgctct caaggatgac   2400
gtgggtttga tttctaagtg tttcacagtg tctgtaaatc aagaccaaag agcctgtcga   2460
tgagactgtt tattaccaga ttcacttctg aattggccag aggaaatctg aatgtattat   2520
```

```
cctgtgtgtg tctaggtaga gatattggaa ggctgccagg ggatttcgaa gtttgcaacc   2580

tttataggat aactgatggc aatattaaga cagacgcctg cttttgcaaa taacttacaa   2640

gactgtaaat tccaaagatc tgaatggggc tttcctgatg ttggtatcta aggcttaggc   2700

ctatagattg atttaccttt ggaattgtgc tccaaatgtc tactgaagct taaccgaaga   2760

actaataaat ggactacagt agctcacgtt acagggaagg agggtaggca gggaggctct   2820

gtgtgttaaa atgagggtct cactgcttta ggattgaagt ggctggaaag agtgatgcct   2880

ggggaaggag atggagttat gagggtactg tggctggtac tttctgtact aaacatttcc   2940

tttttctatt ttaccactaa ttttgtttta aactgtgagc cgtccaagtc agaagaagac   3000

agcaaaaaaa gcaacttttc caacatacaa tttactttta ataaagtatg aatatttcat   3060

tttgagaaca ttccctggaa ttgccacata attcattaaa aacatttttt taagcaacac   3120

ttggaacagt gtttacttta aatccttaat ggccttaatt aattctcaga ttcctgcccc   3180

atcacttaca gaaccaattc actttagagt gactaaaagg aaacgatagc ctagctttct   3240

aaagccacgc tgtgtccctc aattacagag ggtaggaatg ggtatacctc taactgtgca   3300

aagcagagtg aaattcaatt catagaataa caactgctgg gaatatccgt gccaggaaaa   3360

gaaaaatttc tggcaaatat tttgtcactg ctgtaaagca aaatatttgt gaaagtgcca   3420

aaataaagtc tgtcatgcca aaagtaaatc attgtataga ctgacatcca gttttcttca   3480

actgt                                                               3485
```

```
<210> SEQ ID NO 63
<211> LENGTH: 3961
<212> TYPE: DNA
<213> ORGANISM: Homo sapiens

<400> SEQUENCE: 63

gaggtcttcc tgtttttgga gggggcaggc accccagggc cgattgtcgc gaatcacctt     60

cacctctggg ggctcagaat ccctgagcca gaaggccagg gcagggctgg gggataccc c   120

tgctgctcag acaggaaaat gggctcggag cttgcccaat acttcccaga aggacgaggc    180

tgctgaactt ctcattcggg gctccgggac ctggactgta ccccttcctg gcgtcacctc    240

ctcctgtcgc ctggccctcg ccatgcagac cccgcgagcg tcccctcccc gcccggccct    300

gctgcttctg ctgctgctac tgggggggcgc ccacggcctc tttcctgagg agccgccgcc   360

gcttagcgtg gcccccaggg actacctgaa ccactatccc gtgtttgtgg gcagcgggcc    420

cggacgcctg acccccgcag aaggtgctga cgacctcaac atccagcgag tcctgcgggt    480

caacaggacg ctgttcattg ggacagggga caacctctac cgcgtagagc tggagccccc    540

cacgtccacg gagctgcggt accagaggaa gctgacctgg agatctaacc ccagcgacat    600

aaacgtgtgt cggatgaagg gcaaacagga gggcgagtgt cgaaacttcg taaaggtgct    660

gctccttcgg gacgagtcca cgctctttgt gtgcggttcc aacgccttca acccggtgtg    720

cgccaactac agcatagaca ccctgcagcc cgtcggagac aacatcagcg gtatggcccg    780

ctgcccgtac gaccccaagc acgccaatgt tgccctcttc tctgacggga tgctcttcac    840

agctactgtt accgacttcc tagccattga tgctgtcatc taccgcagcc tcggggacag    900

gcccaccctg cgcaccgtga aacatgactc caagtggttc aaagagcctt actttgtcca    960

tgcggtggag tggggcagcc atgtctactt cttcttccgg gagattgcga tggagtttaa   1020

ctacctggag aaggtggtgg tgtcccgcgt ggcccgagtg tgcaagaacg acgtgggagg   1080

ctccccccgc gtgctggaga agcagtggac gtccttcctg aaggcgcggc tcaactgctc   1140
```

tgtacccgga gactcccatt tctacttcaa cgtgctgcag gctgtcacgg gcgtggtcag 1200
cctcgggggc cggcccgtgg tcctggccgt tttttccacg cccagcaaca gcatccctgg 1260
ctcggctgtc tgcgcctttg acctgacaca ggtggcagct gtgtttgaag gccgcttccg 1320
agagcagaag tcccccgagt ccatctggac gccggtgccg gaggatcagg tgcctcgacc 1380
ccggcccggg tgctgcgcag cccccgggat gcagtacaat gcctccagcg ccttgccgga 1440
tgacatcctc aactttgtca agacccaccc tctgatggac gaggcggtgc cctcgctggg 1500
ccatgcgccc tggatcctgc ggaccctgat gaggcaccag ctgactcgag tggctgtgga 1560
cgtgggagcc ggcccctggg gcaaccagac cgttgtcttc ctgggttctg aggcggggac 1620
ggtcctcaag ttcctcgtcc ggcccaatgc cagcacctca gggacgtctg ggctcagtgt 1680
cttcctggag gagtttgaga cctaccggcc ggacaggtgt ggacggcccg gcggtggcga 1740
gacagggcag cggctgctga gcttggagct ggacgcagct tcgggggccc tgctggctgc 1800
cttcccccgc tgcgtggtcc gagtgcctgt ggctcgctgc cagcagtact cggggtgtat 1860
gaagaactgt atcggcagtc aggaccccta ctgcgggtgg gcccccgacg gctcctgcat 1920
cttcctcagc ccgggcacca gagccgcctt tgagcaggac gtgtccgggg ccagcacctc 1980
aggcttaggg gactgcacag gactcctgcg ggccagcctc tccgaggacc gcgcggggct 2040
ggtgtcggtg aacctgctgg taacgtcgtc ggtggcggcc ttcgtggtgg gagccgtggt 2100
gtccggcttc agcgtgggct ggttcgtggg cctccgtgag cggcgggagc tggcccggcg 2160
caaggacaag gaggccatcc tggcgcacgg ggcgggcgag gcggtgctga gcgtcagccg 2220
cctgggcgag cgcagggcgc agggtcccgg gggccggggc ggaggcggtg gcggtggcgc 2280
cggggttccc ccggaggccc tgctggcgcc cctgatgcag aacggctggg ccaaggccac 2340
gctgctgcag ggcgggcccc acgacctgga ctcggggctg ctgcccacgc ccgagcagac 2400
gccgctgccg cagaagcgcc tgcccactcc gcacccgcac ccccacgccc tgggcccccg 2460
cgcctgggac cacggccacc ccctgctccc ggcctccgct tcatcctccc tcctgctgct 2520
ggcgcccgcc cgggcccccg agcagccccc cgcgcctggg gagccgaccc ccgacggccg 2580
cctctatgct gcccggcccg gccgcgcctc ccacggcgac ttcccgctca ccccccacgc 2640
cagcccggac cgccggcggg tggtgtccgc gcccacgggc cccttggacc cagcctcagc 2700
cgccgatggc ctcccgcggc cctggagccc gcccccgacg ggcagcctga ggaggccact 2760
gggcccccac gcccctccgg ccgccaccct gcgccgcacc cacacgttca acagcggcga 2820
ggcccggcct ggggaccgcc accgcggctg ccacgcccgg ccgggcacag acttggccca 2880
cctcctcccc tatgggggg cggacaggac tgcgcccccc gtgccctagg ccgggggccc 2940
cccgatgcct tggcagtgcc agccacggga accaggagcg agagacggtg ccagaacgcc 3000
ggggcccggg gcaactccga gtgggtgctc aagtcccccc cgcgacccac ccgcggagtg 3060
gggggccccc tccgccacaa ggaagcacaa ccagctcgcc ctccccctac ccggggccgc 3120
aggacgctga gacggtttgg gggtgggtgg gcgggaggac tttgctatgg atttgaggtt 3180
gaccttatgc gcgtaggttt tggttttttt tgcagttttg gtttcttttg cggttttcta 3240
accaattgca caactccgtt ctcggggtgg cggcaggcag gggaggcttg gacgccggtg 3300
gggaatgggg ggccacagct gcagacctaa gccctccccc acccctggaa aggtccctcc 3360
ccaacccagg cccctggcgt gtgtgggtgt gcgtgcgtgt gcgtgccgtg ttcgtgtgca 3420
aggggccggg gaggtgggcg tgtgtgtgcg tgccagcgaa ggctgctgtg ggcgtgtgtg 3480
tcaagtgggc cacgcgtgca gggtgtgtgt ccacgagcga cgatcgtggt ggccccagcg 3540
gcctgggcgt tggctgagcc gacgctgggg cttccagaag gcccgggggt ctccgaggtg 3600
ccggttagga gtttgaaccc cccccactct gcagagggaa gcggggacaa tgccggggtt 3660
tcaggcagga gacacgagga gggcctgccc ggaagtcaca tcggcagcag ctgtctaaag 3720
ggcttggggg cctgggggc ggcgaaggtg ggtggggccc ctctgtaaat acggccccag 3780
ggtggtgaga gagtcccatg ccacccgtcc ccttgtgacc tccccccctct gacctccagc 3840 tgaccatgca tgccacgtgg ctggctgggt cctctgccct ctctggagtt tgcctccccc 3900
agccccctcc ccatcaataa aactctgttt acaaccaccg gcaaaaaaaa aaaaaaaaaa 3960
a 3961

<210> SEQ ID NO 64
<211> LENGTH: 4201
<212> TYPE: DNA
<213> ORGANISM: Homo sapiens

<400> SEQUENCE: 64
tccggcccgc acccaccccc aagaggggcc ttcagctttg gggctcagag gcacgacctc 60
ctggggaggg ttaaaaggca gacgcccccc cgccccccgc gcccccgcgc cccgactcct 120
tcgccgcctc cagcctctcg ccagtgggaa gcggggagca gccgcgcggc cggagtccgg 180
aggcgagggg aggtcggccg caacttcccc ggtccacctt aagaggacga tgtagccagc 240
tcgcagcgct gaccttagaa aaacaagttt gcgcaaagtg gagcggggac ccggcctctg 300
ggcagccccg gcggcgcttc cagtgccttc cagccctcgc gggcggcgca gccgcggccc 360
atggagcccg ccggcccggc ccccggccgc ctcgggccgc tgctctgcct gctgctcgcc 420
gcgtcctgcg cctggtcagg agtggcgggt gaggaggagc tgcaggtgat tcagcctgac 480
aagtccgtgt tggttgcagc tggagagaca gccactctgc gctgcactgc gacctctctg 540
atccctgtgg ggcccatcca gtggttcaga ggagctggac caggccggga attaatctac 600
aatcaaaaag aaggccactt cccccgggta acaactgttt cagacctcac aaagagaaac 660
aacatggact tttccatccg catcggtaac atcaccccag cagatgccgg cacctactac 720
tgtgtgaagt tccggaaagg gagccccgat gacgtggagt ttaagtctgg agcaggcact 780
gagctgtctg tgcgcgccaa accctctgcc cccgtggtat cgggccctgc ggcgagggcc 840
acacctcagc acacagtgag cttcacctgc gagtcccacg gcttctcacc cagagacatc 900
accctgaaat ggttcaaaaa tgggaatgag ctctcagact tccagaccaa cgtggacccc 960
gtaggagaga gcgtgtccta cagcatccac agcacagcca aggtggtgct gacccgcgag 1020
gacgttcact ctcaagtcat ctgcgaggtg gcccacgtca ccttgcaggg ggaccctctt 1080
cgtgggactg ccaacttgtc tgagaccatc cgagttccac ccaccttgga ggttactcaa 1140
cagcccgtga gggcagagaa ccaggtgaat gtcacctgcc aggtgaggaa gttctacccc 1200
cagagactac agctgacctg gttggagaat ggaaacgtgt cccggacaga aacggcctca 1260
accgttacag agaacaagga tggtacctac aactggatga gctggctcct ggtgaatgta 1320
tctgcccaca gggatgatgt gaagctcacc tgccaggtgg agcatgacgg gcagccagcg 1380
gtcagcaaaa gccatgacct gaaggtctca gcccacccga aggagcaggg ctcaaatacc 1440
gccgctgaga acactggatc taatgaacgg aacatctata ttgtggtggg tgtggtgtgc 1500
accttgctgg tggccctact gatggcggcc ctctacctcg tccgaatcag acagaagaaa 1560
gcccagggct ccacttcttc tacaaggttg catgagcccg agaagaatgc cagagaaata 1620
acacaggaca caaatgatat cacatatgca gacctgaacc tgcccaaggg gaagaagcct 1680
gctccccagg ctgcggagcc caacaaccac acggagtatg ccagcattca gaccagcccg 1740
cagcccgcgt cggaggacac cctcacctat gctgacctgg acatggtcca cctcaaccgg 1800
acccccaagc agccggcccc caagcctgag ccgtccttct cagagtacgc cagcgtccag 1860
gtcccgagga agtgaatggg accgtggttt gctctagcac ccatctctac gcgctttctt 1920
gtcccacagg gagccgccgt gatgagcaca gccaacccag ttcccggagg gctggggcgg 1980
tgcaggctct gggacccagg ggccagggtg gctcttctct ccccacccct ccttggctct 2040
ccagcacttc ctgggcagcc acggccccct ccccccacat tgccacatac ctggaggctg 2100
acgttgccaa accagccagg gaaccaacct gggaagtggc cagaactgcc tggggtccaa 2160
gaactcttgt gcctccgtcc atcaccatgt gggttttgaa gaccctcgac tgcctccccg 2220
atgctccgaa gcctgatctt ccagggtggg gaggagaaaa tcccacctcc cctgacctcc 2280
accacctcca ccaccaccac caccaccacc accaccacta ccaccaccac ccaactgggg 2340
ctagagtggg gaagatttcc cctttagatc aaactgcccc ttccatggaa aagctggaaa 2400
aaaactctgg aacccatatc caggcttggt gaggttgctg ccaacagtcc tggcctcccc 2460
catccctagg ctaaagagcc atgagtcctg gaggaggaga ggacccctcc caaaggactg 2520
gagacaaaac cctctgcttc cttgggtccc tccaagactc cctggggccc aactgtgttg 2580
ctccacccgg acccatctct cccttctaga cctgagcttg cccctccagc tagcactaag 2640
caacatctcg ctgtggacgc ctgtaaatta ctgagaaatg tgaaacgtgc aatcttgaaa 2700
ctgaggtgtt agaaaacttg atctgtggtg ttttgttttg tttttttttct taaaacaaca 2760
gcaacgtgat cttggctgtc tgtcatgtgt tgaagtccat ggttgggtct tgtgaagtct 2820
gaggtttaac agtttgttgt cctggaggga ttttcttaca gcgaagactt gagttcctcc 2880
aagtcccaga accccaagaa tgggcaagaa ggatcaggtc agccactccc tggagacaca 2940
gccttctggc tgggactgac ttggccatgt tctcagctga gccacgcggc tggtagtgca 3000
gccttctgtg accccgctgt ggtaagtcca gcctgcccag ggctgctgag ggctgcctct 3060
tgacagtgca gtcttatcga gacccaatgc ctcagtctgc tcatccgtaa agtggggata 3120
gtgaagatga cacccctccc caccacctct cataagcact ttaggaacac acagagggta 3180
gggatagtgg ccctggccgt ctatcctacc cctttagtga ccgcccccat cccggctttc 3240
tgagctgatc cttgaagaag aaatcttcca tttctgctct caaaccctac tgggatcaaa 3300
ctggaataaa ttgaagacag ccagggggat ggtgcagctg tgaagctcgg gctgattccc 3360
cctctgtccc agaaggttgg ccagagggtg tgacccagtt accctttaac cccccacccctt 3420
ccagtcgggt gtgagggcct gaccgggccc agggcaagca gatgtcgcaa gccctattta 3480
ttcagtcttc actataactc ttagagttga gacgctaatg ttcatgactc ctggccttgg 3540
gatgcccaag ggatttctgg ctcaggctgt aaaagtagct gagccatcct gcccattcct 3600
ggaggtccta caggtgaaac tgcaggagct cagcatagac ccagctctct gggggatggt 3660
cacctggtga tttcaatgat ggcatccagg aattagctga gccaacagac catgtggaca 3720
gctttggcca gagctcccgt gtggcatctg ggagccacag tgacccagcc acctggctca 3780
ggctagttcc aaattccaaa agattggctt gtaaaccttc gtctccctct cttttaccca 3840
gagacagcac atacgtgtgc acacgcatgc acacacacat tcagtatttt aaaagaatgt 3900
tttcttggtg ccattttcat tttattttat tttttaattc ttggaggggg aaataaggga 3960

```
ataaggccaa ggaagatgta tagctttagc tttagcctgg caacctggag aatccacata   4020

ccttgtgtat tgaaccccag gaaaaggaag aggtcgaacc aaccctgcgg aaggagcatg   4080

gtttcaggag tttattttaa gactgctggg aaggaaacag gccccatttt gtatatagtt   4140

gcaacttaaa ctttttggct tgcaaaatat ttttgtaata aagatttctg ggtaataatg   4200

a                                                                   4201
```

<210> SEQ ID NO 65
<211> LENGTH: 3333
<212> TYPE: DNA
<213> ORGANISM: Homo sapiens

<400> SEQUENCE: 65

```
gtggccgcgg ggcggtgtca tcgcccccgc cccgcccggt ccagccagct cggcccgggg     60

gcttcgggct gtcgggccgg cgctcccttc tctgccaggt ggcgagtaca cctgctcacg    120

taggcgtcat gaggtctccg gttcgagacc tggcccggaa cgatggcgag gagagcacgg    180

accgcacgcc tcttctaccg ggcgccccac gggccgaagc cgctccagtg tgctgctctg    240

ctcgttacaa cttagcaatt ttggcctttt ttggtttctt cattgtgtat gcattacgtg    300

tgaatctgag tgttgcgtta gtggatatgg tagattcaaa tacaacttta gaagataata    360

gaacttccaa ggcgtgtcca gagcattctg ctcccataaa agttcatcat aatcaaacgg    420

gtaagaagta ccaatgggat gcagaaactc aaggatggat tctcggttcc tttttttatg    480

gctacatcat cacacagatt cctggaggat atgttgccag caaaataggg gggaaaatgc    540

tgctaggatt tgggatcctt ggcactgctg tcctcaccct gttcactccc attgctgcag    600

atttaggagt tggaccactc attgtactca gagcactaga aggactagga gagggtgtta    660

catttccagc catgcatgcc atgtggtctt cttgggctcc ccctcttgaa agaagcaaac    720

ttcttagcat ttcatatgca ggagcacagc ttgggacagt aatttctctt cctctttctg    780

gaataatttg ctactatatg aattggactt atgtcttcta ctttttttggt actattggaa    840

tattttggtt tcttttgtgg atctggttag ttagtgacac accacaaaaa cacaagagaa    900

tttcccatta tgaaaaggaa tacattcttt catcattaag aaatcagctt tcttcacaga    960

agtcagtgcc gtgggtaccc attttaaaat ccctgccact ttgggctatc gtagttgcac   1020

acttttctta caactggact ttttatactt tattgacatt attgcctact tatatgaagg   1080

agatcctaag gttcaatgtt caagagaatg ggtttttatc ttcattgcct tatttaggct   1140

cttggttatg tatgatcctg tctggtcaag ctgctgacaa tttaagggca aaatggaatt   1200

tttcaacttt atgtgttcgc agaattttta gccttatagg aatgattgga cctgcagtat   1260

tcctggtagc tgctggcttc attggctgtg attattcttt ggccgttgct ttcctaacta   1320

tatcaacaac actgggaggc ttttgctctt ctggatttag catcaaccat ctggatattg   1380

ctccttcgta tgctggtatc ctcctgggca tcacaaatac atttgccact attccaggaa   1440

tggttgggcc cgtcattgct aaaagtctga cccctgataa cactgttgga gaatggcaaa   1500

ccgtgttcta tattgctgct gctattaatg tttttggtgc cattttcttt acactattcg   1560

ccaaaggtga agtacaaaac tgggctctca atgatcacca tggacacaga cactgaagga   1620

accaataaat aatcctgcct ctattaatgt atttttattt atcatgtaac ctcaaagtgc   1680

cttctgtatt gtgtaagcat tctatgtctt tttttaattg tacttgtatt agatttttaa   1740

ggcctataat catgaaatat cactagttgc cagaataata aaatgaactg tgtttaatta   1800

tgaataatat gtaagctagg acttctactt taggttcaca tacctgcctg ctagtcgggc   1860
```

aacatgaagt aggacagttc tgttgatttt ttagggccat actaaaggga atgagctgaa 1920
acagacctcc tgataccttt gcttaattaa actagatgat aattctcagg tactgataaa 1980
cacctgttgt tgttcacttt cctcataaaa attgtcagct ctctctgaca cttagacctc 2040
aaactttagc atctctgtgg agctgccatc cactgtataa tttcgcctgg caactggact 2100
gaggggagtg tgcccaggca gctgccaagc actccctccc tggcttcagg gtcagagtgc 2160
ccagcgttta tcagaggcag catccaagcc cagagccagt gtcgactctt cggctggtgc 2220
ctttcctctg aggggctatc aatgtgtaga taaagccctg agtaggcaag agcagtgaga 2280
tccactgcta tggtcttgat acatcctcaa actttccctt cccagcacag aggaatattg 2340
gctggcatgc aacctgcaaa agaaaaatgc gaagcggccg ggcacggtgg ctcatgcctg 2400
taatcccagc actttggggg gctgaggtgg gcgaatcatg agatcaggag ttcgagacca 2460
gcctggccag catggtgaaa ccccatctct actaaaaata caaaaaatta gctgggcgtg 2520
gtgacgggcg cctgtaatcc cagatactca ggaggctgag gtaggagaat cacttgaacc 2580
tgggaggtgg aagttgcagt gaaccaagat cacgccactg cactccagcc tgggcgatgg 2640
agcgagactc caactcaaaa aaaaaaaaag aataaagaaa gaaaagtgcg atgcccagtc 2700
aatcacaaat aagatcatcc tggtttaaat ctactctcac atggatcaca gtataaattt 2760
ctatgtgctg tgttttgttc gtttgtattt tgtagagatg ggtctcgtt ttgtcgccca 2820 ggctggtttt gaactcctgg cttcaagcga tcctcctgtc tcggcctcac aaagtgttga 2880
gactacaggc atgagccact gtgcccagcc tgttctatgt ttttaagcta cacgagaatt 2940 tttttttaa ttaattctca ctgtttgttc agtctgtctt catctaagtt tgtgttgcag 3000
tttaaagtta aagtgacttt taaaggccac atcacctgag actagggtaa tcatctttac 3060
ttctggttcc tgaaatcata tttttccagt ggaccatcct ccagtggctg tggttgttga 3120
gcatgctttc agaacaccta tgtggcttaa aacttagttt atgttttgtg ttcaacacta 3180
cgtgtaatat tttaaaactg tttaatgtga tgtgaataca tttatgtaca tttattttta 3240
aatttgtaaa tagctttaaa ttgctatggc aatgtttctt ttataaatca tcaaaataaa 3300
cctttgtgaa ttgaaaaaaa aaaaaaaaaa aaa 3333

<210> SEQ ID NO 66
<211> LENGTH: 3743
<212> TYPE: DNA
<213> ORGANISM: Homo sapiens

<400> SEQUENCE: 66
tttcttctag aagagctttg cgtcttaaac gcccataccg cagacagctg cctggcgggc 60
gacccagccc catcctgatg gccccaggac acaagcccag gagcgccccg gtgcgcgcgg 120
ttccgcggcc caggggcgcc gggtttggtg gcacagcgag ccccctttct ctagcgaaac 180
ctgtttccct ccaatcttgt ggttgcagct ttccgtacgt atgcaaccga ttataaagtc 240
gtgacccaga acagcagctc tggaaatgta acccatgaaa agatccccat aggcactgag 300
atagaaggga tgaacatttt aggattggtc ctgtttgctc tggtgttagg agtggcctta 360
aagaaactag gctccgaagg agaagacctc atccgtttct tcaattccct caacgaggcg 420
acgatggtgc tggtgtcctg gattatgtgc tcagcgaccc ttccctctat gatgaagtgc 480
attgaagaga acaatggtgt ggacaagagg atcagcaggt ttattctccc catcggggcc 540
accgtgaaca tggacggagc agccatcttc cagtgtgtgg ccgcggtgtt cattgcgcaa 600

-continued

```
ctcaacaacg tagagctcaa cgcaggacag attttcacca ttctagtgac tgccacagcg    660
tccagtgttg gagcagcagg cgtgccagct ggaggggtcc tcaccattgc cattatcctg    720
gaggccattg ggctgcctac tcatgacctg cctctgatcc tggctgtgga ctggattgtg    780
gaccggacca ccacggtggt gaatgtggaa ggggatgccc tgggtgcagg cattctccac    840
cacctgaatc agaaggcaac aaagaaaggc gagcaggaac ttgctgaggt gaaagtggaa    900
gccatcccca actgcaagtc tgaggaggag acatcgcccc tggtgacaca ccagaacccc    960
gctggccccg tggccagtgc cccagaactg gaatccaagg agtcggttct gtgatggggc   1020
tgggctttgg gcttgcctgc cagcagtgat gtcccaccct gttcacccag ccgccagtca   1080
tggacacagg gcactgccct tgccaacttt taccctccca agcaatgctt tggcccagtc   1140
gctggcctga ggcttacctc tcggcactgg cattgggctc cccagccgga actggttacc   1200
aaggacaagg acactctgac attcggcttg atccatgtcc aggtgcaact gtgtgtacac   1260
cagggatctg tttggaaaca accccttgag ctgccaggct caagaaatca tggactcaca   1320
gggtcctgtg tggttacatc ttggaaaaaa tgcagatgta tttcactctc cccggtcagc   1380
tctgcatcag gtgttttctg agcaaaccaa ggggggtttat agtcatctgt cgcattgcct   1440
cgagttgcag taattgaaaa aatgctcaaa ttcttagcca tggctggcct ttgctgagct   1500
gggactcagg tgtttaaaga gtttgtgcta tagctaggtg tggatagctt ctgatccctg   1560
ggttctggga gactgcaggt gccgcacatt gtcaagttag aaatactcca ggtgggtgtt   1620
agcactgtgg tggtctctgg tccacagcct taggtaaaca acttagattc tgaggtcaaa   1680
gaaaaaagga gagggaatgc agccttgtgg gggagaagcg gggcagaggg ttctctaatc   1740
taatcaggac aggacaggtt tcacatacaa ttgtcccagt tcgcatccca gccctggggc   1800
acttttctgc ttccttccag aggcctgggc ctctgataac actttggctt tttctccatt   1860
cacgctgatt tggcaaaagg ccagagatgg gcctccttcc ctggggaggt gtgatgtagt   1920
tatcacattc aggacccttg ttgatttatc atctattatt tgaattcaac tggacactct   1980
gtaaaatgct gcactgcagc aaaaacaaaa ccaccaccac cccagagaaa accatgtact   2040
aattggagtg gggtaccccc attcacaggt tcccaggtcc cctggctttg gctgatttca   2100
aaatatagag ccctttcttg ccagtacatc caagtttaaa attatcagcg aaatggtcca   2160
tgtttttcca attacctgct gacacggttc taagctaagt gaaggggaag atctgagagc   2220
gtgctgtttg tggctgttga tgcatattcg tgatgtaaca ggtcctgggg cctcacttta   2280
ccccatttgt aaaatggggc taatgtcacc tgcctcttac ctacctcaga gggatttggt   2340
gaagcaaact gttaatcttc gaaaacgacc atttcacttc ttggatatca agtgctaacc   2400
cagtatgttc ttctttttta tgtaagggac agctttctcc acagagtcct ttctgctggt   2460
gaggacagca tttctgagca gggctttgtt ctctatgtgc attaggactt ttatcatgcc   2520
cttgttctgt gtgtagttac ttgacagcat caaatgccgc ctcttcctaa tgtccttcaa   2580
gttttcatga actagcaacc ccaccttcca ccatggttct gggcgcctga ttttgctgtg   2640
actcccagac ccagccactg tttctgccac cctgtaacag gccattaaag ctccccagtg   2700
ttcagcctcc ttcactccct tgttttccct gttgctatgt gtcacctggg ccctacagac   2760
aggggcacac gcttatggat gtgtgtacca ttgagatgag aatgggtaga tggaacggag   2820
accatcaagc cacacccccct tcttaaaact ggggacatga gcctgagcag aaagggtgaa   2880
gaagagccat gggacacaga gttgacccag ccagggggaa agcccagctc tctttaaacc   2940
agctaagcca ttccagtctc ctgtgaagcc aaaagggacc aggaaccgtg caaaggaaac   3000
```

tggaaacttt tccccgctgg gtagagcatg ttgctgatac tcttctgttt tcaagggaaa 3060
caatcacatt gtttgattcc aaatggtaaa tgaacactca ctattcttca ggcttcagta 3120
aatctttttt tcttccttca tatatatata cacaacacac acacacatat gtatatctat 3180
acacacatgt gtgttgtgta tatgcatgtg tgtgtgtgcg tgtgtgtata gttttagctc 3240
caagccaagc aagtttgtgt ttggatagag gggaacttaa ctattaacta caagttgtat 3300
gtctgtggta tcttgatttt cccatttcta aagatgaatt tcacaaagcc ataaagcgtg 3360
aaattagagc tggacttaag actcattggc cgaccatcct gtgtcctggc ctggccctgc 3420
agtaagaagc gtgtctgggt ctggagaagg gtgcttccga gagtgtgcag gtggcccttc 3480
cccttggagg cgagaagaga gaatgtgctg tctatcttcc tggttttcag tccacagagt 3540
cggtagacca ggggttacgt gactggggaa aatctcacat ctccttgtct gaaaacattt 3600
cccctgctgt tctctttcta acatgttgtg gtaaatctgt tcagatactg ctcatctgac 3660
tgttttgtac atgtgacaat tgccttaaaa cctagcacag tcctcagaaa tgaataccgt 3720
gtttccactg gaaaaaaaaa aaa 3743

<210> SEQ ID NO 67
<211> LENGTH: 2214
<212> TYPE: DNA
<213> ORGANISM: Homo sapiens

<400> SEQUENCE: 67
cctgtttccc aggaacggtc cccggcttcg cgccccaatt tctaacagcc tgcctgtccc 60
ccgggaacgt tctaacatcc ttggggagcg ccccagctac aagacactgt cctgagaacg 120
ctgtcatcac ccgtagttgc aagtttcgga gcggcagtgg gaagcatgcg ggactacgac 180
gaggtgatcg ccttcctggg cgagtggggg cccttccagc gcctcatctt cttcctgctc 240
agcgccagca tcatccccaa tggcttcaat ggtatgtcag tcgtgttcct ggcggggacc 300
ccggagcacc gctgtcgagt gccggacgcc gcgaacctga gcagcgcctg gcgcaacaac 360
agtgtcccgc tgcggctgcg ggacggccgc gaggtgcccc acagctgcag ccgctaccgg 420
ctcgccacca tcgccaactt ctcggcgctc gggctggagc cggggcgcga cgtggacctg 480
gggcagctgg agcaggagag ctgcctggat ggctgggagt tcagccagga cgtctacctg 540
tccaccgtcg tgaccgagtg gaatctggtg tgtgaggaca actggaaggt gcccctcacc 600
acctccctgt tcttcgtagg cgtgctcctc ggctccttcg tgtccgggca gctgtcagac 660
aggtttggca ggaagaacgt tctcttcgca accatggctg tacagactgg cttcagcttc 720
ctgcagattt tctccatcag ctgggagatg ttcactgtgt tatttgtcat cgtgggcatg 780
ggccagatct ccaactatgt ggtagccttc atactaggaa cagaaattct tggcaagtca 840
gttcgtatta tattctctac attaggagtg tgcacatttt ttgcagttgg ctatatgctg 900
ctgccactgt ttgcttactt catcagagac tggcggatgc tgctgctggc gctgacggtg 960
ccgggagtgc tgtgtgtccc gctgtggtgg ttcattcctg aatctccccg atggctgata 1020
tcccagagaa gatttagaga ggctgaagat atcatccaaa aagctgcaaa aatgaacaac 1080
atagctgtac cagcagtgat atttgattct gtggaggagc taaatcccct gaagcagcag 1140
aaagctttca ttctggacct gttcaggact cggaatattg ccataatgac cattatgtct 1200
ttgctgctat ggatgctgac ctcagtgggt tactttgctc tgtctctgga tgctcctaat 1260
ttacatggag atgcctacct gaactgtttc ctctctgcct tgattgaaat tccagcttac 1320

```
attacagcct ggctgctatt gcgaaccctg cccaggcgtt atatcatagc tgcagtactg   1380
ttctggggag gaggtgtgct tctcttcatt caactggtac ctgtggatta ttacttctta   1440
tccattggtc tggtcatgct gggaaaattt gggatcacct ctgctttctc catgctgtat   1500
gtcttcactg ctgagctcta cccaaccctg gtcaggaaca tggcggtggg ggtcacatcc   1560
acggcctcca gagtgggcag catcattgcc ccctactttg tttacctcgg tgcttacaac   1620
agaatgctgc cctacatcgt catgggtagt ctgactgtcc tgattggaat cctcacccct   1680
tttttccctg aaagtttggg aatgactctt ccagaaacct tagagcagat gcagaaagtg   1740
aaatggttca gatctgggaa aaaaacaaga gactcaatgg agacagaaga aaatcccaag   1800
gttctaataa ctgcattctg aaaaaatatc taccccattt ggtgaagtga aaaacagaaa   1860
aataagaccc tgtggagaaa ttcgttgttc ccactgaaat ggactgactg taacgattga   1920
caccaaaatg aaccttgcta tcaagaaatg ctcgtcatac agtaaactct ggatgattct   1980
tccagataat gtccttgctt tacaaaccaa ccatttctag agagtctcct tactcattaa   2040
ttcaatgaaa tggattggta agatgtcttg aaaacatgtt agtcaaggac tggtaaaata   2100
catataaaga ttaacactca tttccaatca tacaaatact atccaaataa aaataacatc   2160
attgtattaa cgcaaatatt aggtgacaac aaaaaaaaaa aaaaaaaaaa aaaa         2214
```

<210> SEQ ID NO 68
<211> LENGTH: 4797
<212> TYPE: DNA
<213> ORGANISM: Homo sapiens

<400> SEQUENCE: 68

```
ggcgggaggg ggcgggaaat cctcggcctc ggtggcggtg gtggacacgt cgagccgggt     60
agaagtggag gggccgttcg aagagtcgtg agggggtgac gggttaagat tcggagagag    120
aggtgctagt ggctggactt gacctggaaa gaatcttctg ctgactctca acttttcctg    180
gaaaaaatgg atcattccca ccatatgggg atgagctata tggactccaa cagtaccatg    240
caaccttctc accatcaccc aaccacttca gcctcacact cccatggtgg aggagacagc    300
agcatgatga tgatgcctat gaccttctac tttggcttta agaatgtgga actactgttt    360
tccggtttgg tgatcaatac agctggagaa atggctggag cttttgtggc agtgttttta    420
ctagcaatgt tctatgaagg actcaagata gcccgagaga gcctgctgcg taagtcacaa    480
gtcagcattc gctacaattc catgcctgtc ccaggaccaa atggaaccat ccttatggag    540
acacacaaaa ctgttgggca acagatgctg agctttcctc acctcctgca aacagtgctg    600
cacatcatcc aggtggtcat aagctacttc ctcatgctca tcttcatgac ctacaacggg    660
tacctctgca ttgcagtagc agcaggggcc ggtacaggat acttcctctt cagctggaag    720
aaggcagtgg tagtggatat cacagagcat tgccattgac atcaaactct atggcgtggc    780
cttatcgatt gcagtgggaa gttgttgaag acttgaagac gtgattcctg ctccaatcat    840
cccttcttgc tcctctttgt gcacgtacac acacacacac acacacacac acacacaccc    900
ctgctcaaca gaggtttagt ttacagtctc tgaactaaag tagtaacctc ccaaattgtt    960
ttttctaata agctgagatt cccatttctc ttaaggagaa gccacccatg agatgtcttt   1020
tccttctcca tcatcttaga gccaagttat atgttcttgt ctaatccatg tagctttttg   1080
ttcaatgact tgatcatctg cttccttttt gaatttttaa cagatagtaa gtaaatttgg   1140
tggtttttttc ccctgggtca gtgatggaaa ggggttaact tcagccagga ttgatggcag  1200
ctgagggaaa ttcttgccca actaaaccca gaactcaaac ttaacattag aaaataaggt   1260
```

ccagggccgg acacagtggc ccatgcctgt aatcccagca ctttgggggg ccaaggcagg 1320
ctggatcacc tgaggacagg agttcgagac cagtctggcc aacatgggga aaccccgtct 1380
ctactaaaaa tacaaaaatt agccgggcat ggtggtgggc gcctgtaatc ccagctactc 1440
agaaggctga ggcaggagaa tcacttgaac ctaggaggcg gaggttgcag tgagccaaga 1500
tggcgccatt gcactccagc ctgggtgaca agagtgaaac tccatctcaa aaaaaaagaa 1560
aagaaggtcc agcttttgga ttcaatgagt gggaaataca ttgtgccttt ctctagatgt 1620
gatacgttat accaaaatct ttgtagtgtg cagagcggtg gtttgagact aaatacaggc 1680
ttagaacttg cagagtgtgt attcttggat ggctgatgca tcgacttgca ttcccactta 1740
acactttgat tagcatgaac ttgccaatca aaaaatgaca atcaatttga gaaaatagaa 1800
atagatattt ttaaataaaa ccattcacag tttactttgt cttgatacct tggtttgtcc 1860
cagctgaagt gaagcaagag agtttgaatt aatttttcca ttataatgtt ttcgcatgtc 1920
tgcctctaaa actgtgattt tcaagcttta gcgtgcatca gaatcacctg tagggcttgt 1980
taaaacacta attgctgggc ctcaacccaa aagcccccaa agtggcactt ctgagttcct 2040
gctgatgtta caagggacca cacttttgag aatctgtgct ttaagctaag gaaatattgc 2100
ctggtgggtt ggctgcctgg tattgggcat ggaaatttga attgctgatt ggtagatggt 2160
gtgtctggac ttaactcacg tagtaaatac tgctgatcaa tacctaatca ttccacattt 2220
attgagctcc acctgtgtgt atgtgtaccc aagcacacat gtgtgaaggg ctatagccaa 2280
agtattttta ctagcctgta tgaaatcact agtccttatt tttaaaggtc tatggtttct 2340
tggaagtagt ttgattgttg agagagacct ttgatctgca gtgtaaatct accagtcatg 2400
ggccagaagg gcaaaagccc agctttctct ttggaaagac tcaggctgtg gtttgttgat 2460
ggccaggttt tcctcaggct ccaacaactg tgcttatacc aagcagatcc tcatcctcca 2520
tataatcatc tttgttattc gtgggggttt aattacatta caagtggcca aaacccctgt 2580
tctcagtgaa gaaccacatt ggatttgtat tctgttcagt tgtagtctac actgcagtct 2640
tattcctggt tcaaactacc tctttaaatt gatttgtctt gtgctggtct gttaaatcct 2700
gccctccttg gtgctagatc cagttgtgcc tcagggcaga ggaaacaaaa cacagctatc 2760
ctgttggcct gtgttgtggt tttgaagttt gtactttctc tgtgggtgcc agttaaatat 2820
tggagagcaa ggaatgtgga cttgtatggc tttgaaccaa gagagggtta tgagcctact 2880
ggattgaggt taaaatccaa gaaccaacat ttagagcttt gtgcttttct ctcattccat 2940
cactttgtaa tgatgatact taacatgagc agggtgaatg acaggtactg acgaagtcca 3000
acacaaaggt ataatacagc ctgttgtcta aagccaagga gtcataaaac catgagaaat 3060
aaataggaat caatagttag tagtgacatt ggtgctctct agaaatctca gcatgagctg 3120
ctatagaata ccctcccagc aacaaaacct aatcagtaag gccagctaga cccaatggct 3180
catgcctgta atcccaacac tttgggaggc caaggtggga ggatggcttg tgtccagaag 3240
ttcgagacca gcctggacaa catagtgaga tcctatctct ataaaaaatc aaaaattagc 3300
caggcatggt ggtgcatacc tatagtcctg gctatttggg aggctgaggc aggaggattg 3360
ctttagccct ggaggtcgag gctgcagtaa gccatgattg cgccactgca ctcagcccgg 3420
gtgacaaagc aagaccctgt ctcagaaaaa aagaaaattc aaggccagtt aagacaaaat 3480
gctatgactt tgaaattcac agaaagaaat aacagtttag attaggtctt caggtattca 3540
ggatagagat aatctcctga aaaacctgaa tttcagagat tcttagactg gctgccaaag 3600

-continued gatgaagcta gtgaaggaga aaaagcttaa attccatctt gagctcttgg attgtgataa 3660
tacaatgatt tcattaactt ttcatttctg tatacctgtt catttggaat ttaatgcttg 3720
acttctttgt tcattttgga tctaaacttc tcttttcttc cttccccatt cacatctatt 3780
agaagactgc atcaccattt ctttggcccc cttactctgt tgtcctttcc cttttctttc 3840
agttttttta atcgcatgtc tagtatatta agtctccata gccctcctga tgcagtagac 3900
agtgctatgc tgtggatata ataccaacca gaaattggca tttataaacc tgttaagaga 3960
ctttaagcat gcttcaagag gcagttgacc cactggaatt tctataaggc tggtacccttt 4020 cccagagtta cagaatctta ggtgccgtct ctagtctgtg agggaggaac tcccagcatc 4080
cccattgccc acaaatggaa tcctcactgt atccactagg agattagaaa ttaaggtttc 4140
ttcactactt ctatggtagg gttgtctgaa attccctttc aggctgtggg tactggtctt 4200
gggttctagt cataaggggt tccttataag gagcaggcgg aggggagtac actttcatgt 4260
gatttaattt tgatcctgcc ctctccagct gctccttcaa aagatacatc aaaagataga 4320
aactctgggc tgggcacagt ggctcacaca ctttgggagg ccaagcgggg gtgcagatca 4380
cctgaggtca ggagtttgag accagcctgg ccaatgtggt gaaaccccat ctctactaaa 4440
aatacaaaaa ttagctgggc gtggtggtgc atgcctgtaa tcccagctac tcgggaggct 4500
gaggcaggag aatcgcttga acccaggagg cggaggttgc agtgagccaa gatggcgcca 4560
ttgcactcca gcctgggcga caagagcaaa actccgtctc aaaaaaaaaa aaaagataca 4620
aagtctgcat ttgatataat gccttaatta ctgggtctac aattaatgtt gactgtttta 4680
gattgtaagc tcctggagag cagtattgct gtagtaggaa tgttttaaca gtgtcatatg 4740
aaaaagaaca aaataaatat tttgattttg tgattctaaa aaaaaaaaaa aaaaaaa 4797

<210> SEQ ID NO 69
<211> LENGTH: 2347
<212> TYPE: DNA
<213> ORGANISM: Homo sapiens

<400> SEQUENCE: 69
ggcgtgggac gtgctgcggc gtcctagctg gcttacaggg cggcggcggg gtgtgtgtcc 60
tctgttaaga gtgctactcg cccggggttg atctgtgcat gccactcctg ggtcagacgg 120
tgaggtcggc gtctgcgagg acgcggcggt ggagtagaag ggcagccgga gacaggcccg 180
gcgccccttc cgaggctaga cggccccagc ttcgcgggga tcatggcatt gctggtggac 240
cgagtgcggg gccactggcg aatcgccgcc gggctcctgt tcaacctgct ggtgtccatc 300
tgcattgtgt tcctcaacaa atggatttat gtgtaccacg gcttccccaa catgagcctg 360
accctggtgc acttcgtggt cacctggctg ggcttgtata tctgccagaa gctggacatc 420
tttgccccca aaagtctgcc gccctccagg ctcctcctcc tggccctcag cttctgtggc 480
tttgtggtct tcactaacct ttctctgcag aacaacacca taggcaccta tcagctggcc 540
aaggccatga ccacgccggt gatcatagcc atccagacct tctgctacca gaaaaccttc 600
tccaccagaa tccagctcac gctgattcct ataactttag gtgtaatcct aaattcttat 660
tacgatgtga agtttaattt ccttggaatg gtgtttgctg ctcttggtgt tttagttaca 720
tccctttatc aagtgtgggt aggagccaaa cagcatgaat tacaagtgaa ctcaatgcag 780
ctgctgtact accaggctcc gatgtcatct gccatgttgc tggttgctgt gcccttcttt 840
gagccagtgt ttggagaagg aggaatattt ggtccctggt cagtttctgc tttgcttatg 900
gtgctgctat ctggagtaat agctttcatg gtgaacttat caatttattg gatcattggg 960
aacacttcac ctgtcaccta taacatgttc ggacacttca agttctgcat tactttattc 1020
ggaggatatg ttttatttaa ggatccactg tccattaatc aggcccttgg cattttatgt 1080
acattatttg gcattctcgc ctatacccac tttaagctca gtgaacagga aggaagtagg 1140
agtaaactgg cacaacgtcc ttaattgggt ttttgtggag aaaagaatgt tgtcccaaga 1200
agataaaaaa tattgttaag tgtgcaagtt attaaaaaaa aaaaattggg ccaggcacgg 1260
tggctcacgc ctgtaatccc agcactttgg gaggccaagg ccagcggatc acttgaggtc 1320
aggagttcga gaccagcctg accaacatgg agaaaccctg tctcaactaa taatacaaaa 1380
ttagccaggc gtggtggcgc atgcctgtaa tcccagctac tcgggaggct gaggcaggag 1440
aatcacttga acccgggagg cggcggttgc agtgagccga gatcgtacca ttgcactcca 1500
gcctgggcaa caagagcgaa actccatttc aaaaaaaaaa aattggtgac agactcaatg 1560
atggaatgat ttgtcggaat taacacaaag cagattttat tcatataatg actttttttt 1620
aagagtctct tttttaaaaa aacttaattc tctaaaaccg aaatggttca tgcttctttt 1680
taaaaatgat tgtataaaat gtatggaatg gttagcctgg tgtggtggtg cacacctgta 1740
atcccagcta cttgggagac tgagacatga gaatcgcttg agcctgggag gcggaggttg 1800
caatgagcca agatcgtacc actgcactcc agcctgggcg acagagcaag acactgtctc 1860
tctctctctc tccatatata tatgtgtgtg tgtgtatata tatatatatg tgtgtgtgtg 1920
tgtgtgtata catatataca catatataca cacacacata catatacatg tgtatatata 1980
taccatccca tatatatgtg ggatatatat atatatatat atggatatgg ttatatatat 2040
gggatggttt ggttggtccc agcaaagtat atgaaaatta aagttctgtg ataatgacaa 2100
aggaattgct gttactgtac tgcaaatatg ctgtgggttc tcggtgttca aactcttcta 2160
aggaaggaca cacagtagct ctctgcttgc tgatagatgg tttcccagtg tgagatttgt 2220
tattttgatc agagtattca aatcagaatt taaatctagt gtttctattt tagtttagct 2280
tcctgattta tataaatgaa atctcattta taaagtataa taaagatgac tgtaagacaa 2340
aatccaa 2347

<210> SEQ ID NO 70
<211> LENGTH: 1681
<212> TYPE: DNA
<213> ORGANISM: Homo sapiens

<400> SEQUENCE: 70
agtcctgggc gaagggggcg gtggttcccc gcggcgctgc gcgcggcggt aattagtgat 60
tgtcttccag cttcgcgaag gctaggggcg cggctgccgg gtggctgcgc ggcgctgccc 120
ccggaccgag gggcagccaa cccaatgaaa ccaccgcgtg ttcgcgcctg gtagagattt 180
ctcgaagaca ccagtgggcc cgttccgagc cctctggacc gcccgtgtgg aaccaaacct 240
gcgcgcgtgg ccgggccgtg ggacaacgag gccgcggaga ctgtttcaat gcatcaaagc 300
tactgacatc tcatggcatg ggcatccagg ttccgctgaa tgcaacagag ttcaactatc 360
tctgtccagc catcatcaac caaattgatg ctagatcttg tctgattcat acaagtgaaa 420
agaaggctga aatccctcca aagacctatt cattacaaat agcctgggtt ggtggtttta 480
tagccatttc catcatcagt ttcctgtctc tgctgggggt tatcttagtg cctctcatga 540
atcgggtgtt tttcaaattt ctcctgagtt tccttgtggc actggccgtt gggactttga 600
gtggtgatgc tttttttacac cttcttccac attctcatgc aagtcaccac catagtcata 660

-continued

```
gccatgaaga accagcaatg gaaatgaaaa gaggaccact tttcagtcat ctgtcttctc    720
aaaacataga agaaagtgcc tattttgatt ccacgtggaa gggtctaaca gctctaggag    780
gcctgtattt catgtttctt gttgaacatg tcctcacatt gatcaaacaa tttaaagata    840
agaagaaaaa gaatcagaag aaacctgaaa atgatgatga tgtggagatt aagaagcagt    900
tgtccaagta tgaatctcaa ctttcaacaa atgaggagaa agtagataca gatgatcgaa    960
ctgaaggcta tttacgagca gactcacaag agccctccca ctttgattct cagcagcctg   1020
cagtcttgga agaagaagag gtcatgatag ctcatgctca tccacaggaa gtctacaatg   1080
aatatgtacc cagagggtgc aagaataaat gccattcaca tttccacgat acactcggcc   1140
agtcagacga tctcattcac caccatcatg actaccatca tattctccat catcaccacc   1200
accaaaacca ccatcctcac agtcacagcc agcgctactc tcgggaggag ctgaaagatg   1260
ccggcgtcgc cactctggcc tggatggtga taatgggtga tggcctgcac aatttcagcg   1320
atggcctagc aattggtgct gcttttactg aaggcttatc aagtggttta agtacttctg   1380
ttgctgtgtt ctgtcatgag ttgcctcatg aattaggtga ctttgctgtt ctactaaagg   1440
ctggcatgac cgttaagcag gctgtccttt ataatgcatt gtcagccatg ctggcgtatc   1500
ttggaatggc aacaggaatt ttcattggtc attatgctga aaatgtttct atgtggatat   1560
ttgcacttac tgctggctta ttcatgtatg ttgctctggt tgatatggta agtttttaag   1620
aagtcttatt acattattga ccaacaataa aatagagaaa atattcaaaa aaaaaaaaaa   1680
a                                                                   1681
```

<210> SEQ ID NO 71
<211> LENGTH: 6512
<212> TYPE: DNA
<213> ORGANISM: Homo sapiens

<400> SEQUENCE: 71

```
gagagctgcc tgctcagaca acagacacgc gaggtcagga agaagccgct tataaattac     60
cgcttccttc gcgccgccgc caacgccgag ccccgaggac cgcaagccca gaggacaagc    120
tgcgccaaga gggagtgcgg agcgttcacc cagcgggtca gagagcgagc gggcaggcag    180
cccccggccg gcggaacccg gcacagccga gcagagcgcg ggcggcgccg cagccacccc    240
agatccagaa ccagaaccac agcccttctg aggagctccc aaaccaagga gatggccacc    300
aaggagaagc tgcagtgtct gaaagatttc cacaaggaca tcctgaagcc ctcaccaggg    360
aagagcccag gcacgcggcc tgaggacgag gctgagggaa aacctccgca gagggagaag    420
tggtctagca agatcgactt tgtgctctct gtggctggcg gcttcgtggg cttgggcaac    480
gtctggcgct tcccgtacct ctgctacaag aatggtggag gtgcgtttct cataccgtat    540
tttattttcc tgtttgggag cggcctgcct gtgtttttct tggagatcat cataggccag    600
tacacctctg aagggggcat cacctgctgg gaaaagatct gccccttgtt ctctggtatc    660
ggctatgcct ccgttgtaat tgtgtccctc ctgaatgtct actacatcgt catcctggcc    720
tgggccacat actacctgtt ccagtccttc cagaaggagc tgccctgggc acactgcaac    780
cacagctgga acacacctca ctgcatggag gacaccatgc gcaagaacaa gagtgtctgg    840
atcaccatca gctccaccaa cttcacctcc cctgtcatcg agttctggga gcgcaacgtg    900
ctgagcttgt cccctggaat cgaccaccca ggctctctga aatgggacct cgctctctgc    960
cttcttttag tctggctagt gtgtttcttc tgcatctgga agggcgtcag gtccactggg   1020
aaggtcgtct acttcacagc cacttttcca ttcgccatgc tcctggtgct gctggtccga   1080
```

-continued

```
gggctgacgc tgccgggcgc gggcgcaggc atcaagttct atctgtatcc tgacatcacc   1140
cgccttgagg acccacaggt gtggattgac gctgggactc agatattctt ctcttatgcc   1200
atctgcctgg gggctatgac ctcgctgggg agctacaaca agtacaagta taactcgtac   1260
agggactgta tgctgctggg atgcctgaac agtggtacca gttttgtgtc tggcttcgca   1320
attttttcca tcctgggctt catggcacaa gagcaagggg tggacattgc tgatgtggct   1380
gagtcaggtc ctggcctggc cttcattgcc tacccaaaag ctgtgacaat gatgccgctg   1440
cccacatttt ggtccattct ttttttttatt atgcttctct tgcttggact ggatagccag   1500
tttgttgaag ttgaaggaca gatcacatcc ttggttgatc tttacccatc cttcctaagg   1560
aagggttatc gtcgggaaat cttcatcgcc ttcgtgtgta gcatcagcta cctgctgggg   1620
ctgacgatgg tgacggaggg tggcatgtat gtgtttcagc tctttgacta ctatgcagct   1680
agcggtgtat gccttttgtg ggttgcattc tttgaatgtt ttgttattgc ctggatatat   1740
ggaggtgata acctttatga tggtattgag gacatgattg gctatcggcc cgggccctgg   1800
atgaagtaca gctgggctgt gatcactcca gttctctgtg ttggatgttt catcttctcg   1860
ctcgtcaagt acgtacccct gacctacaac aaaacatacg tgtaccccaa ctgggccatt   1920
gggctgggct ggagcctggc cctttcctcc atgctctgcg ttcccttggt catcgtcatc   1980
cgcctctgcc agactgaggg gccgttcctt gtgagagtca agtacctgct gaccccaagg   2040
gaacccaacc gctgggctgt ggagcgcgag ggagccacac cttacaactc tcgcaccgtc   2100
atgaacggcg ctctcgtgaa accgacccac atcattgtgg agaccatgat gtgagctctc   2160
tcgggtcgac ggggccggcg gctttcctgc tgtttactaa cattagattc tcataggacc   2220
aggtttacag agctttatat ttgcactagg attttttttt ttttgtaatt gtcacagaaa   2280
atgtaattgt gggtatgtgt gcgtgcgtgt gtgtgtgtgt gtgtatcgtg tgtgtgtgtt   2340
ttgttttgat ttgggggata ttttgtacaa aaagaaaacc cacgggaaga tgtccgtgga   2400
gaggcagagc tttcatactg aattagatgt attttatggg aatttggtaa atttttcttt   2460
gtattttttt ttttacatat aagtatatat acacttagag attgtcatat acttttacca   2520
cttgaattga tcttcttgcc agcaatagat ctcattttca aaagcaattc ttcggtgctg   2580
tgtagctggc agaaagttct gtccagtaaa cgcaggatgg aattttcctg ggactctaca   2640
cccatcttaa ggtggtatac cttccaaatc ctggttcaga tggaagaaat agcaggagag   2700
aggacccatt agctggcaga cccaggggga agaaaggagg gctgtgagga gatacctcat   2760
taaacttggc ttagtgaaga agagagatgc caaaggaatg aaccaaccct tcacataaag   2820
gagactggct gaagctgaat gaggaggccc tatagcagaa gtctgattct aagagcagta   2880
gaaacttgta ccagaagcaa aatcccactt ttaattttga gatggtgagt ggatagtcag   2940
tagaccgtca gaaccactgg ccagagaggg agctgctaga gatccaagaa ggctggcagg   3000
agtgaggctc acaactcagc ctcgcaagag gtggcagagg cacaggaggc cacagtcctt   3060
cctggggcat tccaggcaga gaaggagcag aggctctccc ggcaggagct ggggtctcag   3120
ggctcagatg agtctgttgc atttgaatgg ggtcatagca ggttctggtc attccccaag   3180
caacatctca gcatctctta aagttgcctg caggaatgaa gcatgacata cctgttgagg   3240
gactagggga gtggtgggga ggtgagtgga ccaaaggata taggccccag gcatgcagat   3300
gggcccggtg tcggggaggg gtgctttctt tcctcatctc cccactcccc actctcagcc   3360
tgggagactc ctgccaagcc ctcattaaag atgccaccct gggctgccct ggcacctagc   3420
```

aaggcacacc aagaacagct tttgagtctg tatcctccac tgggggaagt gctcccagtt 3480
cagaacaagg gcagcccgtg gtgctgacct aggatataac aaagctcttc acttcaaaac 3540
ccctgcaata gctgggttta cagacattta ccacctgcgg acccaaaaga gaaggcctag 3600
gagagttttc tagaaggttg ggattgtcag ggtcctggcc cctcagaact ggcttgatca 3660
agggccttat gtggagcaga ggttgtctct gaaccaggag agaaggtact atacctttca 3720
aatccccagg gcagacacac ccccacccag cccctatttg gacctaaact gtgccatttg 3780
aacagtcact tccaagctca gtctaaatga aaccgaaacg tgaccacgca caaaggcagt 3840
cactgcctcg aggggtgcag accgcagaat tttcacagca ggggctcttg gaaccctgga 3900
aaccccccttc ttaaatttgg gaggaggagt atgcctttgg tgtcccccctc ccaaggggca 3960
attctgaacc ccatctttgg caggcataca tatttcactg tttccaaagc tatctactct 4020
gccaaacaac acccagtcct attccaaact ctcaacgatt ctatcttgtt cctgtttttc 4080
tatgtattta tggttgccgt ttgtgtctga tttgatttta ctgtttttc cctgatttta 4140
tggagtagca ttgtgacctg ttttcctttg tcttatataa ctttagtaaa ctaaccactg 4200
tcaatgattg agggcaggtg gcacgtgggg aagaggggac ttggcacgca gtggctacct 4260
gggcatttgt ggtcatttca gtttccatct ccccagcggg ggctccctgg gtgaaaggcc 4320
acagtatttt gggttggtag gcaaattgca acattctgga catggcctga ggaaggcctc 4380
ttcttataag attctcagac caaattctag accaaagaca caggcagacc aagtccccag 4440
gccccgcctg gaaggaagtc gttcctcaac tctccccaag gcacctgtct ccaatcagag 4500
ccctctcgcc cagccagccc tggctctgtg tgcagagcat agctctgcga gtacctgtgt 4560
aataatgctc aaccttcatg tctccgtata aacgaaactt tccatgagag ctcatgactc 4620
tggtccacct gtctatagag aatgggcaaa gtccttcacc tgctttctgc ttgggatggg 4680
tcagaaatgc tgatgcccgc acatagccca gccagccaga tctggaaagg aagcgagggg 4740
gttgtttaaa tcaatttttt aagatgaaga agtgggagac actgcgttga gatgggccat 4800
gctagggcca cagagatttc ctgacggtca gggagagaag ggcctccagg gtcccctaac 4860
ccaacgccct tgttgtaaat gaggtaactg aggctcaggg aggcactgtg agccaggaat 4920
ggattttctt gaaacagctc tagctgcagg ttctccgagg taggtgcagg gaatggtgag 4980
tgtctaacca gggctacatc cagcaacatc ctcaaggtct tcctgacaac caaagacaag 5040
cctttatgga aaaggaaatg cgctcccctc catgttcagg gatgagggga gcagcagcag 5100
ccacactccc accatcctca cagaattcct ggacccatgc ggtggctccg tgagctgggt 5160
gactccagcc tcacctgcac accccagccc tgcacggggc cctccttcct cccagcagcc 5220
cttggtgagc taggaattga gatccctgtt tgtgaaagag ggaactgagg tgcagagaag 5280
ccagaggtgt gccagatcct taggcaggat ttagatgaag tcgccctggc tccagactga 5340
ccccgaggct ctgcggggag tttccaggca gcaggaagtg gccttggatg ctctccttcc 5400
aggacagcat aacccctggg ccatgtgcag ctccttcact gccccctgga tccccagcat 5460
acccccaaag acagtgggga aacacaaggg gagagcacag catggcccct ccagcccact 5520
tcagggcact cttgtatcac ccgggtaccg ccacactggt cccccaccca gccagcatct 5580
cccagcacag cccctctccc tggggaaatg ctctgggtag ccagtctaaa ggcagaggca 5640
cctaactgct ccccgcagcc caccccaccc aagattcaga cacaagccag gaaaggaccc 5700
aagagaaaat ccttcaaggt ggcctgaggt cccatccctc cctcagaccc atgtggtccc 5760
aggccaggct gcctgggaca cggtaaatac cactgtgtgc aaaaatcgaa gtacaaaacc 5820

```
acaagactaa acaaaacaaa cccagagagc caaacttgta gaggtgggca gtccagaaag   5880

cagggggcag ccctccccct ttccttctct ccctgatcct cagaatatat attgttgtaa   5940

taggaagcat ttttgcattg ttctcttgtg ggtgtcacta cagacatgtt ctggcgtgtt   6000

ctccgaggga tggagcatcc tgttatatat ttgacttcaa attgagatgt tggcttcatt   6060

tttttttttt acccaattaa tctcccaatc cctagcaact gtgactctgt atttagcaca   6120

agagaaagct gagaatgtgg gtcttgcctc cttccagaaa tatgtctggc tcatcaggac   6180

attttttttaa aacttcaaaa tatttttaag atattttaaa cttttataaa aaaaaaatca   6240

accaacaaga gacttttctg aggaggaaca tttgtatttg aacaagatcc ttggtgtgta   6300

gttcagtctt gcagtataca agcttttgtg tataaatgtt ttatgatatg attccctgta   6360

ttttgcaggg gtttttttct cttttgcttt ttagataaat atgtatatca atattttaaa   6420

ttcatctttg cttttttttag aggagtttgt aatcacctta taacatgaaa ataaacattt   6480

ccttttttaac atccaaaaaa aaaaaaaaaa aa                                6512
```

```
<210> SEQ ID NO 72
<211> LENGTH: 3550
<212> TYPE: DNA
<213> ORGANISM: Homo sapiens

<400> SEQUENCE: 72

gccgggcccc gccgccgccc gcgcgccccc gggcccccga cacacatgag attcttcagg     60

ctcactttca agtgcttcgt ggactgcttc tgactgcgcc gcccgcgccc cgcaccccgc    120

cgcccgcccg ccgccccgtc ccccggcccg gccgcccccc ggcccccggc cggcccgcgc    180

cctcggggcc ctccccggtg ccgccggtgc cccccgcctg accgccgccc cccgtgaggc    240

gccgcgaccc cggcccggcc gtgcggcccg ccgaggccat ggcgaagaag agcgccgaga    300

acggcatcta tagcgtgtcc ggcgacgaga agaagggccc cctcatcgcg cccgggcccg    360

acggggcccc ggccaagggc gacggccccg tgggcctggg gacacccggc ggccgcctgg    420

ccgtgccgcc gcgcgagacc tggacgcgcc agatggactt catcatgtcg tgcgtgggct    480

tcgccgtggg cttgggcaac gtgtggcgct tcccctacct gtgctacaag aacggcggag    540

gtgtgttcct tattccctac gtcctgatcg ccctggttgg aggaatcccc attttcttct    600

tagagatctc gctgggccag ttcatgaagg ccggcagcat caatgtctgg aacatctgtc    660

ccctgttcaa aggcctgggc tacgcctcca tggtgatcgt cttctactgc aacacctact    720

acatcatggt gctggcctgg ggcttctatt acctggtcaa gtcctttacc accacgctgc    780

cctgggccac atgtggccac acctggaaca ctcccgactg cgtggagatc ttccgccatg    840

aagactgtgc caatgccagc ctggccaacc tcacctgtga ccagcttgct gaccgccggt    900

cccctgtcat cgagttctgg gagaacaaag tcttgaggct gtctggggga ctggaggtgc    960

caggggccct caactgggag gtgacccttt gtctgctggc ctgctgggtg ctggtctact   1020

tctgtgtctg gaagggggtc aaatccacgg gaaagatcgt gtacttcact gctacattcc   1080

cctacgtggt cctggtcgtg ctgctggtgc gtggagtgct gctgcctggc gccctggatg   1140

gcatcattta ctatctcaag cctgactggt caaagctggg gtcccctcag gtgtggatag   1200

atgcggggac ccagattttc ttttcttacg ccattggcct gggggccctc acagccctgg   1260

gcagctacaa ccgcttcaac aacaactgct acaatgggac cagcttcttt gctggcttcg   1320

tggtcttctc catcctgggc ttcatggctg cagagcaggg cgtgcacatc tccaaggtgg   1380
```

-continued

```
cagagtcagg gccgggcctg gccttcatcg cctacccgcg ggctgtcacg ctgatgccag   1440
tggccccact ctgggctgcc ctgttcttct tcatgctgtt gctgcttggt ctcgacagcc   1500
agtttgtagg tgtggagggc ttcatcaccg gcctcctcga cctcctcccg gcctcctact   1560
acttccgttt ccaaagggag atctctgtgg ccctctgttg tgccctctgc tttgtcatcg   1620
atctctccat ggtgactgat ggcgggatgt acgtcttcca gctgtttgac tactactcgg   1680
ccagcggcac caccctgctc tggcaggcct tttgggagtg cgtggtggtg gcctgggtgt   1740
acggagctga ccgcttcatg gacgacattg cctgtatgat cgggtaccga ccttgcccct   1800
ggatgaaatg gtgctggtcc ttcttcaccc cgctggtctg catgggcatc ttcatcttca   1860
acgttgtgta ctacgagccg ctggtctaca acaacaccta cgtgtacccg tggtggggtg   1920
aggccatggg ctgggccttc gccctgtcct ccatgctgtg cgtgccgctg cacctcctgg   1980
gctgcctcct cagggccaag ggcaccatgg ctgagcgctg gcagcacctg acccagccca   2040
tctggggcct ccaccacttg gagtaccgag ctcaggacgc agatgtcagg ggcctgacca   2100
ccctgacccc agtgtccgag agcagcaagg tcgtcgtggt ggagagtgtc atgtgacaac   2160
tcagctcaca tcaccagctc acctctggta gccatagcag cccctgcttc agccccaccg   2220
cacccctcca gggggcctgc ctttccctga cacttttggg gtctgcctgg gggaggaggg   2280
gagaaagcac catgagtgct cactaaaaca actttttcca tttttaataa aacgccaaaa   2340
atatcacaac ccaccaaaaa tagatgcctc tccccctcca gccctagccg agctggtcct   2400
aggccccgcc tagtgcccca cccccaccca cagtgctgca ctcctcctgc ccctgccacg   2460
cccacccccct gcccacctct ccaggctctg ctctgcagca cacccgtggg tgacccctca   2520
ccccagaagc agcagtggca gcttgggaaa tgtgaggaag ggaaggaggg agagacggga   2580
gggaggagag agaggagaag ggaggcaggg gaggggcagc agaaccaagg caaatatttc   2640
agctgggcta taccccctctc cccatccctg ttatagaagc ttagagagcc agccagcaat   2700
ggaaccttct ggttcctgcg ccaatcgcca ccagtatcaa ttgtgtgagc ttgggtgcga   2760
gtgcacgcgt gcgtgagtac ggagagtata tatagatctc tatctcttag caaaggtgaa   2820
tgccagatgt aaatggcgcc tctgggcaaa ggaggcttgt attttgcaca ttttataaaa   2880
acttgagaga atgagatttc tgcttgtata tttctaaaaa gaggaaggag cccaaaccat   2940
cctctcctta ccactcccat ccctgtgagc cctaccttac ccctctgccc ctagccaagg   3000
agtgtgaatt tatagatcta actttcatag gcaaaacaaa agcttcgagc tgttgcgtgt   3060
gtgagtctgt tgtgtggatg tgcgtgtgtg gtccccagcc ccagactgga ttggaaaagt   3120
gcatggtggg ggcctcgggg ctgtccccac gctgtccctt tgccacaagt ctgtggggca   3180
agaggctgca atattccgtc ctgggtgtct gggctgctaa cctggcctgc tcaggcttcc   3240
caccctgtgc ggggcacacc cccaggaagg gaccctggac acggctccca cgtccaggct   3300
taaggtggat gcacttcccg cacctccagt cttctgtgta gcagctttaa cccacgtttg   3360
tctgtcacgt ccagtcccga gacggctgag tgaccccaag aaaggcttcc ccgacaccca   3420
gacagaggct gcagggctgg ggctgggtga gggtggcggg cctgcgggga cattctactg   3480
tgctaaaaag ccactgcaga catagcaata aaaacatgtc attttccaaa gcaggaaaaa   3540
aaaaaaaaaa                                                          3550
```

<210> SEQ ID NO 73
<211> LENGTH: 9648
<212> TYPE: DNA
<213> ORGANISM: Homo sapiens

<400> SEQUENCE: 73
ggtttgtaat gatagggcgg cagcagcagc agcagcagca gtggtggaac gaggaggtgg 60
agaattgaga gcacgatgca tacacaggtg tttctgagta gtaattagat cgctgtgaag 120
gaaaaagcac acctttgagt tttcacctgt gaacactata gcgctgagag agacagtctg 180
aaagcagagg aagacatcga tcagtaacac caagagacac caaagttgaa agttttgttt 240
tctttccctc tgttttattt ttcccccgtg tgtccctact atggtcagaa agcctgttgt 300
gtccaccatc tccaaaggag gttacctgca gggaaatgtt aacgggaggc tgccttccct 360
gggcaacaag gagccacctg ggcaggagaa agtgcagctg aagaggaaag tcactttact 420
gaggggagtc tccattatca ttggcaccat cattggagca ggaatcttca tctctcctaa 480
gggcgtgctc cagaacacgg gcagcgtggg catgtctctg accatctgga cggtgtgtgg 540
ggtcctgtca ctatttggag ctttgtctta tgctgaattg ggaacaacta taaagaaatc 600
tggaggtcat tacacatata ttttggaagt ctttggtcca ttaccagctt ttgtacgagt 660
ctgggtggaa ctcctcataa tacgccctgc agctactgct gtgatatccc tggcatttgg 720
acgctacatt ctggaaccat tttttattca atgtgaaatc cctgaacttg cgatcaagct 780
cattacagct gtgggcataa ctgtagtgat ggtcctaaat agcatgagtg tcagctggag 840
cgcccggatc cagattttct taacctttg caagctcaca gcaattctga taattatagt 900
ccctggagtt atgcagctaa ttaaaggtca aacgcagaac tttaaagacg ccttttcagg 960
aagagattca agtattacgc ggttgccact ggctttttat tatggaatgt atgcatatgc 1020
tggctggttt tacctcaact ttgttactga agaagtagaa aaccctgaaa aaaccattcc 1080
ccttgcaata tgtatatcca tggccattgt caccattggc tatgtgctga caaatgtggc 1140
ctactttacg accattaatg ctgaggagct gctgctttca aatgcagtgg cagtgacctt 1200
ttctgagcgg ctactgggaa atttctcatt agcagttccg atctttgttg ccctctcctg 1260
ctttggctcc atgaacggtg gtgtgtttgc tgtctccagg ttattctatg ttgcgtctcg 1320
agagggtcac cttccagaaa tcctctccat gattcatgtc cgcaagcaca ctcctctacc 1380
agctgttatt gttttgcacc ctttgacaat gataatgctc ttctctggag acctcgacag 1440
tcttttgaat ttcctcagtt ttgccaggtg gcttttttatt gggctggcag ttgctgggct 1500
gatttatctt cgatacaaat gcccagatat gcatcgtcct ttcaaggtgc cactgttcat 1560
cccagctttg ttttccttca catgcctctt catggttgcc ctttccctct attcggaccc 1620
atttagtaca gggattggct tcgtcatcac tctgactgga gtccctgcgt attatctctt 1680
tattatatgg gacaagaaac ccaggtggtt tagaataatg tcagagaaaa taaccagaac 1740
attacaaata atactggaag ttgtaccaga agaagataag ttatgaacta atggacttga 1800
gatcttggca atctgcccaa ggggagacac aaaataggga tttttacttc attttctgaa 1860
agtctagaga attacaactt tggtgataaa caaaaggagt cagttatttt tattcatata 1920
ttttagcata ttcgaactaa tttctaagaa atttagttat aactctatgt agttatagaa 1980
agtgaatatg cagttattct atgagtcgca caattcttga gtctctgata cctacctatt 2040
ggggttagga gaaaagacta gacaattact atgtggtcat tctctacaac atatgttagc 2100
acggcaaaga accttcaaat tgaagactga gatttttctg tatatatggg ttttgtaaag 2160
atggttttac acactataga tgtctatact gtgaaaagtg ttttcaattc tgaaaaaaag 2220
catacatcat gattatggca aagaggagag aaagaaattt attttacatt gacattgcat 2280

```
tgcttcccct tagataccaa tttagataac aaacactcat gctttaatgg attataccca   2340
gagcactttg aacaaaggtc agtggggatt gttgaataca ttaaagaaga gtttctaggg   2400
gctactgttt atgagacaca tccaggagtt atgtttaagt aaaaatcctt gagaatttat   2460
tatgtcagat gtttttttcat tcattatcag gaagttttag ttatctgtca ttttttttt   2520
tcacatcagt ttgatcagga aagtgtataa cacatcttag agcaagagtt agtttggtat   2580
taaatcctca ttagaacaac cacctgtttc actaataact taccccctgat gagtctatct   2640
aaacatatgc attttaagcc ttcaaattac attatcaaca tgagagaaat caccaacaaa   2700
gaagatgttc aaaataatag tcccatatct gtaatcatat ctacatgcaa tgttagtaat   2760
tctgaagttt tttaaattta tggctatttt tacacgatga tgaattttga cagtttgtgc   2820
attttcttta tacattttat attcttctgt taaaatatct cttcagatga aactgtccag   2880
attaattagg aaaaggcata tattaacata aaaattgcaa aagaaatgtc gctgtaaata   2940
agatttacaa ctgatgtttc tagaaaattt ccacttctat atctaggctt tgtcagtaat   3000
ttccacacct taattatcat tcaacttgca aaagagacaa ctgataagaa gaaaattgaa   3060
atgagaatct gtggataagt gtttgtgttc agaagatgtt gttttgccag tattagaaaa   3120
tactgtgagc cgggcatggt ggcttacatc tgtaatccca gcactttggg aggctgaggg   3180
ggtggatcac ctgaggtcgg gagttctaga ccagcctgac caacatggag aaaccccatc   3240
tctactaaaa atacaaaatt agctgggcat ggtggcacat gctggtaatc tcagctattg   3300
aggaggctga ggcaggagaa ttgcttgaac ccgggaggcg gaggttgcag tgagccaaga   3360
ttgcaccact gtactccagc ctgggtgaca aagtcagact ccatctccaa aaaaaaaaga   3420
ttatatatat atatatatgt gtgtgtatgt gtgtgtgtgt gtgtgtgtgt atatatatat   3480
atatatatat acacacacac acacacactt tttatatata tatatatata tatatagtgg   3540
aacttacaaa tgagagtaat ataatgatga aattttgaac tgttatttat aaacatctaa   3600
ggtaaaatgg ttagtcatgg ccagagtatg tttcatcctt taatttttgt ccatttgaaa   3660
ataaggattt ttgaaagaat tataccaatt aaaattatta aaggcaaaca tagaattcat   3720
aaaaaattgt ccaaagtaga aatgatgacc tataatttgg agcatttcca attcagtaat   3780
ttcaattttg ctcttgaaaa catttaatat atatccaaga ctgacatttc tttagctgaa   3840
cctaacgttt gggtctctga gtgaatttat aataactcct tccttcctta gcatagggtt   3900
ttcaaaattt gatttataat tcctatttcc agtaaatatt gttcatttgt ccacatctct   3960
ccctatgata tgttgctgga ggtaagaatt tctttcatat tcctattttt tttttcccca   4020
tagactaggc tcatagaatt taaacaagca aattttcctg agctttttct tgccaaatga   4080
aagaagactg gtaaattctc atagagaggt ttgtgtagtt cttggctctt cctggggtta   4140
atgtgcttat attcacagtg gcaaattggt ctcagacttt aatttattta tttttgattt   4200
gaatttctct ttaaaagtat caatttaaaa ggtaactaga attattcttt ctcattttca   4260
aaagtgattt ttgcattatt aaatttccct gccattgtaa tgccatttca cgcagaaaaa   4320
aagtcagcca gtaattaaga aaaaaagtga tggagattaa gtagtatttt ggcttatttt   4380
taggactcat catgagaaga cacagttcct ttaatcagga aattaatatc cataattttc   4440
actcaaaatt gcagtatgta aagcagattc tcaaaaactc tcctgaacac ttatttatat   4500
atatgttttt atataagtaa aatttttctc atatttttat acgatatgca cacacacaca   4560
tacatgcaca tactacttac tacatgttct gtacttgtac tttgtaccat gcatattcaa   4620
atgtttatat acataagttt attataacat aaacagtaaa agtaatgaat actgtttaaa   4680
```

-continued

```
ataactaata tagtattttt taatttttgt ggggatggat tctcaaatac ttgtgatttt   4740
aaaagattct aaagctaaaa cacaacttga ttttaaaaag aatgattctc cttacacaat   4800
tataaatatt tgcagtaaat attttcctta taatactgtt ttgaccccat ttaaaaagta   4860
ttagattata ttcctttgat ccaatgaaaa ctgaacctta taaatggtta gctgaaagta   4920
gaccttattc ttgtccttct ttagaagagt aaagatttgt cctagggaag atggctgact   4980
tcggttccca acatgcgtat gcatttagac tgtagctcct cagccctgtg gacacaaaat   5040
ttggacagct tattaggtta cgttagcaat gcatgacggt ttctccaaca ctaagatatt   5100
cacgttgaaa cagatttcct gttcgtctta tgtgtctggt aaaattgttt ccccaattac   5160
aatttgacat atcaatagag ggttaacaag agtataatta cataacagaa ttcctcatga   5220
actgtaatca gtctacagga aaatcattat tttatcttga tttgcagatg aatatactgc   5280
taagaaaggg agcaactctg acctttgtta aagttgatct tttgtaattg aggtataagg   5340
tatgaaaaga taaaaaaccg aaggccagag aatcaggaaa tgaaagatag tatggactga   5400
aggtaacaat attttaatgt tatgcaatat agtcagagaa atattaaaaa ttagttgttt   5460
gctgtgcata ggtggatctc gcaggaagct aatgaaacct aagcttcagt gcctctcact   5520
tagacatgtt ccattcgagg tcctgaacct aactttgtat taggaattct gtactaattt   5580
tgttgaagaa gaccagcaaa gttgtgtaca cttctacccc cacaaaatct gcattgtcca   5640
tgtgagtaaa gtaaaataat tcctgttatt tttttctgtt agaaataagt atggaggata   5700
tgtttttaaa aatttatgag ttaattgaaa tatccatata taacaagtga ctttctcaca   5760
atatatatga tgtgatatat agggagatag tttcactttc atcatatttt atacgttgat   5820
tctgaactat agaaaaataa taaatgggat tttaattata gctcttagtt gggaaagaaa   5880
tatagagaga tgtgggattt gaatgcccat gaaagacatt ttattttact tgaatatatt   5940
cttgcttcac tttaccctcc ataatatgtt gtacattagt gctgatcaag tttacagagt   6000
tacattttgc tttcctaacc attcagtcag gaattaaaat atggcattgt ataacaactg   6060
ggaagaagct catagtggat ataaattaga gtagataatg ggtcaccttg atagcctctg   6120
tttacattac ttgtatatgg gcaaaataat tattacctat acgtgtattt aagcttaatt   6180
ttcatataaa cagtattttt aatctatgtt aaaatagata atatctaaaa gtgtgatctc   6240
taggtagtcc ttagtttatt agtactgtac ttcaaaaaga tttttaaata ggtccggcac   6300
ggtggctcat gcctgtaatc ccagcacttt gggaggctga ggcgggcgaa tcacctgagg   6360
tcaggagttc gagatcagcc tggccaacat ggtgaaaccc tgtctcaact aaaaatataa   6420
aaattagccg ggcgtggtgg caggcgcctg taatcccagc tactcgggag gctgaggcag   6480
gagaatcact tgaacccaag ggcagaagc tgcagttagc caagatcgca tcattgcact   6540
ccagcctagg ggacaagagc gcgagacttc atctcaaaaa aaaaaaaaaa aaaaaaaaaa   6600
gatttttaaa taatagctaa aggtatgctc tctaggtcat ccttagttta ttagtactgt   6660
acttaaaaat tattttttaa tagtcaattt tgggagataa ttatttcttt ccttatattt   6720
tccaattagt tggtgtctaa aaataaatgt tttgtctaat tttagatcag gtatacattc   6780
acaaaagcat aaatcatagt ctcacaggaa attcaccaat tttccatatg tcgtgagata   6840
actgtccttt ctacaacctc ataacaatga atttatataa ttacctagat tttcttagtg   6900
tgaatctacc cattagtttt attttcttgg tagttatttt tttccctcct ctctgttact   6960
attggcctta aaatacacag aggacggtta cagtgtccta atagctgtta catgtgtgtg   7020
```

-continued

```
tttcagcgta cttgaatcaa gtgtacattt atagtaccaa taaccgcctt tacagcttta   7080
cagttaacaa ttctctcaca aaactgtaga gcattaggca tctgagagcc atagagggcc   7140
aactttgttc cagagtgaac atgctttttt tcctcaacat atacactact gatttttttt   7200
aaaagtatga ctttcaagtg aattaatgta ttggttagga gaactgcttg ctaagtcctt   7260
attacctctt gttaaagcct cagaaggccg tgctgaaagc cagaggggaa aaaaagagta   7320
atgcacaggt atctcttttg cagtggtgac tgtattttga gtaccttgtg tgacagggta   7380
ttattacagc atcttgtggg aaaacctatt aggcctttgc atgttaaagc tgtataattt   7440
gttgggttgt gagtggtctg acttaaatgt gtattataaa atttagacat caaattttcc   7500
tactaactaa ctttattaga tgcatacttg gaagcacagt catatcacac tgggaggcaa   7560
tgcaatgtgg ttacctggtc ctaggtttga actgtcttat ttcaaaagat ttctgaatta   7620
atttttccct agaatttctc cttcattcca aagtacaaac atactttgaa gaatgaaaca   7680
gattgttccc atgaatgtat gctcatactc gactagaaac gatctatgtt aaatgactgt   7740
gtatatgaat tatttcaagt actaccccaa ataactttct tattgctctg aaagaagaaa   7800
agcaatgtaa atcactatga ttattgcaca aacaaccaga attctccaac aattttaagt   7860
aatctgatcc tcttcttgga gaaaattgtt acctaatagt ttttccttat gaatgttatt   7920
actactggta taaatcaaat ttctataaat ttcctactta agtcttaaga actgggttct   7980
tcctttgatg ttattcatgt tcagaaagga aacaacactt tactctttta ggacaattcc   8040
tagaatctat agtagtatca ggatatattt tgctttaaaa tatattttgg ttattttgaa   8100
tacagacatt ggctccaaat tttcatcttt gcacaatagt atgacttttc actagaactt   8160
ctcaacattt gggaactttg caaatatgag catcatatgt gttaaggctg tatcatttaa   8220
tgctatgaga tacattgttt tctccctatg ccaaacaggt gaacaaacgt agttgttttt   8280
tactgatact aaatgttggc tacctgtgat tttatagtat gcacatgtca gaaaaaggca   8340
agacaaatgg cctcttgtac tgaatacttc ggcaaactta ttgggtcttc attttctgac   8400
agacaggatt tgactcaata tttgtagagc ttgcgtagaa tggattacat ggtagtgatg   8460
cactggtaga aatggttttt agttattgac tcagaattca tctcaggatg aatcttttat   8520
gtctttttat tgtaagcata tctgaattta ctttataaag atggttttag aaagctttgt   8580
ctaaaaattt ggcctaggaa tggtaacttc attttcagtt gccaaggggt agaaaaataa   8640
tatgtgtgtt gttatgttta tgttaacata ttattaggta ctatctatga atgtatttaa   8700
atatttttca tattctgtga caagcattta taatttgcaa caagtggagt ccatttagcc   8760
cagtgggaaa gtcttggaac tcaggttacc cttgaaggat atgctggcag ccatctcttt   8820
gatctgtgct taaactgtaa tttatagacc agctaaatcc ctaacttgga tctggaatgc   8880
attagttatg accttgtacc attcccagaa tttcaggggc atcgtgggtt tggtctagtg   8940
attgaaaaca caagaacaga gagatccagc tgaaaaagag tgatcctcaa tatcctaact   9000
aactggtcct caactcaagc agagtttctt cactctggca ctgtgatcat gaaacttagt   9060
agaggggatt gtgtgtattt tatacaaatt taatacaatg tcttacattg ataaaattct   9120
taaagagcaa aactgcattt tatttctgca tccacattcc aatcatatta gaactaagat   9180
atttatctat gaagatataa atggtgcaga gagactttca tctgtggatt gcgttgtttc   9240
ttagggttcc tagcactgat gcctgcacaa gcatgtgata tgtgaaataa aatggattct   9300
tctatagcta aatgagttcc ctctggggag agttctggta ctgcaatcac aatgccagat   9360
ggtgtttatg ggctatttgt gtaagtaagt ggtaagatgc tatgaagtaa gtgtgtttgt   9420
```

-continued tttcatctta tggaaactct tgatgcatgt gcttttgtat ggaataaatt ttggtgcaat 9480
atgatgtcat tcaactttgc attgaattga attttggttg tatttatatg tattatacct 9540
gtcacgcttc tagttgcttc aaccatttta taaccatttt tgtacatatt ttacttgaaa 9600
atattttaaa tggaaattta aataaacatt tgatagttta cataataa 9648

<210> SEQ ID NO 74
<211> LENGTH: 6384
<212> TYPE: DNA
<213> ORGANISM: Homo sapiens

<400> SEQUENCE: 74
agcttgtccc cgcctagcaa ggagtcggct aagaactgga tcctagcgag gagcccggca 60
cagacagcga atgaccgcag ccagacagtc gctcttgctc ttcctcggcc ctgcggcagg 120
atccgccggt gcaggggcct ctccccggac tccacgcgtg tctggagggc tctcgggtta 180
gggaaggggg ctttggagac gccccgggcg gccgggcggt ggcgggacgc gggcccttta 240
agaaggagcg aggggcgcgg ccaggtaggg gcgggtccag ggcggatcag cgctgcgccg 300
gcgccggccc gggagccgga tttggagcgc gaggcgccgg tgggggcgga gggggctgcg 360
cggcggaggc tcccgtggcc tcggacgctc ctcctagcta gcggccgccg cccgccgccg 420
cctgcgcctc cagctccttc gccccggcgg gcccggccgc cgcttccggc agctcacctg 480
ggaagcgctc acctgggacg cgctcacctg ggacgcgcta cctgcctccg ggcgcctggg 540
cttcaggatg aaggaccgtc tggagcagct gaaggccaag cagctgacac aggatgatga 600
tactgatgcg gttgagattg ctatcgacaa cacggctttt atggacgagt tcttttctga 660
gattgaggaa actcggctta acattgacaa gatctcagaa catgtagagg aggctaagaa 720
actctacagt atcattctct ctgcaccgat tccagagcca aaaaccaagg atgacctaga 780
gcagctcacg actgagatta agaaaagggc caacaacgtc cggaacaaac tgaagagcat 840
ggagaagcat attgaagaag atgaggtcag gtcatcggca gaccttcgga ttcggaaatc 900
ccagcactct gtcctttctc ggaagtttgt ggaggtgatg accaaataca atgaagctca 960
agtggacttc cgagaacgca gcaaagggcg aatccagcgg cagctcgaaa ttactggcaa 1020
aaagacaacc gatgaggagc tggaggagat gttggagagt ggcaacccgg ccatcttcac 1080
ttctgggatc attgactcac agatttccaa gcaagccctc agtgagattg agggacgaca 1140
caaggacatt gtgaggctgg agagcagcat caaggagctt cacgacatgt ttatggacat 1200
cgccatgctg gtggagaatc agggtgagat gttagataac atagagttga atgtcatgca 1260
cacagtggac cacgtggaga aggcacgaga tgaaacgaaa aaagctgtga aataccagag 1320
tcaggcccgg aagaaactga tttcactcca gactggtgtg gccacccttg tcttcagatg 1380
agaatggagt ctgaatggcc ttcctgagag cgagtgcgac ccgttccttt gtttccttgc 1440
aaccaccctt ggacctgact cagctaacaa tctagccctg ggggaatgtg atctacctga 1500
tgcgaccctg agttctcccc agagcctcct cctgccccac cagctctcaa gtaccttttc 1560
tcctggactg tgtggaccca cccagctttc ttcctccctg ttgtgtgtca gattatgcct 1620
tgcacttggg aaagctcttg tgagactctc ccaaggtgct gtatttttct acctcatgga 1680
gtattctccc agaaactgca atgtattttt ttaggggagt atctttaaca aagcagaatg 1740
attcttctaa gtttggcaac aagaaggctt ggatctgagt cttctacctg gcaggatgcc 1800
aatcctgttt gttgtccgta tgtcctgaaa acatgaggga ctggcagatg tcattttggt 1860

-continued

```
ctaaagagct gacttgtttg aaattcagcc ttaaattaag ctcttagttg ttcagcttgg   1920
ggggcaactt tgatttttct ctgtgttgta gtctctcata tttactcaag gagggaccag   1980
gatgatacag tcatctgagg ttatgctttg caaaaggctg acggtatgga atatgtttcc   2040
atgtctgagt cttagaaact ggctgctcat tgttagaaag tgatgctttg tgagactatt   2100
gtcttggggc caaaaataat cagggatttt aaattgggca agggacaagg tgctagaatc   2160
ctaagctctg gaaatatttc atgacactgg tgtattcact catgtgttcc agatgtattc   2220
taattgtgta tgaaatgtat gtacacataa gtgtgtgtgt ctcaggaagt aggaaataaa   2280
aatggaagct attatgacct caaaaaaaaa aagccaactt tgagctagga taaaaattgg   2340
gtaaaggaca tttgcttacc tgcaaatgaa tcactgtgga aatgtgatct tcccatatca   2400
tcaagaaact tgttttctgg atgaatactg ggagaataaa atgagaactc tggagtgagc   2460
taaattgatc ccaattaagt ttttctgctt agcagacaga aggtataatt ttttgacacc   2520
ctttcccacc tggtgcctat gctaggcttg tcctgagaac atccctcagt aacttgatat   2580
tcacatgacc tacaggatgt cccatctgca gggctgagtc agttggggaa caccagaggc   2640
tacacagtag ctcttcctgc tactcggtta atgagcttgg caggttcttt gtctcactga   2700
attcttatca tggaaacagc agcagcagcc gctaggaaat cttcaagtgt agtgtctgtg   2760
ctaacccagt ggtaaatccc ttagatcccc tgctggtctc tggcagtctc cttgattttg   2820
ggtaccatgt atattttccg ctttgacttt aacgctttct aggatagggt aagcaccctt   2880
aattcaggca ctgtccatta gcttcctttg caaaggctac ttatggccgg tcacaatcca   2940
gcactcagac agagccaagg caatatcctc ttgcccatgg ctatgatgtc agacagtgga   3000
tgggctccag caacaagaga caaaataact aaaggccttt gctctcctct gacattgagg   3060
cctggggctt acagtttgga atacaacatg tgaaggtttt tgttgttgtt tgtatttttt   3120
agatgtaaac ttgattattt tattgctaat ttaaaaataa aaatgacttt gtattgattg   3180
tgaaacggtt ctggctctgt ctcgatgcag aaacacaatg atctggtgcc accatgtggt   3240
gatttttatt caggttttag aatgcagttc acaccttttt aagccatgtg ctggatcaga   3300
tggttcaaaa gtgcaatttt tgaacatggt ttaactccca cagaatgcag tgtaactatg   3360
tttgtgtttc agatttgagg tgttcccccc aaaagaattt ggttcagtcc ttgggagtat   3420
ctggctttag gaggaaatgg gggagatctg tcacgatgtt atctagaagg tggaatgacc   3480
ataccaaaca tccttttaat ctaacttgaa tgtctcacca aaaataacat ttctgttggc   3540
attctgggtc ctagaagcca gatccatctc ctttttcctt ctgttgctct cttccttcac   3600
accctcttcc atgtccacat gcacttatct ccctgcagaa tactttttgc gatgatgttt   3660
ctcatgtatt ctttctttcc ttgtctggat gagcagaaga agatcatgat catgatctgc   3720
tgtattatcc ttgcgatcat cttagcttcc accattggga gcatatttgc ctgaaaaagg   3780
tgagccatct gtggggaggg tcagaccttc tttcactgac ttgaaacctt tgtgtcttgg   3840
gggcactcta ggtgccttaa tctgggtggg attaggtgct aataatggtt agagaaaact   3900
aaagaaaggg atgtttcaga gacagaaaag tgagtgaaga atgaactgtt agtaggtagt   3960
ctgtgggagg aggggggaga cagaaggtgg caatctgtcc tataacctgg tgtggcagaa   4020
tgctttgtac aggtgaagga tagtgattcc tgctaaacag tttgagcctt ggtatctgga   4080
agtgacaaaa agaacaagaa ttagttcttg cattaggtgc atcttgaact ttttggaaga   4140
gggccggcca cacagtaaat tcaaattaaa tttcttccct ttcaaggtta atgaaagtta   4200
acacagcctt gtatgtagtc ctttaccccg ggtaagaggg atttggtgat cccagccacg   4260
```

aacaccatgc tatataatct atgatttttt tcctccattt ttctgttatc tcccacagcc 4320
ctcacagatt gatcgactgg catttctaat cctccttcca cttctgtggt accatcactt 4380
ctccacgcag actcctcatc agcttctcct ctttccatta tgaaacttct taagaaacag 4440
ggcaccaatc aactacttat taagaattat gcaaagaata aacgtataca gaattgggcg 4500
gaggacaggg acagggagta cagatacata gctgattagg cagatggttt aaaggaggac 4560
tgcagggtag agaagcaagc agagtgggcg cctctttagg aagtgacaca gcctgcatgt 4620
gcagtatggc tgtgaagggg cagatatcat agcacaccta actcaacagg atcttacttg 4680
aactgctgtg agttggtcaa gtcagggcac ttctgctctt caggctcctc taggtcacac 4740
ctttgaccac cctacatctg tttcctcttt caggctccag tagtagtctt aaaagtgaag 4800
tttatctaag gataagcaca tgcctatctt gctcactgct gtgtccccac tttttagcac 4860
agcgcctgct gcttacaggt actcaaatat ctgctgactt aattacttat aattaagctc 4920
ttatttcagt catggacaaa tccttgggtt tgactcctaa actctttaag gtaccaatga 4980
gaacgtggtt tgttactgtc agaggctgtg taaagccgct tgggaatggg ctgatctgct 5040
tatgcaaaaa tgctaccaac ctttcaaacc ccattaccac aacatgaaaa tttaaagtgc 5100
tttttctatg ggtggtgatg gtggagttct agcaacagcc tcttaatctg tggagaagat 5160
ggctggctcc aggactgtgg ttcaataacg aaatacaggc ccacaaaata aaataggttt 5220
atagcatgac tgaactcaca catcagtaga acactctgtg aaccataaca aagaacagat 5280
aaaggtgtca agtgagaaag gtgaaatgag gttatcactc acttcacctc tcacctgatt 5340
tgtgttgcta gctgaaactg ctggccagta acgtatgtat aagaaactgt tataggccgg 5400
gcacggtggc tcatgcctgt aatcacagca ctttgggagg ccaaggcagg tggatcacca 5460
gactgaccaa catagtgaaa ccccctctct acaaaaaata caaaaattag ccaggcatgg 5520
tggcttgcac ctgtattccc agctacttgg gaggctgagg caggagaatt gcttgaatgc 5580
aagaggcgga agttgcagtg agccgagatc gcgccactgc actccagcct gggcaacaag 5640
agctaaattc catctaaaaa aaaaaaaaaa acaaaaaaaa aaaactgttc ttaatactta 5700
atactgtccc caattccatt caaggttcag ttgtgttcag ctttaaaacc agctatgtga 5760
atgtgagttc tagtgcagat tatttagtga ttatgtaact aaaattgatg aaaaaatcac 5820
actatacaac tgtgaggagc acacaactgc taagtttgta cttttgaaag taaattattc 5880
tttgtttgat accttatttt ttaagaaagt gggattaaaa atattttggt cagtgctgtt 5940
ttctacccac cttcaaaagc caatggtttg atatttctat taatttgtgc ttcctttagt 6000
tttaataggg gatagaagac tgcagctggt tgggtctgga aaacattaat ctgggcaaac 6060
ggagctggag ctatgaggat ctgagtccta gggggccctc attcactagc agtaagaatt 6120
taagtggtgc atggcacata gcactgtact agattctgca ggggcacaaa catagagcca 6180
aacactctcc ctcttggaga atttcagacc cagaaaaggc cacgcagttc taacttttgt 6240
catcggttcc ttttgctaaa aggcaaaggg tatgttcctt gcctattgtc caacataccc 6300
cttccaagat tgtgagaaga tgggtagctg ggcatcaata aatattgaat caattgacct 6360
aaaaaaaaaa aaaaaaaaaa aaaa 6384

<210> SEQ ID NO 75
<211> LENGTH: 4548
<212> TYPE: DNA
<213> ORGANISM: Homo sapiens -continued

<400> SEQUENCE: 75

```
gggactggag gctgccgagg gggccggcgc ccgagtccgg gattcggcca gtggtgctga     60
gcgagtgctg gaccagcggc cgtcctgtgc acctggcctg tgcgcgtgcc cgctgctcgg    120
cttcacccag actaaggcgc gggcagctgc gggaacaggc ggggtgggcg gagggagacc    180
gggaggcacg ggcgccctgt gcgcggagga ggtgaaggcg gccggggccg ggacgccatg    240
tccatggagg accccttctt tgtggtgaaa ggagaggtac agaaagcagt caacactgcc    300
cagggattgt ttcagagatg gacagagctc ctccaggacc cctccacagc aacaagggaa    360
gaaatcgact ggaccaccaa cgagctgaga aataacctcc ggagcataga gtgggatcta    420
gaggaccttg atgaaaccat cagcatagtt gaagcaaatc ctagaaaatt taaccttgat    480
gcaactgaat tgagtataag aaaagccttc attacaagta ctcggcaagt tgtcagggac    540
atgaaagatc agatgtcaac ttcatctgtg caggcattag ctgaaagaaa aaatagacag    600
gcactgctgg gagacagtgg cagccagaac tggagcactg gaacaacaga taaatatggg    660
cgtctggacc gagagctcca gagagccaat tctcatttca ttgaggagca gcaggcacag    720
cagcagttga tcgtggaaca gcaggatgag cagttggagc tggtctctgg cagcatcggg    780
gtgctgaaga acatgtccca gcgcatcgga ggggagctgg aggaacaggc agttatgttg    840
gaagatttct ctcacgaatt ggagagcact cagtcccggc tggacaatgt gatgaagaaa    900
cttgcaaaag tatctcatat gaccagtgat cggcgccaat ggtgtgccat agccatcctc    960
tttgcagtcc tgttggttgt gctcatcctc ttcttagtgc tgtgacggcg gggcctctgg   1020
gtgcgagttc ctcctgcata tgaaccgagg ggaggaggag aagctgagca cgtgtgacat   1080
tgccgtctac tcacattcct atcctggaaa catactgctg cactgacttt tctccgtgtg   1140
accccacaat tgacatggct cctccatccc agcgctggaa gggccagtgg gaagaggaaa   1200
tagatgtctg cactcctggc tgcagctgga caacagaagc cccatgccgc ctgtccagtt   1260
cggaggagaa ctagctgctg ccttgccttc cgggacctcg tttgctgagg agggacttac   1320
agactccact ggtgttttgc tgttgctcat tccatgcatc tttggcagct cttttcttct   1380
gctcagaccc ttccccgtgc tcagacagtg caccgctgtc ccatctaaag aaacctgtca   1440
ggaatacgag cttctgggta tgtttcgttt cccattgctg tagcatttct tatcccctga   1500
gagctgatga ttattgagga cagaaggctc agaaacagtt tgtgacagaa aatgcagtgt   1560
ttcattttc agggataaat gctaagataa aattgctttt ccaggtcatt tttttttgtg   1620
gtaagaataa ctaatggaaa ataatgaaac accctggggt ttgggggtgc taacaacttg   1680
tggctttaac tgacaggagc aattaaaaag agcaagaggg ttctgcattg gcatagctta   1740
gggaagggtt aatgatgtcg ccacaggtca gctcctgatc cttgccgact tgatgttgct   1800
gtaccagggc ttcctcccca gaggtgcagc ttgcgttttg agggtgattg ctacatatgt   1860
tgttgctaaa cagctcagta acacacttga atgaatttgg ataccagatt gtcctcatta   1920
cagttctttt actcttaggg cactctacac tgggggttgg ggttgggagt ggttagtaca   1980
tttattacat ttattaagaa acgtaatgac ataaaaggtt agctctgggc cagacttctc   2040
ttactctgtg ggtaatggca aggatgtgta ggtaaacttg gttctttttt ttccctaaga   2100
tgacagcttg attttatcat ctgcagtcaa ataactgagc caatccaaat ttaaatgata   2160
gatgctttaa ttgagtttaa gtagctgaaa ctgctgagac actaaacttt aaccttctga   2220
tgacttttta aaatgcctca aatgtgcaca tgtatatagg atatttttat aacttccctg   2280
atgaataatc tgatattaaa gtagtatttg gacccagagc cagaactcgg tggtggaggc   2340
```

```
tgctggtctc tcctcaccac cttcttttgc acttggaaag aacagcaaca tctggataga   2400
gttctggctt tgacttctca tttccttgtc tttttgggtg cattcctcag cacacttttt   2460
ttttaaacct ttttgttttg ttttgtttgt atttcatgtg gttttatttg ggggttttgg   2520
ttttttcacc ctttttgtg atttgcaatg atgtgcttgc ccagctaact tttgaattgc   2580
actttttaat aaatattctt aacaattttt gaagaaggat attttatctc atttgagatc   2640
atggtaggtt aagaaaatat gcctgttgat gaaagctaaa agcaaattta tgaaactaaa   2700
agggtgattg acatccatgt ttacactccg ctctaatgtt tgatatataa ataagttatt   2760
ttcaaattag gaaaaaacag tgagtattac aaagggcttc agatgtttag agtactaggt   2820
tatttatgtt ttacaaagtt tgaatcttct ataaactaag aaaggggatg atccttagat   2880
ttgcattaaa atatagaagt cttttaaagt aaatgtgaac cttgtctaag tactgtaatc   2940
cacacaacac attataagaa gcaaaccagc atcttaagga attataaaat taccctattt   3000
aaaagccatg ctattgttct gctattacca gatttattgt gccacacaaa aggatcatgt   3060
gtgtcagcag gggccgtttg gaacaaacct agtcattaat gagtaagata ctcctgttag   3120
ttcagggacc aagttttatg acccagaggc ttaatgatgt ttggatatat ttcaaatcgg   3180
cgtgcttacc tcactgattt aaattatttt ctaaatagtg gccattgtag acctgactca   3240
ggctgaagct aaatagagaa caatttagaa agttaactaa caatacagtg cattctaccc   3300
gtagggccac catgcccttc tgcccctggc tgatttgatc ctgtgtctga tcccattgca   3360
ccctgactgg gcagtcccta cagaaccagt gttaatttga agggcctcca ctcaggctcc   3420
aaatgtggca gccaaagaga acaatccagg gaacctacat ttatttttaa ggacaaatat   3480
ttcctcctca gtggtcctaa tgttcagggc tttagaggga acccaggtgg tctcttcacc   3540
ctgtgtccta gaatgggaga gtaagtagac agtggtgata accccacact gcttataagt   3600
gcatctttat agtatttggg gctttcctac ccctttagcc ttctgtacct agtaccatat   3660
tccagtttta aagaactggc agaatgtgat ggataacaga ggaagagctc aatttatgtt   3720
tattggaaga acattttact taaatgattt gaggggtggg agggagtgaa ctactgagtt   3780
tgccagagtg aaaatccatc tgaaaaactc agctaccttt agtttttagt cctcattttt   3840
ggtcttgtct ctgcggactg tgaagaatca caatgctcta tatgccctgg actgtgtggc   3900
aaatgcaggt tgcagcgtgt gtgttacatg aggatcttcc acaatttcag aatgcacgcc   3960
agagctgaag gggaaactt ggtaacttgc ccattattct ctgcttttag ccagagttaa   4020
acagactgat gggtctggta gccaacaact tggcaacttc cactccttct cacctcgtga   4080
gattaagggc tgtgaaaaga aatctagtct aactccaaca gaaatctgtc tctgttaagt   4140
gttttacctt ctgtaagtag agatggtaga gccaagattt ttcttttggt aatttccctg   4200
tctataaagt gagaccaaag ggatatctgt tccctgttac ctttttggag aattcataac   4260
atttgaagat caaaaaattg aatgataaat atgaatggct tttcaattct gtggactttg   4320
taccatttgg cttcaccttg tactgcaaga tgaatttgta aacaaaacaa aattggactg   4380
tctggaaagc taaagttctg aaatatggaa tgtactgcct ctaatttttc tttgtcttcc   4440
tctcactggc atttttttct ctcccaggtt tcttaagaat aatgtttttt aaaggaggct   4500
ttttgcccat caagaataaa aagaaataaa accaaaaaaa aaaaaaaa                 4548
```

<210> SEQ ID NO 76
<211> LENGTH: 2124
<212> TYPE: DNA

<213> ORGANISM: Homo sapiens

<400> SEQUENCE: 76
ggccgcgctg ccgatcgccg ggaggacccc cgcctcgccg aagacgggcg gggcaagccg 60
agcctcacgg ggtccccgga gctgggccgg gcctccagat ggagaaggcg caacggggag 120
ttcttgagta agccagagcg gtgtccagcg cggtgtagcc gcagccgccg ctgtcaggcg 180
cagcaacggg caaccccgta gaagtcggtc ggcaggtcct ctccaacccg ccgctaccgc 240
gccgctgtgg gagagacccc agcaggagcc caaaggcagc tacgggggcg cgaaggccgc 300
tggcgccgcc tcggccagcc cttcccgcgc ggttccactg ccttaaggat gacagtcgta 360
gggaaccctc gaagttggag ctgccagtgg ttgccaatcc tgatactgtt gctgggcaca 420
ggccatgggc caggggtgga aggcgtgaca cactacaagg ccggcgaccc tgttattctg 480
tatgtcaaca aagtgggacc ctaccataac cctcaggaaa cttaccacta ctatcagctt 540
ccagtctgct gccctgagaa gatacgtcac aaaagcctta gcctgggtga agtgctggat 600
ggggaccgaa tggctgagtc tttgtatgag atccgctttc gggaaaacgt ggagaagaga 660
attctgtgcc acatgcagct cagttctgca caggtggagc agctgcgcca ggccattgaa 720
gaactgtact actttgaatt tgtggtagat gacttgccaa tccggggctt tgtgggctac 780
atggaggaga gtggtttcct gccacacagc cacaagatag gactctggac ccatttggac 840
ttccacctag aattccatgg agaccgaatt atatttgcca atgtttcagt gcgggacgtc 900
aagccccaca gcttggatgg gttacgacct gacgagttcc taggccttac ccacacttat 960
agcgtgcgct ggtctgagac ttcagtggag cgtcggagtg acaggcgccg tggtgacgat 1020
ggtggtttct ttcctcgaac actggaaatc cattggttgt ccatcatcaa ctccatggtg 1080
cttgtgtttt tactggtggg ttttgtggct gtcattctaa tgcgtgtgct tcggaatgac 1140
ctggctcggt acaacttaga tgaggagacc acctctgcag gttctggtga tgactttgac 1200
cagggtgaca atggctggaa aattatccat acagatgtct tccgcttccc cccataccgt 1260
ggtctgctct gtgctgtgct tggcgtgggt gcccagttcc tggcccttgg cactggcatt 1320
attgtcatgg cactgctggg catgttcaat gtgcaccgtc atggggccat taactcagca 1380
gccatcttgt tgtatgccct gacctgctgc atctctggct acgtgtccag ccacttctac 1440
cggcagattg gaggcgagcg ttgggtgtgg aacatcattc tcaccaccag tctcttctct 1500
gtgcctttct tcctgacgtg gagtgtggtg aactcagtgc attgggccaa tggttcgaca 1560
caggctctgc cagccacaac catcctgctg cttctgacgg tttggctgct ggtgggcttt 1620
cccctcactg tcattggagg catctttggg aagaacaacg ccagcccctt tgatgcaccc 1680
tgtcgcacca agaacatcgc ccgggagatt ccaccccagc cctggtacaa gtctactgtc 1740
atccacatga ctgttggagg cttcctgcct ttcaggtatc ctccctttat tccatggcta 1800
ttactgtcag gttcctgacc tcaatttttc ctgtccctac tcatccagta ccctaaccca 1860
acccgttgat ccctggttca gtggtaccat tcagagatca ttaaatggtt cctcctatcc 1920
ccaagcagga ctgagcttga atgatatgag agtgtctcac ttataaagct ctccggagac 1980
atttccccct tcaccttcct ggtttctgac tttaatgcct atggacatca tgtggggttt 2040
aaagcccatt tgatgaccca tttactttgt tgaatacctc tttgtgccag gcaaagaata 2100
aagtggaata aaatggaaaa aaaa 2124

<210> SEQ ID NO 77
<211> LENGTH: 2375

<212> TYPE: DNA
<213> ORGANISM: Homo sapiens

<400> SEQUENCE: 77
gggcgcggag ccccagccga gcctagccct gcccggcccc ggaggacttg caacactccg 60
aggccaggaa cgctccgtct ggaacggcgc aggtcccagc agctggggtt ccccctcagc 120
ccgtgagcag ccatgtccaa ccccagcgcc ccaccaccat atgaagaccg caaccccctg 180
tacccaggcc ctccgccccc tgggggctat gggcagccat ctgtcctgcc aggagggtat 240
cctgcctacc ctggctaccc gcagcctggc tacggtcacc ctgctggcta cccacagccc 300
atgcccccca cccacccgat gcccatgaac tacggcccag gccatggcta tgatggggag 360
gagagagcgg tgagtgatag cttcgggcct ggagagtggg atgaccggaa agtgcgacac 420
acttttatcc gaaaggttta ctccatcatc tccgtgcagc tgctcatcac tgtggccatc 480
attgctatct tcacctttgt ggaacctgtc agcgcctttg tgaggagaaa tgtggctgtc 540
tactacgtgt cctatgctgt cttcgttgtc acctacctga tccttgcctg ctgccaggga 600
cccagacgcc gtttcccatg gaacatcatt ctgctgaccc tttttacttt tgccatgggc 660
ttcatgacgg gcaccatttc cagtatgtac caaaccaaag ccgtcatcat tgcaatgatc 720
atcactgcgg tggtatccat ttcagtcacc atcttctgct ttcagaccaa ggtggacttc 780
acctcgtgca caggcctctt ctgtgtcctg ggaattgtgc tcctggtgac tgggattgtc 840
actagcattg tgctctactt ccaatacgtt tactggctcc acatgctcta tgctgctctg 900
ggggccattt gtttcaccct gttcctggct tacgacacac agctggtcct ggggaaccgg 960
aagcacacca tcagccccga ggactacatc actggcgccc tgcagattta cacagacatc 1020
atctacatct tcacctttgt gctgcagctg atgggggatc gcaattaagg agcaagcccc 1080
cattttcacc cgatcctggg ctctcccttc caagctagag ggctgggccc tatgactgtg 1140
gtctgggctt taggcccctt tccttcccct tgagtaacat gcccagtttc ctttctgtcc 1200
tggagacagg tggcctctct ggctatggat gtgtgggtac ttggtgggga cggaggagct 1260
agggactaac tgttgctctt ggtgggcttg gcagggacta ggctgaagat gtgtcttctc 1320
cccgccacct actgtatgac accacattct tcctaacagc tggggttgtg aggaatatga 1380
aaagagccta ttcgatagct agaagggaat atgaaaggta gaagtgactt caaggtcacg 1440
aggttcccct cccacctctg tcacaggctt cttgactacg tagttggagc tatttcttcc 1500
cccagcaaag ccagagagct ttgtccccgg cctcctggac acataggcca ttatcctgta 1560
ttcctttggc ttggcatctt ttagctcagg aaggtagaag agatctgtgc ccatgggtct 1620
ccttgcttca atcccttctt gtttcagtga catatgtatt gtttatctgg gttagggatg 1680
ggggacagat aatagaacga gcaaagtaac ctatacaggc cagcatggaa cagcatctcc 1740
cctgggcttg ctcctggctt gtgacgctat aagacagagc aggccacatg tggccatctg 1800
ctccccattc ttgaaagctg ctggggcctc cttgcaggct tctggatctc tggtcagagt 1860
gaactcttgc ttcctgtatt caggcagctc agagcagaaa gtaaggggca gagtcatacg 1920
tgtggccagg aagtagccag ggtgaagaga gactcggtgc gggcagggag aatgcctggg 1980
ggtccctcac ctggctaggg agataccgaa gcctactgtg gtactgaaga cttctgggtt 2040
ctttccttct gctaacccag ggagggtcct aagaggaagg tgacttctct ctgtttgtct 2100
taagttgcac tgggggattt ctgacttgag gcccatctct ccagccagcc actgccttct 2160
ttgtaatatt aagtgccttg agctggaatg gggaaggggg acaagggtca gtctgtcggg 2220
tgggggcaga aatcaaatca gcccaaggat atagttagga ttaattactt aatagagaaa 2280
tcctaactat atcacacaaa gggatacaac tataaatgta ataaagttta tgtctagaag 2340
ttaaaaccca aaaaaaaaaa aaaaaaaaaa aaaaa 2375

<210> SEQ ID NO 78
<211> LENGTH: 7717
<212> TYPE: DNA
<213> ORGANISM: Homo sapiens

<400> SEQUENCE: 78
acggaaatga aaggagcact tccgggttcg gcaataacct ggagccggcg gcgtaggttg 60
gctctttagg gcttcacccc gaagctccac cttcgctccc gtctttctgg aaacaccgct 120
ttgatctcgg cggtgcggga caggtacctc ccggctgctg cgggtgccct ggatccagtc 180
ggctgcacca ggcgagcgag acccttccct ggtggaggct cagagttccg gcagggtgca 240
tccggcctgt gtgtggcgcg aggcagggaa gccggtaccc gggtcctggc cccagcgctg 300
acgttttctc tccccttttct tctctcttcg cggttgcggc gtcgcagacg ctagtgtgag 360
cccccatggc agatacgacc ccgaacggcc cccaaggggc gggcgctgtg caattcatga 420
tgaccaataa actggacacg gcaatgtggc tttctcgctt gttcacagtt tactgctctg 480
ctctgtttgt tctgcctctt cttgggttgc atgaagcagc aagcttttac caacgtgctt 540
tgctggcaaa tgctcttacc agtgctctga ggctgcatca aagattacca cacttccagt 600
taagcagagc attcctggcc caggctttgt tagaggacag ctgccactac ctgttgtatt 660
cactcatctt tgtaaattcc tatccagtta caatgagtat cttcccagtc ttgttattct 720
ctttgcttca tgctgccaca tatacgaaaa aggtccttga cgcaaggggc tcaaatagtt 780
tacctctgct gagatctgtc ttggacaaat taagtgctaa tcaacaaaat attctgaaat 840
tcattgcttg caatgaaata ttcctgatgc ctgcgacagt ttttatgctt tttagtggtc 900
aaggaagttt gctccaacct tttatatact atagatttct taccccttcga tattcgtctc 960 gaagaaaccc atattgtcgg accttattta atgaactgag gattgttgtt gaacacataa 1020
taatgaaacc tgcttgccca ctgtttgtga gaagactttg tctccagagc attgccttta 1080
taagcagatt ggcaccaaca gttccatagt ttaacatcta gttaagctac aaatatagta 1140
taagcattat tagcagctgg tacttctgct aggggttgta aattccaggt gttacactga 1200
cctcaatcca atttacataa tttacataaa tgcatctcgg tggaaaaata atcattttct 1260
tggcatgtta aatcaagctt aaaaagtttt gagaaaattt tactgcgctg tgttgctaat 1320
ggttaaagaa gtctgtatct agtgataaat ataccagttt ttttaaaaag atgctgttgt 1380
gcctatatca tgaagtacat taatttctca tgtaaaaaaa atagctctaa aatttgtttc 1440
aacctaattg gtaacctgag tttatatctg gcatgaattc attatggtga tacacatatg 1500
tgaattcagt acattttgag acagtattct accattcagt aattttggtt aatgatttta 1560
acacttctca gtgtatttaa tttcaaattg tttttttaat tggttttatg ctgctttgtt 1620
aggacagatg tgttttgaat gtaccattat aagaagaatt ctatgtatct taaactatga 1680
tcttctaaaa ttttatttcc gtaagtactt ctgtggcctt gagtattttt taaaaggctc 1740
aactgtaagc ctcttagcca gttggataaa tatttggggt cacctagcca ttgaaagcag 1800
aaagcagtag tgacacagct ttcccttcaa agagccattg agaaacattt ctcaaacagg 1860
aaatccttct tttactaatg tggacatata gattattcgt attatagttt gtagaactac 1920
ctagttcaga atcttgactg ccagttttct tggtttctta ggcttgaatt ttcatagaca 1980

-continued

```
attgcaacag tttagatgcc ttttgaaagg aatgtaatga agattcagca tctgactata   2040
tgtgtgtcta tcctgaaata ataatggaga gtatactgta gattacatgt ttacccatca   2100
aatctgactt aaaaggttaa atggaaggtt ttataggtaa ggtaattgat tgggaatggg   2160
gtagggggag gagttgtggg ggaataatgt gcatttcagt ctcaacgcat agataaattt   2220
aggggaattg gatgtattat tcaactttga tttgggttgt aaaatgtgtt aaatcctgtt   2280
cattgaactc ccatcaactc ttataaaatt catgctgatc ttcattaccg ttgcatgatt   2340
ggaaatgttt aaaacattgt acagttttag tatagagaaa tgtaatggtt tttgtgacca   2400
gtttctgtct gcatgtaatt tggatttctc aaatacattc attagtaatt tatcagtaac   2460
attagtttta tttttgttca tctccttatc tataaaaagg ggatattctt aggataaata   2520
catgaaaaat tatacttgat agcttaacta taatcagcta tttttgtatt tttgtaatat   2580
ttgtccacta agctggagaa gcagcctcat acagttgatt ttgtgtatgt ggctagtctt   2640
attgtcacta tgtaagtaat ccaatggttt tagaaactaa actttctaga gcaataaaat   2700
gactataatg ttaagtaaac ataatgttga tttctaatta tgttttaaaa aatgaagtct   2760
tgaattatat caagaaattt tggcagctga agtcatgttt attttgaagc tgttagtttt   2820
ttcctataat ttaaaaagat cttttagatt tatagaagag tcagaaatgt acaagagagt   2880
ttttttgttg ttgtttttgt tttttgagac agagtctgtc tctgtcgcca aggctggagt   2940
gcagtggcgc aatcctggct cactgtagcc tctgcctcct gggttcaagt gcttctcctg   3000
cctcagcctc ccgagtagct gggactacag gtgcacgcca ccacgcctgt agtcccagct   3060
gtattgtaaa aatacaaaat tttagtattt ttagtagaga cagggtttca ccatgttggc   3120
caggatggtc tcgatctcct gacctcgtga tctgcctgcc tcggcctccc aaagtgccgg   3180
gattacaggt gtgagccacc gcgccctgcc aagaagagtt cttttgcata ccctttactc   3240
aggtcctctc atgttaacgt tttacataac tgtagaacat ttatctaaag taagatatta   3300
gcccagaaca atactactaa ctgaagtata aaacttattt gaatttcaac agtttttttt   3360
tcatttctta ttttcctttt gtgtgctctg tttataccat gatccatgat ttttttaaaa   3420
tcatgattgt cttttaaaga tctgtgtgtc tctgttttga gtttttcctg tttattttga   3480
aaagtactgt tggtcaagat aattggtcaa taatccatgt tggttttaac aaaaagcatt   3540
ttaacattaa aaatattaca gtataaaata acactctgtg ctttaaattg aggttttatg   3600
tcattttagc agaattataa tatttctgat atactcatgt ttgacaagtt gaaacagatt   3660
tgtttcttaa aggaaggttt aatatacaaa aaaaggtaat cttaaactta cgaaaaagta   3720
aattttacaa tttgagcatt actagatgtt tagtttgcat gaactcatag ttagaaattc   3780
tgcaatagga atatctacaa ccggctgatt tggaatttga aattatagtg ttacatgtat   3840
acctatcaaa ttaaaattaa ggaaatacaa tagcaatata tagaatgaat gtagtaacag   3900
aaattaactc tttactgcat cattgaactt attgttagtt acaggtttaa aagaagttca   3960
tttaacatcc agtgtgtcta attcttctgg aagtggtgta gtaccattgt tcttctggca   4020
tttttaaata ttaaaccttt ttggatagat ggaagcctta tacaaaatct actttatttt   4080
agcaaggatt ctctgtcctt ttgtatagtt ggtaccttac taatttaaac tctaatatca   4140
atctaaagag aaatttatta tgcaatttgt atttaggttt tttttttttt ttttggaatg   4200
aagttcagag gtagatcctc ctggaagaaa gaaagcaagc gaacttttta aagaaaatta   4260
gacttgaata tttaagaatg tcccttacag agaaaaggcc aactataata ctaagctaaa   4320
```

-continued

```
agttatgaaa aattaatagg ttcttttata gagctaagaa tgatgaaacc atcaatactt   4380
ccttcttcct aaaaatccag atcaaaactt caggttaggt ttctaagttt aggacatgaa   4440
tattattttt ttctggaaaa gaagatgagt atatgtgtaa taagacaagt agaactgaga   4500
gatttagttt tttttttttt taagttttag ttcagaataa cattaatttt gagagattga   4560
ggtaaagaac cttaactaat gctaaggagt ttattttgat taacataggt tattctgacc   4620
accacctctt ccttccttaa tctccttaga atctgacagt ctcaaagctg tcacacaaat   4680
tagactaatt ttgacacttt gaaatgaaaa cttcaaggaa gaagtagcca cggacagtta   4740
tgtttataat cagtaggtgg cactctttcc tcaggtagcc ccccattttc acatgatgtg   4800
tttgaaggtt aaatgccacc aaaagtgctg agtcagctat aaaactaagt ccctgaattc   4860
catggccctt ttaaatatgt aatcattcaa gattgaaaaa aaaaattaag catttttttgt   4920
ttgtttgctt gtttgttttt gagacggagt ttcactcttg ttggccaggc tggagtgcaa   4980
tggcgccatc tcagctcact gcaacctctg cctcccggat tcaagcaatt ctccttcagc   5040
cctccaagta gctggggtta caggtgcccg ccaccatgcc cagctagttt ttgtattttt   5100
agtagagatg aggtttcacc atgttggcca ggctggtctt gaactcctga cctcgtgatc   5160
cccccacctc ggccttccaa agtgctggat tacaggcgtg agccactgtg cctggcttgc   5220
atttttaaaa tactgaatta ttcaaaagaa gtaccctgtc aatatgtgct ttctaggaaa   5280
acagtaaaat aggccacaat ttggagtgac accattcaga tcaaggtcta tccagttttt   5340
tcttttcatg ctaagtgcct acatcaccga aacacactaa tataaaatta tcctttctcc   5400
ttcattttca gatgtgtaaa aaatggtact taaagtgttt tcatgatcat tttgtaggta   5460
gactagatat agcccgttga acctctttta aaatttagac ttttgatagt aatataaaag   5520
catattgaaa tttgtagata ttatatgagg aatggcacct agatttgaaa attatgcttg   5580
gcttgtagag acaactagtt tctctcgctc tttttttttt tttttttttt ttttttgaga   5640
cagattctca ctcagttgcc caggctggag tgcagtggtg cagtcttggc tcactgcaac   5700
ctctgcctcc tgggttaaag cgattctcat gcctcagcct ccctagtagc tgagactaca   5760
ggcgtgcacc accacgccca gctaattttt gtatttttag tagagacagg atttcaccat   5820
gttcaccatg ttggtcaggc tggtcttgaa ctcctggcct caagtgatct gcccgcctcg   5880
acctcccaga gtgctgggat tataggtgtg agccactaag cctggctgag acaactagtt   5940
tcccttaact cattggaatt ctctaggatt aggagaattc cacagagcct atatgatatt   6000
atagctcaac atttagtata ccaaaggcat acccgtgtaa atctaggagt tatttccaga   6060
gattgtttta aggagcagtc ttatattcag ggtagaaagt tatgattgga tctgctgtta   6120
aggagaacaa aggagcttct aaaggtttgg gaggtttact ggtagtaact attctaggaa   6180
atatttatgt tttaaggtga tgttcacatg ggttctttag aaggaacata gtcaagtgtg   6240
atggattaac tctatatagt ctttctcctc ttgtgcgtgt aggaaatctg acctgcagtg   6300
tcagttgatg tgacaagaga taaagaaagc acagtatttt aaaatctaaa gcagattcct   6360
ttcttagaaa acaataggaa aaaattatag atggatgtct ttgctgaaat ctaacaatta   6420
gctcatattc catgagaaag agtggcctaa gaattatttc atgttaccta gccttctgaa   6480
gctactcact tgatgtgcct agcactttga aactaacctt ttctttcttt gttcatgaca   6540
gtttaattcc aaatatttac tattttctct tgtaactgtt agaacagttc cttttgacat   6600
taatttttgc ctacatatat atttttaagt tgagaccaaa tcggtgaagt gttgagcaag   6660
taacatttat gatgtgtgta tattggaaca aatgtaaaag ggttacaaag attagaaaca   6720
```

gagtcataaa aaatggcttg atttataaag gcattacttt tggtgcttta tataatggca 6780
tatattgaac taaaaatttg tatatacagt atgtcagcat ttcttagtaa cttctcttga 6840
atccattttt aatatctaat attgtacagg ttggggagtt acattcttca ggccaatact 6900
atccagacta tataaattta taaaataaat tgaaaaattc attcccctgt attcaagacc 6960
aaagcacata aatgctaatg tagggctcag aggggaaata cagttctcct gcatatttga 7020
gaaaatgtga agtcctttca agaaaatcta ataaacataa taatcatagc ctgctgacac 7080
taaggaaaaa ggacctcatt cactctttct tttatgcagt gatttactgg tccctactga 7140
tttccaaatt ggatcacgat agtaaattat ccatgctggt acctgtgaaa gtaagccctg 7200
ggatccatat ttgttttgtg ttctgcttaa atcagcaaga atgataaatt tgatggtgtg 7260
aaattggaag tatcaagggc tttctttggt gattgaggga aataatgtct ctacttgtaa 7320
tttattgtga cccttttca ctgtatatgc tttgtatgtc taatatttat ttcaatgcaa 7380
attcaattgt tccttcatct gtattgttat atctaagatt ttattgatgt taaaatctaa 7440
ttgtggaata aaaatctctc tggaatttag cagatacaaa aatgttatct tgcaaaagaa 7500
ctaagaacat ttgtagttag aaatcagctt tcctttgagc ttaattgcct ttttgttaga 7560
ataaggtgaa tttgaacaca ctcctcttat cctcagccca tcacaaataa tagagatgcc 7620
atgattttga ggtctgatgt gaaactggta aaaatgtgat ctaaggtgta actggaaaaa 7680
aaaaggaaag aaaaattaca ttgatgcctc agctgtt 7717

<210> SEQ ID NO 79
<211> LENGTH: 4154
<212> TYPE: DNA
<213> ORGANISM: Homo sapiens

<400> SEQUENCE: 79
acttggacgc gcttgcggag gattgcgttg acgagactct tatttattgt caccaacctg 60
tggtggaatt tgcagttgca cattggatct gattcgcccc gccccgaatg acgcctgccc 120
ggaggcagtg aaagtacagc cgcgccgccc caagtcagcc tggacacata aatcagcacg 180
cggccggaga accccgcaat ctctgcgccc acaaaataca ccgacgatgc ccgatctact 240
ttaagggctg aaacccacgg gcctgagaga ctataagagc gttccctacc gccatggaac 300
aacggggaca gaacgccccg gccgcttcgg gggcccggaa aaggcacggc ccaggaccca 360
gggaggcgcg gggagccagg cctgggcccc gggtccccaa gacccttgtg ctcgttgtcg 420
ccgcggtcct gctgttggtc tcagctgagt ctgctctgat cacccaacaa gacctagctc 480
cccagcagag agcggcccca caacaaaaga ggtccagccc ctcagaggga ttgtgtccac 540
ctggacacca tatctcagaa gacggtagag attgcatctc ctgcaaatat ggacaggact 600
atagcactca ctggaatgac ctccttttct gcttgcgctg caccaggtgt gattcaggtg 660
aagtggagct aagtccctgc accacgacca gaaacacagt gtgtcagtgc gaagaaggca 720
ccttccggga agaagattct cctgagatgt gccggaagtg ccgcacaggg tgtcccagag 780
ggatggtcaa ggtcggtgat tgtacaccct ggagtgacat cgaatgtgtc cacaaagaat 840
caggtacaaa gcacagtggg gaagtcccag ctgtggagga gacggtgacc tccagcccag 900
ggactcctgc ctctccctgt tctctctcag gcatcatcat aggagtcaca gttgcagccg 960
tagtcttgat tgtggctgtg tttgtttgca agtctttact gtggaagaaa gtccttcctt 1020
acctgaaagg catctgctca ggtggtggtg gggaccctga gcgtgtggac agaagctcac 1080

-continued

```
aacgacctgg ggctgaggac aatgtcctca atgagatcgt gagtatcttg cagcccaccc   1140
aggtccctga gcaggaaatg gaagtccagg agccagcaga gccaacaggt gtcaacatgt   1200
tgtcccccgg ggagtcagag catctgctgg aaccggcaga agctgaaagg tctcagagga   1260
ggaggctgct ggttccagca aatgaaggtg atcccactga gactctgaga cagtgcttcg   1320
atgactttgc agacttggtg ccctttgact cctgggagcc gctcatgagg aagttgggcc   1380
tcatggacaa tgagataaag gtggctaaag ctgaggcagc gggccacagg gacaccttgt   1440
acacgatgct gataaagtgg gtcaacaaaa ccgggcgaga tgcctctgtc cacaccctgc   1500
tggatgcctt ggagacgctg ggagagagac ttgccaagca gaagattgag gaccacttgt   1560
tgagctctgg aaagttcatg tatctagaag gtaatgcaga ctctgccatg tcctaagtgt   1620
gattctcttc aggaagtcag accttccctg gtttaccttt tttctggaaa aagcccaact   1680
ggactccagt cagtaggaaa gtgccacaat tgtcacatga ccggtactgg aagaaactct   1740
cccatccaac atcacccagt ggatggaaca tcctgtaact tttcactgca cttggcatta   1800
tttttataag ctgaatgtga taataaggac actatggaaa tgtctggatc attccgtttg   1860
tgcgtacttt gagatttggt ttgggatgtc attgttttca cagcactttt ttatcctaat   1920
gtaaatgctt tatttattta tttgggctac attgtaagat ccatctacac agtcgttgtc   1980
cgacttcact tgatactata tgatatgaac ctttttttggg tgggggtgc ggggcagttc   2040
actctgtctc ccaggctgga gtgcaatggt gcaatcttgg ctcactatag ccttgacctc   2100
tcaggctcaa gcgattctcc cacctcagcc atccaaatag ctgggaccac aggtgtgcac   2160
caccacgccc ggctaatttt ttgtattttg tctagatata ggggctctct atgttgctca   2220
gggtggtctc gaattcctgg actcaagcag tctgcccacc tcagactccc aaagcggtgg   2280
aattagaggc gtgagccccc atgcttggcc ttacctttct acttttataa ttctgtatgt   2340
tattatttta tgaacatgaa gaaactttag taaatgtact tgtttacata gttatgtgaa   2400
tagattagat aaacataaaa ggaggagaca tacaatgggg gaagaagaag aagtcccctg   2460
taagatgtca ctgtctgggt tccagccctc cctcagatgt actttggctt caatgattgg   2520
caacttctac aggggccagt cttttgaact ggacaacctt acaagtatat gagtattatt   2580
tataggtagt tgtttacata tgagtcggga ccaaagagaa ctggatccac gtgaagtcct   2640
gtgtgtggct ggtccctacc tgggcagtct catttgcacc catagccccc atctatggac   2700
aggctgggac agaggcagat gggttagatc acacataaca atagggtcta tgtcatatcc   2760
caagtgaact tgagccctgt ttgggctcag gagatagaag acaaaatctg tctcccacgt   2820
ctgccatggc atcaaggggg aagagtagat ggtgcttgag aatggtgtga aatggttgcc   2880
atctcaggag tagatggccc ggctcacttc tggttatctg tcaccctgag cccatgagct   2940
gccttttagg gtacagattg cctacttgag gaccttggcc gctctgtaag catctgactc   3000
atctcagaaa tgtcaattct taaacactgt ggcaacagga cctagaatgg ctgacgcatt   3060
aaggttttct tcttgtgtcc tgttctatta ttgttttaag acctcagtaa ccatttcagc   3120
ctctttccag caaacccttc tccatagtat ttcagtcatg gaaggatcat ttatgcaggt   3180
agtcattcca ggagtttttg gtcttttctg tctcaaggca ttgtgtgttt tgttccggga   3240
ctggtttggg tgggacaaag ttagaattgc ctgaagatca cacattcaga ctgttgtgtc   3300
tgtggagttt taggagtggg gggtgacctt tctggtcttt gcacttccat cctctcccac   3360
ttccatctgg catcccacgc gttgtcccct gcacttctgg aaggcacagg gtgctgctgc   3420
ctcctggtct ttgcctttgc tgggccttct gtgcaggacg ctcagcctca gggctcagaa   3480
```

ggtgccagtc cggtcccagg tcccttgtcc cttccacaga ggccttccta gaagatgcat 3540
ctagagtgtc agccttatca gtgtttaaga tttttctttt atttttaatt tttttgagac 3600
agaatctcac tctctcgccc aggctggagt gcaacggtac gatcttggct cagtgcaacc 3660
tccgcctcct gggttcaagc gattctcgtg cctcagcctc cggagtagct gggattgcag 3720
gcacccgcca ccacgcctgg ctaatttttg tatttttagt agagacgggg tttcaccatg 3780
ttggtcaggc tggtctcgaa ctcctgacct caggtgatcc accttggcct ccgaaagtgc 3840
tgggattaca ggcgtgagcc accagccagg ccaagctatt cttttaaagt aagcttcctg 3900
acgacatgaa ataattgggg gttttgttgt ttagttacat taggctttgc tatatcccca 3960
ggccaaatag catgtgacac aggacagcca tagtatagtg tgtcactcgt ggttggtgtc 4020
ctttcatgct tctgccctgt caaaggtccc tatttgaaat gtgttataat acaaacaagg 4080
aagcacattg tgtacaaaat acttatgtat ttatgaatcc atgaccaaat taaatatgaa 4140
accttatata aaaa 4154

<210> SEQ ID NO 80
<211> LENGTH: 3809
<212> TYPE: DNA
<213> ORGANISM: Homo sapiens

<400> SEQUENCE: 80
ggcagccgcg cccgctgggc cacagaggcc gctgaggccg cggcgcccgc cagcctgtcc 60
cgcgccatgg ccccgcgcgc ccggcggcgc cgcccgctgt tcgcgctgct gctgctctgc 120
gcgctgctcg cccggctgca ggtggctttg cagatcgctc ctccatgtac cagtgagaag 180
cattatgagc atctgggacg gtgctgtaac aaatgtgaac caggaaagta catgtcttct 240
aaatgcacta ctacctctga cagtgtatgt ctgccctgtg gcccggatga atacttggat 300
agctggaatg aagaagataa atgcttgctg cataaagttt gtgatacagg caaggccctg 360
gtggccgtgg tcgccggcaa cagcacgacc ccccggcgct gcgcgtgcac ggctgggtac 420
cactggagcc aggactgcga gtgctgccgc cgcaacaccg agtgcgcgcc gggcctgggc 480
gcccagcacc cgttgcagct caacaaggac acagtgtgca aaccttgcct tgcaggctac 540
ttctctgatg ccttttcctc cacggacaaa tgcagaccct ggaccaactg taccttcctt 600
ggaaagagag tagaacatca tgggacagag aaatccgatg cggtttgcag ttcttctctg 660
ccagctagaa aaccaccaaa tgaaccccat gtttacttgc ccggtttaat aattctgctt 720
ctcttcgcgt ctgtggccct ggtggctgcc atcatctttg gcgtttgcta taggaaaaaa 780
gggaaagcac tcacagctaa tttgtggcac tggatcaatg aggcttgtgg ccgcctaagt 840
ggagataagg aaatgtgact ggaaacagta actccacgtt catctccagc gggcaggtga 900
tgaacttcaa gggcgacatc atcgtggtct acgtcagcca gacctcgcag gagggcgcgg 960
cggcggctgc ggagcccatg ggccgcccgg tgcaggagga gaccctggcg cgccgagact 1020
ccttcgcggg gaacggcccg cgcttcccgg acccgtgcgg cggccccgag ggctgcggg 1080 agccggagaa ggcctcgagg ccggtgcagg agcaaggcgg ggccaaggct tgagcgcccc 1140
ccatggctgg gagcccgaag ctcggagcca gggctcgcga gggcagcacc gcagcctctg 1200
ccccagcccc ggccacccag ggatcgatcg gtacagtcga ggaagaccac ccggcattct 1260
ctgcccactt tgccttccag gaaatgggct tttcaggaag tgaattgatg aggactgtcc 1320
ccatgcccac ggatgctcag cagcccgccg cactggggca gatgtctccc ctgccactcc 1380

-continued

```
tcaaactcgc agcagtaatt tgtggcacta tgacagctat ttttatgact atcctgttct   1440
gtgggggggg gggtctgttt tccccccata tttgtattcc ttttcataac ttttcttgat   1500
atctttcctc cctctttttt aatgtaaagg ttttctcaaa aattctccta aaggtgaggg   1560
tctctttctt ttctctttc ctttttttt tcttttttg gcaacctggc tctggcccag   1620
gctagagtgc agtggtgcga ttatagcccg gtgcagcctc taactcctgg gctcaagcaa   1680
tccaagtgat cctcccacct caaccttcgg agtagctggg atcacagctg caggccacgc   1740
ccagcttcct ccccccgact cccccccag agacacggtc ccaccatgtt acccagcctg   1800
gtctcaaact ccccagctaa agcagtcctc cagcctcggc ctcccaaagt actgggatta   1860
caggcgtgag cccccacgct ggcctgcttt acgtattttc ttttgtgccc ctgctcacag   1920
tgttttagag atggctttcc cagtgtgtgt tcattgtaaa cacttttggg aaagggctaa   1980
acatgtgagg cctggagata gttgctaagt tgctaggaac atgtggtggg actttcatat   2040
tctgaaaaat gttctatatt ctcatttttc taaaagaaag aaaaaaggaa acccgattta   2100
tttctcctga atctttttaa gtttgtgtcg ttccttaagc agaactaagc tcagtatgtg   2160
accttacccg ctaggtggtt aatttatcca tgctggcaga ggcactcagg tacttggtaa   2220
gcaaatttct aaaactccaa gttgctgcag cttggcattc ttcttattct agaggtctct   2280
ctggaaaaga tggagaaaat gaacaggaca tggggctcct ggaaagaaag ggcccgggaa   2340
gttcaaggaa gaataaagtt gaaattttaa tttgcatttt ttttgtctag ataagaatag   2400
cgtgaataga tcctctttta ttcgtaaata atcgtgcatc tgtgggttag ccttgtagaa   2460
gtggaaaaca ttccattttc caatgcattt aaatgtaaag ccaaatctgc atgttgtgaa   2520
tttaagaaaa cttattatcc taaaggtgcc tttctcttgg catcatcccg cttgtgagaa   2580
gcctagagga cgctccaggt ggaaggaaat cccctgggtg gttttatctt ttgttaccca   2640
gtgagcactg gttccccgca aatactgggg aaaagcaaaa atacacaagc aagttaaaat   2700
taattttgca catctgggag gttataaaag aaagcactaa tagtagtcac tgcccagact   2760
ttactggcca caaatgccca gctgaagagc atgactgtgg atcactggtt tttccctcct   2820
gctggaaatg ctggggtggt agcggtcgat taggattttc agtggagaag cacaggacag   2880
ttctgtaatt tatgggactc cttagccaac ataaagaact gcaggaaata actgcacagc   2940
caggaggatc cgttggtggg aatttaccgt cattcctgcc cttttattta acatcatcca   3000
cagagagatg ttatacaaat ggaggaaacc attatacctt ttgatatgga atatattaca   3060
gagttacagt tcacaaagta gaatgctgag ctgaaaaccc gagtttctgc tgtgactgtc   3120
atctcactga gcacttcgct tttctttgct tttatttttt ccttctataa aaaggcaata   3180
atgataattt ataatagttt ccctacccag agatattaga agtatgctac agtgaatgtt   3240
aaagtacctt gagatcctta aatcaaaggt gctatataca taagtaagac tctactttca   3300
gaaaaaggta atattatttc ctgcactgat ccctactaat tctatattga tccaaaggca   3360
actcaatgct aaaaaatgta tagaaaatat aagtctgtgt ctgtgtactg tagagatgta   3420
tgtgacaagt gtaaacaaaa tgaactgaag cagtaatgaa cagttattag gggaacatg   3480
ataaagagat tatattaagc ttatgtttca ccataaaatc ctttttatgg cttactaaaa   3540
ccgagctcac tgtaaaatca tgatccaact tattgctaat ctttatgata tgcttattcc   3600
taatctttat ggtatggtgt caaccgttca tttgtatctt attgctcatt ccctggacca   3660
cagactaggg acagaaaata cttgctttaa taatatatat gctgttgatt tcacaaaaat   3720
ttattaaaat acagcctggg tacccagtga aagagctgaa atggaaatgg agtatcatgt   3780
```

ttcctactca cattttactc agctgtcgg 3809

<210> SEQ ID NO 81
<211> LENGTH: 2258
<212> TYPE: DNA
<213> ORGANISM: Homo sapiens

<400> SEQUENCE: 81
ctcctccagc tcttcctgtc ccgctgttgc aacactgcct cactcttccc ctcccacctt 60
ctctcccctc ctctctgctt taattttctc agaattctct ggactgaggc tccagttctg 120
gcctttgggg ttcaagatca ctgggaccag gccgtgatct ctatgcccga gtctcaaccc 180
tcaactgtca ccccaaggca cttgggacgt cctggacaga ccgagtcccg ggaagcccca 240
gcactgccgc tgccacactg ccctgagccc aaatgggggga gtgagaggcc atagctgtct 300
ggcatgggcc tctccaccgt gcctgacctg ctgctgccac tggtgctcct ggagctgttg 360
gtgggaatat accccctcagg ggttattgga ctggtccctc acctagggga cagggagaag 420
agagatagtg tgtgtcccca aggaaaatat atccaccctc aaaataattc gatttgctgt 480
accaagtgcc acaaaggaac ctacttgtac aatgactgtc caggcccggg gcaggatacg 540
gactgcaggg agtgtgagag cggctccttc accgcttcag aaaaccacct cagacactgc 600
ctcagctgct ccaaatgccg aaaggaaatg ggtcaggtgg agatctcttc ttgcacagtg 660
gaccgggaca ccgtgtgtgg ctgcaggaag aaccagtacc ggcattattg gagtgaaaac 720
cttttccagt gcttcaattg cagcctctgc ctcaatggga ccgtgcacct ctcctgccag 780
gagaaacaga acaccgtgtg cacctgccat gcaggtttct ttctaagaga aaacgagtgt 840
gtctcctgta gtaactgtaa gaaaagcctg gagtgcacga agttgtgcct accccagatt 900
gagaatgtta agggcactga ggactcaggc accacagtgc tgttgcccct ggtcattttc 960
tttggtcttt gccttttatc cctcctcttc attggtttaa tgtatcgcta ccaacggtgg 1020
aagtccaagc tctactccat tgtttgtggg aaatcgacac ctgaaaaaga gggggagctt 1080
gaaggaacta ctactaagcc cctggcccca aacccaagct tcagtcccac tccaggcttc 1140
acccccaccc tgggcttcag tcccgtgccc agttccacct tcacctccag ctccacctat 1200
acccccggtg actgtcccaa ctttgcggct ccccgcagag aggtggcacc accctatcag 1260
ggggctgacc ccatccttgc gacagccctc gcctccgacc ccatccccaa ccccccttcag 1320 aagtgggagg acagcgccca caagccacag agcctagaca ctgatgaccc cgcgacgctg 1380
tacgccgtgg tggagaacgt gcccccgttg cgctggaagg aattcgtgcg gcgcctaggg 1440
ctgagcgacc acgagatcga tcggctggag ctgcagaacg ggcgctgcct gcgcgaggcg 1500
caatacagca tgctggcgac ctggaggcgg cgcacgccgc ggcgcgaggc cacgctggag 1560
ctgctgggac gcgtgctccg cgacatggac ctgctgggct gcctggagga catcgaggag 1620
gcgctttgcg gccccgccgc cctcccgccc gcgcccagtc ttctcagatg aggctgcgcc 1680
cctgcgggca gctctaagga ccgtcctgcg agatcgcctt ccaaccccac ttttttctgg 1740
aaaggagggg tcctgcaggg gcaagcagga gctagcagcc gcctacttgg tgctaacccc 1800
tcgatgtaca tagcttttct cagctgcctg cgcgccgccg acagtcagcg ctgtgcgcgc 1860
ggagagaggt gcgccgtggg ctcaagagcc tgagtgggtg gtttgcgagg atgagggacg 1920
ctatgcctca tgcccgtttt gggtgtcctc accagcaagg ctgctcgggg gcccctggtt 1980
cgtccctgag cctttttcac agtgcataag cagttttttt tgtttttgtt ttgttttgtt 2040

-continued

```
ttgtttttaa atcaatcatg ttacactaat agaaacttgg cactcctgtg ccctctgcct   2100

ggacaagcac atagcaagct gaactgtcct aaggcagggg cgagcacgga acaatggggc   2160

cttcagctgg agctgtggac ttttgtacat acactaaaat tctgaagtta aagctctgct   2220

cttggaaaaa aaaaaaaaaa aaaaaaaaaa aaaaaaaa                             2258


<210> SEQ ID NO 82
<211> LENGTH: 3682
<212> TYPE: DNA
<213> ORGANISM: Homo sapiens

<400> SEQUENCE: 82

gcgagcgcag cggagcctgg agagaaggcg ctgggctgcg agggcgcgag ggcgcgaggg     60

cagggggcaa ccggaccccg cccgcaccca tggcgcccgt cgccgtctgg gccgcgctgg    120

ccgtcggact ggagctctgg gctgcggcgc acgccttgcc cgcccaggtg gcatttacac    180

cctacgcccc ggagcccggg agcacatgcc ggctcagaga atactatgac cagacagctc    240

agatgtgctg cagcaaatgc tcgccgggcc aacatgcaaa agtcttctgt accaagacct    300

cggacaccgt gtgtgactcc tgtgaggaca gcacatacac ccagctctgg aactgggttc    360

ccgagtgctt gagctgtggc tcccgctgta gctctgacca ggtggaaact caagcctgca    420

ctcgggaaca gaaccgcatc tgcacctgca ggcccggctg gtactgcgcg ctgagcaagc    480

aggaggggtg ccggctgtgc gcgccgctgc gcaagtgccg cccgggcttc ggcgtggcca    540

gaccaggaac tgaaacatca gacgtggtgt gcaagccctg tgccccgggg acgttctcca    600

acacgacttc atccacggat atttgcaggc cccaccagat ctgtaacgtg gtggccatcc    660

ctgggaatgc aagcatggat gcagtctgca cgtccacgtc ccccacccgg agtatggccc    720

caggggcagt acacttaccc cagccagtgt ccacacgatc ccaacacacg cagccaactc    780

cagaacccag cactgctcca agcacctcct tcctgctccc aatgggcccc agccccccag    840

ctgaagggag cactggcgac ttcgctcttc cagttggact gattgtgggt gtgacagcct    900

tgggtctact aataatagga gtggtgaact gtgtcatcat gacccaggtg aaaaagaagc    960

ccttgtgcct gcagagagaa gccaaggtgc ctcacttgcc tgccgataag gcccggggta   1020

cacagggccc cgagcagcag cacctgctga tcacagcgcc gagctccagc agcagctccc   1080

tggagagctc ggccagtgcg ttggacagaa gggcgcccac tcggaaccag ccacaggcac   1140

caggcgtgga ggccagtggg gccggggagg cccgggccag caccgggagc tcagattctt   1200

cccctggtgg ccatgggacc caggtcaatg tcacctgcat cgtgaacgtc tgtagcagct   1260

ctgaccacag ctcacagtgc tcctcccaag ccagctccac aatgggagac acagattcca   1320

gcccctcgga gtccccgaag gacgagcagg tccccttctc caaggaggaa tgtgcctttc   1380

ggtcacagct ggagacgcca gagaccctgc tggggagcac cgaagagaag cccctgcccc   1440

ttggagtgcc tgatgctggg atgaagccca gttaaccagg ccggtgtggg ctgtgtcgta   1500

gccaaggtgg gctgagccct ggcaggatga ccctgcgaag gggccctggt ccttccaggc   1560

ccccaccact aggactctga ggctctttct gggccaagtt cctctagtgc cctccacagc   1620

cgcagcctcc ctctgacctg caggccaaga gcagaggcag cgagttgtgg aaagcctctg   1680

ctgccatggc gtgtccctct cggaaggctg gctgggcatg gacgttcggg gcatgctggg   1740

gcaagtccct gactctctgt gacctgcccc gcccagctgc acctgccagc ctggcttctg   1800

gagcccttgg gtttttttgtt tgtttgtttg tttgtttgtt tgtttctccc cctgggctct   1860

gccccagctc tggcttccag aaaaccccag catccttttc tgcagagggg ctttctggag   1920
```

aggagggatg ctgcctgagt cacccatgaa gacaggacag tgcttcagcc tgaggctgag 1980
actgcgggat ggtcctgggg ctctgtgcag ggaggaggtg gcagccctgt agggaacggg 2040
gtccttcaag ttagctcagg aggcttggaa agcatcacct caggccaggt gcagtggctc 2100
acgcctatga tcccagcact ttgggaggct gaggcgggtg gatcacctga ggttaggagt 2160
tcgagaccag cctggccaac atggtaaaac cccatctcta ctaaaaatac agaaattagc 2220
cgggcgtggt ggcgggcacc tatagtccca gctactcaga agcctgaggc tgggaaatcg 2280
tttgaacccg ggaagcggag gttgcaggga gccgagatca cgccactgca ctccagcctg 2340
ggcgacagag cgagagtctg tctcaaaaga aaaaaaaaag caccgcctcc aaatgccaac 2400
ttgtcctttt gtaccatggt gtgaaagtca gatgcccaga gggcccaggc aggccaccat 2460
attcagtgct gtggcctggg caagataacg cacttctaac tagaaatctg ccaatttttt 2520
aaaaaagtaa gtaccactca ggccaacaag ccaacgacaa agccaaactc tgccagccac 2580
atccaacccc ccacctgcca tttgcaccct ccgccttcac tccggtgtgc ctgcagcccc 2640
gcgcctcctt ccttgctgtc ctaggccaca ccatctcctt tcagggaatt tcaggaacta 2700
gagatgactg agtcctcgta gccatctctc tactcctacc tcagcctaga ccctcctcct 2760
cccccagagg ggtgggttcc tcttccccac tccccacctt caattcctgg gccccaaacg 2820
ggctgccctg ccactttggt acatggccag tgtgatccca agtgccagtc ttgtgtctgc 2880
gtctgtgttg cgtgtcgtgg gtgtgtgtag ccaaggtcgg taagttgaat ggcctgcctt 2940
gaagccactg aagctgggat tcctccccat tagagtcagc cttccccctc ccagggccag 3000
ggccctgcag aggggaaacc agtgtagcct tgcccggatt ctgggaggaa gcaggttgag 3060
gggctcctgg aaaggctcag tctcaggagc atggggataa aggagaaggc atgaaattgt 3120
ctagcagagc aggggcaggg tgataaattg ttgataaatt ccactggact tgagcttggc 3180
agctgaacta ttggagggtg ggagagccca gccattacca tggagacaag aagggttttc 3240
caccctggaa tcaagatgtc agactggctg gctgcagtga cgtgcacctg tactcaggag 3300
gctgagggga ggatcactgg agcccaggag tttgaggctg cagcgagcta tgatcgcgcc 3360
actacactcc agcctgagca acagagtgag accctgtctc ttaaagaaaa aaaaagtcag 3420
actgctggga ctggccaggt ttctgcccac attggaccca catgaggaca tgatggagcg 3480
cacctgcccc ctggtggaca gtcctgggag aacctcaggc ttccttggca tcacagggca 3540
gagccgggaa gcgatgaatt tggagactct gtggggcctt ggttcccttg tgtgtgtgtg 3600
ttgatcccaa gacaatgaaa gtttgcactg tatgctggac ggcattcctg cttatcaata 3660
aacctgtttg ttttaaaaaa aa 3682

<210> SEQ ID NO 83
<211> LENGTH: 2894
<212> TYPE: DNA
<213> ORGANISM: Homo sapiens

<400> SEQUENCE: 83
cgagactcca tctcaaaaac aaaacaaata aacgaacaaa aaaacccaca acgtattatt 60
ttcttgttta cgaggtttct tgtctctctg gctccaccag aagaggagca gggacccttc 120
ttgctgttgt tcattgctgc atcccccaca ccgagagcag agcctggcat gggcagaaag 180
tcctcagtcg atatttggtg gccccaagcg aatgaagcat ccaagaaggg aaagctgggg 240
gctccccact gcacttgcca cctgagtcac attttcagaa gcctctggaa agtcgtgcac 300

-continued

```
agcccaggag tgttgagcaa tttcggtttc ctctgaggtt gaaggaccca ggcgtgtcag    360
ccctgctcca gacaccttgg gcatggagga gagtgtcgta cggccctcag tgtttgtggt    420
ggatggacag accgacatcc cattcacgag gctgggacga agccaccgga gacagtcgtg    480
cagtgtggcc cgggtgggtc tgggtctctt gctgttgctg atgggggccg ggctggccgt    540
ccaaggctgg ttcctcctgc agctgcactg gcgtctagga gagatggtca cccgcctgcc    600
tgacggacct gcaggctcct gggagcagct gatacaagag cgaaggtctc acgaggtcaa    660
cccagcagcg catctcacag gggccaactc cagcttgacc ggcagcgggg ggccgctgtt    720
atgggagact cagctgggcc tggccttcct gaggggcctc agctaccacg atggggccct    780
tgtggtcacc aaagctggct actactacat ctactccaag gtgcagctgg gcggtgtggg    840
ctgcccgctg ggcctggcca gcaccatcac ccacggcctc tacaagcgca caccccgcta    900
ccccgaggag ctggagctgt tggtcagcca gcagtcaccc tgcggacggg ccaccagcag    960
ctcccgggtc tggtgggaca gcagcttcct gggtggtgtg gtacacctgg aggctgggga   1020
gaaggtggtc gtccgtgtgc tggatgaacg cctggttcga ctgcgtgatg gtacccggtc   1080
ttacttcggg gctttcatgg tgtgaaggaa ggagcgtggt gcattggaca tgggtctgac   1140
acgtggagaa ctcagagggt gcctcagggg aaagaaaact cacgaagcag aggctgggcg   1200
tggtggctct cgcctgtaat cccagcactt tgggaggcca aggcaggcgg atcacctgag   1260
gtcaggagtt cgagaccagc ctggctaaca tggcaaaacc ccatctctac taaaaataca   1320
aaaattagcc ggacgtggtg gtgcctgcct gtaatccagc tactcaggag gctgaggcag   1380
gataattttg cttaaacccg ggaggcggag gttgcagtga gccgagatca caccactgca   1440
ctccaacctg ggaaacgcag tgagactgtg cctcaaaaaa aagaaaggaa gaaaaaagaa   1500
aactcaggaa acagatcttg ggggacactc cagggaaccc aaaactcaaa ggcggagagc   1560
tcagtgggca ccaccaaggc gagatgaagc cccagcaggc accttcagaa gacccacgta   1620
gactgcagac cctgccacgg acaatactaa ggacaaaaac ccagagactt ggggtctgtg   1680
ggcccccaaa catggggtaa agttgatttg cctgatattc aggaagaagg ggtgaggggt   1740
gggtatttat gcttttgatt cagaagaaag tggggcttgg gattccaggg acttggctgg   1800
gggtgggaaa cttcatccac ttccctactc tcatcatgag tacggacagg gtgggcggga   1860
gactgatcat cgggactcat catgaagagc ccagccccac cccacatact cagatcccac   1920
ccacagactg gtggccacac ctcagcctgg tcacaaagag ttacactcag atacatgagc   1980
acggcagcgt gctcataact gtttaacaac cagctgtcct gggaggggga cagctttgta   2040
atgtttgcca atttccatgg tgtaaatgct accaccatgg ctgatttcat cactgccaag   2100
catagacatc cctaatagga caccacggat ctgtccccgg catccggccc agggcctggc   2160
acaaagcatg ctctagggaa atgcttgctg attgaaagga aggaagaatg actctacagt   2220
cacacctatg gcatcccaca aaatctgtca catggctgca taatctcagc cactctttca   2280
caactataga ctcatacacg cgaagtgcca gattcatgca caaccacaca atcacatgga   2340
agtcacagac ggcatcacag acagtcacag cactgtgtgt atgttataac acaagcacac   2400
aaaactcaga cagcatccca gctacacagc cactcccaga ggtgtcaccg tcacacttgg   2460
taattaatac tcattacatt agacacagac agaccaagtt atagtcagac ctggttacac   2520
acatacacac acacaatatc accatgacaa atacacatta cacacacaca acatcacaat   2580
gacaaacaca cattacacac acaacatcac gatgacaaac acacattaca cacacaacat   2640
cacgatgaca aacacacatt acacacacat cacaatgaca aacacaacat tacacacaca   2700
```

-continued caacatcaca atgacacaca catcacacac acatcacaat gacaaacaca caacattaca 2760
cacatataca cacagcctga gggccctccc cagcccagac taacacatct cggggtgagg 2820
accagacctt gttcataacc ctgggcctct taaccactga tctttgaaat aaatggcaaa 2880
tagttgtacc tgga 2894

<210> SEQ ID NO 84
<211> LENGTH: 1680
<212> TYPE: DNA
<213> ORGANISM: Homo sapiens

<400> SEQUENCE: 84
aaaaagcggc gcgctgtgtc ttcccgcagt ctctcgtcat ggaatacgcc tctgacgctt 60
cactggaccc cgaagccccg tggcctcccg cgccccgcgc tcgcgcctgc cgcgtactgc 120
cttgggccct ggtcgcgggg ctgctgctgc tgctgctgct cgctgccgcc tgcgccgtct 180
tcctcgcctg cccctgggcc gtgtccgggg ctcgcgcctc gcccggctcc gcggccagcc 240
cgagactccg cgagggtccc gagctttcgc ccgacgatcc cgccggcctc ttggacctgc 300
ggcagggcat gtttgcgcag ctggtggccc aaaatgttct gctgatcgat gggcccctga 360
gctggtacag tgacccaggc ctggcaggcg tgtccctgac gggggggcctg agctacaaag 420 aggacacgaa ggagctggtg gtggccaagg ctggagtcta ctatgtcttc tttcaactag 480
agctgcggcg cgtggtggcc ggcgagggct caggctccgt ttcacttgcg ctgcacctgc 540
agccactgcg ctctgctgct ggggccgccg ccctggcttt gaccgtggac ctgccacccg 600
cctcctccga ggctcggaac tcggccttcg gtttccaggg ccgcttgctg cacctgagtg 660
ccggccagcg cctgggcgtc catcttcaca ctgaggccag ggcacgccat gcctggcagc 720
ttacccaggg cgccacagtc ttgggactct tccgggtgac ccccgaaatc ccagccggac 780
tcccttcacc gaggtcggaa taacgtccag cctgggtgca gcccacctgg acagagtccg 840
aatcctactc catccttcat ggagacccct ggtgctgggt ccctgctgct ttctctacct 900
caaggggctt ggcaggggtc cctgctgctg acctcccctt gaggaccctc ctcacccact 960
ccttccccaa gttggacctt gatatttatt ctgagcctga gctcagataa tatattatat 1020
atattatata tatatatata tttctattta aagaggatcc tgagtttgtg aatggacttt 1080
tttagaggag ttgttttggg gggggggggg tcttcgacat tgccgaggct ggtcttgaac 1140
tcctggactt agacgatcct cctgcctcag cctcccaagc aactgggatt catcctttct 1200
attaattcat tgtacttatt tgcttatttg tgtgtattga gcatctgtaa tgtgccagca 1260
ttgtgcccag gctagggggc tatagaaaca tctagaaata gactgaaaga aaatctgagt 1320
tatggtaata cgtgaggaat ttaaagactc atccccagcc tccacctcct gtgtgatact 1380
tgggggctag ctttttttctt tctttctttt ttttgagatg gtcttgttct gtcaaccagg 1440
ctagaatgca gcggtgcaat catgagtcaa tgcagcctcc agcctcgacc tcccgaggct 1500
caggtgatcc tcccatctca gcctctcgag tagctgggac cacagttgtg tgccaccaca 1560
cttggctaac tttttaattt ttttgcggag acggtattgc tatgttgcca aggttgttta 1620
catgccagta caatttataa taaacactca tttttcctcc ctctgaaaaa aaaaaaaaaa 1680

<210> SEQ ID NO 85
<211> LENGTH: 2029
<212> TYPE: DNA
<213> ORGANISM: Homo sapiens

<400> SEQUENCE: 85

```
ggcggcgggc ggcgggcggc ggggaccggg tgcggtggtg gctgcggcgg cggcggcggg     60
agcagcatgg attggggcac tgagctgtgg gatcagttcg aggtgctcga gcgccacacg    120
cagtgggggc tggacctgtt ggacagatat gtaaagttcg tgaaagaacg caccgaagtg    180
gaacaggctt acgccaaaca actgcggagc ctggtgaaaa aatatctgcc caagagacct    240
gccaaggatg atcctgagtc caaattcagc cagcaacagt ccttcgtaca gattctccag    300
gaggtgaatg actttgcagg ccagcgggag ctggtggctg agaacctcag tgtccgtgta    360
tgtcttgagc tgaccaagta ctcacaagag atgaaacagg agaggaagat gcacttccaa    420
gaagggcggc gggcccagca gcagctggaa aatggcttta aacagctgga gaatagtaag    480
cgtaaatttg agcgggactg ccgggaggca gagaaggcag cccagactgc tgaacggcta    540
gaccaggata tcaacgccac caaggctgat gtggagaagg ccaagcagca agcccacctt    600
cggagtcaca tggccgaaga aagcaaaaac gaatatgcgg ctcaactgca gcgcttcaac    660
cgagaccaag cccacttcta tttttcacag atgccccaga tattcgataa gctccaagac    720
atggatgaac gcagggccac ccgcctgggt gccgggtatg ggctcctgtc ggaggccgag    780
ctggaggtgg tgcccataat agccaagtgc ttggagggca tgaaggtggc tgcaaatgct    840
gtggatccca agaacgactc ccacgtcctt atagagctgc acaagtcagg ttttgcccgc    900
ccgggcgacg tggaattcga ggacttcagc cagcccatga accgtgcacc ctccgacagc    960
agtctgggca ccccctcgga tggacggcct gaactccgag gcccgggtcg cagccgcacc   1020
aagcgctggc cttttggcaa gaagaacaag acagtggtga ccgaggattt tagccacttg   1080
cccccagagc agcagcgaaa acggcttcaa cagcagttgg aagaacgcag tcgtgaactt   1140
cagaaggagg ttgaccagag ggaagcccta aagaaaatga aggatgtcta tgagaagaca   1200
cctcagatgg gggaccccgc cagcttggag ccccagatcg ctgaaaccct gagcaacatt   1260
gaacggctga aattggaagt gcagaagtat gaggcgtggc tggcagaagc tgaaagtcga   1320
gtccttagca accggggaga cagcctgagc cggcacgccc ggcctcccga cccccccgct   1380
agcgccccgc cagacagcag cagcaacagc gcatcacagg acaccaagga gagctctgaa   1440
gagcctccct cagaagagag ccaggacacc cccatttaca cggagtttga tgaggatttc   1500
gaggaggaac ccacatcccc cataggtcac tgtgtggcca tctaccactt tgaagggtcc   1560
agcgagggca ctatctctat ggccgagggt gaagacctca gtcttatgga agaagacaaa   1620
ggggacggct ggacccgggt caggcggaaa gagggaggcg agggctacgt gcccacctcc   1680
tacctccgag tcacgctcaa ttgaaccctg ccagagacgg gaagaggggg gctgtcggct   1740
gctgcttctg ggccacgggg agccccagga cctatgcact ttatttctga ccccgtggct   1800
tcggctgaga cctgtgtaac ctgctgcccc ctccaccccc aacccagtcc tacctgtcac   1860
accggacgga cccgctgtgc cttctaccat cgttccacca ttgatgtaca tactcatgtt   1920
ttacatcttt tctttctgcc gctcggctcc ggccattttg ttttatacaa aaatgggaaa   1980
aaaaaaaaag aaattatata aagttcctag aaaaaaaaaa aaaaaaaaa               2029
```

<210> SEQ ID NO 86
<211> LENGTH: 1762
<212> TYPE: DNA
<213> ORGANISM: Homo sapiens

<400> SEQUENCE: 86

```
gacgtcatcg gaggcgtggt cgtccccaaa attagggagg aagaggaaaa aaaaaagcca     60
```

gaaaaagttt tcttttctgg agtcccaaac gaggtgcggg acggaagagg gggtgaaggc 120
cagaggctcg gggcttcaag accgctgtct ggagtccccc tttccaggcc atgtcggggc 180
ccacctggct gcccccgaag cagccggagc ccgccagagc cctcagggg agggcgatcc 240 cccgcggcac cccggggcca ccaccggccc acggagcagc actccagccc caccccaggg 300
tcaatttttg ccccccttcca tctgagcagt gttaccaggc cccagggga ccggaggatc 360 gggggccggc gtgggtgggg tcccatggag tactccagca cacgcagggg ctccctgcag 420
acaggggggg ccttcgccct ggaagcctgg acgccgagat agacttgctg agcagcacgc 480
tggccgagct gaatgggggt cggggtcatg cgtcacggcg accagaccga caggcatatg 540
agcccccgcc acctcctgcc taccgcacgg gctccctgaa gccaaatcca gcctcgccgc 600
tcccagcgtc tccctatggg ggccccactc cagcctctta cactaccgcc agcaccccgg 660
ctggcccagc cttccccgtg caagtgaagg tggcacagcc agtgaggggc tgcggcccac 720
ccaggcgggg agcctctcag gcctctgggc ccctcccggg cccccacttt cctctcccag 780
gccgaggtga agtctggggg cctggctata ggagccagag agagccaggg ccaggggcca 840
aagaggaagc tgctggggtc tctggccctg caggaagagg aagaggaggc gagcacgggc 900
cccaggtgcc cctgagccag cctccagagg atgagctgga taggctgacg aagaagctgg 960
ttcacgacat gaaccacccg cccagcgggg agtactttgg ccagtgtggt ggctgcggag 1020
aagatgtggt tggggatggg gctggggttg tggcccttga tcgcgtcttt cacgtgggct 1080
gctttgtatg ttctacatgc cgggcccagc ttcgcggcca gcatttctac gccgtggaga 1140
ggagggcata ttgcgagggc tgctacgtgg ccaccctgga gaaatgtgcc acgtgctccc 1200
agcccatcct ggaccggatc ctgcgggcta tggggaaggc ctaccaccct ggctgcttca 1260
cctgcgtggt gtgtcaccgc ggcctcgacg gcatcccctt cacagtggat gctacgagcc 1320
agatccactg cattgaggac tttcacagga agtttgcccc aagatgctca gtgtgcggtg 1380
gggccataat gcctgagcca ggtcaggagg agactgtgag aattgttgct ctggatcgaa 1440
gttttcacat tggctgttac aagtgcgagg agtgtgggct gctgctctcc tctgagggcg 1500
agtgtcaggg ctgctacccg ctggatgggc acatcttgtg caaggcctgc agcgcctggc 1560
gcatccagga gctctcagcc accgtcacca ctgactgctg agtcttccta gaagtacctg 1620
ctgggttctc agttccagtt cccatccttt gattgatcac tctccctgac atccacctgt 1680
atgactttgt caccaaatgc tgtcttctct ttctccaatc aagaaataat aatccctcga 1740
gtttacaaaa caaaaaaaaa aa 1762

<210> SEQ ID NO 87
<211> LENGTH: 2783
<212> TYPE: DNA
<213> ORGANISM: Homo sapiens

<400> SEQUENCE: 87
gattgcgagc caggaggagg aagccggcgg tggccccgtc agcagccggc tgctgagagg 60
ccggtaggcg gcggcggtcc cgaggggcgg cggccgcgct gctccctgag aacgggtccc 120
gcagctgggc aggcgggcgg cctgagggcg cggagccatg aagctgtaca gcctcagcgt 180
cctctacaaa ggcgaggcca aggtggtgct gctcaaagcc gcatacgatg tgtcttcctt 240 cagcttttc cagagatcca gcgttcagga attcatgacc ttcacgagtc aactgattgt 300
ggagcgctca tcgaaaggca ctagagcttc tgtcaaagaa caagactatc tgtgccacgt 360

-continued

```
ctacgtccgg aatgatagtc ttgcaggtgt ggtcattgct gacaatgaat acccatcccg    420
ggtggccttt accttgctgg agaaggtact agatgaattc tccaagcaag tcgacaggat    480
agactggcca gtaggatccc ctgctacaat ccattaccca gccctggatg gtcacctcag    540
tagataccag aacccacgag aagctgatcc catgactaaa gtgcaggccg aactagatga    600
gaccaaaatc attctgcaca acaccatgga gtctctgtta gagcgaggtg agaagctaga    660
tgacttggtg tccaaatccg aggtgctggg aacacagtct aaagccttct ataaaactgc    720
ccggaaacaa aactcatgct gtgccatcat gtgatgcagc ctgccagagg cccaatgctg    780
gaatggcacc atcattcaca tcagaactgc agcccctgga aaagaagaga cagccataga    840
cgaggagcca gagtgggggc agactggcca tttttatttt gaagttcctg cgagaaatgg    900
atggtggaag ggtggcgaat gttcaaattc atatgtgtgg tagtgattct tggaaagaat    960
ttgaggtccc caaaggtgta tttttgggca aatgaaacca taaactccga ctggcttctg   1020
tagatgccaa agggctcttt ttcagctaac cctgggaagg ctctgtggga gggaggtcgg   1080
agccagctgt ttctcgatct ttggtatatc tttggatctt atttgtacat taatgatatt   1140
aacactccag tgggggtgg ggagtccctg atgctagggc tggggtgggt ggagtttgaa   1200
gactcttggg aaagcctctc ctggggccac tgttgggggt gggagtgagc ccaccacaga   1260
ggccacaggc aggccccac ttcaggccca aggcctgggg cgggggaac agtcactggg   1320
tctcagattc tgagactgtt gtttagctta cctttctgct aggattggct tcccgcagag   1380
ggcagggccc atcctaagca gcttccaagt cccacaaagg tggcttgtgg gaggatttgg   1440
aaggagctgc attgtgggcg gggagtgtgt gggttgggtt cgtaccagca agtagactag   1500
gaactgagcc caggaaaggg ggatgttttc ctggtgtttg gatggtcagc tgggagtgtc   1560
catcatcagg ggaagatcaa acacaggtgc actcagctgc ccagggcctc tgggacactt   1620
gccttgactt gcaacttgcc ttgaacatca cgatcaaagc agcaggtgct gtggtctctc   1680
aaaattgatt tttatttgac tctgtggctc taagactgcc ttgaaccgcc tgaggcctat   1740
gcatctgaac aagtgggtct ctcccttgag caccaggagt gggtgccagc cggccccgag   1800
gattcccagc accccaccta tggtcttgcc agcataggct tgctagttcc ttcttggtca   1860
gaggtagctg cagaggggg aggccaaggg tttggtctaa gctgtgccct gccacctggc   1920
aggaggccca ctcactgccc aagtcatggc aacaggctgg agcagcccag gagatgggcc   1980
taaaatgttc tggatccctt gggtcctagt gttatgttcc agtctgccca cctgtgctca   2040
ggatgcagcc ctgggatcca gcacccatgg aagcttctgc tgggatggtg tcacctatgg   2100
gttttgaacc agtgtggtat ggtccttggg agctctgctc tgagcttgcc acactgctga   2160
gagcacccac tgtcctgacc agagtctcag tggtcctgac ccccaatgtg ggcaggggct   2220
gggcaggagg gtggggtctg ctgtgggttc agaggactcc acctcctggc tggtttacct   2280
gctgctgccc attttctctg ggtactgctg gccagaggac tttagcctac ccctgaagag   2340
cctgtccatg tcattttcct actgccatag ataccctaag cccagggccc cttgaggccc   2400
agactcagcc tgcccactgg tgccggagac ggagtggagt gggcctggat ccgagggatg   2460
ctacctctcc ctttcccact tgaggaccct ggggagagat gggggcgggg aaaatggagg   2520
tatgaatttg gggtaagagg aagtgagatc tccgcttgca ggtcagcccc tgccttgcag   2580
ggcgggctgg cttgactcag gccctgtgag atagagggcc cagcccagcc ccacccacag   2640
atcccctgct cctgttgtgt tctgttgtaa atcatttggc gagactgtat tttagtaact   2700
gctgcctaac ttccctgtgt tctatttgag aggcgcctgt ctggataaag ttgtcttgaa   2760
```

atttcaaaaa aaaaaaaaaa aaa 2783

<210> SEQ ID NO 88
<211> LENGTH: 3341
<212> TYPE: DNA
<213> ORGANISM: Homo sapiens

<400> SEQUENCE: 88
ccgggccccg gcggctgcgc cgagtccccg cccctccctg ctccgtaggg gtaggagggg 60
gccggcggag tttccctccc cgcccagcgg ccctgggcgg gcttttcggc tgcttctcat 120
aagcaggtgg tttcgtttct ccggcacagg taggtttctc tggcaccgat tcggggcctg 180
cccggacttc gccgcacgct gcagaacctc gcccagcgcc caccatgccc cggcagctca 240
gcgcggcggc cgcgctcttc gcgtccctgg ccgtaatttt gcacgatggc agtcaaatga 300
gagcaaaagc atttccagaa accagagatt attctcaacc tactgcagca gcaacagtac 360
aggacataaa aaaacctgtc cagcaaccag ctaagcaagc acctcaccaa actttagcag 420
caagattcat ggatggtcat atcacctttc aaacagcggc cacagtaaaa attccaacaa 480
ctaccccagc gactacaaaa aacactgcaa ccaccagccc aattacctac accctggtca 540
caacccaggc cacacccaac aactcacaca cagctcctcc agttactgaa gttacagtcg 600
gccctagctt agccccttat tcactgccac ccaccatcac cccaccagct catacaactg 660
gaaccagttc atcaaccgtc agccacacaa ctgggaacac cactcaaccc agtaaccaga 720
ccacccttcc agcaacttta tcgatagcac tgcacaaaag cacaaccggt cagaagcctg 780
ttcaacccac ccatgcccca ggaacaacgg cagctgccca caataccacc cgcacagctg 840
cacctgcctc cacggttcct gggcccaccc ttgcacctca gccatcgtca gtcaagactg 900
gaatttatca ggttctaaac ggaagcagac tctgtataaa agcagagatg gggatacagc 960
tgattgttca agacaaggag tcggtttttt cacctcggag atacttcaac atcgacccca 1020
acgcaacgca agcctctggg aactgtggca cccgaaaatc caaccttctg ttgaattttc 1080
agggcggatt tgtgaatctc acatttacca aggatgaaga atcatattat atcagtgaag 1140
tgggagccta tttgaccgtc tcagatccag agacaattta ccaaggaatc aaacatgcgg 1200
tggtgatgtt ccagacagca gtcgggcatt ccttcaagtg cgtgagtgaa cagagcctcc 1260
agttgtcagc ccacctgcag gtgaaaacaa ccgatgtcca acttcaagcc tttgattttg 1320
aagatgacca ctttggaaat gtggatgagt gctcgtctga ctacacaatt gtgcttcctg 1380
tgattggggc catcgtggtt ggtctctgcc ttatgggtat gggtgtctat aaaatccgcc 1440
taaggtgtca atcatctgga taccagagaa tctaattgtt gcccgggggg aatgaaaata 1500
atggaattta gagaactctt tcatcccttc caggatggat gttgggaaat tccctcagag 1560
tgtgggtcct tcaaacaatg taaaccacca tcttctattc aaatgaagtg agtcatgtgt 1620
gatttaagtt caggcagcac atcaatttct aaatactttt tgtttatttt atgaaagata 1680
tagtgagctg tttattttct agtttccttt agaatatttt agccactcaa agtcaacatt 1740
tgagatatgt tgaattaaca taatatatgt aaagtagaat aagccttcaa attataaacc 1800
aagggtcaat tgtaactaat actactgtgt gtgcattgaa gattttattt tacccttgat 1860
cttaacaaag cctttgcttt gttatcaaat ggactttcag tgcttttact atctgtgttt 1920
tatggtttca tgtaacatac atattcctgg tgtagcactt aactcctttt ccactttaaa 1980
tttgtttttg ttttttgaga cggagtttca ctcttgtcac ccaggctgga gtacagtggc 2040

-continued acgatctcgg cttatggcaa cctccgcctc ccgggttcaa gtgattctcc tgcttcagct 2100
tcccgagtag ctgggattac aggcacacac taccacgcct ggctaatttt tgtattttta 2160
ttatagacgg ggtttcacca tgttggccag actggtcttg aactcttgac ctcaggtgat 2220
ccacccacct cagcctccca aagtgctggg attacaggca tgagccattg cgcccggcct 2280
taaatgtttt ttttaatcat caaaaagaac aacatatctc aggttgtcta agtgttttta 2340
tgtaaaacca acaaaaagaa caaatcagct tatatttttt atcttgatga ctcctgctcc 2400
agaatcgcta gactaagaat taggtggcta cagatggtag aactaaacaa taagcaagag 2460
acaataataa tggcccttaa ttattaacaa agtgccagag tctaggctaa gcactttatc 2520
tatatctcat ttcattctca caacttatag gtgaatgagt aaactgagac ttaagggaac 2580
tgaatcactt aaatgtcacc tggctaactg atggcagagc cagagcttga attcatgttg 2640
gtctgacatc aaggtctttg gtcttctccc tacaccaagt tacctacaag aacaatgaca 2700
ccacactctg cctgaaggct cacacctcat accagcatac gctcacctta cagggaaatg 2760
ggtttatcca ggatcatgag acattagggt agatgaaagg agagctttgc agataacaaa 2820
atagcctatc cttaataaat cctccactct ctggaaggag actgaggggc tttgtaaaac 2880
attagtcagt tgctcatttt tatgggattg cttagctggg ctgtaaagat gaaggcatca 2940
aataaactca aagtattttt aaattttttt gataatagag aaacttcgct aaccaactgt 3000
tctttcttga gtgtatagcc ccatcttgtg gtaacttgct gcttctgcac ttcatatcca 3060
tatttcctat tgttcacttt attctgtaga gcagcctgcc aagaatttta tttctgctgt 3120
tttttttgct gctaaagaaa ggaactaagt caggatgtta acagaaaagt ccacataacc 3180
ctagaattct tagtcaagga ataattcaag tcagcctaga gaccatgttg actttcctca 3240
tgtgtttcct tatgactcag taagttggca aggtcctgac tttagtctta ataaaacatt 3300
gaattgtagt aaaggttttt gtaataaaaa cttactttgg a 3341

<210> SEQ ID NO 89
<211> LENGTH: 3524
<212> TYPE: DNA
<213> ORGANISM: Homo sapiens

<400> SEQUENCE: 89
caggaagagg tatttcttgg ggatgctacc aaggcagaga ctgtgaagaa ggaagaacgt 60
tgcttgggca aaaggagcat attctcagga gacggggccc ctgcctgcca caccaagcat 120
taggccacca ggaagacccc catctgcaag caagcctagc cttccaggga gaaagaggcc 180
cctgcagctc cttcatcatg aactggcaca tgatcatctc tgggcttatt gtggtagtgc 240
ttaaagttgt tggaatgacc ttatttctac tttatttccc acagattttt aacaaaagta 300
acgatggttt caccaccacc aggagctatg gaacagtctc acagattttt gggagcagtt 360
ccccaagtcc caacggcttc attaccacaa ggagctatgg aacagtctgc cccaaagact 420
gggaatttta tcaagcaaga tgttttttct tatccacttc tgaatcatct tggaatgaaa 480
gcagggactt ttgcaaagga aaaggatcca cattggcaat tgtcaacacg ccagagaaac 540
tgaagtttct tcaggacata actgatgctg agaagtattt tattggctta atttaccatc 600
gtgaagagaa aaggtggcgt tggatcaaca actctgtgtt caatggcaat gttaccaatc 660
agaatcagaa tttcaactgt gcgaccattg gcctaacaaa gacatttgat gctgcatcat 720
gtgacatcag ctaccgcagg atctgtgaga agaatgccaa atgatcacag ttccctgtga 780
caagaactat acttgcaact ctttttgaat ccatacaggt cgtctggcca atgattcttt 840

-continued

```
tacttaccta tctgtctacc agtagcggtc cttgcccatt tgggaaactg agcttctttc    900
ttctgcactg ggggactgga tgctagccat ctccaggaga caggatcagt tttacggaaa    960
caactcagtt agtatagaga tgaggtccgc ttctgtagta ctgagcattt ctgactgatc   1020
aaaaaggcct agtctgttga cagggtttgt tttattttag cctcagagta taccatacta   1080
ctagggagta actgtagagt gagaaattat aaacattatt tagggattac catggtggaa   1140
gagggataaa cataggtcct gtgacttcgt ctctgttctc aagggaaccc cattcacatg   1200
cccctcctaa ctccacaagc gagggtagca gaggctctcc tcagtctgaa ctaaggcttg   1260
gccttgggga gggctcctag tgctgagctt ggagcagcac ggacagcagc attgtttatg   1320
ggaatggaga gaggtctggg caggatagga accttcttgg agaccccttt gaagaaaacc   1380
aggcagccaa gggagccaaa cacactagat ttctgttctt cagcaaagcc ctgaagagac   1440
acttaagcta aaaattccct tgtcatattt ctgaaactcc attataacat atgtaactcc   1500
tttgtaacca aaatttaggt aagcaggctt cctttgctct gaaggttttg agtacctggc   1560
tgtatttgtt gagtattttt aaaattttgg atagtctctt aggcaacaat aatcacaata   1620
tattcatccc ttcagttctg gagaaagcct gataccaggc acagcctact gaccccaagg   1680
agcctggcac tgattggcat cacattgatc tagaactggt ccagccgacg aagagtagga   1740
aaagagaagg gctgctcagg gaaacattgg ctgggggcac ggaataagca catagtaaaa   1800
agggaacatc agggtcaaat ggaaatcacc tgagacagga aacagggagt tcatttggcc   1860
acactggaag aaaggcaaga aagaggaaga caagtcttgg agtaccctgg ctgttctcca   1920
cactcacaag acatcagcta tatactctgc ttggtgcata agaaagagaa aagagatgcc   1980
ttttgtgttt tgagtaagaa taattaaacc ataaggaaga ccatgtataa aactgatgga   2040
aataatagtc accaaagtac agcacatacc attttgtgtc taataacaat gtagcacagt   2100
aatgactgta catgtcattg tatgtatacc aaacaagatt gttgtaaatc atattttta   2160
ttacaacact aagttctgct tctgcattcc taggtttcat catttttggc tccttagcat   2220
ggccacttac aattttttaa catgagataa cacatcaggt gtcagaactt gcttgaaggg   2280
aattaccaga agtaatttgt gtttgagatg gggtggaaat tggaattata ttagtagccg   2340
gtggagatac aagttctctg actgtgttgg gaaaggataa gtgctaccgt tgagaaggga   2400
agaaaggctg agtctaggtg gagaaaaata tcaacagaac tctagccaaa ggcaagcccc   2460
agaactcaga caacagaaag gaaatcctaa tccttctgtt ttgagaagag agaactgtag   2520
ttgcttcact tcctatttca tgacagaata actgcaaact tttaagatca ggaaatgtag   2580
acatctagtg atttctttag tagacagttt aatttccccc aagattagga gacacttctg   2640
tgcaggttct aaaaggagcc caatggcctg gggtgggagt ggggagtaga tagggaatat   2700
gtgggatttg gtttaagttc atcattggaa gagttcctgg atccttgcaa gcttagataa   2760
atgtgatctt tattagatag cagtggcatg ctttaaaaaa aaaaaaggca atgaaaattt   2820
agcaagccac tgaatttgag ttttcacttt gtttctaata tgctgtgtga atcagtacag   2880
ttttcttacc ctttcttggt cttaatttcc ttactgataa aatggggtag taatacctat   2940
ctcaaaaaat tattgcacat attaaataac attcctctat gtatctcaat ggcattagac   3000
attaggagaa gcattttgtg gaggatttga agttgagatc ttcatccaag aagtagcttt   3060
tcaatttgct agaagcttaa tgtaggcaag ccacttcatt tttcagaact tgtttactca   3120
tttataatat gggaataaaa atttgtgcaa gtcagagaag ggtgccttaa aaatgttgtg   3180
```

gccaagccac atgagatcaa agacacactt ttcatgacct caaatgtggg cccagcctag 3240
gtcagccaac ccccatccaa cccttagact cacgaacaaa tccacctgag atcagcagag 3300
ccaccctaga tcagctgaaa ctctaagcac aaaaataaaa acttatcact gtataccact 3360
ggagttttct ggttatctct cgtatagcaa aatctaactg atgcaatctc catctggcct 3420
tcatccttct ccctttattg tcctttcgtg tattgttcat ccagcaacca ggatgatctt 3480
gttaaaacat taaacagatt ctgtcactct taaaaaaaaa aaaa 3524

<210> SEQ ID NO 90
<211> LENGTH: 4787
<212> TYPE: DNA
<213> ORGANISM: Homo sapiens

<400> SEQUENCE: 90
gagctggtgc tctcccccag cccctaggga attggagctg aggaggagct gaaaatgcag 60
atttagcatc aagcacagac ctacactcgc tctttctctc cggtacacac agctccccac 120
attcgcaccc ctgcccgcgc gccgggccgc ctgactgcac ggcttcccct ccagccagat 180
gctggagaac acacactgat tcgctgcttt ccaagaccct gttcagtctc tttctctata 240
caaagatttt tttaaaaact atatataaga attctttatt tgcaccctcc ctcccgagtcc 300 cctgctccgc cagcctgcgc gcctcctagc accacttttc actcccaaag aaggatgaag 360
ggtggttgtg tctcccagtg gaaggcggcc gccgggttcc tcttctgtgt catggttttt 420
gcatctgctg agcgaccggt cttcacgaat cattttcttg tggagttgca taaaggggga 480
gaggacaaag ctcgccaagt tgcagcagaa cacggctttg gagtccgaaa gcttcccttt 540
gctgaaggtc tgtaccactt ttatcacaat ggccttgcaa aggccaagag aagacgcagc 600
ctacaccaca agcagcagct ggagagagac cccagggtaa agatggcttt gcagcaggaa 660
ggatttgacc gaaaaaagcg aggttacaga gacatcaatg agatcgacat caacatgaac 720
gatcctcttt ttacaaagca gtggtatctg atcaatactg ggcaagctga tggcactcct 780
ggccttgatt tgaatgtggc tgaagcctgg gagctgggat acacagggaa aggtgttacc 840
attggaatta tggatgatgg gattgactat ctccacccgg acctggcctc caactataat 900
gccgaagcaa gttacgactt cagcagcaac gacccctatc cttaccctcg gtacacagat 960
gactggttta acagccacgg gacccgatgt gcaggagaag tttctgctgc cgccaacaac 1020
aatatctgtg gagttggagt agcatacaac tccaaggttg caggcatccg gatgctggac 1080
cagccattca tgacagacat catcgaggcc tcctccatca gtcatatgcc acagctgatt 1140
gacatctaca gcgccagctg gggccccaca gacaacggca agacagtgga tgggccccgg 1200
gagctcacgc tgcaggccat ggccgatggc gtgaacaagg gccgcggcgg caaaggcagc 1260
atctacgtgt gggcctccgg ggacggcggc agctatgacg actgcaactg cgacggctac 1320
gcctccagca tgtggaccat ctccatcaac tcagccatca acgacggcag gactgccctg 1380
tacgacgaga gctgctcttc caccttggct tccaccttca gcaacgggag gaaaaggaac 1440
cccgaggccg gtgtggcaac cacagatttg tacggcaact gcactctgag gcattctggg 1500
acatctgcag ctgcccccga ggcagctggt gtgtttgcac tggctctgga ggctaacctg 1560
ggtctgacct ggcgggacat gcagcatctg actgtgctca cctccaaacg gaaccagctt 1620
cacgacgagg tccatcagtg gcggcgcaat ggggtcggcc tggaatttaa tcacctcttt 1680
ggctacgggg tccttgatgc aggtgccatg gtgaaaatgg ctaaagactg gaaaaccgtg 1740
cctgagagat tccactgtgt gggaggctcc gtgcaggacc ctgagaaaat accatccact 1800

-continued

```
ggcaagttgg tgctgacact cacaaccgac gcctgtgagg ggaaggaaaa ttttgtccgc   1860
tacctggagc atgtccaggc tgtcatcacg gtcaacgcaa ccagaagagg agacctgaac   1920
atcaacatga cttcccctat gggcaccaag tccattttgc tgagccggcg tccaagggat   1980
gacgactcca aggtgggctt tgacaagtgg cctttcatga ccactcacac gtggggggaa   2040
gacgcccgag gcacctggac cctggagctg ggatttgtcg gcagcgcccc gcagaagggg   2100
gtgctgaagg agtggaccct gatgctgcat ggcactcaga gtgccccgta catcgaccag   2160
gtggtgcggg attaccagtc caagttggcc atgtccaaga aagaggagct ggaggaagag   2220
ctggacgaag ccgtggagag aagcctgaaa agcatcctta acaagaacta gcgctgcaca   2280
tccgcctttc ccaccgccct ccctccccag ctccgcctct gtcctcgctc cacgtttcag   2340
gcaggcacct agcaattcca tcacccgtac aggcaattcc gtcttcttaa tctgaagctt   2400
cactcactgt caatgattat tttcattaca atggaaacaa tctttttttac tctatgcccc   2460
aaatatagcg ttcccaacaa catccatgtc ctatgtgtga ctctaaattc tttatttctg   2520
tcattcaaat gggtgatatc ctgaaaaaaa aaaaaaaaaa aaaactggga cagctttccc   2580
ctcatttttt tttttgtttc tgagaaaaga acgtatttta aaagccacat agagtgactc   2640
caagaacaat tgtccatggt ctcaaacaag gggctgttac ataacaagaa aatcaaagct   2700
gaggacaggg tgtgagcgcc acatctctga aagcacagga gacactgtgc tataaatcct   2760
ttggggagcg atgttttgaa tttagtgaga tttaccaggg atgtagatta aggtgatgtg   2820
attcaaaaga tgccattcat agagagccct agttactgca tggggaaaga gatccaggaa   2880
gcatgagtgc tggatatttt actaccaatg ccaagataat tcactctact cagccggcgt   2940
ggcaaatata aaacttacag agcgtggctg tgctctcacc agctgctgct ctgagttatg   3000
ttaaaatccg ctagagcagc ccaaattttt ctcagtttgt atagagttca tcccagcccc   3060
aattttctgg ggctcctcac atagctaccc aaaagagaaa aaaaattaag acaagcctgg   3120
caacacacct ggtgaagagt agtttactag cttttcaaac aagaatgtcc cttttcctaa   3180
gtcactttga ggtgtctcaa tctgatctga gtgagaggcg acaggagtat tttttttttt   3240
ttacagcttt acacacacag atgtgggctt tgatttccaa gtaatataat ggaagagaaa   3300
tctcatactc ccccacagtt tgatgtcatt aatgtgttgg gaaaaaggcc tctgtcccgg   3360
aagagtcatg ggaggtgaaa ggggcacgtt tgaagatgcg agcgctatct tcacatagtt   3420
ctccagttgt atggagcctc ttctgccaag agagggccat gcaattcatc ccagaggaac   3480
ctgaggcctg aaggaggtga gagaagacct ctgtgaggaa agcacacagt caccttctcg   3540
gcaactaagc agtccctgag accatttaac atgcaacccg aaggttatgg tcaatcccaa   3600
aagtcaccac tccattccca actagacatt accaaagtga cctacccaga gattgcttct   3660
catccccagt cccaatgcac atccattccc aagaaatgct ttgtcttcag cctctccagg   3720
caccatctcc cttcctgtgg gagcagagag cttagcctgg agcacctttc cttcaagcca   3780
gcaacacaga gcactaggtt caattccctg aaggtggcca ctttaagaga gaaatctgaa   3840
aaccccattt gctttctttt ctcccatatt ggcatggatt tctgtcttct ctaacacctt   3900
gtgaccttct ctatatcatg ctttaaagtg taataatatg attttttaaa agaaatttat   3960
tacttgttgc aaaggtcttt ttaaaccagt ttagatttca agaaaaaata aatggaaatc   4020
atcgaaaatt catttcacat taatggtcta aaaataaacc aaaggacatt atgtgtgcat   4080
gtgtgtataa gtgcacacag aaatatatat acatatgtag actatataca tgtgtgtata   4140
```

tatgtgtata tatacataca cttgtataaa tgtatataca catataccta taatgtgtgt 4200
atgtgtattt attgaagaaa cagataccat actcatttct aaaagaatat tcagagaata 4260
tcaagatgat tctggctgaa aaaggccagt ggaaattcag gtgaaaatgt tcatcaattc 4320
ccattgcatc acctctgtaa tttttcagct ctctgtataa acattaaatg tcttatatag 4380
cagcaaaaat ataaaatagt tgtccatatt ttcacaggtg tggtgtaatt tataaaatta 4440
gaaagcaact tatcagctac ttaagagaaa tggcaagttt tgatatgagt atacaatata 4500
taaaaatata tatagtgcta tatatataaa tatttggtct ctatttcatt ttttgcatca 4560
gtattaatac taaaatatgt ctcgctagtg atgtttttat gatatccctg atcctaactg 4620
aagagacagt tatttatagt catttatttt aaaaaatgaa aataagtgaa taataattag 4680
gttaacattg ttgctccctg tgacaaaatt ttataagcaa atttcaaaag acatgttgta 4740
aattaggagg ctcaacaata aaacattatg ctccagaaaa aaaaaaa 4787

<210> SEQ ID NO 91
<211> LENGTH: 5820
<212> TYPE: DNA
<213> ORGANISM: Homo sapiens

<400> SEQUENCE: 91
agccgctgcg cccgagctgg cctgcgagtt cagggctcct gtcgctctcc aggagcaacc 60
tctactccgg acgcacaggc attccccgcg cccctccagc cctcgccgcc ctcgccaccg 120
ctcccggccg ccgcgctccg gtacacacag gatccctgct gggcaccaac agctccacca 180
tggggctggc ctggggacta ggcgtcctgt tcctgatgca tgtgtgtggc accaaccgca 240
ttccagagtc tggcggagac aacagcgtgt ttgacatctt tgaactcacc ggggccgccc 300
gcaaggggtc tgggcgccga ctggtgaagg gccccgaccc ttccagccca gctttccgca 360
tcgaggatgc caacctgatc ccccctgtgc ctgatgacaa gttccaagac ctggtggatg 420
ctgtgcgggc agaaaagggt ttcctccttc tggcatccct gaggcagatg aagaagaccc 480
ggggcacgct gctggccctg gagcggaaag accactctgg ccaggtcttc agcgtggtgt 540
ccaatggcaa ggcgggcacc ctggacctca gcctgaccgt ccaaggaaag cagcacgtgg 600
tgtctgtgga agaagctctc ctggcaaccg gccagtggaa gagcatcacc ctgtttgtgc 660
aggaagacag ggcccagctg tacatcgact gtgaaaagat ggagaatgct gagttggacg 720
tccccatcca aagcgtcttc accagagacc tggccagcat cgccagactc cgcatcgcaa 780
aggggggcgt caatgacaat ttccaggggg tgctgcagaa tgtgaggttt gtctttggaa 840
ccacaccaga agacatcctc aggaacaaag gctgctccag ctctaccagt gtcctcctca 900
cccttgacaa caacgtggtg aatggttcca gccctgccat ccgcactaac tacattggcc 960
acaagacaaa ggacttgcaa gccatctgcg gcatctcctg tgatgagctg tccagcatgg 1020
tcctggaact caggggcctg cgcaccattg tgaccacgct gcaggacagc atccgcaaag 1080
tgactgaaga gaacaaagag ttggccaatg agctgaggcg gcctccccta tgctatcaca 1140
acggagttca gtacagaaat aacgaggaat ggactgttga tagctgcact gagtgtcact 1200
gtcagaactc agttaccatc tgcaaaaagg tgtcctgccc catcatgccc tgctccaatg 1260
ccacagttcc tgatggagaa tgctgtcctc gctgttggcc cagcgactct gcggacgatg 1320
gctggtctcc atggtccgag tggacctcct gttctacgag ctgtggcaat ggaattcagc 1380
agcgcggccg ctcctgcgat agcctcaaca accgatgtga gggctcctcg gtccagacac 1440
ggacctgcca cattcaggag tgtgacaaga gatttaaaca ggatggtggc tggagccact 1500

-continued ggtccccgtg gtcatcttgt tctgtgacat gtggtgatgg tgtgatcaca aggatccggc 1560
tctgcaactc tcccagcccc cagatgaacg ggaaaccctg tgaaggcgaa gcgcgggaga 1620
ccaaagcctg caagaaagac gcctgcccca tcaatggagg ctggggtcct tggtcaccat 1680
gggacatctg ttctgtcacc tgtggaggag gggtacagaa acgtagtcgt ctctgcaaca 1740
accccacacc ccagtttgga ggcaaggact gcgttggtga tgtaacagaa aaccagatct 1800
gcaacaagca ggactgtcca attgatggat gcctgtccaa tccctgcttt gccggcgtga 1860
agtgtactag ctaccctgat ggcagctgga aatgtggtgc ttgtcccect ggttacagtg 1920
gaaatggcat ccagtgcaca gatgttgatg agtgcaaaga agtgcctgat gcctgcttca 1980
accacaatgg agagcaccgg tgtgagaaca cggaccccgg ctacaactgc ctgccctgcc 2040
ccccacgctt caccggctca cagcccttcg gccagggtgt cgaacatgcc acggccaaca 2100
aacaggtgtg caagccccgt aacccctgca cggatgggac ccacgactgc aacaagaacg 2160
ccaagtgcaa ctacctgggc cactatagcg accccatgta ccgctgcgag tgcaagcctg 2220
gctacgctgg caatggcatc atctgcgggg aggacacaga cctggatggc tggcccaatg 2280
agaacctggt gtgcgtggcc aatgcgactt accactgcaa aaaggataat tgccccaacc 2340
ttcccaactc agggcaggaa gactatgaca aggatggaat tggtgatgcc tgtgatgatg 2400
acgatgacaa tgataaaatt ccagatgaca gggacaactg tccattccat tacaacccag 2460
ctcagtatga ctatgacaga gatgatgtgg gagaccgctg tgacaactgt ccctacaacc 2520
acaacccaga tcaggcagac acagacaaca atggggaagg agacgcctgt gctgcagaca 2580
ttgatggaga cggtatcctc aatgaacggg acaactgcca gtacgtctac aatgtggacc 2640
agagagacac tgatatggat ggggttggag atcagtgtga caattgcccc ttggaacaca 2700
atccggatca gctggactct gactcagacc gcattggaga tacctgtgac aacaatcagg 2760
atattgatga agatggccac cagaacaatc tggacaactg tccctatgtg cccaatgcca 2820
accaggctga ccatgacaaa gatggcaagg gagatgcctg tgaccacgat gatgacaacg 2880
atggcattcc tgatgacaag gacaactgca gactcgtgcc caatcccgac cagaaggact 2940
ctgacggcga tggtcgaggt gatgcctgca aagatgattt tgaccatgac agtgtgccag 3000
acatcgatga catctgtcct gagaatgttg acatcagtga gaccgatttc cgccgattcc 3060
agatgattcc tctggacccc aaagggacat cccaaaatga ccctaactgg gttgtacgcc 3120
atcagggtaa agaactcgtc cagactgtca actgtgatcc tggactcgct gtaggttatg 3180
atgagtttaa tgctgtggac ttcagtggca ccttcttcat caacaccgaa agggacgatg 3240
actatgctgg atttgtcttt ggctaccagt ccagcagccg cttttatgtt gtgatgtgga 3300
agcaagtcac ccagtcctac tgggacacca accccacgag ggctcaggga tactcgggcc 3360
tttctgtgaa agttgtaaac tccaccacag ggcctggcga gcacctgcgg aacgccctgt 3420
ggcacacagg aaacacccct ggccaggtgc gcaccctgtg gcatgaccct cgtcacatag 3480
gctggaaaga tttcaccgcc tacagatggc gtctcagcca caggccaaag acgggtttca 3540
ttagagtggt gatgtatgaa gggaagaaaa tcatggctga ctcaggaccc atctatgata 3600
aaacctatgc tggtggtaga ctagggttgt ttgtcttctc tcaagaaatg gtgttcttct 3660
ctgacctgaa atacgaatgt agagatccct aatcatcaaa ttgttgattg aaagactgat 3720
cataaaccaa tgctggtatt gcaccttctg gaactatggg cttgagaaaa cccccaggat 3780
cacttctcct tggcttcctt cttttctgtg cttgcatcag tgtggactcc tagaacgtgc 3840

-continued gacctgcctc aagaaaatgc agttttcaaa aacagactca gcattcagcc tccaatgaat 3900
aagacatctt ccaagcatat aaacaattgc tttggtttcc ttttgaaaaa gcatctactt 3960
gcttcagttg ggaaggtgcc cattccactc tgcctttgtc acagagcagg gtgctattgt 4020
gaggccatct ctgagcagtg gactcaaaag cattttcagg catgtcagag aagggaggac 4080
tcactagaat tagcaaacaa aaccaccctg acatcctcct tcaggaacac ggggagcaga 4140
ggccaaagca ctaaggggag ggcgcatacc cgagacgatt gtatgaagaa aatatggagg 4200
aactgttaca tgttcggtac taagtcattt tcaggggatt gaaagactat tgctggattt 4260
catgatgctg actggcgtta gctgattaac ccatgtaaat aggcacttaa atagaagcag 4320
gaaagggaga caaagactgg cttctggact tcctccctga tccccaccct tactcatcac 4380
ctgcagtggc cagaattagg gaatcagaat caaaccagtg taaggcagtg ctggctgcca 4440
ttgcctggtc acattgaaat tggtggcttc attctagatg tagcttgtgc agatgtagca 4500
ggaaaatagg aaaacctacc atctcagtga gcaccagctg cctcccaaag gaggggcagc 4560
cgtgcttata tttttatggt tacaatggca caaaattatt atcaacctaa ctaaaacatt 4620
ccttttctct tttttcctga attatcatgg agttttctaa ttctctcttt tggaatgtag 4680 attttttta aatgctttac gatgtaaaat atttattttt tacttattct ggaagatctg 4740
gctgaaggat tattcatgga acaggaagaa gcgtaaagac tatccatgtc atctttgttg 4800
agagtcttcg tgactgtaag attgtaaata cagattattt attaactctg ttctgcctgg 4860
aaatttaggc ttcatacgga aagtgtttga gagcaagtag ttgacattta tcagcaaatc 4920
tcttgcaaga acagcacaag gaaaatcagt ctaataagct gctctgcccc ttgtgctcag 4980
agtggatgtt atgggattct ttttttctct gttttatctt ttcaagtgga attagttggt 5040
tatccatttg caaatgtttt aaattgcaaa gaaagccatg aggtcttcaa tactgtttta 5100
ccccatccct tgtgcatatt tccagggaga aggaaagcat atacactttt ttctttcatt 5160
tttccaaaag agaaaaaaat gacaaaaggt gaaacttaca tacaaatatt acctcatttg 5220
ttgtgtgact gagtaaagaa tttttggatc aagcggaaag agtttaagtg tctaacaaac 5280
ttaaagctac tgtagtacct aaaaagtcag tgttgtacat agcataaaaa ctctgcagag 5340
aagtattccc aataaggaaa tagcattgaa atgttaaata caatttctga aagttatgtt 5400
ttttttctat catctggtat accattgctt tatttttata aattattttc tcattgccat 5460
tggaatagat atctcagatt gtgtagatat gctatttaaa taatttatca ggaaatactg 5520
cctgtagagt tagtatttct atttttatat aatgtttgca cactgaattg aagaattgtt 5580 ggtttttct ttttttgtt ttgttttttt tttttttttt ttttgctttt gacctcccat 5640
ttttactatt tgccaatacc tttttctagg aatgtgcttt tttttgtaca catttttatc 5700
cattttacat tctaaagcag tgtaagttgt atattactgt ttcttatgta caaggaacaa 5760
caataaatca tatggaaatt tatatttata aaaaaaaaaa aaaaaaaaaa aaaaaaaaaa 5820

<210> SEQ ID NO 92
<211> LENGTH: 1648
<212> TYPE: DNA
<213> ORGANISM: Homo sapiens

<400> SEQUENCE: 92
cagagaaggc ttaggctccc gagtcaacag ggcattcacc gcctggggcg cctgagtcat 60
caggacactg ccaggagaca cagaacccta gatgccctgc agaatccttc ctgttacggt 120
ccccctccct gaaacatcct tcattgcaat atttccagga aaggaagggg gctggctcgg 180
aggaagagag gtggggaggt gatcagggtt cacagaggag ggaactgaat gacatcccag 240
gattacataa actgtcagag gcagccgaag agttcacaag tgtgaagcct ggaagccggc 300
gggtgccgct gtgtaggaaa gaagctaaag cacttccaga gcctgtccgg agctcagagg 360
ttcggaagac ttatcgacca tggagcgcgc gtcctgcttg ttgctgctgc tgctgccgct 420
ggtgcacgtc tctgcgacca cgccagaacc ttgtgagctg gacgatgaag atttccgctg 480
cgtctgcaac ttctccgaac ctcagcccga ctggtccgaa gccttccagt gtgtgtctgc 540
agtagaggtg gagatccatg ccggcggtct caacctagag ccgtttctaa agcgcgtcga 600
tgcggacgcc gacccgcggc agtatgctga cacggtcaag gctctccgcg tgcggcggct 660
cacagtggga gccgcacagg ttcctgctca gctactggta ggcgccctgc gtgtgctagc 720
gtactcccgc ctcaaggaac tgacgctcga ggacctaaag ataaccggca ccatgcctcc 780
gctgcctctg gaagccacag gacttgcact ttccagcttg cgcctacgca acgtgtcgtg 840
ggcgacaggg cgttcttggc tcgccgagct gcagcagtgg ctcaagccag gcctcaaggt 900
actgagcatt gcccaagcac actcgcctgc cttttcctgc gaacaggttc gcgccttccc 960
ggcccttacc agcctagacc tgtctgacaa tcctggactg ggcgaacgcg gactgatggc 1020
ggctctctgt ccccacaagt tcccggccat ccagaatcta gcgctgcgca acacaggaat 1080
ggagacgccc acaggcgtgt gcgccgcact ggcggcggca ggtgtgcagc cccacagcct 1140
agacctcagc cacaactcgc tgcgcgccac cgtaaaccct agcgctccga gatgcatgtg 1200
gtccagcgcc ctgaactccc tcaatctgtc gttcgctggg ctggaacagg tgcctaaagg 1260
actgccagcc aagctcagag tgctcgatct cagctgcaac agactgaaca gggcgccgca 1320
gcctgacgag ctgcccgagg tggataacct gacactggac gggaatccct tcctggtccc 1380
tggaactgcc ctcccccacg agggctcaat gaactccggc gtggtcccag cctgtgcacg 1440
ttcgaccctg tcggtggggg tgtcgggaac cctggtgctg ctccaagggg cccggggctt 1500
tgcctaagat ccaagacaga ataatgaatg gactcaaact gccttggctt caggggagtc 1560
ccgtcaggac gttgaggact tttcgaccaa ttcaaccctt tgccccacct ttattaaaat 1620
cttaaacaac gggtcaaaaa aaaaaaaa 1648

<210> SEQ ID NO 93
<211> LENGTH: 1616
<212> TYPE: DNA
<213> ORGANISM: Homo sapiens

<400> SEQUENCE: 93
gccaaggctg gggcagggga gtcagcagag gcctcgctcg ggcgcccagt ggtcctgccg 60
cctggtctca cctcgctatg gttcgtctgc ctctgcagtg cgtcctctgg ggctgcttgc 120
tgaccgctgt ccatccagaa ccacccactg catgcagaga aaaacagtac ctaataaaca 180
gtcagtgctg ttctttgtgc cagccaggac agaaactggt gagtgactgc acagagttca 240
ctgaaacgga atgccttcct tgcggtgaaa gcgaattcct agacacctgg aacagagaga 300
cacactgcca ccagcacaaa tactgcgacc ccaacctagg gcttcgggtc cagcagaagg 360
gcacctcaga aacagacacc atctgcacct gtgaagaagg ctggcactgt acgagtgagg 420
cctgtgagag ctgtgtcctg caccgctcat gctcgcccgg ctttggggtc aagcagattg 480
ctacaggggt ttctgatacc atctgcgagc cctgcccagt cggcttcttc tccaatgtgt 540
catctgcttt cgaaaaatgt cacccttgga caagctgtga gaccaaagac ctggttgtgc 600

-continued

```
aacaggcagg cacaaacaag actgatgttg tctgtggtcc ccaggatcgg ctgagagccc    660

tggtggtgat ccccatcatc ttcgggatcc tgtttgccat cctcttggtg ctggtcttta    720

tcaaaaaggt ggccaagaag ccaaccaata aggcccccca ccccaagcag gaaccccagg    780

agatcaattt tcccgacgat cttcctggct ccaacactgc tgctccagtg caggagactt    840

tacatggatg ccaaccggtc acccaggagg atggcaaaga gagtcgcatc tcagtgcagg    900

agagacagtg aggctgcacc cacccaggag tgtggccacg tgggcaaaca ggcagttggc    960

cagagagcct ggtgctgctg ctgctgtggc gtgagggtga ggggctggca ctgactgggc   1020

atagctcccc gcttctgcct gcacccctgc agtttgagac aggagacctg gcactggatg   1080

cagaaacagt tcaccttgaa gaacctctca cttcaccctg gagcccatcc agtctcccaa   1140

cttgtattaa agacagaggc agaagtttgg tggtggtggt gttggggtat ggtttagtaa   1200

tatccaccag accttccgat ccagcagttt ggtgcccaga gaggcatcat ggtggcttcc   1260

ctgcgcccag gaagccatat acacagatgc ccattgcagc attgtttgtg atagtgaaca   1320

actggaagct gcttaactgt ccatcagcag gagactggct aaataaaatt agaatatatt   1380

tatacaacag aatctcaaaa acactgttga gtaaggaaaa aaaggcatgc tgctgaatga   1440

tgggtatgga actttttaaa aaagtacatg cttttatgta tgtatattgc ctatggatat   1500

atgtataaat acaatatgca tcatatattg atataacaag ggttctggaa gggtacacag   1560

aaaacccaca gctcgaagag tggtgacgtc tggggtgggg aagaagggtc tggggg       1616
```

<210> SEQ ID NO 94
<211> LENGTH: 2757
<212> TYPE: DNA
<213> ORGANISM: Homo sapiens

<400> SEQUENCE: 94

```
gacaagtact gagtgaactc aaaccctctg taaagtaaca gaagttagaa ggggaaatgt     60

cgcctctctg aagattaccc aaagaaaaag tgatttgtca ttgctttata gactgtaaga    120

agagaacatc tcagaagtgg agtcttaccc tgaaatcaaa ggatttaaag aaaaagtgga    180

atttttcttc agcaagctgt gaaactaaat ccacaacctt tggagaccca ggaacaccct    240

ccaatctctg tgtgttttgt aaacatcact ggagggtctt ctacgtgagc aattggattg    300

tcatcagccc tgcctgtttt gcacctggga agtgccctgg tcttacttgg gtccaaattg    360

ttggctttca cttttgaccc taagcatctg aagccatggg ccacacacgg aggcagggaa    420

catcaccatc caagtgtcca tacctcaatt tctttcagct cttggtgctg gctggtcttt    480

ctcacttctg ttcaggtgtt atccacgtga ccaaggaagt gaaagaagtg gcaacgctgt    540

cctgtggtca caatgtttct gttgaagagc tggcacaaac tcgcatctac tggcaaaagg    600

agaagaaaat ggtgctgact atgatgtctg gggacatgaa tatatggccc gagtacaaga    660

accggaccat ctttgatatc actaataacc tctccattgt gatcctggct ctgcgcccat    720

ctgacgaggg cacatacgag tgtgttgttc tgaagtatga aaaagacgct ttcaagcggg    780

aacacctggc tgaagtgacg ttatcagtca aagctgactt ccctacacct agtatatctg    840

actttgaaat tccaacttct aatattagaa ggataatttg ctcaacctct ggaggttttc    900

cagagcctca cctctcctgg ttggaaaatg gagaagaatt aaatgccatc aacacaacag    960

tttcccaaga tcctgaaact gagctctatg ctgttagcag caaactggat ttcaatatga   1020

caaccaacca cagcttcatg tgtctcatca agtatggaca tttaagagtg aatcagacct   1080

tcaactggaa tacaaccaag caagagcatt ttcctgataa cctgctccca tcctgggcca   1140
```

-continued

```
ttaccttaat ctcagtaaat ggaattttg tgatatgctg cctgacctac tgctttgccc   1200

caagatgcag agagagaagg aggaatgaga gattgagaag ggaaagtgta cgccctgtat   1260

aacagtgtcc gcagaagcaa ggggctgaaa agatctgaag gtcccacctc catttgcaat   1320

tgacctcttc tgggaacttc ctcagatgga caagattacc ccaccttgcc ctttacgtat   1380

ctgctcttag gtgcttcttc acttcagttg ctttgcagga agtgtctaga ggaatatggt   1440

gggcacagaa gtagctctgg tgaccttgat caaggtgttt tgaaatgcag aattcttgag   1500

ttctggaagg gactttagag aataccagtg ttattaatga caaaggcact gaggcccagg   1560

gaggtgaccc gaattataaa ggccagcgcc agaacccaga tttcctaact ctggtgctct   1620

ttccctttat cagtttgact gtggcctgtt aactggtata tacatatata tgtcaggcaa   1680

agtgctgctg gaagtagaat ttgtccaata acaggtcaac ttcagagact atctgatttc   1740

ctaatgtcag agtagaagat tttatgctgc tgtttacaaa agcccaatgt aatgcatagg   1800

aagtatggca tgaacatctt taggagacta atggaaatat tattggtgtt tacccagtat   1860

tccatttttt tcattgtgtt ctctattgct gctctctcac tcccccatga ggtacagcag   1920

aaaggagaac tatccaaaac taatttcctc tgacatgtaa gacgaatgat ttaggtacgt   1980

caaagcagta gtcaaggagg aaagggatag tccaaagact taactggttc atattggact   2040

gataatctct ttaaatggct ttatgctagt ttgacctcat ttgtaaaata tttatgagaa   2100

agttctcatt taaaatgaga tcgttgttta cagtgtatgt actaagcagt aagctatctt   2160

caaatgtcta aggtagtaac tttccatagg gcctccttag atccctaaga tggctttttc   2220

tccttggtat ttctgggtct ttctgacatc agcagagaac tggaaagaca tagccaactg   2280

ctgttcatgt tactcatgac tcctttctct aaaactgcct tccacaattc actagaccag   2340

aagtggacgc aacttaagct gggataatca cattatcatc tgaaaatctg gagttgaaca   2400

gcaaaagaag acaacatttc tcaaatgcac atctcatggc agctaagcca catggctggg   2460

atttaaagcc tttagagcca gcccatggct ttagctacct cactatgctg cttcacaaac   2520

cttgctcctg tgtaaaacta tattctcagt gtagggcaga gaggtctaac accaacataa   2580

ggtactagca gtgtttcccg tattgacagg aatacttaac tcaataattc ttttcttttc   2640

catttagtaa cagttgtgat gactatgttt ctattctaag taattcctgt attctacagc   2700

agatactttg tcagcaatac taagggaaga aacaaagttg aaccgtttct ttaataa      2757
```

```
<210> SEQ ID NO 95
<211> LENGTH: 2207
<212> TYPE: DNA
<213> ORGANISM: Homo sapiens

<400> SEQUENCE: 95

cacttcctcc ccagacaggg gtagtgcgag gccgggcaca gccttcctgt gtggttttac     60

cgcccagaga gcgtcatgga cctggggaaa ccaatgaaaa gcgtgctggt ggtggctctc    120

cttgtcattt tccaggtatg cctgtgtcaa gatgaggtca cggacgatta catcggagac    180

aacaccacag tggactacac tttgttcgag tctttgtgct ccaagaagga cgtgcggaac    240

tttaaagcct ggttcctccc tatcatgtac tccatcattt gtttcgtggg cctactgggc    300

aatgggctgg tcgtgttgac ctatatctat ttcaagaggc tcaagaccat gaccgatacc    360

tacctgctca acctggcggt ggcagacatc ctcttcctcc tgacccttcc cttctgggcc    420

tacagcgcgg ccaagtcctg ggtcttcggt gtccactttt gcaagctcat ctttgccatc    480
```

-continued

```
tacaagatga gcttcttcag tggcatgctc ctacttcttt gcatcagcat tgaccgctac    540

gtggccatcg tccaggctgt ctcagctcac cgccaccgtg cccgcgtcct tctcatcagc    600

aagctgtcct gtgtgggcat ctggatacta gccacagtgc tctccatccc agagctcctg    660

tacagtgacc tccagaggag cagcagtgag caagcgatgc gatgctctct catcacagag    720

catgtggagg cctttatcac catccaggtg gcccagatgg tgatcggctt tctggtcccc    780

ctgctggcca tgagcttctg ttaccttgtc atcatccgca ccctgctcca ggcacgcaac    840

tttgagcgca acaaggccat caaggtgatc atcgctgtgg tcgtggtctt catagtcttc    900

cagctgccct acaatggggt ggtcctggcc cagacggtgg ccaacttcaa catcaccagt    960

agcacctgtg agctcagtaa gcaactcaac atcgcctacg acgtcaccta cagcctggcc   1020

tgcgtccgct gctgcgtcaa ccctttcttg tacgccttca tcggcgtcaa gttccgcaac   1080

gatctcttca agctcttcaa ggacctgggc tgcctcagcc aggagcagct ccggcagtgg   1140

tcttcctgtc ggcacatccg gcgctcctcc atgagtgtgg aggccgagac caccaccacc   1200

ttctccccat aggcgactct tctgcctgga ctagagggac ctctcccagg gtccctgggg   1260

tggggatagg gagcagatgc aatgactcag gacatccccc cgccaaaagc tgctcaggga   1320

aaagcagctc tcccctcaga gtgcaagccc ctgctccaga agatagcttc accccaatcc   1380

cagctacctc aaccaatgcc aaaaaaagac agggctgata agctaacacc agacagacaa   1440

cactgggaaa cagaggctat tgtcccctaa accaaaaact gaaagtgaaa gtccagaaac   1500

tgttcccacc tgctggagtg aaggggccaa ggagggtgag tgcaaggggc gtgggagtgg   1560

cctgaagagt cctctgaatg aaccttctgg cctcccacag actcaaatgc tcagaccagc   1620

tcttccgaaa accaggcctt atctccaaga ccagagatag tggggagact tcttggcttg   1680

gtgaggaaaa gcggacatca gctggtcaaa caaactctct gaacccctcc ctccatcgtt   1740

ttcttcactg tcctccaagc cagcgggaat ggcagctgcc acgccgccct aaaagcacac   1800

tcatcccctc acttgccgcg tcgccctccc aggctctcaa caggggagag tgtggtgttt   1860

cctgcaggcc aggccagctg cctccgcgtg atcaaagcca cactctgggc tccagagtgg   1920

ggatgacatg cactcagctc ttggctccac tgggatggga ggagaggaca agggaaatgt   1980

caggggcggg gagggtgaca gtggccgccc aaggcccacg agcttgttct ttgttctttg   2040

tcacagggac tgaaaacctc tcctcatgtt ctgctttcga ttcgttaaga gagcaacatt   2100

ttacccacac acagataaag ttttcccttg aggaaacaac agctttaaaa gaaaaagaaa   2160

aaaaaagtct ttggtaaatg gcaaaaaaaa aaaaaaaaaa aaaaaaa                 2207
```

<210> SEQ ID NO 96
<211> LENGTH: 2307
<212> TYPE: DNA
<213> ORGANISM: Homo sapiens

<400> SEQUENCE: 96

```
gattatcaca gattctggag aagagtgagg acttgggttc accacctaca gcctggctcc     60

cgcgacgccg gaggtgaagg tggcttgctc cgaagatgtg gacttgccct gcaccgcccc    120

ctgggatccg caggttccct acacggtctc ctgggtcaag ttattggagg gtggtgaaga    180

gaggatggag acaccccagg aagaccacct caggggacag cactatcatc agaaggggca    240

aaatggttct ttcgacgccc ccaatgaaag gccctattcc ctgaagatcc gaaacactac    300

cagctgcaac tcggggacat acaggtgcac tctgcaggac ccggatgggc agagaaacct    360

aagtggcaag gtgatcttga gagtgacagg atgccctgca cagcgtaaag aagagacttt    420
```

taagaaatac agagcggaga ttgtcctgct gctggctctg gttattttct acttaacact 480
catcattttc acttgtaagt ttgcacggct acagagtatc ttcccagatt tttctaaagc 540
tggcatggaa cgagcttttc tcccagttac ctccccaaat aagcatttag ggctagtgac 600
tcctcacaag acagaactgg tatgagcagg atttctgcag gttcttcttc ctgaagctga 660
ggctcagggg tgtgcctgtc tgttacactg gaggagagaa gaatgagcct acgctgaaga 720
tggcatcctg tgaagtcctt cacctcactg aaaacatctg gaaggggatc ccaccccatt 780
ttctgtgggc aggcctcgaa aaccatcaca tgaccacata gcatgaggcc actgctgctt 840
ctccatggcc accttttcag cgatgtatgc agctatctgg tcaacctcct ggacattttt 900
tcagtcatat aaaagctatg gtgagatgca gctggaaaag ggtcttggga aatatgaatg 960
cccccagctg gcccgtgaca gactcctgag gacagctgtc ctcttctgca tcttggggac 1020
atctctttga attttctgtg ttttgctgta ccagcccaga tgttttacgt ctgggagaaa 1080
ttgacagatc aagctgtgag acagtgggaa atatttagca aataatttcc tggtgtgaag 1140
gtcctgctat tactaaggag taatctgtgt acaaagaaat aacaagtcga tgaactattc 1200
cccagcaggg tcttttcatc tggaaagac atccataaag aagcaataaa gaagagtgcc 1260
acatttattt ttatatctat atgtacttgt caaagaaggt ttgtgttttt ctgcttttga 1320
aatctgtatc tgtagtgaga tagcattgtg aactgacagg cagcctggac atagagaggg 1380
agaagaagtc agagagggtg acaagataga gagctattta atggccggct ggaaatgctg 1440
ggctgacggt gcagtctggg tgctcgccca cttgtcccac tatctgggtg catgatcttg 1500
agcaagttcc ttctggtgtc tgctttctcc attgtaaacc acaaggctgt tgcatgggct 1560
aatgaagatc atatacgtga aaattatttg aaaacatata aagcactata cagattcgaa 1620
actccattga gtcattatcc ttgctatgat gatggtgttt tggggatgag agggtgctat 1680
ccatttctca tgttttccat tgtttgaaac aaagaaggtt accaagaagc ctttcctgta 1740
gccttctgta ggaattcttt tggggaagtg aggaagccag gtccacggtc tgttcttgaa 1800
gcagtagcct aacacactcc aagatatgga cacacgggag ccgctggcag aagggacttc 1860
acgaagtgtt gcatggatgt tttagccatt gttggctttc ccttatcaaa cttgggccct 1920
tcccttcttg gtttccaaag gcattttatt gcttgagtta tatgttcact gtccccctaa 1980
tattagggag taaaacggat accaagttga tttagtgttt ttacctctgt cttggctttc 2040
atgttattaa acgtatgcat gtgaagaaag ggtgtttttc tgttttatat tcaactcata 2100
agactttggg ataggaaaaa tgagtaatgg ttactaggct taatacctgg gtgattacat 2160
aatctgtaca atgaaccccc atgatgtaag tttacctatg taacaaacct gcacttatac 2220
ccatgaactt aaaatgaaag ttaaaaataa aaaacatata caaataaaaa aatcccgact 2280
ttgggatgag tgctaggatg ttgtaaa 2307

<210> SEQ ID NO 97
<211> LENGTH: 2348
<212> TYPE: DNA
<213> ORGANISM: Homo sapiens

<400> SEQUENCE: 97
agatgtgagt cctcaatgag ctataaccac agccataaat atctctcaaa gatgaggaac 60
attctcatga tgttgacact gcaatttttt gacaatttcc caacactctt aagaaacatt 120
ccccaatctc acacgaaaag tgggggtttt aattttcttg ttcaacttct aaagagaaat 180

-continued

```
tggagaagat aaaactggac actggggaga ccacaacttc atgctgcgtg ggatctccca    240
gctacctgca gtggccacca tgtcttgggt cctgctgcct gtactttggc tcattgttca    300
aactcaagca atagccataa agcaaacacc tgaattaacg ctccatgaaa tagtttgtcc    360
taaaaaactt cacattttac acaaaagaga gatcaagaac aaccagacag aaaagcatgg    420
caaagaggaa aggtatgaac ctgaagttca atatcagatg atcttaaatg gagaagaaat    480
cattctctcc ctacaaaaaa ccaagcacct cctggggcca gactacactg aaacattgta    540
ctcacccaga ggagaggaaa ttaccacgaa acctgagaac atggaacact gttactataa    600
aggaaacatc ctaaatgaaa agaattctgt tgccagcatc agtacttgtg acgggttgag    660
aggatacttc acacatcatc accaaagata ccagataaaa cctctgaaaa gcacagacga    720
gaaagaacat gccgtcttta catctaacca ggaggaacaa gacccagcta accacacatg    780
tggtgtgaag agcactgacg ggaaacaagg cccaattcga atctctagat cactcaaaag    840
cccagagaaa gaagactttc ttcgggcaca gaaatacatt gatctctatt tggtgctgga    900
taatgccttt tataagaact ataatgagaa tctaactctg ataagaagct ttgtgtttga    960
tgtgatgaac ctactcaatg tgatatataa caccatagat gttcaagtgg ccttggtagg   1020
tatggaaatc tggtctgatg gggataagat aaaggtggtg cccagcgcaa gcaccacgtt   1080
tgacaacttc ctgagatggc acagttctaa cctggggaaa aagatccacg accatgctca   1140
gcttctcagc gggattagct tcaacaatcg acgtgtggga ctggcagctt caaattcctt   1200
gtgttcccca tcttcggttg ctgttattga ggctaaaaaa aagaataatg tggctcttgt   1260
aggagtgatg tcacatgagc tgggccatgt ccttggtatg cctgatgttc cattcaacac   1320
caagtgtccc tctggcagtt gtgtgatgaa tcagtatctg agttcaaaat tcccaaagga   1380
tttcagtaca tcttgccgtg cacattttga aagatacctt ttatctcaga aaccaaagtg   1440
cctgctgcaa gcacctattc ctacaaatat aatgacaaca ccagtgtgtg ggaaccacct   1500
tctagaagtg ggagaagact gtgattgtgg ctctcctaag gagtgtacca atctctgctg   1560
tgaagcccta acgtgtaaac tgaagcctgg aactgattgc ggaggagatg ctccaaacca   1620
taccacagag tgaatccaaa agtctgcttc actgagatgc taccttgcca ggacaagaac   1680
caagaactct aactgtccca ggaatcttgt gaattttcac ccataatggt ctttcacttg   1740
tcattctact ttctatattg ttatcagtcc aggaaacagg taaacagatg taattagaga   1800
cattggctct ttgtttaggc ctaatctttc tttttacttt ttttttctt ttttcttttt    1860
ttttaaagat catgaatttg tgacttagtt ctgccctttg gagaacaaaa gaaagcagtc   1920
ttccatcaaa tcaccttaaa atgcacggct aaactattca gagttaacac tccagaattg   1980
ttaaattaca agtactatgc tttaatgctt ctttcatctt actagtatgg cctataaaaa   2040
aaataatacc acttgatggg tgaaggcttt ggcaatagaa agaagaatag aattcaggtt   2100
ttatgttatt cctctgtgtt cacttcgcct tgctcttgaa agtgcagtat ttttctacat   2160
catgtcaaga atgattcaat gtaaatattt ttcattttat catgtatatc ctatacacac   2220
atctccttca tcatcatata tgaagtttat tttgagaagt ctacattgct tacattttaa   2280
ttgagccagc aaagaaggct taatgattta ttgaaccata atgtcaataa aaacacaact   2340
tttgaggc                                                             2348
```

<210> SEQ ID NO 98
<211> LENGTH: 2517
<212> TYPE: DNA
<213> ORGANISM: Homo sapiens

<400> SEQUENCE: 98
aaaacactca ttttgtttta tagcatgaca ggctgtctga ttccatcttt ataaccaaag 60
ccaattaaga tcttaaaacc aaacatataa cttcatcttt ttacaagtac ttagagcctg 120
agttgctcca caggaatcca ggaactgggc acaggaaaag gatctaagct ggtggtgtgg 180
gaagatggaa accaacttct ccattcctct gaatgaaact gaggaggtgc tccctgagcc 240
tgctggccac accgttctgt ggatcttctc attgctagtc cacggagtca cctttgtctt 300
cggggtcctg ggcaatgggc ttgtgatctg ggtggctgga ttccggatga cacgcacagt 360
caacaccatc tgttacctga acctggccct agctgacttc tctttcagtg ccatcctacc 420
attccgaatg gtctcagtcg ccatgagaga aaaatggcct tttggctcat tcctatgtaa 480
gttagttcat gttatgatag acatcaacct gtttgtcagt gtctacctga tcaccatcat 540
tgctctggac cgctgtattt gtgtcctgca tccagcctgg gcccagaacc atcgcaccat 600
gagtctggcc aagagggtga tgacgggact ctggattttc accatagtcc ttaccttacc 660
aaatttcatc ttctggacta caataagtac tacgaatggg gacacatact gtattttcaa 720
ctttgcattc tggggtgaca ctgctgtaga gaggttgaac gtgttcatta ccatggccaa 780
ggtctttctg atcctccact tcattattgg cttcagcgtg cctatgtcca tcatcacagt 840
ctgctatggg atcatcgctg ccaaaattca cagaaaccac atgattaaat ccagccgtcc 900
cttacgtgtc ttcgctgctg tggtggcttc tttcttcatc tgttggttcc cttatgaact 960
aattggcatt ctaatggcag tctggctcaa agagatgttg ttaaatggca aatacaaaat 1020
cattcttgtc ctgattaacc caacaagctc cttggccttt tttaacagct gcctcaaccc 1080
aattctctac gtctttatgg gtcgtaactt ccaagaaaga ctgattcgct ctttgcccac 1140
tagtttggag agggccctga ctgaggtccc tgactcagcc cagaccagca acacagacac 1200
cacttctgct tcacctcctg aggagacgga gttacaagca atgtgaggtc ggggatattt 1260
ttgggctctg tctctttcta ccctgcgtta agcggaaaaa aaaaattctg acagtgtttt 1320
tcttcctctt tcataccacc accaccacaa tcatcaacat aaaggaagtc tgtaccaaat 1380
ctgtaggggg tttttcccac aaccaagcaa tagacaccag ctgggtgtcc tacaattaaa 1440
ttccaacact atctacctgg agctactgtc agatcccaca ggtttaaggg ctcattcccc 1500
aagtctgctc ctccagttga gacacaagtc acaaatccag gcttctgaga cttcggacca 1560
accagcttca atcagggttc ccactacccc ctctttgggg gtagagtggc tcatggaact 1620
cagagaaaca tttatttcgg cttgctggtt tattataaaa gcaaggttta ttataaaaga 1680
tactacaaag gatacagatg aagaggcaca tagggcaagg tacggggttc cacgccctcc 1740
ctgagtgcat caccctctgg gaacctccgt gtgttcacgt ctcatgaagc tctccaaatc 1800
cagtcctctt gggtttttat ggaagcttca tgatgtcagc attctttcct ccagtgtata 1860
ggatgggatc ctctctgggg agggtcttaa gacccacaat tagaaaggca agggaagatt 1920
agagtcctgc tttggggtag atgaaaggaa aggagagaga ttctgtttcc tgaggcttaa 1980
tacacccaac attataacaa aggactgtag caagggctat gggagttctg aagcagaaac 2040
catgggctaa aaccaacata catcttaata ccagataccc taatcccagt cctaacttca 2100
tttaaccttg gtcacattga gtcattccag gatgagtggc tcaagtattt cctcagggaa 2160
aatacttctg tgccccctga tttgagggta agaagtagat aatgaggcca ctgtgggtgt 2220
tattttttca tgtctggacc tcagcctata tcctgagact aagtggaagt gggaaaagag 2280

```
tacaagagaa gagacaaagt ggggatattt gtaaggctta gatgagatag tgttttttta   2340

gaaaaaaact ttatcttacc attaagtaaa atgtttgcca taggctttct ggggctttct   2400

ctttttaaag tcagactgtt gaaggtttct tctattctta tttgttaaga gttttctttt   2460

attgtttaaa tcatgaatga atgttgaatt ttattaaatg cagtttctgt aaatatt      2517


<210> SEQ ID NO 99
<211> LENGTH: 2790
<212> TYPE: DNA
<213> ORGANISM: Homo sapiens

<400> SEQUENCE: 99

ccctttctgt atttgagttc taccgtcagt cctggcatta tttctctctc tacaaggagc     60

cttaggaggt acggggagct cgcaaatact ccttttggtt tattcttacc accttgcttc    120

tgtgttcctt gggaatgctg ctgtgcttat gcatctggtc tctttttgga gctacagtgg    180

acaggcattt gtgacagcac tatgggactg agtaacattc tctttgtgat ggccttcctg    240

ctctctggtg ctgctcctct gaagattcaa gcttatttca atgagactgc agacctgcca    300

tgccaatttg caaactctca aaaccaaagc ctgagtgagc tagtagtatt ttggcaggac    360

caggaaaact tggttctgaa tgaggtatac ttaggcaaag agaaatttga cagtgttcat    420

tccaagtata tgggccgcac aagttttgat tcggacagtt ggaccctgag acttcacaat    480

cttcagatca aggacaaggg cttgtatcaa tgtatcatcc atcacaaaaa gcccacagga    540

atgattcgca tccaccagat gaattctgaa ctgtcagtgc ttgctaactt cagtcaacct    600

gaaatagtac caatttctaa tataacagaa aatgtgtaca taaatttgac ctgctcatct    660

atacacggtt acccagaacc taagaagatg agtgttttgc taagaaccaa gaattcaact    720

atcgagtatg atggtattat gcagaaatct caagataatg tcacagaact gtacgacgtt    780

tccatcagct tgtctgtttc attccctgat gttacgagca atatgaccat cttctgtatt    840

ctggaaactg acaagacgcg gcttttatct tcacctttct ctatagagct tgaggaccct    900

cagcctcccc cagaccacat tccttggatt acagctgtac ttccaacagt tattatatgt    960

gtgatggttt tctgtctaat tctatggaaa tggaagaaga agaagcggcc tcgcaactct   1020

tataaatgtg gaaccaacac aatggagagg gaagagagtg aacagaccaa gaaaagagaa   1080

aaaatccata tacctgaaag atctgatgaa gcccagcgtg tttttaaaag ttcgaagaca   1140

tcttcatgcg acaaaagtga tacatgtttt taattaaaga gtaaagccca tacaagtatt   1200

cattttttct accctttcct ttgtaagttc ctgggcaacc tttttgattt cttccagaag   1260

gcaaaaagac attaccatga gtaataaggg ggctccagga ctccctctaa gtggaatagc   1320

ctccctgtaa ctccagctct gctccgtatg ccaagaggag actttaattc tcttactgct   1380

tcttttcact tcagagcaca cttatgggcc aagcccagct taatggctca tgacctggaa   1440

ataaaattta ggaccaatac ctcctccaga tcagattctt ctcttaattt catagattgt   1500

gttttttttt taaatagacc tctcaatttc tggaaaactg ccttttatct gcccagaatt   1560

ctaagctggt gccccactga attttgtgta cctgtgacta aacaactacc tcctcagtct   1620

gggtgggact tatgtattta tgaccttata gtgttaatat cttgaaacat agagatctat   1680

gtactgtaat agtgtgatta ctatgctcta gagaaaagtc taccccctgct aaggagttct   1740

catccctctg tcagggtcag taaggaaaac ggtggcctag ggtacaggca acaatgagca   1800

gaccaaccta aatttgggga aattaggaga ggcagagata gaacctggag ccacttctat   1860

ctgggctgtt gctaatattg aggaggcttg ccccacccaa caagccatag tggagagaac   1920
```

tgaataaaca ggaaaatgcc agagcttgtg aaccctgttt ctcttgaaga actgactagt 1980
gagatggcct ggggaagctg tgaaagaacc aaaagagatc acaatactca aaagagagag 2040
agagagaaaa aagagagatc ttgatccaca gaaatacatg aaatgtctgg tctgtccacc 2100
ccatcaacaa gtcttgaaac aagcaacaga tggatagtct gtccaaatgg acataagaca 2160
gacagcagtt tccctggtgg tcagggaggg gttttggtga tacccaagtt attgggatgt 2220
catcttcctg gaagcagagc tggggaggga gagccatcac cttgataatg ggatgaatgg 2280
aaggaggctt aggactttcc actcctggct gagagaggaa gagctgcaac ggaattagga 2340
agaccaagac acagatcacc cggggcttac ttagcctaca gatgtcctac gggaacgtgg 2400
gctggcccag catagggcta gcaaatttga gttggatgat tgtttttgct caaggcaacc 2460
agaggaaact tgcatacaga gacagatata ctgggagaaa tgactttgaa aacctggctc 2520
taaggtggga tcactaaggg atggggcagt ctctgcccaa acataaagag aactctgggg 2580
agcctgagcc acaaaaatgt tcctttattt tatgtaaacc ctcaagggtt atagactgcc 2640
atgctagaca agcttgtcca tgtaatattc ccatgttttt accctgcccc tgccttgatt 2700
agactcctag cacctggcta gtttctaaca tgttttgtgc agcacagttt ttaataaatg 2760
cttgttacat tcatttaaaa aaaaaaaaaa 2790

<210> SEQ ID NO 100
<211> LENGTH: 2312
<212> TYPE: DNA
<213> ORGANISM: Homo sapiens

<400> SEQUENCE: 100
ctccacaggt ccgccccaat ccccgctcac acttgggaaa cttgggactg cgctggggcc 60
gcgtgtggca cctcaggggg gcggcccccg gcctcaagag gagggggagg agaaggagga 120
agaggaggaa gtgagcccga aggatccgct cggagctgtt tgtccagctg tttctattcg 180
cacccggagc agtacagcca gaagggggcc gagccgaagg tggctggctt taggcgctaa 240
tttccaactc ttttcctcac agcttgtctt ttccaggcac cctggagtcc cctcaggcca 300
gctcggtggg cgcgcacctg ccagccgccc ctgacctcgc aggccaggcg acctccgagc 360
ctgagaagat ggcccagtcc aagctcgatt gccgctcacc tgtcggcctc gactgctgca 420
actgctgcct ggacctggcc catcggagtg ggctccagcg aggcagcagc ggggagaaca 480
acaacccggg cagccctaca gtgagcaact ttcggcagct gcaggaaaag ctggtctttg 540
agaacctcaa taccgacaag ctcaacagca taatgcggca ggattcgcta gagccggtgc 600
tgcgggaccc ctgctacctg atcaacgagg gcatctgcaa ccgcaacatc gaccagacca 660
tgctctccat cctgctcttc ttccacagtg cctccggagc cagcgtggtg gccatagaca 720
acaagatcga acaggccatg gatctggtga agaatcatct gatgtatgct gtgagagagg 780
aggtggagat cctgaaggag cagatccgag agctggtgga gaagaactcc cagctagagc 840
gtgagaacac cctgttgaag accctggcaa gcccagagca gctggagaag ttccagtcct 900
gtctgagccc tgaagagcca gctcccgaat ccccacaagt gcccgaggcc cctggtggtt 960
ctgcggtgta agtggctctg tcctcagggt gggcagagcc actaaacttg ttttacctag 1020
ttctttccag tttgtttttg gctccccaag catcatctca cgaggagaac tttacaccta 1080
gcacagctgg tgccaagaga tgtcctaagg acatggccac ctgggtccac tccagcgaca 1140 gaccccctgac aagagcaggt ctctggaggc tgagttgcat ggggcctagt aacaccaagc 1200

```
cagtgagcct ctaatgctac tgcgccctgg gggctcccag ggcctgggca acttagctgc   1260
aactggcaaa ggagaagggt agtttgaggt gtgacaccag tttgctccag aaagtttaag   1320
gggtctgttt ctcatctcca tggacatctt caacagcttc acctgacaac gactgttcct   1380
atgaagaagc cacttgtgtt ttaagcagag gcaacctctc tcttctcctc tgtttcgtga   1440
aggcagggga cacagatggg agagattgag ccaagtcagc cttctgttgg ttaatatggt   1500
ataatgcatg gctttgtgca cagcccagtg tgggattaca gctttgggat gaccgcttac   1560
aaagttctgt ttggttagta ttggcatagt ttttctatat agccataaat gcgtatatat   1620
acccataggg ctagatctgt atcttagtgt agcgatgtat acatatacac atccacctac   1680
atgttgaagg gcctaaccag ccttgggagt attgactggt cccttacctc ttatggctaa   1740
gtctttgact gtgttcattt accaagttga cccagtttgt cttttaggtt aagtaagact   1800
cgagagtaaa ggcaaggagg ggggccagcc tctgaatgcg gccacggatg ccttgctgct   1860
gcaacccttt ccccagctgt ccactgaaac gtgaagtcct gttttgaatg ccaaacccac   1920
cattcactgg tgctgactac atagaatggg gttgagagaa gatcagtttg ggcttcacag   1980
tgtcatttga aaacgttttt tgttttgttt tgtaattatt gtggaaaact ttcaagtgaa   2040
cagaaggatg gtgtcctact gtggatgagg gatgaacaag ggatggcttt tgatccaatg   2100
gagcctggga ggtgtgccca gaaagcttgt ctgtagcggg ttttgtgaga gtgaacactt   2160
tccacttttt gacaccttat cctgatgtat ggttccagga tttggatttt gattttccaa   2220
atgtagcttg aaatttcaat aaactttgct ctgtttttct aaaaataaaa aaaaaaaaaa   2280
aaaaaaaaaa aaaaaaaaaa aaaaaaaaaa aa                                 2312
```

```
<210> SEQ ID NO 101
<211> LENGTH: 1944
<212> TYPE: DNA
<213> ORGANISM: Homo sapiens

<400> SEQUENCE: 101

aatttctcac tgcccctgtg ataaactgtg gtcactggct gtggcagcaa ctattataag     60
atgctctgaa aactcttcag acactgaggg gcaccagagg agcagactac aagaatggca    120
cacgctatgg aaaactcctg gacaatcagt aaagagtacc atattgatga agaagtgggc    180
tttgctctgc caaatccaca ggaaaatcta cctgattttt ataatgactg gatgttcatt    240
gctaaacatc tgcctgatct catagagtct ggccagcttc gagaaagagt tgagaagtta    300
aacatgctca gcattgatca tctcacagac cacaagtcac agcgccttgc acgtctagtt    360
ctgggatgca tcaccatggc atatgtgtgg ggcaaaggtc atggagatgt ccgtaaggtc    420
ttgccaagaa atattgctgt tccttactgc caactctcca agaaactgga actgcctcct    480
attttggttt atgcagactg tgtcttggca aactggaaga aaaaggatcc taataagccc    540
ctgacttatg agaacatgga cgttttgttc tcatttcgtg atggagactg cagtaaagga    600
ttcttcctgg tctctctatt ggtggaaata gcagctgctt ctgcaatcaa agtaattcct    660
actgtattca aggcaatgca aatgcaagaa cgggacactt tgctaaaggc gctgttggaa    720
atagcttctt gcttggagaa agcccttcaa gtgtttcacc aaatccacga tcatgtgaac    780
ccaaaagcat ttttcagtgt tcttcgcata tatttgtctg gctggaaagg caaccccccag    840
ctatcagacg gtctggtgta tgaagggttc tgggaagacc caaaggagtt tgcagggggc    900
agtgcaggcc aaagcagcgt ctttcagtgc tttgacgtcc tgctgggcat ccagcagact    960
gctggtggag gacatgctgc tcagttcctc caggacatga gaagatatat gccaccagct   1020
```

cacaggaact tcctgtgctc attagagtca aatccctcag tccgtgagtt tgtcctttca 1080
aaaggtgatg ctggcctgcg ggaagcttat gacgcctgtg tgaaagctct ggtctccctg 1140
aggagctacc atctgcaaat cgtgactaag tacatcctga ttcctgcaag ccagcagcca 1200
aaggagaata agacctctga agacccttca aaactggaag ccaaaggaac tggaggcact 1260
gatttaatga atttcctgaa gactgtaaga agtacaactg agaaatccct tttgaaggaa 1320
ggttaatgta acccaacaag agcacatttt atcatagcag agacatctgt atgcattcct 1380
gtcattaccc attgtaacag agccacaaac taatactatg caatgtttta ccaataatgc 1440
aatacaaaag acctcaaaat acctgtgcat ttcttgtagg aaaacaacaa aaggtaatta 1500
tgtgtaatta tactagaagt tttgtaatct gtatcttatc attggaataa aatgacattc 1560
aataaataaa aatgcataag atatattctg tcggctgggc gcggtggctc acgcctgtaa 1620
tcccagcact ttgggaggcc gaggcgggcg gatcacaagg tcaggagatc gagaccatct 1680
tggctaacac ggtgaaaccc cgtctctact aaaaatacaa aaaattagcc gggcgcggtg 1740
gcgggcacct gtagtcccag ctactcggga ggctgaggca ggagaatggc gtgaacctgg 1800
gaggcggagc ttgcagtgag ccaagattgt gccactgcaa tccggcctgg gctaaagagc 1860
gggactccgt ctcaaaaaaa aaaaaaaaaa gatatattct gtcataataa ataaaaatgc 1920
ataagatata aaaaaaaaaa aaaa 1944

<210> SEQ ID NO 102
<211> LENGTH: 5266
<212> TYPE: DNA
<213> ORGANISM: Homo sapiens

<400> SEQUENCE: 102
gcttaaaaat ttctgtgtct tacacagaag atagaaaaaa tagagtgtct ccaattggat 60
ggatttttta aaaaatttgg ttattgtaat ggatttattt tttcttagag ctgagctgat 120
tgtactttgg ccaactaatg ggttaatact gtcaagggaa attagccctg actaaacatt 180
gccgctggct catgaatgca ctaggcttgg ggcagtataa aaactcagag aaatcagtgt 240
gtaggagaca cagaaatcag tgtcactcag tgacagaagc aacaataatt gtgaaaaata 300
cttcagcagt tatggactca tctgtcattc aaaggaaaaa agtagctgtc attggtggtg 360
gcttggttgg ctcattacaa gcatgctttc ttgcaaagag gaatttccag attgatgtat 420
atgaagctag ggaagatact cgagtggcta ccttcacacg tggaagaagc attaacttag 480
ccctttctca tagaggacga caagccttga aagctgttgg cctggaagat cagattgtat 540
cccaaggtat tcccatgaga gcaagaatga tccactctct ttcaggaaaa aagtctgcaa 600
ttccctatgg gacaaagtct cagtatattc tttctgtaag cagagaaaat ctaaacaagg 660
atctattgac tgctgctgag aaatacccca atgtgaaaat gcactttaac cacaggctgt 720
tgaaatgtaa tccagaggaa ggaatgatca cagtgcttgg atctgacaaa gttcccaaag 780
atgtcacttg tgacctcatt gtaggatgtg atggagccta ttcaactgtc agatctcacc 840
tgatgaagaa acctcgcttt gattacagtc agcagtacat tcctcatggg tacatggagt 900
tgactattcc acctaagaac ggagattatg ccatggaacc taattatctg catatttggc 960
ctagaaatac ctttatgatg attgcacttc ctaacatgaa caaatcattc acatgtactt 1020
tgttcatgcc ctttgaagag tttgaaaaac ttctaaccag taatgatgtg gtagatttct 1080
tccagaaata ctttccggat gccatccctc taattggaga gaaactccta gtgcaagatt 1140

-continued

```
tcttcctgtt gcctgcccag cccatgatat ctgtaaagtg ctcttcattt cactttaaat   1200
ctcactgtgt actgctggga gatgcagctc atgctatagt gccgtttttt gggcaaggaa   1260
tgaatgcggg ctttgaagac tgcttggtat ttgatgagtt aatggataaa ttcagtaacg   1320
accttagttt gtgtcttcct gtgttctcaa gattgagaat cccagatgat cacgcgattt   1380
cagacctatc catgtacaat tacatagaga tgcgagcaca tgtcaactca agctggttca   1440
tttttcagaa gaacatggag agatttcttc atgcgattat gccatcgacc tttatccctc   1500
tctatacaat ggtcactttt tccagaataa gataccatga ggctgtgcag cgttggcatt   1560
ggcaaaaaaa ggtgataaac aaaggactct tttcttggg atcactgata gccatcagca    1620
gtacctacct acttatacac tacatgtcac cacgatcttt cctccgcttg agaagaccat   1680
ggaactggat agctcacttc cggaatacaa catgtttccc cgcaaaggcc gtggactccc   1740
tagaacaaat ttccaatctc attagcaggt gatagaaagg ttttgtggta gcaaatgcat   1800
gatttctctg tgaccaaaat taagcatgaa aaaaatgttt ccattgccat atttgattca   1860
ctagtggaag atagtgttct gcttataatt aaactgaatg tagagtatct ctgtatgtta   1920
attgcaatta ctggttgggg ggtgcatttt aaaagatgaa acatgcagct tccctacatt   1980
acacacactc aggttgagtc attctaacta taaaagtgca atgactaaga tccttcactt   2040
ctctgaaagt aaggccctag atgcctcagg gaagacagta atcatgcctt ttctttaaaa   2100
gacacaatag gactcgcaac agcattgact caacacctag gactaaaaat cacaacttaa   2160
ctagcatgtt aactgcactt ttcattacgt gaatggaact tacctaacca cagggctcag   2220
acttactaga taaaaccaga aatggaaata aggaattcag gggagttcca gagacttaca   2280
aaatgaactc attttatttt cccaccttca aatataagta ttatcatcta tctgtttatc   2340
gtctatctat ctatcatcta tctatctatc tatcatctat ctatctatct atctatctat   2400
ctatctatct atctatctct atttatttat gtatttagag atcaggtctc actctgttga   2460
ccaggctgga gtgcagtggt gagatctggg ttcactgcaa cctctgcctc ctgggctcaa   2520
gcaatcctcc cacttcagcc tcccaaatag ctggggctac catggtattt ttcagtagag   2580
accgggtctt gccatgctgc ccaggccagt ctcaaactcc tggcctcatg tgatctgccc   2640
acctcagcct cccaaagtac agggattaga gttgtgagcc accgctgcca gcccagagtt   2700
accctctaaa gataagaaaa aggctattaa tatcatacta agtgaaggac aggaaagggt   2760
tttattcata aattaaatgt ctacatgtgc cagaatggaa aggaaacaag gggagacaac   2820
ttttatagaa atacaaagcc attactttat tcaatttcag accctcagaa gcaatttact   2880
aatttattct tcgactacat actgcagcag aaccagcaat acacttgatt tttaaaagca   2940
catttagtga aatgttttct ttggttcatc cttctttaac aggctgctga gtcactcaga   3000
aatccttcaa acatgattaa ttatgaagat gaaacactag agtcatataa gaaataaaaa   3060
ttgggcaata aaataaaatg attcagtgtt tcttttctat attgtcaatg aaaaccttga   3120
gttctaataa tccatgttca gtttgtaggg aaagaaaaaa taatttttcc ttctacccac   3180
tttaggttcc ttggctgggg cccctataac aaaagacaga ttgacaagag aaaaacaaac   3240
ataaatttat tagcgggtat atgtaatata tatgtgggaa atacagggga atgagcaaat   3300
ctcaaagagc tggcgtctta gaactccctg gcttatatag catcgacaaa gaacagtaaa   3360
tttttagaga aacaacaaaa caaagaaaaa gagctttgag tctgtagggg cagcaatttg   3420
ggggaagcaa atatatggga gtttgccttg tagattcctc tggtgctggt ctccaggctg   3480
acaaggattc aaagttgtct ctgaaactcc tctttgtcat actgcacata taaaacgtct   3540
```

tttgtttcca acaagaggat tttctttttc attctagaat tatctccttg ataacttgat 3600
cagatatagg acatgacact gaatagagtc caacagtaca aaaaaaattc agtatgttct 3660
agctacttca cacatgtgta cgcgacagtt atttttacag taaggtattt tcgagaaaaa 3720
tgcattacgt gttttggaaa atagagtaat ttaaaaaata tatttgaaat gaaaatctcc 3780
aacacattag aagatgatga tgttagatgc ccatcgtgtg ccacaagtgg ttttttcatt 3840
atgtaaagca cccgttgaat taaaagaatt tgtttttgtt caacctcttc ctgaggccca 3900
agagcatatg ggcaattcgg atttcctgct ggaccacaag gttctgttga tattacatag 3960
aacgggtatt ccagacactt cttatgatga aagtccaaaa gtggcatcca atttaaggcc 4020
ccatctttcg ttgccattct tcattcctac aaaggacgaa cttggattac atcaactttg 4080
gacccattgg ttttgtcgct gtcgtcaact gacagtgatt catcactggt gatgataaaa 4140
atgatggaag aagagttgaa agtcactttt ttctttggcc tgtccccatc tttctgtgac 4200
atcacaatgg gtctgatctg catttcactt ccagctgctg gtaggtcttt agcaggcctc 4260
tggcacctca gcagtcggag gcacagaagc tgcaaaaggg atcttcgaaa ctgggcagag 4320
aaaaaataaa gtggaatatt aagtaaaagt tgggcactaa tctggattaa cattcgagga 4380
aatcagttga gctgaattta agttgttttt tgtttgttag caggtgtgga tgtggggtta 4440
tgtggtcatg ctcagatcta cctaaatcac cccagagctt tatgtctttt attcattcta 4500
attcttatta accggaatat gtaggaccat ttcaatacct tgtaatcctc caagcttcaa 4560
tctgcacaca ctttctatga gggcaggtac aactattaag agattttgaa cattaagtta 4620
gtccacaaat attcagtggg catctactag gtgacagcca ctgtgctata attagagact 4680
ttttactata agcatcaaaa acagataagg ctcttcctgg cagagtttac agcctggtgt 4740
acttgctaat gtctctttaa ttaggtgaag aatttttttt ttctatcgaa attactaatc 4800
agttggggaa aaaaatacta tagcagacag cactaatgtc atcaacaaac attgttcttc 4860
tccgtgtcct gggtacaaca tcgaataata tttcttggcc tcctttccgc ttctcctctc 4920
tgctgttcct ctctacaaga acctgggagg ccaacgccta aagatcataa tatcacacaa 4980
tggaaggaac ctagattcct aaatgactgc ataggacaga tcccatctcc tccacccaat 5040
acattattag actgaactgt gacctgaaat gagcaataaa ctctgtatta attcactgaa 5100
atgttggggt tgcttgttat agtagtcggt ccatcatgac cagtaaaaca taaatcaaaa 5160
gttaatgtaa ttgttatccc attatttaga gcgaaataaa tgttgaatat atggactttc 5220
tcagattagg aaataccaat taaaaatata ataaatagct acattg 5266

<210> SEQ ID NO 103
<211> LENGTH: 2217
<212> TYPE: DNA
<213> ORGANISM: Homo sapiens

<400> SEQUENCE: 103
ccccgccgcc gccgcccttc gcgccctggg ccatctccct cccacctccc tccgcggagc 60
agccagacag cgagggcccc ggccgggggc aggggggacg ccccgtccgg ggcacccccc 120
cggctctgag ccgcccgcgg ggccggcctc ggcccggagc ggaggaagga gtcgccgagg 180
agcagcctga ggccccagag tctgagacga gccgccgccg cccccgccac tgcggggagg 240
agggggagga ggagcgggag gagggacgag ctggtcggga gaagaggaaa aaaacttttg 300
agacttttcc gttgccgctg ggagccggag gcgcggggac ctcttggcgc gacgctgccc 360

-continued

```
cgcgaggagg caggacttgg ggaccccaga ccgcctccct ttgccgccgg ggacgcttgc    420
tccctccctg ccccctacac ggcgtccctc aggcgccccc attccggacc agccctcggg    480
agtcgccgac ccggcctccc gcaaagactt ttccccagac ctcgggcgca ccccctgcac    540
gccgccttca tccccggcct gtctcctgag cccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
taccttttgc cgggagaccc ccagcccctg caggggcggg gcctccccac cacaccagcc    840
ctgttcgcgc tctcggcagt gccgggggc gccgcctccc ccatgccgcc ctccgggctg    900
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagcccccc gagccagggg   1080
gaggtgccgc ccggcccgct gcccgaggcc gtgctcgccc tgtacaacag cacccgcgac   1140
cgggtggccg gggagagtgc agaaccggag cccgagcctg aggccgacta ctacgccaag   1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg   1440
ctggcaccca gcgactcgcc agagtggtta tcttttgatg tcaccggagt tgtgcggcag   1500
tggttgagcc gtggagggga aattgagggc tttcgcctta gcgcccactg ctcctgtgac   1560
agcagggata acacactgca agtggacatc aacgggttca ctaccggccg ccgaggtgac   1620
ctggccacca ttcatggcat gaaccggcct ttcctgcttc tcatggccac cccgctggag   1680
agggcccagc atctgcaaag ctcccggcac cgccgagccc tggacaccaa ctattgcttc   1740
agctccacgg agaagaactg ctgcgtgcgg cagctgtaca ttgacttccg caaggacctc   1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccgggcg cctcggcggc gccgtgctgc gtgccgcagg cgctggagcc gctgcccatc   1980
gtgtactacg tgggccgcaa gcccaaggtg gagcagctgt ccaacatgat cgtgcgctcc   2040
tgcaagtgca gctgaggtcc cgccccgccc cgccccgccc cggcaggccc ggccccaccc   2100
cgccccgccc ccgctgcctt gcccatgggg gctgtattta aggacacccg tgccccaagc   2160
ccacctgggg ccccattaaa gatggagaga ggactgcgga aaaaaaaaaa aaaaaaa      2217
```

<210> SEQ ID NO 104
<211> LENGTH: 1629
<212> TYPE: DNA
<213> ORGANISM: Homo sapiens

<400> SEQUENCE: 104

```
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca cccacttccc aggcaacctg cctaacatgc    180
ttcgagatct ccgagatgcc ttcagcagag tgaagacttt ctttcaaatg aaggatcagc    240
tggacaactt gttgttaaag gagtccttgc tggaggactt taagggttac ctgggttgcc    300
```

aagccttgtc tgagatgatc cagttttacc tggaggaggt gatgccccaa gctgagaacc 360
aagacccaga catcaaggcg catgtgaact ccctgggggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caacccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt tttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260
gatcacttga ggtcaggagt tcctaaccag cctggtcaac atggtgaaac cccgtctcta 1320
ctaaaaatac aaaaattagc cgggcatggt ggcgcgcacc tgtaatccca gctacttggg 1380
aggctgaggc aagagaattg cttgaaccca ggagatggaa gttgcagtga gctgatatca 1440
tgcccctgta ctccagcctg ggtgacagag caagactctg tctcaaaaaa taaaaataaa 1500
aataaatttg gttctaatag aactcagttt taactagaat ttattcaatt cctctgggaa 1560
tgttacattg tttgtctgtc ttcatagcag attttaattt tgaataaata aatgtatctt 1620
attcacatc 1629

<210> SEQ ID NO 105
<211> LENGTH: 12
<212> TYPE: PRT
<213> ORGANISM: Artificial Sequence
<220> FEATURE:
<223> OTHER INFORMATION: peptide

<400> SEQUENCE: 105

His His Leu Gly Gly Ala Lys Gln Ala Gly Asp Val
1 5 10

<210> SEQ ID NO 106
<211> LENGTH: 10515
<212> TYPE: DNA
<213> ORGANISM: Homo sapiens

<400> SEQUENCE: 106
ggaggaggga gagcacaggc tttgaccgat agtaacctct gcgctcggtg cagccgaatc 60
tataaaagga actagtcccg gcaaaaaccc cgtaattgcg agcgagagtg agtggggccg 120
ggacccgcag agccgagccg acccttctct cccgggctgc ggcagggcag ggcggggagc 180
tccgcgcacc aacagagccg gttctcaggg cgctttgctc cttgtttttt ccccggttct 240
gttttctccc cttctccgga aggcttgtca aggggtagga gaaagagacg caaacacaaa 300
agtggaaaac agttaatgac cagccacggc gtccctgctg tgagctctgg ccgctgcctt 360
ccagggctcc cgagccacac gctgggggtg ctggctgagg gaacatggct tgttggcctc 420
agctgaggtt gctgctgtgg aagaacctca ctttcagaag aagacaaaca tgtcagctgc 480
tgctggaagt ggcctggcct ctatttatct tcctgatcct gatctctgtt cggctgagct 540
acccacccta tgaacaacat gaatgccatt ttccaaataa agccatgccc tctgcaggaa 600
cacttccttg ggttcagggg attatctgta atgccaacaa cccctgtttc cgttacccga 660
ctcctgggga ggctcccgga gttgttggaa actttaacaa atccattgtg gctcgcctgt 720
tctcagatgc tcggaggctt cttttataca gccagaaaga caccagcatg aaggacatgc 780
gcaaagttct gagaacatta cagcagatca agaaatccag ctcaaacttg aagcttcaag 840
atttcctggt ggacaatgaa accttctctg ggttcctgta tcacaacctc tctctcccaa 900
agtctactgt ggacaagatg ctgagggctg atgtcattct ccacaaggta tttttgcaag 960
gctaccagtt acatttgaca agtctgtgca atggatcaaa atcagaagag atgattcaac 1020
ttggtgacca agaagtttct gagctttgtg gcctaccaag ggagaaactg gctgcagcag 1080
agcgagtact tcgttccaac atggacatcc tgaagccaat cctgagaaca ctaaactcta 1140
catctccctt cccgagcaag gagctggctg aagccacaaa aacattgctg catagtcttg 1200
ggactctggc ccaggagctg ttcagcatga gaagctggag tgacatgcga caggaggtga 1260
tgtttctgac caatgtgaac agctccagct cctccaccca aatctaccag gctgtgtctc 1320
gtattgtctg cgggcatccc gagggagggg ggctgaagat caagtctctc aactggtatg 1380
aggacaacaa ctacaaagcc ctctttggag gcaatggcac tgaggaagat gctgaaacct 1440
tctatgacaa ctctacaact ccttactgca atgatttgat gaagaatttg gagtctagtc 1500
ctctttcccg cattatctgg aaagctctga agccgctgct cgttgggaag atcctgtata 1560
cacctgacac tccagccaca aggcaggtca tggctgaggt gaacaagacc ttccaggaac 1620
tggctgtgtt ccatgatctg gaaggcatgt gggaggaact cagccccaag atctggacct 1680
tcatggagaa cagccaagaa atggaccttg tccggatgct gttggacagc agggacaatg 1740
accacttttg ggaacagcag ttggatggct tagattggac agcccaagac atcgtggcgt 1800
tttggccaa gcacccagag gatgtccagt ccagtaatgg ttctgtgtac acctggagag 1860
aagctttcaa cgagactaac caggcaatcc ggaccatatc tcgcttcatg gagtgtgtca 1920
acctgaacaa gctagaaccc atagcaacag aagtctggct catcaacaag tccatggagc 1980
tgctggatga gaggaagttc tgggctggta ttgtgttcac tggaattact ccaggcagca 2040
ttgagctgcc ccatcatgtc aagtacaaga tccgaatgga cattgacaat gtggagagga 2100
caaataaaat caaggatggg tactgggacc ctggtcctcg agctgacccc tttgaggaca 2160
tgcggtacgt ctgggggggc ttcgcctact tgcaggatgt ggtggagcag gcaatcatca 2220
gggtgctgac gggcaccgag aagaaaactg gtgtctatat gcaacagatg ccctatccct 2280
gttacgttga tgacatcttt ctgcgggtga tgagccggtc aatgcccctc ttcatgacgc 2340
tggcctggat ttactcagtg gctgtgatca tcaagggcat cgtgtatgag aaggaggcac 2400
ggctgaaaga gaccatgcgg atcatgggcc tggacaacag catcctctgg tttagctggt 2460
tcattagtag cctcattcct cttcttgtga gcgctggcct gctagtggtc atcctgaagt 2520
taggaaacct gctgccctac agtgatccca gcgtggtgtt tgtcttcctg tccgtgtttg 2580
ctgtggtgac aatcctgcag tgcttcctga ttagcacact cttctccaga gccaacctgg 2640
cagcagcctg tgggggcatc atctacttca cgctgtacct gccctacgtc ctgtgtgtgg 2700

-continued

```
catggcagga ctacgtgggc ttcacactca agatcttcgc tagcctgctg tctcctgtgg   2760
cttttgggtt tggctgtgag tactttgccc tttttgagga gcagggcatt ggagtgcagt   2820
gggacaacct gtttgagagt cctgtggagg aagatggctt caatctcacc acttcggtct   2880
ccatgatgct gtttgacacc ttcctctatg gggtgatgac ctggtacatt gaggctgtct   2940
ttccaggcca gtacggaatt cccaggccct ggtattttcc ttgcaccaag tcctactggt   3000
ttggcgagga aagtgatgag aagagccacc ctggttccaa ccagaagaga atatcagaaa   3060
tctgcatgga ggaggaaccc acccacttga agctgggcgt gtccattcag aacctggtaa   3120
aagtctaccg agatgggatg aaggtggctg tcgatggcct ggcactgaat ttttatgagg   3180
gccagatcac ctccttcctg ggccacaatg gagcggggaa gacgaccacc atgtcaatcc   3240
tgaccgggtt gttccccccg acctcgggca ccgcctacat cctgggaaaa gacattcgct   3300
ctgagatgag caccatccgg cagaacctgg gggtctgtcc ccagcataac gtgctgtttg   3360
acatgctgac tgtcgaagaa cacatctggt tctatgcccg cttgaaaggg ctctctgaga   3420
agcacgtgaa ggcggagatg gagcagatgg ccctggatgt tggtttgcca tcaagcaagc   3480
tgaaaagcaa aacaagccag ctgtcaggtg gaatgcagag aaagctatct gtggccttgg   3540
cctttgtcgg gggatctaag gttgtcattc tggatgaacc cacagctggt gtggaccctt   3600
actcccgcag gggaatatgg gagctgctgc tgaaataccg acaaggccgc accattattc   3660
tctctacaca ccacatggat gaagcggacg tcctggggga caggattgcc atcatctccc   3720
atgggaagct gtgctgtgtg ggctcctccc tgtttctgaa gaaccagctg ggaacaggct   3780
actacctgac cttggtcaag aaagatgtgg aatcctccct cagttcctgc agaaacagta   3840
gtagcactgt gtcatacctg aaaaaggagg acagtgtttc tcagagcagt tctgatgctg   3900
gcctgggcag cgaccatgag agtgacacgc tgaccatcga tgtctctgct atctccaacc   3960
tcatcaggaa gcatgtgtct gaagcccggc tggtggaaga catagggcat gagctgacct   4020
atgtgctgcc atatgaagct gctaaggagg gagcctttgt ggaactcttt catgagattg   4080
atgaccggct ctcagacctg ggcatttcta gttatggcat ctcagagacg accctggaag   4140
aaatattcct caaggtggcc gaagagagtg gggtggatgc tgagacctca gatggtacct   4200
tgccagcaag acgaaacagg cgggccttcg gggacaagca gagctgtctt cgcccgttca   4260
ctgaagatga tgctgctgat ccaaatgatt ctgacataga cccagaatcc agagagacag   4320
acttgctcag tgggatggat ggcaaagggt cctaccaggt gaaaggctgg aaacttacac   4380
agcaacagtt tgtggccctt ttgtggaaga gactgctaat tgccagacgg agtcggaaag   4440
gatttttgc tcagattgtc ttgccagctg tgtttgtctg cattgccctt gtgttcagcc   4500
tgatcgtgcc accctttggc aagtacccca gcctggaact tcagccctgg atgtacaacg   4560
aacagtacac atttgtcagc aatgatgctc ctgaggacac gggaaccctg gaactcttaa   4620
acgccctcac caaagaccct ggcttcggga cccgctgtat ggaaggaaac ccaatcccag   4680
acacgccctg ccaggcaggg gaggaagagt ggaccactgc cccagttccc cagaccatca   4740
tggacctctt ccagaatggg aactggacaa tgcagaaccc ttcacctgca tgccagtgta   4800
gcagcgacaa aatcaagaag atgctgcctg tgtgtccccc aggggcaggg gggctgcctc   4860
ctccacaaag aaaacaaaac actgcagata tccttcagga cctgacagga agaaacattt   4920
cggattatct ggtgaagacg tatgtgcaga tcatagccaa aagcttaaag aacaagatct   4980
gggtgaatga gtttaggtat ggcggctttt ccctgggtgt cagtaatact caagcacttc   5040
ctccgagtca agaagttaat gatgccatca aacaaatgaa gaaacaccta aagctggcca   5100
```

aggacagttc tgcagatcga tttctcaaca gcttgggaag atttatgaca ggactggaca 5160
ccaaaaataa tgtcaaggtg tggttcaata acaagggctg gcatgcaatc agctctttcc 5220
tgaatgtcat caacaatgcc attctccggg ccaacctgca aaagggagag aaccctagcc 5280
attatggaat tactgctttc aatcatcccc tgaatctcac caagcagcag ctctcagagg 5340
tggctctgat gaccacatca gtggatgtcc ttgtgtccat ctgtgtcatc tttgcaatgt 5400
ccttcgtccc agccagcttt gtcgtattcc tgatccagga gcgggtcagc aaagcaaaac 5460
acctgcagtt catcagtgga gtgaagcctg tcatctactg gctctctaat tttgtctggg 5520
atatgtgcaa ttacgttgtc cctgccacac tggtcattat catcttcatc tgcttccagc 5580
agaagtccta tgtgtcctcc accaatctgc ctgtgctagc ccttctactt ttgctgtatg 5640
ggtggtcaat cacacctctc atgtacccag cctcctttgt gttcaagatc cccagcacag 5700
cctatgtggt gctcaccagc gtgaacctct tcattggcat taatggcagc gtggccacct 5760
ttgtgctgga gctgttcacc gacaataagc tgaataatat caatgatatc ctgaagtccg 5820
tgttcttgat cttcccacat ttttgcctgg gacgagggct catcgacatg gtgaaaaacc 5880
aggcaatggc tgatgccctg gaaaggtttg gggagaatcg ctttgtgtca ccattatctt 5940
gggacttggt gggacgaaac ctcttcgcca tggccgtgga aggggtggtg ttcttcctca 6000
ttactgttct gatccagtac agattcttca tcaggcccag acctgtaaat gcaaagctat 6060
ctcctctgaa tgatgaagat gaagatgtga ggcgggaaag acagagaatt cttgatggtg 6120
gaggccagaa tgacatctta gaaatcaagg agttgacgaa gatatataga aggaagcgga 6180
agcctgctgt tgacaggatt tgcgtgggca ttcctcctgg tgagtgcttt gggctcctgg 6240
gagttaatgg ggctggaaaa tcatcaactt tcaagatgtt aacaggagat accactgtta 6300
ccagaggaga tgctttcctt aacaaaaata gtatcttatc aaacatccat gaagtacatc 6360
agaacatggg ctactgccct cagtttgatg ccatcacaga gctgttgact gggagagaac 6420
acgtggagtt ctttgccctt ttgagaggag tcccagagaa agaagttggc aaggttggtg 6480
agtgggcgat tcggaaactg ggcctcgtga agtatggaga aaaatatgct ggtaactata 6540
gtggaggcaa caaacgcaag ctctctacag ccatggcttt gatcggcggg cctcctgtgg 6600
tgtttctgga tgaacccacc acaggcatgg atcccaaagc ccggcggttc ttgtggaatt 6660
gtgccctaag tgttgtcaag gaggggagat cagtagtgct tacatctcat agtatggaag 6720
aatgtgaagc tctttgcact aggatggcaa tcatggtcaa tggaaggttc aggtgccttg 6780
gcagtgtcca gcatctaaaa aataggtttg gagatggtta tacaatagtt gtacgaatag 6840
cagggtccaa cccggacctg aagcctgtcc aggatttctt tggacttgca tttcctggaa 6900
gtgttctaaa agagaaacac cggaacatgc tacaatacca gcttccatct tcattatctt 6960
ctctggccag gatattcagc atcctctccc agagcaaaaa gcgactccac atagaagact 7020
actctgtttc tcagacaaca cttgaccaag tatttgtgaa ctttgccaag gaccaaagtg 7080
atgatgacca cttaaaagac ctctcattac acaaaaacca gacagtagtg gacgttgcag 7140
ttctcacatc ttttctacag gatgagaaag tgaaagaaag ctatgtatga agaatcctgt 7200
tcatacgggg tggctgaaag taaagaggaa ctagactttc ctttgcacca tgtgaagtgt 7260
tgtggagaaa agagccagaa gttgatgtgg gaagaagtaa actggatact gtactgatac 7320
tattcaatgc aatgcaattc aatgcaatga aaacaaaatt ccattacagg ggcagtgcct 7380
ttgtagccta tgtcttgtat ggctctcaag tgaaagactt gaatttagtt ttttacctat 7440

```
acctatgtga aactctatta tggaacccaa tggacatatg ggtttgaact cacacttttt   7500
ttttttttt tgttcctgtg tattctcatt ggggttgcaa caataattca tcaagtaatc   7560
atggccagcg attattgatc aaaatcaaaa ggtaatgcac atcctcattc actaagccat   7620
gccatgccca ggagactggt ttcccggtga cacatccatt gctggcaatg agtgtgccag   7680
agttattagt gccaagtttt tcagaaagtt tgaagcacca tggtgtgtca tgctcacttt   7740
tgtgaaagct gctctgctca gagtctatca acattgaata tcagttgaca gaatggtgcc   7800
atgcgtggct aacatcctgc tttgattccc tctgataagc tgttctggtg gcagtaacat   7860
gcaacaaaaa tgtgggtgtc tccaggcacg ggaaacttgg ttccattgtt atattgtcct   7920
atgcttcgag ccatgggtct acagggtcat ccttatgaga ctcttaaata tacttagatc   7980
ctggtaagag gcaaagaatc aacagccaaa ctgctggggc tgcaagctgc tgaagccagg   8040
gcatgggatt aaagagattg tgcgttcaaa cctagggaag cctgtgccca tttgtcctga   8100
ctgtctgcta acatggtaca ctgcatctca agatgtttat ctgacacaag tgtattattt   8160
ctggcttttt gaattaatct agaaaatgaa aagatggagt tgtattttga caaaaatgtt   8220
tgtacttttt aatgttattt ggaattttaa gttctatcag tgacttctga atccttagaa   8280
tggcctcttt gtagaaccct gtggtataga ggagtatggc cactgcccca ctatttttat   8340
tttcttatgt aagtttgcat atcagtcatg actagtgcct agaaagcaat gtgatggtca   8400
ggatctcatg acattatatt tgagtttctt tcagatcatt taggatactc ttaatctcac   8460
ttcatcaatc aaatattttt tgagtgtatg ctgtagctga aagagtatgt acgtacgtat   8520
aagactagag agatattaag tctcagtaca cttcctgtgc catgttattc agctcactgg   8580
tttacaaata taggttgtct tgtggttgta ggagcccact gtaacaatac tgggcagcct   8640
ttttttttt ttttttaatt gcaacaatgc aaaagccaag aaagtataag ggtcacaagt   8700
ctaaacaatg aattcttcaa cagggaaaac agctagcttg aaaacttgct gaaaaacaca   8760
acttgtgttt atggcattta gtaccttcaa ataattggct ttgcagatat tggatacccc   8820
attaaatctg acagtctcaa atttttcatc tcttcaatca ctagtcaaga aaaatataaa   8880
aacaacaaat acttccatat ggagcatttt tcagagtttt ctaacccagt cttatttttc   8940
tagtcagtaa acatttgtaa aaatactgtt tcactaatac ttactgttaa ctgtcttgag   9000
agaaaagaaa aatatgagag aactattgtt tggggaagtt caagtgatct ttcaatatca   9060
ttactaactt cttccacttt ttccagaatt tgaatattaa cgctaaaggt gtaagacttc   9120
agatttcaaa ttaatctttc tatatttttt aaatttacag aatattatat aacccactgc   9180
tgaaaaagaa aaaaatgatt gttttagaag ttaaagtcaa tattgatttt aaatataagt   9240
aatgaaggca tatttccaat aactagtgat atggcatcgt tgcattttac agtatcttca   9300
aaaatacaga atttatagaa taatttctcc tcatttaata tttttcaaaa tcaaagttat   9360
ggtttcctca ttttactaaa atcgtattct aattcttcat tatagtaaat ctatgagcaa   9420
ctccttactt cggttcctct gatttcaagg ccatatttta aaaaatcaaa aggcactgtg   9480
aactattttg aagaaaacac aacattttaa tacagattga aaggacctct tctgaagcta   9540
gaaacaatct atagttatac atcttcatta atactgtgtt accttttaaa atagtaattt   9600
tttacatttt cctgtgtaaa cctaattgtg gtagaaattt ttaccaactc tatactcaat   9660
caagcaaaat ttctgtatat tccctgtgga atgtacctat gtgagtttca gaaattctca   9720
aaatacgtgt tcaaaaattt ctgcttttgc atctttggga cacctcagaa aacttattaa   9780
caactgtgaa tatgagaaat acagaagaaa ataataagcc ctctatacat aaatgcccag   9840
```

cacaattcat tgttaaaaaa caaccaaacc tcacactact gtatttcatt atctgtactg 9900
aaagcaaatg ctttgtgact attaaatgtt gcacatcatt cattcactgt atagtaatca 9960
ttgactaaag ccatttgtct gtgttttctt cttgtggttg tatatatcag gtaaaatatt 10020
ttccaaagag ccatgtgtca tgtaatactg aaccactttg atattgagac attaatttgt 10080
acccttgtta ttatctacta gtaataatgt aatactgtag aaatattgct ctaattcttt 10140
tcaaaattgt tgcatccccc ttagaatgtt tctatttcca taaggattta ggtatgctat 10200
tatcccttct tataccctaa gatgaagctg tttttgtgct ctttgttcat cattggccct 10260
cattccaagc actttacgct gtctgtaatg ggatctattt ttgcactgga atatctgaga 10320
attgcaaaac tagacaaaag tttcacaaca gatttctaag ttaaatcatt ttcattaaaa 10380
ggaaaaaaga aaaaaaattt tgtatgtcaa taactttata tgaagtatta aaatgcatat 10440
ttctatgttg taatataatg agtcacaaaa taaagctgtg acagttctgt tggtctacag 10500
aaaaaaaaaa aaaaa 10515

<210> SEQ ID NO 107
<211> LENGTH: 1624
<212> TYPE: DNA
<213> ORGANISM: Homo sapiens

<400> SEQUENCE: 107
gttgcttgga tcagtctagg tgcagctgcc ggatccttca gcgtctgcat ctcggcgtcg 60
ccccgcgtac cgtcgcccgg ctctccgccg ctctcccggg gtttcggggc acttgggtcc 120
cacagtctgg tcctgcttca ccttcccctg acctgagtag tcgccatggc acaggttctc 180
agaggcactg tgactgactt ccctggattt gatgagcggg ctgatgcaga aactcttcgg 240
aaggctatga aaggcttggg cacagatgag gagagcatcc tgactctgtt gacatcccga 300
agtaatgctc agcgccagga aatctctgca gcttttaaga ctctgtttgg cagggatctt 360
ctggatgacc tgaaatcaga actaactgga aaatttgaaa aattaattgt ggctctgatg 420
aaaccctctc ggctttatga tgcttatgaa ctgaaacatg ccttgaaggg agctggaaca 480
aatgaaaaag tactgacaga aattattgct tcaaggacac ctgaagaact gagagccatc 540
aaacaagttt atgaagaaga atatggctca agcctggaag atgacgtggt gggggacact 600
tcagggtact accagcggat gttggtggtt ctccttcagg ctaacagaga ccctgatgct 660
ggaattgatg aagctcaagt tgaacaagat gctcaggctt tatttcaggc tggagaactt 720
aaatggggga cagatgaaga aaagtttatc accatctttg gaacacgaag tgtgtctcat 780
ttgagaaagg tgtttgacaa gtacatgact atatcaggat ttcaaattga ggaaaccatt 840
gaccgcgaga cttctggcaa tttagagcaa ctactccttg ctgttgtgaa atctattcga 900
agtatacctg cctaccttgc agagaccctc tattatgcta tgaagggagc tgggacagat 960
gatcataccc tcatcagagt catggtttcc aggagtgaga ttgatctgtt taacatcagg 1020
aaggagttta ggaagaattt tgccacctct ctttattcca tgattaaggg agatacatct 1080
ggggactata agaaagctct tctgctgctc tgtggagaag atgactaacg tgtcacgggg 1140
aagagctccc tgctgtgtgc ctgcaccacc ccactgcctt ccttcagcac ctttagctgc 1200
atttgtatgc cagtgcttaa cacattgcct tattcatact agcatgctca tgaccaacac 1260
atacacgtca tagaagaaaa tagtggtgct tctttctgat ctctagtgga gatctctttg 1320
actgctgtag tactaaagtg tacttaatgt tactaagttt aatgcctggc cattttccat 1380

```
ttatatatat tttttaagag gctagagtgc ttttagcctt ttttaaaaac tccatttata   1440

ttacatttgt aaccatgata ctttaatcag aagcttagcc ttgaaattgt gaactcttgg   1500

aaatgttatt agtgaagttc gcaactaaac taaacctgta aaattatgat gattgtattc   1560

aaaagattaa tgaaaaataa acatttctgt ccccctgaaa aaaaaaaaaa aaaaaaaaaa   1620

aaaa                                                                1624


<210> SEQ ID NO 108
<211> LENGTH: 760
<212> TYPE: DNA
<213> ORGANISM: Homo sapiens

<400> SEQUENCE: 108

gaggaaccga gaggctgaga ctaacccaga aacatccaat tctcaaactg aagctcgcac     60

tctcgcctcc agcatgaaag tctctgccgc ccttctgtgc ctgctgctca tagcagccac    120

cttcattccc caagggctcg ctcagccaga tgcaatcaat gccccagtca cctgctgtta    180

taacttcacc aataggaaga tctcagtgca gaggctcgcg agctatagaa gaatcaccag    240

cagcaagtgt cccaaagaag ctgtgatctt caagaccatt gtggccaagg agatctgtgc    300

tgaccccaag cagaagtggg ttcaggattc catggaccac ctggacaagc aaacccaaac    360

tccgaagact tgaacactca ctccacaacc caagaatctg cagctaactt attttcccct    420

agctttcccc agacaccctg ttttatttta ttataatgaa ttttgtttgt tgatgtgaaa    480

cattatgcct taagtaatgt taattcttat ttaagttatt gatgttttaa gtttatcttt    540

catggtacta gtgtttttta gatacagaga cttggggaaa ttgcttttcc tcttgaacca    600

cagttctacc cctgggatgt tttgagggtc tttgcaagaa tcattaatac aaagaatttt    660

ttttaacatt ccaatgcatt gctaaaatat tattgtggaa atgaatattt tgtaactatt    720

acaccaaata aatatatttt tgtacaaaaa aaaaaaaaaa                          760


<210> SEQ ID NO 109
<211> LENGTH: 815
<212> TYPE: DNA
<213> ORGANISM: Homo sapiens

<400> SEQUENCE: 109

agaggagcag aggggctgag accaaaccag aaacctccaa ttctcatgtg gaagcccatg     60

ccctcaccct ccaacatgaa agcctctgca gcacttctgt gtctgctgct cacagcagct    120

gctttcagcc cccaggggct tgctcagcca gttgggatta atacttcaac tacctgctgc    180

tacagattta tcaataagaa aatccctaag cagaggctgg agagctacag aaggaccacc    240

agtagccact gtccccggga agctgtaatc ttcaagacca aactggacaa ggagatctgt    300

gctgacccca cacagaagtg ggtccaggac tttatgaagc acctggacaa gaaaacccaa    360

actccaaagc tttgaacatt catgactgaa ctgaaaacaa gccatgactt gagaaacaaa    420

taatttgtat accctgtcct ttctcagagt ggttctgaga ttattttaat ctaattctaa    480

ggaatatgag ctttatgtaa taatgtgaat catggttttt cttagtagat tttaaaagtt    540

attaatattt taatttaatc ttccatggat tttggtgggt tttgaacata aagccttgga    600

tgtatatgtc atctcagtgc tgtaaaaact gtgggatgct cctcccttct ctacctcatg    660

ggggtattgt ataagtcctt gcaagaatca gtgcaaagat ttgctttaat tgttaagata    720

tgatgtccct atggaagcat attgttatta tataattaca tatttgcata tgtatgactc    780

ccaaattttc acataaaata gatttttgta taaca                               815
```

<210> SEQ ID NO 110
<211> LENGTH: 1872
<212> TYPE: DNA
<213> ORGANISM: Homo sapiens

<400> SEQUENCE: 110
ttaattacaa aaactaatga ctaagagaga ggtggctaga gctgaggccc ctgagtcagg 60
ctgtgggtgg gatcatctcc agtacaggaa gtgagacttt catttcctcc tttccaagag 120
agggctgagg gagcagggtt gagcaactgg tgcagacagc ctagctggac tttgggtgag 180
gcggttcagc catgaggctg gctgtgcttt tctcgggggc cctgctgggg ctactggcag 240
cccaggggac agggaatgac tgtcctcaca aaaaatcagc tactttgctg ccatccttca 300
cggtgacacc cacggttaca gagagcactg gaacaaccag ccacaggact accaagagcc 360
acaaaaccac cactcacagg acaaccacca caggcaccac cagccacgga cccacgactg 420
ccactcacaa ccccaccacc accagccatg gaaacgtcac agttcatcca acaagcaata 480
gcactgccac cagccaggga ccctcaactg ccactcacag tcctgccacc actagtcatg 540
gaaatgccac ggttcatcca acaagcaaca gcactgccac cagcccagga ttcaccagtt 600
ctgcccaccc agaaccacct ccaccctctc cgagtcctag cccaacctcc aaggagacca 660
ttggagacta cacgtggacc aatggttccc agccctgtgt ccacctccaa gcccagattc 720
agattcgagt catgtacaca acccagggtg gaggagaggc ctggggcatc tctgtactga 780
accccaacaa aaccaaggtc cagggaagct gtgagggtgc ccatccccac ctgcttctct 840
cattccccta tggacacctc agctttggat tcatgcagga cctccagcag aaggttgtct 900
acctgagcta catggcggtg gagtacaatg tgtccttccc ccacgcagca cagtggacat 960
tctcggctca gaatgcatcc cttcgagatc tccaagcacc cctggggcag agcttcagtt 1020
gcagcaactc gagcatcatt ctttcaccag ctgtccacct cgacctgctc tccctgaggc 1080
tccaggctgc tcagctgccc cacacagggg tctttgggca aagtttctcc tgccccagtg 1140
accggtccat cttgctgcct ctcatcatcg gcctgatcct tcttggcctc ctcgccctgg 1200
tgcttattgc tttctgcatc atccggagac gcccatccgc ctaccaggcc ctctgagcat 1260
ttgcttcaaa ccccagggca ctgagggggt tggggtgtgg tggggggggta cccttatttc 1320 ctcgacacgc aactggctca aagacaatgt tattttcctt ccctttcttg aagaacaaaa 1380
agaaagccgg gcatgacggc tcatgcctgt aatcccagca ctttgggagg ctgaggcagg 1440
tggatcactg gaggtcagga gtttgagacc agcctggcca acatggtgaa accctgtctc 1500
tactaaaaat acaattagcc aggtgtggcg gcgtaatccc agctggcctg taatcccagc 1560
tacttgggag gctgaggcag aactgcttga acccaggagg tggaggttgc agtgagccgt 1620
catcgcgcca ctaagccaag atcgcgccac tgcactccag cctgggcgac agagccagac 1680
tgtctcaaat aaataaatat gagataatgc agtcgggaga agggagggag agaattttat 1740
taaatgtgac gaactgcccc cccccccccc ccagcaggag agcagcaaaa tttatgcaaa 1800
tctttgacgg ggttttcctt gtcctgccag gattaaaagc catgagtttc ttgtcaaaaa 1860
aaaaaaaaaa aa 1872

<210> SEQ ID NO 111
<211> LENGTH: 3225
<212> TYPE: DNA
<213> ORGANISM: Homo sapiens

<400> SEQUENCE: 111

```
atttccggag gggaggcccc gcggctgccg ccgccatttc gggcgctgct gtgaagctga      60
aaccggagcc ggtccgctgg gcggcgggcg ccgggggccg gaggggcgcg cgcggcggcg     120
gcaccccagc gtttaggcgc ggaggcagcc atggcgggca acttcgactc ggaggagcgg     180
agtagctggt actgggggag gttgagtcgg caggaggcgg tggcgctgct gcagggccag     240
cggcacgggg tgttcctggt gcgggactcg agcaccagcc ccggggacta tgtgctcagc     300
gtctcagaga actcgcgcgt ctcccactac atcatcaaca gcagcggccc gcgcccgccg     360
gtgccaccgt cgcccgccca gcctccgccc ggggtgagcc cctccagact ccgaatagga     420
gatcaagagt ttgattcatt gcctgcttta ctggaattct acaaaataca ctatttggac     480
actacaacgt tgatagaacc agtttccaga tccaggcagg gtagtggagt gattctcagg     540
caggaggagg cggagtatgt gcgagccctc tttgacttta atgggaatga tgaggaagat     600
cttcccttta agaaaggaga catcttgaga atccgggaca agcctgaaga gcagtggtgg     660
aatgcggagg acagcgaagg caagagaggg atgattccag tcccttacgt cgagaagtat     720
agacctgcct ccgcctcagt atcggctctg attggaggta accaggaggg ttcccaccca     780
cagccactgg gtgggccgga gcctgggccc tatgcccaac ccagcgtcaa cactccgctc     840
cctaacctcc agaatgggcc catatatgcc agggttatcc agaagcgagt ccccaatgcc     900
tacgacaaga cagccttggc tttggaggtc ggtgagctgg taaaggttac gaagattaat     960
gtgagtggtc agtgggaagg ggagtgtaat ggcaaacgag gtcacttccc attcacacat    1020
gtccgtctgc tggatcaaca gaatcccgat gaggacttca gctgagtata gttcaacagt    1080
tttgctgaca gatgggaaca atcttttttt ttttttttcca actgccatct atacaatttt    1140
cttacagatg tcaaaagcag tctagtttat ataagcattc tgttacctgt gatatttttt    1200
agactgaact gctccattcc tagtcttaat taccatattc agggtacgaa ctggagggct    1260
tgtgtgttag cttctgaatt ggcaattgga ggcggtagtg gtcgtgcctg tgtgtatcag    1320
aagggatagg tatcttgcct cctttctctc aggcagtgca aatcaccctg tggaaaaccg    1380
atggacagga aggagtgtta cacactgctt accctgattt attcagtggt tttgttttca    1440
ttctggaacc atactatcaa atggcgacag actgttccgt tccacccccg tgaagtaatc    1500
atgcaccgtg tgaatagtat caagcaggat tgctttcatt gtatggagca tgaccagcgt    1560
gtgactcatt ctgacatttc agatcctaag aattctaaga acactactag aagcatttgt    1620
tccctcctag tcaatgcttc atactttttc ttgggattct tttagccctt gacattcttg    1680
tcccccaaac ctgtaagtag gtgaattcct aagataagtg tgtattttca ttccaggtga    1740
aaagcaggat gtaccgagca ctttattcag tgcatagctt taagccagtg ttggattcac    1800
taagtggaca gccagtctcc cagctctctg ccttccccaa aagggtcgta gtaggtcacc    1860
cttctacagc agctaactag agtcctaact aatgggatcc agcagggcca tttctccaga    1920
gggccagtat cctattagga gactcttgga attcttaggt tctactcaag agtggaagga    1980
ccaatcacct ctgatattct gtggaaggtt ttggggtcaa attctgccct ctgcattctg    2040
tgcaacttgt ataaaagtca agttagtatt acatgaattt ggggtagggt tagtgctttg    2100
aaaaaatgtt gaaccggctg ggcgcggtgg ctcacgtctg taatcccagc actttgggag    2160
gccgaggcgg gtggatcatg aggtcaggag ttcgagacca gcctggccaa catagtgaaa    2220
ccccatctct gctaaagata taaaaaatta gcccggcgtg gtggtgcacg cctgtaatcc    2280
cagctactcg ggaggctgag gcaggagaat tgcttcaacc tgggaggtgg aggctgcagt    2340
```

gagccgagat cgcaccactg cgttccagcc tgagcgacag ggcaagactc agtctcaaaa 2400
aaaaaaaaaa ggaaaaaaaa aagaaaaaaa aatgttgaac caattgtgaa ttacttatgt 2460
attattcatt tctcatgggg agagtaatgc tgttgaagaa cattacattg taaactgcct 2520
tcatttttgg ctctttgttt atgttcaggt ttagtttaca aacccattta agtatggaat 2580
gatttatatg gggtcaggtg ctccacaaaa tagacctatg agaccaaaaa tgacctaggc 2640
tatttagacg acagcatgaa acttccacgt tagttctcag tctataaagg cacttaccgg 2700
tctctggtgt ggtatgacca atagaaacac cttatagttt gctttggacc tcattttgga 2760
aaaataatct gcctttctaa ttgttctgca taggttaaaa tgataaattt acattctttg 2820
aacctatacc agattgtggt gtccgagtga ccggcacact gtctgacaca cagtcagtgt 2880
gcacgtattt gtctgagtga atgaggagac ctgagaaacc ggtgacgtgg cacagggaag 2940
ccagctggcc caggattccg tacatggccg caagcagact aacgcgttga cgctaattta 3000
atgtatttta cctcacacta aggtcatgct tgataaagac gttaaactca acttgtaaaa 3060
tggtagccca gtgctatgca cagagtgggt gctcattagt gttgaatgaa cacatttgta 3120
atactacatg taattccatc tgactgcttt gttaaatttt cagttagaac gtagatactg 3180
taaagtccac acacacatta aatcttgttt tcctgaaagt atggc 3225

<210> SEQ ID NO 112
<211> LENGTH: 1184
<212> TYPE: DNA
<213> ORGANISM: Homo sapiens

<400> SEQUENCE: 112
cacagagccc gggccgcagg cacctcctcg ccagctcttc cgctcctctc acagccgcca 60
gacccgcctg ctgagcccca tggcccgcgc tgctctctcc gccgccccca gcaatccccg 120
gctcctgcga gtggcactgc tgctcctgct cctggtagcc gctggccggc gcgcagcagg 180
agcgtccgtg gccactgaac tgcgctgcca gtgcttgcag accctgcagg gaattcaccc 240
caagaacatc caaagtgtga acgtgaagtc ccccggaccc cactgcgccc aaaccgaagt 300
catagccaca ctcaagaatg ggcggaaagc ttgcctcaat cctgcatccc ccatagttaa 360
gaaaatcatc gaaaagatgc tgaacagtga caaatccaac tgaccagaag ggaggaggaa 420
gctcactggt ggctgttcct gaaggaggcc ctgcccttat aggaacagaa gaggaaagag 480
agacacagct gcagaggcca cctggattgt gcctaatgtg tttgagcatc gcttaggaga 540
agtcttctat ttatttattt attcattagt tttgaagatt ctatgttaat attttaggtg 600
taaaataatt aagggtatga ttaactctac ctgcacactg tcctattata ttcattcttt 660
ttgaaatgtc aaccccaagt tagttcaatc tggattcata tttaatttga aggtagaatg 720
ttttcaaatg ttctccagtc attatgttaa tatttctgag gagcctgcaa catgccagcc 780
actgtgatag aggctggcgg atccaagcaa atggccaatg agatcattgt gaaggcaggg 840
gaatgtatgt gcacatctgt tttgtaactg tttagatgaa tgtcagttgt tatttattga 900
aatgatttca cagtgtgtgg tcaacatttc tcatgttgaa actttaagaa ctaaaatgtt 960
ctaaatatcc cttggacatt ttatgtcttt cttgtaaggc atactgcctt gtttaatggt 1020
agttttacag tgtttctggc ttagaacaaa ggggcttaat tattgatgtt ttcatagaga 1080
atataaaaat aaagcactta tagaaaaaac tcgtttgatt tttgggggga aacaagggct 1140
acctttactg gaaaatctgg tgatttataa aaaaaaaaaa aaaa 1184

<210> SEQ ID NO 113
<211> LENGTH: 1234
<212> TYPE: DNA
<213> ORGANISM: Homo sapiens

<400> SEQUENCE: 113
gagctccggg aatttccctg gcccgggact ccgggctttc cagccccaac catgcataaa 60
aggggttcgc cgttctcgga gagccacaga gcccgggcca caggcagctc cttgccagct 120
ctcctcctcg cacagccgct cgaaccgcct gctgagcccc atggcccgcg ccacgctctc 180
cgccgccccc agcaatcccc ggctcctgcg ggtggcgctg ctgctcctgc tcctggtggc 240
cgccagccgg cgcgcagcag gagcgcccct ggccactgaa ctgcgctgcc agtgcttgca 300
gaccctgcag ggaattcacc tcaagaacat ccaaagtgtg aaggtgaagt cccccggacc 360
ccactgcgcc caaaccgaag tcatagccac actcaagaat gggcagaaag cttgtctcaa 420
ccccgcatcg cccatggtta agaaaatcat cgaaaagatg ctgaaaaatg gcaaatccaa 480
ctgaccagaa ggaaggagga agcttattgg tggctgttcc tgaaggaggc cctgccctta 540
caggaacaga agaggaaaga gagacacagc tgcagaggcc acctggattg cgcctaatgt 600
gtttgagcat cacttaggag aagtcttcta tttatttatt tatttattta tttgtttgtt 660
ttagaagatt ctatgttaat attttatgtg taaaataagg ttatgattga atctacttgc 720
acactctccc attatattta ttgtttattt taggtcaaac ccaagttagt tcaatcctga 780
ttcatattta atttgaagat agaaggtttg cagatattct ctagtcattt gttaatattt 840
cttcgtgatg acatatcaca tgtcagccac tgtgatagag gctgaggaat ccaagaaaat 900
ggccagtgag atcaatgtga cggcagggaa atgtatgtgt gtctattttg taactgtaaa 960
gatgaatgtc agttgttatt tattgaaatg atttcacagt gtgtggtcaa catttctcat 1020
gttgaagctt taagaactaa aatgttctaa atatcccttg gacattttat gtctttcttg 1080
taaggcatac tgccttgttt aatgttaatt atgcagtgtt tccctctgtg ttagagcaga 1140
gaggtttcga tatttattga tgttttcaca aagaacagga aaataaaata tttaaaaata 1200
taaaaaaaaa aaaaaaaaaa aaaaaaaaaa aaaa 1234

<210> SEQ ID NO 114
<211> LENGTH: 2505
<212> TYPE: DNA
<213> ORGANISM: Homo sapiens

<400> SEQUENCE: 114
agtggggaga gatgagtgta gataaaagga gtgcagaagg cacgaggaag ccacagtgct 60
ccggatcctc caatcttcgc tcctccaatc tccgctcctc cacccagttc aggaacccgc 120
gaccgctcgc agcgctctct tgaccactat gagcctcctg tccagccgcg cggcccgtgt 180
ccccggtcct tcgagctcct tgtgcgcgct gttggtgctg ctgctgctgc tgacgcagcc 240
agggcccatc gccagcgctg gtcctgccgc tgctgtgttg agagagctgc gttgcgtttg 300
tttacagacc acgcaaggag ttcatcccaa aatgatcagt aatctgcaag tgttcgccat 360
aggcccacag tgctccaagg tggaagtggt agcctccctg aagaacggga aggaaatttg 420
tcttgatcca gaagcccctt ttctaaagaa agtcatccag aaaattttgg acggtggaaa 480
caaggaaaac tgattaagag aaatgagcac gcatggaaaa gtttcccagt cttcagcaga 540
gaagttttct ggaggtctct gaacccaggg aagacaagaa ggaaagattt tgttgttgtt 600
tgtttatttg tttttccagt agttagcttt cttcctggat tcctcacttt gaagagtgtg 660
aggaaaacct atgtttgccg cttaagcttt cagctcagct aatgaagtgt ttagcatagt 720
acctctgcta tttgctgtta ttttatctgc tatgctattg aagttttggc aattgactat 780
agtgtgagcc aggaatcact ggctgttaat ctttcaaagt gtcttgaatt gtaggtgact 840
attatatttc caagaaatat tccttaagat attaactgag aaggctgtgg atttaatgtg 900
gaaatgatgt ttcataagaa ttctgttgat ggaaatacac tgttatcttc acttttataa 960
gaaataggaa atattttaat gtttcttggg gaatatgtta gagaatttcc ttactcttga 1020
ttgtgggata ctatttaatt atttcacttt agaaagctga gtgtttcaca ccttatctat 1080
gtagaatata tttccttatt cagaatttct aaaagtttaa gttctatgag ggctaatatc 1140
ttatcttcct ataattttag acattcttta tctttttagt atggcaaact gccatcattt 1200
acttttaaac tttgatttta tatgctattt attaagtatt ttattaggag taccataatt 1260
ctggtagcta aatatatatt ttagatagat gaagaagcta gaaaacaggc aaattcctga 1320
ctgctagttt atatagaaat gtattctttt agtttttaaa gtaaaggcaa acttaacaat 1380
gacttgtact ctgaaagttt tggaaacgta ttcaaacaat ttgaatataa atttatcatt 1440
tagttataaa aatatatagc gacatcctcg aggccctagc atttctcctt ggatagggga 1500
ccagagagag cttggaatgt taaaaacaaa acaaaacaaa aaaaaacaag gagaagttgt 1560
ccaagggatg tcaatttttt atccctctgt atgggttaga ttttccaaaa tcataatttg 1620
aagaaggcca gcatttatgg tagaatatat aattatatat aaggtggcca cgctggggca 1680
agttccctcc ccactcacag ctttggcccc tttcacagag tagaacctgg gttagaggat 1740
tgcagaagac gagcggcagc ggggagggca gggaagatgc ctgtcgggtt tttagcacag 1800
ttcatttcac tgggattttg aagcatttct gtctgaatgt aaagcctgtt ctagtcctgg 1860
tgggacacac tggggttggg ggtgggggaa gatgcggtaa tgaaaccggt tagtcagtgt 1920
tgtcttaata tccttgataa tgctgtaaag tttattttta caaatatttc tgtttaagct 1980
atttcacctt tgtttggaaa tccttccctt ttaaagagaa aatgtgacac ttgtgaaaag 2040
gcttgtagga aagctcctcc cttttttttct ttaaaccttt aaatgacaaa cctaggtaat 2100
taatggttgt gaatttctat ttttgctttg tttttaatga acatttgtct ttcagaatag 2160
gattctgtga taatatttaa atggcaaaaa caaaacataa ttttgtgcaa ttaacaaagc 2220
tactgcaaga aaaataaaac atttcttggt aaaaacgtat gtatttatat attatatatt 2280
tatatataat atatattata tatttagcat tgctgagctt tttagatgcc tattgtgtat 2340
cttttaaagg ttttgaccat tttgttatga gtaattacat atatattaca ttcactatat 2400
taaaattgta ctttttttact atgtgtctca ttggttcata gtctttattt tgtcctttga 2460
ataaacatta aaagatttct aaacttcaaa aaaaaaaaaa aaaaa 2505

<210> SEQ ID NO 115
<211> LENGTH: 2343
<212> TYPE: DNA
<213> ORGANISM: Homo sapiens

<400> SEQUENCE: 115
ggtgcgtccg cgggtggctg ccccgcaggt gcgcgcggcc ggggctggcg gcgactctct 60
ccaccgggcc gcccgggagg ctcatgcagc gcggctgggt cccgcggcgc ccggatcggg 120
gaagtgaaag tgcctcggag gaggagggcc ggtccggcag tgcagccgcc tcacaggtcg 180
gcggacgggc caggcgggcg gcctcctgaa ccgaaccgaa tcggctcctc gggccgtcgt 240

-continued

```
cctcccgccc ctcctcgccc gccgccggag ttttctttcg gtttcttcca agattcctgg    300
ccttccctcg acggagccgg gcccagtgcg ggggcgcagg gcgcgggagc tccacctcct    360
cggctttccc tgcgtccaga ggctggcatg gcgcgggccg agtactgagc gcacggtcgg    420
ggcacagcag ggccgggggg tgcagctggc tcgcgcctcc tctccggccg ccgtctcctc    480
cggtccccgg cgaaagccat tgagacacca gctggacgtc acgcgccgga gcatgtctgg    540
gagtcagagc gaggtggctc catccccgca gagtccgcgg agccccgaga tgggacggga    600
cttgcggccc gggtcccgcg tgctcctgct cctgcttctg ctcctgctgg tgtacctgac    660
tcagccaggc aatggcaacg agggcagcgt cactggaagt tgttattgtg gtaaaagaat    720
ttcttccgac tccccgccat cggttcagtt catgaatcgt ctccggaaac acctgagagc    780
ttaccatcgg tgtctatact acacgaggtt ccagctcctt tcctggagcg tgtgtggggg    840
caacaaggac ccatgggttc aggaattgat gagctgtctt gatctcaaag aatgtggaca    900
tgcttactcg gggattgtgg cccaccagaa gcatttactt cctaccagcc ccccaatttc    960
tcaggcctca gagggggcat cttcagatat ccacacccct gcccagatgc tcctgtccac   1020
cttgcagtcc actcagcgcc ccaccctccc agtaggatca ctgtcctcgg acaaagagct   1080
cactcgtccc aatgaaacca ccattcacac tgcgggccac agtctggcag ctgggcctga   1140
ggctggggag aaccagaagc agccggaaaa aaatgctggt cccacagcca ggacatcagc   1200
cacagtgcca gtcctgtgcc tcctggccat catcttcatc ctcaccgcag ccctttccta   1260
tgtgctgtgc aagaggagga gggggcagtc accgcagtcc tctccagatc tgccggttca   1320
ttatatacct gtggcacctg actctaatac ctgagccaag aatggaagct tgtgaggaga   1380
cggactctat gttgcccagg ctgttatgga actcctgagt caagtgatcc tcccaccttg   1440
gcctctgaag gtgcgaggat tataggcgtc acctaccaca tccagcctac acgtatttgt   1500
taatatctaa cataggacta accagccact gccctctctt aggcccctca tttaaaaacg   1560
gttatactat aaaatctgct tttcacactg ggtgataata acttggacaa attctatgtg   1620
tattttgttt tgttttgctt tgctttgttt tgagacggag tctcgctctg tcatccaggc   1680
tggagtgcag tggcatgatc tcggctcact gcaacccccca tctcccaggt tcaagcgatt   1740
ctcctgcctc ctcctgagta gctgggacta caggtgctca ccaccacacc cggctaattt   1800
tttgtatttt tagtagagac ggggtttcac catgttgacc aggctggtct cgaactcctg   1860
acctggtgat ctgcccaccc aggcctccca aagtgctggg attaaaggtg tgagccacca   1920
tgcctggccc tatgtgtgtt ttttaactac taaaaattat ttttgtaatg attgagtctt   1980
ctttatggaa acaactggcc tcagcccttg cgcccttact gtgattcctg gcttcatttt   2040
ttgctgatgg ttccccctcg tcccaaatct ctctcccagt acaccagttg ttcctccccc   2100
acctcagccc tctcctgcat cctcctgtac ccgcaacgaa ggcctgggct ttcccaccct   2160
ccctccttag caggtgccgt gctgggacac catacgggtt ggtttcacct cctcagtccc   2220
ttgcctaccc cagtgagagt ctgatcttgt ttttattgtt attgctttta ttattattgc   2280
ttttattatc attaaaactc tagttcttgt tttgtctctc cgaatgaaaa aaaaaaaaaa   2340
aaa                                                                 2343
```

<210> SEQ ID NO 116
<211> LENGTH: 2692
<212> TYPE: DNA
<213> ORGANISM: Homo sapiens

<400> SEQUENCE: 116

-continued

```
cctacccgcg cgcaggccaa gttgctgaat caatggagcc ctccccaacc cgggcgttcc      60
ccagcgaggc ttccttccca tcctcctgac caccggggct tttcgtgagc tcgtctctga     120
tctcgcgcaa gagtgacaca caggtgttca aagacgcttc tggggagtga gggaagcggt     180
ttacgagtga cttggctgga gcctcagggg cgggcactgg cacggaacac accctgaggc     240
cagccctggc tgcccaggcg gagctgcctc ttctcccgcg ggttggtgga cccgctcagt     300
acggagttgg ggaagctctt tcacttcgga ggattgctca acaaccatgc tgggcatctg     360
gaccctccta cctctggttc ttacgtctgt tgctagatta tcgtccaaaa gtgttaatgc     420
ccaagtgact gacatcaact ccaagggatt ggaattgagg aagactgtta ctacagttga     480
gactcagaac ttggaaggcc tgcatcatga tggccaattc tgccataagc cctgtcctcc     540
aggtgaaagg aaagctaggg actgcacagt caatggggat gaaccagact gcgtgccctg     600
ccaagaaggg aaggagtaca cagacaaagc ccatttttct tccaaatgca gaagatgtag     660
attgtgtgat gaaggacatg gcttagaagt ggaaataaac tgcacccgga cccagaatac     720
caagtgcaga tgtaaaccaa actttttttg taactctact gtatgtgaac actgtgaccc     780
ttgcaccaaa tgtgaacatg gaatcatcaa ggaatgcaca ctcaccagca acaccaagtg     840
caaagaggaa gtgaagagaa aggaagtaca gaaaacatgc agaaagcaca gaaaggaaaa     900
ccaaggttct catgaatctc caactttaaa tcctgaaaca gtggcaataa atttatctga     960
tgttgacttg agtaaatata tcaccactat tgctggagtc atgacactaa gtcaagttaa    1020
aggctttgtt cgaaagaatg gtgtcaatga agccaaaata gatgagatca agaatgacaa    1080
tgtccaagac acagcagaac agaaagttca actgcttcgt aattggcatc aacttcatgg    1140
aaagaaagaa gcgtatgaca cattgattaa agatctcaaa aaagccaatc tttgtactct    1200
tgcagagaaa attcagacta tcatcctcaa ggacattact agtgactcag aaaattcaaa    1260
cttcagaaat gaaatccaaa gcttggtcta gagtgaaaaa caacaaattc agttctgagt    1320
atatgcaatt agtgtttgaa aagattctta atagctggct gtaaatactg cttggttttt    1380
tactgggtac attttatcat ttattagcgc tgaagagcca acatatttgt agatttttaa    1440
tatctcatga ttctgcctcc aaggatgttt aaaatctagt tgggaaaaca aacttcatca    1500
agagtaaatg cagtggcatg ctaagtaccc aaataggagt gtatgcagag gatgaaagat    1560
taagattatg ctctggcatc taacatatga ttctgtagta tgaatgtaat cagtgtatgt    1620
tagtacaaat gtctatccac aggctaaccc cactctatga atcaatagaa gaagctatga    1680
ccttttgctg aaatatcagt tactgaacag gcaggccact ttgcctctaa attacctctg    1740
ataattctag agattttacc atatttctaa actttgttta taactctgag aagatcatat    1800
ttatgtaaag tatatgtatt tgagtgcaga atttaaataa ggctctacct caaagacctt    1860
tgcacagttt attggtgtca tattatacaa tatttcaatt gtgaattcac atagaaaaca    1920
ttaaattata atgtttgact attatatatg tgtatgcatt ttactggctc aaaactacct    1980
acttctttct caggcatcaa aagcattttg agcaggagag tattactaga gctttgccac    2040
ctctccattt ttgccttggt gctcatctta atggcctaat gcacccccaa acatggaaat    2100
atcaccaaaa aatacttaat agtccaccaa aaggcaagac tgcccttaga aattctagcc    2160
tggtttggag atactaactg ctctcagaga aagtagcttt gtgacatgtc atgaacccat    2220
gtttgcaatc aaagatgata aaatagattc ttatttttcc cccacccccg aaaatgttca    2280
ataatgtccc atgtaaaacc tgctacaaat ggcagcttat acatagcaat ggtaaaatca    2340
```

tcatctggat ttaggaattg ctcttgtcat acccccaagt ttctaagatt taagattctc 2400
cttactacta tcctacgttt aaatatcttt gaaagtttgt attaaatgtg aattttaaga 2460
aataatattt atatttctgt aaatgtaaac tgtgaagata gttataaact gaagcagata 2520
cctggaacca cctaaagaac ttccatttat ggaggatttt tttgcccctt gtgtttggaa 2580
ttataaaata taggtaaaag tacgtaatta aataatgttt ttggtaaaaa aaaaaaaaaa 2640
aaaaaaaaaa aaaaaaaaaa aaaaaaaaaa aaaaaaaaaa aaaaaaaaaa aa 2692

<210> SEQ ID NO 117
<211> LENGTH: 1629
<212> TYPE: DNA
<213> ORGANISM: Homo sapiens

<400> SEQUENCE: 117
acacatcagg ggcttgctct tgcaaaacca aaccacaaga cagacttgca aaagaaggca 60
tgcacagctc agcactgctc tgttgcctgg tcctcctgac tggggtgagg gccagcccag 120
gccagggcac ccagtctgag aacagctgca cccacttccc aggcaacctg cctaacatgc 180
ttcgagatct ccgagatgcc ttcagcagag tgaagacttt ctttcaaatg aaggatcagc 240
tggacaactt gttgttaaag gagtccttgc tggaggactt taagggttac ctgggttgcc 300
aagccttgtc tgagatgatc cagttttacc tggaggaggt gatgccccaa gctgagaacc 360
aagacccaga catcaaggcg catgtgaact ccctggggga gaacctgaag accctcaggc 420
tgaggctacg gcgctgtcat cgatttcttc cctgtgaaaa caagagcaag gccgtggagc 480
aggtgaagaa tgcctttaat aagctccaag agaaaggcat ctacaaagcc atgagtgagt 540
ttgacatctt catcaactac atagaagcct acatgacaat gaagatacga aactgagaca 600
tcagggtggc gactctatag actctaggac ataaattaga ggtctccaaa atcggatctg 660
gggctctggg atagctgacc cagccccttg agaaacctta ttgtacctct cttatagaat 720
atttattacc tctgatacct caacccccat ttctatttat ttactgagct tctctgtgaa 780
cgatttagaa agaagcccaa tattataatt tttttcaata tttattattt tcacctgttt 840
ttaagctgtt tccatagggt gacacactat ggtatttgag tgttttaaga taaattataa 900
gttacataag ggaggaaaaa aaatgttctt tggggagcca acagaagctt ccattccaag 960
cctgaccacg ctttctagct gttgagctgt tttccctgac ctccctctaa tttatcttgt 1020
ctctgggctt ggggcttcct aactgctaca aatactctta ggaagagaaa ccagggagcc 1080
cctttgatga ttaattcacc ttccagtgtc tcggagggat tcccctaacc tcattcccca 1140
accacttcat tcttgaaagc tgtggccagc ttgttattta taacaaccta aatttggttc 1200
taggccgggc gcggtggctc acgcctgtaa tcccagcact ttgggaggct gaggcgggtg 1260
gatcacttga ggtcaggagt tcctaaccag cctggtcaac atggtgaaac cccgtctcta 1320
ctaaaaatac aaaaattagc cgggcatggt ggcgcgcacc tgtaatccca gctacttggg 1380
aggctgaggc aagagaattg cttgaaccca ggagatggaa gttgcagtga gctgatatca 1440
tgcccctgta ctccagcctg ggtgacagag caagactctg tctcaaaaaa taaaaataaa 1500
aataaatttg gttctaatag aactcagttt taactagaat ttattcaatt cctctgggaa 1560
tgttacattg tttgtctgtc ttcatagcag attttaattt tgaataaata aatgtatctt 1620
attcacatc 1629

<210> SEQ ID NO 118
<211> LENGTH: 4267

<212> TYPE: DNA
<213> ORGANISM: Homo sapiens

<400> SEQUENCE: 118
attcgcctct gggaggttta ggaagcggct ccgggtcggt ggccccagga cagggaagag 60
cgggcgctat ggggagccgg acgccagagt cccctctcca cgccgtgcag ctgcgctggg 120
gcccccggcg ccgacccccg ctgctgccgc tgctgttgct gctgctgccg ccgccaccca 180
gggtcggggg cttcaactta gacgcggagg ccccagcagt actctcgggg cccccgggct 240
ccttcttcgg attctcagtg gagttttacc ggccgggaac agacggggtc agtgtgctgg 300
tgggagcacc caaggctaat accagccagc caggagtgct gcagggtggt gctgtctacc 360
tctgtccttg ggtgccagc cccacacagt gcacccccat tgaatttgac agcaaaggct 420
ctcggctcct ggagtcctca ctgtccagct cagagggaga ggagcctgtg gagtacaagt 480
ccttgcagtg gttcggggca acagttcgag cccatggctc ctccatcttg gcatgcgctc 540
cactgtacag ctggcgcaca gagaaggagc cactgagcga ccccgtgggc acctgctacc 600
tctccacaga taacttcacc cgaattctgg agtatgcacc ctgccgctca gatttcagct 660
gggcagcagg acagggttac tgccaaggag gcttcagtgc cgagttcacc aagactggcc 720
gtgtggtttt aggtggacca ggaagctatt tctggcaagg ccagatcctg tctgccactc 780
aggagcagat tgcagaatct tattaccccg agtacctgat caacctggtt caggggcagc 840
tgcagactcg ccaggccagt tccatctatg atgacagcta cctaggatac tctgtggctg 900
ttggtgaatt cagtggtgat gacacagaag actttgttgc tggtgtgccc aaagggaacc 960
tcacttacgg ctatgtcacc atccttaatg gctcagacat tcgatccctc tacaacttct 1020
caggggaaca gatggcctcc tactttggct atgcagtggc cgccacagac gtcaatgggg 1080
acgggctgga tgacttgctg gtgggggcac ccctgctcat ggatcggacc cctgacgggc 1140
ggcctcagga ggtgggcagg gtctacgtct acctgcagca cccagccggc atagagccca 1200
cgcccaccct taccctcact ggccatgatg agtttggccg atttggcagc tccttgaccc 1260
ccctggggga cctggaccag gatggctaca atgatgtggc catcggggct ccctttggtg 1320
gggagaccca gcagggagta gtgtttgtat ttcctggggg cccaggaggg ctgggctcta 1380
agccttccca ggttctgcag cccctgtggg cagccagcca caccccagac ttctttggct 1440
ctgcccttcg aggaggccga gacctggatg gcaatggata tcctgatctg attgtggggt 1500
cctttggtgt ggacaaggct gtggtataca ggggccgccc catcgtgtcc gctagtgcct 1560
ccctcaccat cttccccgcc atgttcaacc cagaggagcg gagctgcagc ttagagggga 1620
accctgtggc ctgcatcaac cttagcttct gcctcaatgc ttctggaaaa cacgttgctg 1680
actccattgg tttcacagtg gaacttcagc tggactggca gaagcagaag ggaggggtac 1740
ggcgggcact gttcctggcc tccaggcagg caaccctgac ccagaccctg ctcatccaga 1800
atggggctcg agaggattgc agagagatga agatctacct caggaacgag tcagaatttc 1860
gagacaaact ctcgccgatt cacatcgctc tcaacttctc cttggacccc caagccccag 1920
tggacagcca cggcctcagg ccagccctac attatcagag caagagccgg atagaggaca 1980
aggctcagat cttgctggac tgtggagaag acaacatctg tgtgcctgac ctgcagctgg 2040
aagtgtttgg ggagcagaac catgtgtacc tgggtgacaa gaatgccctg aacctcactt 2100
tccatgccca gaatgtgggt gagggtggcg cctatgaggc tgagcttcgg gtcaccgccc 2160
ctccagaggc tgagtactca ggactcgtca gacacccagg gaacttctcc agcctgagct 2220

-continued

```
gtgactactt tgccgtgaac cagagccgcc tgctggtgtg tgacctgggc aaccccatga   2280
aggcaggagc cagtctgtgg ggtggccttc ggtttacagt ccctcatctc cgggacacta   2340
agaaaaccat ccagtttgac ttccagatcc tcagcaagaa tctcaacaac tcgcaaagcg   2400
acgtggtttc ctttcggctc tccgtggagg ctcaggccca ggtcaccctg aacggtgtct   2460
ccaagcctga ggcagtgcta ttcccagtaa gcgactggca tccccgagac cagcctcaga   2520
aggaggagga cctgggacct gctgtccacc atgtctatga gctcatcaac caaggcccca   2580
gctccattag ccagggtgtg ctggaactca gctgtcccca ggctctggaa ggtcagcagc   2640
tcctatatgt gaccagagtt acgggactca actgcaccac caatcacccc attaacccaa   2700
agggcctgga gttggatccc gagggttccc tgcaccacca gcaaaaacgg gaagctccaa   2760
gccgcagctc tgcttcctcg ggacctcaga tcctgaaatg cccggaggct gagtgtttca   2820
ggctgcgctg tgagctcggg cccctgcacc aacaagagag ccaaagtctg cagttgcatt   2880
tccgagtctg ggccaagact ttcttgcagc gggagcacca gccatttagc ctgcagtgtg   2940
aggctgtgta caaagccctg aagatgccct accgaatcct gcctcggcag ctgccccaaa   3000
aagagcgtca ggtggccaca gctgtgcaat ggaccaaggc agaaggcagc tatggcgtcc   3060
cactgtggat catcatccta gccatcctgt ttggcctcct gctcctaggt ctactcatct   3120
acatcctcta caagcttgga ttcttcaaac gctccctccc atatggcacc gccatggaaa   3180
aagctcagct caagcctcca gccacctctg atgcctgagt cctcccaatt tcagactccc   3240
attcctgaag aaccagtccc cccaccctca ttctactgaa aaggaggggt ctgggtactt   3300
cttgaaggtg ctgacggcca gggagaagct cctctcccca gcccagagac atacttgaag   3360
ggccagagcc agggggtga ggagctgggg atccctcccc cccatgcact gtgaaggacc   3420
cttgtttaca cataccctct tcatggatgg gggaactcag atccagggac agaggcccca   3480
gcctccctga agcctttgca ttttggagag tttcctgaaa caacttggaa agataactag   3540
gaaatccatt cacagttctt tgggccagac atgccacaag gacttcctgt ccagctccaa   3600
cctgcaaaga tctgtcctca gccttgccag agatccaaaa gaagccccca gctaagaacc   3660
tggaacttgg ggagttaaga cctggcagct ctggacagcc ccaccctggt gggccaacaa   3720
agaacactaa ctatgcatgg tgccccagga ccagctcagg acagatgcca cacaaggata   3780
gatgctggcc cagggcccag agcccagctc caaggggaat cagaactcaa atggggccag   3840
atccagcctg gggtctggag ttgatctgga acccagactc agacattggc acctaatcca   3900
ggcagatcca ggactatatt tgggcctgct ccagacctga tcctggaggc ccagttcacc   3960
ctgatttagg agaagccagg aatttcccag gaccctgaag gggccatgat ggcaacagat   4020
ctggaacctc agcctggcca gacacaggcc ctccctgttc cccagagaaa ggggagccca   4080
ctgtcctggg cctgcagaat ttgggttctg cctgccagct gcactgatgc tgcccctcat   4140
ctctctgccc aacccttccc tcaccttggc accagacacc caggacttat ttaaactctg   4200
ttgcaagtgc aataaatctg acccagtgcc cccactgacc agaactagaa aaaaaaaaaa   4260
aaaaaaa                                                             4267
```

<210> SEQ ID NO 119
<211> LENGTH: 3319
<212> TYPE: DNA
<213> ORGANISM: Homo sapiens

<400> SEQUENCE: 119

```
ggtggctacc gctcccggct tggcgtcccg cgcgcacttc ggcgatggct tttccgccgc     60
```

-continued

```
ggcgacggct gcgcctcggt ccccgcggcc tcccgcttct tctctcggga ctcctgctac    120
ctctgtgccg cgccttcaac ctagacgtgg acagtcctgc cgagtactct ggccccgagg    180
gaagttactt cggcttcgcc gtggatttct tcgtgcccag cgcgtcttcc cggatgtttc    240
ttctcgtggg agctcccaaa gcaaacacca cccagcctgg gattgtggaa ggagggcagg    300
tcctcaaatg tgactggtct tctacccgcc ggtgccagcc aattgaattt gatgcaacag    360
gcaatagaga ttatgccaag gatgatccat tggaatttaa gtcccatcag tggtttggag    420
catctgtgag gtcgaaacag gataaaattt tggcctgtgc cccattgtac cattggagaa    480
ctgagatgaa acaggagcga gagcctgttg gaacatgctt tcttcaagat ggaacaaaga    540
ctgttgagta tgctccatgt agatcacaag atattgatgc tgatggacag ggattttgtc    600
aaggaggatt cagcattgat tttactaaag ctgacagagt acttcttggt ggtcctggta    660
gcttttattg gcaaggtcag cttatttcgg atcaagtggc agaaatcgta tctaaatacg    720
accccaatgt ttacagcatc aagtataata accaattagc aactcggact gcacaagcta    780
tttttgatga cagctatttg ggttattctg tggctgtcgg agatttcaat ggtgatggca    840
tagatgactt tgtttcagga gttccaagag cagcaaggac tttgggaatg gtttatattt    900
atgatgggaa gaacatgtcc tccttataca attttactgg cgagcagatg gctgcatatt    960
tcggattttc tgtagctgcc actgacatta atggagatga ttatgcagat gtgtttattg   1020
gagcacctct cttcatggat cgtggctctg atggcaaact ccaagaggtg gggcaggtct   1080
cagtgtctct acagagagct tcaggagact tccagacgac aaagctgaat ggatttgagg   1140
tctttgcacg gtttggcagt gccatagctc ctttgggaga tctggaccag gatggtttca   1200
atgatattgc aattgctgct ccatatgggg gtgaagataa aaaaggaatt gtttatatct   1260
tcaatggaag atcaacaggc ttgaacgcag tcccatctca aatccttgaa gggcagtggg   1320
ctgctcgaag catgccacca agctttggct attcaatgaa aggagccaca gatatagaca   1380
aaaatggata tccagactta attgtaggag cttttggtgt agatcgagct atcttataca   1440
gggccagacc agttatcact gtaaatgctg gtcttgaagt gtaccctagc attttaaatc   1500
aagacaataa aacctgctca ctgcctggaa cagctctcaa agtttcctgt tttaatgtta   1560
ggttctgctt aaaggcagat ggcaaaggag tacttcccag gaaacttaat ttccaggtgg   1620
aacttctttt ggataaactc aagcaaaagg gagcaattcg acgagcactg tttctctaca   1680
gcaggtcccc aagtcactcc aagaacatga ctatttcaag ggggggactg atgcagtgtg   1740
aggaattgat agcgtatctg cgggatgaat ctgaatttag agacaaactc actccaatta   1800
ctatttttat ggaatatcgg ttggattata gaacagctgc tgatacaaca ggcctgcaac   1860
ccattcttaa ccagttcacg cctgctaaca ttagtcgaca ggctcacatt ctacttgact   1920
gtggtgaaga caatgtctgt aaacccaagc tggaagtttc tgtagatagt gatcaaaaga   1980
agatctatat tggggatgac aaccctctga cattgattgt taaggctcag aatcaaggag   2040
aaggtgccta cgaagctgag ctcatcgttt ccattccact gcaggctgat ttcatcgggg   2100
ttgtccgaaa caatgaagcc ttagcaagac tttcctgtgc atttaagaca gaaaaccaaa   2160
cccgccaggt ggtatgtgac cttggaaacc caatgaaggc tggaactcaa ctcttagctg   2220
gtcttcgttt cagtgtgcac cagcagtcag agatggatac ttctgtgaaa tttgacttac   2280
aaatccaaag ctcaaatcta tttgacaaag taagcccagt tgtatctcac aaagttgatc   2340
ttgctgtttt agctgcagtt gagataagag gagtctcgag tcctgatcat atctttcttc   2400
```

cgattccaaa ctgggagcac aaggagaacc ctgagactga agaagatgtt gggccagttg 2460
ttcagcacat ctatgagctg agaaacaatg gtccaagttc attcagcaag gcaatgctcc 2520
atcttcagtg gccttacaaa tataataata acactctgtt gtatatcctt cattatgata 2580
ttgatggacc aatgaaccgc acttcagata tggagatcaa ccctttgaga attaagatct 2640
catctttgca gacaactgaa aagaatgaca cggttgccgg gcaaggtgag cgggaccatc 2700
tcatcactaa gcgggatctt gccctcagtg aaggagatat tcacactttg ggttgtggag 2760
ttgctcagtg cttgaagatt gtctgccaag ttgggagatt agacagagga aagagtgcaa 2820
tcttgtacgt aaagtcatta ctgtggactg agacttttat gaataaagaa aatcagaatc 2880
attcctattc tctgaagtcg tctgcttcat ttaatgtcat agagtttcct tataagaatc 2940
ttccaattga ggatatcacc aactccacat tggttaccac taatgtcacc tggggcattc 3000
agccagcgcc catgcctgtg cctgtgtggg tgatcatttt agcagttcta gcaggattgt 3060
tgctactggc tgttttggta tttgtaatgt acaggatggg ctttttttaaa cgggtccggc 3120 cacctcaaga agaacaagaa agggagcagc ttcaacctca tgaaaatggt gaaggaaact 3180
cagaaactta actgcagttt ttaagttatg ctacatcttg acccactaga attagcaact 3240
ttattataga tttaaacttt cttcatgagg agtaaaaatc caaggcttta ctgctgatag 3300
tgctaattgg cattaacca 3319

<210> SEQ ID NO 120
<211> LENGTH: 2387
<212> TYPE: DNA
<213> ORGANISM: Homo sapiens

<400> SEQUENCE: 120
agacacctct gccctcacca tgagcctctg gcagcccctg gtcctggtgc tcctggtgct 60
gggctgctgc tttgctgccc ccagacagcg ccagtccacc cttgtgctct tccctggaga 120
cctgagaacc aatctcaccg acaggcagct ggcagaggaa tacctgtacc gctatggtta 180
cactcgggtg gcagagatgc gtggagagtc gaaatctctg gggcctgcgc tgctgcttct 240
ccagaagcaa ctgtccctgc ccgagaccgg tgagctggat agcgccacgc tgaaggccat 300
gcgaacccca cggtgcgggg tcccagacct gggcagattc caaacctttg agggcgacct 360
caagtggcac caccacaaca tcacctattg gatccaaaac tactcggaag acttgccgcg 420
ggcggtgatt gacgacgcct ttgcccgcgc cttcgcactg tggagcgcgg tgacgccgct 480
caccttcact cgcgtgtaca gccgggacgc agacatcgtc atccagtttg gtgtcgcgga 540
gcacggagac gggtatccct tcgacgggaa ggacgggctc ctggcacacg cctttcctcc 600
tggccccggc attcagggag acgcccattt cgacgatgac gagttgtggt ccctgggcaa 660
gggcgtcgtg gttccaactc ggtttggaaa cgcagatggc gcggcctgcc acttcccctt 720
catcttcgag ggccgctcct actctgcctg caccaccgac ggtcgctccg acggcttgcc 780
ctggtgcagt accacggcca actacgacac cgacgaccgg tttggcttct gccccagcga 840
gagactctac acccaggacg gcaatgctga tgggaaaccc tgccagtttc cattcatctt 900
ccaaggccaa tcctactccg cctgcaccac ggacggtcgc tccgacggct accgctggtg 960
cgccaccacc gccaactacg accgggacaa gctcttcggc ttctgcccga cccgagctga 1020
ctcgacggtg atggggggca actcggcggg ggagctgtgc gtcttcccct tcactttcct 1080
gggtaaggag tactcgacct gtaccagcga gggccgcgga gatgggcgcc tctggtgcgc 1140
taccacctcg aactttgaca gcgacaagaa gtggggcttc tgcccggacc aaggatacag 1200

-continued tttgttcctc gtggcggcgc atgagttcgg ccacgcgctg ggcttagatc attcctcagt 1260
gccggaggcg ctcatgtacc ctatgtaccg cttcactgag gggccccct tgcataagga 1320 cgacgtgaat ggcatccggc acctctatgg tcctcgccct gaacctgagc cacggcctcc 1380
aaccaccacc acaccgcagc ccacggctcc cccgacggtc tgccccaccg gacccccac 1440 tgtccacccc tcagagcgcc ccacagctgg ccccacaggt cccccctcag ctggccccac 1500
aggtcccccc actgctggcc cttctacggc cactactgtg cctttgagtc cggtggacga 1560
tgcctgcaac gtgaacatct tcgacgccat cgcggagatt gggaaccagc tgtatttgtt 1620
caaggatggg aagtactggc gattctctga gggcaggggg agccggccgc agggcccctt 1680
ccttatcgcc gacaagtggc ccgcgctgcc ccgcaagctg gactcggtct ttgaggagcg 1740
gctctccaag aagcttttct tcttctctgg gcgccaggtg tgggtgtaca caggcgcgtc 1800
ggtgctgggc ccgaggcgtc tggacaagct gggcctggga gccgacgtgg cccaggtgac 1860
cggggccctc cggagtggca gggggaagat gctgctgttc agcgggcggc gcctctggag 1920
gttcgacgtg aaggcgcaga tggtggatcc ccggagcgcc agcgaggtgg accggatgtt 1980
ccccggggtg cctttggaca cgcacgacgt cttccagtac cgagagaaag cctatttctg 2040
ccaggaccgc ttctactggc gcgtgagttc ccggagtgag ttgaaccagg tggaccaagt 2100
gggctacgtg acctatgaca tcctgcagtg ccctgaggac tagggctccc gtcctgcttt 2160
ggcagtgcca tgtaaatccc cactgggacc aaccctgggg aaggagccag tttgccggat 2220
acaaactggt attctgttct ggaggaaagg gaggagtgga ggtgggctgg gccctctctt 2280
ctcacctttg tttttgttg gagtgtttct aataaacttg gattctctaa cctttaaaaa 2340
aaaaaaaaaa aaaaaaaaaa aaaaaaaaaa aaaaaaaaaa aaaaaaa 2387

<210> SEQ ID NO 121
<211> LENGTH: 3761
<212> TYPE: DNA
<213> ORGANISM: Homo sapiens

<400> SEQUENCE: 121
aaatttagat tttgcaaacc tgtgcattga tgagagtgct attgaaacac attaagaaag 60
attttcaacg caggaatgtg tcatttcctt tcttcatgta ccagatgctg aaatactatg 120
agataaagat tttaggtttc aattgtaaag agagagaagt ggataaatca gtgctgcttt 180
ctttaggacg aaagaagtat ggagcagtgg gatcactttc acaatcaaca ggaggacact 240
gatagctgct ccgaatctgt gaaatttgat gctcgctcaa tgacagcttt gcttcctccg 300
aatcctaaaa acagcccttc ccttcaagag aaactgaagt ccttcaaagc tgcactgatt 360
gccctttacc tcctcgtgtt tgcagttctc atccctctca ttggaatagt ggcagctcaa 420
ctcctgaagt gggaaacgaa gaattgctca gttagttcaa ctaatgcaaa tgatataact 480
caaagtctca cgggaaaagg aaatgacagc gaagaggaaa tgagatttca agaagtcttt 540
atggaacaca tgagcaacat ggagaagaga atccagcata ttttagacat ggaagccaac 600
ctcatggaca cagagcattt ccaaaatttc agcatgacaa ctgatcaaag atttaatgac 660
attcttctgc agctaagtac cttgttttcc tcagtccagg gacatgggaa tgcaatagat 720
gaaatctcca agtccttaat aagtttgaat accacattgc ttgatttgca gctcaacata 780
gaaaatctga atggcaaaat ccaagagaat accttcaaac aacaagagga aatcagtaaa 840
ttagaggagc gtgtttacaa tgtatcagca gaaattatgg ctatgaaaga agaacaagtg 900

-continued

```
catttggaac aggaaataaa aggagaagtg aaagtactga ataacatcac taatgatctc    960
agactgaaag attgggaaca ttctcagacc ttgagaaata tcactttaat tcaaggtcct   1020
cctggacccc cgggtgaaaa aggagatcga ggtcccactg gagaaagtgg tccacgagga   1080
tttccaggtc caataggtcc tccgggtctt aaaggtgatc ggggagcaat tggctttcct   1140
ggaagtcgag gactcccagg atatgccgga aggccaggaa attctggacc aaaaggccag   1200
aaaggggaaa aggggagtgg aaacacatta actccattta cgaaagttcg actggtcggt   1260
gggagcggcc ctcacgaggg gagggtggag atactccaca gcggccagtg gggtacaatt   1320
tgtgacgatc gctgggaagt gcgcgttgga caggtcgtct gtaggagctt gggataccca   1380
ggtgttcaag ccgtgcacaa ggcagctcac tttggacaag gtactggtcc aatatggctg   1440
aatgaagtgt tttgttttgg gagagaatca tctattgaag aatgtaaaat tcggcaatgg   1500
gggacaagag cctgttcaca ttctgaagat gctggagtca cttgcacttt ataatgcatc   1560
atattttcat tcacaactat gaaatcgctg ctcaaaaatg attttattac cttgttcctg   1620
taaaatccat ttaatcaata tttaagagat taagaatatt gcccaaataa tattttagat   1680
tacaggatta atatattgaa caccttcatg cttactattt tatgtctata tttaaatcat   1740
tttaacttct ataggttttt aaatggaatt ttctaatata atgacttata tgctgaattg   1800
aacattttga agtttatagc ttccagatta caaaggccaa gggtaataga aatgcatacc   1860
agtaattggc tccaattcat aatatgttca ccaggagatt acaatttttt gctcttcttg   1920
tctttgtaat ctatttagtt gattttaatt actttctgaa taacggaagg gatcagaaga   1980
tatcttttgt gcctagattg caaaatctcc aatccacaca tattgtttta aaataagaat   2040
gttatccaac tattaagata tctcaatgtg caataacttg tgtattagat atcaatgtta   2100
atgatatgtc ttggccacta tggaccaggg agcttatttt tcttgtcatg tactgacaac   2160
tgtttaattg aatcatgaag taaattgaaa gcaggacata tgagaaaact gaccatcagt   2220
atatttgtcc agataattgg tggatcaaaa atgccactta acaggaagtt tagtttgtta   2280
tgcactttaa atggaataat tagcttgtta caattctagg acatggtgtt taaaatttaa   2340
atctgattaa tccattttaa caaacaatgc aaacatcttc agtgcagaag gaagagtggt   2400
ttcaactgtt tggagtcttt tatgaagtca gtcaacattt acaaccaaag ggcggggggg   2460
ggggtggggg gtgcgtcttt agtcctaaag ggacaataac tctgagcatg ccccaaaaaa   2520
gtagtttagc aacctttttgt tggtagtcaa cccatcccca gggccatagt gtagagtgtg   2580
aaaagctacc ctgaaaccca gtaattctac cctgaaagtg actgcctgca gaaagaccag   2640
cagttgatat taaagcgcaa atgaattcaa cctcagccct gaaaataaca gaattctgaa   2700
gtttcctatg actaattcac aaaaaaagta attgtaaact agtactatta tggaattact   2760
ctactgttct ttctttaata gtggcaaatg aaagcataag cttaagcatt ttttcatatt   2820
ctgaagtctc accacacata ataaccaagt ggtagactca cagccgtcca acttaaaaag   2880
gcaaaacctt accttggaat tggaattact gtaaacagcc tactgaaaat gcatttttat   2940
catgtaacat tcttctactt gtttaacatt gctgattttc tctggcagca taattttgtg   3000
gttaagagaa tgaattctga atgtacactt tctgtctcaa accctggctg taatttcagc   3060
tagttaataa ttctttgtgt tcagttccac tatctaggta ttttcttcaa aaggtaaata   3120
caatggtttc tgaaagaatc atttgcatta tcagcctgtt tgggatgtct gagatcagtg   3180
cctctgggtt gttaatactg tattgctgta tggtatatgt atgctgattt actacttatg   3240
cgtaagtggt atgcatggga tgtctgaaat cagtgcctat gggttgtcaa tagtattaac   3300
```

```
tattagtgtt aactgttagt attaactatt agtattatta acactaataa tagtactatt   3360

actattacta tttttatttt aaaataaaat ttacctttaa aataataata gtactattgc   3420

tagtactagt actattgcta ttactagtac tattactagt actagtacta tgacactgtt   3480

aatagtacta ttaacaaccc ataggcactt gggatgtctg agatcagtgc ctatgggttg   3540

ttaatactat attgctgtat ggtatatgca tgctgattta ccacttatgc atagatatat   3600

ctttaataag taatctaaaa atcctttttg tatttgagag aatctactaa gttcagtcca   3660

gtcaagaaaa gaacctaata gcaccaatac aaattgagga cttaatttac tttggaatgt   3720

tgaattgcat ttgttccatt aaaaaaaaca gaaatttgcg a                        3761
```

```
<210> SEQ ID NO 122
<211> LENGTH: 2533
<212> TYPE: DNA
<213> ORGANISM: Homo sapiens

<400> SEQUENCE: 122

attcttctat tagataacag tagctattta aatacttctg cagaagctca catattttta     60

gtttgttgaa gttcgtgact gcttcactct ctcattctta gcttgaattt ggaaatgact    120

tttgatgacc taaagatcca gactgtgaag gaccagcctg atgagaagtc aaatggaaaa    180

aaagctaaag gtcttcagtt tctttactct ccatggtggt gcctggctgc tgcgactcta    240

ggggtccttt gcctgggatt agtagtgacc attatggtgc tgggcatgca attatcccag    300

gtgtctgacc tcctaacaca agagcaagca aacctaactc accagaaaaa gaaactggag    360

ggacagatct cagcccggca acaagcagaa gaagcttcac aggagtcaga aaacgaactc    420

aaggaaatga tagaaaccct tgctcggaag ctgaatgaga aatccaaaga gcaaatggaa    480

cttcaccacc agaatctgaa tctccaagaa acactgaaga gagtagcaaa ttgttcagct    540

ccttgtccgc aagactggat ctggcatgga gaaaactgtt acctattttc ctcgggctca    600

tttaactggg aaaagagcca agagaagtgc ttgtctttgg atgccaagtt gctgaaaatt    660

aatagcacag ctgatctgga cttcatccag caagcaattt cctattccag ttttccattc    720

tggatggggc tgtctcggag gaaccccagc tacccatggc tctgggagga cggttctcct    780

ttgatgcccc acttatttag agtccgaggc gctgtctccc agacataccc ttcaggtacc    840

tgtgcatata tacaacgagg agctgtttat gcggaaaact gcattttagc tgccttcagt    900

atatgtcaga agaaggcaaa cctaagagca cagtgaattt gaaggctctg gaagaaaaga    960

aaaaagtctt tgagttttat tctggaattt aagctattct ttgtcacttg ggtgccaaac   1020

atgagagccc agaaaactgt catttagctg gctgcagaac tcctttgcag aaactggggt   1080

tccaggtgcc tggcaccttt atgtcaacat tttgattct agctacctgt attatttcac    1140

ctagcttgtc ccaagcttcc ctgccagcct gaagtccatt ttccccttttt tattttaaaa  1200

tttgactcct cttcaagctt gaaaaccctc tgaactcagt cttctttacc tcattatcac   1260

cttcccctca cactcctaaa attgcatgaa agacagaaca tggagaactt gctcaagtgc   1320

aggcagagag caaaaagggg aaatatgtct gggaaaaagt gcacgtgaag aaacaaagaa   1380

ggacagaggc cattccgaaa tcaagaaact catgttctta actttaaaaa aggtatcaat   1440

ccttggtttt taaactgtgg tccatctcca gactctacca cttacggaca gacagacaga   1500

cagacacaca cacacacaca cacacacatt ttgggacaag tggggagccc aagaaagtaa   1560

ttagtaagtg agtggtcttt tctgtaagct aatccacaac ctgttaccac ttcctgaatc   1620
```

-continued agttattatt tcttcatttt tttttctacc agaggacaga ttaatagatt taacccttca 1680
caacagttct tgttagaatc atgggatgtg tggcccagag gtaagaatag aatttctttc 1740
cctaaagaac ataccttttg tagatgaact cttctcaact ctgttttgct atgctataat 1800
tccgaaacat acaagacaaa aaaaatgaag acactcaatc tagaacaaac taagccaggt 1860
atgcaaatat cgctgaatag aaacagatgg aattagaaat atatcttcta tttttaggct 1920
tctatttcct ttccacccac tcttcacagg ctattctact ttaaaggaag ccttttttatt 1980 ttgctgcaca caatctagca ggaatctttt ttttttttta agagctgtgt catccttatg 2040
taggcaagag atgtttgctt ttgttaaaag ctttattgag atataattaa cataaaataa 2100
actgaacata tttaaagtgt actatttgat aagttttcac accttgtgga gaacatgcat 2160
actacaatta agagagtgaa catatccatc atccctcaaa gtgtcacaat gctcctcctg 2220
atgactcctc cccagaaaac caccaatcgg ctttcatttt gcattttgta gttttatgtg 2280
aatggaatca tatagtatgt cttttttttt tgtctggctt ctttcacttt gcataattat 2340
tttgagattc atatgtctcc atcttgatgc tcgtatgaat tcattctttt aaatgttgaa 2400
tattcccttg tatggatata ccacaattca tttacccatt tacttgttga tgacatttgg 2460
gttgttttag ttttgggata ttacaaataa agctgctgtg aacatttgtg tacaagaaaa 2520
aaaaaaaaaa aaa 2533

<210> SEQ ID NO 123
<211> LENGTH: 2680
<212> TYPE: DNA
<213> ORGANISM: Homo sapiens

<400> SEQUENCE: 123
atatagagca ggcgccgcgg gtcgcagcac agtgcggaga ccgcagcccc ggagcccggg 60
ccagggtcca cctgtccccg cagcgccggc tcgcgccctc ctgccgcagc caccgagccg 120
ccgtctagcg ccccgacctc gccaccatga gagccctgct ggcgcgcctg cttctctgcg 180
tcctggtcgt gagcgactcc aaagtgagtg cgctcttgct ttgactgatg ctgcccaagg 240
acctctgatc agcaccaggg gagaggaggg gctgctcagg gagctggggt cctccggatt 300
ccatccacag cagggccaga ctctccccag gaaatgggac agggtggcag cggaggcttg 360
agaaccacgg gggttggcac tggctggcaa gggaggaaga ggccgccggg actgccccag 420
cctgcgggca tctggtagat gaagcttgct tgggtcaatc catttctcct ggctggaaac 480
ccatggtctt ccatttgaga actagatacg aacaggcgaa ctgtgactgt ctaaatggag 540
gaacatgtgt gtccaacaag tacttctcca acattcactg gtgcaactgc ccaaagaaat 600
tcggagggca gcactgtgaa atagataagt caaaaacctg ctatgagggg aatggtcact 660
tttaccgagg aaaggccagc actgacacca tgggccggcc ctgcctgccc tggaactctg 720
ccactgtcct tcagcaaacg taccatgccc acagatctga tgctcttcag ctgggcctgg 780
ggaaacataa ttactgcagg aacccagaca accggaggcg accctggtgc tatgtgcagg 840
tgggcctaaa gccgcttgtc caagagtgca tggtgcatga ctgcgcagat ggaaaaaagc 900
cctcctctcc tccagaagaa ttaaaatttc agtgtggcca aaagactctg aggccccgct 960
ttaagattat tgggggagaa ttcaccacca tcgagaacca gccctggttt gcggccatct 1020
acaggaggca ccgggggggc tctgtcacct acgtgtgtgg aggcagcctc atcagccctt 1080
gctgggtgat cagcgccaca cactgcttca ttgattaccc aaagaaggag gactacatcg 1140
tctacctggg tcgctcaagg cttaactcca acacgcaagg ggagatgaag tttgaggtgg 1200
aaaacctcat cctacacaag gactacagcg ctgacacgct tgctcaccac aacgacattg 1260
ccttgctgaa gatccgttcc aaggagggca ggtgtgcgca gccatcccgg actatacaga 1320
ccatctgcct gccctcgatg tataacgatc cccagtttgg cacaagctgt gagatcactg 1380
gctttggaaa agagaattct accgactatc tctatccgga gcagctgaaa atgactgttg 1440
tgaagctgat ttcccaccgg gagtgtcagc agccccacta ctacggctct gaagtcacca 1500
ccaaaatgct gtgtgctgct gacccacagt ggaaaacaga ttcctgccag ggagactcag 1560
ggggacccct cgtctgttcc ctccaaggcc gcatgacttt gactggaatt gtgagctggg 1620
gccgtggatg tgccctgaag gacaagccag gcgtctacac gagagtctca cacttcttac 1680
cctggatccg cagtcacacc aaggaagaga atggcctggc cctctgaggg tccccaggga 1740
ggaaacgggc accacccgct ttcttgctgg ttgtcatttt tgcagtagag tcatctccat 1800
cagctgtaag aagagactgg gaagataggc tctgcacaga tggatttgcc tgtgccaccc 1860
accagggcga acgacaatag ctttaccctc aggcataggc ctgggtgctg gctgcccaga 1920
cccctctggc caggatggag ggtggtcct gactcaacat gttactgacc agcaacttgt 1980
ctttttctgg actgaagcct gcaggagtta aaaagggcag ggcatctcct gtgcatgggt 2040
gaagggagag ccagctcccc cgacggtggg catttgtgag gcccatggtt gagaaatgaa 2100
taatttccca attaggaagt gtaacagctg aggtctcttg agggagctta gccaatgtgg 2160
gagcagcggt ttggggagca gagacactaa cgacttcagg gcagggctct gatattccat 2220
gaatgtatca ggaaatatat atgtgtgtgt atgtttgcac acttgtgtgt gggctgtgag 2280
tgtaagtgtg agtaagagct ggtgtctgat tgttaagtct aaatatttcc ttaaactgtg 2340
tggactgtga tgccacacag agtggtcttt ctggagaggt tataggtcac tcctggggcc 2400
tcttgggtcc cccacgtgac agtgcctggg aatgtattat tctgcagcat gacctgtgac 2460
cagcactgtc tcagtttcac tttcacatag atgtcccttt cttggccagt tatcccttcc 2520
ttttagccta gttcatccaa tcctcactgg gtggggtgag gaccactcct gtacactgaa 2580
tatttatatt tcactatttt tatttatatt tttgtaattt taaataaaag tgatcaataa 2640
aatgtgattt ttctgatgac aaaaaaaaaa aaaaaaaaaa 2680

<210> SEQ ID NO 124
<211> LENGTH: 1570
<212> TYPE: DNA
<213> ORGANISM: Homo sapiens

<400> SEQUENCE: 124
gccgagccag ccccttcacc accagccggc cgcgccccgg gaagggaagt ttgtggcgga 60
ggaggttcgt acgggaggag ggggaggcgc ccacgcatct ggggctgact cgctctttcg 120
caaaacgtct gggaggagtc cctggggcca caaaactgcc tccttcctga ggccagaagg 180
agagaagacg tgcagggacc ccgcgcacag gagctgccct cgcgacatgg gtcacccgcc 240
gctgctgccg ctgctgctgc tgctccacac ctgcgtccca gcctcttggg gcctgcggtg 300
catgcagtgt aagaccaacg gggattgccg tgtggaagag tgcgccctgg gacaggacct 360
ctgcaggacc acgatcgtgc gcttgtggga agaaggagaa gagctggagc tggtggagaa 420
aagctgtacc cactcagaga agaccaacag gaccctgagc tatcggactg gcttgaagat 480
caccagcctt accgaggttg tgtgtgggtt agacttgtgc aaccagggca actctggccg 540
ggctgtcacc tattcccgaa gccgttacct cgaatgcatt tcctgtggct catcagacat 600

```
gagctgtgag aggggccggc accagagcct gcagtgccgc agccctgaag aacagtgcct    660

ggatgtggtg acccactgga tccaggaagg tgaagaaggg cgtccaaagg atgaccgcca    720

cctccgtggc tgtggctacc ttcccggctg cccgggctcc aatggtttcc acaacaacga    780

caccttccac ttcctgaaat gctgcaacac caccaaatgc aacgagggcc caatcctgga    840

gcttgaaaat ctgccgcaga atggccgcca gtgttacagc tgcaagggga acagcaccca    900

tggatgctcc tctgaagaga ctttcctcat tgactgccga ggccccatga atcaatgtct    960

ggtagccacc ggcactcacg aaccgaaaaa ccaaagctat atggtaagag gctgtgcaac   1020

cgcctcaatg tgccaacatg cccacctggg tgacgccttc agcatgaacc acattgatgt   1080

ctcctgctgt actaaaagtg gctgtaacca cccagacctg gatgtccagt accgcagtgg   1140

ggctgctcct cagcctggcc ctgcccatct cagcctcacc atcaccctgc taatgactgc   1200

cagactgtgg ggaggcactc tcctctggac ctaaacctga aatccccctc tctgccctgg   1260

ctggatccgg gggacccctt tgcccttccc tcggctccca gccctacaga cttgctgtgt   1320

gacctcaggc cagtgtgccg acctctctgg gcctcagttt tcccagctat gaaaacagct   1380

atctcacaaa gttgtgtgaa gcagaagaga aaagctggag gaaggccgtg ggccaatggg   1440

agagctcttg ttattattaa tattgttgcc gctgttgtgt tgttgttatt aattaatatt   1500

catattattt attttatact tacataaaga ttttgtacca gtggacaagg ccaaaaaaaa   1560

aaaaaaaaaa                                                          1570
```

<210> SEQ ID NO 125
<211> LENGTH: 3032
<212> TYPE: DNA
<213> ORGANISM: Homo sapiens

<400> SEQUENCE: 125

```
tggcactcca ggctgcctcc aagagcaggg ttggtagagc tgagggatga gagatttgcc     60

tgtcctggag agtcaccacc cttccagctt tggggaggcc cccagggaaa gtgagggaga    120

agatatatga agattgctga attacgtgcc tccttcggag aaccccaccc agtcccgggc    180

ccagggcagt aacttgccca ttggaaaggg gaaagcagag gccacactca gtgacaatgg    240

ccacaaggaa cattggctag catgtggatg acctctgttt ccttacaggc tctgaagccc    300

ttccatgaat ccccggaaga aggtggacct gaaactcatt atcgtcggag ccattggtgt    360

gggaaagacc tccctccttc accaatatgt gcacaagacg ttttatgagg aataccagac    420

cacactgggg gccagcatcc tctccaagat tatcatattg ggtgacacaa ctttgaagtt    480

acagatctgg gacacgggcg gtcaggagcg gttccgctcc atggtgtcca cgttctacaa    540

gggctccgat ggctgcatcc tagcttttga tgtcaccgac ctggagtctt ttgaagccct    600

ggatatctgg cggggtgatg tcctggccaa gattgtcccc atggagcagt cctaccccat    660

ggtgttgttg gggaacaaga tcgatctggc agaccggaag gtaccccagg aagtagctca    720

aggctggtgt agagagaaag atattcctta ctttgaagtc agtgccaaga atgacatcaa    780

tgtggtgcaa gcgtttgaga tgctggccag tagggctctg tcgaggtacc agagcatctt    840

agaaaatcac ctcacagaat ccatcaagct ctcgccagac cagtcaagga gcagatgctg    900

ctgacctcca gacgcctgct ctggaagccc agaaacagag cctgccccga gcctggtcac    960

cccaggcttg agaacaggtg accatccccc tccagcccca ctgcctgccc aagcacagtg   1020

caggggggcct aagctctgcg gcagagccct tgaccctggt gctgggccca gagtcagagg   1080

gcagcccctg gctcaggctg agtatagtga gagcgtctgg atgaagcccg gaatgtcaga   1140
```

gccaaaccct ggtcctgcag aagtcacagt ttccgcagtg gctccagctt tccccaccca 1200
tccacccctc aaacactccc gctccagaac acacatctcc gcagaccggc cactgattgg 1260
agtctggtta catcctcctg tggacagacc ttcctcaccc gctcccacct cacacccctc 1320
agccacaagc aaagctttgg acaatggcac agctcagcct ccttcaacga gcagactaag 1380
gagtaaaggt ctggacccca catgctgggc ccgcctcagc tcctggcaga agctgtcgtg 1440
cctgagaccc cctctgctcc ctccagggta gaagactgag ggagcacagg agaagccaca 1500
agggaccatg gctcattcct ccttgctggg tgctcaggca actcacataa atctctgagt 1560
ctcaatttgt ttatctgtcc tgtgggggtg agatgtgcct tgccccctgt atcacagtgt 1620
ggttttgagg accagaagct gtgcttaaat ccagtagctg ttgtcaatat gcatttattt 1680
acttctttga caagtttatt tttgcgtatc tactatgtac gatgcattga agtccagtga 1740
caaacaaaac acagggactc tgccctcctg gagccgacat ctggtgaggg agagacgcag 1800
actctagaca gatatttcca aatagcaggt aagtgctata aacaaaggga aacagggtaa 1860
tgggatagag tgacaggggg tgggatgagt tgctatttta gatgaagtgg tccaggaggg 1920
cttccctgag gaggtggcat ttggtctgag ggctagagaa tgagaaagca gctgtcacct 1980
gagagctgga gaaagaacat tccagggaga gggagcatca agacccaaag ccctgaggca 2040
aaaacaagct tgccatgttc caggaacagt gaaaggacat ccattgacct aatactcaaa 2100
gctgctgtcc caaagacaaa gcaaagggga cccagctccc ttgggtggct cctagatgct 2160
ctgctgcctg accaccagag ggcagcagtg ctccttctct tccaggctga gcagaaagtg 2220
gatgctcatg aacgttttag gagctggggt tttgtccttc agatgctcaa agcttgttca 2280
tgggcttgga ggcatgttta gccctttggg atttgtaagg cagagaattc caatttctta 2340
agcctagtaa gaaatgagca aaaacttcaa tatatatgac tcaggcaaga aatcagcatc 2400
tgtggcaaat actagaatga aatgcaagaa agctcactgc aaggagtctc cctccctgca 2460
gattccaagg ctggaatctt tttcttctgg ctccaggcag cacagacagg gcctagcctg 2520
gagagggtgg acaagatgtc ctctcagggt cttcaatggc caagtccaag cccactgcag 2580
aatctttctg tctacccgta agtatccttt cctgagttcc aggcaaagct ggggatgtta 2640
gcctatgact gtcatctgac ttggaaggta cacctagggg ccgggggggag gtcagcaggg 2700 gagtttggga gccacttctc cccccacgtg gcactggagt gtgaactggc tcattctgga 2760
caccagcatg gagccagcac gggaacaggg gggcagccta gagcacaagc tctatctgtg 2820
tccttcagag ctcctgggaa acatgatgcg ccctcatggg aatggcattt tgcatatcac 2880
acaggctgtc ctgggagtca ggcagactgg attgtcacgt gcggtgtgca tgcagcagct 2940
tgtgcactgc agtggacctg tggaccattt ctaaaggtgc acaacaaata ataaatgtgt 3000
ccttctttgt ttttaaaaaa aaaaaaaaaa aa 3032

<210> SEQ ID NO 126
<211> LENGTH: 2828
<212> TYPE: DNA
<213> ORGANISM: Homo sapiens

<400> SEQUENCE: 126
agcgccccgg aagtgatctg tggcggctgc tgcagagccg ccaggaggag ggtggatctc 60
cccagagcaa agcgtcggag tcctcctcct ccttctcctc ctcctcctcc tcctcctcca 120
gccgcccagg ctcccccgcc acccgtcaga ctcctccttc gaccgctccc ggcgcggggc 180

-continued

```
cttccaggcg acaaggaccg agtaccctcc ggccggagcc acgcagccgc ggcttccgga    240
gccctcgggg cggcggactg gctcgcggtg cagattcttc ttaatccttt ggtgaaaact    300
gagacacaaa atggctgcaa ataagcccaa gggtcagaat tctttggctt tacacaaagt    360
catcatggtg ggcagtggtg gcgtgggcaa gtcagctctg actctacagt tcatgtacga    420
tgagtttgtg gaggactatg agcctaccaa agcagacagc tatcggaaga aggtagtgct    480
agatggggag gaagtccaga tcgatatctt agatacagct gggcaggagg actacgctgc    540
aattagagac aactacttcc gaagtgggga ggggttcctc tgtgttttct ctattacaga    600
aatggaatcc tttgcagcta cagctgactt cagggagcag attttaagag taaaagaaga    660
tgagaatgtt ccatttctac tggttggtaa caaatcagat ttagaagata aaagacaggt    720
ttctgtagaa gaggcaaaaa acagagctga gcagtggaat gttaactacg tggaaacatc    780
tgctaaaaca cgagctaatg ttgacaaggt atttttttgat ttaatgagag aaattcgagc    840
gagaaagatg gaagacagca aagaaaagaa tggaaaaaag aagaggaaaa gtttagccaa    900
gagaatcaga gaaagatgct gcattttata atcaaagccc aaactccttt cttatcttga    960
ccatactaat aaatataatt tataagcatt gccattgaag gcttaattga ctgaaattac   1020
tttaacattt tggaaattgt tgtatatcac taaaagcatg aattggaact gcaatgaaag   1080
tcaaatttac tttaaaaaga aattaatatg gcttcaccaa gaagcaaagt tcaacttatt   1140
tcataattgc ctacatttat catggtcctg aatgtagcgt gtaagcttgt gtttcttggg   1200
cagtctttct tgaaattgaa gaggtgaaat gggggtgggg agtgggagga aaggtgactt   1260
cctctggtgt ttattataaa gcttaaattt tatatcattt taaaatgtct tggtcttcta   1320
ctgccttgaa aaatgacaat tgtgaacatg atagttaaac taccactttt tttaaccatt   1380
attatgcaaa atttagaaga aaagttattg gcatggttgt tgcatatagt taaactgaga   1440
gtaattcatc tgtgaatctg ctttaattac ctggtgagta acttagaaaa gtggtgtaaa   1500
cttgtacatg gaatttttttg aatatgcctt aatttagaaa ctgaaaaata tctggttata   1560
tcattctggg tgtgttctta ctgacaccag gggtccgctg ccccatgtgt cctggtgaga   1620
aaatatatgc ctggcacagc ttttgtatag aaaattcttg agaagtaact gtccgctaga   1680
agtctgtcca aatttaaaat gtgtgccata ttctggttct tgaaaataag attccagagc   1740
tctttgatcg cttttaataa actgcaagtt cattttaaat gaagggccag catatatact   1800
tgcaagataa ttttcagctg caaggattca gcaccagtta tgtttgaatg aaccctcctt   1860
ttctctgaga ttctggtccc tggaaatccc tttctgctag tggtgagcat gtaagtgtta   1920
agtttttaat ctgggagcag ggcataggaa gaaaatgtca gtagtgctaa tgcattttgc   1980
actagaacgc ttcgggaaaa tattcatgct tgccatctgt tcatttctaa atttatattc   2040
ataaagttac agtttgatac aggaattatt aggagtaatt cttttctgtt tctgtttata   2100
atgaagaaca ctgtagctac attttcagaa gttaacatca agccatcaaa cctgggtata   2160
gtgcagaaaa cgtggcacac actgaccaca cattaggctg tgtcaccatt gtgtggtgta   2220
cctgctggaa gaattctagc atgctacttg gggacataat ttcagtggga aatatgccac   2280
tgaccgattt tttttttttc ctctttgcag tggggctagg acagttgatt caacaaagta   2340
ttttttttctt ttttctcagt cctaatttga acaggtcaaa gatgtgttca ggcattccag   2400
gtaacaggtg tgtatgtaaa gttaaaaata ggctttttag gaactcactc tttagatatt   2460
tacatccagc ttctcatgtt aaatatttgt ccttaaaggg tttgagatgt acatctttca   2520
tttcgtattt ctcataggct atgccatgtg cggaattcaa gttaccaatg taacactggc   2580
```

```
cagcgggccc agcaatctcc atgtgtactt attacagtct tatttaacca ggggtcctaa   2640

ccactaacat tgtgactttg ctttgagacc tttcctctcc tgggtactga ggtgctatga   2700

agccaactga caaagatgca tcacgtgtct taggctgatg ccactacccg atttgtttat   2760

ttgcaatttg agccatttaa agaccaataa acttcctttt ttaaaatgtt aaaaaaaaaa   2820

aaaaaaaa                                                            2828


<210> SEQ ID NO 127
<211> LENGTH: 3502
<212> TYPE: DNA
<213> ORGANISM: Homo sapiens

<400> SEQUENCE: 127

tttcctcagg aaaagccctg agaggaagca gggagggggt tgggagctgt gggggccaga     60

cgaacccgag cgctcccacc gagctgcctg ccatggggct ggggctgctg ctcccgctgc    120

tgctgctctg gactcggggg actcaggggt ccgagctgga ccccaaaggg cagcacgtct    180

gtgtggccag cagcccctct gctgagctgc agtgctgcgc aggctggagg cagaaggatc    240

aagaatgcac catccccatc tgtgaggggc cggacgcctg ccagaaagac gaggtgtgtg    300

tgaagccggg cctctgtcga tgcaagcctg gattctttgg ggcccactgc agctcccgct    360

gcccgggcca gtactggggc cccgactgcc gtgagagctg cccctgccac ccgcacggcc    420

agtgcgagcc agccacgggc gcgtgccagt gccaggccga ccgctgggga gcccgctgcg    480

agttcccgtg cgcctgcggc ccccacgggc gctgcgaccc cgcgaccggc gtgtgccact    540

gcgaacccgg ctggtggtcg tccacgtgcc gccgcccgtg ccagtgcaac accgcggcgg    600

cgcgctgcga gcaggccacg ggcgcctgcg tgtgcaagcc gggctggtgg gggcgccgct    660

gcagcttccg ctgcaactgc cacggctccc cgtgcgagca ggactccggc cgctgcgcct    720

gccggccggg ctggtggggt cccgaatgcc agcagcagtg cgagtgtgtg cggggccgct    780

gcagcgccgc ctccggcgag tgcacctgcc cgcccggctt ccgcggagcg cgctgcgagc    840

tgccctgccc ggcaggcagc cacggggtgc agtgcgcaca cagctgtggc cgctgcaaac    900

acaatgagcc gtgctctcca gacacaggca gctgtgagtc ctgcgagccg ggctggaacg    960

ggacccagtg ccagcagccc tgcctgcctg gcacctttgg cgagagctgc gaacagcagt   1020

gccctcactg ccgacatggg gaggcctgtg agccagatac tggccactgt cagcgctgtg   1080

accctggctg gctggggccc aggtgtgaag acccctgccc cactggtacc tttggggaag   1140

actgtggctc tacctgcccc acctgtgttc aggggtcctg tgatactgtg acaggggact   1200

gtgtctgcag tgccggctac tgggggccca gctgcaacgc ctcctgccca gccggtttcc   1260

atggaaacaa ctgctcagtt ccttgtgaat gcccagaggg actctgccac cctgtctctg   1320

ggtcctgcca gccaggctct ggcagtcggg acactgccct catcgcgggc agccttgtgc   1380

ctctgctgct gctcttcctg ggccttgcct gctgtgcctg ctgctgctgg gccccccgat   1440

cagacctcaa ggacaggcca gcgagagatg gagctaccgt gtccaggatg aagctgcagg   1500

tctgggggac actgaccagc ttgggctcca cgctgccctg ccgttccctc agctcccaca   1560

agctaccctg ggtgacagtc tcacatcacg acccggaggt ccccttcaac cacagcttca   1620

tcgagccgcc ctctgccggc tgggccactg atgactcctt ctcatccgat cctgagtctg   1680

gagaggcaga tgaggttcct gcctactgtg tgccacccca agaagggatg gtccctgtgg   1740

cccaggcagg gtcgtcagag gccagcctgg ctgcaggtgc tttcccgccc cctgaggacg   1800
```

-continued

```
cctccacgcc attcgccatc ccgcgcacct ccagcctagc tcgggccaag cggccatcgg   1860

tctccttcgc ggaaggtacc aagtttgcac cacagagtcg ccgaagctca ggggagctct   1920

ccagcccgct ccgaaagccc aagaggctct cccgggggc gcagtcgggt cctgagggcc   1980

gggaagccga agagtccaca ggcccagagg aagcagaagc ccccgagtcc tttccggcgg   2040

ctgccagtcc cggggattca gccactggcc accggcggcc cccacttggt ggccggacag   2100

tggctgagca cgtggaagcc attgagggca gcgtccagga gagctcgggc cctgtgacca   2160

cgatctacat gctggcaggg aagccccgcg gatccgaagg ccctgtccgc tctgtcttcc   2220

gccattttgg tagcttccag aaaggccagg cggaagccaa ggtcaagagg gccatcccta   2280

agcctccgcg ccaggccctg aatcggaaaa agggcagccc tggccttgcc tctggctctg   2340

tcggccagag ccccaactca gccccaaaag ctgggcttcc tggggccaca gggcctatgg   2400

cagtcagacc agaggaagcg gtccgggggc tgggggctgg caccgagagt tcaaggagag   2460

cccaggagcc agtctctggc tgtggctccc cagaacagga tccccagaag caggctgaag   2520

aggaaaggca ggaggaacct gagtatgaga atgttgtacc catctccagg ccaccagaac   2580

cctgatgacc ttgaatttgg ggagtgggga gagtggatgg actagactgt gctgtgtgct   2640

ggaaaatgat cccggggcca ggacagacaa accagagcct ctgcgcctcc acagggaaaa   2700

ggcaaggctt ccaggccagt tggcccaggc ccctggcagt gctcccggag gggcccagga   2760

aggcctgggc agagaccctg taggatgggg tcaggaaggg ttgcctgcag ggacttttgc   2820

tctgctgtcc tggaccctgt gtgcctcata agggctattc tttctttcac gtgcaaaaca   2880

tttttctgaa atagcaaaca acctacatgt ttgctgataa aagattggct aaacaaattt   2940

ttttttttt ttttgagaca gaatctccct ctgtccccca ggctggagtg cagtggtgcg   3000

atctcggctc actgcaagct ctgcctcccg ggttcacgcc cttctcctgc ctcagcctcc   3060

cgagtagctg ggactacagg tgccctccac cacgcttggc taattttttt gtatatttaa   3120

tagagacagg gtttcaccat gttagccagg atggtctcga tctcctgacc tcgtgatcca   3180

cctgcctcgg cctcccaaag tgctgggatg acaggcatga gccaccacgc ctggtctatg   3240

aactttttaa aaaggatgta tgtgtataaa aacagattca agggaaaggc actaaatggt   3300

tttttcctct ggaagatgag attgtaggtg atatttattt tcttctgaaa cttttgtata   3360

gtttgcaaat tttctacagt gaacattctt ttttactttt gttactagat tgaatttgat   3420

aaagtataat aaaaagcaat gatctttgtt aaaaaaataa aaagtactaa cattacagac   3480

atgtaaaaaa aaaaaaaaaa aa                                            3502
```

<210> SEQ ID NO 128
<211> LENGTH: 4201
<212> TYPE: DNA
<213> ORGANISM: Homo sapiens

<400> SEQUENCE: 128

```
tccggcccgc acccaccccc aagaggggcc ttcagctttg gggctcagag gcacgacctc     60

ctggggaggg ttaaaaggca gacgccccc cgcccccgc gcccccgcgc cccgactcct    120

tcgccgcctc cagcctctcg ccagtgggaa gcggggagca gccgcgcggc cggagtccgg   180

aggcgagggg aggtcggccg caacttcccc ggtccacctt aagaggacga tgtagccagc   240

tcgcagcgct gaccttagaa aaacaagttt gcgcaaagtg gagcggggac ccggcctctg   300

ggcagccccg gcggcgcttc cagtgccttc cagccctcgc gggcggcgca gccgcggccc   360

atggagcccg ccggcccggc ccccggccgc ctcgggccgc tgctctgcct gctgctcgcc   420
```

```
gcgtcctgcg cctggtcagg agtggcgggt gaggaggagc tgcaggtgat tcagcctgac    480
aagtccgtgt tggttgcagc tggagagaca gccactctgc gctgcactgc gacctctctg    540
atccctgtgg ggcccatcca gtggttcaga ggagctggac caggccggga attaatctac    600
aatcaaaaag aaggccactt cccccgggta acaactgttt cagacctcac aaagagaaac    660
aacatggact tttccatccg catcggtaac atcaccccag cagatgccgg cacctactac    720
tgtgtgaagt tccggaaagg gagccccgat gacgtggagt ttaagtctgg agcaggcact    780
gagctgtctg tgcgcgccaa accctctgcc cccgtggtat cgggccctgc ggcgagggcc    840
acacctcagc acacagtgag cttcacctgc gagtcccacg gcttctcacc cagagacatc    900
accctgaaat ggttcaaaaa tgggaatgag ctctcagact tccagaccaa cgtggacccc    960
gtaggagaga gcgtgtccta cagcatccac agcacagcca aggtggtgct gacccgcgag   1020
gacgttcact ctcaagtcat ctgcgaggtg gcccacgtca ccttgcaggg ggaccctctt   1080
cgtgggactg ccaacttgtc tgagaccatc cgagttccac ccaccttgga ggttactcaa   1140
cagcccgtga gggcagagaa ccaggtgaat gtcacctgcc aggtgaggaa gttctacccc   1200
cagagactac agctgacctg gttggagaat ggaaacgtgt cccggacaga aacggcctca   1260
accgttacag agaacaagga tggtacctac aactggatga gctggctcct ggtgaatgta   1320
tctgcccaca gggatgatgt gaagctcacc tgccaggtgg agcatgacgg gcagccagcg   1380
gtcagcaaaa gccatgacct gaaggtctca gcccacccga aggagcaggg ctcaaatacc   1440
gccgctgaga acactggatc taatgaacgg aacatctata ttgtggtggg tgtggtgtgc   1500
accttgctgg tggccctact gatggcggcc ctctacctcg tccgaatcag acagaagaaa   1560
gcccagggct ccacttcttc tacaaggttg catgagcccg agaagaatgc cagagaaata   1620
acacaggaca caaatgatat cacatatgca gacctgaacc tgcccaaggg gaagaagcct   1680
gctccccagg ctgcggagcc caacaaccac acggagtatg ccagcattca gaccagcccg   1740
cagcccgcgt cggaggacac cctcacctat gctgacctgg acatggtcca cctcaaccgg   1800
acccccaagc agccggcccc caagcctgag ccgtccttct cagagtacgc cagcgtccag   1860
gtcccgagga agtgaatggg accgtggttt gctctagcac ccatctctac gcgctttctt   1920
gtcccacagg gagccgccgt gatgagcaca gccaacccag ttcccggagg gctggggcgg   1980
tgcaggctct gggacccagg ggccagggtg gctcttctct ccccacccct ccttggctct   2040
ccagcacttc ctgggcagcc acggccccct ccccccacat tgccacatac ctggaggctg   2100
acgttgccaa accagccagg gaaccaacct gggaagtggc cagaactgcc tggggtccaa   2160
gaactcttgt gcctccgtcc atcaccatgt gggttttgaa gaccctcgac tgcctccccg   2220
atgctccgaa gcctgatctt ccagggtggg gaggagaaaa tcccacctcc cctgacctcc   2280
accacctcca ccaccaccac caccaccacc accaccacta ccaccaccac ccaactgggg   2340
ctagagtggg gaagatttcc cctttagatc aaactgcccc ttccatggaa aagctggaaa   2400
aaaactctgg aacccatatc caggcttggt gaggttgctg ccaacagtcc tggcctcccc   2460
catccctagg ctaaagagcc atgagtcctg gaggaggaga ggacccctcc caaaggactg   2520
gagacaaaac cctctgcttc cttgggtccc tccaagactc cctggggccc aactgtgttg   2580
ctccacccgg acccatctct cccttctaga cctgagcttg cccctccagc tagcactaag   2640
caacatctcg ctgtggacgc ctgtaaatta ctgagaaatg tgaaacgtgc aatcttgaaa   2700
ctgaggtgtt agaaaacttg atctgtggtg ttttgttttg ttttttttct taaaacaaca   2760
```

-continued

```
gcaacgtgat cttggctgtc tgtcatgtgt tgaagtccat ggttgggtct tgtgaagtct   2820
gaggtttaac agtttgttgt cctggaggga ttttcttaca gcgaagactt gagttcctcc   2880
aagtcccaga accccaagaa tgggcaagaa ggatcaggtc agccactccc tggagacaca   2940
gccttctggc tgggactgac ttggccatgt tctcagctga gccacgcggc tggtagtgca   3000
gccttctgtg accccgctgt ggtaagtcca gcctgcccag ggctgctgag ggctgcctct   3060
tgacagtgca gtcttatcga gacccaatgc ctcagtctgc tcatccgtaa agtggggata   3120
gtgaagatga cacccctccc caccacctct cataagcact ttaggaacac acagagggta   3180
gggatagtgg ccctggccgt ctatcctacc cctttagtga ccgcccccat cccggctttc   3240
tgagctgatc cttgaagaag aaatcttcca tttctgctct caaaccctac tgggatcaaa   3300
ctggaataaa ttgaagacag ccagggggat ggtgcagctg tgaagctcgg gctgattccc   3360
cctctgtccc agaaggttgg ccagagggtg tgacccagtt accctttaac ccccaccctt   3420
ccagtcgggt gtgagggcct gaccgggccc agggcaagca gatgtcgcaa gccctattta   3480
ttcagtcttc actataactc ttagagttga gacgctaatg ttcatgactc ctggccttgg   3540
gatgcccaag ggatttctgg ctcaggctgt aaaagtagct gagccatcct gcccattcct   3600
ggaggtccta caggtgaaac tgcaggagct cagcatagac ccagctctct gggggatggt   3660
cacctggtga tttcaatgat ggcatccagg aattagctga gccaacagac catgtggaca   3720
gctttggcca gagctcccgt gtggcatctg ggagccacag tgacccagcc acctggctca   3780
ggctagttcc aaattccaaa agattggctt gtaaaccttc gtctccctct cttttaccca   3840
gagacagcac atacgtgtgc acacgcatgc acacacacat tcagtatttt aaaagaatgt   3900
tttcttggtg ccattttcat tttattttat tttttaattc ttggaggggg aaataaggga   3960
ataaggccaa ggaagatgta tagctttagc tttagcctgg caacctggag aatccacata   4020
ccttgtgtat tgaaccccag gaaaaggaag aggtcgaacc aaccctgcgg aaggagcatg   4080
gtttcaggag tttattttaa gactgctggg aaggaaacag gccccatttt gtatatagtt   4140
gcaacttaaa ctttttggct tgcaaaatat ttttgtaata aagatttctg ggtaataatg   4200
a                                                                   4201
```

<210> SEQ ID NO 129
<211> LENGTH: 5820
<212> TYPE: DNA
<213> ORGANISM: Homo sapiens

<400> SEQUENCE: 129

```
agccgctgcg cccgagctgg cctgcgagtt cagggctcct gtcgctctcc aggagcaacc     60
tctactccgg acgcacaggc attccccgcg cccctccagc cctcgccgcc ctcgccaccg    120
ctcccggccg ccgcgctccg gtacacacag gatccctgct gggcaccaac agctccacca    180
tggggctggc ctggggacta ggcgtcctgt tcctgatgca tgtgtgtggc accaaccgca    240
ttccagagtc tggcggagac aacagcgtgt ttgacatctt tgaactcacc ggggccgccc    300
gcaaggggtc tgggcgccga ctggtgaagg gccccgaccc ttccagccca gctttccgca    360
tcgaggatgc caacctgatc ccccctgtgc ctgatgacaa gttccaagac ctggtggatg    420
ctgtgcgggc agaaaagggt ttcctccttc tggcatccct gaggcagatg aagaagaccc    480
ggggcacgct gctggccctg gagcggaaag accactctgg ccaggtcttc agcgtggtgt    540
ccaatggcaa ggcgggcacc ctggacctca gcctgaccgt ccaaggaaag cagcacgtgg    600
tgtctgtgga agaagctctc ctggcaaccg gccagtggaa gagcatcacc ctgtttgtgc    660
```

```
aggaagacag ggcccagctg tacatcgact gtgaaaagat ggagaatgct gagttggacg    720
tccccatcca aagcgtcttc accagagacc tggccagcat cgccagactc cgcatcgcaa    780
agggggcgt  caatgacaat ttccaggggg tgctgcagaa tgtgaggttt gtctttggaa    840
ccacaccaga agacatcctc aggaacaaag gctgctccag ctctaccagt gtcctcctca    900
cccttgacaa caacgtggtg aatggttcca gccctgccat ccgcactaac tacattggcc    960
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
tgactgaaga gaacaaagag ttggccaatg agctgaggcg gcctccccta tgctatcaca   1140
acggagttca gtacagaaat aacgaggaat ggactgttga tagctgcact gagtgtcact   1200
gtcagaactc agttaccatc tgcaaaaagg tgtcctgccc catcatgccc tgctccaatg   1260
ccacagttcc tgatggagaa tgctgtcctc gctgttggcc cagcgactct gcggacgatg   1320
gctggtctcc atggtccgag tggacctcct gttctacgag ctgtggcaat ggaattcagc   1380
agcgcggccg ctcctgcgat agcctcaaca accgatgtga gggctcctcg gtccagacac   1440
ggacctgcca cattcaggag tgtgacaaga gatttaaaca ggatggtggc tggagccact   1500
ggtccccgtg gtcatcttgt tctgtgacat gtggtgatgg tgtgatcaca aggatccggc   1560
tctgcaactc tcccagcccc cagatgaacg ggaaaccctg tgaaggcgaa gcgcgggaga   1620
ccaaagcctg caagaaagac gcctgcccca tcaatggagg ctggggtcct tggtcaccat   1680
gggacatctg ttctgtcacc tgtggaggag ggtacagaa  acgtagtcgt ctctgcaaca   1740
accccacacc ccagtttgga ggcaaggact gcgttggtga tgtaacagaa aaccagatct   1800
gcaacaagca ggactgtcca attgatggat gcctgtccaa tccctgcttt gccggcgtga   1860
agtgtactag ctaccctgat ggcagctgga aatgtggtgc ttgtccccct ggttacagtg   1920
gaaatggcat ccagtgcaca gatgttgatg agtgcaaaga agtgcctgat gcctgcttca   1980
accacaatgg agagcaccgg tgtgagaaca cggaccccgg ctacaactgc ctgccctgcc   2040
ccccacgctt caccggctca cagcccttcg gccagggtgt cgaacatgcc acggccaaca   2100
aacaggtgtg caagccccgt aacccctgca cggatgggac ccacgactgc aacaagaacg   2160
ccaagtgcaa ctacctgggc cactatagcg accccatgta ccgctgcgag tgcaagcctg   2220
gctacgctgg caatggcatc atctgcgggg aggacacaga cctggatggc tggcccaatg   2280
agaacctggt gtgcgtggcc aatgcgactt accactgcaa aaaggataat tgccccaacc   2340
ttcccaactc agggcaggaa gactatgaca aggatggaat tggtgatgcc tgtgatgatg   2400
acgatgacaa tgataaaatt ccagatgaca gggacaactg tccattccat tacaacccag   2460
ctcagtatga ctatgacaga gatgatgtgg gagaccgctg tgacaactgt ccctacaacc   2520
acaacccaga tcaggcagac acagacaaca atggggaagg agacgcctgt gctgcagaca   2580
ttgatggaga cggtatcctc aatgaacggg acaactgcca gtacgtctac aatgtggacc   2640
agagagacac tgatatggat ggggttggag atcagtgtga caattgcccc ttggaacaca   2700
atccggatca gctggactct gactcagacc gcattggaga tacctgtgac aacaatcagg   2760
atattgatga agatggccac cagaacaatc tggacaactg tccctatgtg cccaatgcca   2820
accaggctga ccatgacaaa gatggcaagg gagatgcctg tgaccacgat gatgacaacg   2880
atggcattcc tgatgacaag gacaactgca gactcgtgcc caatcccgac cagaaggact   2940
ctgacggcga tggtcgaggt gatgcctgca aagatgattt tgaccatgac agtgtgccag   3000
```

-continued

```
acatcgatga catctgtcct gagaatgttg acatcagtga gaccgatttc cgccgattcc   3060
agatgattcc tctggacccc aaagggacat cccaaaatga ccctaactgg gttgtacgcc   3120
atcagggtaa agaactcgtc cagactgtca actgtgatcc tggactcgct gtaggttatg   3180
atgagtttaa tgctgtggac ttcagtggca ccttcttcat caacaccgaa agggacgatg   3240
actatgctgg atttgtcttt ggctaccagt ccagcagccg cttttatgtt gtgatgtgga   3300
agcaagtcac ccagtcctac tgggacacca accccacgag ggctcaggga tactcgggcc   3360
tttctgtgaa agttgtaaac tccaccacag ggcctggcga gcacctgcgg aacgccctgt   3420
ggcacacagg aaacacccct ggccaggtgc gcaccctgtg gcatgaccct cgtcacatag   3480
gctggaaaga tttcaccgcc tacagatggc gtctcagcca caggccaaag acgggtttca   3540
ttagagtggt gatgtatgaa gggaagaaaa tcatggctga ctcaggaccc atctatgata   3600
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa cccccaggat   3780
cacttctcct tggcttcctt cttttctgtg cttgcatcag tgtggactcc tagaacgtgc   3840
gacctgcctc aagaaaatgc agttttcaaa aacagactca gcattcagcc tccaatgaat   3900
aagacatctt ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaaggggag ggcgcatacc cgagacgatt gtatgaagaa aatatggagg   4200
aactgttaca tgttcggtac taagtcattt tcaggggatt gaaagactat tgctggattt   4260
catgatgctg actggcgtta gctgattaac ccatgtaaat aggcacttaa atagaagcag   4320
gaaagggaga caaagactgg cttctggact tcctccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata tttttatggt tacaatggca caaaattatt atcaacctaa ctaaaacatt   4620
ccttttctct tttttcctga attatcatgg agttttctaa ttctctcttt tggaatgtag   4680
attttttta aatgctttac gatgtaaaat atttattttt tacttattct ggaagatctg   4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
aaatttaggc ttcatacgga aagtgtttga gagcaagtag ttgacattta tcagcaaatc   4920
tcttgcaaga acagcacaag gaaaatcagt ctaataagct gctctgcccc ttgtgctcag   4980
agtggatgtt atgggattct tttttctct gttttatctt ttcaagtgga attagttggt   5040
tatccatttg caaatgtttt aaattgcaaa gaaagccatg aggtcttcaa tactgtttta   5100
ccccatccct tgtgcatatt tccagggaga aggaaagcat atacactttt ttctttcatt   5160
tttccaaaag agaaaaaaat gacaaaaggt gaaacttaca tacaaatatt acctcatttg   5220
ttgtgtgact gagtaaagaa tttttggatc aagcggaaag agtttaagtg tctaacaaac   5280
ttaaagctac tgtagtacct aaaaagtcag tgttgtacat agcataaaaa ctctgcagag   5340
aagtattccc aataaggaaa tagcattgaa atgttaaata caatttctga aagttatgtt   5400
```

tttttctat catctggtat accattgctt tatttttata aattattttc tcattgccat 5460
tggaatagat atctcagatt gtgtagatat gctatttaaa taatttatca ggaaatactg 5520
cctgtagagt tagtatttct atttttatat aatgtttgca cactgaattg aagaattgtt 5580 ggtttttct tttttttgtt ttgttttttt tttttttttt ttttgctttt gacctcccat 5640
ttttactatt tgccaatacc tttttctagg aatgtgcttt tttttgtaca catttttatc 5700
cattttacat tctaaagcag tgtaagttgt atattactgt ttcttatgta caaggaacaa 5760
caataaatca tatggaaatt tatatttata aaaaaaaaaa aaaaaaaaaa aaaaaaaaaa 5820

<210> SEQ ID NO 130
<211> LENGTH: 931
<212> TYPE: DNA
<213> ORGANISM: Homo sapiens

<400> SEQUENCE: 130
tttcgtcggc ccgcccccttg gcttctgcac tgatggtggg tggatgagta atgcatccag 60
gaagcctgga ggcctgtggt ttccgcaccc gctgccaccc ccgcccctag cgtggacatt 120
tatcctctag cgctcaggcc ctgccgccat cgccgcagat ccagcgccca gagagacacc 180
agagaaccca ccatggcccc ctttgagccc ctggcttctg gcatcctgtt gttgctgtgg 240
ctgatagccc ccagcagggc ctgcacctgt gtcccacccc acccacagac ggccttctgc 300
aattccgacc tcgtcatcag ggccaagttc gtggggacac cagaagtcaa ccagaccacc 360
ttataccagc gttatgagat caagatgacc aagatgtata aagggttcca agccttaggg 420
gatgccgctg acatccggtt cgtctacacc cccgccatgg agagtgtctg cggatacttc 480
cacaggtccc acaaccgcag cgaggagttt ctcattgctg gaaaactgca ggatggactc 540
ttgcacatca ctacctgcag ttttgtggct ccctggaaca gcctgagctt agctcagcgc 600
cggggcttca ccaagaccta cactgttggc tgtgaggaat gcacagtgtt tccctgttta 660
tccatcccct gcaaactgca gagtggcact cattgcttgt ggacggacca gctcctccaa 720
ggctctgaaa agggcttcca gtcccgtcac cttgcctgcc tgcctcggga gccagggctg 780
tgcacctggc agtccctgcg gtcccagata gcctgaatcc tgcccggagt ggaagctgaa 840
gcctgcacag tgtccaccct gttcccactc ccatctttct tccggacaat gaaataaaga 900
gttaccaccc agcagaaaaa aaaaaaaaaa a 931

<210> SEQ ID NO 131
<211> LENGTH: 1686
<212> TYPE: DNA
<213> ORGANISM: Homo sapiens

<400> SEQUENCE: 131
cagacgctcc ctcagcaagg acagcagagg accagctaag agggagagaa gcaactacag 60 acccccccctg aaaacaaccc tcagacgcca catcccctga caagctgcca ggcaggttct 120
cttcctctca catactgacc cacggctcca ccctctctcc cctggaaagg acaccatgag 180
cactgaaagc atgatccggg acgtggagct ggccgaggag gcgctcccca agaagacagg 240
ggggccccag ggctccaggc ggtgcttgtt cctcagcctc ttctccttcc tgatcgtggc 300
aggcgccacc acgctcttct gcctgctgca ctttggagtg atcggccccc agagggaaga 360
gttccccagg gacctctctc taatcagccc tctggcccag gcagtcagat catcttctcg 420
aaccccgagt gacaagcctg tagcccatgt tgtagcaaac cctcaagctg aggggcagct 480

-continued

```
ccagtggctg aaccgccggg ccaatgccct cctggccaat ggcgtggagc tgagagataa    540
ccagctggtg gtgccatcag agggcctgta cctcatctac tcccaggtcc tcttcaaggg    600
ccaaggctgc cctccaccc atgtgctcct cacccacacc atcagccgca tcgccgtctc     660
ctaccagacc aaggtcaacc tcctctctgc catcaagagc ccctgccaga gggagacccc    720
agagggggct gaggccaagc cctggtatga gcccatctat ctgggagggg tcttccagct    780
ggagaagggt gaccgactca gcgctgagat caatcggccc gactatctcg actttgccga    840
gtctgggcag gtctactttg ggatcattgc cctgtgagga ggacgaacat ccaaccttcc    900
caaacgcctc ccctgcccca atccctttat taccccctcc ttcagacacc ctcaacctct    960
tctggctcaa aaagagaatt gggggcttag ggtcggaacc caagcttaga actttaagca   1020
acaagaccac cacttcgaaa cctgggattc aggaatgtgt ggcctgcaca gtgaagtgct   1080
ggcaaccact aagaattcaa actggggcct ccagaactca ctggggccta cagctttgat   1140
ccctgacatc tggaatctgg agaccaggga gcctttggtt ctggccagaa tgctgcagga   1200
cttgagaaga cctcacctag aaattgacac aagtggacct taggccttcc tctctccaga   1260
tgtttccaga cttccttgag acacggagcc cagccctccc catggagcca gctccctcta   1320
tttatgtttg cacttgtgat tatttattat ttatttatta tttatttatt tacagatgaa   1380
tgtatttatt tgggagaccg gggtatcctg ggggacccaa tgtaggagct gccttggctc   1440
agacatgttt tccgtgaaaa cggagctgaa caataggctg ttcccatgta gccccctggc   1500
ctctgtgcct tcttttgatt atgtttttta aaatatttat ctgattaagt tgtctaaaca   1560
atgctgattt ggtgaccaac tgtcactcat tgctgagcct ctgctcccca ggggagttgt   1620
gtctgtaatc gccctactat tcagtggcga gaaataaagt ttgcttagaa aagaaaaaaa   1680
aaaaaa                                                              1686
```